US006265434B1

(12) United States Patent
Caldwell et al.

(10) Patent No.: US 6,265,434 B1
(45) Date of Patent: Jul. 24, 2001

(54) PYRROLIDINE MODULATORS OF CHEMOKINE RECEPTOR ACTIVITY

(75) Inventors: Charles Caldwell; Kevin T. Chapman, both of Scotch Plains; Jeffrey Hale; Dooseop Kim, both of Westfield; Christopher Lynch, Scotch Plains; Malcolm MacCoss, Freehold; Sander G. Mills, Scotch Plains; Keith Rosauer, Matawan; Christopher Willoughby, Edison; Scott Berk, Maplewood, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/543,024

(22) Filed: Apr. 4, 2000

Related U.S. Application Data

(60) Provisional application No. 60/128,035, filed on Apr. 6, 1999.

(51) Int. Cl.[7] .................... A61K 31/40; A61K 31/445; C07D 211/00; C07D 409/00; C07D 207/00

(52) U.S. Cl. ...................... 514/429; 514/428; 514/408; 514/315; 546/184; 546/208; 546/212; 548/400

(58) Field of Search .................... 514/429, 428, 514/408, 315; 546/184, 208, 212; 548/400, 570, 577

(56) References Cited

U.S. PATENT DOCUMENTS

| 5,468,469 | 11/1995 | Aszalos et al. ...................... 514/150 |
| 5,684,032 | 11/1997 | Elliott et al. ......................... 514/414 |
| 5,776,954 | 7/1998 | de Laszlo et al. ................... 514/340 |

FOREIGN PATENT DOCUMENTS

WO 99/09984    3/1999    (WO).

OTHER PUBLICATIONS

C. Dorn et al, "Discovery of Potent Human CCR5 Antagonists for the Treatment of HIV–I Infection", Abstract 117, 219th National Meeting of the American Chemical Society, San Francisco, CA, Mar. 2000.
L. Meurer et al, "Discovery of Potent Human CCR5 Antagonists for the Treatment of HIV–II Infection", Abstract 118, 219th National Meeting of the American Chemical Society, San Francisco, CA, Mar. 2000.
P. Finke et al, "Discovery of Potent Human CCR5 Antagonists for the Treatment of HIV–III Infection", Abstract 119, 219th National Meeting of the American Chemical Society, San Francisco, CA, Mar. 2000.
C. Caldwell et al, "Discovery of Potent Human CCR5 Antagonists for the Treatment of HIV–IV Infection", Abstract 120, 219th National Meeting of the American Chemical Society, San Francisco, CA, Mar. 2000.

J. J. Gomez–Reino et al., "Association of Rheumatoid Arthritis with a Functional Chemokine Receptor, CCR5", Arthritis & Rheumatism, vol. 42, No. 5, May 1999, pp. 989–992.
H. Hotoda, "Small–molecule inhibitors of HIV–1 entry via chemokine receptors", Drugs of the Future, vol. 24, No. 12, 1999, pp. 1355–1362.
T. J. Schall, "Biology of the Rantes/sis Cytokine Family", Cytokine, vol. 3, No. 3, May 1991, pp. 165–183.
P. M. Murphy, "The Molecular Biology of Leukocyte Chenoattractant Receptors", Annual Review of Immunology, vol. 12, 1994, pp. 593–633.
H. Deng et al., "Identification of a major co–receptor for primary isolates of HIV–1", Nature, vol. 381, Jun. 1996, pp. 661–666.
R. Horuk, "Molecular properties of the chemokine receptor family", Trends Pharm. Science, vol. 15, 1994, pp. 159–165.
A. Ben–Baruch et al., "Monocyte Chemotactic Protein–3 (MCP3) Interacts with Multiple Leukocyte Receptors", J. Biol. Chem., vol. 270, No. 38, Sep. 1995, pp. 22123–22128.
K. Neote et al., "Molecular Cloning, Functional Expression, and Signaling Characteristics of C–C Chemokine Receptor", Cell, vol. 72, Feb. 1993, pp. 415–425.
C. Combadiere et al., "Cloning and Functional Expression of a Human Eosinophil CC Chemokine Receptor", J. Biol. Chem., vol. 270, No. 27, Jul. 1995, pp. 16491–16494.
C. A. Power et al., "Molecular Cloning and Functional Expression of a Novel Cc Chemokine Receptor cDNA from a Human Basophilic Line", J. Biol. Chem., vol. 270, No. 33, Aug. 1995, pp. 19495–19500.
M. Samson et al., "Molecular Cloning and Functional Expression of a New Human CC–Chemokine Receptor Gene", Biochemistry, vol. 35, 1996, pp. 3362–3367.

(List continued on next page.)

Primary Examiner—Richard L. Raymond
Assistant Examiner—Sudhaker B. Patel
(74) Attorney, Agent, or Firm—Kenneth R. Walton; Melvin Winokur

(57) ABSTRACT

The present invention is directed to pyrrolidine compounds of the formula 1:

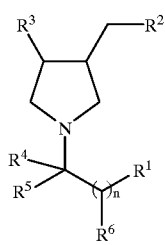

(wherein $R^1$, $R^2$, $R^3$, $R^4$, $R^5$, $R^6$ and n are defined herein) which are useful as modulators of chemokine receptor activity. In particular, these compounds are useful as modulators of the chemokine receptors CCR–5 and/or CCR–3.

36 Claims, No Drawings

OTHER PUBLICATIONS

A. Chaudhuri et al., "Expression of the Duffy Antigen in K562 Cells,", J. Biol. Chem., vol. 269, No. 11, Mar. 1994, pp. 7835–7838.

H. Kita et al., "Chemokines Active on Eosinophils: Potential Roles in Allergic Inflammation", J. Exp. Med., vol. 183, Jun. 1996, pp. 2421–2426.

D. Smith et al., "Blocking of HIV–1 Infectivity by a Soluable, Secreted Form of the CD4 Antigen", Science, vol. 238, 1987, pp. 1704–1707.

J. A. Levy, "Infection by Human Immunodeficiency Virus—DC4 is not Enough", N. Eng. J. Med., vol. 335, No. 20, Nov. 1996), pp. 1528–1530.

T. Dragic et al., "HIV–1 entry into CD4+cells is mediated by the chemokine receptor CC–CKR5", Nature, vol. 381, Jun. 1996, pp. 667–673.

L. Wu et al., "CD4–induced interaction of primary HIV–1 gp120 glycoproteins with the chemokine receptor CCR–5", Nature, vol. 384, Nov. 1996, pp. 179–183.

A. Trkola et al., "CD4–dependent, antibody–sensitive interactions between HIV–1 and its co–receptor CCR–5", Nature, vol. 384, Nov. 1996, pp. 184–187.

M. Samson et al., "Resistence to HIV–1 infection in caucasian individuals bearing mutant alleles of the CCR–5 cehmokine receptor gene", Nature, vol. 382, Aug. 1996, pp. 722–725.

C. M. Hill et al., "Natural resistence to HIV?", Nature, vol. 382, Aug. 1996, pp. 668–669.

Y. Huang et al., "The Role of a mutant CCR5 allele in HIV–1 transmission and disease progression", Nature Medicine, vol. 2, No. 11, 1996, pp. 1240–1243.

L. Zhang et al., "HIV–1 subtype and second–receptor use", Nature, vol. 383, Oct. 1996, p. 768.

W. S. Blair et al., "HIV–1 entry—an expanding portal for drug discovery", DDT, vol. 5, May 2000, pp. 183–194.

M. Baba et al., "A small–molecule, nonpeptide CCR5 antagonist with highly potent and selective anti HIV–1 activity", Proc. Natl. Acad. Sci., vol. 96, May 1999, pp. 5698–5703.

R. Horuk et al., "Chemokine Receptor Antagonists", Med. Res. Rev., vol. 20, No. 2, 2000, pp. 155–168.

M. Shiraishi et al., "Discovery of Novel, Potent , and Selective Small–Molecule CCR5 Antagonists as Anti–HIV–1 Agents: Synthesis and Biological Evaluation of Anilide Derivatives with a Quanternary Ammonium Moiety", J. Med. Chem., vol. 43, 2000, pp. 2049–2063.

PYRROLIDINE MODULATORS OF CHEMOKINE RECEPTOR ACTIVITY

This application claims the benefit of U.S. Provisional Application No. 60/128,035, filed Apr. 6, 1999, the disclosure of which is hereby incorporated by reference in its entirety.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine,* 3, 165–183 (1991) and Murphy, *Rev. Immun.,* 12, 593–633 (1994)). There are two classes of chemokines, C-X-C (α) and C-C (β), depending on whether the first two cysteines are separated by a single amino acid (C-X-C) or are adjacent (C-C). The α-chemolines, such as interleukin-8 (IL-8), neutrophil-activating protein-2 (NAP-2) and melanoma growth stimulatory activity protein (MGSA) are chemotactic primarily for neutrophils, whereas β-chemokines, such as RANTES, MIP-1α, MIP-1β, monocyte chemotactic protein-1 (MCP-1), MCP-2, MCP-3 and eotaxin are chemotactic for macrophages, T-cells, eosinophils and basophils (Deng, et al., *Nature,* 381, 661–666 (1996)).

The chemokines bind specific cell-surface receptors belonging to the family of G-protein-coupled seven-transmembrane-domain proteins (reviewed in Horuk, *Trends Pharm. Sci.* 15, 159–165 (1994)) which are termed "chemokine receptors." On binding their cognate ligands, chemokine receptors transduce an intracellular signal though the associated trimeric G protein, resulting in a rapid increase in intracellular calcium concentration. There are at least sixteen human chemokine receptors that bind or respond to β-chemokines with the following characteristic pattern: CCR-1 (or "CKR-1" or "CC-CKR-1") [MIP-1α, MIP-1β, MCP-3, RANTES] (Ben-Barruch, et al., *J. Biol. Chem.,* 270, 22123–22128 (1995); Beote, et al, *Cell,* 72, 415–425 (1993)); CCR-2A and CCR-2B (or "CKR-2A"/ "CKR-2A" or "CC-CKR-2A"/"CC-CKR-2A") [MCP-1, MCP-3, MCP4]; CCR-3 (or "CKR-3" or "CC-CKR-3") [eotaxin, RANTES, MCP-3] (Combadiere, et al., *J. Biol. Chem.,* 270, 16491–16494 (1995); CCR4 (or "CKR-4" or "CC-CKR-4") [MIP-1α, RANTES, MCP-1] (Power, et al., *J. Biol. Chem,* 270, 19495–19500 (1995)); CCR-5 (or "CKR-5" or "CC-CKR-5") [MIP-1α, RANTES, MIP-1β] (Sanson, et al., *Biochemistry,* 35, 362–3367 (1996)); and the Duffy blood-group antigen [RANTES, MCP-1] (Chaudhun, et al., *J. Biol. Chem.,* 269, 7835–7838 (1994)). The β-chemokines include eotaxin, MIP ("macrophage inflammatory protein"), MCP ("monocyte chemoattractant protein") and RANTES ("regulation-upon-activation, normal T expressed and secreted").

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. A review of the role of chemokines in allergic inflammation is provided by Kita, H., et al., *J. Exp. Med.* 183, 2421–2426 (1996). Accordingly, agents which modulate chemokine receptors would be useful in such disorders and diseases. Compounds which modulate chemokine receptors would be especially useful in the treatment and prevention of atopic conditions including allergic rhinitis, dermatitis, conjunctivitis, and particularly bronchial asthma.

A retrovirus designated human immunodeficiency virus (HIV-1) is the etiological agent of the complex disease that includes progressive destruction of the immune system (acquired immune deficiency syndrome; AIDS) and degeneration of the central and peripheral nervous system. This virus was previously known as LAV, HTLV-III, or ARV.

Certain compounds have been demonstrated to inhibit the replication, of HIV, including soluble CD4 protein and synthetic derivatives (Smith, et al., Science, 238, 1704–1707 (1987)), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 glycoprotein of the cell.

Entry of HIV-1 into a target cell requires cell-surface CD4 and additional host cell cofactors. Fusin has been identified as a cofactor required for infection with virus adapted for growth in transformed T-cells, however, fusin does not promote entry of macrophagetropic viruses which are believed to be the key pathogenic strains of HIV in vivo. It has recently been recognized that for efficient entry into target cells, human immunodeficiency viruses require a chemokine receptors, most probably CCR-5 or CXCR4, as well as the primary receptor CD4 (Levy, *N. Engl. J. Med.,* 335(20), 1528–1530 (Nov. 14, 1996). The principal cofactor for entry mediated by the envelope glycoproteins of primary macrophage-trophic strains of HIV-1 is CCR-5, a receptor for the β-chemokines RANTES, MIP-1α and MIP-10 (Deng, et al., *Nature,* 381, 661666 (1996)). IRV attaches to the CD4 molecule on cells through a region of its envelope protein, gp120. It is believed that the CD-4 binding site on the gp120 of HIV interacts with the CD4 molecule on the cell surface, and undergoes conformational changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with-the cell membrane, and entry of the viral core into the cell. It has been shown that β-chemokine ligands prevent MIV-1 from fusing with the cell (Dragic, et al., *Nature,* 381, 667–673 (1996)). It has further been demonstrated that a complex of gp120 and soluble CD4 interacts specifically with CCR-5 and inhibits the binding of the natural CCR-5 ligands MIP-1α and MIP-1β (Wu, et al., *Nature,* 384, 179–183 (1996); Trkola, et al., *Nature,* 384, 184–187 (1996)).

Humans who are homozygous for mutant CCR-5 receptors which do not serve as co-receptors for IV-1 in vitro appear to be unusually resistant to HIV-1 infection and are not immuno-compromised by the presence of this genetic variant (*Nature,* 382, 722–725 (1996)). Absence of CCR-5 appears to confer substantial protection from HIV-1 infection (*Nature,* 382, 668–669 (1996)). Other chemokine receptors may be used by some strains of HIV-1 or may be favored by non-sexual routes of transmission. Although most HIV-1 isolates studied to date utilize CCR-5 or fusin, some can use both as well as the related CCR-2B and CCR-3 as co-receptors (*Nature Medicine,* 2(11), 1240–1243 (1996)). Nevertheless, drugs targeting chemokine receptors may not be unduly compromised by the genetic diversity of HIV-1 (Zhang, et al., *Nature,* 383, 768 (1996)). Accordingly, an agent which could block chemokine receptors in humans who possess normal chemokine receptors should prevent infection in healthy individuals and slow or halt viral progression in infected patients. By focusing on the host's cellular immune response to HIV infection, better therapies towards all subtypes of HIV may be provided. These results indicate that inhibition of chemokine receptors presents a viable method for the prevention or treatment of infection by HIV and the prevention or treatment of AIDS.

The peptides eotaxin, RANTES, MIP-1α, MIP-1β, MCP-1, and MCP-3 are known to bind to chemokine receptors. As noted above, the inhibitors of HIV-1 replication present in supernatants of CD8+T cells have been characterized as the chemokines RANTES, MIP-1α and MIP-1β.

SUMMARY OF THE INVENTION

The present invention is directed to compounds which inhibit the entry of human immunodeficiency virus (HIV) into target cells and are of value in the prevention of infection by HIV, the treatment of infection by HIV and the prevention and/or treatment of the resulting acquired immune deficiency syndrome (AIDS). The present invention also relates to pharmaceutical compositions containing the compounds and to a method of use of the present compounds and other agents for the prevention and treatment of AIDS and viral infection by HIV.

The present invention is further directed to compounds which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention is directed to compounds of formula I:

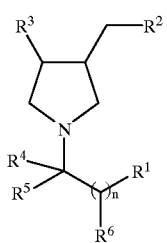

wherein:
$R^1$ is selected from:
(1) —$CO_2H$,
(2) —$NO_2$,
(3) -tetrazolyl,
(4) -hydroxyisoxazole,
(5) —$SO_2NH$—($CO_3$ alkyl)-$R^9$, wherein $R^9$ is independently selected from: hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$ alkyl, $C_{1-3}$ alkoxy and trifluoromethyl,
(6) —$SO_2NHCO$—($C_{0-3}$ alkyl)-$R^9$, wherein $R^9$ is independently selected from: hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$ alkyl, $C_{1-3}$ alkoxy and trifluoromethyl, and
(7) —$P(O)(OH)_2$;
$R^2$ is selected from the group consisting of:

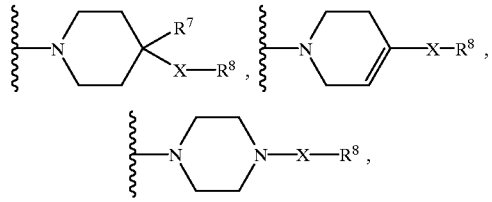

wherein $R^7$ is selected from:
(1) hydrogen,
(2) $C_{1-6}$ alkyl, which is unsubstituted or substituted with 1–4 substituents where the substituents are independently selected from: hydroxy, cyano, and halo,
(3) cyano,
(4) hydroxy, and
(5) halo,
wherein X is selected from:
$C_{1-10}$ alkyl and -($C_{0-6}$ alkyl)$C_{3-6}$cycloalkyl($C_{0-6}$ alkyl)-, which is unsubstituted or substituted with 1–7 substituents where the substituents are independently selected from:
(a) halo,
(b) hydroxy,
(c) —O—$C_{1-3}$ alkyl,
(d) trifluoromethyl,
(e)-($C_{1-3}$ alkyl)hydroxy, and
(f) ethylenedioxy
and wherein $R^8$ is selected from:
phenyl, naphthyl, biphenyl, indanyl, tetrahydronapthyl and heterocycle, which is unsubstituted or substituted with 1–7 of $R^{11}$ where $R^{11}$ is independently selected from:
(a) halo,
(b) cyano,
(c) hydroxy,
(d) $C_{1-6}$ alkyl, which is unsubstituted or substituted with 1–5 of $R^{12}$ where $R^{12}$ is independently selected from: halo, cyano, hydroxy, $C_{1-6}$ alkoxy, —$CO_2H$, —$CO_2$($C_{1-6}$ alkyl), phenyl, trifluoromethyl, and —$NR^9R^{10}$, wherein $R^9$ is defined above and $R^{10}$ is independently selected from the definitions of $R^9$,
(e) —O—$C_{1-6}$ alkyl, which is unsubstituted or substituted with 1–5 of $R^{12}$,
(f) —$CF_3$,
(g) —$CBF_2$,
(h) —$CH_2F$,
(i) —$NO_2$,
(j) phenyl,
(k) —$CO_2R^9$,
(l) tetrazolyl,
(m) —$NR^9R^{10}$,
(n) —$NR^9COR^{10}$,
(o) —$NR^9$—$CO_2R^{10}$,
(p) —CO—$NR^9R^{10}$,
(q) —OCO—$N^9R^{10}$,
(r) —$NR^9CO$—$NR^9R^{10}$,
(s) —$S(O)_m$—$R^9$, wherein m is an integer selected from 0, 1 and 2, (t) $S(O)_2NR^9R^{10}$,
(u) $-NR^9S(O)_2-R^{10}$,
(v) $-NR^9S(O)_2-NR^9R^{10}$, and
(w) $C_{1-6}$ fluoroalkoxy;

$R^3$ is selected from the group consisting of: phenyl and heterocycle,
  which is unsubstituted or substituted with 1–7 substituents where the substituents are independently selected from:
  (a) halo,
  (b) trifluoromethyl,
  (c) hydroxy,
  (d) $C_{1-3}$ alkyl,
  (e) $-O-C_{1-3}$ alkyl,
  (f) $-CO_2R^9$,
  (g) $-NR^9R^{10}$, and
  (h) $-CONR^9R^{10}$;

$R^4$ is selected from:
  $C_{1-10}$ alkyl, $C_{3-8}$ cycloalkyl, -($C_{1-3}$ alkyl)-$C_{3-8}$ cycloalkyl, $C_{2-10}$ alkenyl, $C_{2-10}$ alkynyl, phenyl, -($C_{1-6}$ alkyl)-phenyl, naphthyl, biphenyl, heterocycle, hydrogen, cyclohexenyl, dihydronaphthyl, tetrahydronaphthyl, and octahydronaphthyl,
    which is unsubstituted or substituted with 1–7 of $R^{11}$ where $R^{11}$ is independently as defined above;

$R^5$ is selected from:
  hydrogen or $C_{1-6}$ alkyl, wherein the alkyl is unsubstituted or substituted with 1–7 substituents where the substituents are independently selected from:
  (a) halo,
  (b) trifluoromethyl,
  (c) hydroxy,
  (d) $C_{1-3}$ alkyl,
  (e) $-O-C_{1-3}$ alkyl,
  (f) $-CO_2R^9$,
  (g) $-NR^9R^{10}$, and
  (h) $-CONR^9R^{10}$,
or where $R^4$ and $R^5$ may be joined together to form a $C_{3-8}$ cycloalkyl ring which may be unsubstituted or substituted with 1–7 of $R^{11}$;

$R^6$ is independently selected from:
  hydrogen or $C_{1-6}$ alkyl, wherein the alkyl is unsubstituted or substituted with 1–7 substituents where the substituents are independently selected from:
  (a) halo,
  (b) trifluoromethyl,
  (c) hydroxy,
  (d) $C_{1-3}$ alkyl, (e) $-O-C_{1-3}$ alkyl, (f) $-CO_2R^9$, (g) $-NR^9R^{10}$, and (h) $-CONR^9R^{10}$;

n is an integer selected from 0, 1, 2 and 3;
and pharmaceutically acceptable salts thereof and individual diastereomers thereof.

In one embodiment, the present invention is directed to compounds of formula I, wherein:

$R^1$ is selected from:
  (1) $-CO_2H$,
  (2) $-NO_2$,
  (3)-tetrazolyl,
  (4)-hydroxyisoxazole,
  (5) $-SO_2NH-(C_{0-3}$ alkyl)-$R^9$, wherein $R^9$ is independently selected from: hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$ alkyl, $C_{1-3}$ alkoxy and trifluoromethyl, and
  (6) $-P(O)(OH)_2$;

$R^2$ is selected from the group consisting of:

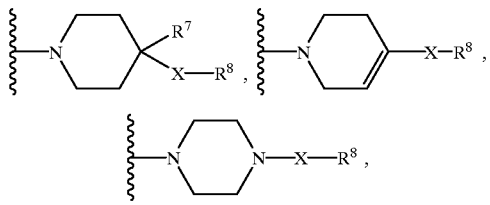

wherein $R^7$ is selected from:
  (1) hydrogen,
  (2) $C_{1-6}$ alkyl, which is unsubstituted or substituted with 1–4 substituents where the substituents are independently selected from: hydroxy, cyano, and halo,
  (3) cyano,
  (4) hydroxy, and
  (5) halo,
wherein X is selected from:
  $C_{1-10}$ alkyl and -($C_{0-6}$ alkyl)$C_{3-6}$cycloalkyl($C_{0-6}$ alkyl)-,
    which is unsubstituted or substituted with 1–7 substituents where the substituents are independently selected from:
    (a) halo,
    (b) hydroxy,
    (c) $-O-C_{1-3}$ alkyl, and
    (d) trifluoromethyl,
and wherein $R^8$ is selected from:
  phenyl, naphthyl, biphenyl, indanyl, tetrahydronapthyl and heterocycle,
    which is unsubstituted or substituted with 1–7 of $R^{11}$ where $R^{11}$ is independently selected from:
    (a) halo,
    (b) cyano,
    (c) hydroxy,
    (d) $C_{1-6}$ alkyl, which is unsubstituted or substituted with 1–5 of $R^{12}$ where $R^{12}$ is independently selected from: halo, cyano, hydroxy, $C_{1-6}$ alkoxy, $-CO_2H$, $-CO_2(C_{1-6}$ alkyl), phenyl, trifluoromethyl, and $-NR^9R^{10}$, wherein $R^9$ is defined above and $R^{10}$ is independently selected from the definitions of $R^9$,
    (e) $-O-C_{1-6}$ alkyl, which is unsubstituted or substituted with 1–5 of $R^{12}$,
    (f) $-CF_3$,
    (g) $-CBF_2$,
    (h) $-CH_2F$,
    (i) $-NO_2$,
    (j) phenyl,
    (k) $-CO_2R^9$,
    (l) tetrazolyl,
    (m) $-NR^9R^{10}$,
    (n) $-NR^9-COR^{10}$,
    (o) $-NR^9-CO_2R^{10}$,
    (p) $-CO-NR^9R^{10}$,
    (q) $-OCO-NR^9R^{10}$,
    (r) $-NR^9CO-NR^9R^{10}$,
    (s) $-S(O)_m-R^9$, wherein m is an integer selected from 0, 1 and 2,
    (t) $-S(O)_2-NR^9R^{10}$,
    (u) $-NR^9S(O)_2-R^{10}$, and
    (v) $-NR^9S(O)_2-NR^9R^{10}$;

$R^3$ is selected from the group consisting of:
  phenyl and heterocycle,
    which is unsubstituted or substituted with 1–7 substituents where the substituents are independently selected from:

(a) halo,
(b) trifluoromethyl,
(c) hydroxy,
(d) $C_{1-3}$ alkyl,
(e) —O—$C_{1-3}$ alkyl,
(f) —$CO_2R^9$,
(g) —$NR^9R^{10}$, and
(h) —$CONR^9R^{10}$;

$R^4$ is selected from:
$C_{1-10}$ alkyl, $C_{3-8}$ cycloalkyl, -($C_{1-3}$ alkyl)-$C_{3-8}$ cycloalkyl, $C_{2-10}$ alkenyl, $C_{2-10}$ alkynyl, phenyl, -($C_{1-6}$ alkyl)-phenyl, naphthyl, biphenyl, heterocycle, hydrogen, cyclohexenyl, dihydronaphthyl, tetrahydronaphthyl, and octahydronaphthyl,
which is unsubstituted or substituted with 1–7 of $R^{11}$ where $R^{11}$ is independently as defined above;

$R^5$ is selected from:
hydrogen or $C_{1-6}$ alkyl, wherein the alkyl is unsubstituted or substituted with 1–7 substituents where the substituents are independently selected from:
(a) halo,
(b) trifluoromethyl,
(c) hydroxy,
(d) $C_{1-3}$ alkyl,
(e) —O—$C_{1-3}$ alkyl,
(f) —$CO_2R^9$,
(g) —$NR^9R^{10}$, and
(h) —$CONR^9R^{10}$, or where $R^4$ and $R^5$ may be joined together to form a $C_{3-8}$ cycloalkyl ring which may be unsubstituted or substituted with 1–7 of $R^{11}$;

$R^6$ is independently selected from:
hydrogen or $C_{1-6}$ alkyl, wherein the alkyl is unsubstituted or substituted with 1–7 substituents where the substituents are independently selected from:
(a) halo,
(b) trifluoromethyl,
(c) hydroxy,
(d) $C_{1-3}$ alkyl,
(e) —O—$C_{1-3}$ alkyl,
(f) —$CO_2R^9$,
(g) —$NR^9R^{10}$, and
(h) —$CONR^9R^{10}$;

n is an integer selected from 0, 1, 2 and 3;
and pharmaceutically acceptable salts thereof and individual diastereomers thereof.

Preferred compounds of the present invention include those of formula Ia:

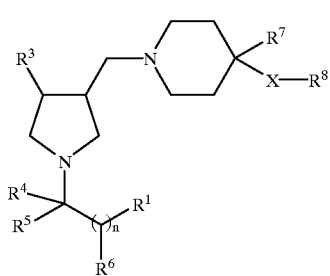

Ia wherein $R^1$, $R^3$, $R^4$, $R^5$, $R^6$, $R^7$, $R^8$, X and n are defined herein;
and pharmaceutically acceptable salts and individual diastereomers thereof.

More preferred compounds of the present invention include those of formula Ic:

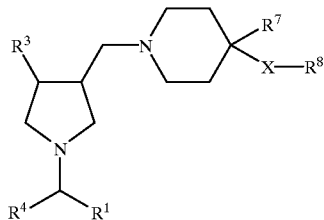

Ic wherein $R^1$, $R^3$, $R^4$, $R^7$, $R^8$ and X are defined herein;
and pharmaceutically acceptable salts and individual diastereomers thereof.

Highly preferred compounds of the present invention include those of formula Id:

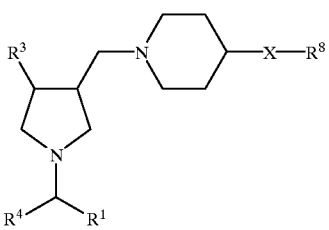

Id wherein $R^1$, $R^3$, $R^4$, $R^8$, and X are defined herein;
and pharmaceutically acceptable salts and individual diastereomers thereof.

More highly preferred compounds of the present invention include those of formula Ie:

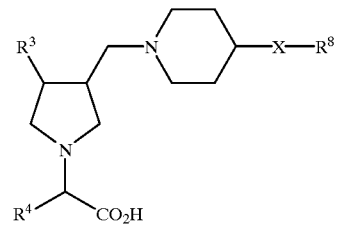

Ie wherein $R^3$, $R^4$, $R^8$ and X are defined herein;
and pharmaceutically acceptable salts and individual diastereomers thereof.

In the present invention it is preferred that $R^1$ is selected from:
(1) —$CO_2H$,
(2) —$P(O)(OH)_2$, and
(3) -tetrazolyl.

In the present invention it is more preferred that $R^1$ is selected from:
(1) —$CO_2H$, and
(2) tetraolyl.

In the present invention it is even more preferred that $R^1$ is —$CO_2H$.

In the present invention it is preferred that $R^2$ is

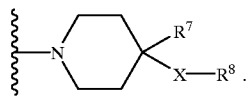

In the present invention it is more preferred that $R^2$ is

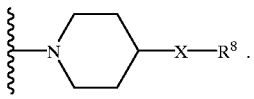

In the present invention it is preferred that $R^3$ is selected from the group consisting of:
phenyl and thienyl,
which may be unsubstituted or substituted with 1–5 substituents where the substituents are independently selected from:
(a) halo,
(b) trifluoromethyl,
(c) hydroxy,
(d) $C_{1-3}$ alkyl, and
(e) —O—$C_{1-3}$ alkyl.

In the present invention it is more preferred that $R^3$ is selected from the group consisting of:
phenyl and thienyl,
which may be unsubstituted or substituted with 1–5 substituents where the substituents are independently selected from:
(a) fluoro,
(b) chloro,
(c) trifluoromethyl,
(d) hydroxy, and
(e) $C_{1-3}$ alkyl.

In the present invention it is even more preferred that $R^3$ is selected from the group consisting of:
phenyl, which may be unsubstituted or substituted with 1–5 substituents where the substituents are independently selected from:
(a) fluoro, and
(b) chloro; and
unsubstituted thienyl.

In the present invention it is most preferred that $R^3$ is unsubstituted phenyl, 3-fluorophenyl or 3-thienyl.

In the present invention it is preferred that $R^4$ is $C_{1-10}$ alkyl, $C_{3-8}$ cycloalkyl, or -($C_{1-3}$ alkyl)-$C_{3-8}$ cycloalkyl,
which is unsubstituted or substituted with 1–5 substituents where the substituents are independently selected from:
(a) halo,
(b) hydroxy,
(c)-$C_{1-6}$ alkyl, which is unsubstituted or substituted with halo, cyano, —$CO_2H$, hydroxy or trifluoromethyl,
(d) —O—$C_{1-6}$ alkyl, which is unsubstituted or substituted halo, cyano, —$CO_2H$, hydroxy or trifluoromethyl,
(e) —$CF_3$,
(f) —$CHF_2$,
(g) —$CH_2F$, and
(h) —$CO_2H$.

In the present invention it is more preferred that $R^4$ is selected from: isopropyl, isobutyl, sec-butyl, t-butyl, cyclohexyl, cyclopentyl, cyclobutyl, cyclopropyl, —$CH_2$-cyclohexyl, —$CH_2$-cyclopentyl, —$CH_2$-cyclobutyl, and —$CH_2$-cyclopropyl. In an aspect of this embodiment, in the present invention it is more preferred that $R^4$ is selected from: isopropyl, isobutyl, sec-butyl, cyclohexyl, cyclopentyl, cyclobutyl, cyclopropyl, —$CH_2$-cyclohexyl, —$CH_2$-cyclopentyl, —$CH_2$-cyclobutyl, and —$CH_2$-cyclopropyl.

In the present invention it is even more preferred that $R^4$ is selected from: isopropyl, sec-butyl, t-butyl, cyclohexyl, cyclopentyl, cyclobutyl, cyclopropyl, —$CH_2$-cyclobutyl, and —$CH_2$-cyclopropyl. In an aspect of this embodiment, in the present invention it is more preferred that that $R^4$ is selected from: isopropyl, cyclohexyl, cyclopentyl, cyclobutyl, cyclopropyl, —$CH_2$-cyclobutyl, and —$CH_2$-cyclopropyl.

In the present invention it is most preferred that $R^4$ is selected from: cyclohexyl, isopropyl, sec-butyl, t-butyl, —$CH_2$-cyclobutyl and —$CH_2$-cyclopropyl. In an aspect of this embodiment, in the present invention it is most preferred that $R^4$ is selected from: cyclohexyl, isopropyl, —$CH_2$-cyclobutyl and —$CH_2$-cyclopropyl.

In the present invention it is preferred that $R^5$ is hydrogen.
In the present invention it is preferred that $R^6$ is hydrogen or unsubstituted $C_{1-6}$ alkyl.
In the present invention it is more preferred that $R^6$ is hydrogen.
In the present invention it is preferred that $R^7$ is hydrogen, fluoro, hydroxy or $C_{1-6}$ alkyl.
In the present invention it is more preferred that $R^7$ is hydrogen or fluoro.
In the present invention it is even more preferred that $R^7$ is hydrogen.

In the present invention it is preferred that X is $C_{1-6}$ alkyl, which is unsubstituted or substituted with 1–7 substituents where the substituents are independently selected from:
(a) halo,
(b) hydroxy,
(c) —O—$C_{1-3}$ alkyl, and
(d) trifluoromethyl.

In the present invention it is more preferred that X is $C_{2-4}$ alkyl, which is unsubstituted or substituted with 1–6 substituents where the substituents are independently selected from:
(a) halo,
(b) —O—$C_{1-3}$ alkyl, and
(c) trifluoromethyl.

In the present invention it is even more preferred that X is $C_{2-4}$ alkyl, which is unsubstituted or substituted with 1–6 substituents where the substituents are fluoro.

In the present invention it is most preferred that X is n-propyl or —$CH_2CH_2CF_2$—.

In the present invention it is preferred that $R^8$ is selected from: phenyl, naphthyl, benzoimidazolyl, benzofurazanyl, isoxazolyl, pyrazinyl, pyridazinyl, pyridyl, pyrimidyl, and tetrazolopyridyl,
which is unsubstituted or substituted with 1–7 substituents where the substituents are independently selected from:
(a) halo,
(b) cyano,
(c) hydroxy,
(d) $C_{1-6}$ alkyl, which is unsubstituted or substituted with 1–5 of $R^{12}$ where $R^{12}$ is independently selected from; halo, cyano, hydroxy, $C_{1-6}$ alkoxy, —$CO_2H$, phenyl, —$CO_2(C_{1-6}$ alkyl), trifluoromethyl, and —$NR^9R^{10}$, wherein $R^9$ and $R^{10}$ are independently selected from:

hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$ alkyl, $C_{1-3}$ alkoxy and trifluoromethyl;
(e) —O—$C_{1-6}$ alkyl, which is unsubstituted or substituted with 1–5 of $R^{12}$,
(f) —$CF_3$,
(g) —$CHF_2$,
(h) —$CH_2F$,
(i) —$NO_2$,
(j) phenyl,
(k) —$CO_2R^9$,
(l) tetrazolyl,
(m) —$NR^9R^{10}$,
(n) —$NR^9$—$COR^{10}$,
(o) —$NR^9$—$CO_2R^{10}$,
(p) —CO—$NR^9R^{10}$,
(q) —OCO—$NR^9R^{10}$,
(r) —$NR^9CO$—$NR^9R^{10}$,
(s) —$S(O)_m$—$R^9$, wherein m is an integer selected from 0, 1 and 2,
(t) —$S(O)_2$—$NR^9R^{10}$,
(u) —$NR^9S(O)_2$—$R^{10}$, and
(v) —$NR^9S(O)_2$—$NR^9R^{10}$.

In the present invention it is more preferred that $R^8$ is selected from: phenyl, benzofurazanyl, benzoimidazolyl, isoxazole, pyridyl, and tetrazolopyridyl;

which is unsubstituted or substituted with 1–5 substituents where the substituents are independently selected from:
(a) halo,
(b) cyano,
(c) —$NO_2$,
(d) —$CF_3$,
(e) —$CBF_2$,
(f) —$CH_2F$,
(g) tetrazolyl,
(h) $C_{1-6}$ alkyl, which is unsubstituted or substituted with phenyl,
(i) —O—$C_{1-6}$ alkyl, and
(j) —$SO_2CH_3$.

In an aspect of the preceding embodiment, $R^8$ is selected from: phenyl, benzofurazanyl, benzoimidazolyl, isoxazole, and pyridyl, which is unsubstituted or substituted with 1–5 substituents where the substituents are independently selected from (a)–(i), as defined in the preceding paragraph.

In the present invention it is even more preferred that $R^8$ is phenyl, which is unsubstituted or substituted with 1–3 substituents where the substituents are independently selected from:
(a) fluoro,
(b) chloro,
(c) cyano,
(d) —$NO_2$, and
(e) —$CF_3$.

In the present invention it is most preferred that $R^8$ is selected from: phenyl, 2-cyanophenyl, 3-cyanophenyl, 4-cyanophenyl, 4-fluorophenyl, 2,4-difluorophenyl, 3,4-difluorophenyl, 3,5-difluorophenyl, 2,6-difluorophenyl, 2,4,6-trifluorophenyl, 4-nitrophenyl, 4-chlorophenyl, 3-chlorophenyl, 4-(trifluoromethyl)phenyl, and 3,5-bis(trifluoromethyl)phenyl.

In the present invention it is preferred that n is an integer selected from 0 and 1.

In the present invention it is more preferred that n is an integer which is 0.

It is to be understood that embodiments of the present invention include, but are not limited to, compounds of formula I wherein $R^1$, $R^2$, $R^3$, $R^4$, $R^5$, $R^6$, $R^7$, $R^8$, X, and n are defined in accordance with one of the embodiments or aspects thereof as set forth above. Any and all possible combinations of preferred, more preferred, even more preferred, highly preferred, more highly preferred, and/or most preferred definitions of these variables are within the scope of the present invention.

The compounds of the instant invention have at least two asymmetric centers at the ring junction of the substituents bearing $R^2$ and $R^3$. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The relative configurations of the more preferred compounds of this invention are of the trans orientation, i.e. as depicted:

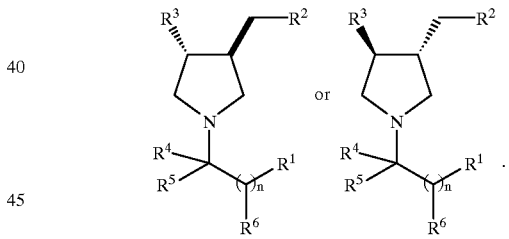

The relative configurations of the most preferred compounds of this invention with respect to the configuration of the substituent on the pyrrolidine nitrogen are of the orientation as depicted:

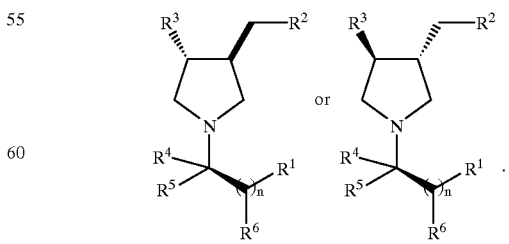

In a preferred aspect the present invention is a compound of formula (II):

(II)

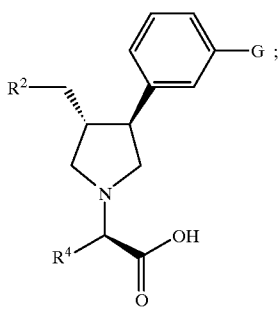

wherein

R² is selected from the group consisting of

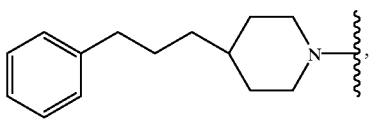

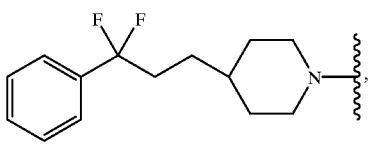

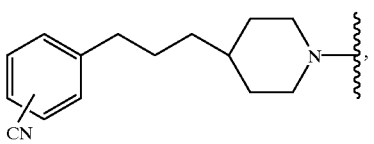

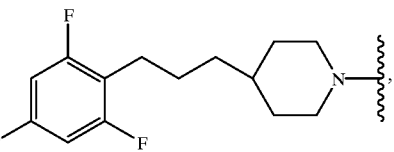

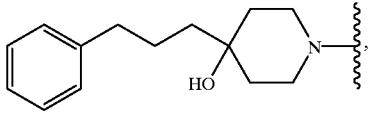

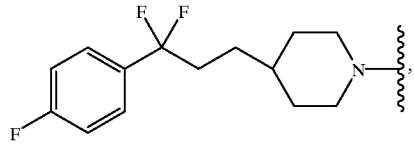

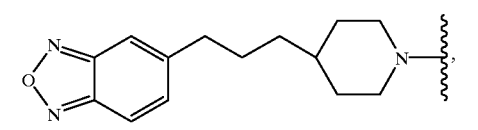

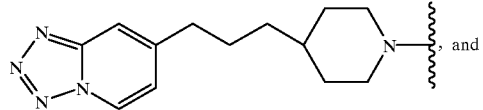, and

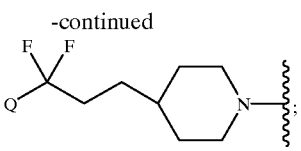

R⁴ is selected from the group consisting of

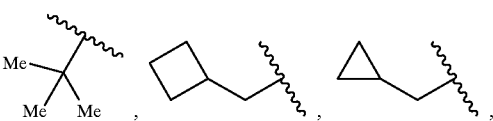

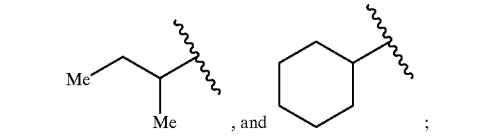, and ;

Q is pyridyl, pyrazinyl, pyrimidinyl, thiazolyl, thienyl, or pyrazolyl, any one of which is unsubstituted or substituted with methyl or trifluoromethyl; and G is hydrogen or fluoro;

and pharmaceutically acceptable salts thereof and individual diastereomers thereof.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, halo or halogen as used herein are intended to include chloro, fluoro, bromo and iodo. Similarly, $C_{1-8}$, as in $C_{1-8}$ alkyl is defined to identify the group as having 1, 2, 3, 4, 5, 6, 7 or 8 carbons in a linear or branched arrangement, such that $C_{1-8}$ alkyl specifically includes methyl, ethyl, propyl, butyl, pentyl, hexyl, heptyl and octyl. Likewise, $C_0$, as in $C_0$ alkyl is defined to identify the presence of a direct covalent bond.

As with "$C_{1-8}$ alkyl", the term "$C_{1-6}$ alkyl" means linear or branched chain alkyl groups having from 1 to 6 carbon atoms and includes all of the hexyl alkyl, pentyl alkyl, etc. isomers.

The term "$C_3$–$C_8$ cycloalkyl" refers to a cyclic ring selected from cyclopropyl, cyclobutyl, cyclopentyl, cyclohexyl, cycloheptyl, and cyclooctyl. The term "$C_3$–$C_6$ cycloalkyl" refers to a cyclic ring selected from cyclopropyl, cyclobutyl, cyclopentyl, and cyclohexyl. Similar terms (e.g., "$C_4$–$C_6$ cycloalkyl") have analogous meanings.

The term "$C_{1-6}$ alkoxy" means an —O—alkyl group wherein alkyl is $C_{1-6}$ alkyl as defined above. Suitable alkoxy groups include, but are not limited to, methoxy, ethoxy, n-propoxy, isopropoxy, n-butoxy, isobutoxy, tert-butoxy, and sec-butoxy.

The term "$C_{1-6}$ fluoroalkoxy" means a $C_{1-6}$ alkoxy group as defined above in which the alkyl group is substituted with one or more fluorine atoms. Exemplary fluoroalkoxy groups include, but are not limited to, trifluoromethoxy, 2,2,2-trifluoroethoxy, fluoromethoxy, and difluoromethoxy.

The tern "-($C_{1-3}$ alkyl)hydroxy" refers to a $C_{1-3}$ alkyl group as defined above which is substituted on one its carbons by a hydroxy group. Exemplary groups include hydroxymethyl, hydroxyethyl, 3-hydroxy-n-propyl, 2-hydroxy-n-propyl, and so forth.

The term "heterocycle" (which may alternatively be referred to as "heterocyclic") refers to a 4- to 8-membered monocyclic ring, a 7- to 11-membered bicyclic system, or a 10 to 15-membered tricyclic ring system, any ring of which is saturated or unsaturated (partially or totally), and which consists of carbon atoms and one or more heteroatoms (e.g., from 1 to 4 heteroatoms) selected from N, O and S, and wherein the nitrogen and sulfur heteroatoms may optionally be oxidized, the nitrogen heteroatom may optionally be quaternized, and a ring carbon may optionally be oxidized (i.e., is substituted with oxo). The heterocyclic ring may be attached at any heteroatom or carbon atom, provided that attachment results in the creation of a stable structure. A preferred heterocycle is a 4 to 8-membered monocyclic ring or a 7- to 11-membered bicyclic system, as defined and described above.

The term "heterocycle" as used herein is intended to include the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzyl, tetrahydrofuranyl, and tetrahydrothienyl, and N-oxides thereof.

The term "heterocycle" as used herein is also intended to include, but is not limited to, the following groups: methylenedioxyphenyl, imidazopyridyl, imidazopyrimidinyl, imidazopyridazinyl, imidazopyrazinyl, imidazottiazinyl, imidazothipheyl, pyrazolopyridyl, pyrazolopyrimidinyl, pyrazolopyridazinyl, pyrazolopyrazinyl, pyrazolotriazinyl, pyrazolothiophenyl, triazolopyridyl, triazolopyrimidinyl, triazolopyridazinyl, triazolopyrazinyl, triazolothiophenyl, tetrahydroimidazopyridinyl, tetrahydropyrazolopyridinyl, tetrahydrotriazopyridinyl, tetrahydrotriazolopyridazinyl, and tetrahydroindazolyl.

The term "heterocycle" as used herein is also intended to include, but is not limited to, the following groups: tetrahydroirnidazopyrimidyl, tetrahydroimidazopyrazinyl, tetrahydroimidazopyridazinyl, tetrahydrotriazolopyirnidyl, tetrahydrotriazolopyrazinyl, tetrahydropyrazolopyrimidyl, tetrahydropyrazolopyrazinyl, imidazothiazolyl, and imidazothiadiazolyl.

The term "heterocycle" as used herein is also intended to include, but is not limited to, oxopyridinyl (e.g., 2-oxopyridinyl), oxopiperidinyl, and oxopyrazolyl.

The term "heterocycle" as used herein is also intended to include, but is not limited to, thiochromanyl, 1,1-dioxothiochromanyl, thieno-tetrahydrothiopyranyl, and 1,1-dioxo-thieno-tetrahydrothiopyranyl.

The terms "thiophenyl" and "thienyl" have the same meaning herein and are used interchangeably. Similarly, the following pairs of terms are used interchangeably: "indazolyl" and "benzopyrazolyl"; "pyridinyl" and "pyridyl".

In the expression " . . . which is unsubstituted or substituted with . . . ", "which" is intended to refer back to all preceding chemical groups in the particular definition in which the expression appears, unless a contrary meaning is expressed or is implied by the context. Furthermore, the term "substituted" in the expression includes mono and poly-substitution by a named substituent to the extent such single and multiple substitution is chemically allowed in any of the named chemical groups. Thus, for example, the expression "is independently selected from: hydrogen, $C_{1-6}$ alkyl, $C_{5-6}$ cycloalkyl, benzyl or phenyl, which is unsubstituted or substituted with 1–3 substituents . . . ", encompasses hydrogen, $C_{1-6}$ alkyl, $C_{5-6}$ cycloalkyl, benzyl, phenyl, mono- and di- and tri-substituted $C_{1-6}$ alkyl, mono- and di- and tri-substituted $C_{5-6}$ cycloalkyl, mono and di- and tri-substituted benzyl and mono- and di- and tri-substituted phenyl.

Exemplifying the invention is the use of the compounds disclosed in the Examples and herein.

Specific compounds within the present invention include a compound which is selected from the group consisting of:

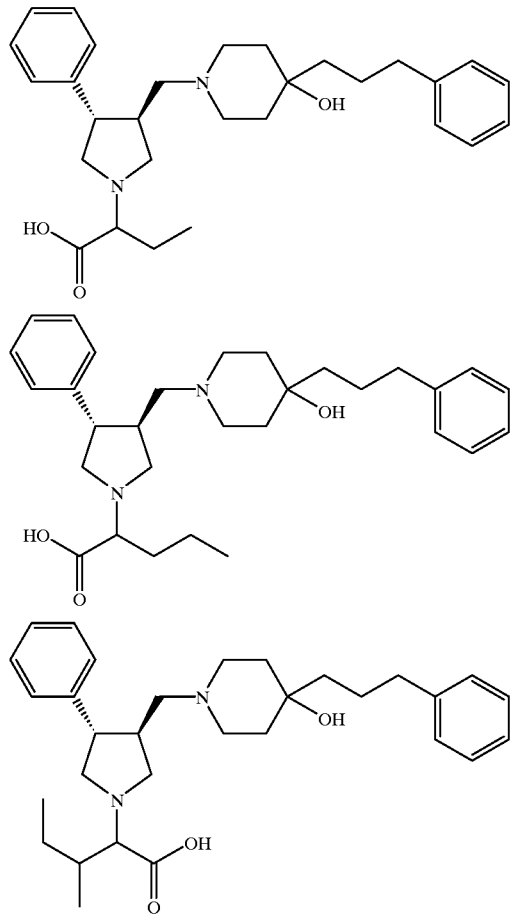

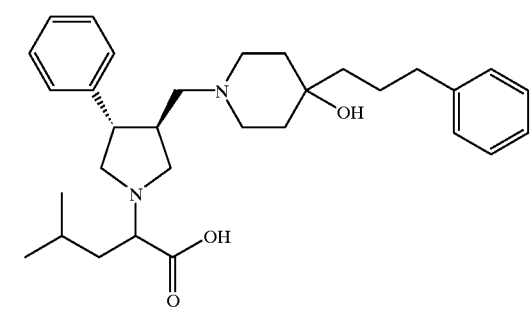
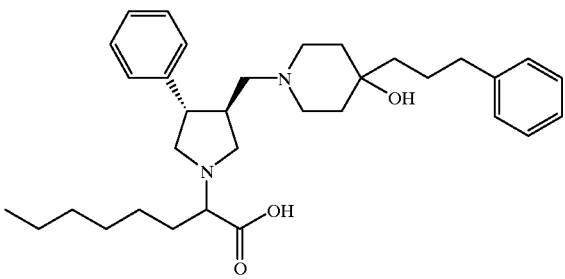
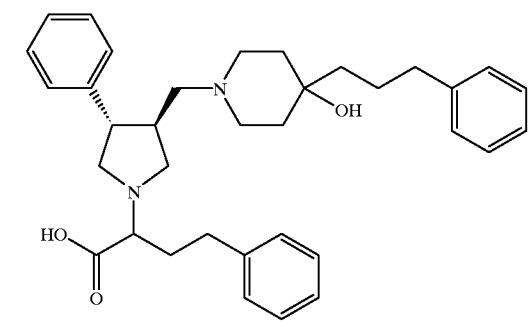
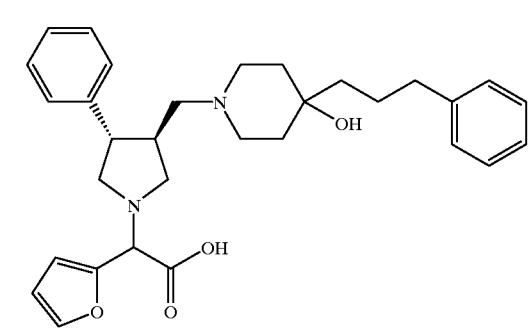
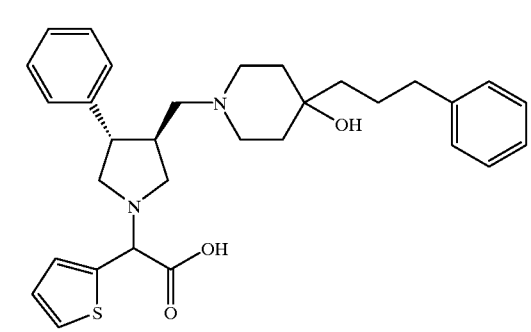
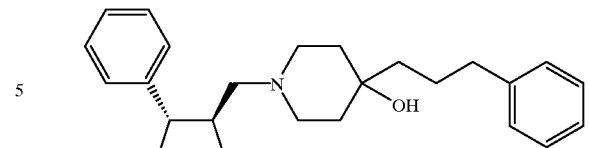
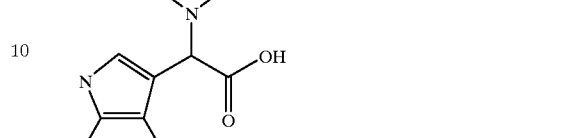
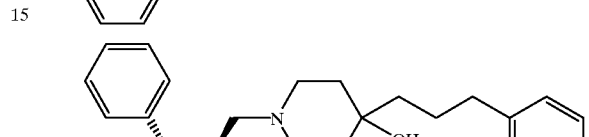
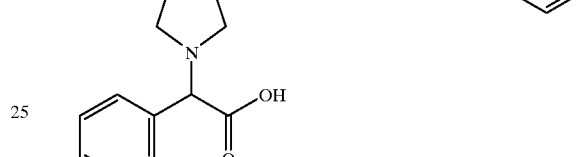
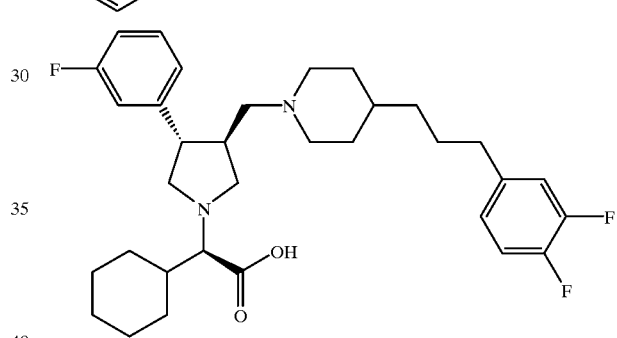
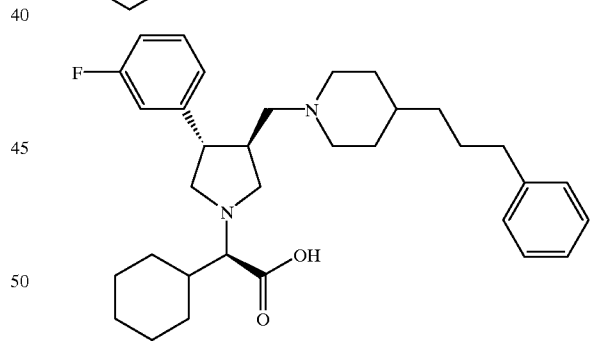
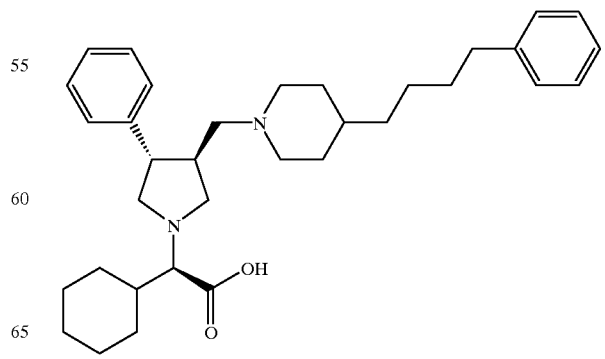

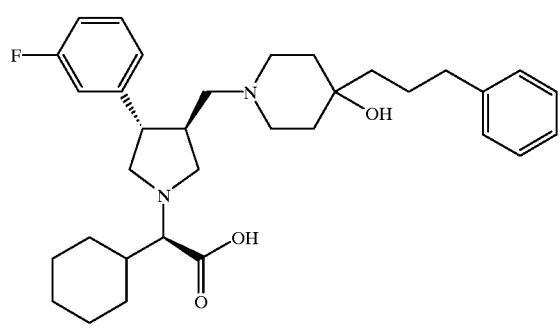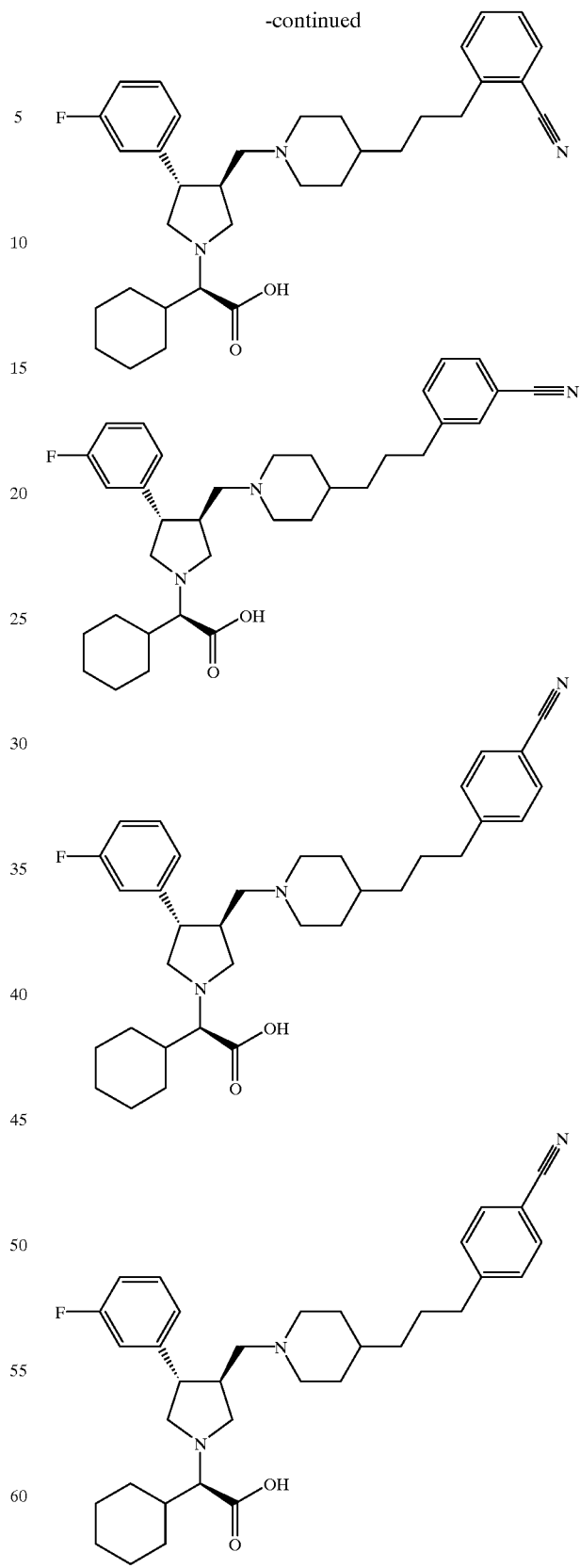

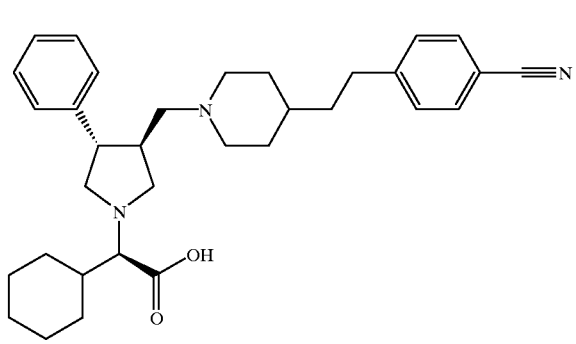
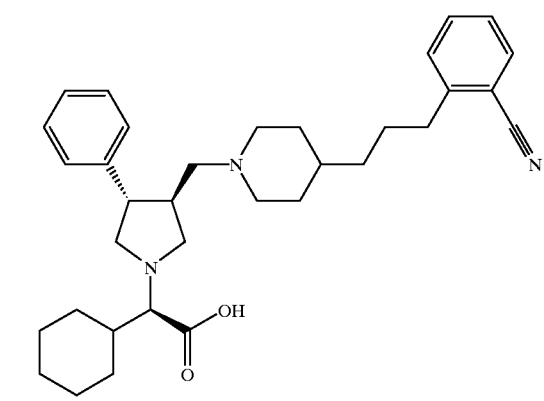
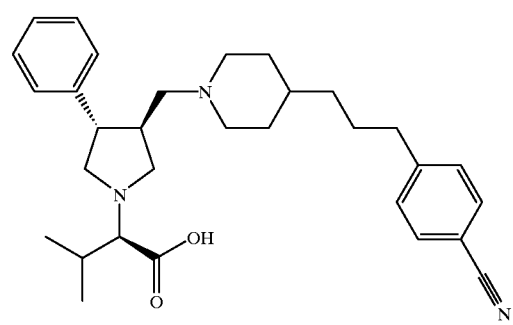
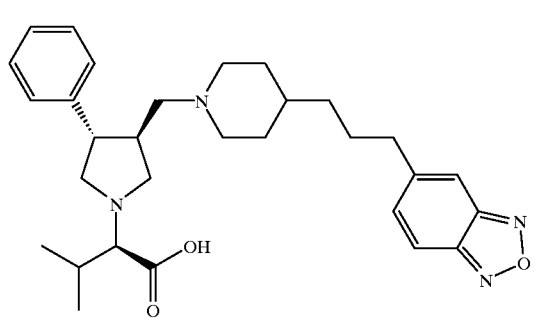
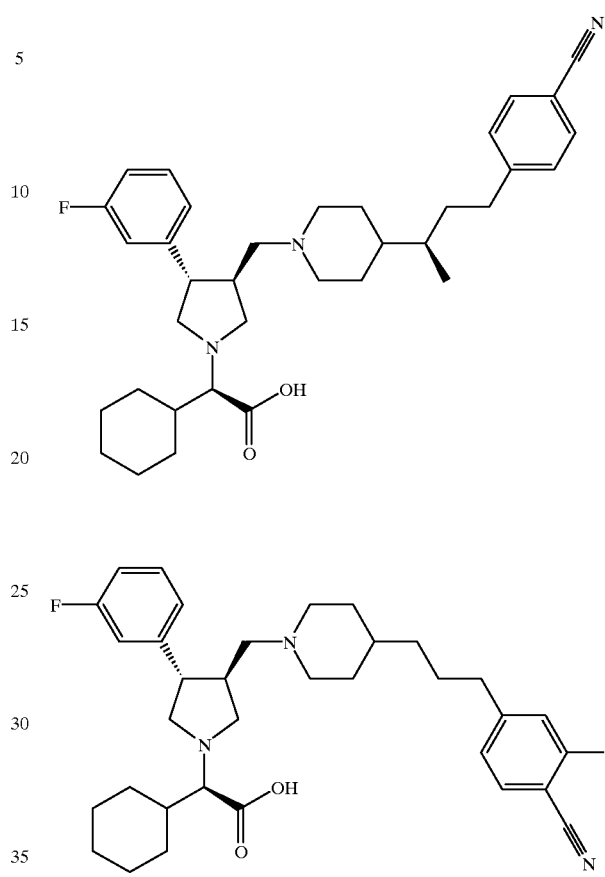
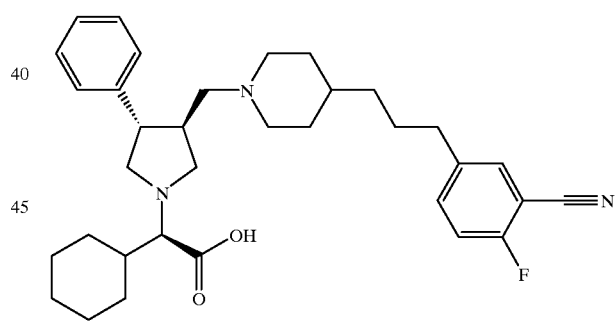
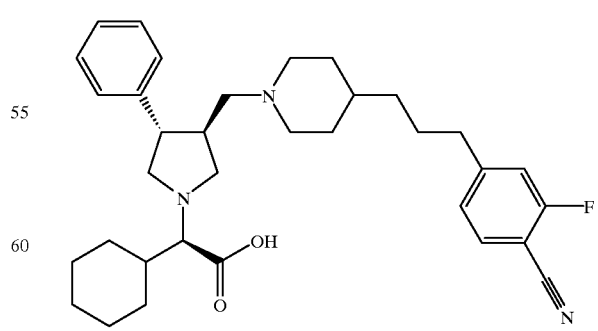

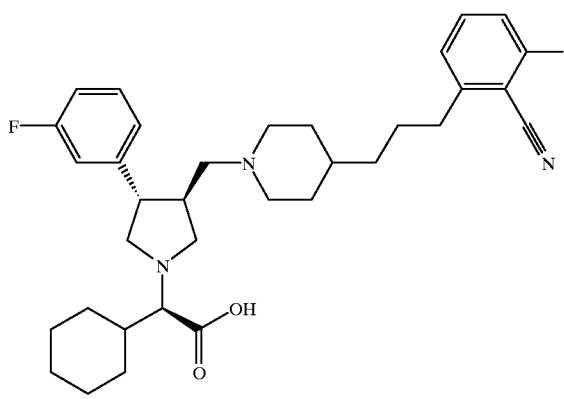
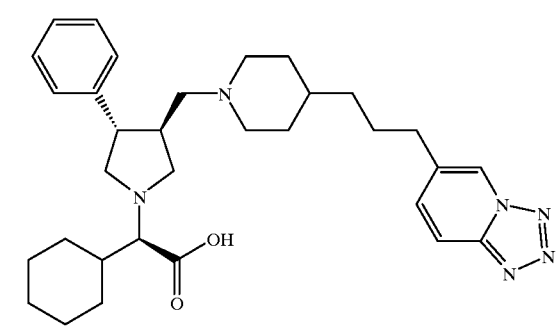
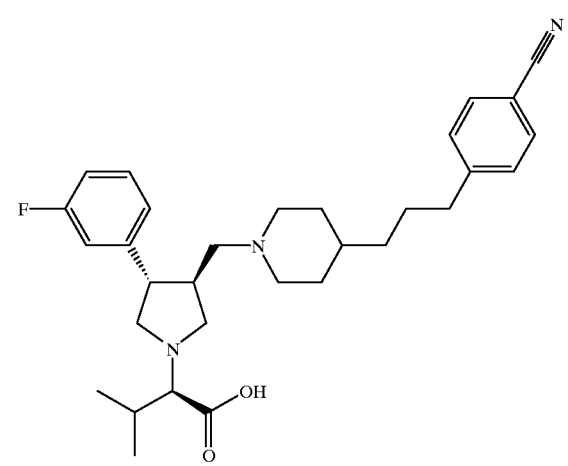
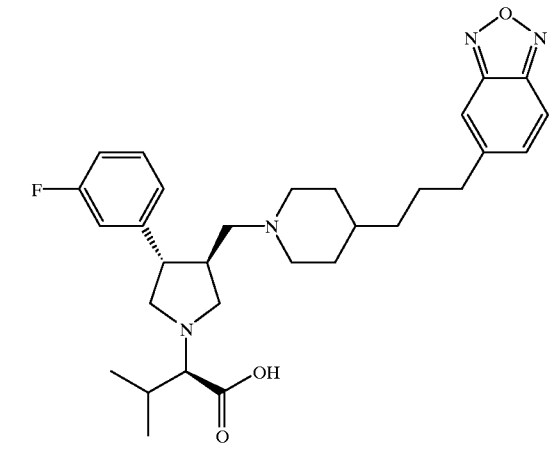
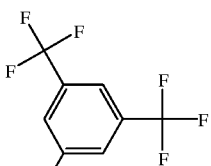
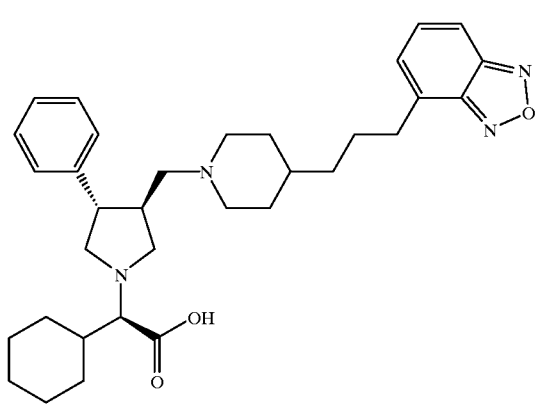

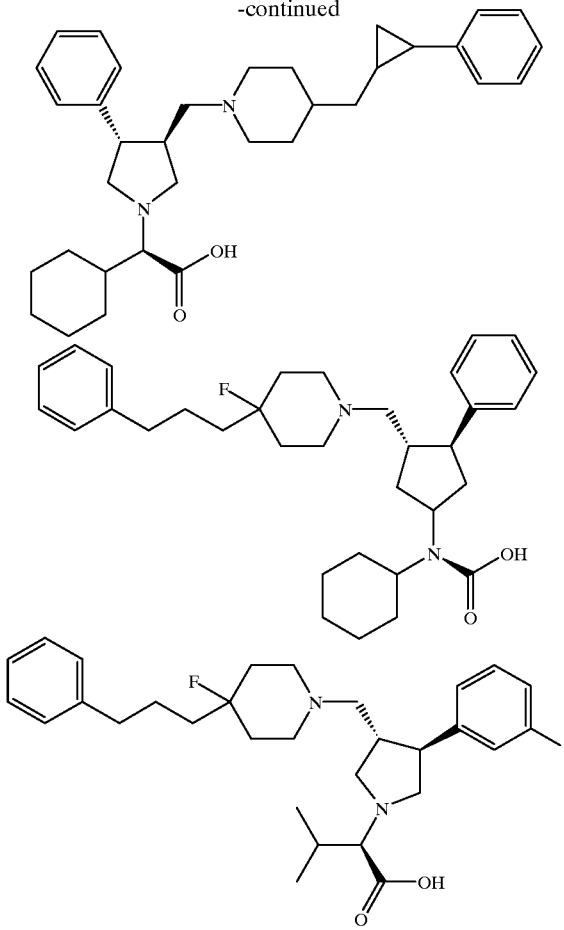
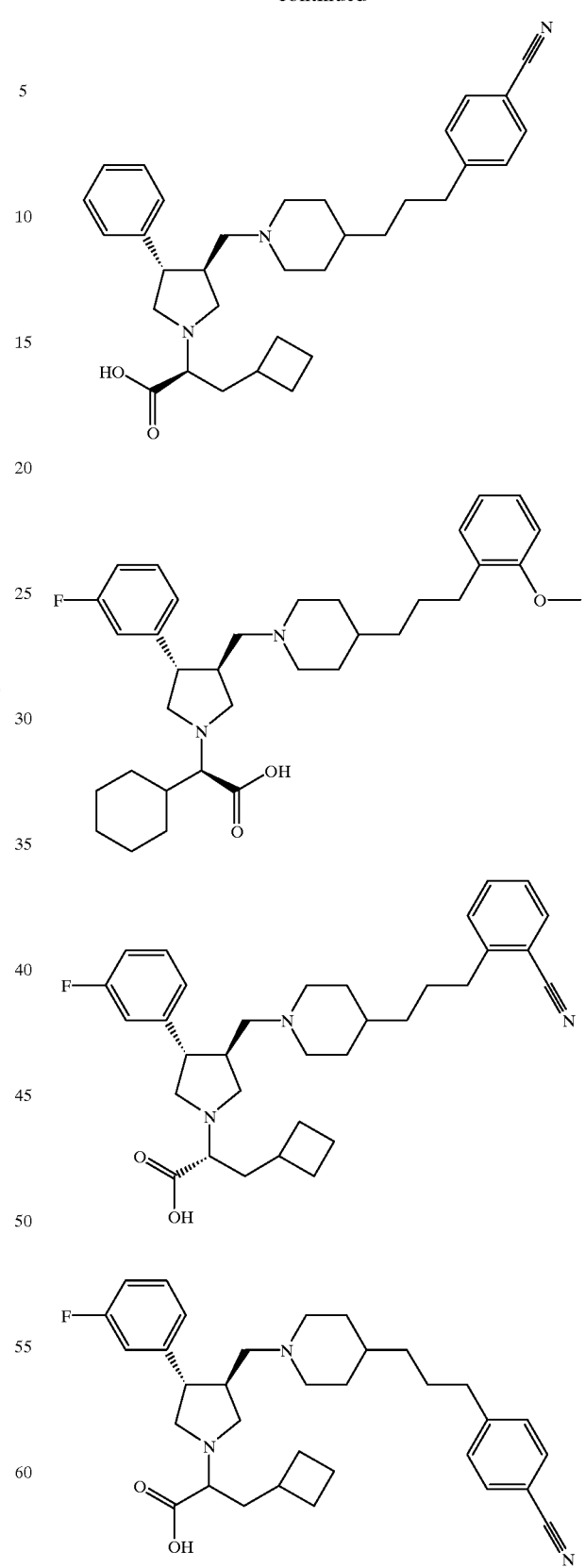

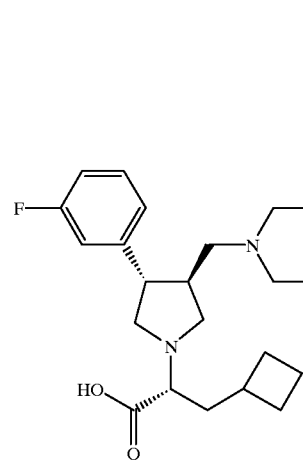
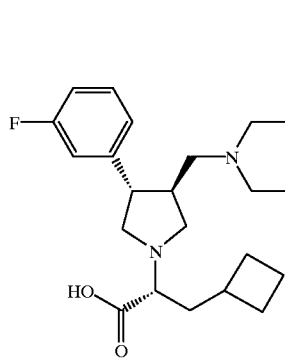
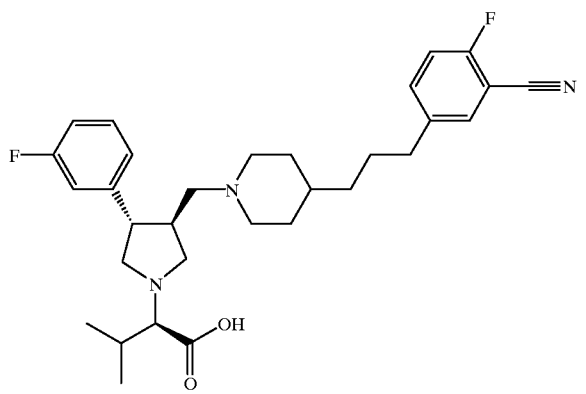
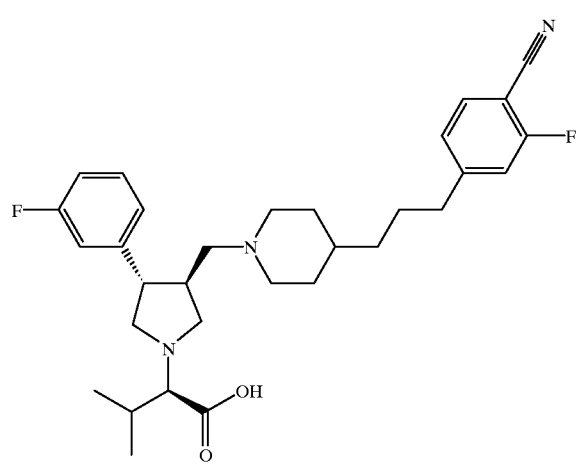
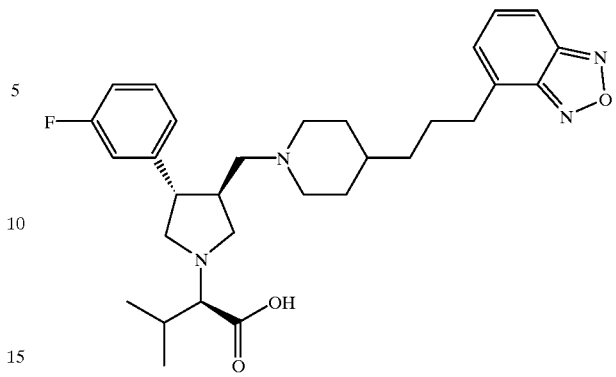
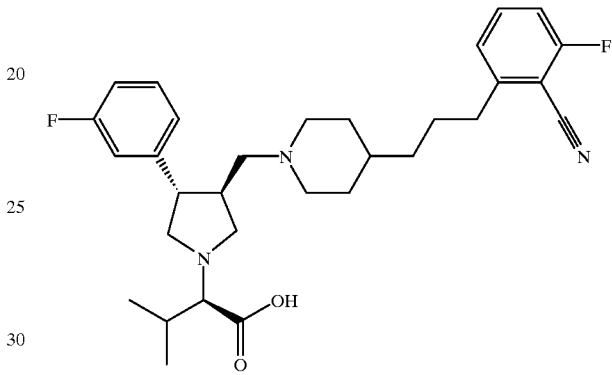
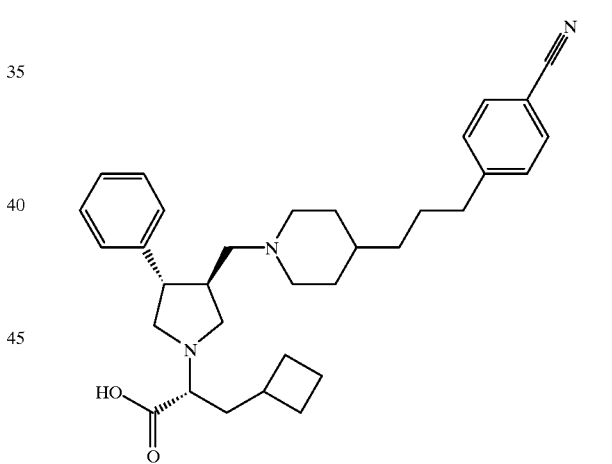
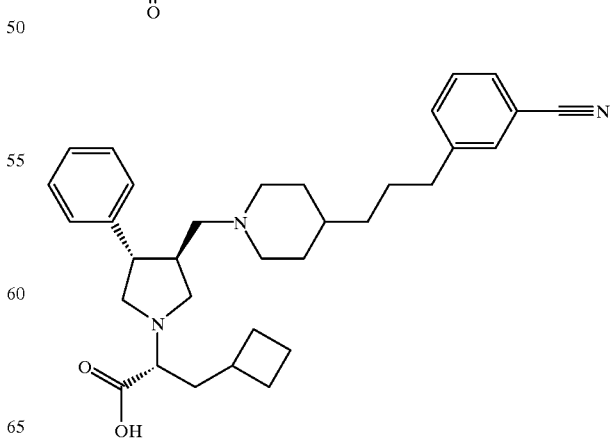

29
-continued
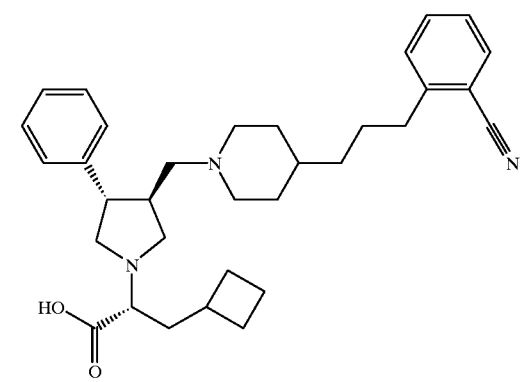
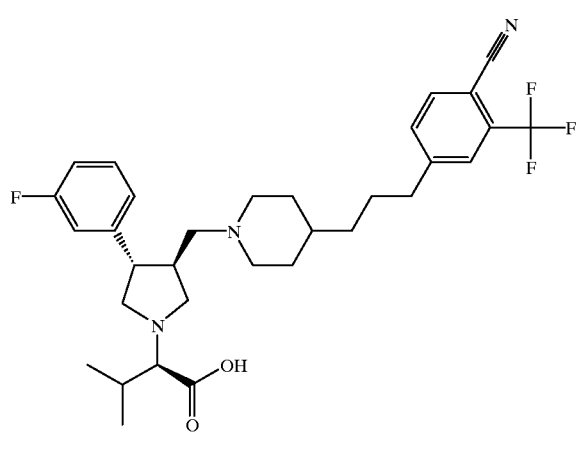
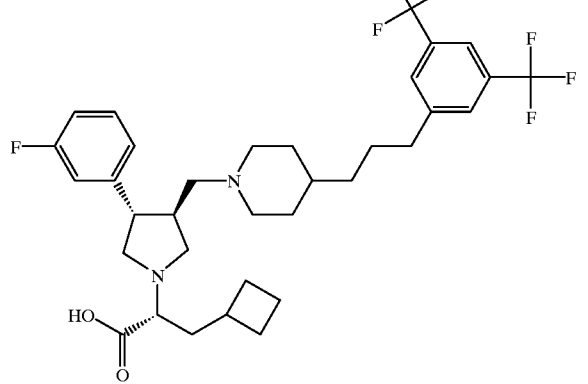
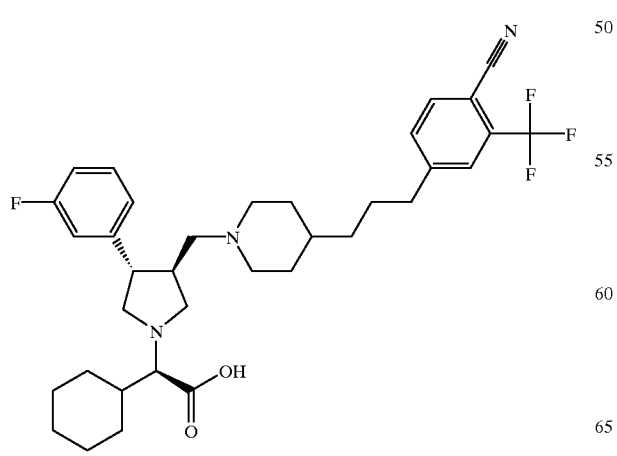
30
-continued
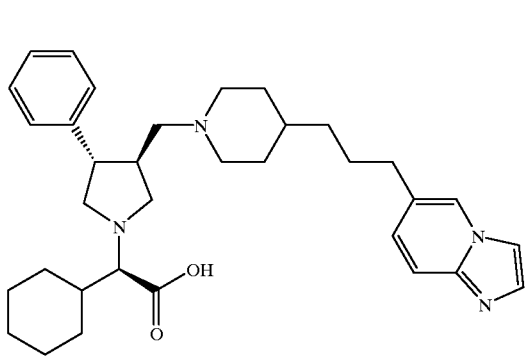
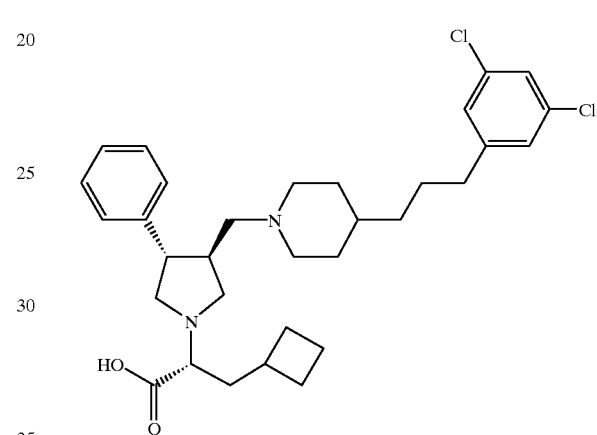
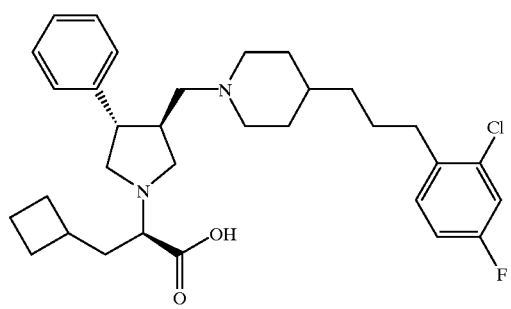
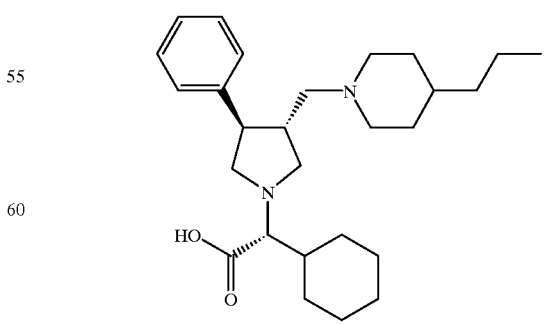

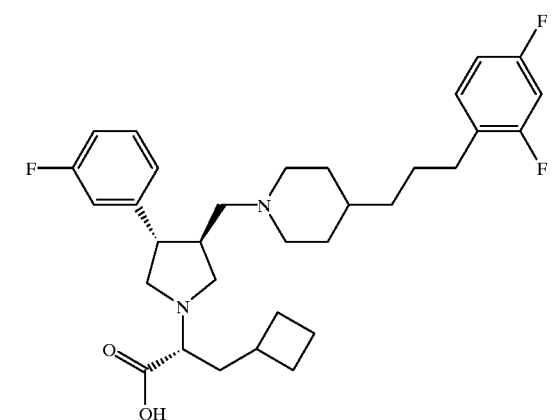
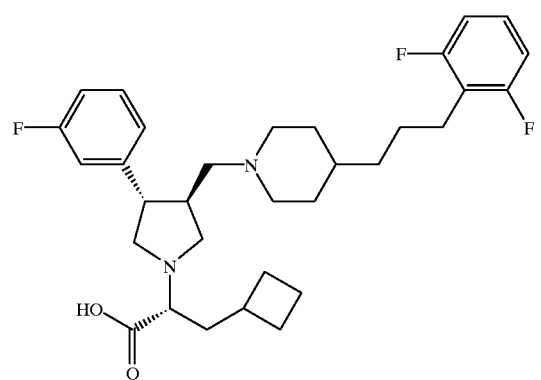
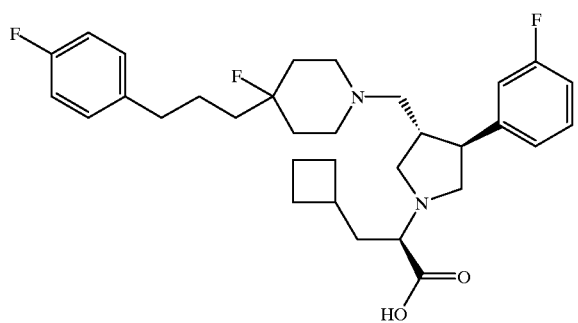
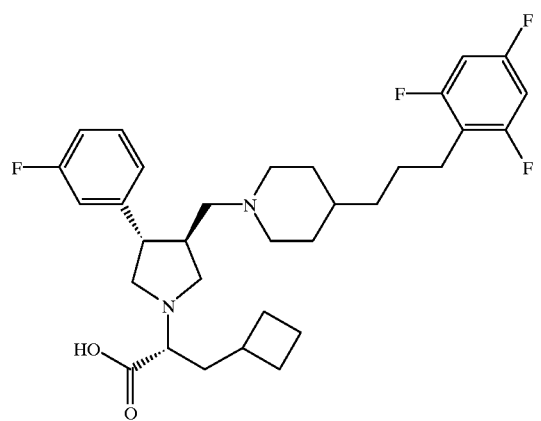
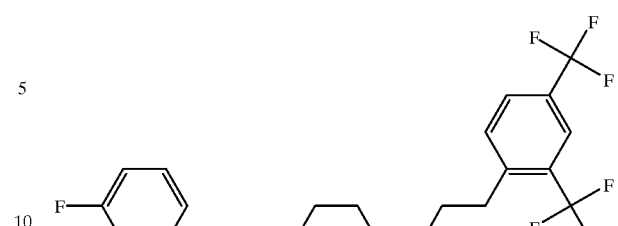
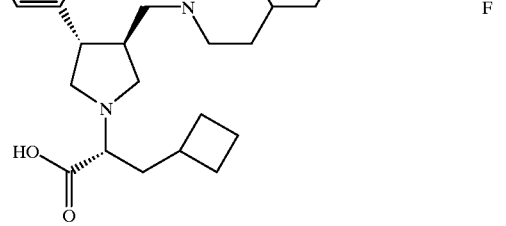
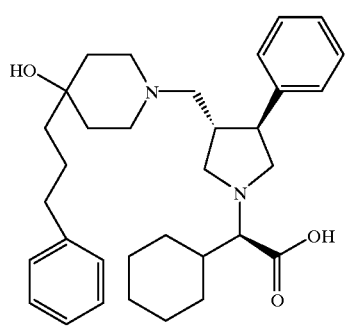
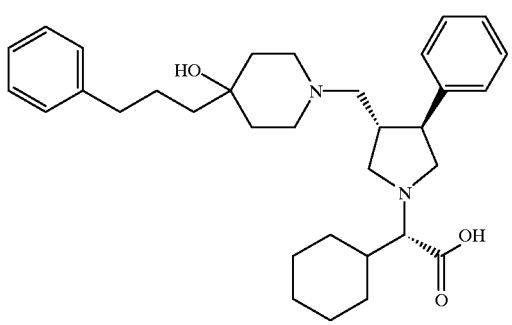
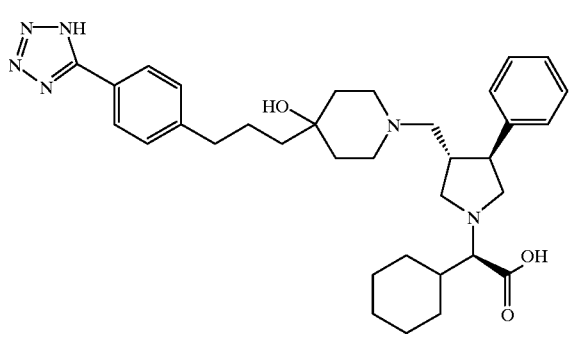

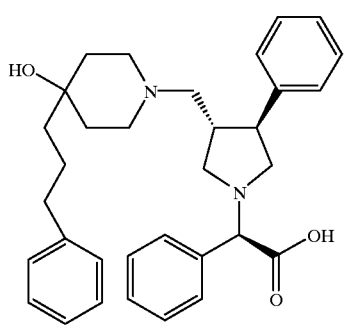
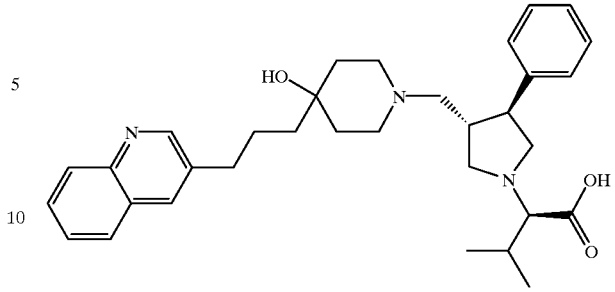

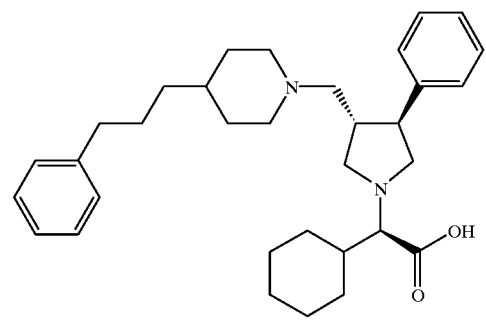
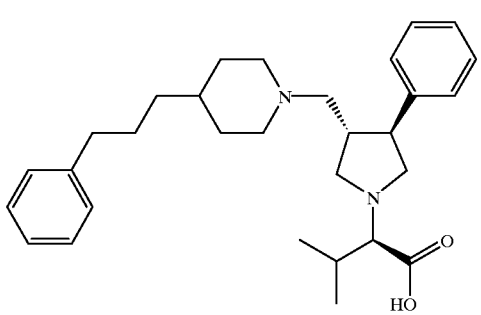
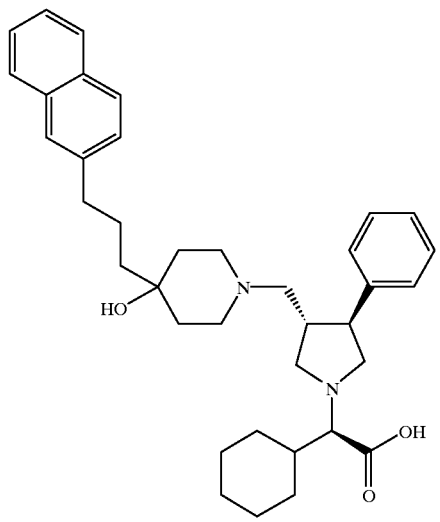
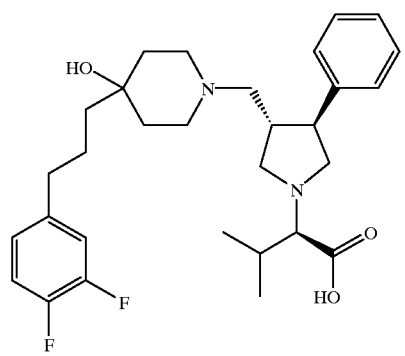
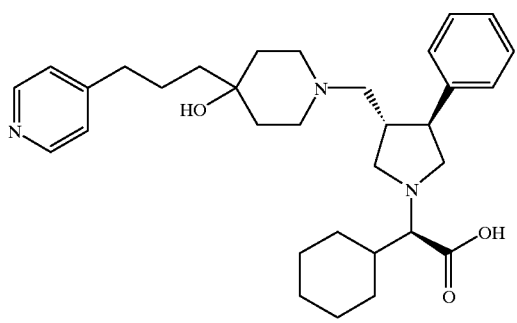
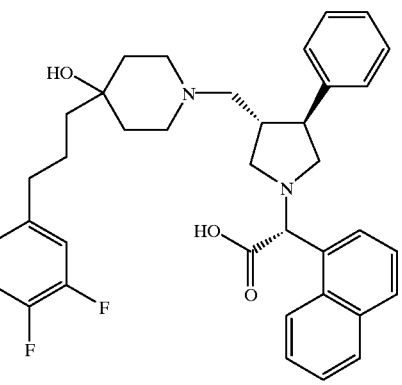
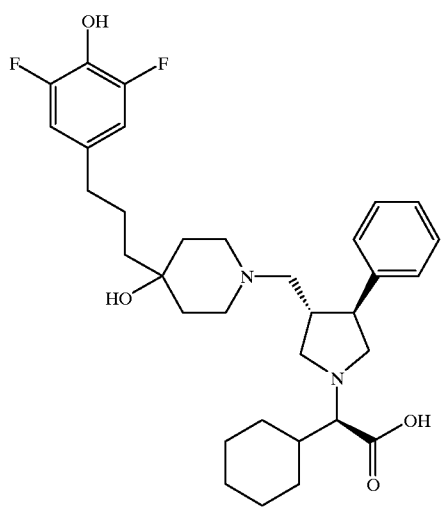
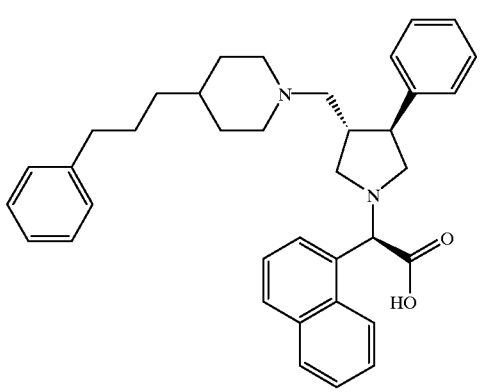

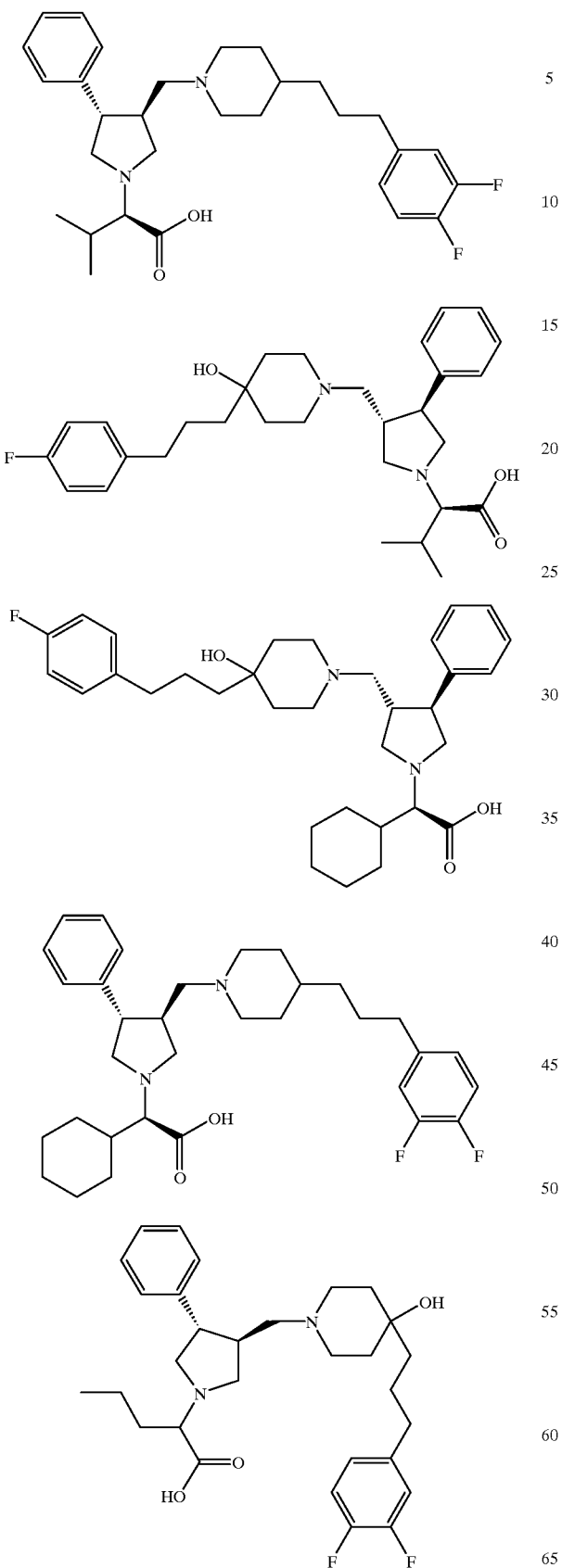
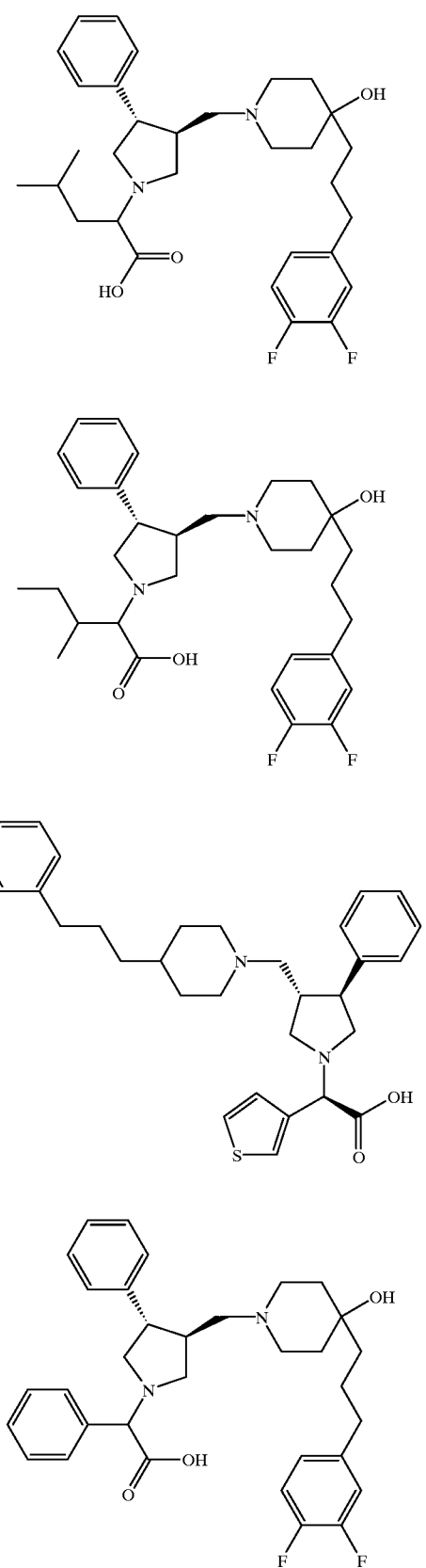

39
-continued
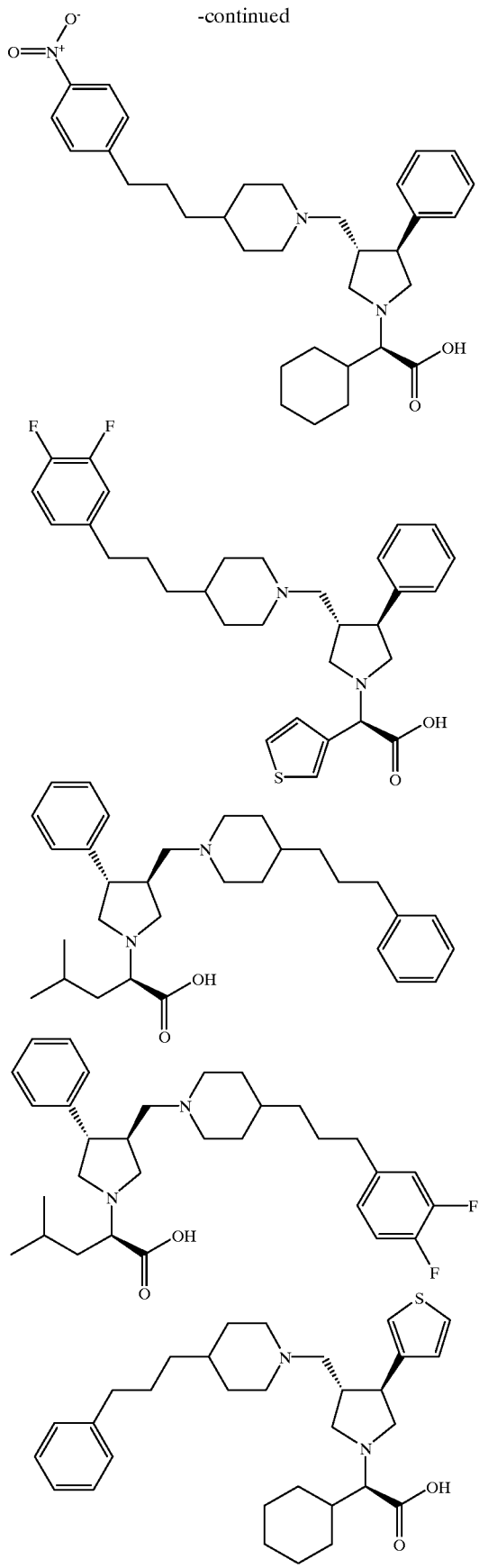
40
-continued
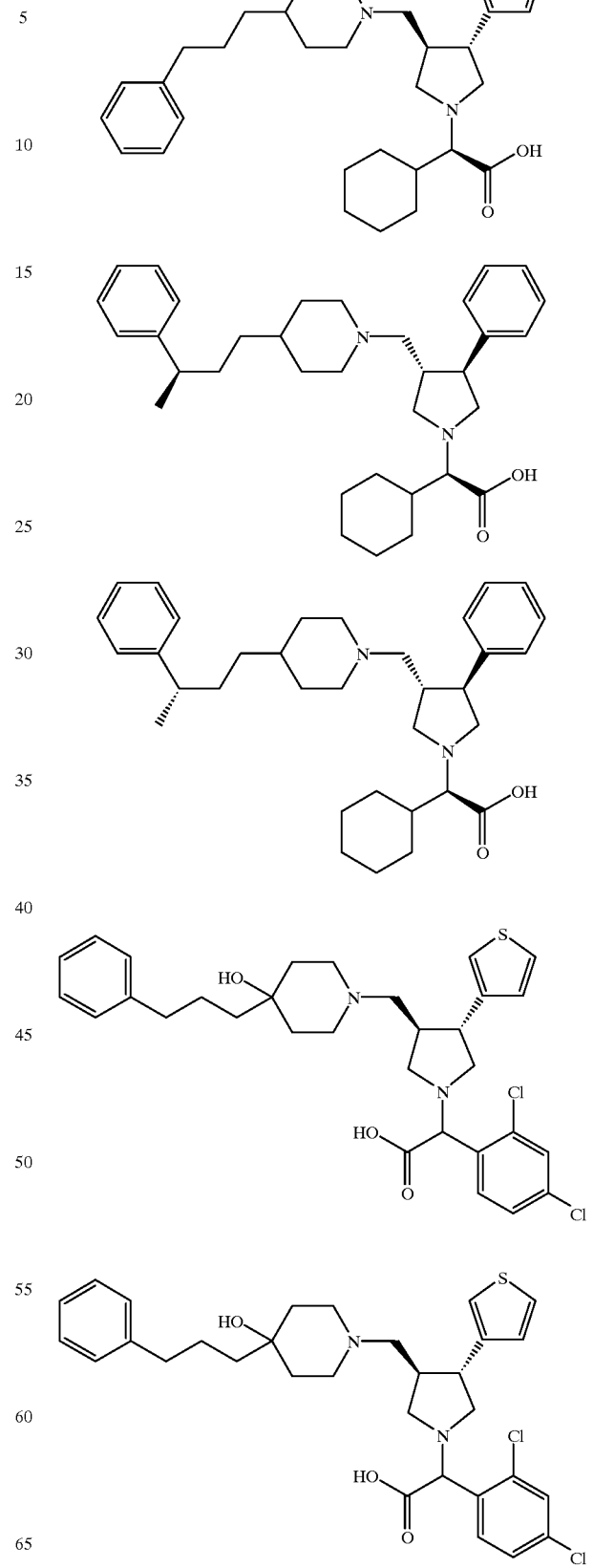

41
-continued
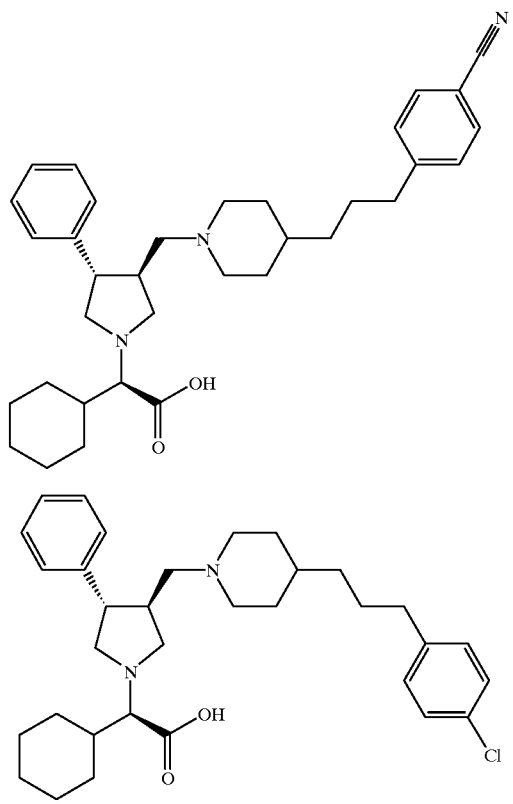
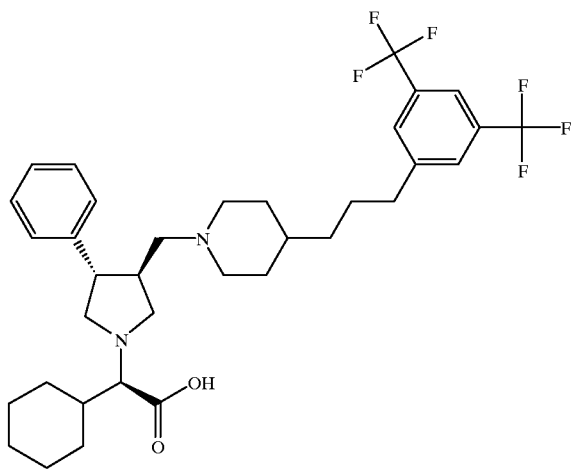
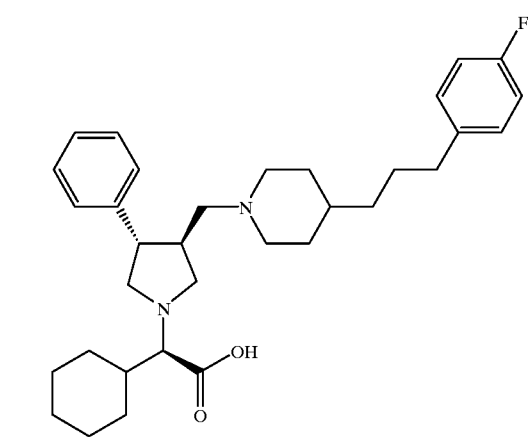
42
-continued
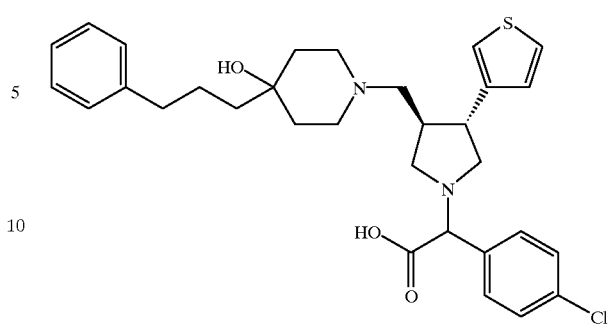
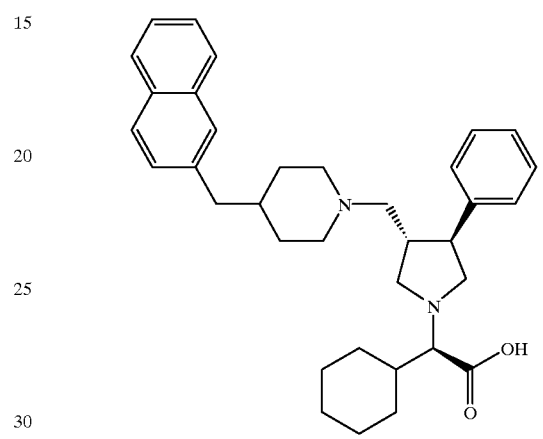
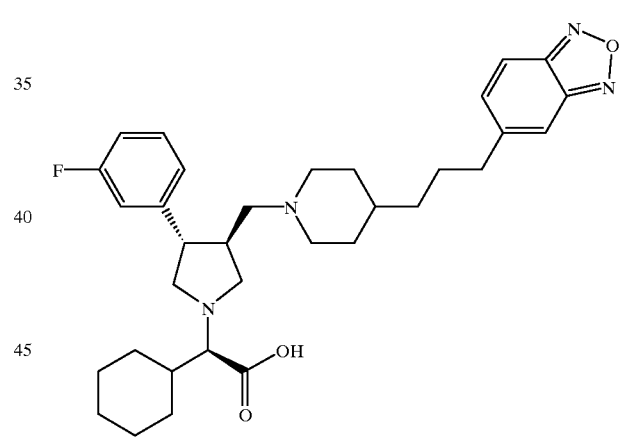
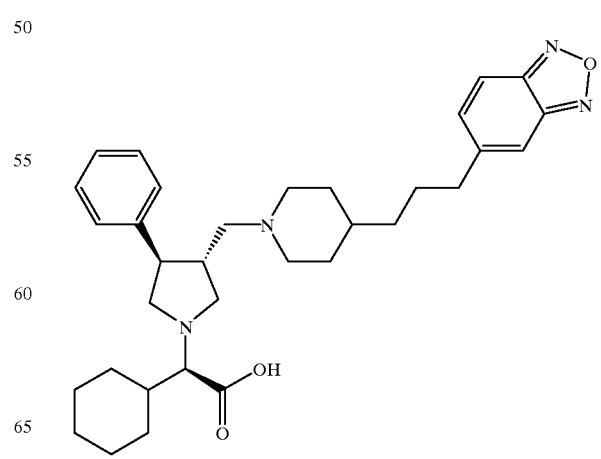

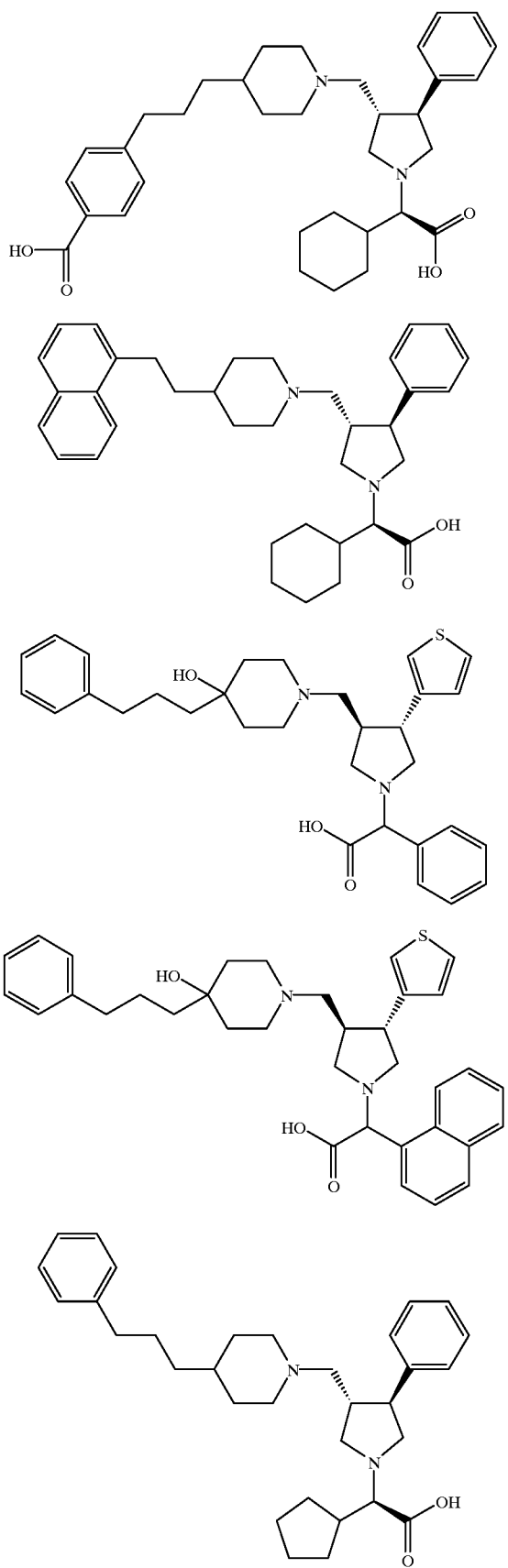
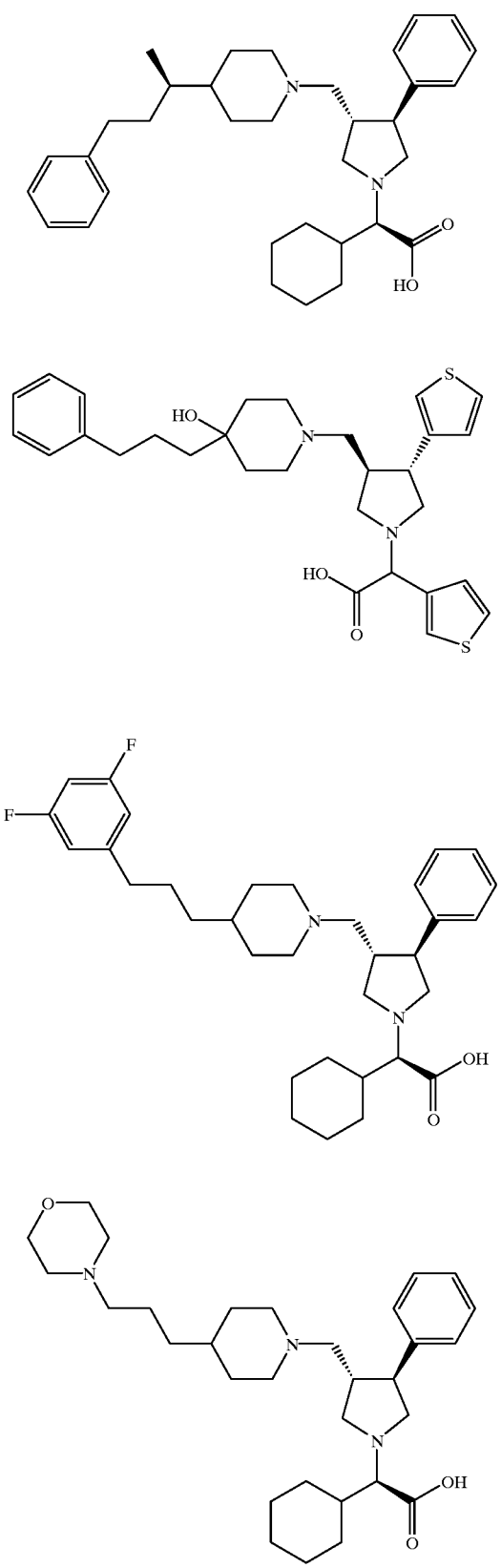

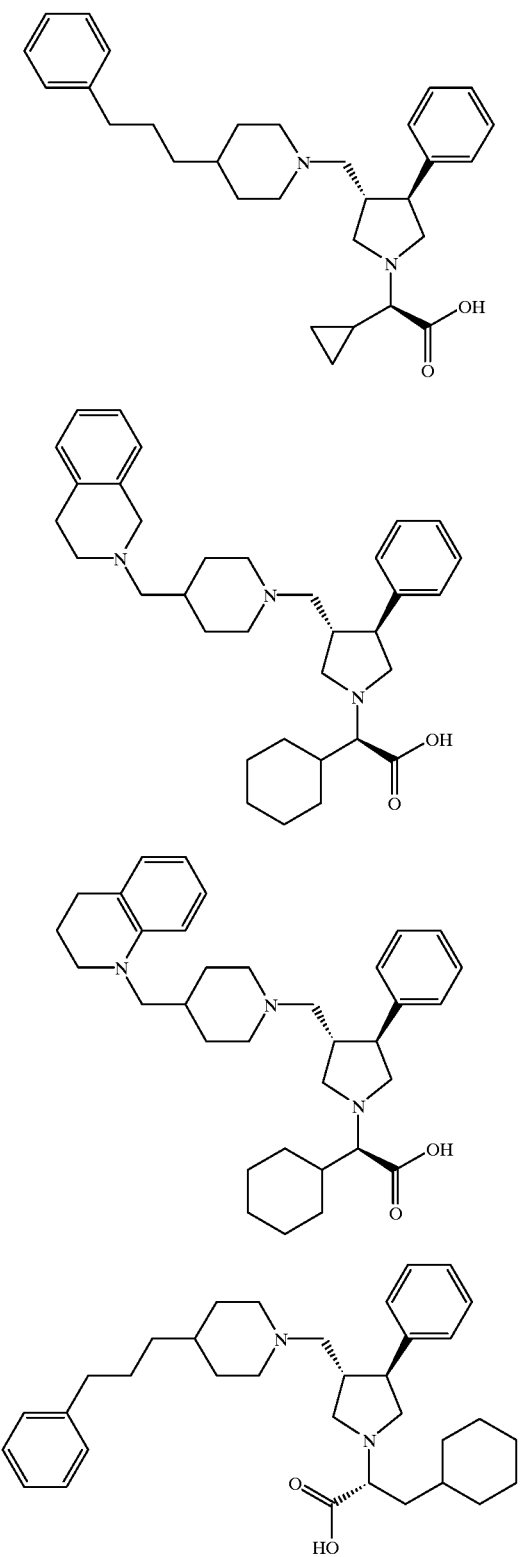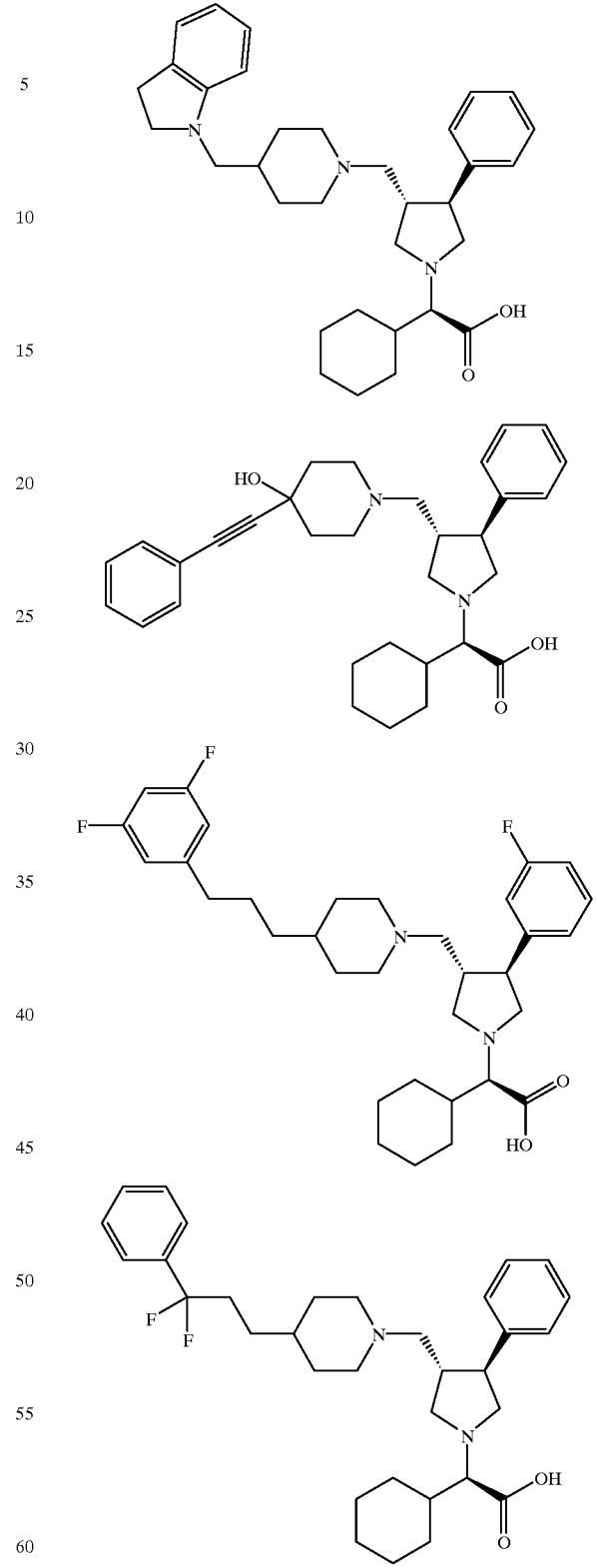

47
-continued
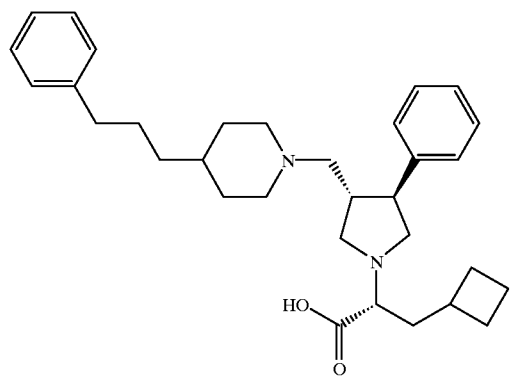
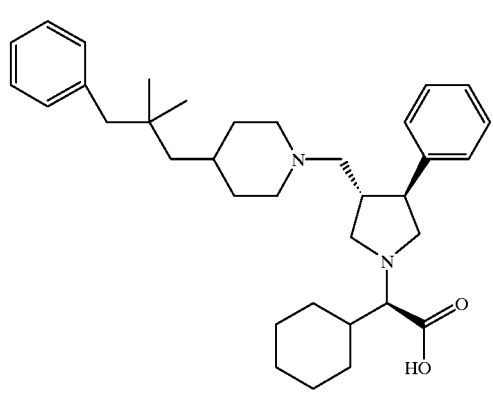
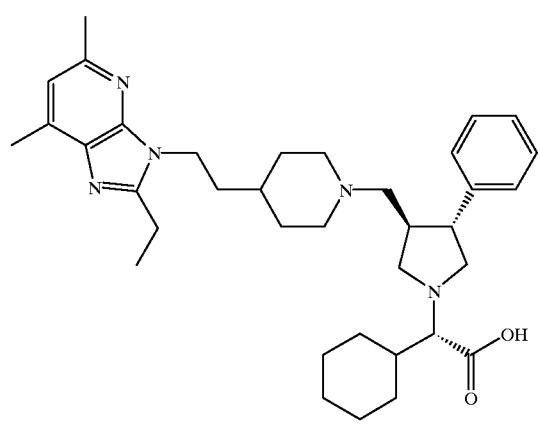
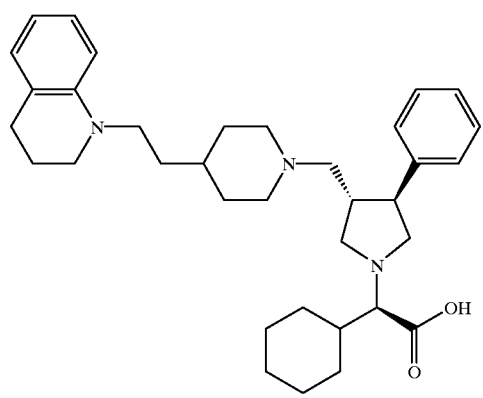
48
-continued
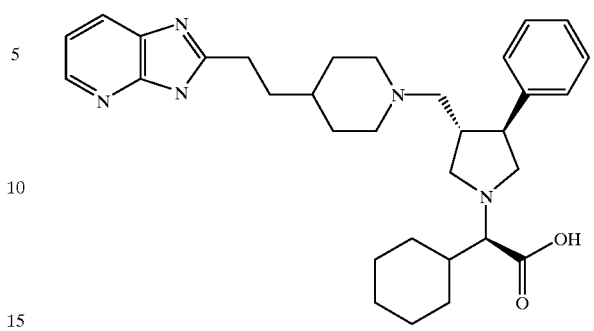
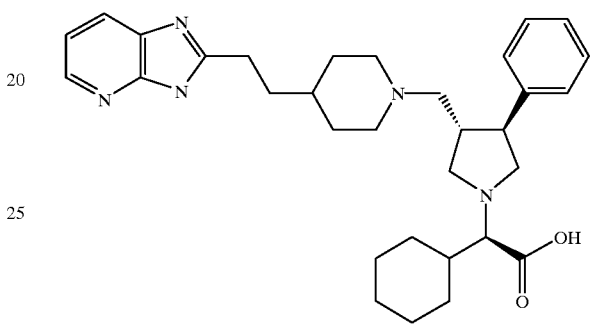
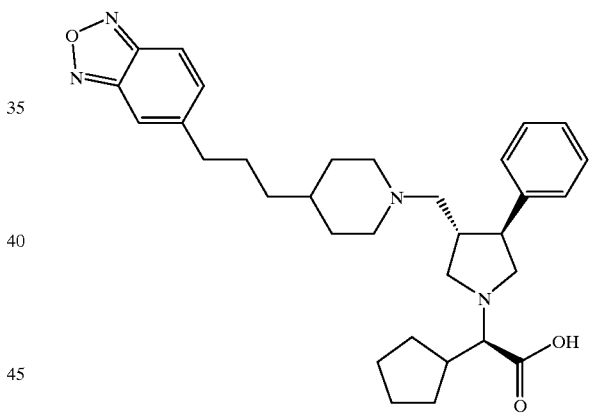

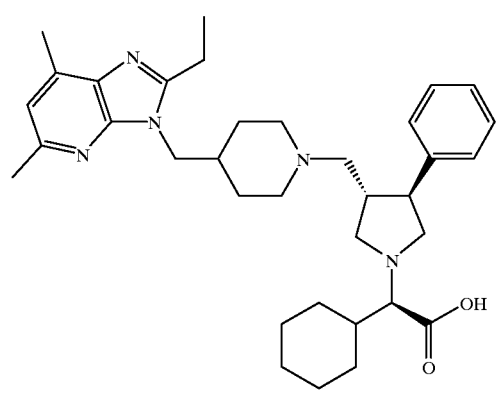
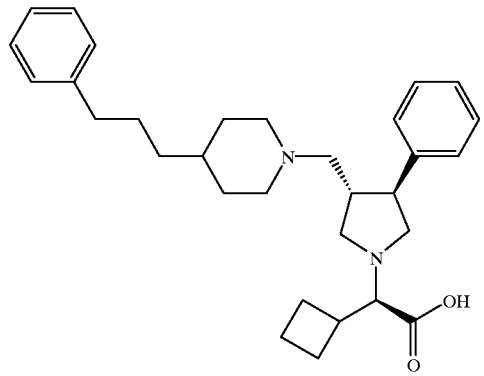
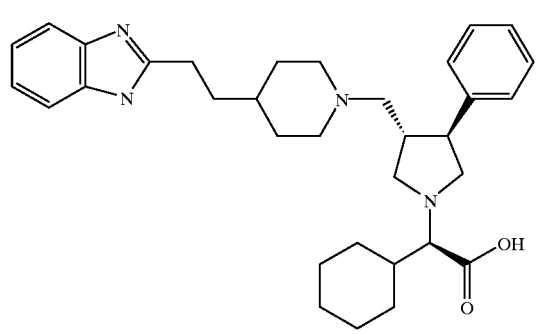
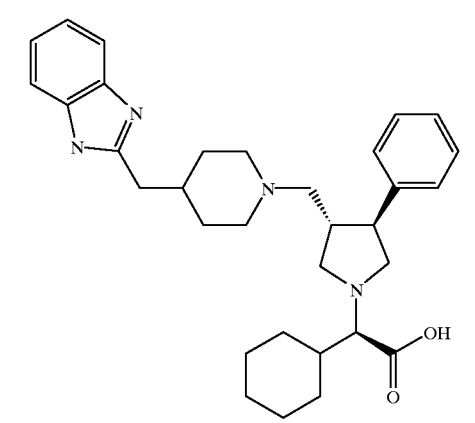
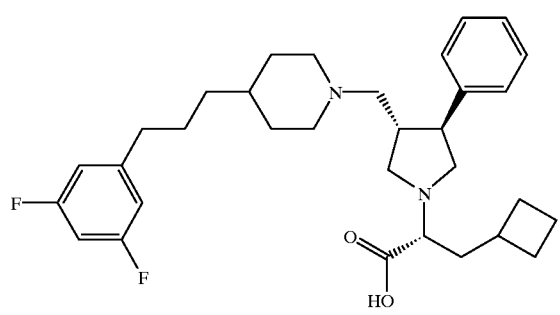
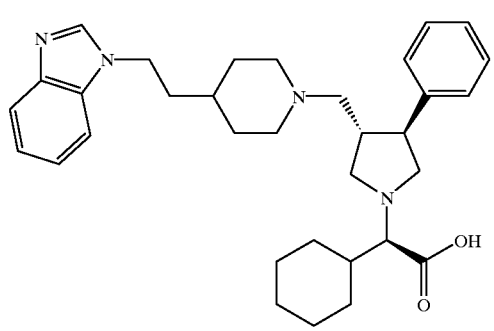
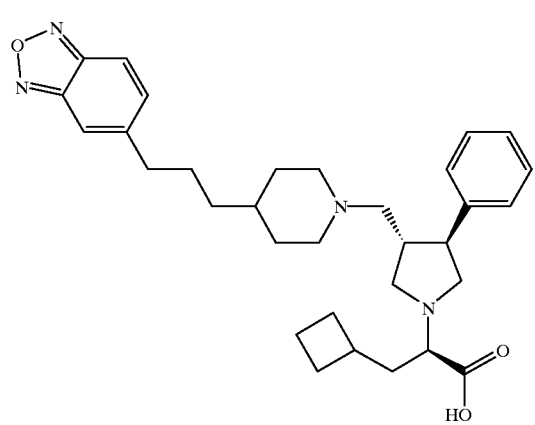

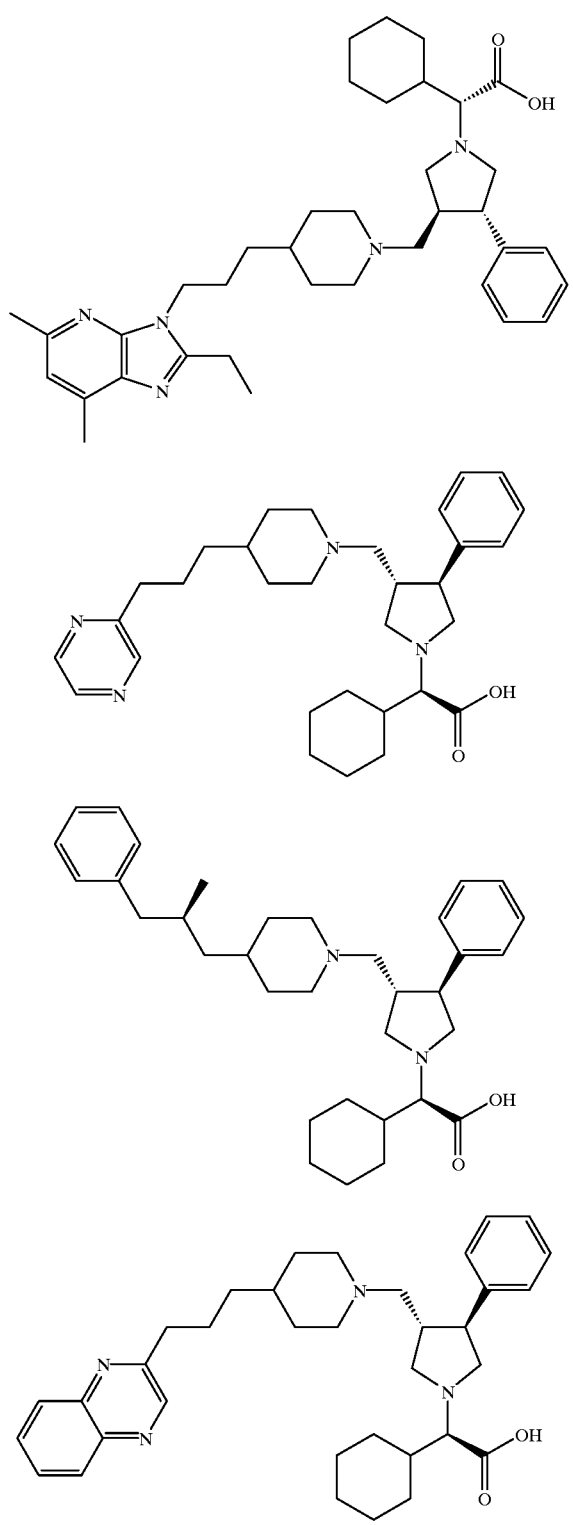
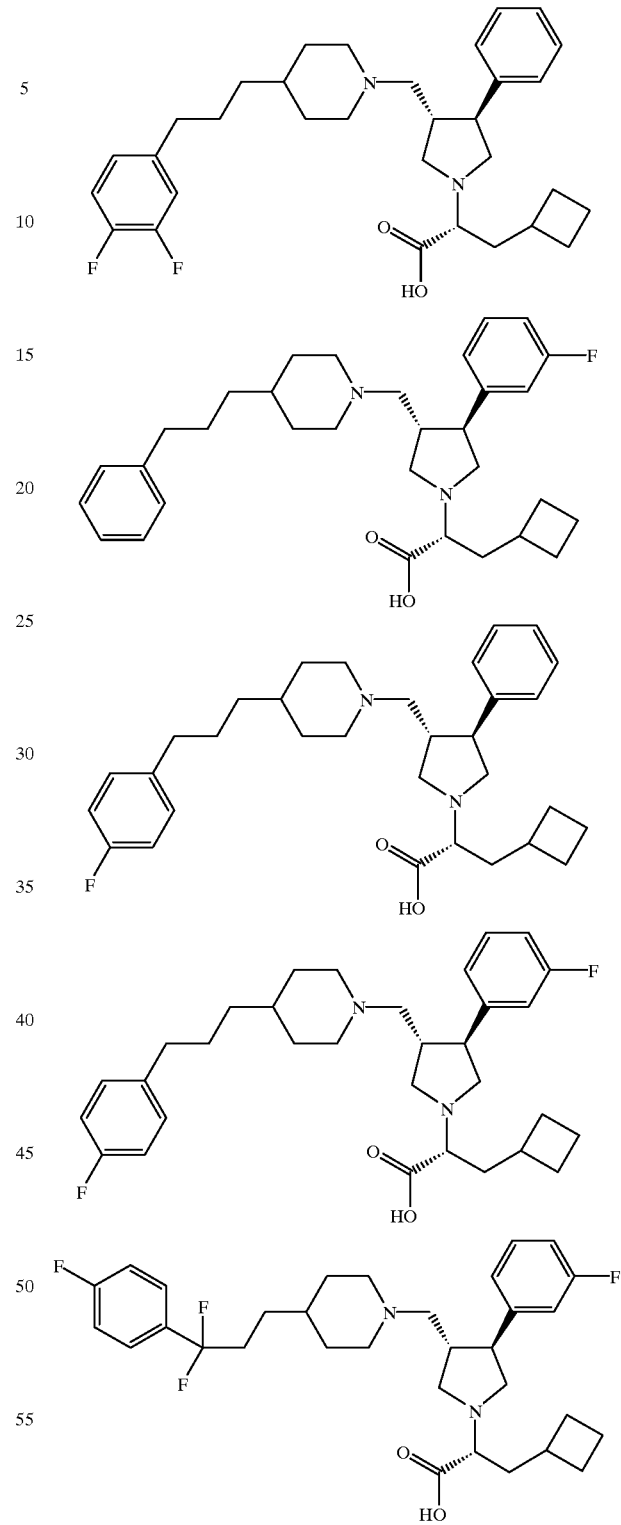

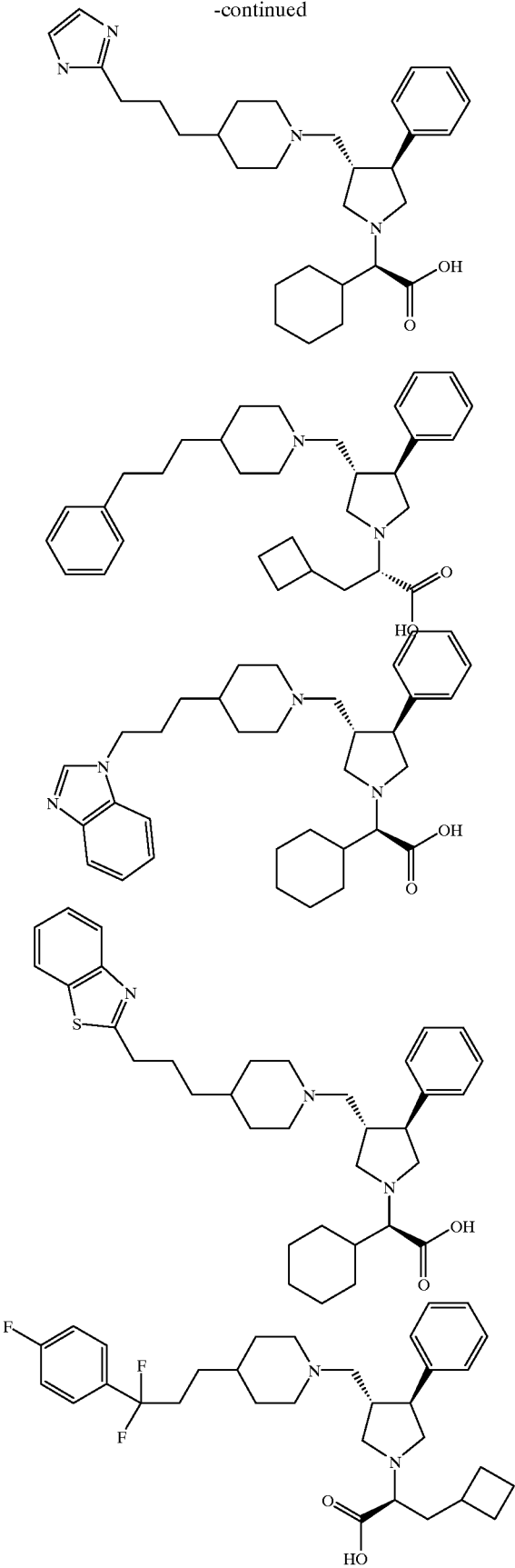

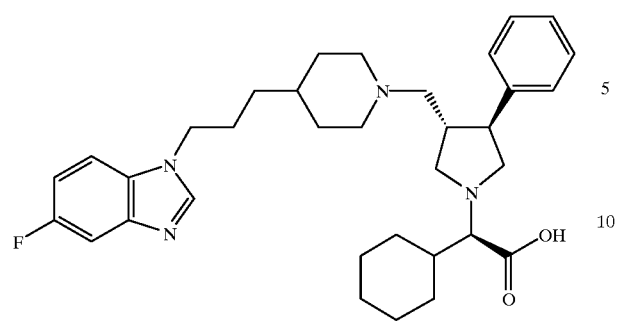
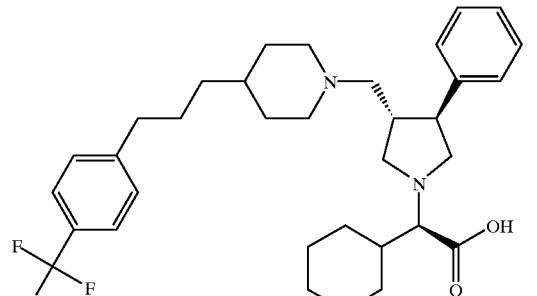
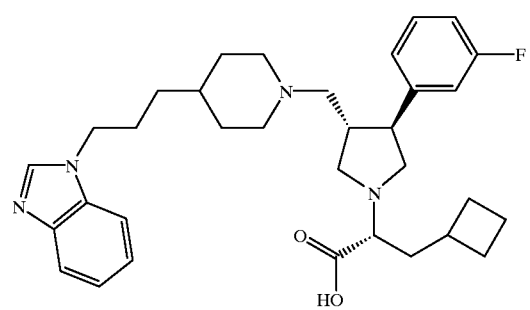
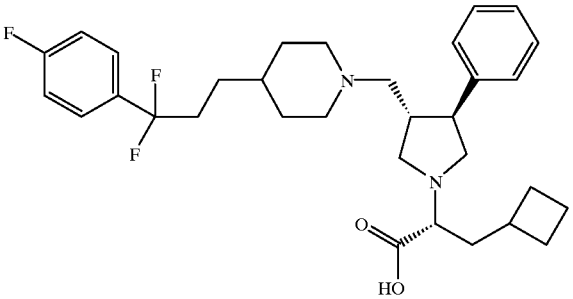
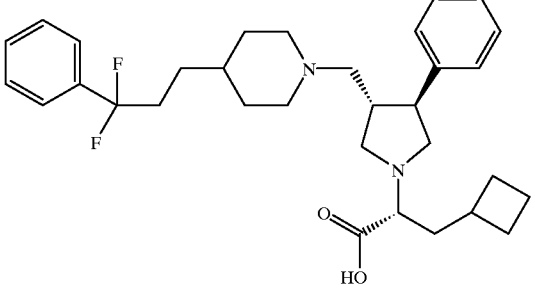
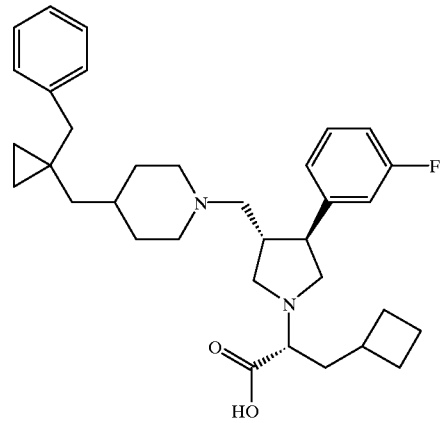

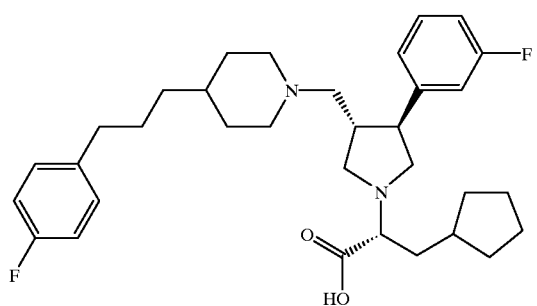
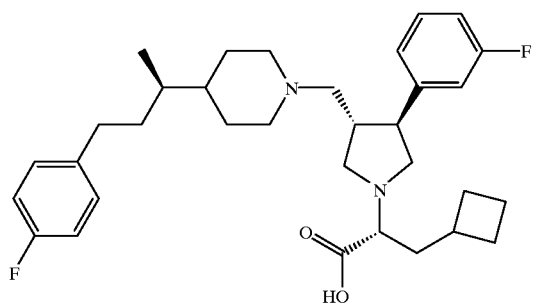
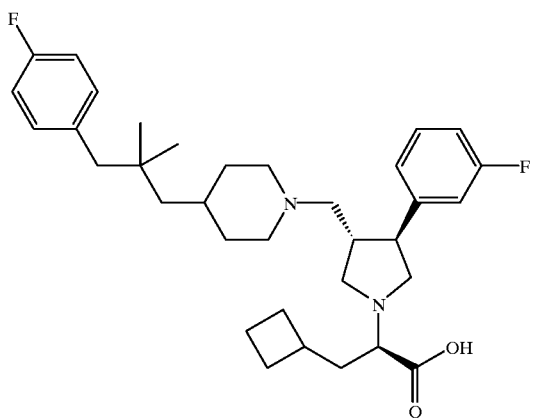
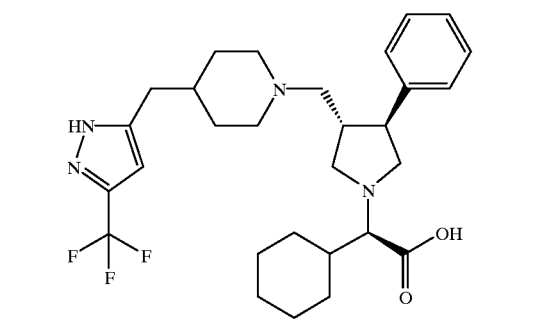
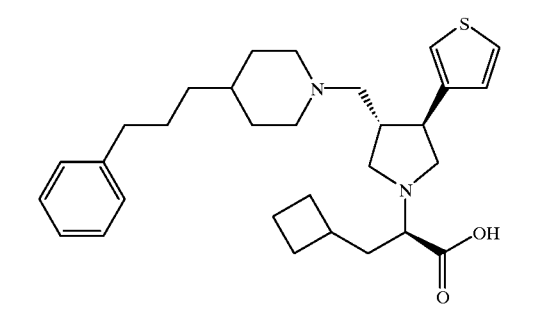
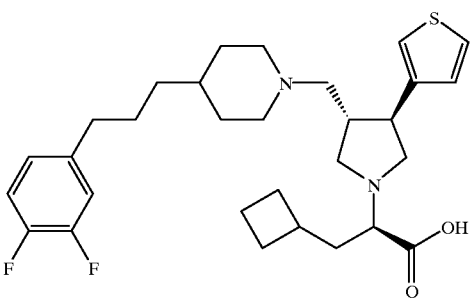
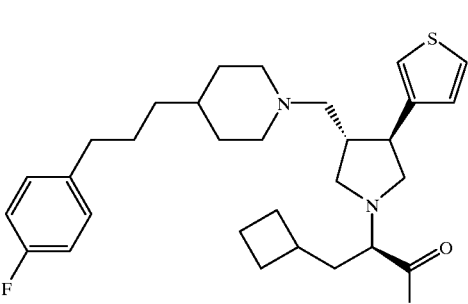
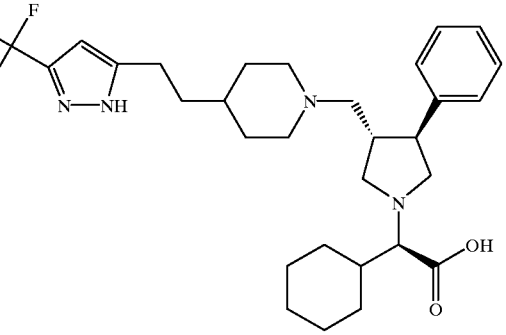
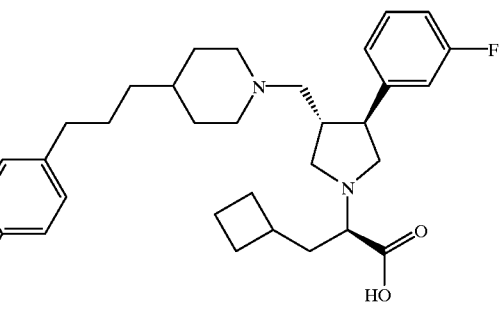
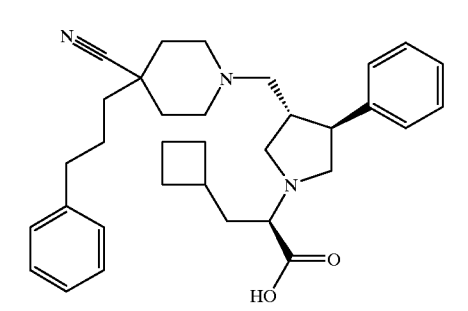

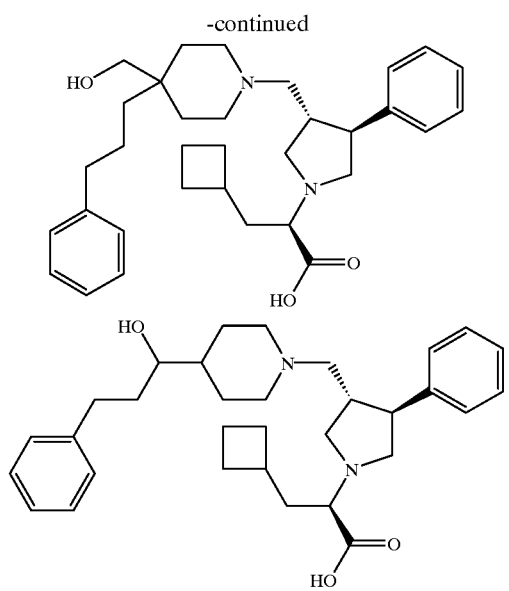
and pharmaceutically acceptable salts thereof and individual diastereomers thereof.
Specific compounds within the present invention also include compounds selected from the group consisting of:
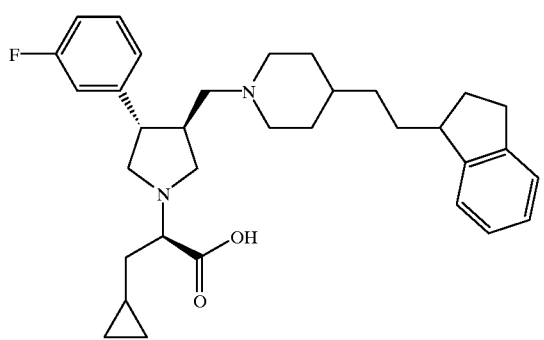
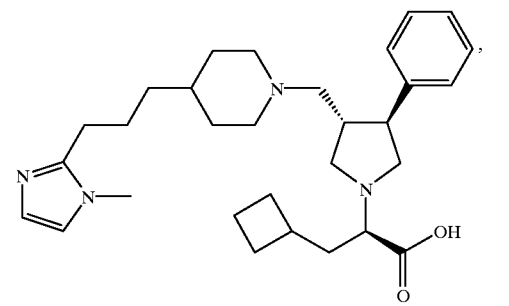
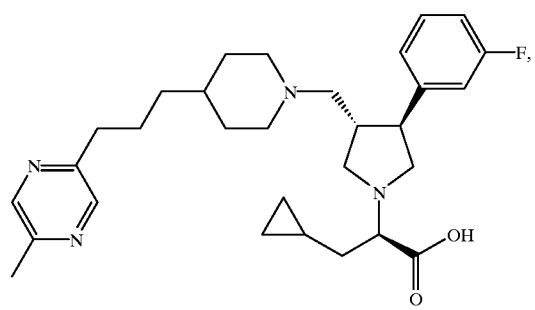
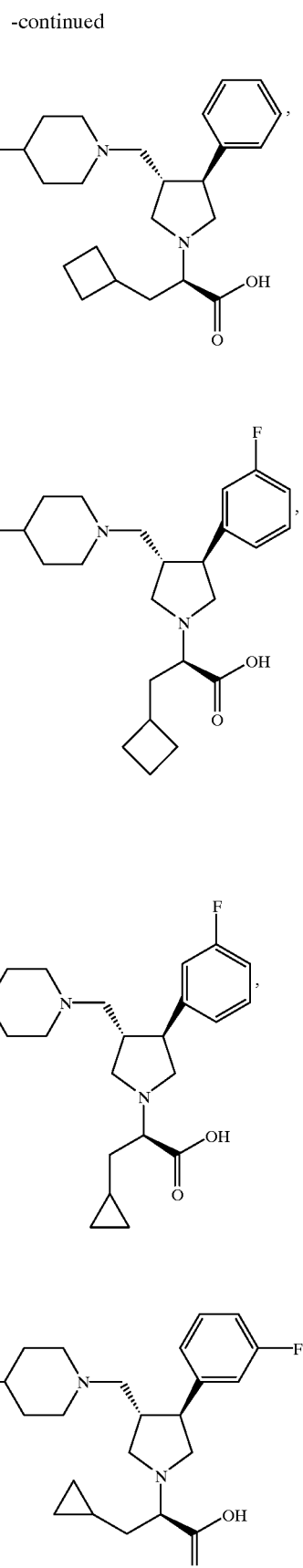

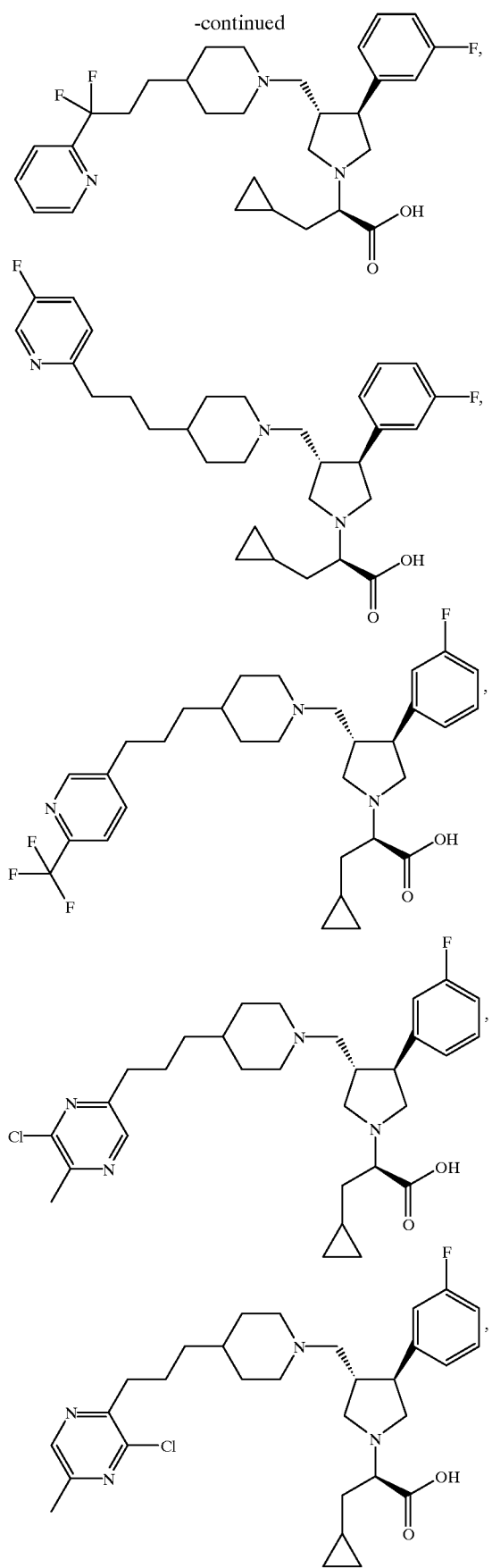

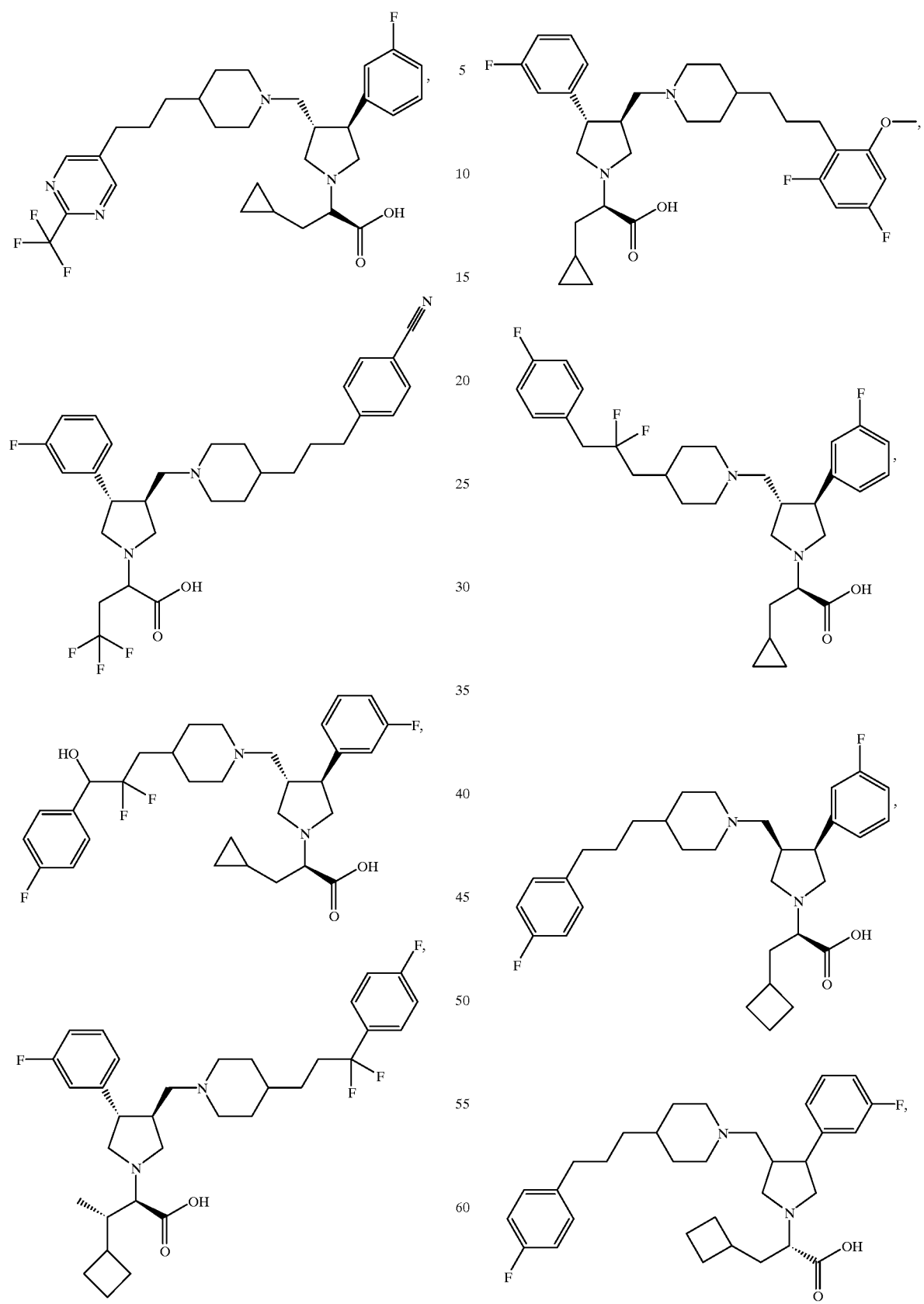

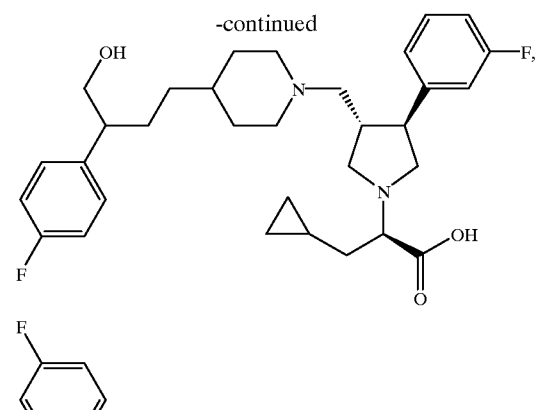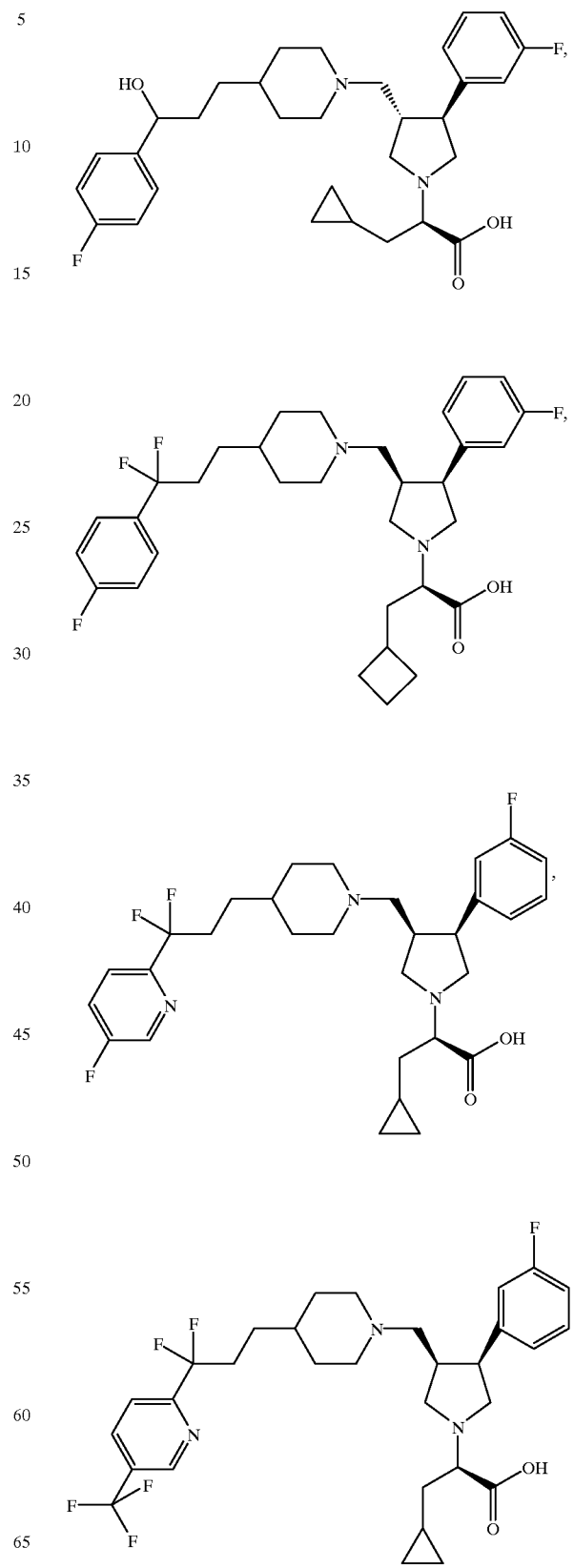

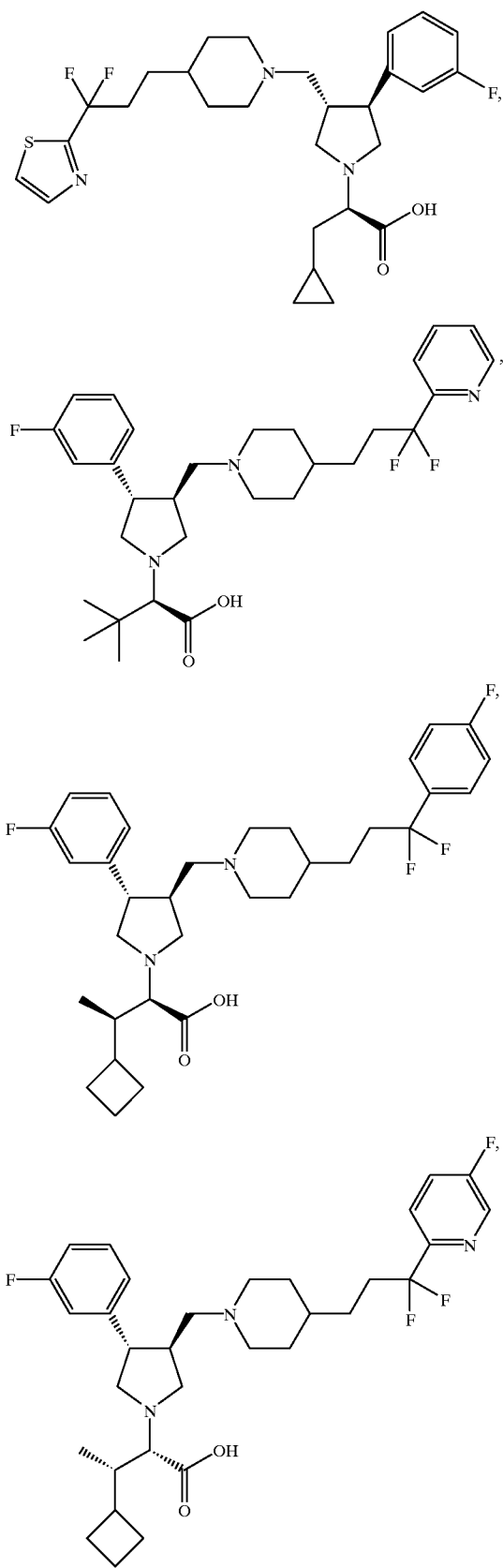
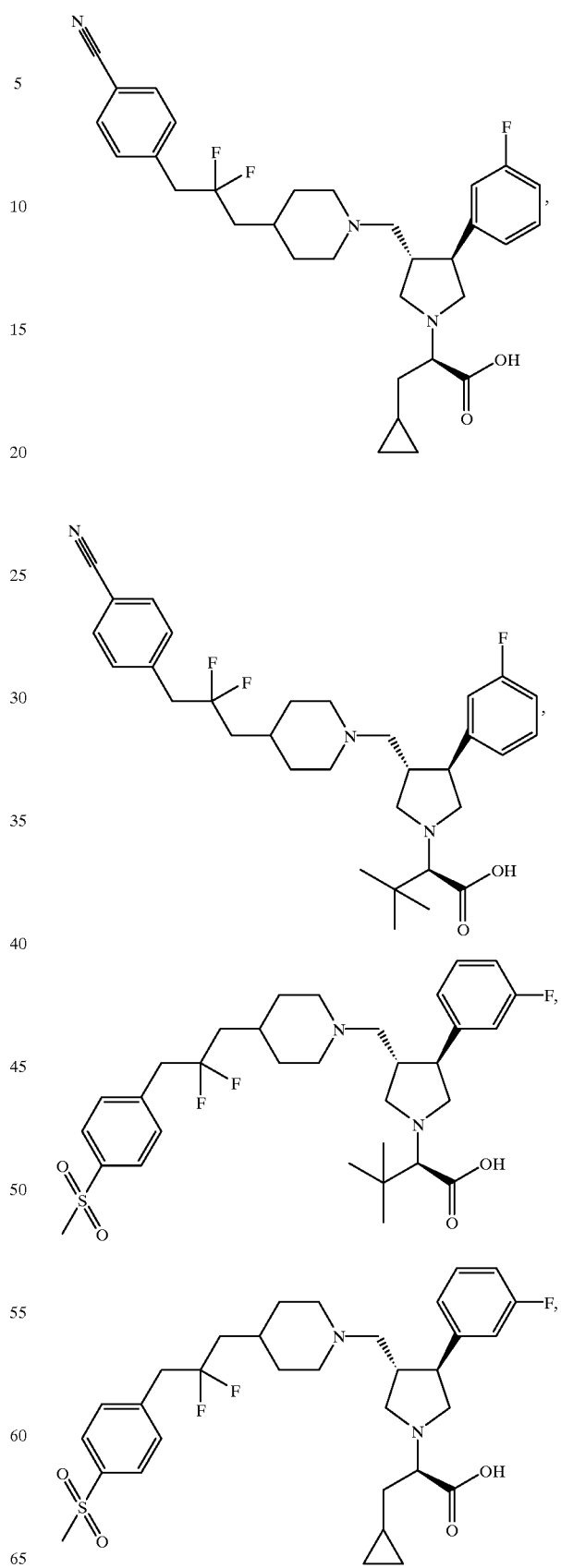

-continued
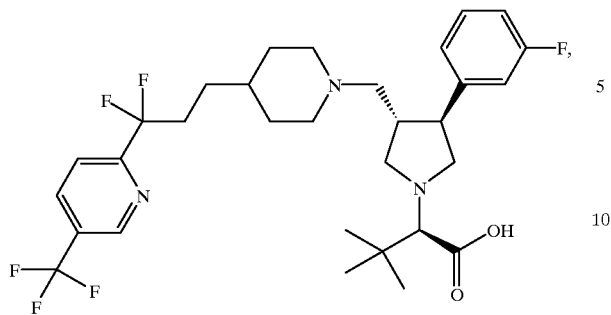
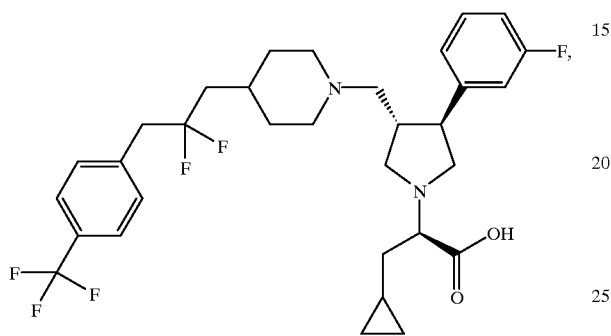
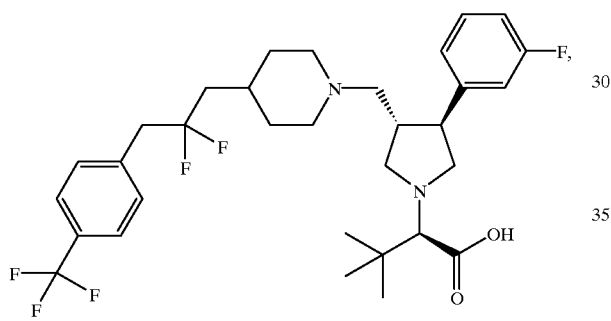
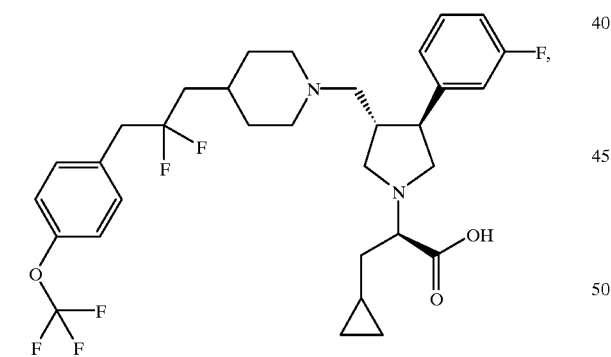

-continued
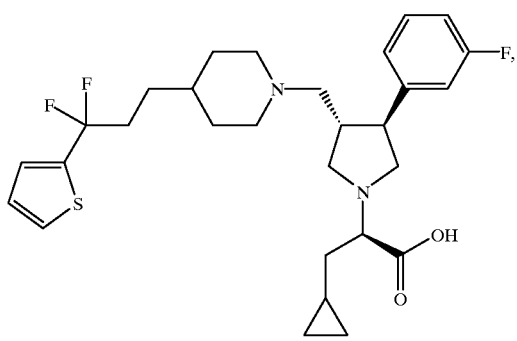
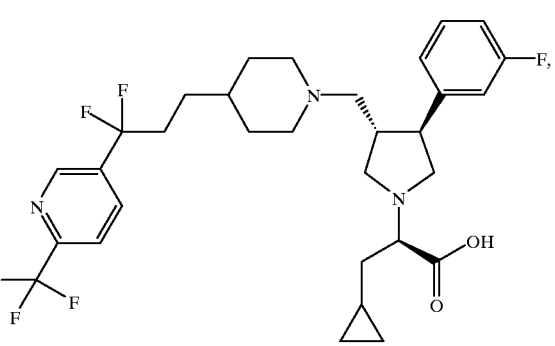
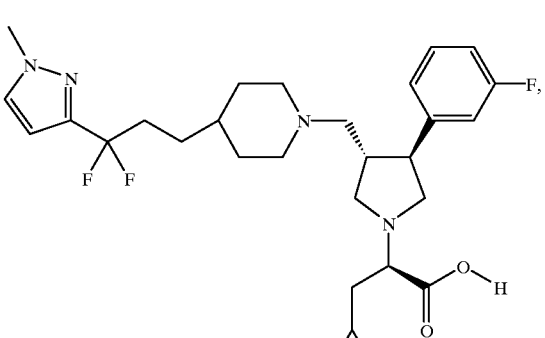
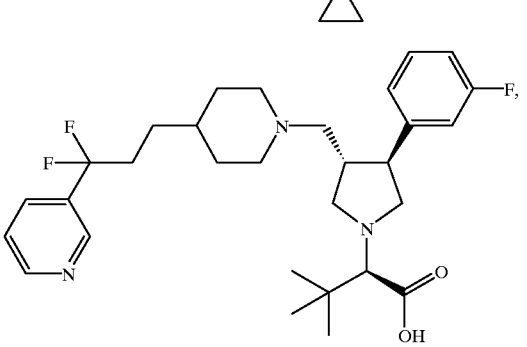
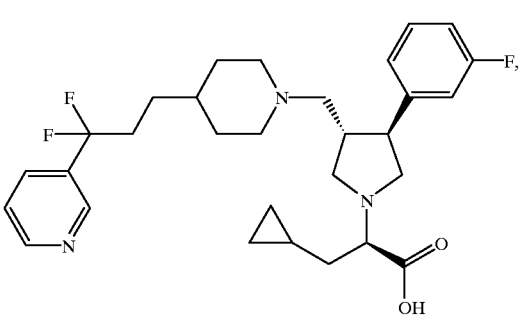

-continued

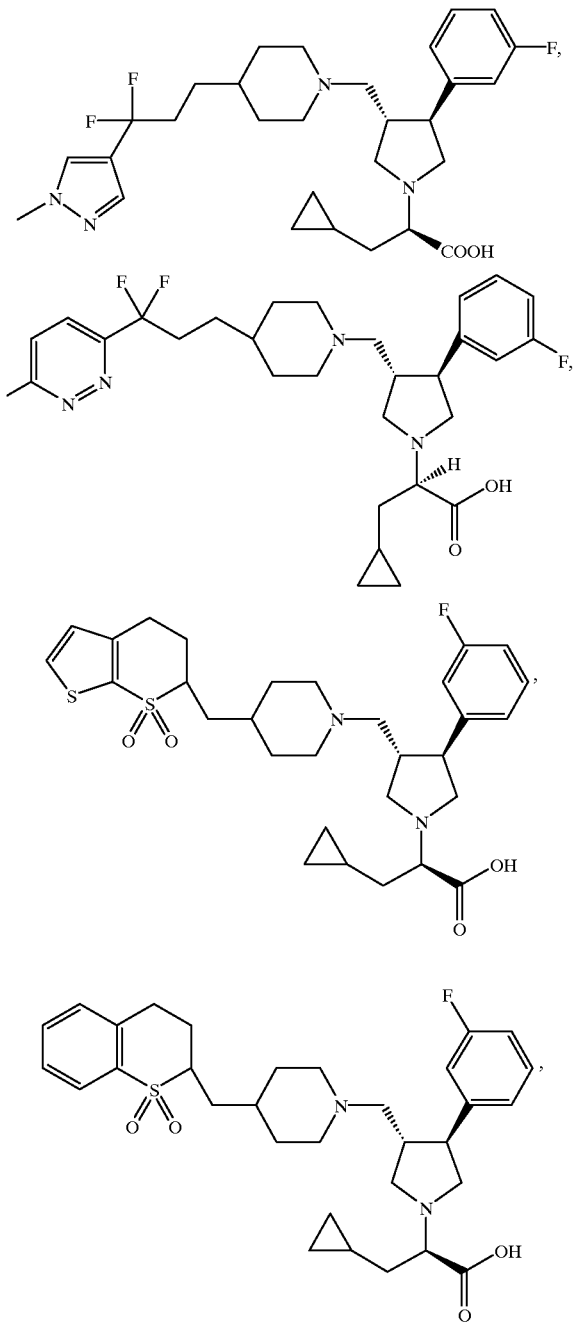

and pharmaceutically acceptable salts thereof and individual diastereomers thereof.

The subject compounds are useful in a method of modulating chemokine receptor activity in a patient in need of such modulation comprising the administration of an effective amount of the compound.

The present invention is directed to the use of the foregoing compounds as modulators of chemokine receptor activity. In particular, these compounds are useful as modulators of the chemokine receptors, including CCR-5 and/or CCR-3.

The utility of the compounds in accordance with the present invention as modulators of chemokine receptor activity may be demonstrated by methodology known in the art, such as the assay for chemokine binding as disclosed by Van Riper, et al., *J. Exp. Med.,* 177 851–856 (1993) which may be readily adapted for measurement of CCR-5 binding, and the assay for CCR-3 binding as disclosed by Daugherty, et al., *J. Exp. Med.,* 183, 2349–2354 (1996). Cell lines for expressing the receptor of interest include those naturally expressing the receptor, such as EOL-3 or THP-1, or a cell engineered to express a recombinant receptor, such as CHO, RBL-2H3, HEK-293. For example, a CCR3 transfected AML14.3D10 cell line has been placed on restricted deposit with American Type Culture Collection in Rockville, Md. as ATCC No. CRL-12079, on Apr. 5, 1996. The utility of the compounds in accordance with the present invention as inhibitors of the spread of HIV infection in cells may be demonstrated by methodology known in the art, such as the HIV quantitation assay disclosed by Nunberg, et al., *J. Virology,* 65 (9), 4887–4892 (1991).

In particular, the compounds of the following examples had activity in binding to the CCR-5 or the CCR-3 receptor in the aforementioned assays, generally with an $IC_{50}$ of less than about 1 $\mu$M. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes.

Accordingly, the present invention is directed to compounds which are useful in the prevention and/or treatment of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited. For example, eosinophilic infiltration to inflammatory sites (e.g., in asthma) can be inhibited according to the present method.

Similarly, an instant compound which promotes one or more functions of a mammalian chemokine receptor (e.g., a human chemokine) is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, eosinophils can be recruited to combat parasitic infections.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with promoters of chemokine receptor function, include, but are not limited to: immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; immunosuppression due congenital deficiency in receptor function or other causes; and infectious diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migrans (e.g., Toxocara), eosinophilic gastroenteritis (e.g., Anisaki spp., Phocanema ssp.), cutaneous larva migrans (*Ancylostona braziliense, Ancylostoma caninum*).

The compounds of the present invention are accordingly useful in the prevention and treatment of a wide variety of inflammatory and immunoregulatory disorders and diseases, allergic conditions, atopic conditions, as well as autoimmune pathologies.

In another aspect, the instant invention may be used to evaluate putative specific agonists or antagonists of chemokine receptors, including CCR-5 and/or CCR-3. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-5 and/or CCR-3. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of these compounds in the prevention or treatment of infection by a retrovirus, in particular, the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a preferred aspect of the present invention, a subject compound may be used in a method of inhibiting the binding of a chemokine to a chemokine receptor, such as CCR-5 or CCR-3, of a target cell, which comprises contacting the target cell with an amount of the compound which is effective at inhibiting the binding of the chemokine to the chemokine receptor.

The subject treated in the methods above is a mammal, preferably a human being, male or female, in whom modulation of chemokine receptor activity is desired. "Modulation" as used herein is intended to encompass antagonism, agonism, partial antagonism, inverse agonism and/or partial agonism. In a preferred aspect of the present invention, modulation refers to antagonism of chemokine receptor activity.

The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

Combined therapy to modulate chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compounds of the pressent invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, caiprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CXCRA, CCR-1, CCR-2, CCR-3 and CCR-5; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone and pioglitazone); (l) preparations of interferon beta (interferon beta-lac, interferon beta-1β); (m) other compounds such as 5-aminosalicylic acid and prodrugs thereof, antimetabolites such as azathioprine and 6-mercaptopurine, and cytotoxic cancer chemotherapeutic agents. The weight ratio of the compound of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The present invention is further directed to combinations of the present compounds with one or more agents useful in the prevention or treatment of AIDS. For example, the compounds of this invention may be effectively administered, whether at periods of preexposure and/or post-exposure, in combination with effective amounts of the AIDS antivirals, immunomodulators, anti-infectives, or vaccines known to those of ordinary skill in the art.

| Drug Name | Manufacturer | Indication |
|---|---|---|
| ANTIVIRALS | | |
| 097 | Hoechst/Bayer | HIV infection, AIDS, ARC (non-nucleoside reverse transcriptase inhibitor) |
| 141 W94 | Glaxo Wellcome | HIV infection, AIDS, ARC (protease inhibitor) |
| 1592U89 | Glaxo Wellcome | HIV infection, AIDS, ARC |
| Acemannan | Carrington Labs (Irving, TX) | ARC |

| Drug Name | Manufacturer | Indication |
|---|---|---|
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| (-)6-Chloro-4(S)-cyclopropylethynyl-4(S)-trifluoro-methyl-1,4-dihydro-2H-3,1-benzoxazin-2-one | Merck | HIV infection, AIDS, ARC (non-nucleoside reverse transcriptase inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (protease inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| EL10 | Elan Corp, PLC (Gainesville, GA) | HIV infection |
| Efavirenz (DMP 266) (-)6-Chloro-4(S)-cyclopropylethynyl-4(S)-trifluoro-methyl-1,4-dihydro-2H-3,1-benzoxazin-2-one, | DuPont (SUSTIVA ®), Merck (STOCRIN ®) | HIV infection, AIDS, ARC (non-nucleoside RT inhibitor) |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| GW 141 | Glaxo Welcome | HIV infection, AIDS, ARC (protease inhibitor) |
| GW 1592 | Glaxo Welcome | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| Compound A | Merck | HIV infection, AIDS, ARC, asymptomatic HIV positive |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (protease inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| T-20 | Trimeris | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| Amprenivir VX-478 | Vertex | HIV infection, AIDS; ARC |
| Zalcitabine | Hoffmann-La Roche | HIV infection; AIDS, ARC, with AZT |
| Zidovudine; AZT | Glaxo Wellcome | HIV infection, AIDS, ARC, Kaposi's sarcoma, in combination with other therapies |
| ABT-378 | Abbott | HIV infection, AIDS, ARC (protease inhibitor) |
| JE2147/AG1776 | Agouron | HIV infection, AIDS, ARC (protease inhibitor) |
| T-20 T-1249 | Trimeris | HIV infection, AIDS, ARC (fusion inhibitor) |

-continued

| Drug Name | Manufacturer | Indication |
|---|---|---|
| BMS 232632 | Bristol-Myers-Squibb | HIV infection, AIDS, ARC (protease inhibitor) |
| IMMUNO-MODULATORS | | |
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246, 738 | American Cyanamid Lederie Labs | AIDS, Kaposi's sarcoma |
| EL10 | Elan Corp, PLC (Gainesville, GA) | HIV infection |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute | HIV infection |
| Tumor Necrosis Factor; TNF | Genentech | ARC, in combination w/gamma Interferon |
| etanercept | Immunex Corp (Enbrel ®) | rheumatoid arthritis |
| infliximab | Centocor (Remicade ®) | rheumatoid arthritis and Crohn's disease |

-continued

| Drug Name | Manufacturer | Indication |
|---|---|---|
| ANTI-INFECTIVES | | |
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Omidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidial diarrhea |
| Intraconazole-R51211 | Janssen Pharm. | histoplasmosis; cryptococcal meningitis |
| Trimetrexate | Warner-Lambert | PCP |
| OTHER | | |
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/AIDS |
| Soluble CD4 Protein and Derivatives | — | HIV infection |
| Testosterone | Alza, Smith Kline | AIDS-related wasting |
| Total Enteral Nutrition | Norwich Eaton Pharmaceuticals | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Preferred combinations are simultaneous or alternating treatments with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. Preferred agents for combination therapy include: Zidovudine, Lamivudine, Stavudine, Efavirenz, Ritonavir, Nelfinavir, Abacavir, Indinavir, 141-W94 (4-amino-N-((2 syn,3S)-2-hydroxy-4phenyl-3-((S)-tetrahydrofuran-3-yloxycarbonylamino)-butyl)N-isobutyl-benzenesulfonamide), N-(2(R)-hydroxy-1(S)-indanyl)-2(R)-phenylmethyl-4-(S)hydroxy-5-(1-(4-(2-benzo[b]furanylmethyl)-2(S)-N'(t-butylcarbox-amido)-piperazinyl))-pentaneamide, and Delavirdine. A preferred inhibitor of HIV protease is indinavir, which is the sulfate salt of N-(2(R)-hydroxy-1(S)-indanyl)-2(R)-phenylmethyl-4-(S)-hydroxy-5-(1-(4-(3-pyridyi-methyl)-2(S)-N'-(t-butylcarbo-xamido)-piperazinyl))-pentane-amide ethanolate, and is synthesized according to U.S. Pat. No. 5,413,999. Indinavir is generally administered at a dosage of 800 mg three times a day. Other preferred inhibitors of HIV protease include nelfinavir and ritonavir. Preferred non-nucleoside inhibitors of HIV reverse transcriptase include (−) 6-chloro-4-(S)-cyclopropylethynyl-4-(S)-trifluoromethyl-1,4-dihydro-2H-3,1-benzoxazin-2-one, which may be prepared by methods disclosed in EP 0,582,455. The preparation of ddC, ddI and AZT are also described in EPO 0,484,071. These combinations may have unexpected effects on limiting the spread and degree of infection of HIV. Preferred combinations with the compounds of the present invention include the following: (1) Zidovudine and Lamivudine; (2) Stavudine and Lamivudine; (3) Efavirenz; (4) Ritoavir; (5) Nelfinavir; (6) Abacavir; (7) Indinavir, (8) 141-W94; and (9) Delavirdine. Preferred combinations with the compounds of the present invention further include the following (1) indinavir, with efavirenz or (−) 6-chloro-4-(S)-cyclopropylethynyl-4-(S)-trifluoromethyl-1,4-dihydro-2H-3,1-benzoxazin-2-one, and, optionally, AZT and/or 3TC and/or ddI and/or ddC; (2) indinavir, and any of AZT and/or ddI and/or ddC.

Compound A in the foregoing Table is N-(2(R)-hydroxy-1(S)-indanyl)-2(R)-phenylmethyl-4-(S)-hydroxy-5-(1-(4-(2-benzo[b]furanylmethyl)-2(S-N'-(t-butylcarboxamido)-piperazinyl))pentaneamide, preferably administered as the sulfate salt. Compound A can be prepared as described in U.S. Pat. No. 5,646,148.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy- propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.) The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made from known procedures or as illustrated.

SCHEME 1

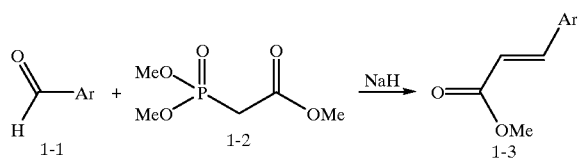

The preparation of cinnamate esters such as 1-3 as intermediates that can be used for the synthesis of compounds within the scope of the instant invention is detailed in Scheme 1. Cinnamate esters of structure 1-3 can be obtained commercially or can be synthesized by reacting a suitable aromatic aldehyde 1-1 with a phosphonoacetate such as 1-2 or a stabilized Wittig reagent in the presence of sodium hydride or other bases such as sodium, lithium or potassium hexamethyldisilazide, potassium t-butoxide, and the like. The aldehyde 1-1 can be obtained commercially or can be prepared in a variety of ways from commercial materials (see March J. "Advanced Organic Chemistry", 4th ed., John Wiley & Sons, New York, pp. 1270–1271 (1992)).

SCHEME 2

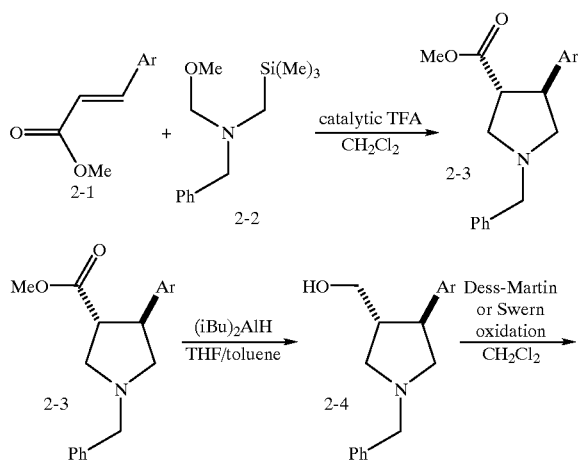

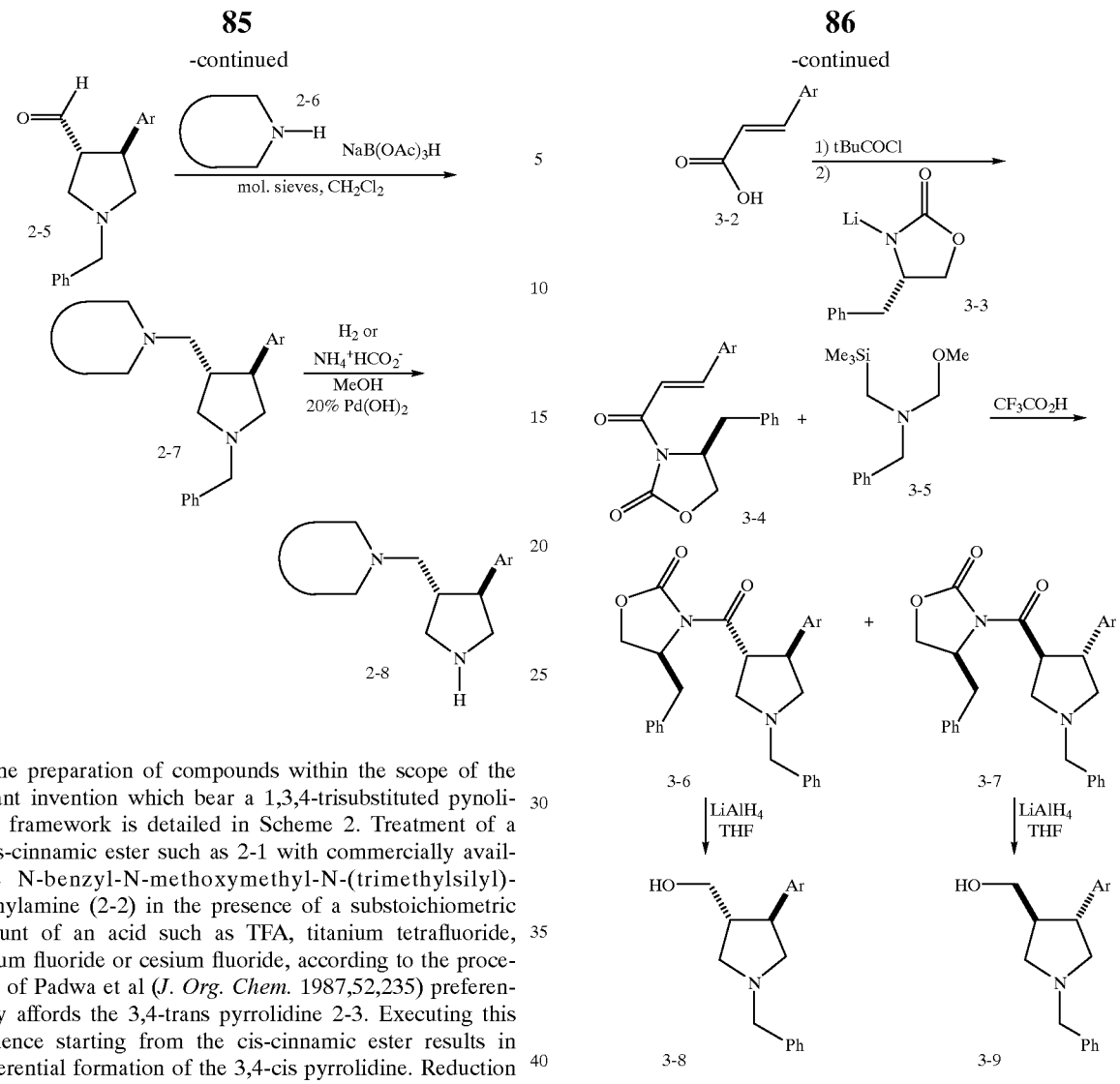

The preparation of compounds within the scope of the instant invention which bear a 1,3,4-trisubstituted pyrolidine framework is detailed in Scheme 2. Treatment of a trans-cinnamic ester such as 2-1 with commercially available N-benzyl-N-methoxymethyl-N-(trimethylsilyl)-methylamine (2-2) in the presence of a substoichiometric amount of an acid such as TFA, titanium tetrafluoride, lithium fluoride or cesium fluoride, according to the procedure of Padwa et al (*J. Org. Chem.* 1987,52,235) preferentially affords the 3,4-trans pyrrolidine 2-3. Executing this sequence starting from the cis-cinnamic ester results in preferential formation of the 3,4-cis pyrrolidine. Reduction of ester 2-3, for example, with diisobutylaluminum hydride, lithium aluminium hydride, or sodium bis(2-methoxyethoxy)aluminum hydride, provides the primary alcohol 24. Oxidation to the aldehyde 2-5 can be carried out under numerous conditions, such as with the Dess-Martin periodinane, with DMSO and oxalyl chloride at low temperature, followed by triethylamine (Swern oxidation), or with various chromium trioxide-based reagents (see March J. "Advanced Organic Chemistry", 4th ed., John Wiley & Sons, New York, pp. 1167–1171 (1992)). Reductive amination with cyclic amine 2-6 then provides diamine 2-7, which can itself be a chemokine receptor modulator. Alternatively, the N-benzyl group is cleaved in a hydrogen atmosphere or with ammonium formate in the presence of 20% palladium hydroxide to provide the secondary amine 2-8.

SCHEME 3

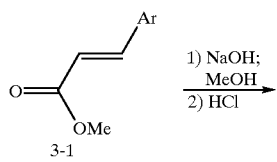

Scheme 3 shows the preparation of optically pure pyrrolidine intermediates. Hydrolysis of unsaturated ester 3-1 provided acid 3-2, which is converted to diacyl derivative 3-4 by activation of the acid group, for example by formation of a mixed anhydride with pivaloyl chloride, followed by reaction with the lithium salt of 4-(S)-benzyloxazolidin-2-one (3-3). Treatment of 3-4 with commercially available N-benzyl-N-methoxymethyl-N-(trimethylsilyl)-methylamine (2-2) in the presence of a substoichiometric amount of an acid such as TEA, titanium tetrafluoride, lithium fluoride or cesium fluoride according to the procedure of Padwa et al (*J. Org. Chem.* 1987, 52, 235) affords the diastereomeric pyrrolidines 3-6 and 3-7, which can be separated by flash chromatography, preparative thin layer chromatography, medium pressure liquid chromatography, high pressure liquid chromatography, fractional crystallization, or similar methods known in the art. The separated products are then individually reduced, for example with lithium alumium hydride (LAH) or other strong hydride reducing agents, to provide pyrrolidines 3-8 and 3-9 in optically enriched form.

SCHEME 4

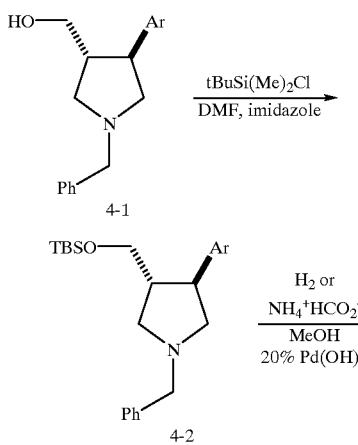

Preparation of a protected pyrrolidine for use as an intermediate in the synthesis of compounds in the instant invention is shown in Scheme 4. The pyrrolidine 4-1 (prepared as shown in Schemes 2 and 3) is protected with a suitable protecting group such as t-butyl-dimethylsilyl to provide silyl ether 4-2. Other silyl groups can also be used in this role, as can other protecting groups for a hydroxy residue (see Greene, T. W.; Wuts, P. G. M. "Protective Groups in Organic Synthesis", 2nd edition, Wiley-Interscience, New York, pp. 10–143 (1991)), subject to the group being stable to conditions used to remove the benzyl group and being removable under conditions that would not adversely affect the remainder of the molecule. Removal of the benzyl group on nitrogen is then carried out by hydrogenolysis, for example by transfer hydrogenation with ammonium formate in the presence of 20% palladium hydroxide or with catalytic hydrogenation with 10% palladium on carbon under one or more atmospheres of hydrogen. Alternatively, compound 4-1 can be debenzylated first under the conditions noted above and then silylated on the hydroxy group, to provide 4-3.

SCHEME 5

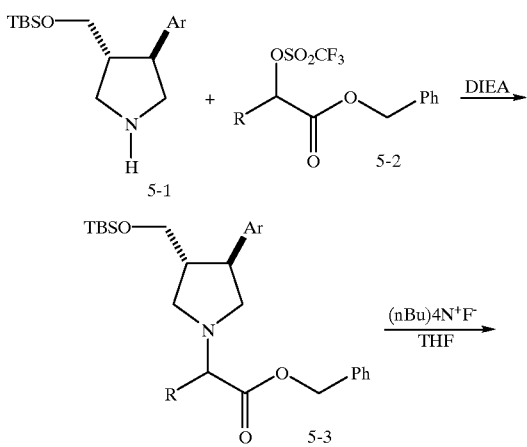

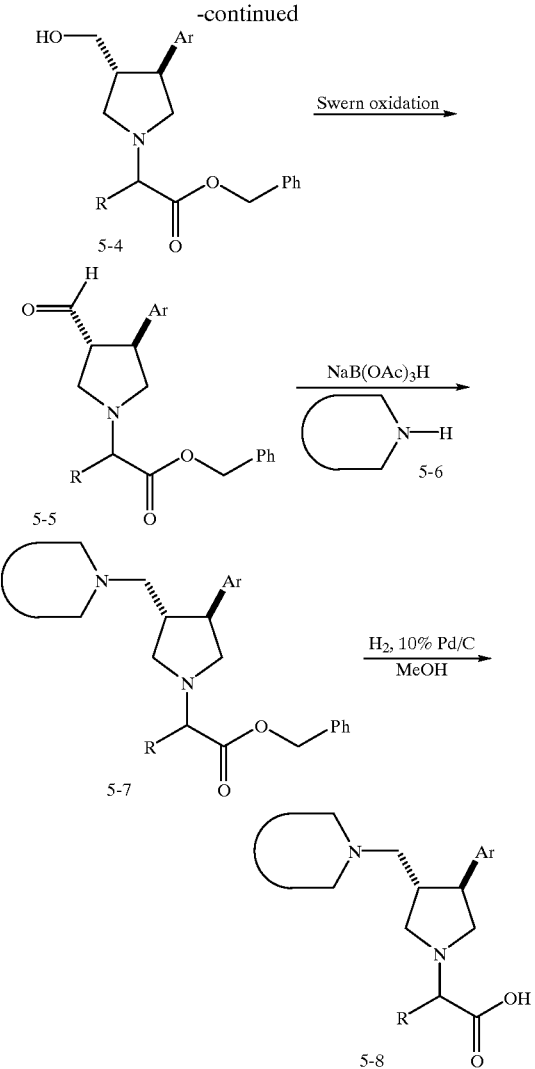

Preparation of some 1,3,4-trisubstituted pyrrolidines within the scope of the instant invention is given in Scheme 5. Alkylation of pyrrolidine 5-1 with the trifluoromethanesulfonate (triflate) ester of a suitable alpha-hydroxy ester derivative 5-2 in the presence of a hindered base such as DIEA ((N,N-(diisopropyl)ethylamine) or a sparingly soluble base such as potassium carbonate provides the N-substituted product 5-3. Triflate ester 5-2 is prepared by treating the parent alpha-hydroxy ester with triflic anhydride in the presence of a suitable hindered tertiary amine, such as DIEA, 2,6-lutidine or 2,6di-t-butyl-4-methylpyridine at or below room temperature in a suitable inert solvent such as dichloromethane or 1,2-dichloroethane. Alternatively, other leaving groups can be employed to activate the alpha-position on ester 5-2 instead of a triflate, such as chloride, bromide, iodide, methanesulfonate, p-toluenesulfonate, etc. Deprotection of silyl ether 5-3 is carried out with tetrabutylammonium fluoride in THF, to afford alcohol 5-4. Alternatively, acidic conditions can be used to remove the silyl group, for example aqueous trifluoroacetic acid, hydrogen fluoride in pyridine, hydrochloric acid, etc. Oxidation of 5-4 to the aldehyde 5-5 is accomplished using the Swern oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Reductive amination with cyclic amine 5-6 then provides di amine 5-7, which can itself be a chemokine receptor antagonist. Cleavage of the benzyl group with catalytic hydrogenation, for example under an atmosphere of hydrogen in the presence of 10% palladium on carbon as catalyst in methanol or ethanol as solvent, provides acid 5-8. Alternatively, the benzyl ester can be cleaved by treatment with strong aqueous base if the remainder of the molecule is stable to those conditions.

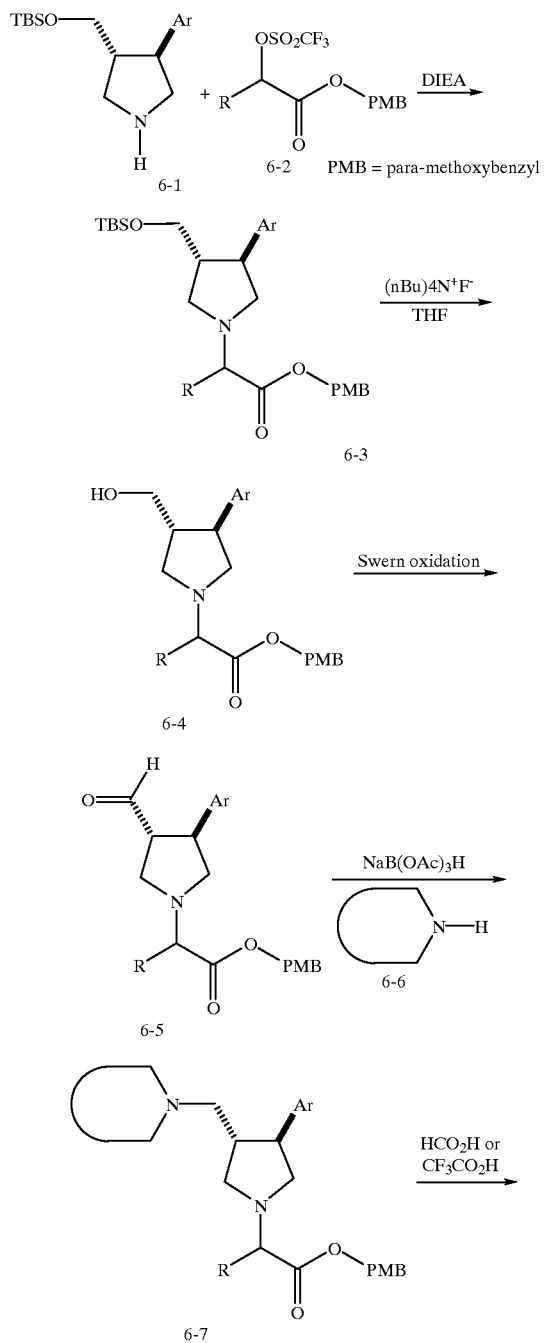

-continued

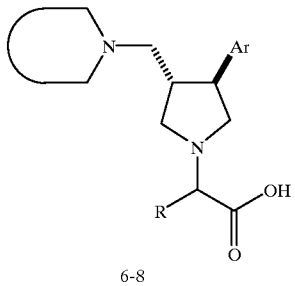

6-8

Preparation of 1,3,4-trisubstituted pyrrolidines within the scope of the instant invention wherein the carboxylic acid protecting group is cleavable under mild acidic conditions is given in Scheme 6. Alkylation of pyrrolidine 6-1 with the triflate ester of a suitable alpha-hydroxy ester derivative 6-2 in the presence of a hindered base such as DIEA or a sparingly soluble base such as potassium carbonate provides the N-substituted product 6-3 (PNMB=para-methoxybenzyl). Triflate ester 6-2 is prepared by treating the parent alpha-hydroxy ester with triflic anhydride in the presence of a suitable hindered tertiary amine, such as DIEA, 2,6-lutidine or 2,6-di-t-butyl-4-methylpyridine at or below room temperature in a suitable inert solvent such as dichloromethane or 1,2-dichloroethane. Alternatively, other leaving groups can be employed to activate the alpha-position on ester 6-2 instead of a triflate, such as chloride, bromide, iodide, methanesulfonate, p-toluenesulfonate, etc. Deprotection of silyl ether 6-3 is carried out with tetrabutylammonium fluoride in THF, to afford alcohol 6-4. Alternatively, mildly acidic conditions in some cases can be used to selectively remove the silyl group, for example aqueous trifluoroacetic acid, hydrogen fluoride in pyridine, hydrochloric acid, etc. Oxidation of 6-4 to the aldehyde 6-5 is accomplished using the Swern oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Reductive amination with cyclic amine 6-6 then provides diamine 6-7, which can itself be a chemokine receptor antagonist. Cleavage of the PMB group with acid, for example with formic acid or trifluoroacetic acid plus anisole, provides acid 6-8. Alternatively, the ester can be cleaved by treatment with strong aqueous base or by catalytic hydrogenation if the remainder of the molecule is stable to those conditions.

SCHEME 7

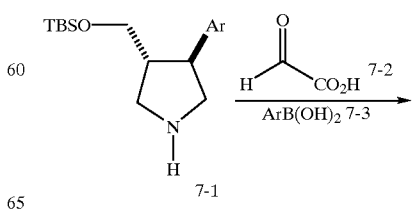

7-1

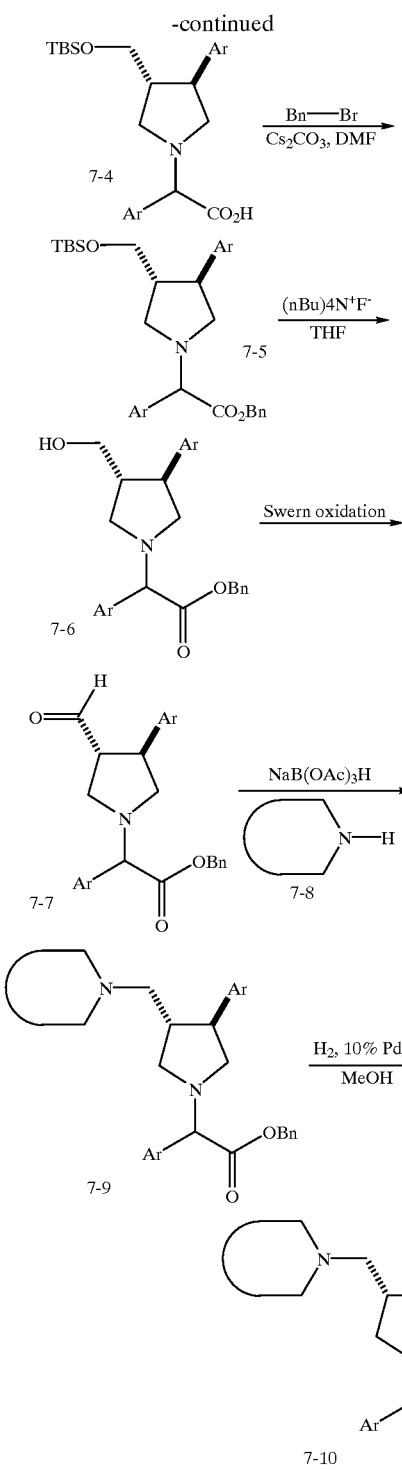

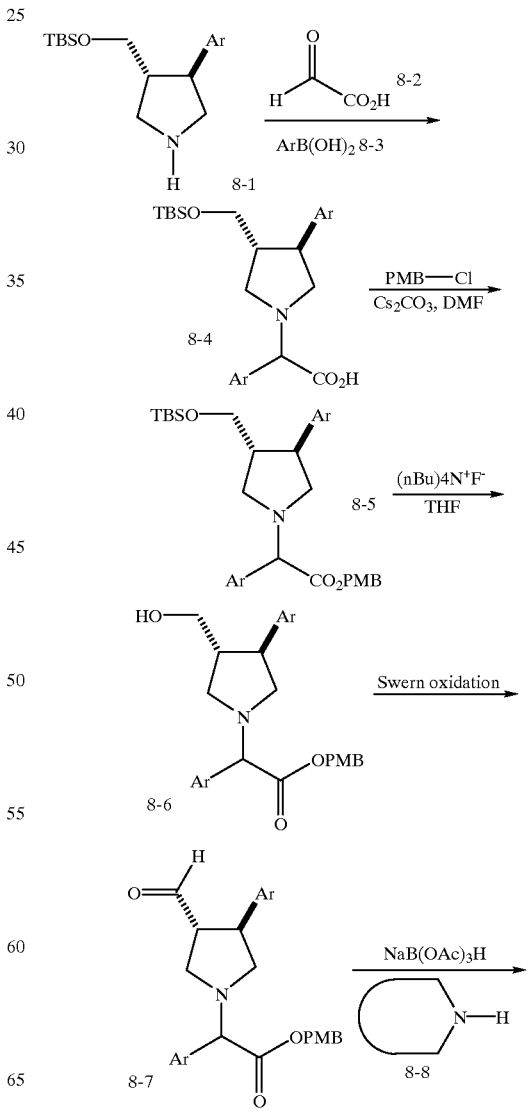

provides alcohol 7-6. Alternatively, simultaneous removal of the silyl group of 7-4 and formation of the ester can be carried out by heating 7-4 in an anhydrous solution of the esterifying alcohol in the presence of acid, such as toluenesulfonic acid, triflic acid, hydrochloric acid, and the like. The alcohol 7-6 is oxidized to aldehyde 7-7 using the Swern oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Reductive amination with cyclic amine 7-8 then provides diamine 7-9, which can itself be a chemokine receptor antagonist. Deprotection of the benzyl ester is carried out with catalytic hydrogenation, for example under an atmosphere of hydrogen in the presence of 10% palladium on carbon as catalyst in methanol or ethanol as solvent, provides acid 7-10. Alternatively, the benzyl ester can be cleaved by treatment with strong aqueous base if the remainder of the molecule is stable to those conditions.

SCHEME 8

An alternative route for the synthesis of pyrrolidines with a 1-(α-arylacetic acid) substituent is given in Scheme 7. Reaction of the protected pyrrolidine 7-1 with glyoxylic acid in the presence of an aryl boronic acid 7-3 provides the N-aralkylated product 74 (see Petasis, N. A.; Goodman, A.; Zavialov, I. A. *Tetrahedron* 1997,53, 16463–16470; and PCT Int. Appl. WO 9800398). Protection of the acid by alkylation with benzyl bromide in DMF in the presence of cesium carbonate provides ester 7-5. Deprotection of the silyl group with tetrabutylammonium fluoride in THF, or with mild acid such as aqueous trifluoroacetic acid, then

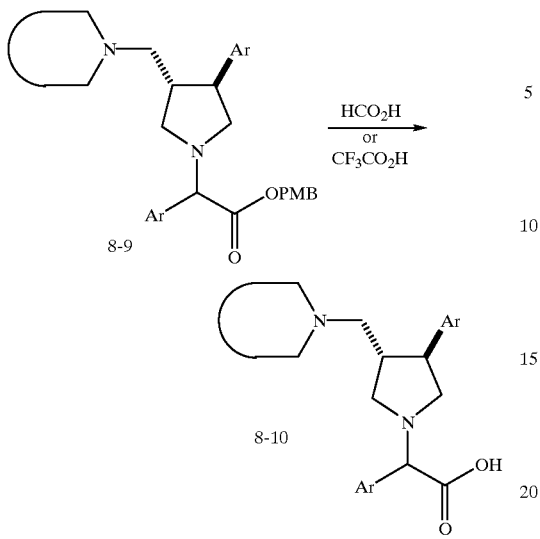

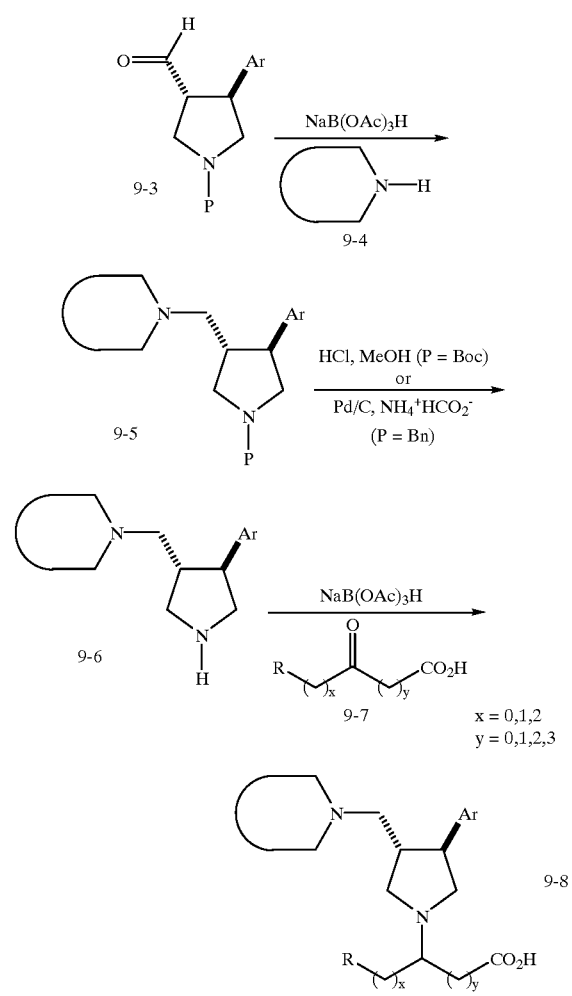

An alternative route for the synthesis of pyrrolidines with a 1-(α-arylacetic acid) substituent, wherein the carboxylic acid protecting group can be cleaved in mild acid, is given in Scheme 8. Reaction of the protected pyrrolidine 8-1 with glyoxylic acid in the presence of an arylboronic acid 8-3 provides the N-aralkylated product 8-4, according to the procedure of Petasis, N. A.; Goodman, A.; Zavialov, I. A. *Tetrahedron* 1997,53, 16463–16470 (see also PCT Int. Appl. WO 9800398). Protection of the acid by alkylation with para-methoxybenzyl chloride in DMF in the presence of cesium carbonate provides ester 8-5. Deprotection of the silyl group with tetrabutylammonium fluoride in THF, provides alcohol 8-6. The alcohol 8-6 is oxidized to aldehyde 8-7 using the Swern oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Reductive amination with cyclic amine 8-8 then provides diamine 8-9, which can itself be a chemokine receptor antagonist. Deprotection of the p-methoxybenzyl ester is carried out by treatment with formic acid, trifluoroacetic acid plus anisole, or other moderate acids, at temperatures from 0 degrees C to 120 degrees C, to provide the chemokine receptor antagonist 8-10.

SCHEME 9

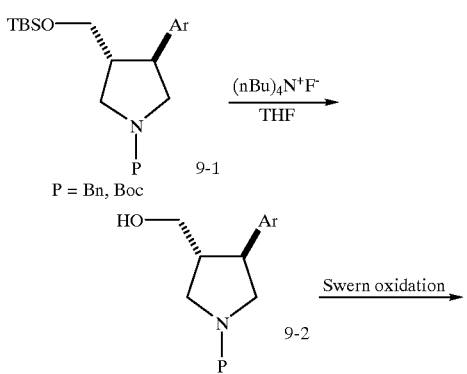

Another method of preparing compounds within the scope of the instant invention is given in Scheme 9. Doubly protected pyrrolidine 9-1 (obtained either as shown in Scheme 4 for 4-2 when P=benzyl or by protection of 4-3 with Boc anhydride in THF/water in the presence of triethylamine when P=Boc) is desilylated with tetrabutylammonium fluoride in THF to provide alcohol 9-2. Oxidation of 9-2 to 9-3 is carried out using Swern's oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Reductive amination with cyclic amine 9-4 then provides diamine 9-5, which can itself be a chemokine receptor antagonist. Deprotection of the pyrrolidine nitrogen, when P=Boc, can be carried out with HCl in methanol or with trifluoroacetic acid and anisole in dichloromethane, to give secondary amine 9-6. When P=benzyl, debenzylation is carried out in the presence of palladium on carbon as a catalyst, using either hydrogen gas or ammonium formate to effect transfer hydrogenation. Reductive amination with keto-acid 9-7 then provides pyrrolidine 9-8.

SCHEME 10

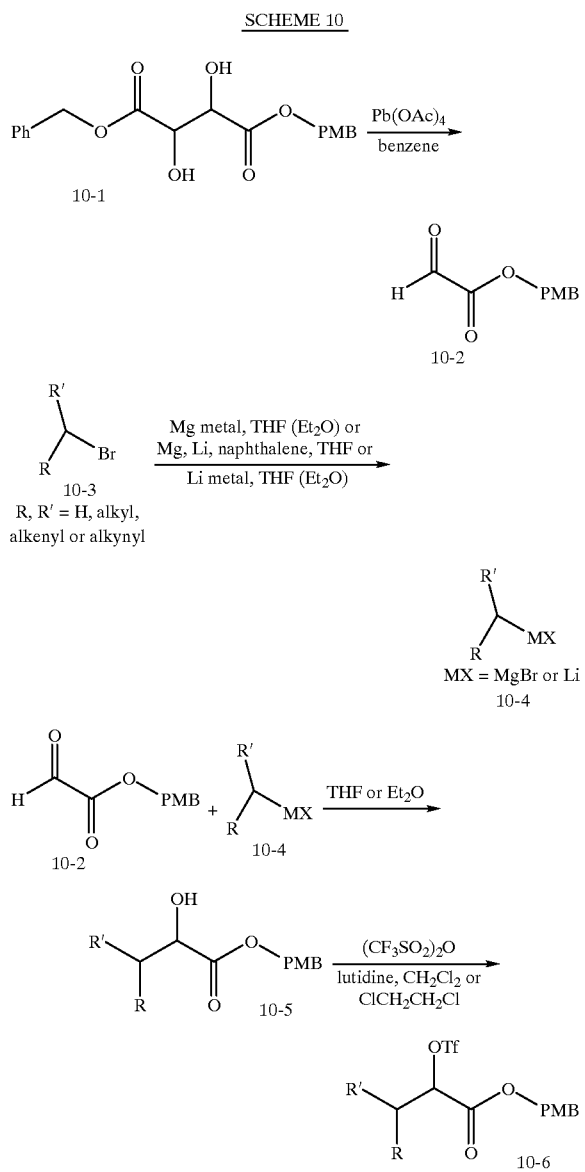

SCHEME 11

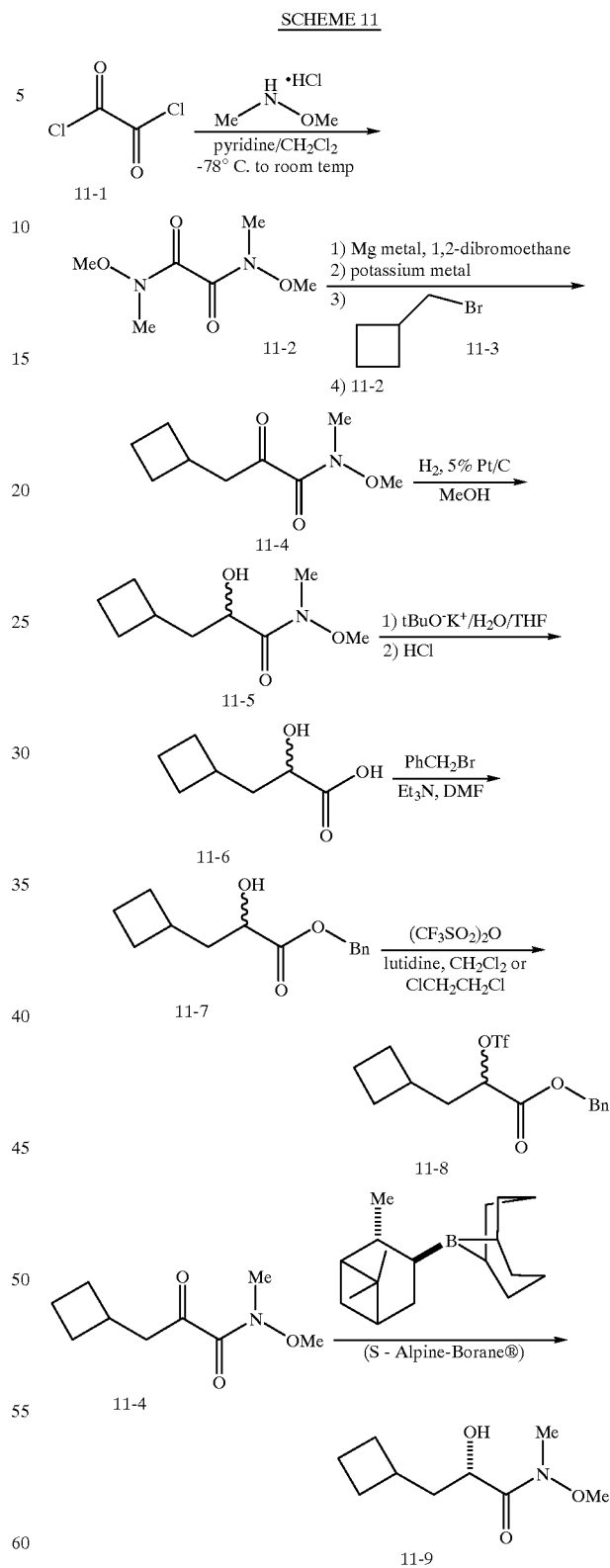

Scheme 10 illustrates preparation of intermediate 2-alkyl-2-trifluoromethanesulfonoxyacetic acid derivatives when the 1-alkyl-1-hydroxyacetic acid is not commerically available. Treatment of the para-methoxybenzyl ester of tartaric acid with lead tetraacetate in benzene provides the glyoxylic ester 10-2. Separately, a commercially available alkyl bromide (such as cyclobutylmethyl bromide) is treated with magnesium metal (in the absence or presence of lithium/naphthalene) or with lithium metal to provide the organometallic intermediate 10-4. Adding 10-4 to the aldehyde 10-2 provides the 2-hydroxy-ester 10-5. Formation of the trifluoromethanesulfonate ester is carried out under standard conditions (for example, with trifluoromethansulfonic anhydride in the presence of a hindered base such as 2,6-lutidine or DIEBA in a halogenated solvent at between −78 degrees C to room temperature, preferably near 0 degrees C, to give 10-6, which is then employed as described above.

Scheme 11 illustrates an alternate preparation of intermediate 2-alkyl-2-trifluoromethanesulfonoxyacetic acid derivatives; in this example, the side chain is exemplified by a cyclobutylmethyl subunit. Treatment of oxalyl chloride (11-1) with N-methyl-N-methoxyamine hydrochloride in the presence of pyridine yields the bis amide 11-2 (also called the bis-Weinreb amide). In a separate vessel, formation of magnesium dibromide in THF, followed by addition of potassium metal, forms a very reactive grade of magnesium metal. Addition of a suitable aliphatic bromide or iodide, for example cyclobutylmethyl bromide (11-3), provides the desired organomagnesium reagent in situ. Addition of bis-amide 11-2, followed by suitable workup, affords the keto-ester 11-4. This compound is reduced by hydrogenation in the presence of 5% platinum on carbon and triethylamine to the racemic alcohol 11-5. Hydrolysis with potassium t-butoxide in THF/water followed by acidification yields the hydroxy acid 11-6. Acid 11-6 is then protected, for example as the benzyl ester, by treatment with benzyl bromide and triethylamine in DMF, to provide 11-7. This ester is then activated with triflic anhydride (or other triflating agents) under the usual conditions. Alternatively, ketoester 11-4 can be reduced enantioselectively, for example with B-isopinocampheyl-9-borabicyclo[3.3.1]nonane (also known as S-Alpine-borane®) to provide S-hydroxy derivative 11-9, which can be carried through the rest of the sequence as for 11-5.

SCHEME 12

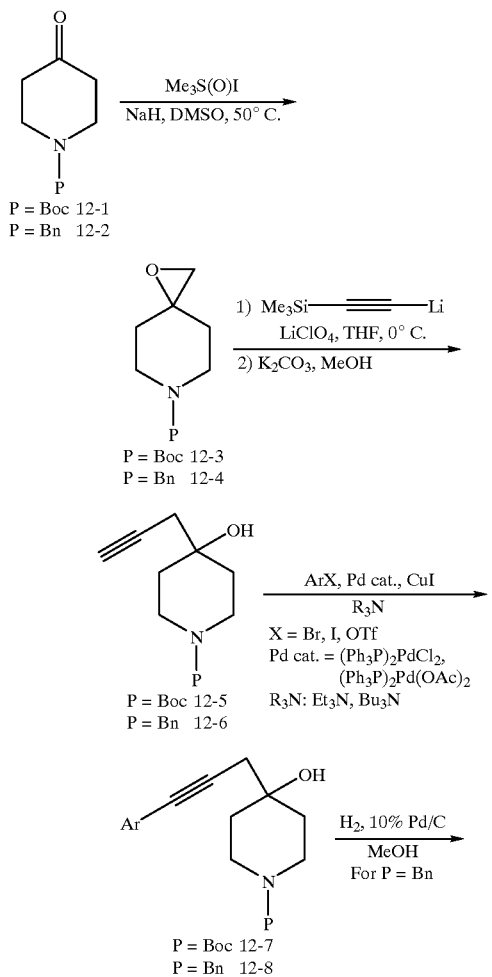

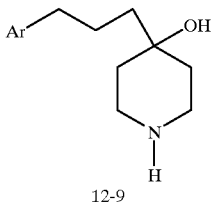

12-9

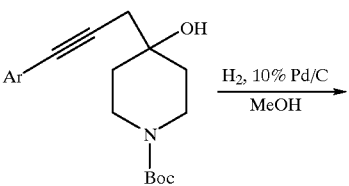

12-7

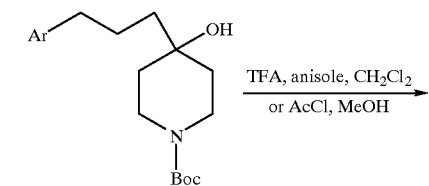

12-10

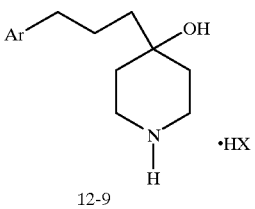

12-9

One route for the preparation of 4-hydroxy-4-(3-arylpropyl)-piperidines is given in Scheme 12. Treatment of commercially available 4-piperidones 12-1 or 12-2 with trimethylsulfoxonium iodide and sodium hydride in dimethyl sulfoxide at or above room temperature provides spiro epoxides 12-3 or 12-4. Addition of the lithium salt of (trimethylsilyl)acetylene to these epoxides in the presence of lithium perchlorate in THF at 0 degrees C, followed by treatment of the crude intermediate with potassium carbonate in methanol, affords the acetylenic alcohols 12-5 or 12-6. Heating of these alkynes with an aromatic halide or triflate in the presence of copper(I) iodide, a palladium catalyst such as bis(triphenylphosphine)palladium dichloride or bis (triphenylphosphine)palladium diacetate in the presence of a tertiary amine base such as triethylamine or tributylamine, then provides coupling products 12-7 or 12-8. In the case of the N-benzyl protected intermediate 12-8, hydrogenationl-hydrogenolysis under standard conditions (for example 10% Pd/C in an atmosphere of hydrogen) provides desired intermediate 12-9. For the Boc protected species 12-7, hydrogenation as above provides the saturated piperidine 12-10, and treatment of this compound under anhydrous acidic conditions (for example, trifluoroacetic acid and anisole in methylene chloride, or acetyl chloride in methanol) then yields the salt of intermediate 12-9. This compound is then utilized as the cyclic secondary amine component as shown above in Scheme 2 and in Schemes 5 through 9. Alternatively, if 4-piperidone is attached directly to the functionalized alkylpyrrolidine framework described above, then the chemistry described herein can be carried out treating the aforementioned alkylpyrrolidine segment as 'P' given in Scheme 12.

SCHEME 13

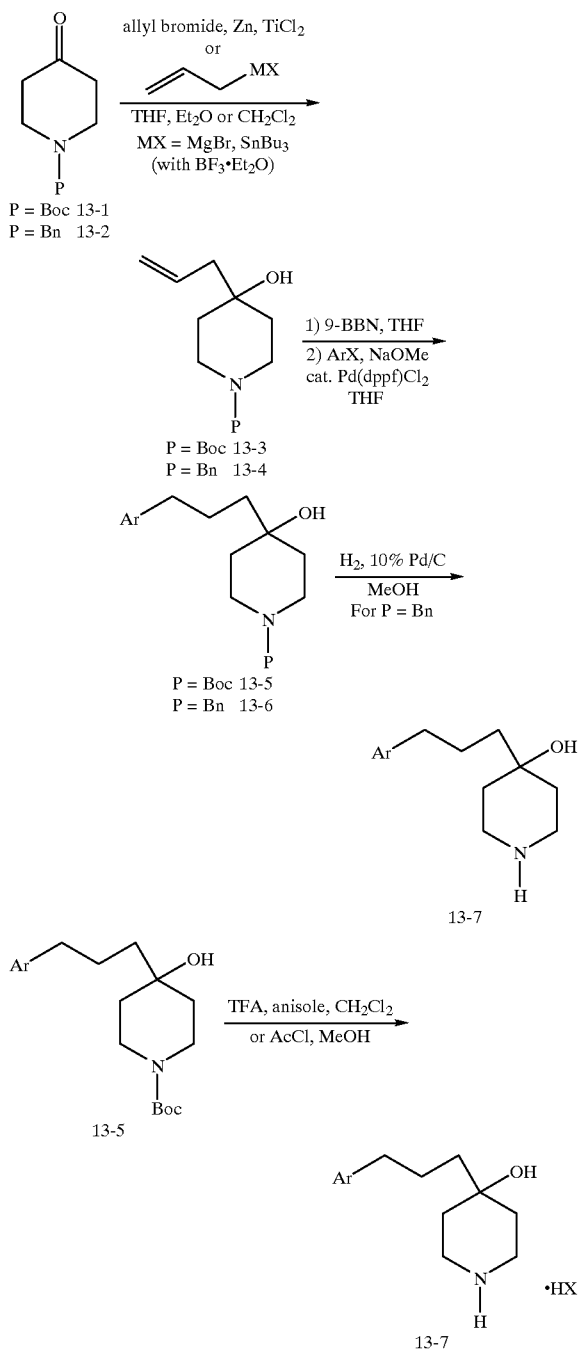

An alternative route for the preparation of 4-hydroxy-4-(3-arylpropyl)piperidines is given in Scheme 13 Treatment of commercially available 4-piperidones 13-1 or 13-2 with a suitable allyl metal compound (such as allylmagnesium bromide or allyltributylstannane (in the presence of boron trifluoride etherate) in THF, ether or dichloromethane, provides adducts 13-3 or 13-4. Hydroboration with a dialkylborane, such as 9-borabicyclo[3.3.1]nonane (9-BBN), followed by treatment with an aryl halide (the halides preferably being bromide or iodide) or aryl triflate and sodium methoxide in the presence of a suitable soluble palladium catalyst, for example Pd(dppf)Cl$_2$ (dppf= diphenylphosphioferrocene), in warm to refluxing TW, provides the 3-arylpropyl derivatives 13-5 and 13-6. For benzylamine 13-6, hydrogenolysis under standard conditions provides the desired intermediate 13-7. For Boc substituted piperidine 13-5, exposure to suitable anhydrous acidic conditions (for example trifluoroacetic acid and anisole in methylene chloride at temperatures from 0–25 degrees C) affords the salt of 13-7. This compound is then utilized as the cyclic secondary amine component as shown above in Scheme 2 and in Schemes 5 through 9. Alternatively, if no functionality are present in the alkyl pyrrolidine framework that would be adversely effected by the above mentioned chemistry, then 4-piperidone may be attached directly to the alkylpyrrolidine framework described above, and the chemistry described in this paragraph can be carried out equating the alkylpyrrolidine segment to the group 'P' given in Scheme 13, structures 1 through 6.

SCHEME 14

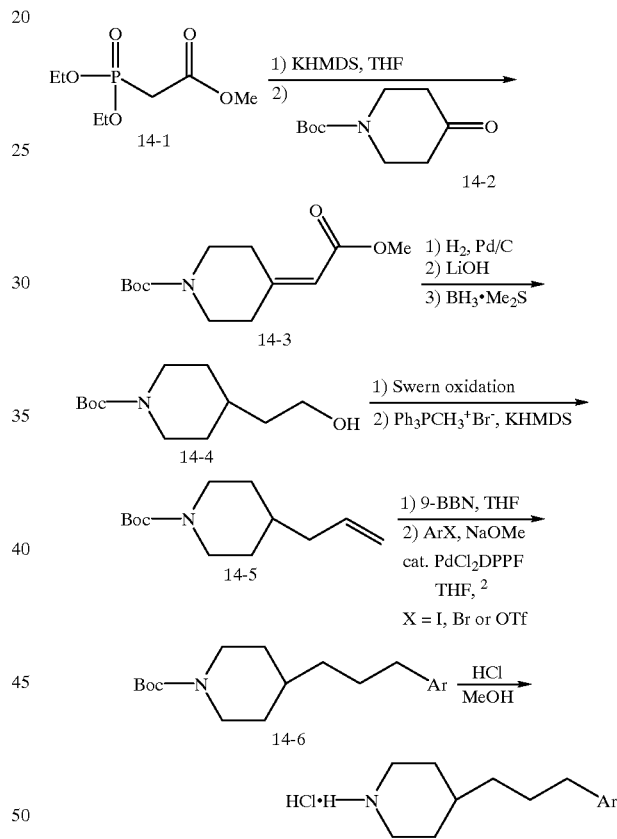

A route for the preparation of 4-(3-arylpropyl)piperidines is given in Scheme 14. Treatment of phosphonoacetate 14-1 with KHMDS followed by addition of commercially available N-Boc -4-piperidone 14-2 provides unsaturated ester 14-3. Hydrogenation of 14-3 followed by hydrolysis to the acid and then reduction with borane-methyl sulfide then affords primary alcohol 14-4. Mild oxidation of 14-4 under Swern conditions provides the corresponding aldehyde, which upon treatment with the Wittig reagent prepared from methyltriphenylphosphonium iodide and KHMDS yields olefin 14-5. Hydroboration with a dialkylborane, such as 9-borabicyclo[3.3.1]nonane (9-BBN), followed by treatment with an aryl halide (the halides preferably being bromide or iodide) or aryl triflate in the presence of a suitable soluble palladium catalyst, for example Pd(dppf)Cl$_2$, in warm to refluxing THF, provides the 3-arylpropyl derivative 14-6. Removal of the Boc group under acidic conditions, for example with HCl in methanol or with trifluoroacetic acid in methylene chloride, then affords the 1-unsubstituted piperidine 14-7, which can then be employed as the secondary amine component in the syntheses described above in Scheme 2 and in Schemes 5 through 9.

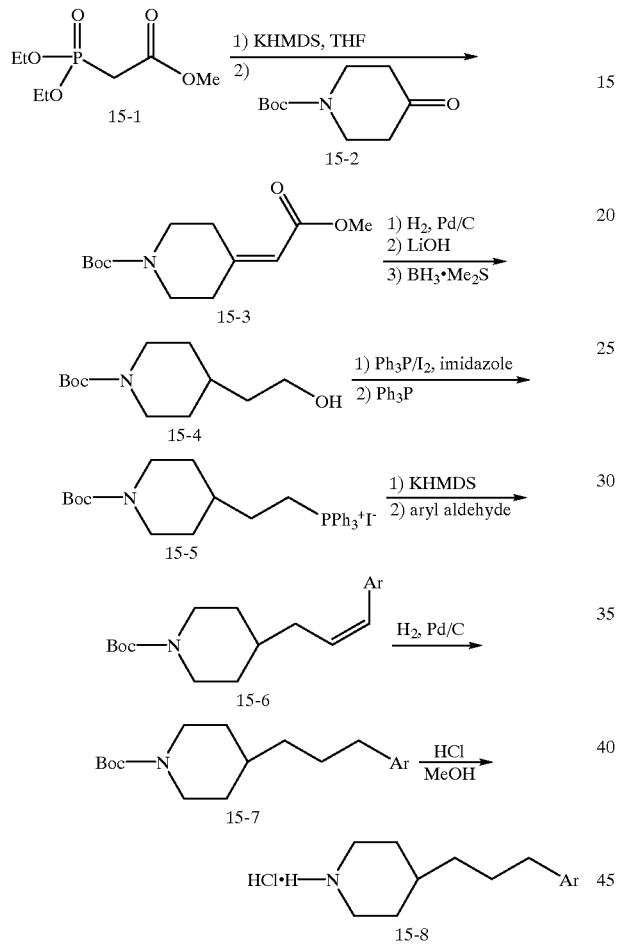

Another route for the preparation of 4-(3-arylpropyl) piperidines is given in Scheme 15. Treatment of phosphonoacetate 15-1 with KHMDS followed by addition of commercially available N-Boc-4-piperidone 15-2 provides unsaturated ester 15-3. Hydrogenation of 15-3 followed by hydrolysis to the acid and then reduction with boran•methyl sulfide then affords primary alcohol 15-4. Formation of the alkyl iodide with triphenylphosphine and iodine in the presence of imidazole followed by treatment with triphenylphosphine provides phosphonium salt 15-5. Deprotonation with a suitable base, for example, KHMDS, LiHMDS, NaHMDS, NaH, LDA, or KH affords the Wittig agent in situ, which upon treatment with a suitable aromatic aldehyde yields the unsaturated derivative 15-6. Hydrogenation under standard conditions provides 15-7, and removal of the Boc group with HCl in methanol or with other acidic conditions then provides the 1-unsubstituted piperidine 15-8, which can then be employed as the secondary amine component in the syntheses described above in Scheme 2 and in Schemes 5 through 9.

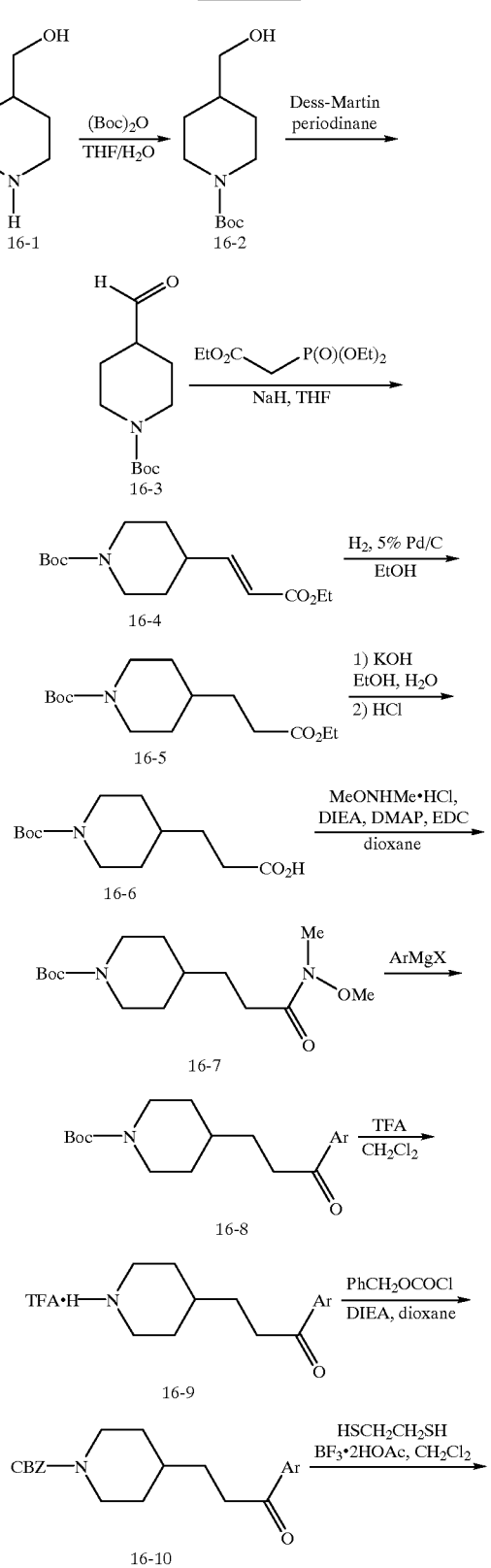

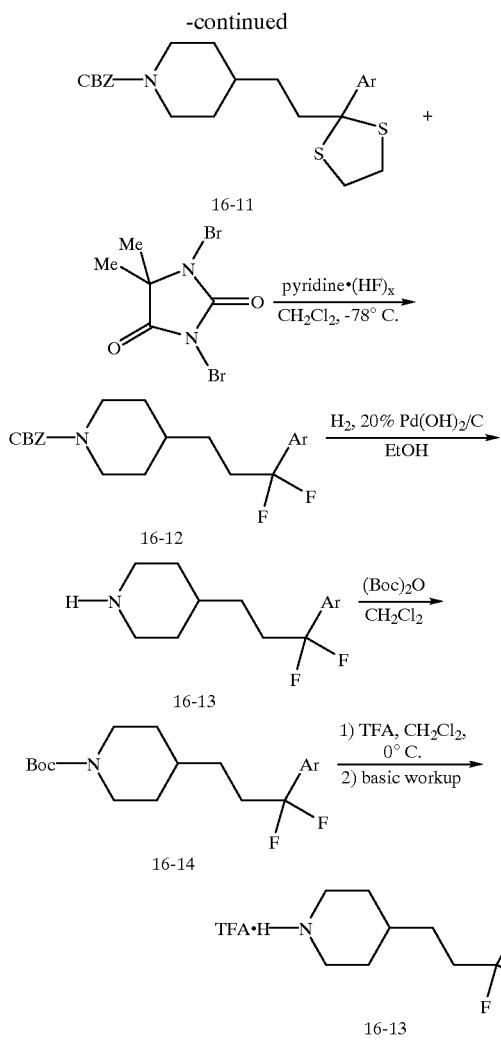

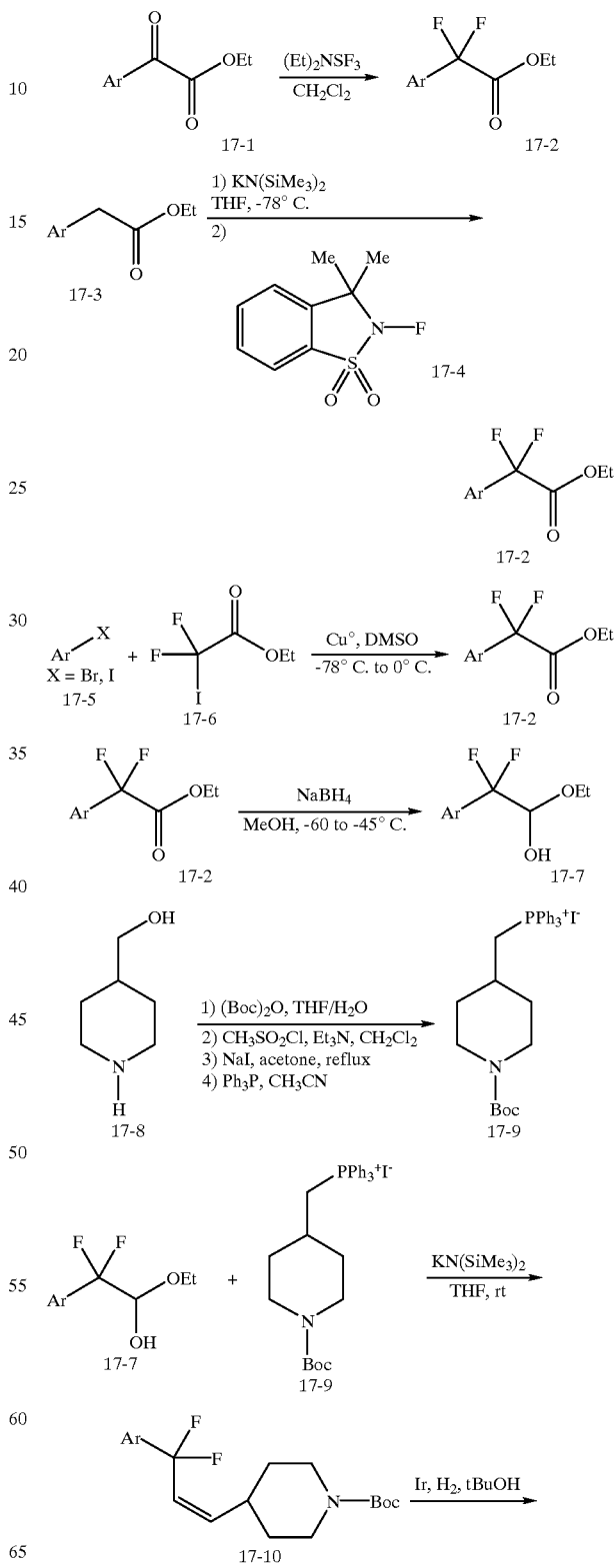

under acidic conditions at or near 0 degrees C. A controlled, basic workup then provides 16-13, suitable for use as described above.

SCHEME 17

Preparation of piperidines with a 4-(3-aryl-3,3,-difluoropropyl) side chain is given in Scheme 16. Treatment of commercially available 16-1 with Boc anydride provides protected piperidine 16-2. Oxidation, for example with the Dess-Martin reagent, by a Swern oxidation, or other known methods provides aldehyde 16-3. Condensation under Horner-Wadsworth-Emmons conditions affords unsaturated ester 164, which is hydrogenated to ester 16-5 and then hydrolyzed to acid 16-6. Formation of the N-methyl-N-methoxy amide 16-7 is carried out employing standard activating agents such as EDC. Weinreb amide 16-7 is then allowed to react with an arylmetal reagent, such as an aryl magnesium halide or an aryllithium, to provide ketone 16-8. Cleavage of the protecting Boc group under acidic conditions yields 16-9, which is reprotected with a carbobenzyloxy group under standard conditions, to afford 16-10. Formation of dithiolane 16-11 with ethanedithiol and boron trifluoride is followed by treatment with 1,3-dibromo-3,3-dimethylhydantoin and pyridine-hydrogen fluoride complex at or around -78 degrees C, to provide gem-difluoro derivative 16-12. Removal of the CBZ group under reductive conditions provides piperidine 16-13, which may be employed directly as the secondary amine in chemistry described above. Alternatively, if additional purification is desired, 16-13 may be protected with a Boc group to afford 16-14. After suitable purification, the Boc group is removed

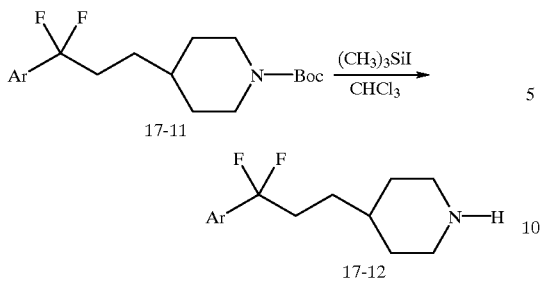

An alternate preparation of piperidines with a 4-(3-aryl-3,3,-difluoropropyl) side chain is given in Scheme 17. Preparation of the intermediate 17-2 can be accomplished in three ways. First, ketoester 17-1 can be fluorinated with diethylaminosulfur trifluoride (DAST) under standard conditions to provide α,α-difluoroester 17-2. Second, arylacetic ester 17-3 can be fluorinated by treatment with a strong base, such as potassium hexamethyldisilazide, followed by addition of a suitable fluorinating agent, such as the N-fluoro reagent 17-4, to give 17-2. Alternatively, an aryl iodide or aryl bromide 17-5 can be treated with ethyl α,α-difluoro-α-iodoacetate (17-6) in the presence of copper metal to provide 17-2. Treatment of ester 17-2 with sodium borohydride at low temperature then provides key intermediate 17-7. Preparation of intermediate 17-9 is carried out by first protecting commercially available 4-(hydroxymethyl)piperidine as the N-Boc derivative, then forming the methanesulfonyl ester under standard conditions, displacing the mesylate group with an iodide, and finally treating the iodide with triphenylphosphine. Coupling of 17-7 with phosphonium salt 17-9 in the presence of a strong base, such as potassium hexamethyldisilazide, sodium hydride, lithium diisopropylamide, or similar reagents, affords olefin 17-10. Reduction of the double bond of 17-10 is effected by treatment with iridium metal in t-butanol or hexane under an atmosphere of hydrogen, to give 17-11. Alternatively, reduction using palladium on carbon, platinum or Raney nickel in the presence of hydrogen can be used, as can diimide, which can be generated from azodicarboxylic acid in situ. The nitrogen protecting group is removed by treatment with trimethylsilyl iodide under anhydrous conditions, to afford piperidine 17-12, which is suitable for use as described above. Alternatively, the Boc group can be removed under acidic, anhydrous conditions, for example with TFA in methylene chloride or with HCl in methanol.

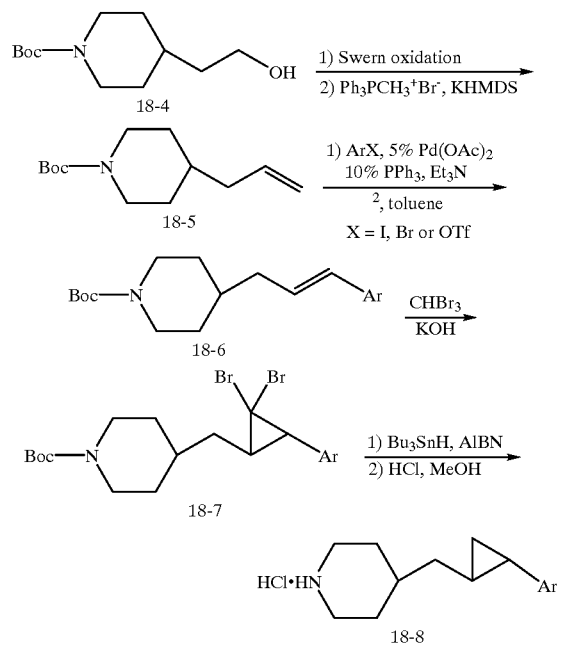

A route for the preparation of 4-(2-arylcycloprop-1-yl)methyl)piperidines is given in Scheme 18. Treatment of phosphonoacetate 18-1 with KHMDS followed by addition of commercially available N-Boc-4piperidone 18-2 provides unsaturated ester 18-3. Hydrogenation of 18-3 followed by hydrolysis to the acid and then reduction with boranemethyl sulfide then affords primary alcohol 18-4. Mild oxidation of 18-4 under Swern conditions provides the corresponding aldehyde, which upon treatment with the Wittig reagent prepared from methyltriphenylphosphonium iodide and KHMDS yields olefin 18-5. Palladium-catalysed arylation of 18-5 then affords unsaturated derivative 18-6. Addition of dibromocarbene (generated in situ from bromoform and potassium hydroxide) provides cyclopropyl derivative 18-7. Debromination is carried out by slow addition of tributyltin hydride in the presence of the radical initiator AIBN. Removal of the nitrogen protecting group under acidic conditions, for example, hydrochloric acid in methanol, affords cyclopropyl piperidine 18-8, which can then be employed as the secondary amine component in the syntheses described above in Scheme 2 and in Schemes 5 through 9.

SCHEME 18

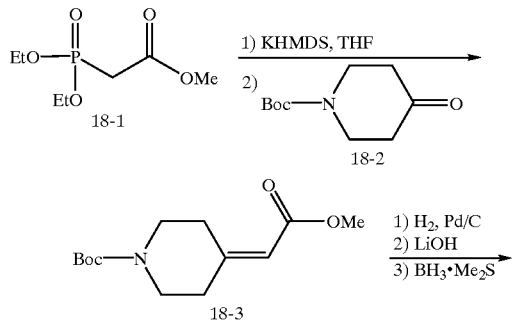

SCHEME 19

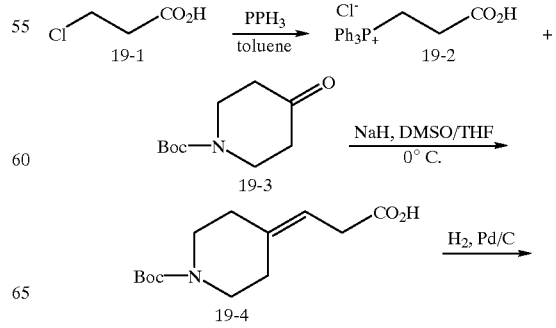

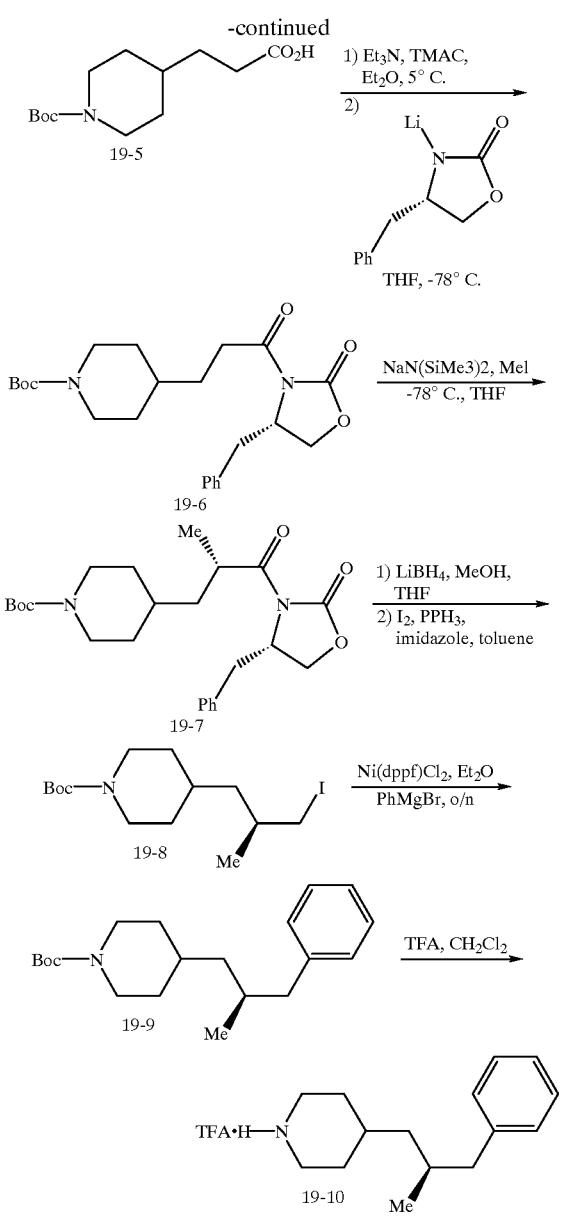

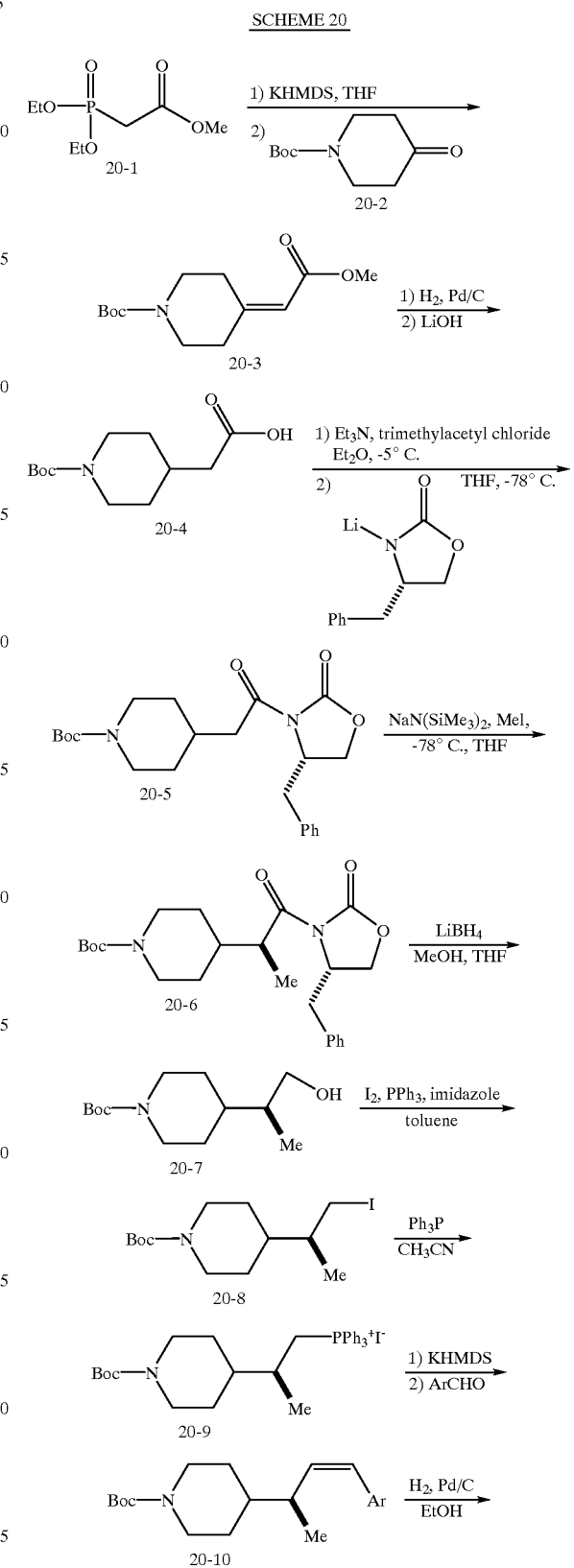

19-10. Piperidine 19-10 can then be employed as the secondary amine component in the syntheses described above in Scheme 2 and in Schemes 5 through 9.

A route for the preparation of 4-(3-aryl-2-methylpropyl) piperidines is given in Scheme 19. Treatment of commercially available 3-chloropropionic acid (19-1) with triphenylphosphine in refluxing toluene provides phosphonium salt 19-2. Treatment with sodium hydride in DMSO/THF provides the ylide in situ, which upon addition of piperidone 19-3 affords the adduct 19-4. Reduction of the double bond, for example with hydrogen gas in the presence of a palladium catalyst, gives acid 19-5. Treatment of 19-5 with trimethylacetyl chloride (SMAC) and triethylamine generates the mixed anhydride in situ, which upon treatment with the lithium salt of 4-(S)-benzyl-2-oxazolidone yields 19-6. Deprotonation of 19-6 with sodium hexamethyldisilazide, followed by addition of methyl iodide, provides alpha-methyl derivative 19-7. Reduction of acyl-oxazolidone 19-7 with lithium borohydride produces the corresponding primary alcohol, which is converted to primary iodide 19-8 with iodine, triphenylphosphine and imidazole in toluene. Coupling with phenyl magnesium bromide in the presence of Ni(dppf)Cl$_2$ affords aralkyl derivative 19-9, which is then deprotected under acidic conditions to provide piperidine

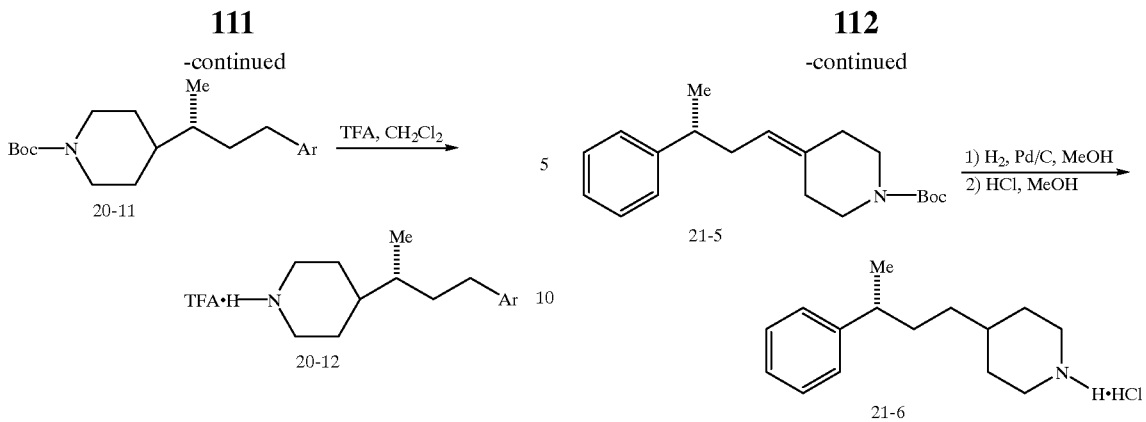

A route for the preparation of 4-(3-aryl-1-methylpropyl) piperidines is given in Scheme 20. Addition of the anion of phosphonoester 20-1 to piperidone 20-2 provides unsaturated ester 20-3. Reduction of the double bond and hydrolysis of the ester affords acid 20-4. Treatment of 20-4 with triethylamine and trimethylacetyl chloride provides the mixed anhydride in situ, which is then coupled with the lithium salt of 4-(S)-benzyl-2-oxazolidone, to yield acyl oxazolidone 20-5. Deprotonation with sodium hexamethyldisilazide followed by addition of methyl iodide provides 20-6. Reduction of 20-6 with lithium borohydride affords alcohol 21-7, which upon treatment with iodine, triphenylphosphine and imidazole in toluene is converted to iodide 20-8. Treatment with triphenylphosphine gives phosphonium salt 20-9, which is converted to the ylide with potassium hexamethyldisilazide. Addition of an aryl aldehyde generates unsaturated aryl derivative 20-10. Hydrogenation provides saturated piperidine 20-11, which is then deprotected under acidic conditions to afford 20-12, which can then be employed as the secondary amine component in the syntheses described above in Scheme 2 and in Schemes 5 through 9.

A route for the preparation of 4-(3-aryl-3-methylpropyl) piperidines is given in Scheme 21. Treatment of commercially available 4-(R)-phenylbutyric acid (21-1) with ethyl chloroformate and triethylamine forms the asymmetric anhydride in situ, which upon treatment with sodium borohydride provides primary alcohol 21-1. Alternatively, this conversion can be carried out by treatment of 21-1 with borane-THF. Activation of the hydroxy group of 21-2 with methanesulfonyl chloride in the presence of a hindered base such as N,N-(diisopropyl)ethylamine, followed by displacement with sodium iodide in refluxing acetone affords iodide 21-3. Heating with triphenylphosphine in toluene provides the phosphonium salt 21-4. Deprotonation of this salt with a strong base, for example n-butyllithium generates the Wittig reagent in situ, which is then allowed to react with N-Boc-4-piperidone, to yield olefin 21-5. Hydrogenation of the double bond followed by treatment with acid, for example HCl in methanol, then provides the secondary amine salt 21-6, which can then be employed as the secondary amine component in the syntheses described above in Scheme 2 and in Schemes 5 through 9.

SCHEME 21

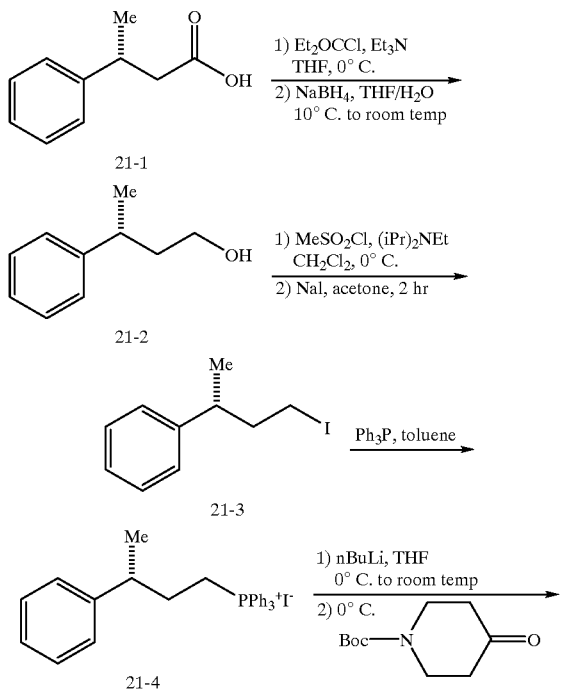

SCHEME 22

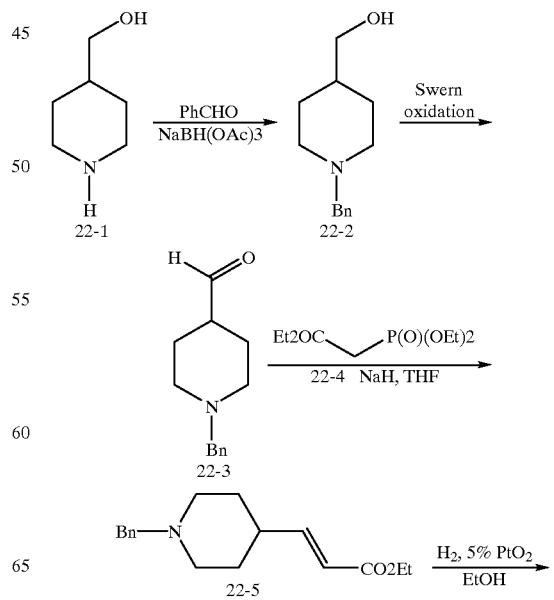

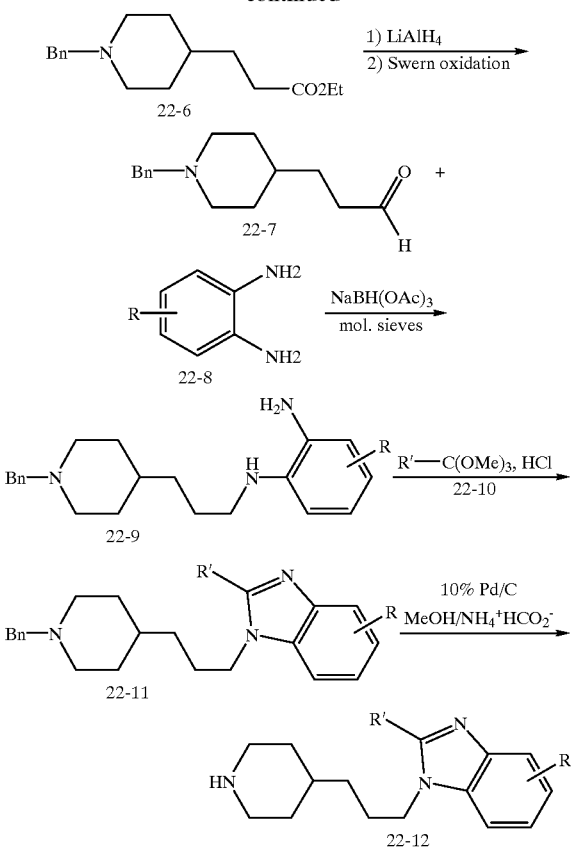

A route for the preparation of 4-(3-(benzimidazol-2-yl) propyl)piperidines is given in Scheme 22. Protection of piperidine 22-1 under reductive amination conditions provides benzylamine 22-2. Oxidation to aldehyde 22-3 is carried out under standard conditions, for example with by Swern oxidation. Addition of ester 22-4 provides unsaturated olefin 22-5, which upon reduction affords ester 22-6. Reduction with lithium aluminum hydride or other strong hydride reducing agents followed by mild oxidation provides aldehyde 22-7. Upon combination with diamine 22-8 under reductive conditions affords the N-alkylated derivative 22-9. Treatment with orthoformate derivative 22-10 in the presence of acid yields benzimidazole 22-11, which upon hydrogenation with palladium on carbon under transfer hydrogenation conditions generates piperidine 22-12, which can then be employed as the secondary amine component in the syntheses described above in Scheme 2 and in Schemes 5 through 9.

GENERAL

Concentration of solutions was carried out on a rotary evaporator under reduced pressure. Flash chromatography was carried out on silica gel (230-400 mesh). NMR spectra were obtained in CDCl$_3$ solution unless otherwise noted. Coupling constants (J) are in hertz (Hz).

Abbreviations: diethyl ether (ether), triethylamine (TEA), NN-diisopropylethylamine (DIEA) saturated aqueous (sat'd), room temperature (rt), hour(s) (h), minute(s) (min).

HPLC CONDITIONS

HPLC A. Retention time using the following conditions: Column: YMC ODS A, 5µ, 4.6×50 mm; Gradient Eluant: 10:90 to 90:10 v/v CH$_3$CH$_3$CN/H$_2$O+0.5% TFA over 4.5 min, hold 30 sec; Detection: PDA, 210–400 nm; Flow Rate: 2.5 mL/min.

HPLC B. Retention time using the following conditions: Column: Analytical Sales & Services Advantage HL C18 5µ 4.6×100 mm column; Gradient Eluant: 10:90 to 90:10 v/v CH$_3$CN/H$_2$O+0.5% TFA over 10 min, hold 2 min; Detection: PDA, 200–400 nm; Flow Rate: 2.25 ml/min.

EXAMPLE 1

2-(R)-(3-(S)-((4-Hydroxy-4-(3-phenylpropyl)piperidin-1-yl)methyl)$_4$-(S)-phenylpyrrolidin-1-yl)-2-(cyclohexyl) acetic acid Step A: 3-((E)-Cinnamoyl)+(S)-benzyloxazolidin-2-one A solution of 222 g (1.5 mol) of trans-cinnamic acid and 250 mL (1.77 mol) of TEA in 3 L of THF at −78° C. was treated with 200 mL of trimethylacetyl chloride maintaining the internal temperature at less than −65° C. The resulting mixture was warmed to 0° C., then cooled to −78° C.

In a separate flask, a solution of 4-(S)-benzyl-oxazolidin-2-one in 2.05 L of THF at −20° C. was treated with 660 mL of 2.5 M n-butyllithium in hexanes over 45 min. The resulting turbid mixture was cooled to −78° C. and then transferred via cannula to the flask containing the mixed anhydride. The resulting mixture was allowed to warm to rt and was stirred for 20 h. The reaction was quenched with 300 mL of sat'd NH$_4$Cl; the resulting mixture was partitioned between EtOAc and H$_2$O and the layers were separated. The organic layer was dried over MgSO$_4$. The aqueous layer was extracted with 2×EtOAc; the extracts were dried and all of the organic extracts were combined. Partial concentration in vacuo caused precipitation of a solid; the mixture was diluted with hexanes and allowed to stand at it for 1.5 h. The precipitate was filtered and dried to afford 402.2 g (87%) of the title compound: $^1$H NMR (500 MHz) δ 2.86 (dd, J=13.5, 9.5, 1H), (3.38, J=13.5, 3.5, 1H), 4.20–4.27 (m, 21), 4.78–4.83 (m, 1H), 7.24–7.42 (5H), 7.63–7.65 (m, 1H), 7.92 (app d, J=2.5, 1H).

Step B: 3-(1-Benzyl-4-(S)-phenylpyrrolidine-3-(R)-yl)-carbonyl)-4-(S)-benzyloxazolidin-2-one and 3-(1-benzyl-4-(R)-phenyl-pyrrolidine-3-(S)-carbonyl)-4-(S)-benzyloxazolidin-2-one A solution of 402 g (1.3 mol) of 3-((E)-cinnamoyl)-4-(S)-benzyloxazolidin-2-one (from EXAMPLE 1, Step A) and 474 g (2.0 mol) of N-methoxymethyl-N-trimethylsilylmethyl benzyl amine in 4 L of CH$_2$Cl$_2$ at −10° C. was treated with 6 mL of TFA. The resulting mixture was stirred cold for 4 h and then was treated with an additional 4 mL of TFA. The reaction mixture was warmed to rt and stirred for 20 h. The reaction was quenched with 2 L of sat'd NaHCO$_3$ and the layers were separated. The organic layer was washed with 1 L of sat'd NaCl and concentrated. Chromatography on 10 kg of silica gel using 4:1 v/v hexanes/EtOAc (24 L), then 7:3 v/v hexanes/EtOAc (36 L), then 3:2 v/v hexanes/EtOAc (32 L) afforded 260.9 g (45%) of 3-(1-benzyl-4-(S)-phenylpyrrolidine-3-(R)-carbonyl)-4-(S)-benzyloxazolidin-2-one and 247.5 g (43%) of 3-(1-benzyl-4-(R)-phenylpyrrolidine-3-(S)-carbonyl)-4-(S)-benzyloxazolidin-2-one. For 3-(1-benzyl-4-(S)-phenylpyrrolidine-3-(R)-carbonyl)-4-(S)-benzyloxazolidin-2-one: $^1$H NMR (500 MHz) δ 2.66 (t, J=8.0, 11H), 2.78 (dd, J=13.0, 9.0, 11H), 2.87 (dd, J=9.0, 4.5, 1H), 3.21–3.27 (m, 2H), 3.64 (d, J=11.5, 1H), 3.77 (d, J=11.5, 1H), 4.104.15 (m, 2H), 4.61–4.65 (m, 1H), 7.16–7.38 (15H). For 3-(1-benzyl-4-(R)-phenylpyrrolidine-3-(S)-carbonyl)-4-(S) benzyloxazolidin-2-one: $^1$H NMR (500 MHz) δ 2.69–2.76 (m, 2H), 2.82 (dd, J=9.5, 5.5, 1H), 3.14–3.22 (3H), 3.64 (d, J=13.0, 1H), 3.74 (d, J=13.0, 1H), 4.074.12 (m, 2H), 4.16 (t, J=9.0, 1H), 4.26–4.30 (m, 1H), 4.654.69 (m, 1H), 7.03–7.40 (15H).

Step C: 1-Benzyl-3-(R)-hydroxymethyl-4-(S)-phenylpyrrolidine

A solution of 3-(1-benzyl-4-(S)-phenylpyrrolidine-3-(R)-carbonyl)-4-(S)-benzyloxazolidin-2-one (from EXAMPLE 1, Step B) in 2.5 L of THF at 10° C. was treated with 1.18 L of 1.0 M lithium aluminum hydride solution in THF over a period of 2 h. The resulting mixture was warmed to rt and stirred for 20 h. The reaction was quenched by adding 40 mL of $H_2O$, then 40 mL of 2.0 N NaOH, then 115 mL of $H_2O$ and then was stirred at rt for 1.5 h. The mixture was filtered and the filtrate was concentrated. Chromatography on 4 kg of silica using 4:1 hexanes/acetone (14 L), then 7:3 hexanes/acetone as the eluant afforded 108.4 g (69%) of the title compound: $^1$H NMR (400 MHz) 2.38–2.46 (m, 2H), 2.78–2.88 (3H), 3.20–3.26 (2H), 3.65 (dd, J=12.0,4.0, 1H), 3.66 (app s, 2H), 3.74 (dd, J=12.0, 4.0, 1H), 7.18–7.34 (10H); ESI-MS 268 (M+H); HPLC A: 2.35 min.

Step D: 1-Benzyl-3-(R)-(t-butyldimethylsilyloxymethyl)-4-(S)-phenyl pyrrolidine

A solution of 82.0 g (0.31 mol) of 1-benzyl-3-(R)-hydroxymethyl-4-(S)-phenyl pyrrolidine (from EXAMPLE 1, Step C) and 46.5 g (0.36 mol) of DIEA in 1 L of $CH_2Cl_2$ was treated with 54.2 g (0.36 mol) of t-butyldimethylsilyl chloride and the resulting mixture was stirred at rt for 20 h. The reaction was quenched with 750 mL of sat'd $NaHCO_3$ and the layers were separated. The organic layer was combined with 150 g of silica gel and aged for 45 min. The mixture was filtered and the filtrate was concentrated to afford 117 g (100%) of the title compound.

Step E: 3-(R)-(t-Butyldimethylsilyloxymethyl)-4-(S)-phenyl pyrrolidine

A mixture of 117 g (0.31 mol) of 1-benzyl-3-(R)-(t-butyldimethylsilyloxymethyl)-4-(S)-phenyl pyrrolidine (from EXAMPLE 1, Step D), 31.5 g (0.50 mol) ammonium formate and 20.0 g of 20% palladium hydroxide on carbon in 1.5 L of MeOH was heated at 55° C. for 2.5 h. The mixture was cooled and filtered through a pad of Celite. The filtrate was concentrated. The residue was dissolved in 1 L of $CH_2Cl_2$, washed with 300 mL of 10% $NH_4OH$ solution, 200 mL of sat'd NaCl, dried over $MgSO_4$ and concentrated to afford 89.2 g (99%) of the title compound: $^1$H NMR (400 MHz) δ –0.09 (s, 3H), –0.08 (s, 3H), 0.77 (s, 9H), 2.25–2.30 (m, 1H), 2.84–2.96 (4H), 3.18 (dd, J=11.2,3.2, 1H), 3.29–3.36 (m, 1H), 3.44 (dd, J=10.0, 6.0), 3.56 (dd, J=10.0, 4.4, 1H); ESI-MS 292 (M+H); HPLC A: 3.44 min.

Step F: Benzyl (S)-Hexahydromandelate

A solution of 500 mg (3.2 mmol) of (S)-hexahydromandelic acid and 238 mg (0.6 mmol) of tetrabutylammonium iodide in 6.5 mL of $CHCl_3$ was treated with 6.5 mL of 0.5 N KOH and 0.38 mL (3.2 mmol) of benzyl bromide then stirred at 70° C. for 1.5 h. The reaction was cooled to rt and the layers were separated. The aqueous phase was extracted with 2×50 mL $CH_2Cl_2$. The organic phases were combined, dried over $Na_2SO_4$ and concentrated. Flash chromatography using 17:3 v/v hexanes/EtOAc as the eluant afforded 616 mg (77%) of the title compound: $R_F$: 0.37 (4:1 v/v hexanes/EtOAc); $^1$H NMR (300 MHz) δ 1.11–1.38 (m, 11H), 2.65 (d, J=6.3 Hz, 1H), 4.06 (dd, J=6.3, 3.5 Hz, 1H), 5.22 (s, 2H), 7.30–7.39 (m, 5H).

Step G: 2-(R)-(3-(R)-(t-Butyldimethylsilyloxymethyl)-4-(S)-phenylpyrrolidin-1-yl)-2-(cyclohexyl)acetic acid, benzyl ester A solution of 330 mg (1.3 mmol) of benzyl (S)-hexahydromandelate (from EXAMPLE 1, Step F) in 6.5 mL of $CH_2Cl_2$ at –78° C. was treated with 0.26 mL (1.5 mmol) of trifluoromethanesulfonic anhydride. The resulting mixture was stirred cold for 5 min and then treated with 0.30 mL (2.6 mmol) of 2,6-lutidine maintaining the internal temperature below –70° C. The resulting mixture was stirred cold for 15 min and then was treated with 0.46 mL (2.6 mmol) of DIEA. The resulting mixture was stirred cold for 15 min and then was treated with a solution of 300 mg (1.0 mmol) of 3-(R)-(t-butyldimethylsilyloxymethyl)-4-(S)-phenylpyrrolidine (from EXAMPLE 1, Step E) in 1.0 mL $CH_2Cl_2$. The reaction was warmed to 0° C. and stirred for 5 h. The reaction was partitioned between 50 mL of ether and 25 ml of $H_2O$ and the layers were separated. The aqueous layer was extracted with 25 mL of ether. The combined organic phases were dried over $MgSO_4$ and concentrated. Flash chromatography using 9:1 v/v hexanes/EtOAc as the eluant afforded 221 mg (31%) of the title compound: $R_F$: 0.72 (4:1 v/v hexanes/EtOAc); $^1$H NMR (500 MHz) δ 0.002 (s, 3H), 0.005 (s, 3H), 0.87 (s, 9H), 0.98–1.80 (9H), 2.01–2.07 (m, 2H), 2.33–2.37 (m, 1H), 2.70–2.74 (m, 2H), 2.90 (q, J=8.0, 1H), 3.12 (t, J=8.0, 1H), 3.20–3.24 (m, 2H), 3.49 (dd, J=7.5, 8.5, 1H), 3.58 (dd, J=5.0, 10.0), 5.18 (s, 2H), 7.18–7.41 (10H).

Step H: 2-(R(3-(R)-(Hydroxymethyl)-4-(S)-phenylpyrrolidin-1-yl)-2-(cyclohexyl)acetic acid, benzyl ester A solution of 217 mg (0.4 mmol) of 2-(R)-(3-(R)-(t-butyldimethylsilyloxymethyl)-4-(S)-phenylpyrrolidin-1-yl)-2-(cyclohexyl)acetic acid, benzyl ester (from Example 1, Step G) in 4 mL of THF was treated with 0.63 mL of 1.0 M tetrabutylammonium fluoride solution in THF and stirred at rt for 2 h. The reaction was concentrated. Flash chromatography on silica gel using 3:2 v/v hexanes/EtOAc as the eluant afforded 177 mg (100%) of the title compound: $R_F$: 0.09 (4:1 v/v hexanes/EtOAc); $^1$H NMR (500 MHz) δ 0.94–1.03 (m, 2H), 1.06–1.28 (4H), 1.61–1.83 (3H), 1.96 (app d, J=13.0, 2H), 2.32–2.36 (m, 1H), 2.64 (t, J=8.5, 1H), 2.79 (dd, J=5.0, 9.0, 1H), 3.07 (q, J=7.5, 11H), 3.16–3.21 (m, 2H), 3.30 (t, J=8.5, 1H), 3.51 (app q, J=7.0, 1H), 3.63 (dABq, J=6.0, 10.0, 2H), 5.18 (ABq, J=12.0, 2H), 7.18–7.41 (10H)

Step I: 2-(R)(3-(R)-Formyl (S)-phenylpyrrolidin-1-yl)-2-(cyclohexyl)acetic acid, benzyl ester A solution of 0.095 mL (1.1 mmol) of oxalyl chloride in 1.5 mL of $CH_2Cl_2$ at –78° C. was treated with 0.155 mL (2.2 mmol) of DMSO in 0.1 mL of $CH_2Cl_2$ and the resulting mixture was stirred cold for 5 min. A solution of 177 mg (0.42 mmol) of 2-(R)-(3-(R)-(hydroxymethyl)-4-(S)-phenylpyrrolidin-1-yl)-2-(cyclohexyl)acetic acid, benzyl ester (from Example 1, Step H) in 1.5 mL of $CH_2Cl_2$ was added and the resulting mixture was stirred cold for 15 min. The resulting mixture was treated with 0.75 mL (4.2 mmol) of DIEA. The reaction was warmed to 0° C., stirred for 20 min and quenched with $H_2O$. The mixture was partitioned between 50 mL of $CH_2Cl_2$ and 50 mL of $H_2O$ and the layers were separated. The aqueous layer was extracted with 50 mL of $CH_2Cl_2$. The combined organic phases were dried over $Na_2SO_4$ and concentrated to give the title compound which was used without further purification: $R_F$: 0.50 (4:1 v/v hexanes/EtOAc); $^1$H NMR (500 MHz) δ 0.94–1.03 (m, 2H), 1.05–1.29 (4H), 1.59 (app d, J=12.5, 11H), 1.67–1.84 (3H), 1.96 (app d, J=12.5, 1H), 2,71 (t, J=8.5, 1H), 2.93–2.96 (m, 1H), 3.17–3.22 (3H), 3.32 (t, J=8.5, 1H), 3.55 (q, J=8.0, 1H), 5.19 (app s, 2H), 7.19–7.41 (10H), 9.64 (d, J=2.0, 1H).

Step J: 2-(R)-(3-(S)-((4-Hydroxy-4-(3-phenylpropyl)piperidin-1-yl)methyl)-4-(S)-phenylpyrrolidin-1-yl)-2-(cyclohexyl)acetic acid, benzyl ester A solution of 87 mg (0.21 mmol) of 2-(R)-(3-(R)-formyl-4-(S)-phenylpyrrolidin-1-yl)-2-(cyclohexyl)acetic acid, benzyl ester (from EXAMPLE 1, Step I) and 69 mg (0.26 mmol) of 4hydroxy-4-(3-phenylpropyl)-piperidine.HCl in 5 mL of $CH_2Cl_2$ at rt was treated with 0.045 mL (0.25 mmol) of DIEA and 86 mg (0.40 mmol) of sodium triacetoxyborohydride and stirred at rt for 1 h. The reaction was diluted with 25 mL of $CH_2Cl_2$ and washed with 25 mL of 1.0 N $NaHCO_3$. The layers were separated and the aqueous layer was extracted with 25 mL of $CH_2Cl_2$. The combined organic phases were washed with 50 mL of sat'd NaCl, dried over $Na_2SO_4$ and concentrated. Flash chromatography on silica gel using 50:1 v/v $CH_2Cl_2$/MeOH as the eluant afforded 110 mg (83%) of the title compound: $R_F$: 0.46 (20:1 v/v $CH_2Cl_2$/MeOH); $^1H$ NMR (300 MHz) δ 0.91–2.85 (m, 32H), 3.16–3.27 (m, 3H), 5.15 (ABq, J=12.2 Hz, 2H), 7.15–7.41 (m, 15H); $NH_3$-CI-MS 609 (M+H).

Step K: 2-(R)-(3-(S)-((4-Hydroxy-4-(3-phenylpropyl)piperidin-1-yl)methyl)-4-(S)-phenylpyrrolidin-1-yl)-2-(cyclohexyl)acetic acid A mixture of 20 mg (0.032 mmol) 2-(R)-(3-(S)-((4-hydroxy-4-(3-phenylpropyl)piperidin-1-yl)methyl)-4-(S)-phenylpyrrolidin-1-yl)-2-(cyclohexyl)acetic acid, benzyl ester (from EXAMPLE 1, Step J) and 3 mg of 10% palladium on carbon in 0.5 mL of MeOH was stirred under one atmosphere of hydrogen for 18 h. The reaction was filtered through a 0.45 nylon filter and concentrated to give 16.5 mg (97%) of the title compound: ESI-MS 519 (M+H); HPLC B: 5.07 min.

EXAMPLE 2
2-(R)-(3-(S)-((4-Hydroxy-4-(3-(4-(1H-tetrazol-5-yl)phenyl)propyl)piperidin-1-yl)methyl)-4-(S)-phenylpyrrolidin-1-yl)-2-(cyclohexyl)acetic acid Step A: 5-(t-Butoxycarbonyl)-5-aza-1-oxa-spiro[2.5]heptane A mixture of 5.50 g (25.0 mmol) of trimethylsulfoxonium iodide and 15 mL of DMSO was cooled to 5° C. and then was treated with 1.20 g (30.0 mmol) of sodium hydride (60 wt % in mineral oil). The cooling was removed and the mixture was stirred at for 30 min. The mixture was recooled to 5° C. and then was treated with 5.00 g (25.0 mmol) of 1-t-butoxycarbonyl-piperidin-4-one. The resulting mixture was warmed to rt and then was stirred in an oil bath set at 50° C. for 30 min. The reaction was cooled and quenched with 100 mL of $H_2O$. The quenched mixture was extracted with 300 mL of ether; the extract was washed with 3×100 mL of $H_2O$, dried over $MgSO_4$ and concentrated. Flash chromatography on 150 g of silica gel using 3:1 v/v hexanes/ether as the eluant afforded 2.84 g (53%) of the title compound: H NMR (500 MHz) δ 1.43–1.49 (m, 2H), 1.47 (s, 9H), 1.77–1.82 (m, 2H), 2.69 (s, 21), 3.40–3.46 (m, 2H), 3.68–3.78 (m, 2H).

Step B: 1-t-Butoxycarbonyl-4-hydroxy(prop-2-ynyl)piperidine

A solution of 3.53 g (36.0 mmol) of trimethylsilylacetylene in 50 mL of THF at −10° C. was treated with 36.0 mL of 1.0 M lithium bis(trimethylsilyl) amide solution in THF and the resulting mixture was stirred cold for 30 min. The resulting mixture was treated with a solution of 2.56 g (12.0 mmol) of 5-(t-butoxycarbonyl)-5-aza-1-oxa-spiro[2.5]heptane (from EXAMPLE 2, Step A) in 15 mL of THF and 2.55 g (24.0 mmol) of lithium perchlorate. The reaction was warmed to rt and stirred for 20 h. The reaction was quenched with 100 mL of sat'd $NH_4Cl$ and the resulting mixture was extracted with 250 mL of ether. The ether extract was concentrated, dissolved in 50 mL of MeOH and stirred in the presence of 3.45 g (25.0 mmol) of $K_2CO_3$ for 1 hr. The mixture was partitioned between 250 mL of ether and 50 mL of $H_2O$ and the layers were separated. The organic layer was dried over $MgSO_4$ and concentrated. Flash chromatography on 125 g of silica gel using 3:2 v/v hexanes/ether as the eluant afforded 2.67 g (94%) of the title compound: $^1H$ NMR (300 MHz) δ 1.46 (s, 9H), 1.53–1.70 (4H), 1.92 (br s, 1H), 2.12 (t, J=2.7, 1H), 2.38 (d, J=2.7,22H), 3.11–3.21 (m, 2H), 3.81–3.88 (m, 2H).

Step C: 1-Bromo(1H-tetrazol-5-yl)benzene

A mixture of 546 mg (3.0 mmol) of 4-(bromo)benzonitrile, 227 mg (3.5 mmol) of sodium azide and 187 mg (3.5 mmol) of $NH_4Cl$ in 5 mL of DMF was stirred at 100° C. for 20 h. The mixture was cooled and concentrated. The residue was dissolved in 20 mL of $H_2O$ and the pH adjusted to 2 with 2 N HCl solution. The solid that precipitated was filtered, rinsed with $H_2O$, then ether and dried to afford 395 mg (58%) of the title compound: El-MS 226+224 (20%, M+H), 198+196 (100%, M-$N_2$+H).

Step D: 1-t-Butoxycarbonyl-4-hydroxy-4-(3-(4-(1H-tetrazol-5-yl)phenyl)propyn-2-yl)piperidine A mixture of 160 mg (0.68 mmol) of 1-t-butoxycarbonyl-4-hydroxy-4-(prop-2-ynyl)piperidine (from EXAMPLE 2, Step B), 210 mg (0.93 mmol) of 1-bromo-4-(1H-tetrazol-5-yl)benzene (from EXAMPLE 2, Step C), 42 mg (0.06 mmol) of dichlorobis(triphenylphosphine)palladium and 5.7 mg (0.03 mmol) of copper iodide in 5 mL of TEA and 2.5 mL of DMF under argon atmosphere was stirred in an oil bath set at 80° C. for 1.5 h. The reaction was cooled and concentrated. The residue was partitioned between 50 mL of $CH_2Cl_2$ and 40 mL of 0.5 N HCl and the layers were separated. The organic layer was dried over $MgSO_4$ and concentrated. Flash chromatography on 12 g of silica gel using 3:1 v/v $CH_2Cl_2$/EtOAc+1% HOAc as the eluant afforded 112 mg (43%) of the title compound: $^1H$ NMR (500 MHz) δ 1.44 (s, 9H), 1.55–1.77, 4H), 2.63 (s, 2H), 3.05–3.20 (m, 2H), 3.84 (app d, J=13.0, 2H), 4.84 (s, 11H), 7.58 (d, J=8.5, 2H), 7.96 (d, J=8.5, 2H).

Step E: 1-t-Butoxycarbonyl-4-hydroxy-4-(3-(4-(1H-tetrazol-5-yl)phenyl)propyl)piperidine A mixture of 131 mg (0.34 mmol) of 1-t-butoxycarbonyl-4-hydroxy-4-(3-(4-(1H-tetrazol-5-yl)phenyl)propyn-2-yl)piperidine (from EXAMPLE 2, Step D) and 60 mg of 10% palladium on carbon in 30 mL of MeOH was hydrogenated on a Parr Shaker at 40 psi for 16 h. The catalyst was filtered and the filtrate concentrated. Flash chromatography on 12 g of silica gel using 2:1 v/v $CH_2Cl_2$/EtOAc +1% HOAc as the eluant afforded 106 mg (80%) of the title compound: $^1H$ NMR (500 MHz) δ 1.34–1.58 (6H), 1.47 (s, 9H), 1.70–1.75 (m, 2H), 2.64 (t, J=7.0,22H), 3.06–3.26 (m, 2H), 3.78 (d, J=12.5, 2H), 7.24 (d, J=8.0, 2H), 7.92 (d, J=8.0, 2H).

Step F: 4-Hydroxy-4-(3-(4-(1H-tetrazol-5-yl)phenyl)propyl)piperidine

A solution of 105 mg (0.27 mmol) of 1-t-butoxycarbonyl-4-hydroxy-4-(3-(4-(1H-tetrazol-5-yl)phenyl)-propyl)piperidine (from EXAMPLE 2, Step E) in 5 mL of 0.5 N HCl in MeOH was stirred at rt for 20 h. The solution was concentrated and dried under vacuum to afford the title compound: HPLC B: 3.10 min.

Step G: 2-(R)-(3-(S)-((4-Hydroxy-4-(3-(4-(1H-tetrazol-5-yl)phenyl)propyl)piperidin-1-yl)methyl)-4-(S)-phenylpyrrolidin-1-yl)-2-(cyclohexyl)acetic acid, benzyl ester The title compound was prepared from 43 mg (0.10 mmol) of 2-(R)-3-(R)-formyl-4-(S)phenylpyrrolidin-1-yl)-2-(cyclohexyl)acetic acid, benzyl ester (from EXAMPLE 1, Step I) and 36 mg (0.11 mmol) of 4-hydroxy-4-(3-(4-(1H-tetrazol-5-yl)phenyl)propyl)piperidine (from EXAMPLE 2, Step F) using a procedure analogous to that described in EXAMPLE 1, Step J. Flash chromatography on silica gel using 20:1 v/v CH$_2$Cl$_2$/MeOH, then 4:1 v/v CH$_2$Cl$_2$/MeOH provided 38 mg (53%) of the title compound: R$_F$: 0.50 (40:10:1 v/v/v CH$_2$Cl$_2$/MeOH/NH$_4$OH); $^1$H NMR (300 MHz) δ 0.85–1.80 (16H), 1.85–2.05 (3H), 2.42 (m, 1H), 2.60–2.80 (3H), 2.85–3.2 (8H), 3.28 (m, 1H), 3.45 (m, 1H), 3.65 (m, 1H), 5.13 (ABq, J=12,22H), 7.00 (d, J=8.0, 2H), 7.14–7.35 (m, 10H), 7.84 (d, J=8.0, 2H).

Step H: 2-(R)-(3-(S((4-Hydroxy-4-(3-(4-(1H-tetrazol-5-yl)phenyl)propyl)piperidin-1-yl)methyl)-4-(S)phenylpyrrolidin-1-yl)-2-(cyclohexyl)acetic acid The title compound was prepared from 38 mg (0.056 mmol) of 2-(R)-(3-(S)-((4-hydroxy-4-(3-(4-(1H-tetrazol-5-yl)phenyl)propyl) piperidin-1-yl)methyl)-4-(S)-phenylpyrrolidin-1-yl)-2-(cyclohexyl)acetic acid, benzyl ester (from EXAMPLE 2, Step G using a procedure analogous to that described in EXAMPLE 1, Step K to provide 33 mg (100%) of the title compound: ESI-MS 587 (M+H).

EXAMPLE 3

2-(R)-(3-(S)-((4-Hydroxy-4-(3-phenylpropyl)piperidin-1-yl)methyl)-4-(S)-phenylpyrrolidin-1-yl)phenylacetic acid Step A: (S)-Mandelic acid, benzyl ester The title compound was prepared from 0.50 g (3.2 mmol) of (S)-mandelic acid using a procedure analogous to that described in EXAMPLE 1, Step F to provide 0.50 g (64%, ee>99%) of the title compound: HPLC: Chiralcel OD 4.6× 250 mm column, 4:1 v/v hexanes/iPrOH, 0.5 mL/min, 220 nm. Retention Times: (S)-enantiomer: 15.5 min; (R)-enantiomer 26.2 min.

Step B: 2-(R/S)-(3-(S((t-Butyldimethylsilyloxy)-1-yl)methyl)-4-(S)-phenylpyrrolidin-1-yl)-phenylacetic acid, benzyl ester The title compound was prepared from 215 mg (0.88 mmol) of (S)-mandelic acid, benzyl ester (from EXAMPLE 3, Step A) using a procedure analogous to that described in EXAMPLE 1, Step G to provide 277 mg (76%) of the title compound as a mixture of diastereomers. R$_F$: 0.68 (4:1 v/v hexanes/EtOAc): $^1$H NMR (300 MHz) δ 0.0 (2 s, 6H), 0.86 (s, 9H), 2.40 (m, 1H), 2.63 (m, 1H), 2.75–2.94 (m, 3H), 3.04 (m, 1H), 3.57–3.61 (m, 2H), 4.13 (s, 1H), 5.15 (ABq, J=12.5, 2H), 7.19–7.54 (m, 15l).

Step C: 2-(R)-(3-(R)-(Hydroxymethyl)-4-(S)-phenylpyrrolidin-1-yl)-phenylacetic acid, benzyl ester and 2-(S)-(3-(S)-(hydroxymethyl)-4-(S)-phenylpyrrolidin-1-yl)-phenylacetic acid, benzyl ester The title compounds were prepared from 268 mg (0.51 mmol) of 2-(R/S)-(3-(R)-(t-butyldimethylsilyloxymethyl)-4-(S)-phenylpyrrolidin-1-yl)-phenylacetic acid, benzyl ester (from EXAMPLE 3, Step B) using a procedure analogous to that described in EXAMPLE 1, Step H. The diastereomers were separated by HPLC (Chiralcel AD 2.0×25 cm column, 7:3 v/v hexanes/iPrOH, 9.0 mL/min, 220 nm) to provide 80 mg of 2-(R)-(3-(R)-(hydroxymethyl)-4-(S)-phenylpyrrolidin-1-yl)-phenylacetic acid, benzyl ester and 34.5 mg of 2-(S)-(3-(R)-(hydroxymethyl)-4-(S)-phenylpyrrolidin-1-yl)-phenylacetic acid, benzyl ester. For 2-(R)-(3-(R)-(hydroxymethyl)-4-(S)-phenylpyrrolidin-1-yl)-phenylacetic acid, benzyl ester: HPLC retention time: 15.3 min; $^1$H NMR (300 MHz) δ 2.39–3.18 (m, 6H), 3.59–3.75 (m, 2H), 4.09 (s, 1H), 5.13 (s, 2H), 7.15–7.48 (m, 15H). For 2-(S)-(3-(R)-(hydroxymethyl)-4-(S)-phenylpyrrolidin-1-yl)-phenylacetic acid, benzyl ester: HPLC retention time: 21.5 min; $^1$H NMR (300 MHz) δ 2.1–2.9 (m, 5H), 3.18–3.32 (m, 2H), 3.58–3.71 (m, 2H), 4.19 (s, 1H), 5.11 (ABq, J=12.3, 2H), 7.17–7.49 (m, 15H).

Step D: 2-(R)-(3-(R)-Formyl-4-(S)-phenylpyrrolidin-1-yl)-phenylacetic acid, benzyl ester The title compound was prepared from 80 mg (0.19 mmol) of 2-(R)-(3-(R)-(hydroxymethyl)-4-(S)-phenylpyrrolidin-1-yl)phenylacetic acid, benzyl ester (from EXAMPLE 3, Step C) using a procedure analogous to that described in EXAMPLE 1, Step I to provide 79 mg (100%) of the title compound which was used in Step E without further purification: R$_F$: 0.69 (3:2 v/v hexanes/EtOAc); $^1$H NMR (300 MHz) δ 2.70–3.32 (m, 5H), 3.61 (q, J=7.4 Hz, 1H), 4.15 (s, 1H), 5.12 (s, 2H), 7.13–7.48 (m, 15H), 9.68 (d, J=1.9 Hz, 1H).

Step E: 2-(R)-(3-(S)-((4-Hydroxy-4-(3-phenylpropyl)piperidin-1-yl)methyl)-4-(S)-phenylpyrrolidin-1-yl)phenylacetic acids benzyl ester The title compound was prepared from 26 mg (0.066 mmol) of 2-(R)-(3-(S)-formyl-4-(S)phenylpyrrolidin-1-yl)phenylacetic acid, benzyl ester (from Step D) and 20 mg (0.078 mmol) of 4-hydroxy-4-(3-phenylpropyl)-piperidine.HCl using a procedure analogous to that described in EXAMPLE 1, Step J to provide 28 mg (70%) of the title compound: R$_F$: 0.37 (19:1 v/v CH$_2$Cl$_2$/MeOH); $^1$H NMR (300 MHz) δ 1.41–2.94 (m, 22H), 4.11 (s, 1H), 5.11 (m, 2H), 7.13–7.49 (m, 20H).

Step F: 2-(R)-(3-(S)-((4Hydroxy-4-(3-phenylpropyl)piperidin-1-yl)methyl)-4-(S)-phenylpyrrolidin-1-yl) phenylacetic acid The title compound was prepared from 28 mg (0.046 mmol) of 2-(R)-(3-(S)-((4-hydroxy-4-(3-phenylpropyl)piperidin-1-yl)methyl)-4-(S)-phenylpyrrolidin-1-yl) phenylacetic acid, benzyl ester (from EXAMPLE 3, Step E) using a procedure analogous to that described in EXAMPLE 1, Step K to provide 21.5 mg (89%) of the title compound: ESI-MS 513 (M+H); HPLC B: 5.6 min.

EXAMPLE 4

2-(S)-(3-(S)-((4Hydroxy-4-(3-phenylpropyl)piperidin-1-yl)methyl)-4-(S)-phenylpyrrolidin-1-yl)phenylacetic acid Step A: 2-(S)-(3-(R)-Formyl-4-(S)-phenylpyrrolidin-1-yl)-phenylacetic acid, benzyl ester The title compound was prepared from 34.5 mg (0.085 mmol) of 2-(S)-(3-(R)-(hydroxymethyl)-4-(S)-phenylpyrrolidin-1-yl)-phenylacetic acid, benzyl ester (from EXAMPLE 3, Step C) using a procedure analogous to that described in EXAMPLE 1, Step I to provide 34 mg (100%) of the title compound which was used without further purification: R$_F$: 0.69 (3:2 v/v hexanes/EtOAc); $^1$H NMR (300 MHz) δ 2.66 (m, 1H), 2.89 (m, 1H), 2.98–3.10 (m, 2H), 3.24 (t, J=8.5 Hz, 1H), 3.65 (m, 1H), 4.16 (s, 1H), 5.11 (ABq, J=12.3 Hz, 2H), 7.18–7.48 (m, 15H), 9.68 (d, J=1.8 Hz, 1H).

Step B: 2-(S)-(3-(S)-((4-Hydroxy-4-(3-phenylpropyl)piperidin-1-yl)methyl)-4-(S)-phenylpyrrolidin-1-yl)-phenylacetic acid, benzyl ester The title compound was prepared from 34 mg (0.085 mmol) of 2-(S)-(3-(R)-formyl-4-(S)-phenylpyrrolidin-1-yl)-phenylacetic acid, benzyl ester (from EXAMPLE 4, Step A) and 22 mg of 4hydroxy-4-(3-phenylpropyl)-piperidine.HCl using a procedure analogous to that described in EXAMPLE 1, Step J to provide 34 mg (66%) of the title compound: R$_F$: 0.37 (19:1 v/v CH$_2$Cl$_2$/MeOH). $^1$H NMR (300 MHz) δ 1.2–3.1 (m, 221), 4.12 (s, 1H), 5.10 (ABq, J=12.5 Hz, 2H), 7.14–7.48 (m, 20H).

Step C: (2-(S(3-(S)-((4Hydroxy-4-(3-phenylpropyl)piperidin-1-yl)methyl)-4-(S)-phenylpyrrolidin-1-yl)-phenylacetic acid The title compound was prepared from 34 mg (0.056 mmol) of 2-(S)-(3-(S)-((4-hydroxy-4-(3-phenylpropyl)piperidin-1-yl)methyl)-4-(S)-phenylpyrrolidin-1-yl)-phenylacetic acid, benzyl ester (from EXAMPLE 4, Step B) using a procedure analogous to that described in EXAMPLE 1, Step K to provide 23 mg (79%) of the title compound: ESI-MS 513 (M+H).

EXAMPLE 5
2-(R)-(3-(S)-((4-Hydroxy-4-(3-phenylpropyl)piperidin-1-yl)methyl)-4-(S)-phenylpyrrolidin-1-yl)-3-methylbutanoic acid Step A: (S)-2-Hydroxy-3-methylbutanoic acid, benzyl ester The title compound was prepared from 2.0 g (16.9 mmol) of (S)-2-hydroxy-3-methylbutanoic acid using a procedure analogous to that described in EXAMPLE 1, Step F to provide 2.22 g (63%) of the title compound: $R_F$: 0.39 (4:1 v/v hexanes/EtOAc); $^1$H NMR (300 MHz) δ 0.83 (d, J=7.0, 3H), 1.01 (d, J=7.0, 3H), 2.08 (m, 1H), 2.67 (d, J=6.3, 1H), 4.08 (dd, J=6.0, 3.6, 1H), 5.22 (ABq, J=12.1, 2H), 7.34–7.39 (m, 5H).

Step B: 2-(R)-(3-(R)-(t-Butyldimethylsilyloxymethyl)-4-(S)-phenylpyrrolidin-1-yl)-3-methylbutanoic acid, benzyl ester The title compound was prepared from 3-(R)-(t-butyldimethyl-silyloxymethyl)-4-(S)-phenyl pyrrolidine (from EXAMPLE 1, Step E) and (S)-2-hydroxy-3-methylbutanoic acid, benzyl ester (from EXAMPLE 5, Step A) using a procedure analogous to that described in EXAMPLE 1, Step G. For the title compound: $R_F$: 0.66 (4:1 v/v hexanes/EtOAc); $^1$H NMR (300 MHz) δ 0.0 (2s, 6H), 0.83–1.10 (m, 15H), 2.07–3.64 (m, 101), 5.18 (s, 2H), 7.18–7.44 (m, 10H).

Step C: 2-(R)-(3-(R)-(Hydroxymethyl)-4-(S)-phenylpyrrolidin-1-yl)-3-methylbutanoic acid, benzyl ester The title compound was prepared from 234 mg (0.48 mmol) of 2-(R)-(3-(R)-(t-butyldimethylsilyloxymethyl)-4-(S)-phenylpyrrolidin-1-yl)-3-methylbutanoic acid, benzyl ester (from EXAMPLE 5, Step B) using a procedure analogous to that described in EXAMPLE 1, Step H to provide 130 mg of the title compound (73%) as a colorless oil: $R_F$: 0.60 (3:2 v/v hexanes/EtOAc); $^1$H NMR (300 MHz) 80.91 (d, J=6.7, 3H), 1.05 (d, J=6.7, 3H), 2.03–3.70 (m, 10H), 5.18 (ABq, J=12.1, 2H), 7.16–7.41 (m, 101H).

Step D: 2-(R)-(3-(R)Formyl-4-(S)-phenylpyrrolidin-1-yl)-3-methylbutanoic-acid, benzyl ester The title compound was prepared from 130 mg (0.35 mmol) of 2-(R)-(3-(R)-(hydroxymethyl)(S)phenylpyrrolidin-1-yl)-3-methylbutanoic acid, benzyl ester (from EXAMPLE 5, Step C) using a procedure analogous to that described in EXAMPLE 1, Step I to provide 129 mg (100%) of the title compound which was used without further purification: $R_F$: 0.77 (3:2 v/v hexanes/EtOAc); $^1$H NMR (300 MHz) δ 0.89 (d, J=6.8, 3H), 1.00 (d, J=6.8, 3H), 2.08 (m, 11H), 2.66 (dd, J=8.9, 8.0, 1H), 2.92 (m, 1H), 3.08 (d, J=10.0, 1H), 3.17 (d, J=6.6, 1H), 3.28 (t, J=8.4, 1H), 3.53 (m, 1H), 5.17 (s, 2H), 7.16–7.38 (m, 10H), 9.63 (d, J=2.1, 1H).

Step E: 2-(R)-(3-(S)-((4-Hydroxy-4-(3-phenylpropyl)piperidin-1-yl)methyl)-4-(S)-phenylpyrrolidin-1-yl)-3-methylbutanoic acid, benzyl ester The title compound was prepared from 30 mg (0.081 mmol) of 2-(R)-(3-(R)-formyl-4-(S)-phenylpyrrolidin-1-yl)-3-methylbutanoic acid, benzyl ester (from EXAMPLE 5, Step D) and 25 mg (0.097 mmol) of 4-hydroxy(3-phenylpropyl)-piperidine. HCl using a procedure analogous to that described in EXAMPLE 1, Step J to provide 36 mg (67%) of the title compound: $R_F$: 0.41 (19:1 v/v CH$_2$Cl$_2$/MeOH). $^1$H NMR (300 MHz) δ 0.89 (d, J=6.6, 3H), 1.00 (d, J=6.6, 3H),1.39–1.69 (m, 8H), 2.00–3.22 (m, 16H), 5.16 (ABq, J=12.1, 21), 7.15–7.41 (m, 15H).

Step F: 2-(R)-(34S)-((4-Hydroxy-4-(3-phenylpropyl) piperidin-1-yl)methyl)-4-(S)-phenylpyrrolidin-1-yl)-3-methylbutanoic acid The title compound was prepared from 31 mg (0.054 mmol) of 2-(R)-(3-(S)-((4hydroxy-4-(3-phenylpropyl) piperidin-1-yl)methyl)-4-(S)-phenylpyrrolidin-1-yl)-3-methylbutanoic acid, benzyl ester (from EXAMPLE 5, Step E) using a procedure analogous to that described in EXAMPLE 1, Step K to provide 25.5 mg (98%) of the title compound: ESI-MS 479 (M+H).

EXAMPLE 6
2-(R)-3-(S)-((4-Hydroxy-4-(3-(quinolin-3-yl)propyl) piperidin-1-yl)methyl)-4-(S)-phenylpyrrolidin-1-yl)-3-methylbutanoic acid Step A: 4-Hydroxy-4-(3-(quinolin-3-yl)propyl) piperidine.HCl The title compound was prepared from 1-t-butoxycarbonyl-4-hydroxy-4-(2-propynyl)piperidine (from EXAMPLE 2, Step B) using procedures analogous to those described in EXAMPLE 2, Steps D–F. For the title compound: $^1$H NMR (500 MHz, CD$_3$OD), 1.64–1.68 (m, 2H), 1.75–1.81 (4H), 1.92–1.97 (m, 2H), 3.07 (t, J=8.0, 2H), 3.21–3.30 (4H), 7.98 (t, J=7.0, 1H), 8.12–8.16 (m, 1H), 8.24 (d, J=8.5, 1H), 8.31 (d, J=8.5, 1H), 9.09 (s, 1H), 9.21 (d, J=2.0, 1H).

Step B: 2-(R)-(3-(S)-((4-Hydroxy-4-(3-(quinolin-3-yl)prop-1-yl)piperidin-1-yl)methyl)-4-(S)-phenylpyrrolidin-1-yl)-3-methylbutanoic acid, benzyl ester The title compound was prepared from 24 mg (0.067 mmol) of 2-(R)-(3-(R)-formyl-4-(S)-phenylpyrrolidin-1-yl)-3-methylbutanoic acid, benzyl ester (from EXAMPLE 5, Step D) and 22.5 mg (0.073 mmol) of 4-hydroxy-4-(3-(quinolin-3-yl)propyl)piperidine.HCl from EXAMPLE 6, Step A using a procedure analogous to that described in EXAMPLE 1, Step J to provide 32.5 mg (75%) of the title compound: $R_F$: 0.21 (19:1 v/v CH$_2$Cl$_2$/MeOH); $^1$H NMR (300 MHz) δ 0.88 (d, J=6.7,33H), 1.01 (d, J=6.7, 3H), 1.42–3.22 (m, 24H), 5.16 (ABq, 2H), 7.15–7.41 (m, 10H), 7.49–7.54 (m, 1H), 7.62–7.68 (m, 1H), 7.75 (d, J=8.0, 1H), 7.91 (s, 1H), 8.06 (d, J=8.2, 1H), 8.75 (d, J=2.1, 1H).

Step C: 2-(R)-(3-(S)-((4-Hydroxy-4-(3-(quinolin-3-yl)prop-1-yl)piperidin-1-yl)methyl)-4-(S)-phenylpyrrolidin-1-yl)-3-methylbutanoic acid The title compound was prepared from 32.5 mg (0.052 mmol) of 2-(R)-(3-(S)-((4-hydroxy-4-(3-(quinolin-3-yl) propyl)piperidin-1-yl)methyl)-4-(S)-phenylpyrrolidin-1-yl)-3-methylbutanoic acid, benzyl ester (from EXAMPLE 6, Step B) using a procedure analogous to that described in EXAMPLE 1, Step K to provide 22.5 mg (81%) of the title compound: ESI-MS 530.5 (M+H).

EXAMPLE 7
2-(R)-(3-(S)-((4-Hydroxy-4-(3-phenylpropyl)piperidin-1-yl)methyl)-4-(S) phenylpyrrolidin-1-yl)propanoic acid Step A: (S)-Lactic acid benzyl ester The title compound was prepared from 1.5 mL of 85% (S)-L-lactic acid in H$_2$O using a procedure analogous to that described in EXAMPLE 1, Step F to provide 1.57 g (51%) of the title compound: $^1$H NMR (300 MHz) δ 1.43 (d, J=6.9, 3H), 2.78 (m, 1H), 4.32 (m, 1H), 5.21 (s, 2H), 7.25–7.41 (m, 5H).

Step B: 2-(R)-(3-(R)-(t-Butyldimethylsilyloxymethyl)-4-(S)-phenylpyrrolidin-1-yl )propanoic acid, benzyl ester The title compound was prepared from 242 mg (1.3 mmol) of (S)-lactic acid, benzyl ester (from EXAMPLE 7, Step A) and 310 mg (1.0 mmol) of 3-(R)-(t-butyldimethylsilyloxymethyl)-4-(S)-phenylpyrrolidine (from EXAMPLE 1, Step E) using a procedure analogous to that described in EXAMPLE 1, Step G to provide 301 mg (62%) of the title compound: $R_F$: 0.47 (4:1 v/v hexanes/

EtOAc). 1H NMR (300 MHz) δ 0.0 (s, 6H), 0.85 (s, 9H), 1.41 (d, J=6.0 Hz, 3H), 2.41–3.62 (m, 9H), 5.17 (s, 2H), 7.16–7.38 (m, 10H).

Step C: 2-(R)-(3-(R)-(Hydroxymethyl)-4-(S)-phenylpyrrolidin-1-yl)propanoic acid, benzyl ester The title compound was prepared from 200 mg (0.44 mmol) of 2-(R)-(3)-(t-butyldimethylsilyloxymethyl)-4-(S)-phenylpyrrolidin-1-yl)propanoic acid, benzyl ester (from EXAMPLE 7, Step B) using a procedure analogous to that described in EXAMPLE 1, Step H to provide 130 mg (87%) of the title compound: $R_F$: 0.20 (1:1 v/v hexanes/EtOAc); $^1$H NMR (300 MHz) δ 1.43 (d, J=6.9, 3H), 2.45 (m, 1H), 2.78 (m, 1H), 2.95 (m, 1H), 3.07–3.21 (m, 2H), 3.35 (t, J=8.5, 1H), 3.45 (m, 1H), 3.58 (dd, J=10.5, 6.1, 1H), 3.70 (dd, J=10.5,4.4, 1H), 5.19 (ABq, J=12.1, 2H), 7.18–7.39 (m, 10H).

Step D: 2-(R(3-(R)-Formyl-4-(S)-phenylpyrrolidin-1-yl)-propanoic acid, benzyl ester The title compound was prepared from 130 mg (0.38 mmol) of 2-(R)-(3-(R)-(hydroxymethyl)-4-(S)-phenylpyrrolidin-1-yl)propanoic acid, benzyl ester (from EXAMPLE 7, Step C) using a procedure analogous to that described in EXAMPLE 1, Step I to provide 128 mg (100%) of the title compound which was used without further purification: $R_F$: 0.58 (1:1 v/v hexanes/EtOAc); $^1$H NMR (300 MHz) δ 1.41 (d, J=7.1, 3H), 2.78–3.61 (m, 7H), 5.17 (ABq, J=12.2, 2H), 7.22–7.38 (m, 10H), 9.66 (d, J=2.1, 1H).

Step E: 2-(R)-(3-(S)-((4-Hydroxy-4-(3-phenylpropyl)piperidin-1-yl)methyl)-4-(S)-phenylpyrrolidin-1-yl) propanoic acid, benzyl ester The title compound was prepared from 30 mg (0.088 mmol) of 2-(R)-(3-(R)-formyl-4-(S)-phenylpyrrolidin-1-yl)propanoic acid, benzyl ester (from EXAMPLE 7, Step D) and 27 mg (0.10 mmol) of 4-hydroxy-4-(3-phenylpropyl)-piperidine. HCl using a procedure analogous to that described in EXAMPLE 1, Step J to provide 25.5 mg (53%) of the title compound: $R_F$: 0.28 (19:1 v/v $CH_2Cl_2$/MeOH); $^1$H NMR (300 MHz) S 1.241.69 (m, 11H), 2.16–3.39 (m, 15H), 5.16 (ABq, J=12.2,22H), 7.15–7.38 (m, 15H).

Step F: 2-(R)-(3-(S)-((4-Hydroxy-4-(3-phenylpropyl) piperidin-1-yl)methyl)-4-(S)-phenylpyrrolidin-1-yl propanoic acid The title compound was prepared from 25.5 mg (0.047 mmol) of 2-(R)-(3-(S)-((4-hydroxy-4-(3-phenylpropyl) piperidin-1-yl)methyl)-4-(S)-phenylpyrrolidin-1-yl)-propanoic acid, benzyl ester (from Step E) using a procedure analogous to that described in EXAMPLE 1, Step K to provide 20.5 mg (96%) of the title compound: ESI-MS 451 (M+H).

EXAMPLE 8

2-(3-(S)-((4-Hydroxy-4-(3-phenylpropylpiperidin-1-yl) methyl)-4-(S)-phenylpyrrolidin-1-yl)acetic acid Step A: 243-(R)-(t-Butyldimethylsilyloxymethyl)-4-(S)-phenylpyrrolidin-1-yl)acetic acid, benzyl ester A solution of 302 mg (1.0 mmol) of 3-(R)(t-butyldimethyl-silyloxymethyl)-4-(S)-phenylpyrrolidine (from EXAMPLE 1, Step E) in 7 mL of dichloroethane was treated with 0.195 mL (1.1 mmol) of DIEA, 76 mg (0.21 mmol) of tetrabutylammonium iodide and 0.162 mL (1.0 mmol) of benzyl 2-bromoacetate. After stirring at rt for 2 h, the reaction was poured into 50 mL of $CH_2Cl_2$ and 50 mL of sat'd NaCl. The layers were separated and the aqueous layer was extracted with 50 mL of $CH_2Cl_2$. The combined organics were dried over $Na_2SO_4$ and concentrated. Flash chromatography on silica gel using 4:1 v/v hexanes/EtOAc afforded 370 mg (82%) of the title compound: $R_F$: 0.41 (4:1 v/v hexanes/EtOAc); $^1$H NMR (300 MHz) δ 0.0 (s, 6H), 0.85 (s, 9H), 2.45 (m, 1H), 2.78–3.13 (m, 5H), 3.45 (ABq, J=16.7, 2H), 3.54–3.66 (m, 2H), 5.18 (s, 2H), 7.18–7.36 (m, 10H).

Step B: 2-(3-(R)-(Hydroxymethyl)-4-(S)-phenylpyrrolidin-1-yl)-acetic acid, benzyl ester The title compound was prepared from 363 mg (0.82 mmol) of 2-(3-(R)-(t-butyldimethylsilyloxymethyl)-4-(S)-phenylpyrrolidin-1-yl)-acetic acid, benzyl ester (from EXAMPLE 8, Step A) using a procedure analogous to that described in EXAMPLE 1, Step H to provide 153 mg (57%) of the title compound: $R_F$: 0.13 (3:2 v/v hexanes/EtOAc). $^1$H NMR (300 MHz) δ 2.54–3.76 (m, 10H), 5.18 (ABq, J=12.1, 2H), 7.21–7.38 (m, 101H).

Step C: 2-(3-(R)-Formyl-4-(S)-phenylpyrrolidin-1-yl)acetic acid, benzyl ester

The title compound was prepared from 153 mg (0.47 mmol) of 2-(3-(R)-(hydroxymethyl)-4-(S)-phenylpyrrolidin-1-yl)acetic acid, benzyl ester (from EXAMPLE 8, Step B) using a procedure analogous to that described in EXAMPLE 1, Step I to provide 152 mg (100%) of the title compound which was used without further purification: $R_F$: 0.42 (3:2 v/v hexanes/EtOAc); $^1$H NMR (300 MHz) δ 2.86 (t, J=8.3, 1H), 3.05–3.07 (m, 2H), 3.27–3.32 (m, 2H), 3.47 (ABq, J=16.9, 2H), 3.67 (m, 1H), 5.18 (ABq, 2H), 7.23–7.38 (m, 10H), 9.72 (d, J=1.2, 1H).

Step D: 2-(3-(S)-((4-Hydroxy-4-(3-phenylpropyl)piperidin-1-yl)methyl)-4-(S)-phenylpyrrolidin-1-yl)acetic acid, benzyl ester The title compound was prepared from 30 mg (0.094 mmol) of 2-(3-(R)-formyl-4-(S)-phenylpyrrolidin-1-yl) acetic acid, benzyl ester (from EXAMPLE 8, Step C) and 28 mg (0.10 mmol) of 4-hydroxy-4-(3-phenylpropyl)-piperidine.HCl using a procedure analogous to that described in EXAMPLE 1, Step J to provide 34.5 mg (70%) of the title compound: $R_F$: 0.26 (19:1 v/v $CH_2Cl_2$/MeOH); $^1$H NMR (300 MHz) δ 1.24–1.69 (m, 8H), 2.16–3.14 (m, 14H), 3.43 (ABq, J=16.8, 2H), 5.16 (ABq, J=12.2, 2H), 7.15–7.37 (m, 15H).

Step E: 2-(3-(S)-((4Hydroxy-4-(3-phenylpropyl)piperidin-1-yl)methyl)-4-(S)-phenylpyrrolidin-1-yl)acetic acid The title compound was prepared from 34.5 mg (0.065 mmol) of 2-(3-(S)-((4-hydroxy-4-(3-phenylpropyl) piperidin-1-yl)methyl)-4-(S)-phenylpyrrolidin-1-yl)acetic acid, benzyl ester (from EXAMPLE 8, Step D) using a procedure analogous to that described in EXAMPLE 1, Step K to provide 28 mg (98%) of the title compound: ESI-MS 437 (M+H).

EXAMPLE 9

2-(S)-(3-(S)-((4-Hydroxy-4-(3-phenylpropyl)piperidin-1-yl)methyl)-4-(S)-phenylpyrrolidin-1-yl)-2-(cyclohexyl) acetic acid The title compound was prepared using procedures analogous to those described in EXAMPLE 1, Steps A–K, except that (R)-hexahydromandelic acid was substituted for (S)hexahydromandelic acid in Step F: ESI-MS: 519 (M+H).

EXAMPLE 10

2-(R)-(3-(S)-((4-(3-Phenylpropyl)piperidin-1-yl)methyl)-4-(S)phenylpyrrolidin-1-yl)-2-(2-chlorophenyl)acetic acid Step A: 2-(R/S(3-(R)-(t-Butyldimethylsilyloxymethyl)-4-(S)-phenylpyrrolidin-1-yl)-2-(2-chlorophenyl)acetic acid A solution of 306 mg (1.0 mmol) of 3-(S)-(t-butyldimethylsilyloxymethyl)-4-(S)-phenylpyrrolidine (from EXAMPLE 1, Step E), 83 mg (1.1 mmol) of glyoxylic acid monohydrate and 161 mg (1.0 mmol) of 2-chlorobenzeneboronic acid in 7.5 mL of $CH_2Cl_2$ was heated at reflux for 4.5 h. The reaction was concentrated and the crude product was used without further purification: $R_F$: 0.13 (95:5:1 v/v/v $CH_2Cl_2$/MeOH/$NH_4OH$).

Step B: 2-(R/S)-(3-(R)-(t-Butyldimethylsilyloxymethyl)-4-(S)-phenylpyrrolidin-1-yl)-2-(2-chlorophenyl)acetic acid, (4-methoxy)benzyl ester A mixture of crude 2-(R/S)-(3-(R)-(t-butyldimethylsilyloxymethyl)-4-(S)-phenylpyrrolidin-1-yl)-(2-chlorophenyl)acetic acid (from EXAMPLE 10, Step A), 338 mg (1.0 mmol) of cesium carbonate and 0.14 mL (1.0 mmol) of 4-(methoxy)benzyl chloride in 3 mL of DMF was stirred at rt for 22 h. The reaction mixture was diluted with 100 mL of ether and washed with 100 mL of 1.0 N $NaHCO_3$. The layers were separated and the aqueous phase was extracted with 100 mL of ether. The combined organic phases were dried over $MgSO_4$ and concentrated. Flash chromatography using 9:1 v/v hexanes/EtOAc as the eluant afforded 377 mg (63%, two steps) of the title compound: $R_F$: 0.68 (4:1 v/v hexanes/EtOAc). For the pair of diastereomers: $^1$H NMR (300 MHz) δ 0.0, 0.01, 0.02,0.04 (4s, 6H), 0.86,0.88 (2s, 9H), 2.42 (m, 1H), 2.67 (m, 1H), 2.84–3.10 (m, 4H), 3.57–3.62 (m, 2H), 3.83 (s, 31), 4.80, 4.81 (2s, 1H), 5.10 (ABq, J=12.1, 2H), 6.83–6.87 (m, 2H), 7.20–7.41 (m, 10H), 7.73 (m, 1H).

Step C: 2-(R)-(3-(R)-(Hydroxymethyl)-4-(S)-phenylpyrrolidin-1-yl)-2-(2-chlorophenyl)acetic acid, 4-(methoxy)benzyl ester The title compound was prepared from 185 mg (0.31 mmol) of 2-(R/S)-(3-(R)-(t-butyldimethylsilyloxymethyl)-3-(S)-phenylpyrrolidin-1-yl)-(2-chlorophenyl)acetic acid, 4-(methoxy)benzyl ester (from EXAMPLE 10, Step B) using a procedure analogous to that described in EXAMPLE 1, Step H. The diastereomers were separated by HPLC (Chiralcel-OJ 2×25 cm column, 2:1:1 v/v/v hexanes/iPrOH/EtOH, 9.0 mL/min, 220 nm) to provide 47 mg of 2-(R)(3-(R)-(hydroxymethyl)-4-(S)phenylpyrrolidin-1-yl)-(2-chlorophenyl)acetic acid, 4-(methoxy)benzyl ester and 51 mg of 2-(S)-(3-(R)-(hydroxymethyl)-4-(S)-phenylpyrrolidin-1-yl)-(2-chlorophenyl)acetic acid, 4-(methoxy)benzyl ester. For 2-(R)(3-(R)-(Hydroxymethyl)-4-(S)-phenylpyrrolidin-1-yl)-(2-chlorophenyl)acetic acid, 4-(methoxy)benzyl ester: HPLC retention time: 16.7 min; $^1$H NMR (300 MHz) δ 1.9 (br m, 1H), 2.4 (m, 1H), 2.6 (m, 1H), 2.9–3.2 (m, 4H), 3.6–3.8 (m, 5H), 4.8 (s, 1H), 5.1 (s, 2H), 6.8 (d, 2H), 7.1–7.4 (m, 10H), 7.6 (m, 1H). For 2-(S)-(3-(R)-(Hydroxymethyl)-4-(S)-phenylpyrrolidin-1-yl)-(2-chlorophenyl)acetic acid, 4-(methoxy)benzyl ester: HPLC retention time: 21.1 min.

Step D: 2-(R)-(3-()-Formyl-4-(S)-phenylpyrrolidin-1-yl)-2-(2-chlorophenyl)acetic acid, 4-(methoxy)benzyl ester The title compound was prepared from 40 mg (0.085 mmol) of 2-(R)-(3-(R)-(hydroxymethyl)-4-(S)-phenylpyrrolidin-1-yl)-(2-chlorophenyl)acetic acid, 4-(methoxy)benzyl ester (from EXAMPLE 10, Step C) using a procedure analogous to that described in EXAMPLE 1, Step I to provide 39 mg (100%) of the title compound which was used without further purification: $R_F$: 0.31 (4:1 v/v hexanes/EtOAc); $^1$H NMR (300 MHz) δ 2.73–3.60 (m, 6H), 3.79 (s, 3H), 4.83 (s, 1H), 5.08 (s, 2H), 6.79–6.84 (m, 2H), 7.16–7.38 (m, 10H), 7.60 (m, 1H), 9.68 (d, J=1.6, 1H).

Step E: 2-(R)-(3-(S)-((4-(3-Phenylpropyl)piperidin-1-yl)methyl)-4-(S)-phenylpyrrolidin-1-yl)-2-(2-chlorophenyl)acetic acid, 4-(methoxy)benzyl ester The title compound was prepared from 39 mg (0.085 mmol) of 2-(R)-(3-(R)-formyl-4-(S)-phenylpyrrolidin-1-yl)-(2-chlorophenyl)acetic acid, 4-(methoxy)benzyl ester (from EXAMPLE 10, Step D) and 4-(3-phenylpropyl)piperidine.HCl using a procedure analogous to that described in EXAMPLE 1, Step J to provide 38 mg (69%) of the title compound: $R_F$: 0.28 (4:1 v/v hexanes/EtOAc); $^1$H NMR (300 MHz) δ 1.05–1.23 (m, 5H), 1.47–1.75 (m, 7H), 2.30–2.97 (m, 11H), 4.76 (s, 1H), 5.06 (s, 2H), 6.78–6.83 (m, 2H), 7.13–7.36 (m, 15H), 7.68 (m, 1H).

Step F: 2-(R)-(3-(S)-((4-(3-Phenylpropyl)piperidin-1-yl)methyl)-4-(S)-phenylpyrrolidin-1-yl)-2-(2-chlorophenyl)acetic acid A solution of 19 mg (0.029 mmol) of 2-(R)-(3-(S)-((4-(3-phenylpropyl)piperidin-1-yl)methyl)-4-(S)phenylpyrrolidin-1-yl)-(2-chlorophenyl)acetic acid, 4-(methoxy)benzyl ester (from EXAMPLE 10, Step E) in 0.5 mL of 96% formic acid was stirred at rt for 1.5 h. The reaction was concentrated. Flash chromatography on silica gel using 19:1 v/v $CH_2Cl_2$/MeOH, then 90:10:1 v/v/v $CH_2Cl_2$/MeOH/$NH_4OH$ afforded 15 mg (96%) of the title compound: $R_F$: 0.44 (90:10:1 v/v/v $CH_2Cl_2$/MeOH/$NH_4O$); $^1$H NMR(300 MHz, $CD_3OD$) 80.88–1.49 (m, 10H), 2.08 (m, 1H), 2.37–3.26 (m, 11H), 3.53 (m, 1H), 4.59 (s, 1H), 7.00–7.26 (m, 13H), 7.76 (m, 1H); ESI-MS 531.5 (M+H).

EXAMPLE 11

2-(R)-(3-(S)-((4-(3-Phenylpropyl)piperidin-1-yl)methyl)-4-(S)-phenylpyrrolidin-1-yl)-2-(1-naphthyl)acetic acid The title compound was prepared using procedures analogous to those described in EXAMPLE 10, Steps A–E and EXAMPLE 1, Step K, except that 1-napthylboronic acid was substituted for 2-chlorobenzeneboronic acid in EXAMPLE 10, Step A, benzyl bromide was substituted for 4-(methoxy)benzyl chloride in EXAMPLE 10, Step B and the diastereomers in EXAMPLE 10, Step C were separated by HPLC using the following conditions: Chiralcel-OJ 2×25 cm column, 7:3 v/v hexanes/iPrOH, 9.0 mL/min, 220 nm. For the title compound: $^1$H NMR (300 MHz, $CD_{30}D$) δ 0.7–3.8 (m, 23H), 4.9 (br s, 1H), 7.0–7.3 (m, 10H), 7.4–7.6 (m, 3H), 7.8–8.0 (m, 3H), 8.6 (br d, 1H); ESI-MS 547 (M+H).

EXAMPLE 12

2-(R)-(3-(S)-((4-Hydroxy-4-(3-(3,4-difluorophenyl)propyl)piperidin-1-yl)methyl)-4-(S)-phenylpyrrolidin-1-yl)-2-(1-naphthyl)acetic acid Step A: 1-(t-Butoxycarbonyl)-4-(prop-2-enyl)-4-hydroxypiperidine A dry round bottom flask was purged with nitrogen and charged with 1-t-butoxycarbonyl-4-piperidinone (20 g, 100 mmol), titanocene dichloride (1.2 g, 5 mmol) and zinc dust (7.8 g, 120 mmol) in 100 mL dry THF. Allyl bromide (11.3 mL, 130 mmol) was added and the mixture was stirred for 5 h at rt. The mixture was diluted with 700 mL EtOAc, washed with 2.0 M HCl (2×200 ML), 100 mL of sat'd NaCl, dried over $MgSO_4$ and concentrated. Flash chromatography (650 g silica, 10/1 $CH_2Cl_2$/$Et_2O$ eluant) afforded 10.9 g (45%) of the title compound: $^1$H NMR (300 MHz) δ 1.4–1.6 (13H), 2.2–2.25 (d, 2H), 3.1–3.2 (m, 2H), 3.75–3.85 (m, 2H), 5.1–5.25 (m, 2H), 5.78–5.92 (m, 1H).

Step B: 4-Hydroxy-4-(3-(3,4-Difluorophenylpropyl)piperidine.HCl

A solution of 1-(t-butoxycarbonyl)-4-(prop-2-enyl)-4-hydroxypiperidine (3.0 g, 12.4 mmol, from EXAMPLE 12, Step A) in 5 mL of THF was cooled to 0° C. and 9-BBN (52 mL, 0.5 M in THF, 26.1 mmol) was added. The mixture was warmed to rt and stirred for 5 h. 3,4-Difluoro-1-bromobenzene (1.4 mL, 12.4 mmol), potassium carbonate (3.61 g, 26.1 mmol) and 1,2-bis(diphenylphosphino) ferrocenyl palladium dichloride (760 mg, 0.93 mmol) was added followed by 60 mL of DMF. The mixture was heated to 55° C. overnight then diluted with 300 mL ether. The organic phase was washed with H₂O (2×200 mL) and sat'd NaCl (100 mL) then dried over MgSO₄ and concentrated. The residue was dissolved in 30 mL 4/1 v/v CH₂Cl₂/TFA and stirred for 30 min. The solvent was removed and the residue was dissolved in 200 mL EtOAc then extracted with 2 N HCl (2×100 mL). The combined aqueous portions were made basic with NaOH and extracted with CH₂Cl₂ (3×70 mL). The organic phases were combined and dried over Na₂SO₄ and concentrated to give the free amine. The amine was converted to the HCl salt by dissolving it in methanolic HCl, removing the solvent and drying under vacuum. 1.42 g (44%) of product was obtained: $^1$H NMR (300 MHz, CD₃OD). δ 1.4–1.98 (8H), 2.58–2.63 (t, 2H), 3.18–3.23 (m, 4H), 6.95–7.01 (m, 1H), 7.08–7.1 (m, 2H).

Step C: 2-(R)-(3-(S)-((4-Hydroxy-4-(3-(3,4-difluorophenyl)-propyl)piperidin-1-yl)methyl)+(S)-phenylpyrrolidin-1-yl)-2-(1-naphthyl)acetic acid, benzyl ester The title compound was prepared from 25 mg (0.057 mmol) of 2-(R)-(3-(R)-formyl-4-(S)-phenylpyrrolidin-1-yl)-(1-naphthyl)acetic acid, benzyl ester (from EXAMPLE 11) and 17 mg (0.058 mmol) of 4-hydroxy-4-(3-(3,4-difluorophenyl)propyl)piperidine.HCl (from EXAMPLE 12, Step B) using a procedure analogous to that described in EXAMPLE 1, Step J to provide 36 mg (90%) of the title compound: $R_F$: 0.62 (19:1 v/v CH₂Cl₂/MeOH); $^1$H NMR (300 MHz) δ 1.24–1.65 (m, 10H), 2.04–2.16 (m, 2H), 2.30–2.62 (m, 7H), 2.78–3.02 (m, 4H), 4.88 (s, 1H), 5.08 (s, 1H), 6.82–7.30 (m, 13H), 7.40–7.55 (m, 3H), 7.70 (d, J=7.1, 1H), 7.78–7.86 (m, 2H), 8.56 (d, J=8.0, 1H).

Step D: 2-(R)-(3-(S((4-Hydroxy-4-(3-(3,4-difluorophenyl)-propyl)piperidin-1-yl)methyl)-4-(S)-phenylpyrrolidin-1-yl)-2-(1-naphthyl)acetic acid The title compound was prepared from 36 mg (0.052 mmol) of 2-(R)-(3-(S)-((4-hydroxy-4-(3-(3,4difluorophenyl)propyl)piperidin-1-yl)methyl)-4-(S)-phenylpyrrolidin-1-yl)-(1-naphthyl)acetic acid, benzyl ester (from EXAMPLE 12, Step C) using a procedure analogous to that described in EXAMPLE 1, Step K to provide 22 mg (70%) of the title compound: $^1$H NMR (300 MHz) δ 0.5–1.5 (m, 9H), 2.1–3.7 (m, 13H), 4.0 (br m, 1H), 4.7 (br m, 1H), 6.7 (m, 1H), 6.8 (m, 1H), 7.0–7.2 (m, 6H), 7.47.6 (m, 3H), 7.7 (br d, 1H), 7.8 (br d, 1H), 7.9 (br m, 1H), 8.9 (br m, 1H); ESI-MS 599.5 (M+H).

EXAMPLE 13
2-(R)-(3-(S)-((4-(3-Phenylpropyl)piperidin-1-yl)methyl)-4-(S)-phenylpyrrolidin-1-yl)-3-(thienyl)acetic acid The title compound was prepared using procedures analogous to those described in EXAMPLE 10, except that thiophene 3-boronic acid was substituted for 2-chlorobenzeneboronic acid in Step A and the diastereomers in Step C were separated by HPLC using the following conditions: Chiralcel OJ 2×25 cm column, 1:1 v/v hexanes/EtOH, 9.0 mL/min, 220 nm. For the title compound: $R_F$: 0.29 (90:10:1 v/v/v CH₂Cl₂/MeOH/NH₄OH); $^1$H NMR (300 MHz, CD₃OD) δ 0.89–1.48 (m, 9H), 1.98 (m, 1H), 2.28–2.48 (m, 4H), 2.68–3.15 (m, 8H), 3.50 (m, 1H), 4.30 (s, 1H), 6.96–7.23 (m, 12H), 7.39 (s, 1H); ESI-MS 503 (M+H).

EXAMPLE 14
(2-(R)-(3-(S)-((4-(3-(3,4-Difluorophenyl)propyl)piperidin-1-yl)methyl)-4-(S)-phenylpyrrolidin-1-yl)(3-thienyl)acetic acid The title compound was prepared using procedures aanlogous to those described in EXAMPLE 13, except that 4-(3-(3,4-difluorophenyl)propyl)piperidine. HCL (from EXAMPLE 119, Step C) was substituted for 4-(3-phenylpropyl)piperdine.HCl in Step E. For the title compound: $R_F$: 0.29 (90:10:1 v/v/v CH₂Cl₂/MeOH/NH₄OH); $^1$H NMR (300 MHz, CD₃OD) δ 0.94–3.44 (m, 23H), 4.28 (br s, 1H), 6.78–7.41 (m, 11H); ESI-MS 539 (M+H).

EXAMPLE 15
2-(R)-(3-(S)-((4-(3-Phenylpropyl)piperidin-1-yl)methyl)-4-(S)-phenylpyrrolidin-1-yl)-2-(cyclopentyl)acetic acid
Step A: Cyclopentylacetic acid, 4-(methoxy)benzyl ester The title compound was prepared from 3 mL (23.9 mmol) of cyclopentylacetic acid using a procedure analogous to that described in EXAMPLE 10, Step B to provide 5.90 g (99%) of the title compound: $R_F$: 0.61 (4:1 v/v hexanes/EtOAc); $^1$H NMR (300 MHz) δ 1.10–1.17 (m, 2H), 1.50–1.63 (m, 4H), 1.75–1.83 (m, 2H), 2.20–2.35 (m, 3H), 3.81 (s, 3H), 5.04 (s, 2H), 6.88 (d, J=8.7, 2H), 7.28 (d, J=8.7, 2H).

Step B: (R/S)-2-Hydroxy-cyclopentylacetic acid, 4-(methoxy)benzyl ester

A solution of 450 mg (1.81 mmol) of cyclopentylacetic acid, 4-(methoxy)benzyl ester (from EXAMPLE 15, Step A) in 6 mL of THF was added to 2.15 mL of 1.0 M sodium bis(trimethylsilyl)amide solution in THF at −78° C. and the resulting mixture was stirred cold for 15 min. A solution of 700 mg (2.67 mmol) of (benzenesulfonyl)phenyloxaziridine in 3 mL of THF was the added and the resulting mixture was stirred at −78° C. for 1 h. The reaction was quenched with sat'd NH₄Cl and warmed to rt. The mixture was concentrated and the residue was dissolved in 100 mL of ether and washed with 100 mL of sat'd NaCl. The phases were separated and the aqueous layer was extracted with 100 mL of ether. The combined organic layers were dried over MgSO₄ and concentrated. Flash chromatography on silica gel using 9:1 v/v hexanes/EtOAc as the eluant afforded 233 mg (48%) of the title compound: $R_F$: 0.37 (4:1 v/v hexanes/EtOAc); $^1$H NMR (300 MHz) δ 1.36–1.69 (m, 8H), 2.22 (m, 11H), 3.81 (s, 3H), 4.14 (d, J=4.9, 11H), 5.14 (ABq, J=11.8, 2H), 6.89 (d, J=8.8, 2H), 7.29 (d, J=8.8, 2H).

Step C: 2-(R/S)-(3-(R)-(t-Butyldimethylsilyloxymethyl)-4-(S)-phenylpyrrolidin-1-yl)-2-(cyclopentyl)acetic acid, (4-methoxy)benzyl ester The title compound was prepared from 233 mg (0.88 mol) of (R/S)-2-hydroxy-cyclopentylacetic acid, 4-(methoxy)benzyl ester (from EXAMPLE 15, Step B) and 209 mg (0.71 mmol) of 3-(R)-(t-butyldimethylsilyloxymethyl)-4-(S)-phenylpyrrolidine (from EXAMPLE 1, Step E) using a procedure analogous to that described in EXAMPLE 1, Step G to provide 326 mg (84%) of the title compounds as a mixture of diastereomers: $R_F$: 0.64 (4:1 v/v hexanes/EtOAc); $^1$H NMR (300 Hz) δ 0.0 (2 s, 6H), 0.84, 0.85 (2 s, 9H), 1.18 (m, 11H), 1.42–1.82 (m, 7H), 2.23–2.34 (m, 2H), 2.65–3.18 (m, 6H), 3.43–3.59 (m, 2H), 3.81 (s, 3H), 5.01–5.19 (m, 2H), 6.85–6.91 (m, 2H), 7.14–7.36 (m, 7H).

Step D: 2-(R)-(3-(R)-(Hydroxymethyl)-4-(S)-phenylpyrrolidin-1-yl)-2-(cyclopentyl)acetic acid, 4-(methoxy)benzyl ester The title compound was prepared from 326 mg (0.60 mmol) of 2-(R/S)-(3-(R)-(t-butyldimethylsilyloxymethyl)-4-(S)-phenylpyrrolidin-1-yl)-2-(cyclopentyl)acetic acid, 4methoxy)benzyl ester (from EXAMPLE 15, Step C) using a procedure analogous to that described in EXAMPLE 1, Step H, except that the diastereomers were separated by HPLC (Chiralpak AD 2×25 cm column, 17:3 v/v hexanes/iPrOH, 9.0 mL/min, 220 nm) to provide 68 mg of 2-(R)-(3-(R)-(hydroxymethyl)-4-(S)-phenylpyrrolidin-1-yl)-2-(cyclopentyl)acetic acid, 4-(methoxy)benzyl ester and 66 mg of 2-(S)-(3-(R)-(hydroxymethyl)-4-(S)- phenylpyrrolidin-1-yl)-2-(cyclopentyl)acetic acid, 4-(methoxy)benzyl ester. For 2-(R)-(3-(R)-(hydroxymethyl)-4-(S)-phenylpyrrolidin-1-yl)-2-(cyclopentyl)acetic acid, 4-(methoxy)benzyl ester: HPLC retention time: 24.4 min; $^1$H NMR (300 MHz) δ 1.15–1.88 (m, 8H), 2.25–2.34 (m, 3H), 2.62 (t, J=8.4, 1H), 2.83 (dd, J=9.4, 4.4, 1H), 3.04–3.19 (m, 3H), 3.29 (t, J=8.4, 1H), 3.55 (dd, J=10.3, 5.6, 1H), 3.68 (dd, J=10.3, 4.4, 1H), 3.80 (s, 3H), 5.10 (s, 2H), 6.87 (d, J=8.7, 2H), 7.14–7.33 (m, 7H). For 2-(S)-(3-(R)-(hydroxymethyl)-4-(S)-phenylpyrrolidin-1-yl)-2-(cyclopentyl)acetic acid, 4-(methoxy)benzyl ester. HPLC retention time: 18.05 min.

Step E: 2-(R)(3-(R)-Formyl-4-(S)-phenylpyrrolidin-1-yl)-2-(cyclopentyl)acetic acid, 4-(methoxy)benzyl ester The title compound was prepared from 68 mg (0.16 mmol) of 2-(R)-(3-(R)-(hydroxymethyl)-4-(S)-phenylpyrrolidin-1-yl)-2-(cyclopentyl)acetic acid, 4-(methoxy)benzyl ester (from EXAMPLE 15, Step D) using a procedure analogous to that described in EXAMPLE 1, Step I to provide 67 mg (100%) of the title compound which was used without further purification: $R_F$: 0.48 (4:1 v/v hexanes/EtOAc); $^1$H NMR (300 MHz) δ 1.14–1.83 (m, 8H), 2.29 (m, 1H), 2.69–3.77 (m, 7H), 3.80 (s, 3H), 5.10 (s, 2H), 6.87 (d, J=8.7,22H), 7.16–7.33 (m, 7H), 9.61 (d, J=2.1, 1H).

Step F: 2-(R)-(3-(S)-((4-(3-Phenylpropyl)piperidin-1-yl)methyl)-4-(S)-phenylpyrrolidin-1-yl)-2-(cyclopentyl)acetic acid, 4-(methoxy)benzyl ester The title compound was prepared from 22 mg (0.053 mmol) of 2-(R)-(3-(R)-formyl-4-(S)-phenylpyrrolidin-1-yl)-2-(cyclopentyl)acetic acid, 4-(methoxy)benzyl ester (from EXAMPLE 15, Step E) and 13 mg (0.054 mmol) of 4-(3-phenylpropyl)piperidine.HCl using a procedure analogous to that described in EXAMPLE 1, Step J to provide 26.5 mg (81%) of the title compound: $R_F$: 0.25 (4:1 v/v hexanes/EtOAc); $^1$H NMR (300 MHz) δ 1.18–1.95 (m, 18H), 2.21–2.89 (m, 11H), 3.14–3.29 (m, 4H), 3.80 (s, 3H), 5.09 (ABq, J=11.9, 2H), 6.87 (d, J=8.7, 2H), 7.14–7.35 (m, 12H).

Step G: 2-(R)-(3-(S)-((4-(3-Phenylpropyl)piperidin-1-yl)methyl)-4-(S)-phenylpyrrolidin-1-yl)-2-(cyclopentyl)acetic acid The title compound was prepared from 26.5 mg (0.043 mmol) of 2-(R)-(3-(S((4-(3-phenylpropyl)piperidin-1-yl)methyl)-4-(S)-phenylpyrrolidin-1-yl)-2-(cyclopentyl)acetic acid, 4-(methoxy)benzyl ester (from EXAMPLE 15, Step F) using a procedure analogous to that described in EXAMPLE 10, Step F to provide 20 mg (95%) of the title compound: $R_F$: 0.33 (90:10:1 v/v/v CH$_2$Cl$_2$/MeOH/NH$_4$OH); 1H NMR (300 MHz, CD$_3$OD) δ 1.02–1.17 (m, 5H), 1.42–1.83 (m, 12H), 2.00–3.04 (m, 10H), 3.18–3.28 (m, 3H), 3.46–3.58 (m, 3H), 6.98–7.28 (m, 10H); ESI-MS 489 (M+H).

EXAMPLE 16

(2-(R)-(3-(S)-((4-(3-Phenylpropyl)piperidin-1-yl)methyl)-4-(S)-phenylpyrrolidin-1-yl)-2-(cyclopropyl)acetic acid The title compound was prepared using procedures analogous to those described in EXAMPLE 15, except that cyclopropylacetic acid was substituted for cyclopentylacetic acid in Step A. For the title compound: $R_F$: 0.21 (90:10:1 v/v/v CH$_2$Cl$_2$/MeOH/NH$_4$OH); $^1$H NMR (300 MHz, CD$_3$OD) δ 0.45–3.83 (m, 29H), 6.97–7.26 (m, 10H); ESI-MS 461 (M+H).

EXAMPLE 17

2-(R)-(3-(S)-((4-(3-Phenylpropyl)piperidin-1-yl)methyl)-4-(S)-phenylpyrrolidin-1-yl)-(3-cyclohexyl)propanoic acid Step A: (R/S)-3-Cyclohexyl-2-hydroxy-propanoic acid, 4-(methoxy)benzyl ester A solution of 0.50 g (2.32 mmol) of 4-(methoxy)benzylglyoxylate (azeotropically dried with 2×25 mL of toluene) in 2 mL of ether at −78° C. was treated with 7 mL of 0.5 M of cyclohexylmethylmagnesium bromide (prepared from 1.0 mL (7.1 mmol) of bromomethylcyclohexane, 174 mg (7.1 mmol) of Mg, 0.1 mL (1.1 mmol) of 1,2-dibromoethane in 14 mL of ether) and the resulting mixture was stirred cold for 1 h. The reaction was quenched with 1 N NaHCO$_3$ and the quenched mixture was partitioned between 100 mL of ether and 100 mL of sat'd NaHCO$_3$. The aqueous layer was separated and extracted with 100 mL of ether. The combined organic layers were dried over MgSO$_4$ and concentrated. Flash chromatography on silica gel using 4:1 v/v hexanes/EtOAc afforded 180 mg (26%) of the title compound: $R_F$: 0.32 (4:1 v/v hexanes/EtOAc); $^1$H NMR (300 MHz) δ 0.84–1.82 (m, 13H), 3.81 (s, 3H), 4.23 (m, 1H), 5.14 (s, 2H), 6.90 (d, J=8.7, 2H), 7.29 (d, J=8.7, 2H).

Step B: 2-(R)-(3-(S)-((4-(3-Phenylpropyl)piperidin-1-yl)methyl)-4-(S)-phenylpyrrolidin-1-yl)-3-(cyclohexyl)propanoic acid The title compound was prepared from (R/S)-3-cyclohexyl-2-hydroxypropanoic acid, 4-(methoxy)benzyl ester (from EXAMPLE 17, Step A) using procedures analogous to those described in EXAMPLE 15, Steps C–G, except that the diastereomers in Step D were separated by HPLC using the following conditions: Chiralpak AD 2×25 cm column, 17:3 v/v hexanes/iPrOH, 9.0 mL/min, 220 nm. For the title compound: $R_F$: 0.46 (90:10:1 v/v/v CH$_2$Cl$_2$/MeOH/NH$_4$OH). $^1$H NMR (300 MHz, CD$_3$OD) δ 0.7–3.6 (m, 37H), 7.0–7.3 (m, 10H); ESI-MS 517 (M+H).

EXAMPLE 18

2-(R)-(3-(S)-((4-(3-Phenylpropyl-1piperidin-1-yl)methyl)-4-(S)-phenylpyrrolidin-1-yl)-2-(cyclobutyl)acetic acid The title compound was prepared using procedures analogous to those described in EXAMPLE 17, except that bromomethylcyclobutane was substituted for bromomethylcyclohexane in Step A and the diastereomers in Step D were separated on HPLC using the following conditions: Chiralcel OJ 2×25 cm column, 7:3 v/v hexanes/iPrOH, 9.0 mL/min, 220 nm. For the title compound: $R_F$: 0.49 (90:10:1 v/v/v CH$_2$Cl$_2$/MeOH/NH$_4$OH); $^1$H NMR (300 MHz, CD$_3$OD) δ 0.95–3.48 (m, 31H), 6.97–7.23 (m, 10H); ESI-MS 475 (M+H).

EXAMPLE 19

2-(R)-(3(S)-((4-(3-Phenylpropyl)piperidin-1-yl)methyl)-4-(S)-phenylpyrrolidin-1-yl)-(3-cyclobutyl)propanoic acid Step A: N,N'-Dimethyl-N,N'-dimethoxy oxamide A mixture of 48.0 g (0.49 mol) of N,O-dimethylhydroxylamine HCl in 250 mL of 3:2 v/v CH$_2$Cl$_2$/pyridine was cooled to −78° C. and treated with 17.4 mL (0.2 mol) of oxalyl chloride maintaining the internal temperature at less than −70° C. The resulting mixture was allowed to warm to rt and stirred for 20 h. The reaction was quenched with 250 mL of sat'd NaCl and the quenched mixture was extracted with 3×400 mL of CH$_2$Cl$_2$. The extracts were combined, dried over MgSO$_4$ and concentrated. Recrystallization from 250 mL of methyl t-butyl ether afforded 24.28 g (69%) of the title compound: $^1$H NMR (500 MHz) δ 3.25 (s, 6H), 3.75 (s, 6H).

Step B: N-Methyl-N-methoxy 2-oxo-3-cyclobutyl propanamide

A suspension of 4.86 g (0.20 mol) of magnesium turnings in 250 mL of THF was treated with 2.0 mL (0.022 mol) of 1,2-dibromoethane and then warmed until gas evolution from the surface of the Mg was visible. 15.2 mL (0.178 mol) of 1,2-dibromoethane was added at rate to maintain a gentle reflux. After the addition, the resulting mixture was heated at reflux for 30 min, then cooled to rt. Potassium (15.6 g, 0.40 mol) was added in ~1 g portions; the mixture was warmed until the potassium started to react and a fine black precipitate formed. This was repeated until all of the potassium was added to the reaction mixture. The resulting suspension of Mg was cooled to 0° C.

The finely divided Mg was treated with 22.5 mL (0.20 mol) of bromomethylcyclobutane maintaining the internal temperature at <5° C. The resulting mixture was stirred cold for 1 h, then was treated with 26.40 g (0.15 mol) of N,N'-dimethyl-N,N'-dimethoxy oxamide (from EXAMPLE 19, Step A) in portions as a solid. The resulting mixture was stirred at 0° C. for 16 h. The reaction was poured onto a mixture of 100 mL conc. HCl and 500 g of ice under $N_2$ atmosphere. The quenched mixture was extracted with 1.5 L of EtOAc. The extract was washed with 500 mL of sat'd NaCl, dried over $MgSO_4$ and concentrated. Flash chromatography on 500 g of silica gel using 3:1 v/v hexanes/EtOAc as the eluant afforded 22.3 g (80%) of the title compound: $^1$H NMR (500 MHz) δ 1.66–1.76 (m, 2H), 1.82–1.98 (m, 2H), 2.12–2.22 (m, 2H), 2.74–2.84 (3H), 3.20 (s, 3H), 3.66 (s, 3H).

Step C: N-Methyl-N-methoxy 2-(S)-hydroxy-3-cyclobutyl propanamide

A mixture of 11.40 g (61.5 mmol) of N-methyl-N-methoxy 2-oxo-3-cyclobutyl propanamide (from EXAMPLE 19, Step B) and 0.5 N (R)-Alpine Borane® solution in THF was concentrated and stirred at rt for 5 days. The mixture was cooled to 0° C. and quenched with 6.8 mL (75.0 mmol) of isobutyraldehyde. The resulting mixture was diluted with 200 mL of ether and treated with 7.5 mL (125 mmol) of ethanolamine. The precipitate that formed was filtered and the filtrate was concentrated. Flash chromatography on 500 g of silica gel using 9:1 v/v $CH_2Cl_2$/EtOAc as the eluant afforded 1 1.48 g (99%, ee=91%) of the title compound: $^1$H NMR (500 MHz) δ 1.59–1.70 (m, 2H), 1.67 (s, 1H), 1.77–1.83 (m, 2H), 1.82–1.92 (m, 1H), 2.03–2.13 (m, 2H), 2.53–2.60 (m, 1H), 3.23 (s, 3H), 3.72 (s, 3H), 4.31 (app d, J=5.5, 1H); HPLC: Chiralpak AS 4.6×250 mm column, 75/25 hexanes/iPrOH, 0.5 mL/min, 210 nm. (S)-Enantiomer=13.3 min, (R)-enantiomer=17.2 min.

Step D: 2-(S)Hydroxy-3-cyclobutyl propanoic acid

A suspension of 33.66 g (0.3 mol) of potassium t-butoxide in 50 mL of THF was treated with 5.40 mL (0.3 mol) of $H_2O$. The resulting mixture was treated with a solution of 11.48 g (0.061 mol) of N-methyl-N-methoxy 2-(S)-hydroxy-3-cyclobutyl propanamide (from EXAMPLE 19, Step C) in 20 mL of THF and stirred at rt for 20 h. The mixture was concentrated and the residue was partitioned between 300 mL of ether and 200 mL of $H_2O$ and the layers were separated. The pH of the aqueous layer was adjusted to 2 with conc. HCl and extracted with 300 mL of EtOAc. The extract was washed with 100 mL of sat'd NaCl, dried over $MgSO_4$ and concentrated to afford 7.50 g (85%) of the title compound: $^1$H NMR (500 MHz) δ 1.66–1.76 (m, 2H), 1.78–1.98 (4H), 2.06–2.16 (m, 2H), 2.51–2.61 (m, 1H), 4.20 (dd, J=8.0,4.0, 1H).

Step E: 4-(Methoxy)benzyl 2-(S)-hydroxy-3-(cyclobutyl) propanoate

A mixture of 432 mg (3.0 mmol) of 2-(S)-hydroxy-3-cyclobutyl propanoic acid (from EXAMPLE 19, Step D), 0.61 mL of 4-(methoxy)benzyl chloride and 0.63 mL of TEA was stirred at rt for 20 h. The reaction mixture was partitioned between 100 mL of ether and 50 mL of $H_2O$ and the layers were separated. The organic layer was washed with 50 mL of sat'd $NaHCO_3$, 50 mL of 2.0 N HCl, 2×50 mL of $H_2O$ and 50 mL of sat'd NaCl, dried over $MgSO_4$ and concentrated. Flash chromatography on 30 g of silica gel using 4:1 v/v hexanes/ether as the eluant afforded 598 mg (75%) of the title compound: $^1$H NMR (500 MHz) δ 1.56–1.94 (6H), 1.98–2.12 (m, 2H), 2.44–2.56 (m, 1H),2.64 (br s, 1H), 3.82 (s, 3H), 4.11–4.13 (m, 1H), 5.19 (ABq, J=25.0, 2H), 6.90 (d, J=9.0, 2H), 7.30 (d, J=9.0, 2H).

Step F: 2-(R)-(3-(R)-Formyl-4-(S)-phenylpyrrolidin-1-yl)-3-(cyclobutyl)propanoic acid, 4-(methoxy)benzyl ester The title compound was prepared from 3-(R)-(t-butyldimethylsilyloxymethyl)-4-(S)-phenylpyrrolidine (from EXAMPLE 1, Step E) and 4-(methoxy)benzyl 2-(S)-hydroxy-3-(cyclobutyl)propanoate (from EXAMPLE 19, Step E) using procedures analogous to those described in EXAMPLE 1, Steps G–I.

Step G: 2-(R)-(3-(S((4-(3-Phenylpropyl)piperidin-1-yl) methyl)-4-(S)-phenylpyrrolidin-1-yl)-3-(cyclobutyl) propanoic acid, 4-methoxybenzyl ester The title compound was prepared from 21 mg (0.049 mmol) of 2-(R)-(3-(R)-formyl-4-(S)-phenylpyrrolidin-1-yl)-3-(cyclobutyl)propanoic acid, 4-(methoxy)benzyl ester (from EXAMPLE 19, Step F) and 11.5 mg (0.047 mmol) of 4-(3-phenylpropyl)piperidine.HCl using a procedure analogous to that described in EXAMPLE 1, Step J to provide 18.5 mg (61%) of the title compound: $R_F$: 0.27 (4:1 v/v hexanes/EtOAc); $^1$H NMR (300 MHz) δ 1.05–3.29 (m, 33H), 3.80 (s, 3H), 5.08 (ABq, J=11.9,22H), 6.87 (d, J=8.4, 2H), 7.14–7.34 (m, 12H).

Step H: 2-(R)-(3-(S)-((4-(3-phenylpropyl)piperidin-1-yl) methyl)-4-(S)-phenylpyrrolidin-1-yl)-3-(cyclobutyl) propanoic acid The title compound was prepared from 18.5 mg (0.030 mmol) of 2-(R)-(3-(S)-((4-(3-phenylpropyl)piperidin-1-yl) methyl)-4-(S)-phenylpyrrolidin-1-yl)-3-(cyclobutyl) propanoic acid, 4-(methoxy)benzyl ester (from EXAMPLE 19, Step G) using a procedure analogous to that described in EXAMPLE 10, Step F to provide 15 mg (100%) of the title compound: $R_F$: 0.40 (90:10:1 v/v/v $CH_2Cl_2$/MeOH(OH); $^1$H NMR (300 MHz, $CD_3OD$) δ 1.01–3.55 (m, 33H), 6.97–7.25 (m, 10H); ESI-MS 489 (M+H).

EXAMPLE 20

2-(R)-(3-(S)-((4-(3-(4-Fluorophenyl)propyl)piperidin-1-yl) methyl)-4-(S)-(3-fluoro-phenyl)pyrrolidin-1-yl)-3-(cyclopentyl)propanoic acid Step A: N-Methoxy-N-methyl cyclopentylacetamide A solution of 2.0 mL (15.9 mmol) of cyclopentylacetic acid in 80 mL of $CH_2Cl_2$ at 0° C. was treated with 3.7 mL (33.6 mmol) of N-methyl-morpholine and 2.2 mL (16.9 mmol) of isobutyl chloroformate. After stirring for 20 min, 1.61 g (16.5 mmol) of N,O-dimethylhydroxylamine HCl was added. The reaction was warmed to rt and stirred for 3 h. The reaction was partitioned between 200 mL of EtOAc and 200 mL 2.0 N HCl. After separating the phases, the organic layer was washed with 200 mL of 1.0 N $NaHCO_3$, dried over $Na_2SO_4$ and concentrated. Flash chromatography on silica gel using 4:1 v/v hexanes/EtOAc afforded 2.28 g (83%) of the title compound: $R_F$: 0.27 (4:1 v/v hexanes/EtOAc). $^1$H NMR (300 MHz) δ 1.12–1.23 (m, 2H), 1.51–1.89 (m, 6H), 2.28 (m, 1H), 2.44 (d, J=7.5, 2H), 3.18 (s, 3H), 3.67 (s, 3H).

Step B: Cyclopentylmethylene phenyl ketone

A solution of 1.98 g (11.5 mmol) of N-methoxy-N-methyl-cyclopentylacetamide (from EXAMPLE 20, Step A) in 115 mL of THF at 0° C. was treated with 13.0 mL of 1.8 M phenyllithium in cyclohexane/ether solution over 40 min. After stirring for 1 h, the reaction was quenched with 2.0 N HCl and warmed to rt. The quenched reaction was partitioned between 200 mL of ether and 200 mL 2.0 N HCl and the layers were separated. The organic layer was washed with 200 mL of 1.0 N NaHCO₃, dried over Na₂SO₄ and concentrated. Flash chromatography on silica gel using 9:1 v/v hexanes/EtOAc afforded 1.57 g (72%) of the title compound: $R_F$: 0.66 (4:1 v/v hexanes/EtOAc); ¹H NMR (300 MHz) δ 1.14–1.22 (m, 2H), 1.52–1.67 (m, 4H), 1.82–1.92 (m, 2H), 2.37 (m, 1H), 2.98 (d, J=7.1, 2H), 7.26–7.61 (m, 5H).

Step C: (S)-2-Cyclopentyl-1-phenylethanol

A solution of 2.7 mL of 1.0 M (R)-2-methyl-CBS-oxazaborolidine solution in toluene in 4 mL of CH₂Cl₂ at −25° C. was treated with 1.4 mL of 2.0 M borane.methyl sulfide in THF and stirred cold for 10 min. A solution of 501 mg (2.66 mmol) of cyclopentylmethylene phenyl ketone (from EXAMPLE 20, Step B) in 2 mL of CH₂Cl₂ was added over 25 min and the resulting mixture was stirred cold for 45 min. The reaction was quenched by pouring it into cold (−25° C.) MeOH. The quenched reaction was warmed to rt and stirred for 45 min until gas evolution ceased. The mixture was concentrated and the residue dissolved in 20 mL of MeOH and concentrated again. Flash chromatography on silica gel using 17:3 v/v hexanes/EtOAc afforded 413 mg (81%) of the title compound: $R_F$: 0.53 (4:1 v/v hexanes/EtOAc); ¹H NMR (300 MHz) δ 1.10–1.17 (m, 2H), 1.47–1.89 (m, 9H), 4.69 (m, 1H), 7.25–7.35 (m, 5H).

Step D: Acetic acid, (S)-2-cyclopentyl-1-phenylethyl ester

A solution of 406 mg (2.13 mmol) of (S)-2-cyclopentyl-1-phenylethanol (from EXAMPLE 20, Step C) in 9 mL of pyridine was treated with 1 mL of acetic anhydride. After stirring for 6 h, the reaction was concentrated. Flash chromatography on silica gel using 7.5% EtOAc in hexane afforded 495 mg (100%) of the title compound: $R_F$: 0.75 (4:1 v/v hexanes/EtOAc); ¹H NMR (300 MHz) δ 1.10–1.21 (m, 2H), 1.44–2.04 (m, 9H), 2.05 (s, 3H), 5.75 (dd, J=8.0, 6.1, 1H), 7.25–7.34 (m, 5H).

Step E: (S)-2-Acetoxy-3-cyclopentylpropanoic acid

A solution of 479 mg (2.0 mmol) of acetic acid, (S)-2-cyclopentyl-1-phenylethyl ester (from EXAMPLE 20, Step D) in 14 mL of 2:2:3 v/v/v CCl₄/CH₃CN/H₂O was treated with 6.59 g (28.9 mmol) of periodic acid and 7.8 mg (0.037 mmol) of RuCl₃.H₂O. The reaction was warmed to 33° C. and stirred for 4 h. After cooling to 0° C., 100 mL of ether was added. After stirring for 10 min and separating the phases, the aqueous layer was extracted with 2×100 mL of ether. The combined organic layers were dried over Na₂SO₄ and concentrated to give 395 mg (95%) of the title compound: $R_F$: 0.62 (90:10:1 v/v/v CH₂Cl₂/MeOH/HOAc); ¹H NMR (300 MHz) 81.09–1.98 (m, 11H), 2.14 (s, 3), 5.03 (dd, J=8.8,4.3, 1H), 8.9 (br, 1H).

Step F: 2-(S)Hydroxy-3-(cyclopentyl)propanoic acid

A solution of 395 mg (1.97 mmol) of 2-(S)-acetoxy-3cyclopentyl propanoic acid (from EXAMPLE 20, Step E) in 10 mL MeOH and 1 mL of H₂O was treated with 1.29 g (9.33 mmol) of K₂CO₃ and stirred at rt for 30 h. The volatiles were removed under reduced pressure. The crude product was partitioned between 100 mL of ether and 100 mL of H₂O and the layers were separated. The aqueous layer was acidified to pH 1–2 using 2.0 N HCl and extracted with 3×150 mL of EtOAc. The combined organic layers were dried over Na₂SO₄ and concentrated to give 287 mg (92%) of the title compound: ¹H NMR (300 MHz) δ 1.11–2.15 (m, 11H), 4.27 (dd, J=8.1, 4.7, 1H), 6.5 (br, 1H).

Step G: 2-(S)-Hydroxy-3-(cyclopentyl)propanoic acid, benzyl ester

A solution of 287 mg (1.81 mmol) of 2-(S)-hydroxy-3-(cyclopentyl)propanoic acid (from EXAMPLE 20, Step F) in 8 mL of DMF was treated with 0.38 mL (2.72 mmol) of TEA and 0.33 mL (2.77 mmol) of benzyl bromide and stirred at rt for 22 h. The reaction was diluted with 200 ml of ether and washed with 200 mL of H₂O, 200 mL of 2.0 N HCl, 200 mL of 1.0 N NaHCO₃, 200 mL of H₂O and 200 mL of sat'd NaCl. The organic layer was dried over MgSO₄ and concentrated. Flash chromatography on silica gel using 17:3 v/v hexanes/EtOAc afforded 102 mg (22%, ee=95.5%) of the title compound: $R_F$: 0.40 (4:1 v/v hexanes/EtOAc); ¹H NMR (300 MHz) δ 1.04–1.17 (m, 2H), 1.46–1.87 (m, 8H), 1.99 (m, 1H), 2.65 (m, 1H), 4.22 (dd, J=7.8,4.8, 1H), 5.23 (ABq, J=12.3, 2H), 7.32–7.41 (m, 5H). HPLC Conditions: Chiralpak AS 4.6×250 mm column, 17:3 v/v hexanes/iPrOH, 0.5 mL/min, 220 nm. Retention times: (S)-Enantiomer=12.2 min; R-enantiomer=15.3 min.

Step H: 3-(R)-(t-Butyldimethylsilyloxymethyl)-4-(S)-(3-fluorophenyl) pyrrolidine The title compound was prepared using procedures analogous to those described in EXAMPLE 1, Steps A–E, except that trans-(3-fluoro)cinnamic acid was subtituted for trans-cinnamic acid in Step A. For the title compound: ¹H NMR (400 MHz) δ 0.013 (s, 3H), 0.016 (s, 3H), 0.87 (s, 9H), 2.09 (br s, 1H), 2.30–2.37 (m, 1H), 2.88–2.90 (3H), 2.23 (dd, J=8.0, 11.2, 1H), 3.39 (dd, J=6.8, 10.0. 11), 3.56 (dd, J=6.0, 10.0, 1H), 3.64 (dd, J=5.2, 10.0), 6.86–6.91 (m, 1H), 6.95 (dt, J=12.0, 2.4, 1H), 7.01 (d, J=7.6, 1H), 7.22–7.27 (m, 1M; ESI-MS 310 (M+H); HPLC A: 3.05 min.

Step I: 2-(R)-(3-(R)-(t-Butyldimethylsilyloxymethyl)-4-(S)-(3-fluorophenyl)pyrrolidin-1-yl)-3-(cyclopentyl)propanoic acid, benzyl ester The title compound was prepared from 100 mg (0.40 mmol) of 2-(S)-hydroxy-3-(cyclopentyl)propanoic acid, benzyl ester (from EXAMPLE 20, Step G) and 154 mg (0.49 mmol) of 3-(R)-(t-butyldimethylsilyloxy-methyl)-4-(S)-(3-fluorophenyl)pyrrolidine (from EXAMPLE 20, Step H) using a procedure analogous to that described in EXAMPLE 1, Step G to provide 189 mg (87%) of the title compound: $R_F$: 0.59 (4:1 v/v hexanes/EtOAc); ¹H NMR (300 MHz) δ 0.0 (s, 6H), 0.84 (s, 9H), 1.05–1.09 (m, 2H), 1.45–1.84 (m, 9H), 2.32 (m, 1H), 2.64 (br t, 1H), 2.74 (br t, 1H), 2.94 (br q, 1H), 3.04–3.15 (m, 2H), 3.37–3.57 (m, 3H), 5.16 (s, 2H), 6.83–6.98 (m, 3H), 7.16–7.39 (m, 6H).

Step J: 2-(R)-(3-(R)-(Hydroxymethyl)-4-(S)-(3-fluorophenyl)pyrrolidin-1-yl)-3-(cyclopentyl)propanoic acid, benzyl ester The title compound was prepared from 189 mg (0.35 mmol) of 2-(R)-(3-(R)-(t-butyldimethylsilyloxymethyl)-4-(S)-(3-fluorophenyl)pyrrolidin-1-yl)-3-cyclopentylpropanoic acid, benzyl ester (from EXAMPLE 20, Step I) using a procedure analogous to that described in EXAMPLE 1, Step H to provide 143 mg (95%) of the title compound: $R_F$: 0.71 (4:1 v/v hexanes/EtOAc); ¹H NMR (300 MHz) δ 1.02–1.11 (m, 2H), 1.44–2.04 (m, 9H), 2.33 (m, 1H), 2.66 (br t, 1H), 2.79 (m, 1H), 3.06–3.14 (m, 1H), 3.29 (m, 1H), 3.41 (m, 1H), 3.56 (dd, J=10.4, 6.0, 1H), 3.67 (dd, J=10.4, 4.5, 1H), 5.17 (ABq, J=12.1, 2H), 6.85–6.98 (m, 3H), 7.19–7.40 (m, 6H).

Step K: 2-(R)-(3-(R)-Formyl-4-(S)-(3-fluorophenyl) pyrrolidin-1-yl)-3-(cyclopentyl)propanoic acid, benzyl ester The title compound was prepared from 143 mg (0.33 mmol) of 2-(R)-(3-(R)-(hydroxymethyl)-4-(S)-(3-fluorophenyl)pyrrolidin-1-yl)-3-cyclopentylpropanoic acid, benzyl ester (from EXAMPLE 20, Step J) using a procedure analogous to that described in EXAMPLE 1, Step I to provide 129 mg (91%) of the title compound. $R_F$: 0.41 (4:1 v/v hexanes/EtOAc); ¹H NMR (300 MHz) δ 1.04–1.12 (m, 2H), 1.45–2.04 (m, 9H), 2.75 (br t, 1H), 2.94 (m, 1H), 3.14–3.30 (m, 3H), 3.42–3.58 (m, 2H), 5.17 (s, 2H), 6.88–6.99 (m, 3H), 7.20–7.39 (m, 6H) 9.62 (d, J=2.0, 1H).

Step L: 2-(R)-(3-(S((4-(3-(4-Fluorophenyl)propyl)piperidin-1-yl)methyl)-4-(S)-(3-fluorophenyl)pyrrolidin-1-yl)-3-(cyclopentyl)propanoic acid, benzyl ester The title compound was prepared from 20 mg (0.047 mmol) of 2-(R)-(3-(R)-formyl-4-(S)-(3-fluorophenyl)pyrrolidin-1-yl)-3-cyclopentylpropanoic acid, benzyl ester (from EXAMPLE 20, Step K) and 13 mg of 4-(3-(4-fluorophenyl)propyl)piperidine.HCl (from EXAMPLE 96, Step B) using a procedure analogous to that described in EXAMPLE 1, Step J to provide 26 mg (89%) of the title compound: $R_F$: 0.20 (4:1 v/v hexanes/EtOAc); $^1$H NMR (300 MHz) δ 1.01–1.83 (m, 22H), 2.21–2.88 (m, 10H), 3.12–3.19 (m, 2H), 3.37 (m, 1H), 5.16 (ABq, J=12.1 Hz, 2H), 6.83–7.39 (m, 13H).

Step M: 2-(R)-(3-(S)-((4-(3-(4-Fluorophenyl)propyl)piperidin-1-yl)methyl)-4-(S)-(3-fluorophenyl)pyrrolidin-1-yl)-3-(cyclopentyl)propanoic acid The title compound was prepared from 26 mg (0.041 mmol) of 2-(R)-(3-(S)-((4-(3-(4-fluorophenyl)propyl)piperidin-1-yl)methyl)-4-(S)-(3-fluorophenyl)pyrrolidin-1-yl)-3-cyclopentylpropanoic acid, benzyl ester (from EXAMPLE 20, Step L) using a procedure analogous to that described in EXAMPLE 1, Step K to provide 20 mg (90%) of the title compound: $^1$H NMR (300 MHz, CD$_3$OD) δ 0.95–2.02 (m, 20H), 2.28–3.22 (m, 12H1), 3.35–3.57 (m, 3H), 6.80–7.29 (m, 8H); ESI-MS 539 (M+H); HPLC A: 3.28 min.

EXAMPLE 21

2-(R)-(3-(S)-((4-(3-(4-Fluorophenyl)propyl)piperidin-1-yl)methyl)-4-(S)-(3-fluorophenyl)pyrrolidin-1-yl)-3-(cyclopropyl)propanoic acid Step A: 2-(S)-Hydroxy-3-(cyclopropyl)propanoic acid A 1 L, 3-neck flask was equipped with two dropping funnels, one containing 21.3 mL of 2.0 N H$_2$SO$_4$ and the other containing 21.3 mL of 2.0 N NaNO$_2$. A mixture of 5.00 g (38.7 mmol) of 2-(S)amino-3-(cyclopropyl)propanoic acid in 28 mL of H$_2$O at 0° C. was treated with a sufficient amount of the acid solution to dissolve the solid. The remaining H$_2$SO$_4$ solution and the NaNO$_2$ solution were added, maintaining the internal temperature at less than 5° C. The resulting mixture was stirred cold for 3 h, then warmed to rt and stirred for 20 h. The reaction mixture was saturated with NaCl and extracted with 4×100 mL of EtOAc. The extracts were dried over MgSO$_4$ and concentrated to afford 4.30 g (85%) of the title compound: $^1$H NMR (300 MHz) δ 0.13–0.18 (m, 2H), 0.48–0.54 (m, 2H), 0.89 (m, 1H), 1.67–1.76 (m, 2H), 4.37 (dd, J=6.4, 4.7 Hz, 1H).

Step B: 2-(S)-Hydroxy-3-(cyclopropyl)propanoic acid, 4-(methoxy)benzyl ester

The title compound was prepared from 1.0 g (7.6 mmol) of 2-(S)-hydroxy-3-(cyclopropyl)propanoic acid (from EXAMPLE 21, Step A), 1.6 mL (11.4 mmol) of TEA and 1.6 mL (11.8 mmol) of 4-(methoxy)benzyl chloride in 10 mL of DMF using a procedure analogous to that described in EXAMPLE 20, Step G to provide 1.70 g (88%, ee=97.5%) of the title compound: $R_F$: 0.20 (4:1 v/v hexanes/EtOAc); $^1$H NMR (300 MHz) δ–0.01–0.09 (m, 2H), 0.40–0.45 (m, 2H), 0.84 (m, 1H), 1.55–1.67 (m, 2H), 2.82 (br m, 1H), 3.81 (s, 3H), 4.25 (br m, 1H), 5.14 (ABq, J=11.8, 2H), 6.90 (d, J=8.7, 2H), 7.29 (d, J=8.7, 2H). HPLC Conditions:

Chiralcel OB 4.6×250 mm column, 13:7 v/v hexanes/EtOH, 0.5 mL/min, 220 nm. Retention times: (S)-enantiomer, 20.4 min; (R)-enantiomer, 17.3 min.

Step C: 2-(R)-(3-(R)-(t-Butyldimethylsilyloxymethyl)-4-(S)-(3-fluoro-phenyl)pyrrolidin-1-yl)-3-(cyclopropyl)propanoic acid, 4-(methoxy)benzyl ester The title compound was prepared from 200 mg (0.8 mmol) of 2-(S)-hydroxy-3-cyclopropyl propanoic acid, 4-(methoxy)benzyl ester (from EXAMPLE 21, Step B) and 321 mg (1.0 mmol) of 3-(R)-(t-butyldimethylsilyloxymethyl)-4-(S)-(3-fluorophenyl)pyrrolidine (from EXAMPLE 20, Step H) using a procedure analogous to that described in EXAMPLE 1, Step G to provide 396 mg (91%) of the title compound: $R_F$: 0.59 (4:1 a/v hexanes/EtOAc); $^1$H NMR (300 MHz) δ 0.01–0.14 (m, 81), 0.39–0.54 (m, 2H), 0.72 (m, 11H), 0–85 (s, 9H), 1.61–1.72 (m, 2H), 2.34 (m, 1H), 2.64 (br t, 1H), 2.75 (br t, 1H), 2.95–3.17 (m, 31), 3.38–3.60 (m, 3H), 3.82 (s, 3H), 5.13 (s, 3H), 6.85–7.00 (m, 5H), 7.18–7.36 (m, 3H).

Step D: 2-(R(3-(R)(Hydroxymethyl)-4-(S)-(3-fluorophenyl)pyrrolidin-1-yl)-3-(cyclopropyl)propanoic acid, (methoxy)benzyl ester The title compound was prepared from 4.0 g (7.36 mmol) of 2-(R)-(3(R)-(t-butyldimethylsilyloxymethyl)-4-(S)-(3-fluorophenyl)pyrrolidin-1-yl)-3-(cyclopropyl)propanoic acid, 4-(methoxy)benzyl ester (from EXAMPLE 21, Step C) using a procedure analogous to that described in EXAMPLE 1, Step H to provide 3.0 g (95%) of the title compound: $R_F$: 0.25 (1:1 v/v hexanes/EtOAc); $^1$H NMR (300 MHz) δ 0.0–0.09 (m, 2H), 0.36–0.47 (m, 21), 0.69 (m, 1H), 1.56–1.74 (m, 2H), 2.20–2.36 (m, 2H), 2.63 (t, J=8.3, 1H), 2.78 (dd, J=9.0,4.9, 1H), 3.03–3.13 (m, 2H), 3.26 (t, J=8.4, 11), 3.38 (dd, J=8.4,6.1, 11), 3.53–3.71 (m, 2H), 3.80 (s, 3H), 5.11 (ABq, J=11.8,22H), 6.85–6.98 (m, 5H), 7.18–7.34 (m, 3H).

Step E: 2-(R)-(3-(R)-Formyl-4-(S)-(3-fluorophenyl)pyrrolidin-1-yl)-3-(cyclopropyl)propanoic acid, 4-(methoxy)benzyl ester The title compound was prepared from 3.0 g (7.0 mmol) of 2-(R)-(3-(R)-(hydroxymethyl)-4-(S)-(3-fluorophenyl)pyrrolidin-1-yl)-3-(cyclopropyl)propanoic acid, 4-(methoxy)benzyl ester (from EXAMPLE 21, Step D) using a procedure analogous to that described in EXAMPLE 1, Step I to provide 2.27 g (76%) of the title compound: $R_F$: 0.40 (7:3 v/v hexanes/EtOAc); $^1$H NMR (300 MHz) δ 0.01–0.10 (m, 2H), 0.360.49 (m, 2H), 0.69 (m, 11H), 1.54–1.76 (m, 2H), 2.64–3.61 (m, 7H), 3.80 (s, 3H), 5.12 (s, 2H), 6.84–7.04 (m, 5H), 7.21–7.34 (m, 3H) 9.63 (d, J=1.9, 1H).

Step F: 2-(R)-(3-(S((4-(3-(4-Fluorophenyl)propyl)piperidin-1-yl)methyl)-4-(S)-(3-fluorophenyl)pyrrolidin-1-yl)-3cyclopropylpropanoic acid, 4-(methoxy)benzyl ester The title compound was prepared from 33.5 mg (0.07 mmol) of 2-(R)-(3-(R)-formyl-4-(S)-(3-fluorophenyl)pyrrolidin-1-yl)-3-(cyclopropyl)propanoic acid, 4-(methoxy)benzyl ester (from EXAMPLE 21, Step E) and 20.5 mg (0.07 mmol) of 4-(3-(4-fluorophenyl)propyl)-piperidine.HCl (from EXAMPLE 96, Step B) using a procedure analogous to that described in EXAMPLE 1, Step J to provide 40 mg (80%) of the title compound: $R_F$: 0.47 (1:1 v/v hexanes/EtOAc); $^1$H NMR (300 MHz) δ 0.01–0.07 (m, 2H), 0.34–0.47 (m, 2H), 0.68 (m, 1H), 0.96–3.41 (m, 26H), 3.80 (s, 3H), 5.12 (ABq, J=11.9, 21), 6.82–7.34 (m, 12H).

Step G: 2-(R)-(3-(S)-((4-(3-(4-Fluorophenyl)propyl)piperidin-1-yl)methyl)-4-(S)-(3-fluorophenyl)pyrrolidin-1-yl)-3-(cyclopropyl)propanoic acid The title compound was prepared from 40 mg (0.06 mmol) of 2-(R)-(3-(S)-((4-(3-(4-fluorophenyl)propyl)piperidin-1-yl)methyl)-4-(S)(3-fluorophenyl)pyrrolidin-1-yl)-3-(cyclopropyl)propanoic acid, 4-(methoxy)benzyl ester (from EXAMPLE 21, Step F) using a procedure analogous to that described in EXAMPLE 10, Step F to provide 30 mg (93%) of the title compound. $R_F$: 0.37 (90:10:1 v/v/v CH$_2$Cl$_2$/MeOH/NH$_4$OH); HPLC A: 2.96 min; ESI-MS 511 (M+H). $^1$H NMR (300 MHz, CD$_3$OD) δ 0.02–0.06 (m, 2H), 0.35–0.42 (m, 2H), 0.69 (m, 1H), 0.96–3.54 (m, 26H), 6.78–7.27 (m, 8H).

EXAMPLE 22

2-(R)-(3-(S)-((4-(3-(Benzofurazan-4-yl)propyl)piperidin-1-yl)methyl)-4-(S)-phenylpyrrolidin-1-yl)-2-(cyclopentyl) acetic acid The title compound was prepared using procedures analogous to those described in EXAMPLE 15, except that 4-(3-(Benzofurazan-4-yl)propyl)piperidine. HCl (from EXAMPLE 117, Step B) was substituted for 4-(3-phenylpropyl)piperidine. HCl in Step F. For the title compound: R$_F$: 0.48 (90:10:1 CH$_2$Cl$_2$/MeOH/NH$_4$OH); $^1$H NMR (300 MHz, CD$_3$OD) δ 1.05–3.64 (m, 33H), 7.12–7.74 (m, 8H); ESI-MS 531.7 (M+H).

EXAMPLE 23

2-(R)-(3-(S)-((4-(3-(3,5-Difluorophenyl)propyl)piperidin-1-yl)methyl)-4-(S)-phenylpyrrolidin-1-yl)-3-(cyclobutyl) propanoic acid Step A: 2-(R)-(3-(S)-((4-(3-(3,5-Difluorophenyl)propyl)piperidin-1-yl)methyl)-4-(S)-phenylpyrrolidin-1-yl)-3-(cyclobutyl)-propanoic acid, (4-methoxy)benzyl ester The title compound was prepared from 19 mg (0.04 mmol) of 2-(R)-(3-(R)-formyl-4-(S)-phenylpyrrolidin-1-yl)-3-(cyclobutyl)propanoic acid, (4-methoxy)benzyl ester (from EXAMPLE 19, Step F) and 12.5 mg (0.04 mmol) of 4-(3-(3,5-difluorophenyl)propyl)piperidine.HCl (from EXAMPLE 95, Step E) using a procedure analogous to that described in EXAMPLE 1, Step J to provide 15.4 mg (53%) of the title compound: R$_F$: 0.40 (1:1 v/v hexanes/EtOAc); $^1$H NMR (300 MHz) δ 1.04–3.27 (m, 33H), 3.80 (s, 3H), 5.04–5.13 (m, 2H), 6.57–6.69 (m, 21), 6.87 (d, J 8.8, 2H), 7.14–7.33 (m, 8H).

Step B: 2-(R)-(3-(S)-((4-(3-(3,5-Difluorophenyl)propyl)piperidin-1-yl)methyl)-4-(S)-phenylpyrrolidin-1-yl)-3-(cyclobutyl)-propanoic acid The title compound was prepared from 15.4 mg (0.02 mmol) of 2-(R)-(3-(S)-((4-(3-(3,5-difluorophenyl)propyl)piperidin-1-yl)methyl)-4-(S)-phenylpyrrolidin-1-yl)-3-(cyclobutyl)propanoic acid, (4-methoxy)benzyl ester (from EXAMPLE 23, Step A) using a procedure analogous to that described in EXAMPLE 10, Step F to provide 11.6 mg (92%) of the title compound: R$_F$: 0.42 (90:10:1 v/v/v CH$_2$Cl$_2$/MeOH/NH$_4$OH); $^1$H NMR (300 MHz, CD$_3$OD) δ 0.99–3.65 (m, 33H), 6.55–6.68 (m, 3H), 7.14–7.31 (m, 5H); ESI-MS 525 (M+H).

EXAMPLE 24

2-(R)-(3-(S)-((4-(3-(Benzofurazan-4-yl)propyl)piperidin-1-yl)methyl)-4-(S)-phenylpyrrolidin-1-yl)-3-(cyclobutyl) propanoic acid Step A: 2-(R)-(3-(S)-((4-(3-(Benzofurazan-4-yl)-propyl)piperidin-1-yl)methyl)-4-(S)-phenylpyrrolidin-1-yl)-3-(cyclobutyl) propanoic acid, (4-methoxy)benzyl ester The title compound was prepared from 20 mg (0.07 mmol) of 2-(R)-(3-(R)formyl-4-(S)-phenylpyrrolidin-1-yl)-3-(cyclobutyl)propanoic acid, (4-methoxy)benzyl ester (from EXAMPLE 19, Step F) and 13.7 mg (0.04 mmol) of 4-(3-(benzofurazanyl)propyl)piperidine.HCl (from EXAMPLE 117, Step B) using a procedure analogous to that described in EXAMPLE 1, Step J to provide 10.6 mg (35%) of the title compound: R$_F$: 0.36 (1:1 v/v hexanes/EtOAc); $^1$H NMR (300 MHz) δ 0.80–3.32 (m, 33H), 3.80 (s, 31), 5.04–5.13 (m, 2H), 6.88 (d, J=8.6, 21), 7.15–7.37 (m, 8H), 7.51 (s, 1H), 7.73 (d, J=9.3, 1H).

Step B: 2-(R)-(3-(S)-((4-(3-(Benzofurazan-4-yl)-propyl)piperidin-1-yl)methyl)-4-(S)-phenylpyrrolidin-1-yl)-3-(cyclobutyl propanoic acid The title compound was prepared from 10.6 mg (0.01 mmol) of 2-(R)-(3-(S)-((4-(3-(benzofurazan-4-yl)propyl)piperidin-1-yl)methyl)-4-(S)-phenylpyrrolidin-1-yl)-3-(cyclobutyl)propanoic acid, (4-methoxy)benzyl ester (from EXAMPLE 24, Step A) using a procedure analogous to that described in EXAMPLE 10, Step F to provide 8.5 mg (100%) of the title compound: R$_F$: 0.37 (90:10:1 v/v/v CH$_2$Cl$_2$/MeOH/NH$_4$OH) $^1$H NMR (300 MHz, CD$_3$OD) δ 1.01–3.58 (m, 33H), 7.15–7.37 (m, 6H), 7.47 (s, 1H), 7.68 (d, J=9.2, 1H).

EXAMPLE 25

2-(R)-(3-(S)-((4-(3-(3,4-Difluorophenyl)propyl)piperidin-1-yl)methyl)-4-(S)-phenylpyrrolidin-1-yl)-3-(cyclobutyl) propanoic acid Step A: 2-(S)Hydroxy-3-(cyclobutyl)propanoic acid, benzyl ester The title compound was prepared using procedures analogous to those described in EXAMPLE 19, Steps A–E, except that benzyl bromide was substituted for (4-methoxy)benzyl chloride in Step E. For the title compound: $^1$H NMR (500 MHz), δ 1.58–1.70 (m, 2H), 1.72–1.82 (m, 2H), 1.84–1.92 (m, 2H), 1.98–2.10 (m, 2H), 2.46–2.58 (m, 1H), 2.63 (br s, 1H), 4.15 (dd, J=7.5, 3.0), 7.33–7.40 (m, 5H).

Step B: 2-(R)-(3-(R)-Formyl-4-(S)-(phenyl)pyrrolidin-1-yl)- 3-(cyclobutyl)propanoic acid, benzyl ester The title compound was prepared from 3-(R)-(t-butyldimethylsilyloxymethyl)-4-(S)-phenyl pyrrolidine (from EXAMPLE 1, Step E) and 2-(S)-hydroxy-3-(cyclobutyl)propanoic acid, benzyl ester (from EXAMPLE 25, Step A) using procedures analogous to those described in EXAMPLE 1, Steps G–I. For the title compound: $^1$H NMR (300 MHz) δ 1.542.08 (m, 8H), 2.31 (m, 1H), 2.75 (t, J=8.6 Hz, 1H), 2.96 (m, 1H), 3.11–3.35 (m, 4H), 3.56 (q, J=7.9 Hz, H3), 5.16 (s, 2H), 7.19–7.39 (m, 10H), 9.63 (d, J=2.2 Hz, 1H).

Step C: 2-(R)-(3-(S)-((4-(3-(3,4-Difluorophenyl)propyl) piperidin-1-yl)methyl)-4-(S)-phenylpyrrolidin-1-yl)-3-(cyclobutyl) propanoic acid, benzyl ester The title compound was prepared from 26 mg (0.06 mmol) of 2-(R)-(3-(R)-formyl-4-(S)-phenylpyrrolidin-1-yl)-3-(cyclobutyl)propanoic acid, benzyl ester (from EXAMPLE 25, Step B) and 17.5 mg (0.06 mmol) of 4-(3-(3,4-difluorophenyl)propyl)piperidine.HCl (from EXAMPLE 119, Step C) using a procedure analogous to that described in EXAMPLE 1, Step J to provide 18.6 mg (47%) of the title compound: R$_F$: 0.33 (1:1 v/v hexanes/EtOAc); $^1$H NMR (500 MHz) δ 1.15–3.29 (m, 33H), 5.17 (ABq, 2H), 6.8–7.4 (m, 13H).

Step D: 2-(R(3-(S)-(4-(3-(3,4-Difluorophenyl)propyl) piperidin-1-yl)methyl)-4-(S)-phenylpyrrolidin-1-yl)-3-(cyclobutyl) propanoic acid The title compound was prepared from 18.6 mg (0.02 mmol) of 2-(R)-(3-(S)-(4-(3-(3A-difluorophenyl)propyl) piperidin-1-yl)methyl)-4-(S)-phenylpyrrolidin-1-yl)-3-(cyclobutyl)propanoic acid, benzyl ester (from EXAMPLE 25, Step C) using a procedure analogous to that described in EXAMPLE 1, Step K to provide 14.1 mg (93%) of the title compound: R$_F$: 0.29 (90:10:1 v/v/v CH$_2$Cl$_2$/MeOH/NH$_4$OH); $^1$H NMR (300 MHz, CD$_3$OD) δ 1.02–3.55 (m, 33H), 6.79–7.28 (m, 81); ESI-MS 525 (M+H); HPLC A: 2.77 min.

EXAMPLE 26

2-(R)-(3-(S)-((4-(3-Phenylpropyl)piperidin-1-yl)methyl)-4-(S)-(3-fluorophenyl)pyrrolidin-1-yl)-3-(cyclobutyl)propanoic acid Step A: 2-(R)-(3-(R(Formyl)-4-(S)-(3-fluorophenyl)pyrrolidin-1-yl)-3-(cyclobutyl)propanoic acid, benzyl ester The title compound was prepared from 3-(R)-(t-butyldimethylsilyloxymethyl)-4-(S)-(3-fluorophenyl)pyrrolidine (from EXAMPLE 20, Step H) and 2-(S)-hydroxy-3-(cyclobutyl)propanoic acid, benzyl ester (from EXAMPLE 25, Step A) using procedures analogous to those described in EXAMPLE 1, Steps G–I. For the title compound: $R_F$: 0.60 (7:3 v/v hexane/EtOAc); $^1$H NMR (300 MHz) 1.57–2.08 (m, 8H), 2.29 (m, 1H), 2.73 (br t, 1H), 2.92 (m, 1H), 3.14–3.34 (m, 4H), 3.56 (br q, 1H), 5.16 (s, 2H), 6.886.99 (m, 3H), 7.20–7.39 (m, 6H), 9.62 (d, J=2.0, 1H).

Step B: 2-(R)-(3-(S)-((4-(3-Phenylpropyl)piperidin-1-yl)methyl)-4 (S)-(3-fluorophenyl)pyrrolidin-1-yl)-3-(cyclobutyl)propanoic acid, benzyl ester The title compound was prepared from 23.2 mg (0.052 mmol) of 2-(R)-(3-(R)-formyl-4-(S)-(3-fluorophenyl)pyrrolidin-1-yl)-3-(cyclobutyl)propanoic acid, benzyl ester (from EXAMPLE 26, Step A) and 12.8 mg (0.052 mmol) of 4-(3-phenylpropyl)piperidine.HCl using a procedure analogous to that described in EXAMPLE 1, Step J to provide 31.7 mg (96%) of the title compound: $R_F$: 0.57 (1:1 v/v hexanes/EtOAc); $^1$H NMR (300 MHz) δ 1.13–3.27 (m, 33H), 5.14 (s, 2H), 6.86–6.99 (m, 3H), 7.14–7.38 (m, 11H).

Step C: 2-(R)-(3-(S)-((4-(3-Phenylpropyl)piperidin-1-yl)methyl)-4-(S)-(3-fluorophenyl)pyrrolidin-1-yl)-3-(cyclobutyl)propanoic acid The title compound was prepared from 31.7 mg (0.051 mmol) of 2-(R)-(3-(S)-((4-(3-phenylpropyl)piperidin-1-yl)methyl)-4-(S)-(3-fluorophenyl)pyrrolidin-1-yl)-3-(cyclobutyl)propanoic acid, benzyl ester (from EXAMPLE 26, Step B) using a procedure analogous to that described in EXAMPLE 1, Step K to provide 23.5 mg (91%) of the title compound: RE: 0.50 (90:10:1 v/v/v CH$_2$Cl$_2$/MeOH NOH); $^1$H NMR (300 MHz, CD$_3$OD) δ 0.98–3.54 (m, 33H), 6.88–7.29 (m, 9H); ESI-MS 507 (M+H); HPLC A: 2.75 min.

EXAMPLE 27

2-(R)-(3-(S)-((4-(3-(3,4-Difluorophenyl)propyl)piperidin-1-yl)methyl)-4-(S)-(3-fluorophenyl)pyrrolidin-1-yl)-3-(cyclobutyl)propanoic acid Step A: 2-(R)-(3-(S)-((4-(3-(3,4-Difluorophenyl)propyl)piperidin-1-yl)methyl)-4-(S)-(3-fluorophenyl)pyrrolidin-1-yl)-3-(cyclobutyl)propanoic acid, benzyl ester The title compound was prepared from 25.6 mg (0.062 mmol) of 2-(R)-(3-(R)-formyl-4-(S)-(3-fluorophenyl)pyrrolidin-1-yl)-3-(cyclobutyl)propanoic acid, benzyl ester (from EXAMPLE 26, Step A) and 17.9 mg of 4-(3-(3,4-difluorophenyl)propyl)piperidine.HCl (from EXAMPLE 119, Step C) using a procedure analogous to that described in EXAMPLE 1, Step J to provide 36.2 mg (91%) of the title compound: $R_F$: 0.53 (7:3 v/v hexanes/EtOAc); $^1$H NMR (300 MHz) δ 1.02–3.26 (m, 33H), 5.15 (s, 2H), 6.81–7.37 (m, 12H).

Step B: 2-(R)-(3-(S((4-(3-(3,4-Difluorophenyl)propyl)piperidin-1-yl)methyl)-4-(S)-(3-fluorophenyl)pyrrolidin-1-yl)-3-(cyclobutyl)propanoic acid The title compound was prepared from 36.2 mg (0.058 mmol) of 2-(R)-(3-(S)-((4-(3-(3, 4-difluorophenyl)propyl)piperidin-1-yl)methyl)-4-(S)-(3-fluorophenyl)pyrrolidin-1-yl)-3-(cyclobutyl)propanoic acid, benzyl ester (from EXAMPLE 27, Step A) using a procedure analogous to that described in EXAMPLE 1, Step K to provide 28.1 mg (89%) of the title compound: $R_F$: 0.43 (90:10:1 v/v/v CH$_2$Cl$_2$/MeOH/NH$_4$OH); $^1$H NMR (300 MHz, CD$_3$OD) δ 0.963.52 (m, 33H), 6.78–7.26 (m, 71); ESI-MS 543 (M+H); HPLC A: 2.83 min.

EXAMPLE 28

2-(R)-(3-(S)-(4-(3-phenylpropyl)piperidin-1-yl)methyl)-4-(S)-phenylpyrrolidin-1-yl)-3-methylbutanoic acid The title compound was prepared using procedures analogous to those described in EXAMPLE 5, substituting 4-(3-phenylpropyl)piperidine.HCl for 4-hydroxy-4-(3-phenylpropyl) piperidine.HCl in Step E. For the title compound: $^1$H NMR (500 MHz, CD$_3$OD) δ 1.03 (d, J=7.0, 3H), 1.15 (d, J=7.0, 3H), 1.12–1.23 (4H), 1.55–1.65 (4H), 1.83 (app t, J=6.5, 1H), 2.05 (app t, J=6.0, 1H, 2.19–2.23 (m, 1H), 2.36–2.39 (m, 11), 2.49–2.52 (m, 1H), 2.55 (t, J=7.5, 2H), 2.73–2.78 (m, 2H), 2.92 (app d, J=11.5, 1H), 3.08–3.14 (m, 1H), 3.30–3.42 (m, 2H), 3.47 (app d, J=4.5, 1H), 3.58 (dd, J=11.0, 8.0, 2H), 7.09–7.37 (10H); HPLC B: 5.24 min.

EXAMPLE 29

2-(R)-(3-(S)-((4-(3-((4-Carboxy)phenyl)propyl)piperidin-1-yl)methyl)-4-(S)-phenylpyrrolidin-1-yl)-2-(cyclohexyl)acetic acid Step A: 1-t-Butoxycarbonyl(3-((4-carbomethoxy)phenyl)propyl) piperidine The title compound was prepared using procedures analogous to those described in EXAMPLE 95, Steps A–D, substituting methyl (4-formyl)benzoate for 3,5-difluorobenzaldehyde in Step C. For the title compound: $^1$H NMR (500 MHz) δ 1.07 (dq, J=4.5, 12.5, 2H), 1.25–1.29 (m, 2H), 1.34–1.48 (m, 2H), 1.45 (s, 9H), 1.57–1.68 (3H), 2.65 (t, J=7.5, 2H, 2.66–2.72 (m, 2H), 3.90 (s, 3H), 3.99–4.10 (m, 2H), 7.23 (d, J=8.0, 21, 7.95 (d, J=8.0, 2H).

Step B: 4-(3-((4-Carbomethoxy)phenyl)propyl) piperidine.TFA

A solution of 37 mg (0.1 mmol) of 1-t-butoxycarbonyl-4-(3-((4-carbomethoxy)phenyl)propyl)piperidine (from EXAMPLE 29, Step A) in CH$_2$Cl$_2$ at 0° C. was treated with 1.0 mL of TFA. The cooling bath was removed and the solution was stirred at rt for 1 h. The mixture was concentrated. The residue was dissolved in 2×5 mL of ether and concentrated to remove excess TFA. The crude product was used in Step C without further purification.

Step C: 2-(R)-(3-(S)-((4-(3-((4-Carbomethoxy)phenyl)propyl)piperidin-1-yl)methyl)-4-(S)-phenylpyrrolidin-1-yl)-2-(cyclohexyl)acetic acid, (4-methoxy)benzyl ester The title compound was prepared from 50 mg (0.11 mmol) of 2-(R)-(3-(R)-formyl-4-(S)-phenylpyrrolidin-1-yl)-2-(cyclohexyl)acetic acid, (4-methoxy)benzyl ester (from EXAMPLE 33, Step E) and 0.1 mol of 4-(3-((4-carbomethoxy)phenyl) propyl)piperidine TFA (from EXAMPLE 29, Step B) using a procedure analogous to that described in EXAMPLE 1, Step J to afford 33 mg (48%) of the title compound: $^1$H NMR (500 MHz), 0.60–1.28 (9H), 1.46–1.80 (11H), 1.95 (app d, J=13.0, 1H),2.18–2.36 (3H), 2.54 (dd, J=6.5,9.0, 1H), 2.60–2.64 (m, 2H), 2.66 (t, J=8.5, 2H), 2.77–2.82 (m, 2H), 3.13–3.21 (3H), 3.80 (s, 3H), 3.90 (s, 3H), 5.09 (ABq, J=12.0, 2H), 6.87 (d, J=9.0, 2H), 7.15–7.23 (5H), 7.25 (d, J=7.0, 2H), 7.32 (d, J=9.0,21), 7.93 (d, J=7.0, 2H).

Step D: 2-(R)-(3-(S)-((4-(3-(4-(Carbomethoxy)phenyl)propyl)piperidin-1-yl)methyl)-4-(S)-phenylpyrrolidin-1-yl)-2-(cyclohexyl)acetic acid The title compound was prepared from 33 mg (0.05 mmol) of 2-(R)-(3-(S)-(4-(3-((4-2-carbomethoxy)phenyl)propyl)piperidin-1-yl)methyl)-4-(S)-phenyl pyrrolidin-1-yl)-3-methylbutanoic acid, (4-methoxy)benzyl ester (from EXAMPLE 29, Step C) using a procedure analogous to that described in EXAMPLE 10, Step F to afford 27 mg of the title compound.

Step E: 2-(R)-(3-(S((4-(3-(4-(Carboxy)phenylpropyl)piperidin-1-yl)methyl)-4-(S)-phenylpyrrolidin-1-yl)-2-(cyclohexyl)acetic acid A solution of 27 mg (0.05 mmol) of 2-(R)-(3-(S)-(4-(3-(4-(carbomethoxy)phenyl)propyl)piperidin-1-yl)methyl)-4-(S)-phenylpyrrolidin-1-yl)-3-methylbutanoic acid (from EXAMPLE 29, Step D) in 3 mL of MeOH was treated with 0.2 mL of 5.0 N NaOH and the resulting mixture was heated at reflux for 1 h. The mixture was cooled and concentrated. The residue was partially dissolved in $H_2O$ and the solids filtered and dried to afford 11 mg (42%, 2 steps) of the title compound: ESI-MS 547 (M+H); HPLC B: 6.57 min.

EXAMPLE 30

2-(R)-(3-(S)-(4-(3-(R)-1-Phenyl-but-3-yl)piperidin-1-yl)methyl)-4-(S)-phenylpyrrolidin-1-yl)-2-(cyclohexyl)acetic acid Step A: 3-(1-(t-Butoxycarbonyl)piperidin-4-yl)acetyl-4-(S)-benzyloxazolidin-2-one A mixture of 2.73 g (11.1 mmol) of 1-(t-butoxycarbonyl)piperidin-4-yl acetic acid and 2.00 mL (14.4 mmol) of TEA in 150 mL of ether at 0° C. was treated with 1.62 mL (13.2 mmol) of trimethylacetyl chloride. The resulting mixture was stirred cold for 45 min, then was cooled to –78° C.

A solution of 2.13 g (4.0 mmol) of 4-(S)-benzyloxazolidin-2-one in 30 mL of TIFF at –78° C. was treated with 2.50 mL of 1.6 M n-butyllithium solution in hexanes and stirred cold for 30 min. The resulting mixture was added via cannula to the mixed anhydride solution and the resulting mixture was warmed to 0° C. and stirred for 30 min. The reaction was quenched with 75 mL of sat'd $NH_4Cl$ and the quenched mixture was partitioned between 300 mL of ether and 75 mL of $H_2O$. The layers were separated and the organic layer was washed with 75 mL of sat'd $NaHCO_3$, 75 mL of sat'd NaCl, dried over $MgSO_4$ and concentrated. Flash chromatography on 150 g of silica gel using 1:1 v/v hexanes/ether afforded 3.62 g (81%) of the title compound: $^1H$ NMR (500 MHz) δ 1.17–1.28 (m, 2H), 1.46 (s, 9H), 1.68–1.80 (m, 2H), 2.04–2.09 (m, 1H), 2.742.82 (m, 2H), 2.89 (dABq, J=3.5, 11.5, 2H), 3.29 (dd, J=13.0,2.5, 1H), 3.98–4.23 (4H), 4.66–4.70 (m, 1H), 7.20–7.35 (5H).

Step B: 3-(2-(S)-((t-Butoxycarbonyl)piperidin)-4-yl)propionyl)-4-(S)-benzyloxazolidin-2-one A solution of 3.60 g (8.9 mmol) of 3-(1-(t-butoxycarbonyl) piperidin-4-yl)acetyl-4-(S)-benzyloxazolidin-2-one (from EXAMPLE 30, Step A) in 50 mL of THF at –78° C. was treated with 12.0 mL of 1.0 M sodium bis(trimethylsilyl)amide solution in THF. The resulting mixture was stirred cold for 30 min and then treated with 1.00 mL (16.1 mmol) of iodomethane maintaining the internal temperature below –70° C. The reaction was warmed to 0° C., stirred for 30 min then quenched with 100 mL of sat'd $NH_4Cl$. The quenched mixture was extracted with 300 mL of ether. The extract was washed with 100 mL of 5% $Na_2SO_3$, 100 mL of sat'd $NaHCO_3$, 100 mL of sat'd NaCl, dried over $MgSO_4$ and concentrated. Flash chromatography on 100 g of silica gel using 4:1 v/v hexanes/EtOAc as the eluant afforded impure product. Recrystallization from 4:1 v/v hexanes/ether afforded 2.68 g (72%) of the pure title compound: $^1H$ NMR (500 MHz) δ 1.16–1.27 (m, 21), 1.20 (d, J=7.0, 3H), 1.45 (s, 9H), 1.58–1.63 (m, 1H), 1.73 (app d, J=13.0, 1H), 1.77–1.84 (m, 1H), 2.62–2.78 (m, 2H), 2.77 (dd, J=13.5, 9.5, 1H), 3.27 (dd, J=13.5, 3.5, 1H), 3.65–3.69 (m, 1H), 4.00–4.23 (4H), 4.66–4.70 (m, 1H), 7.20–7.35 (5H).

Step C: 2-(S)-((t-Butoxycarbonyl)piperidin-4)-yl)propanoic acid

A solution of 2.58 g (6.2 mmol) of 3-(2-(S)-((t-butoxycarbonyl) piperidin-4-yl)propionyl)-4-(S)-benzyloxazolidin-2-one (from EXAMPLE 30, Step B) in 120 mL of 4:1 v/v $THF/H_2O$ at 0° C. was treated with 2.6 mL of 30% $H_2O_2$ solution and 300 mg (7.1 mmol) of $LiOH.H_2O$. The resulting mixture was stirred at 0° C. for 1 h, then at rt for 4 h. The reaction was quenched with 20 mL of 1.3 M $Na_2SO_3$ and 30 mL of 1.0 M $NaHCO_3$. The THF was removed in vacuo and the aqueous mixture was extracted with 150 mL $CH_2Cl_2$. The aqueous layer was acidified to pH=2 with 2.0 N HCl and extracted with 150 mL of ether. The extract was washed with 100 ML of sat'd NaCl, dried over $MgSO_4$ and concentrated. Recrystallization from 4:1 v/v hexanes/ether afforded 1.42 g (89%) of the title compound.

Step D: 2-(S)-((t-Butoxycarbonyl)piperidin-4yl)propanol

A mixture of 1.29 g (5.0 mmol) of 2-(S)-((t-butoxycarbonyl) piperidin-4-yl)propanoic acid (from EXAMPLE 30, Step C) and 0.70 mL (5.0 mmol) of TEA in 30 mL of THF at 0° C. was treated with 0.43 mL (5.0 mmol) of ethyl chloroformate and the resulting mixture was stirred cold for 30 min. The solids were filtered. The filtrate was added to a cooled (0° C.) mixture of 0.50 g (13.0 mmol) of $NaBH_4$ in 10 mL of $H_2O$, maintaining the internal temperature at less than 10° C. The resulting mixture was warmed to rt and stirred for 1 h. The reaction was layered with 75 mL of ether and quenched with 25 mL of 1.0 N HCl. The layers were separated. The organic layer was washed with 25 mL of 1.0 N NaOH, 25 mL of sat'd NaCl, dried over $MgSO_4$ and concentrated to afforded 1.90 g (88%) of the title compound: $^1H$ NMR (500 MHz) δ 0.90 (d, J=6.5, 3H), 1.17–1.66 (5H), 1.45 (s, 9H), 2.65 (br s, 2H), 3.56 (dABq, J=5.5, 10.5), 4.13 (br s, 2H1).

Step E: 1-Iodo-2-(S)-((t-butoxycarbonyl)piperidin-4-yl)propane

A solution of 1.57 g (6.0 mmol) of triphenylphosphine and 0.41 g (6.0 mmol) of imidazole in 40 mL of $CH_2Cl_2$ was treated with 1.52 g (6.0 mmol) of iodine and stirred at rt for 30 min. A solution of 1.15 g (4.7 mmol) of 2-(S)-((t-butoxycarbonyl)piperidin-4-yl)propanol (from EXAMPLE 30, Step D) in 10 mL of $CH_2Cl_2$ was added and the resulting mixture was stirred at rt for 20 h. The reaction mixture was partitioned between 200 mL of ether and 100 mL of $H_2O$ and the layers were separated. The organic layer was washed with 100 mL of sat'd $NaHCO_3$, 100 mL of 5% $Na_2SO_3$, 100 mL of sat'd NaCl, dried over $MgSO_4$ and concentrated. Flash chromatography on 60 g of silica gel using 10:1 v/v hexanes/ether as the eluant afforded 1.57 g (95%) of the title compound: $^1H$ NMR (500 MHz) δ 0.98 (d, J=6.5, 3H), 1.10–1.20 (m, 2H), 1.26–1.36 (m, 1H), 1.40–1.50 (m, 1H), 1.45 (s, 9H), 1.64 (app d, J=11.0, 11H), 2.67 (br s, 2H), 3.19–3.28 (m, 2H), 4.13 (br s, 2H).

Step F: 2-(S)-((t-Butoxycarbonyl)piperidin-4-yl)prop-1-yl triphenylphosphonium iodide A solution of 1.56 g (4.4 mmol) of 1-iodo-2-(S)-((t-butoxycarbonyl)piperidin-4-yl)propane (from EXAMPLE 30, Step E) and 1.31 g (5.0 mmol) of triphenylphosphine in 5 mL of $CH_3CN$ was heated at reflux for 48 h. The mixture was cooled and concentrated. The residue was triturated with ether and $CH_2Cl_2$ and the resulting solid filtered and dried to afford 1.97 g (72%) of the title compound.

Step G: 1-(t-Butoxycarbonyl)-4-(1-(phenyl)-(3S)-but-1-en-3-yl)piperidine

A suspension of 308 mg (0.5 mmol) (2-(S)-(t-butoxycarbonyl) piperidin-4-yl)propyl triphenylphosphonium iodide (from EXAMPLE 30, Step F) in 3 mL of toluene was treated with 1.40 mL of 0.5 M potassium bis(trimethylsilyl)amide solution in toluene and the resulting mixture was stirred at rt for 2 h. The mixture was cooled to 0° C., treated with 0.055 mL (0.54 mmol) of benzaldehyde and stirred cold for 2h. The mixture was partitioned between 40 mL of ether and 20 mL of sat'd NaCl and the layers were separated. The organic layer was dried over $MgSO_4$ and concentrated. Flash chromatography on 8 g of silica gel using 2:1 v/v hexanes/$CH_2Cl_2$, then 1:2 v/v hexanes/$CH_2Cl_2$ as the eluant afforded 42 mg (27%) of the title compound.

Step H: 1-(t-Butoxycarbonyl)-4-(3-(R)-1-phenyl-(3R)-but-3-yl)piperidine

A mixture of 42 mg (0.13 mmol) of 1-(t-butoxycarbonyl)-4-(3-(S)-(1-phenyl)but-1-enyl)piperidine (from EXAMPLE 30, Step G) and 15 mg of 10% palladium on carbon was stirred under an atmosphere of $H_2$ for 20 h. The catalyst was filtered and the filtrate was concentrated to afford 42 mg (100%) of the title compound.

Step I: 2-(R)-(3-(S)-(4-(3(R)-1-phenyl-but-3-yl)piperidin-1-yl)methyl)-4-(S)-phenylpyrrolidin-1-yl)-2-(cyclohexyl) acetic acid The title compound was prepared from 2-(R)-(3-(R)-formyl-(S)-phenylpyrrolidin-1-yl)-2-(cyclohexyl)acetic acid, benzyl ester (from EXAMPLE 1, Step 1) and 1-(t-butoxycarbonyl)-4-(3(R)-1-phenyl-but-3-yl) piperidine (from EXAMPLE 30, Step H) using procedures analogous to those described in EXAMPLE 29, Steps B and C and EXAMPLE 10, Step F. For the title compound: ESI-MS 517 (M+H); HPLC B: 7.82 min.

EXAMPLE 31

2-(R)-(3-(S)-((4-(3-(quinolin-3-yl)propyl)piperidin-1-yl)methyl)-4-(S)-phenylpyrrolidin-1-yl)-2-(cyclohexyl)acetic acid Step A: 1-(t-Butoxycarbonyl)-4-(3-(quinolin-3-yl)propyl) piperidine A solution of 260 mg (1.15 mmol) of 1-(t-butoxycarbonyl)-4-(prop-2-enyl)piperidine (from EXAMPLE 33, Step B) in 3 mL of THF under argon was treated with 2.30 mL of 0.5 M 9-BBN solution in THF. The resulting mixture was stirred at rt for 2 h, then treated with 68 mg (1.25 mmol) of NaOMe. The resulting mixture was stirred until it was homogeneous (~15 min) and then was treated with 0.155 mL (1.15 mmol) of 3-(bromo)quinoline and 41 mg (0.05 mmol) of [1,1'-bis(triphenyl-phosphino)ferrocene]dichloropalladium.$CH_2Cl_2$. The resulting mixture was heated at reflux for 30 min, cooled and quenched with 20 mL of 1.0 N NaOH. The quenched reaction was extracted with 2×50 mL of ether; the extracts were dried over $MgSO_4$, combined and concentrated. Flash chromatography on 15 g of silica gel using 4:1 v/v hexanes/EtOAc as the eluant afforded 240 mg (59%) of the title compound: $^1$H NMR (300 MHz) B 1.00–1.16 (m, 2H), 1.25–1.40 (m, 2H), 1.45 (s, 9H), 1.60–1.80 (5H), 2.62–2.72 (m, 2H), 2.79 (t, J=7.8,22H), 4.06 (br s, 2H), 7.52 (m, 1H), 7.66 (m, 1H), 7.76 (dd, J=8.0, 1.6, 1H), 7.91 (d, J=1.6, 1H), 8.77 (d, J=2.2, 1H).

Step B: 4-(3-(Quinolin-3-yl propyl)piperidine.2 HCl

A solution of 240 mg (0.68 mmol) of 1-(t-butoxycarbonyl)-4-(3-(quinolin-3-yl)propyl)piperidine (from EXAMPLE 31, Step A) in 8 mL of 1.0 M HCl solution in MeOH was stirred at rt for 48 h. The solution was concentrated and the residue crystallized from EtOAc to afford 182 mg (82%) of the title compound: $^1$H NMR (500 MHz, $CD_3OD$) δ 1.37–149 (4H), 1.67–1.74 (m, 1H), 1.85–1.91 (m, 2H), 1.99 (app d, J=13.5, 2H), 2.99 (app t, J=11.5, 2H), 3.05 (t, J=8.0, 2H), 3.38 (app d, J=12.5), 7.97 (t, J=7.0, 1H), 8.13 (dt. J=1.0, 7.0, 1H), 8.24 (d, J=8.5, 1H), 8.31 (d, J=8.0, 1H), 9.10 (s, 1H), 9.21 (d, J=1.0, 1H).

Step C: 2-(R(3-(S)-((4-(3-(Quinolin-3-yl)propyl)piperidin-1-yl)methyl)-4-(S)-phenylpyrrolidin-1-yl)-2-(cyclohexyl) acetic acid The title compound was prepared from 2-(R)-(3-(R)-formyl-4-(S)-phenylpyrrolidin-1-yl)-2-(cyclohexyl)acetic acid, (4-methoxy)benzyl ester (from EXAMPLE 33, Step E) and 4-(3-(quinolin-3-yl)propyl)piperidine 2 HCl (from EXAMPLE 31, Step B) using procedures analogous to those described in EXAMPLE 1, Step J and EXAMPLE 10, Step F. For the title compound: $^1$H NMR (500 MHz, $CD_3OD$) δ 1.10–1.32 (9H), 1.44 (app q, J=11.5, 1H), 1.60–1.90 (1OH), 2.04 (app t, J=11.5, 1H), 2.35 (app d, J=16.0, 1H), 2.53 (app t, J=11.0, 1H), 2.73–2.81 (4H), 2.94 (app d, J=10.0, 1H), 3.11 (app q, J=8.0, 1H), 3.32–3.44 (br s, 2H), 3.45 (d, J=3.5, 1H), 3.56–3.60 (m, 2H), 7.25–7.28 (2H), 7.33–7.36 (3H), 7.57 (t, J=7.5, 1H), 7.69 (t, J=7.5, 1H), 7.87 (d, J=8.0, 1H), 7.97 (d, J=8.0, 1H), 8.11 (app s, 1H), 8.69 (d, J=2.0, 1H); ESI-MS 554 (M+H); HPLC B: 5.83 min.

EXAMPLE 32

2-(R)-(3-(S)-((4-(3-(Phenyl)-2,2-((1-benzylcycloprop-1-yl)methyl)piperidin-1-yl)methyl)-4-(S)-(3-fluoro) phenylpyrrolidin-1-yl)-3-(cyclobutyl)propanoic acid Step A: 1-(t-Butoxycarbonyl)-2-(iodomethyl)piperidine The title compound was prepared from 1-(t-butoxycarbonyl)-4-(carboxy)piperidine using procedures analogous to those described in EXAMPLE 30, Steps D and E. For the title compound: $^1$H NMR (500 MHz) δ 1.11–1.18 (m, 2H), 1.46 (s, 1H), 1.57–1.66 (m, 11H), 1.83 (d, J=13.0, 2H), 2.69 (br s, 2H), 3.10 (d, J=5.0, 2H), 4.13 (br s, 2H).

Step B: 1-(t-Butoxycarbonyl)-4-(2,2-bis(carboethoxy)ethyl) piperidine

A mixture of 645 mg (2.0 mmol) of 1-(t-butoxycarbonyl)-4-(iodomethyl)piperidine (from EXAMPLE 32, Step A), 660 mg (2.5 mmol) of 18-crown-6, 550 mg (4.0 mmol) of potassium carbonate and 0.60 mL of diethylmalonate in 12 mL of toluene was heated at 80° C. for 20h. The mixture was cooled, partitioned between 75 mL of ether and 50 mL of $H_2O$ and the layers were separated. The organic layer was washed with 50 mL of 5% $Na_2S_2O_3$, 50 mL of sat'd NaCl, dried over $MgSO_4$ and concentrated. Flash chromatography on 30 g of silica gel using 4:1 v/v hexanes/EtOAc, then 2:1 v/v hexanes/EtOAc as the eluant afforded 630 mg (89%) of the title compound: $^1$H NMR (500 MHz) δ 1.07–1.14 (m, 21), 1.24–1.28 (m, 6H), 1.38–1.45 (m, 1H), 1.45 (s, 9H), 1.66 (d, J=13.0, 2H), 1.83–1.87 (m, 2H), 2.65 (t, J=7.5,22H), 3.41–3.45 (m, 1H), 4.07 (app d, J=12.5,22H), 4.194.22 (m, 2H).

Step C: 1-(t-Butoxycarbonyl)-4-(3-phenyl-2,2-bis (carboethoxy)propyl) piperidine A solution of 628 mg (1.76 mmol) of 1-(t-butoxycarbonyl)-4-(2,2-bis(carbethoxy)ethyl)piperidine (from EXAMPLE 32, Step B) in 8 mL of THF at 0° C. was treated with 2.0 mL of 1.0 M sodium bis(trimethylsilyl) amide solution in THF and stirred cold for 10 min. The resulting mixture was treated with 0.35 mL (2.9 mmol) of benzyl bromide then warmed to rt and stirred for 1 h. The reaction was quenched with 10 mL of sat'd $NH_4Cl$ and the quenched mixture was partitioned between 50 mL of ether and 25 mL of $H_2O$. The layers were separated and the organic layer was washed with 25 mL of sat'd NaCl, dried over $MgSO_4$ and concentrated. Flash chromatography on 30 g of silica gel using 4:1 v/v hexanes/ether afforded 760 mg (96%) of the title compound: $^1$H NMR (500 MHz) δ 1.08–1.16 (m, 2H), 1.23 (t, J=7.0,66H), 1.45 (s, 9H), 1.54–1.58 (m, 2H), 1.60–1.66 (m, 1H), 1.78 (d, J=6.0, 2H), 2.68 (app t, J=11.5, 21), 3.28 (s, 2H), 4.01 (br s, 2H), 4.15 (q, J=7.0, 4H), 7.06–7.25 (5H).

Step D: 1-Benzyl-4-(3-phenyl-2,2-bis(carboethoxy)propyl) piperidine

A solution of 520 mg (1.16 mmol) of 1-(t-butoxycarbonyl)-4-(3-phenyl-2,2-bis(carboethoxy)propyl) piperidine (from EXAMPLE 32, Step C) in 5 mL of $CH_2Cl_2$ at 0° C. was treated with 5 mL of TFA. The resulting mixture was warmed to rt and stirred for 1.5 h. The reaction was concentrated and triturated with ether. The solid that formed was filtered and dried to afford 617 mg of 4-(3-phenyl-2,2-bis(carboethoxy) propyl)piperidine.TFA.

A mixture of the TEA salt, 0.15 mL (1.5 mmol) of benzaldehyde, 0.16 mL (1.1 mmol) of TEA and 675 mg (3.2 mmol) of sodium triacetoxyborohydride in 10 mL of $CH_2Cl_2$ was stirred at rt for 2.5 h. The reaction mixture was partitioned between 100 mL of ether and 50 mL of 1.0 N NaOH and the layers were separated. The organic layer was washed with 50 mL of sat'd NaCl, dried over $MgSO_4$ and concentrated. Flash chromatography on 25 g of silica gel using 3:1 v/v hexanes/EtOAc as the eluant afforded 445 mg (88%) of the title compound: $^1$H NMR (300 MHz) δ 1.21 (t, J=7.2,66H), 1.21–1.31 (m, 2H), 1.50–1.60 (3H), 1.79 (d, J=5.7, 2H), 1.94 (app t, J=10.8,22H), 2.84 (d, J=11.7,22H), 3.26 (s, 2H), 3.47 (s, 2H), 4.15 (q, J=7.2,44H) 7.05–7.40 (10H).

Step E: 1-Benzyl-4-(3-phenyl-2,2-bis(hydroxymethyl) propyl) piperidine

A mixture of 430 mg (1.0 mmol) of 1-benzyl-4-(3-phenyl-2,2-bis(carboethoxy)propyl)piperidine (from EXAMPLE 32, Step D) and 65 mg (1.7 mmol) of lithium aluminum hydride was heated at reflux for 1 h. The reaction was cooled and quenched with 10 mL of 1.0 N NaOH. The quenched mixture was partitioned between 50 mL of ether and 25 mL of $H_2O$ and the layers were separated. The organic layer was dried over $MgSO_4$ and concentrated. The resulting solid was triturated with ether, filtered and dried to afford 204 mg (59%) of the title compound: $^1$H NMR (500 MHz) δ 1.16 (d, J=5.0,2H), 1.32–1.36 (m, 2H), 1.45–1.49 (m, 1H), 1.66 (d, J=12.0, 2H), 1.76 (br s, 2H), 1.97 (app t, J=11.5, 2H), 2.40 (br s, 2H), 2.73 (s, 2H), 2.83 (app d, J=11.5, 2H), 3.48 (s, 2H), 3.58 (ABq, J=10.5, 4H), 7.19–7.31 (10H).

Step F: -Benzyl-4-(3-phenyl-2,2-bis(iodomethyl)propyl) piperidine

A solution of 393 mg (1.5 mmol) of triphenylphosphine and 102 mg (1.5 mmol) of imidazole in 10 mL of $CH_3CN$ was treated with 381 mg (1.5 mmol) of iodine. The resulting mixture was treated with 202 mg (0.57 mmol) of 1-(benzyl)-4-(3-phenyl-2,2-bis(hydroxymethyl)propyl)_piperidine (from EXAMPLE 32, Step E) and the heated at reflux for 20 h. The mixture was cooled and concentrated. The residue was partitioned between 40 mL of EtOAc and 25 mL of sat'd $NaHCO_3$ and the layers were separated. The organic layer was washed with 25 mL of 5% $Na_2S_2O_3$, mL of sat'd NaCl, dried over $MgSO_4$ and concentrated. Flash chromatography on 12 g of silica gel using 4:1 v/v hexanes/ether afforded 258 mg (79%) of the title compound: $^1$H NMR (500 MHz) δ 1.40–1.50 (5H), 1.56–1.66 (2H), 1.76 (app d, J=13.0, 2H), 1.99 (app t, J=13.0, 2H), 2.80 (s, 2H), 2.86 (app d, J=13.5, 2H), 3.20 (ABq, J=13.0,44H), 3.49 (s, 2H), 7.23–7.38 (10H); ESI-MS 574 (M+H); HPLC A: 3.57 min.

Step G: 1-Benzyl-4-(3-phenyl-2,2'-((1-benzylcycloprop-1-yl)methyl))piperidine

A mixture of 255 mg (0.45 mmol) of 1-benzyl-4-(3-phenyl-2,2-bis(iodomethyl)propyl)piperidine (from EXAMPLE 32, Step F) and 38 mg (1.0 mmol) of lithium aluminum hydride in 5 mL of THF was heated at reflux for 20 h. The reaction was cooled and quenched with 5 mL of 1.0 N NaOH. The quenched mixture was partitioned between 50 mL of ether and 25 mL of $H_2O$ and the layers were separated. The organic layer was dried over $MgSO_4$ and concentrated. Flash chromatography on 6 g of silica gel using 20:1 v/v $CH_2Cl_2$/EtOAc afforded 51 mg (35%) of the title compound: $^1$H NMR (500 MHz) 0.28–0.30 (m, 2H), 0.40–0.42 (m, 2H), 1.12 (d, J=7.0,22H), 1.18–1.25 (m, 2H), 1.54–1.58 (m, 1H), 1.72 (app d, J=13.5, 2H), 1.97 (app t, J=10.5, 2H), 2.57 (s, 2H), 2.87 (app d, J=13.5, 2H), 3.51 (s, 2H), 7.18–7.31 (10H).

Step H: 4-(3-Phenyl-2,2'-(spirocycloproyl)propyl) piperidine.HCl

A solution of 50 mg (0.16 mmol) of 1-benzyl-4-(3-phenyl-2,2'-(spirocycloproyl)propyl)piperidine (from EXAMPLE 32, Step G) and 0.035 mL (0.16 mmol) of 1-chloroethyl chloroformate in 2 mL of 1,2-dichloroethane was heated at reflux for 2 h. The mixture was cooled and concentrated. The residue was dissolved in 3 mL of MeOH and heated at reflux for 1 h. The mixture was cooled and concentrated. The residue was triturated with ether, filtered and dried to afford 34 mg (82%) of the title compound: $^1$H NMR (500 MHz, $CD_3OD$) δ 0.32–0.34 (m, 2H), 0.50–0.52 (m, 21), 1.17 (d, J=7.0,22H), 1.29–1.34 (m, 2H), 1.92–1.99 (3H), 2.63 (s, 2H), 2.98 (app t, J=13.0,22H), 3.34 (app d, J=13.0,22H), 7.16–7.24 (5H); ESI-MS 229; HPLC A: 2.75 min.

Step I: 2-(R)-(3-(S((4-(3-(Phenyl)-2,2'-(spirocyclopropyl) propyl) piperidin-1-yl)methyl)-4-(S)-(3-fluoro) phenylpyrrolidin-1-yl)-3-(cyclobutyl)propanoic acid A mixture of 55 mg (0.13 mmol) of 2-(R)-(3-(R)-(formyl)-4-(S)-(3-fluorophenyl)pyrrolidin-1-yl)-3-(cyclobutyl)propanoic acid, benzyl ester (from EXAMPLE 26, Step A), 0.02 mL (0.14 mmol) of TEA and 12 mg of 10% palladium on carbon in 3 mL of MeOH was stirred under and atmosphere of hydrogen for 1 h. The catalyst was filtered and the filtrate concentrated. The residue was combined with 33 mg (0.12 mmol) of 4-(3-phenyl-2,2'-(spirocycloproyl) propyl)piperidine.HCl (from EXAMPLE 32, Step H), 0.02 mL (0.14 mmol) of TEA and 100 mg (0.47 mmol) of sodium triacetoxyborohydride in 5 mL of $CH_2Cl_2$ and the resulting mixture was stirred at rt for 20 h. The reaction was quenched 3 mL of MeOH and 0.5 mL of $NH_4OH$ and concentrated. Flash chromatography on 4 g of silica gel using $CH_2Cl_2$, then 100:4:0.4 v/v/v $CH_2Cl_2$/MeOH/$NH_4OH$ , then 100:8:0.8 v/v/v $CH_2Cl_2$/MeOH/$NH_4OH$ as the eluant afforded 57 mg of the title compound: ESI-MS 533 (M+H); HPLC A: 2.93 min.

EXAMPLE 33

2-(R)-(3-(S)-((4-(3-(Benzofurazan-3-yl)propyl)piperidin-1-yl)methyl)-4-(S)-phenylpyrrolidin-1-yl)-2-(cyclohexyl) acetic acid Step A: ((1-t-Butoxycarbonyl)piperidin-4-yl)acetaldehyde A solution of oxalyl chloride (1.23 mL, 14.1 mmol) in 50 mL $CH_2Cl_2$ was cooled to −78° C. DMSO (2.0 mL, 28.3 mmol), was added slowly via syringe. After 10 min, 1-(t-butoxycarbonyl)-4-(2-hydroxyethyl)piperidine (2.7 g, 11.8 mmol, from EXAMPLE 113, Step A) in 15 mL $CH_2Cl_2$ was added. The cold mixture was stirred for an additional 20 min then TEA (8.2 mL, 59 mmol) was added. The mixture was warmed to rt and stirred for 1.5 h then diluted with 300 mL $CH_2Cl_2$. The organic phase was washed with 1 M NaOH then dried over $Na_2SO_4$ and concentrated. Flash chromatography (125 g silica, 2.5/1 hexane/EtOAc) afforded 2.25 g (84%) of the title compound: $^1$H NMR (300 MHz) a 1.1–1.2 (m, 2H), 1.45 (s, 9H), 1.65–1.75 (m, 2H), 1.99–2.13 (m, 1H), 2.38–2.4 (d, 2H), 2.65–2.8 (m, 2H), 4.03–4.15 (m, 2H), 9.78 (s, 1H)

Step B: 1-(t-Butoxycarbonyl)-4-(pro-2-enyl)piperidine

A solution of methyltriphenylphosphonium bromide (5.3 g, 14.8 mmol) in 50 mL THF was cooled to 0° C. under nitrogen. Potassium bis(trimethylsilyl)amide (27.7 L, 0.5 M toluene solution, 13.9 mmol) was added and the mixture was stirred for 30 min. A solution of ((1-t-butoxycarbonyl) piperidin-4-yl)acetaldehyde (2.25 g, 9.9 mmol, from EXAMPLE 33, Step A) in 10 mL THF was added and the mixture was warmed to rt and stirred for 30 min. The mixture was diluted with 200 mL EtOAc and washed with H2O and sat'd NaCl (100 mL each).

The organic phase was dried over $Na_2SO_4$ and concentrated to give an oil which was purified by flash chromatography (75 g silica, 10:1 v/v hexane/EtOAc eluant) to afford 1.61 g (71%) of the title compound: $^1$H NMR (300 MHz) δ 1.03–1.18 (m, 2H), 1.45 (s, 9H), 1.4–1.5 (m, 1H), 1.6–1.7 (m, 2H), 1.99–2.13 (t, 1H), 2.62–2.75 (m, 2H), 4.03–4.15 (m, 2H), 4.98–5.12 (m, 2H), 5.7–5.83 (m, 1H).

Step C: 3-Bromobenzofurazan

To a solution of 2,6-dibromoaniline (10 g, 40 mmol) in 160 mL of glacial acetic acid was added 30 mL of 30% hydrogen peroxide. The mixture was left for 48 h at which point crystals had precipitated out. The crystals were collected by filtration, washed with acetic acid and H2O then dried under high vacuum to give 6.24 g (60%) of 2,6-dibromonitrosobenzene. This material (2.6 g, 10 mmol) was dissolved in 25 mL of DMSO along with 650 mg (10 mmol) sodium azide. The mixture was heated to 100° C. for lh then cooled to rt and diluted with 200 mL EtOAc and 150 mL $H_2O$. The layers were separated and the organic phase was washed with $H_2O$ and sat'd NaCl then dried over $Na_2SO_4$ and concentrated. Flash chromatography (75 g silica, 10:1 v/v hexane/EtOAc eluant) afforded 1.7 g (85%) of the title compound: $^1$H NMR (300 MHz) δ 7.25–7.35 (dd, 1H), 7.6–7.65 (d, 1H), 7.78–7.82 (d, 1H)

Step D: 4-(3-(Benzofurazan-3-yl)propyl)piperidine.HCl

A solution of 1-t-butoxycarbonyl-4-(prop-2-enyl) piperidine (330 mg, 1.46 mmol, from EXAMPLE 33, Step B) in 0.5 mL dry THF was cooled to 0° C. and a solution of 9-BBN (3.2 mL, 0.5 M in THF, 1.61 mmol) was added. The mixture was warmed to rt and stirred for 5 h. Potassium carbonate (405 mg, 2.93 mmol), 1,2-bis(diphenylphosphino) ferrocenyl palladium dichloride (60 mg, 0.073 mmol) and 3-bromobenzofurazan (292 mg, 1.46 mmol, from EXAMPLE 33, Step C) were added followed by 5 mL of dry DMF. The resulting mixture was heated to 55° C. overnight then diluted with 50 mL EtOAc. The solution was washed with $H_2O$ (3x) and sat'd NaCl then dried over $Na_2SO_4$ and concentrated. Flash chromatography (15 g silica, 5:1 v/v hexane/EtOAc eluant) afforded the 1-t-butoxycarbonyl derivative of the title compound. Heating in 1% conc. HCl/MeOH at 50° C. for 2h followed by removal of solvent and drying under vacuum afforded 155 mg (38%) of the title compound: $^1$H NMR (300 MHz, $CD_3OD$) δ 1.31–1.42 (m, 4H), 1.6–1.75 (m, 1H), 1.842.0 (m, 4H), 2.9–3.1 (m, 4H), 3.3–3.4 (m, 2H), 7.25–7.3 (d, 1H), 7.47.5 (dd, 11), 7.7–7.75 (d, 1H).

Step E: 2-(R)-(3-(R)-Formyl-4-(S)-phenylpyrrolidin-1-yl)-2-(cyclohexyl)acetic acid, (4-methoxy)benzyl ester The title compound was prepared using procedures analogous to those described in EXAMPLE 1, Steps A–I, except that (4-methoxy)benzyl chloride was substituted for benzyl bromide in Step F. For the title compound: $^1$H NMR (500 MHz) δ 0.95–1.04 (m, 2H), 1.13–1.30 (31), 1.70 (app d, J=12.5, 1H), 1.66–1.83 (4H), 1.95 (app d, J=12.5, 1H), 2.66–2.70 (m, 1H), 2.91–2.95 (m, 1H), 3.16–3.23 (3H), 3.27–3.33 (m, 1H), 3.52–3.56 (m, 1H), 3.83 (s, 3H), 5.12 (s, 2H), 6.88–6.91 (m, 2H), 7.17–7.19 (m, 2H), 7.22–7.26 (m, 1H), 7.29–7.35 4H), 9.64 (d, J=2.0, 1H).

Step F: 2-(R)-(3-(S((4-(3-(Benzofurazan-3-yl)propyl) piperidin-1-yl)methyl)-4-(S)-phenylpyrrolidin-1-yl)-2-(cyclohexyl)acetic acid A solution of 2-(R)-(3-(R)-formyl-4-(S)-phenylpyrrolidin-1-yl)-2-(cyclohexyl)acetic acid, (4-methoxy)benzyl ester (30 mg, 0.069 mmol, from EXAMPLE 33, Step E), 4-(3-(benzofurazan-3-yl)propyl) piperidine.HCl (23 mg, 0.083 mmol from EXAMPLE 33, Step D), sodium triacetoxyborohydride, 29 mg (0.14 mmol) and TEA (0.012 mL, 0.083 mmol) in 0.5 mL 1,2-dichloroethane was stirred for 3 h. The solvent was removed and the product was purified by preparative HPLC (YMC Combiprep ODS-A 20×50 mm column, gradient: 5% acetonitrile/H2O w/0.1% TFA for 1 mn then ramp to 100% acetonitrile/$H_2O$ w/ 0.1% TFA over 6 min, flow: 20 mL/min). The material was stirred in 3 mL formic acid for 8 h. After removal of solvent, purification was accomplished by flash chromatography (3 g silica gel, 19:1 v/v $CH_2Cl_2$/MeOH, then 19:1:0.2 v/v/v $CH_2Cl_2$/MeOH/$NH_4OH$ as the eluants) to give 21 mg (56%) of the title compound: $^1$H NMR (500 MHz) δ 1.02–1.98 (22H), 2.05–2.09 (m, 1H), 2.27–2.33 (m, 1H), 2.6–3.4 (1OH), 3.8–3.9 (m, 1H), 7.07–7.09 (d, 1H J=6 Hz), 7.2–7.33 (m, 6H), 7.63–7.66 (d, 1H, J=9); ESI-MS 545 (M+H).

EXAMPLE 34

2-(R)-(3-(S)-((4-(3-(Tetrazolo[4,5-a]pyridin-5-yl)propyl) piperidin-1-yl)methyl)-4-(S)-phenylpyrrolidin-1-yl)-2-(cyclohexyl)acetic acid Step A: 5-Bromo-tetrazolo[4.5-a]pyridine 2,5-Dibromopyridine (1.0 g, 4.2 mmol), sodium azide (412 mg, 6.3 mmol) and $NH_4Cl$ (339 mg, 6.3 mmol) were heated in 20 mL DMF to 100° C. for 16 h. The mixture was diluted with 150 mL EtOAc, washed with $H_2O$ (2x) and sat'd NaCl then dried over $Na_2SO_4$ and concentrated. Flash chromatography (30 g silica, 2/1 hexane/EtOAc eluant) afforded 212 mg (25%) of the title compound.

Step B: 3-(Tetrazolo[4,5-a]pyridin-5-yl) propylpiperidine.HCl

The title compound was prepared from 4-(prop-2-enyl)-1-(t-butoxycarbonyl)piperidine (225 mg, 1.0 mmol, from EXAMPLE 33, Step B) and (5-bromo)pyrido[1,2-b]-1,2,3-triazole (200 mg, 1 mmol from EXAMPLE 34, Step A) using the procedure described in EXAMPLE 33, Step D to obtain 62 mg (22%) of the title compound.

Step C: 2-(R)-(3-(S)-((4-(3-(Tetrazolo[4,5-a]pyridin-5-yl) propyl)piperidin-1-yl)methyl)-4-(S)-phenylpyrrolidin-1yl)-2-(cyclohexyl)acetic acid A solution of 2-(R)-(3-(R)formyl-4-(S)-phenylpyrrolidin-1-yl)-2-(cyclohexyl)acetic acid, (4-methoxy)benzyl ester (33 mg, 0.075 mmol, from EXAMPLE 33, Step E), 3-(tetrazolo[4,5-a]pyridin-5-yl)propylpiperidine.HCl (27 mg, 0.097 mmol from EXAMPLE 34, Step B) sodium triacetoxyborohydride, 32 mg (0.15 mmol) and TEA (0.014 mL, 0.097 mmol), in 1.0 mL 1,2-dichloroethane was stirred overnight. The solvent was removed and the product was purified by preprative HPLC (column: YMC Combiprep ODS-A 20×50 mm, gradient: 5% acetonitrile/$H_2O$ w/ 0.1% TFA for 1 min then ramp to 100% acetonitrile/$H_2O$ w/ 0.1% TFA over 6 min, flow: 20 mL/min). The material was stirred in 3 mL formic acid for 8 h. After removal of solvent the purification was accomplished by preprative HPLC (column: YMC Combiprep ODS-A 20×50 mm, gradient: 5% acetonitrile/$H_2O$ w/ 0.1% TFA for 1 min then ramp to 100% acetonitrile/$H_2O$ w/0.1% TFA over 6 min, flow: 20 mL/min) to give 11 mg (27%) of the title compound: $^1$H NMR (500 MHz) δ 1.02–1.98 (22H), 2.05–2.1 (m, 1H), 2.1–2.2 (m, 1H), 2.3–2.4 (m, 1H), 2.6–3.4 (8H), 3.8–3.9 (t, 2H), 4.51–4.55 (m, 1H), 7.2–7.33 (m, 5H), 7.48–7.49 (d, 1H, J=9 Hz), 7.94–7.96 (d, 1H, J=9 Hz): ESI-MS, M/z; (M+H)= 545.5 (obs), 545.3 (calc.).

EXAMPLE 35

2-(R)-(3-(S)((4-(3-(2-Cyanophenyl)propyl)piperidin-1-yl) methyl)-4-(S)(3-fluorophenyl)-pyrrolidin-1-yl)-3-(cyclobutylpropanoic acid Step A: 3-(2-Cyanophenyl)propyl piperidine.HCl The title compound was prepared from 4-(prop-2-enyl)-1-t-butoxycarbonyl piperidine (475 mg, 2.1 mmol, from EXAMPLE 33, Step B) and 2-bromobenzonitrile (382 mg, 2.1 mmol) using a procedure analogous to that described in EXAMPLE 33, Step D to obtain 336 mg (61%) of the title compound: $^1$H NMR (300 MHz, CD$_3$OD) δ 1.31–1.42 (m, 4H), 1.61.80 (m, 5H), 1.9–2.1 (m, 2H), 2.8–2.9 (t, 2H), 2.9–3.02 (m, 2H), 3.3–3.4 (m, 2H), 7.33–7.4 (m, 1H), 7.41–7.55 (d, 1H), 7.65–7.7 (m, 1H), 7.7–7.8 (d, 1H).

Step B: 2-(R)-((3-(Formyl)-4-(S)-3-(fluoro) phenylpyrrolidin-1-yl)-3-(cyclobutyl)propanoic acid, benzyl ester The title compound was prepared from 3-(R)-t-butyldimethylsilyloxymethyl-4-(S)-(3-fluoro)phenyl pyrrolidine (from EXAMPLE 20, Step H) using procedures analogous to those described in EXAMPLE 1, Steps F–I. For the title compound: $^1$H NMR (500 MHz) δ 0.95–1/05 (m, 2H), 1.14–1.29 (3H), 1.59 (app d, J=13.1, 1H), 1.66–1.83 (4H), 1.93 (app d, J=13.2, 1H), 2.65–2.69 (m, 1H), 2.88–2.93 (m, 1H), 3.15 (dd, J=5.0, 9.6, 1H), 3.20–3.24 (m, 2H), 3.27–3.30 (m, 1H), 3.55 (dd, J=7.5, 14.9, 1H), 5.18 (ABq, J=12.1, 2H), 6.89–6.97 (3H), 7.23–7.27 (m, 1H), 7.33–7.40 (5H), 9.63 (d, J=2.0, 1H).

Step C: 2-(R)-(3-(S)-((4-(3-(2-Cyanophenyl)propyl)piperidin-1-yl)methyl)-4-(S)-(3-fluorophenyl)pyrrolidin-1-yl)-3-(cyclobutyl)propanoic acid A solution of 2-(R)((3-(R)-formyl)-4-(S)-3-(fluoro)phenyl-pyrrolidin-1-yl)-3-(cyclobutyl)propanoic acid, benzyl ester (28 mg, 0.068 mmol, from EXAMPLE 35, Step B), 3-(2-cyanophenyl)propyl piperidine.HCl (20 mg, 0.075 mmol from EXAMPLE 35, Step A) sodium triacetoxyborohydride, 29 mg (0.14 mmol) and TEA (0.012 mL, 0.083 mmol) in 1 mL 1,2-dichloroethane was stirred for 3 h. The crude mixture was filtered through a pad of silica (3 g) eluting with 19:1 v/v CH$_2$Cl$_2$/MeOH. The solvent was removed and the residue was dissolved in 2 mL MeOH and stirred with 10% palladium on carbon (12 mg, 0.011 mmol) under 1 atm of hydrogen for 20 h. The reaction mixture was filtered through a 0.45 micorn nylon filter and concentrated to afford pure product: $^1$H NMR (500 MHz) δ 1.3–1.3 (5H),1.6–2.4 (H), 2.47–2.57 (m, 1H), 2.79–2.82 (t, 2H, J=7.5 Hz), 2.8–3.55 (H), 3.95–4.05 (m, 1H), 6.946.98 (m, 1H), 7.08–7.1 (d, 1H, J=8.5 Hz), 7.1–7.2 (m, 1H), 7.27–7.33 (m, 3H), 7.48–7.50 (m, 1H), 7.58–7.60 (d, 1H, J=7 Hz): ESI-MS, M/z; (M+H)=532.5 (obs), 532.33 (calc.).

EXAMPLE 36

2-(R)-(3-(S)-((4-(3-(4Cyanophenyl)propyl)piperidin-1-yl) methyl)+(S)-(3-fluorophenyl)-pyrrolidin-1-yl)-3-(cyclobutyl)propanoic acid Step A: 3-(4-Cyanophenyl)propylpiperidine.HCl The title compound was prepared from 4-(prop-2-enyl)-1-t-butoxycarbonyl piperidine (475 mg, 2.1 mmol, from EXAMPLE 33, Step B) and 4 bromobenzonitrile (382 mg, 2.1 mmol) using a procedure analogous to that described in EXAMPLE 33, Step D to obtain 337 mg (61%) of the title compound: $^1$H NMR (300 MHz, CD$_3$OD) δ 1.31–1.42 (m, 4H), 1.58–1.75 (m, 5H), 1.9–2.1 (m, 2H), 2.67–2.77 (t, 2H), 2.9–3.0 (m, 2H), 3.3–3.4 (m, 2H), 7.35–7.4 (d, 2H), 7.6–7.63 (d, 2H).

Step B: 2-(R)-(3-(S)-((4-(3-(4-Cyanophenyl)propyl) piperidin-1-yl)methyl)-4-(S)-(3-fluorophenyl)-pyrrolidin-1-yl)-3-(cyclobutyl)propanoic acid A solution of 2-(R)-((3-(R)-formyl)-4-(S)-(3-fluorophenyl)pyrrolidin-1-yl)-3-(cyclobutyl)propanoic acid, benzyl ester (28 mg, 0.068 mmol, from EXAMPLE 35, Step B), 3-(4-cyanophenyl)propyl piperidine.HCl (20 mg, 0.075 mmol from EXAMPLE 36, Step A) sodium triacetoxyborohydride, 29 mg (0.14 mmol) and TEA (0.012 mL, 0.083 mmol) in 1 mL 1,2-dichloroethane was stirred for 3 h. The crude mixture was filtered through a pad of silica (3 g) eluting with 19:1 v/v CH$_2$Cl$_2$/MeOH. The solvent was removed and the residue was dissolved in 2 mL MeOH and stirred with 10% palladium on carbon (12 mg, 0.011 mmol) under 1 atm of hydrogen for 20 h. The reaction mixture was filtered through a 045 micron nylon filter and concentrated. The product was purified by flash chromatography (3 g silica gel, 19:1 v/v CH$_2$Cl$_2$/MeOH, then 19:1:0.2 CH$_2$Cl$_2$/MeOH/NH$_{40}$H as the eluant) to give 26 mg (67%) of the title compound: $^1$H NMR (500 MHz) δ 1.2–1.4 (5H),1.58–2.15 (14H), 2.27–2.33 (m, 11), 2.45–2.5 (m, 11), 2.62–2.65 (t, 2H, J=7.5), 2.8–3.35 (91), 3.75–3.85 (m, 1H), 6.91–6.96 (t, 1H, J=7), 7.0–7.03 (d, 1H, J=9.5), 7.07–7.09 (m, 1H), 7.24–7.25 (d, 2H, J=8), 7.24–7.28 (m, 1H), 7.55–7.57 (d, 21, J=8 ); ESI-MS 532 (M+H).

EXAMPLES 37–41

The compounds in Table 1 were prepared according to the following procedure: A solution of 3-(S)-((4-hydroxy-4-(3-phenylpropyl)piperidin-1-yl)methyl)-4-(S)-phenylpyrrolidine (25 mg, 0.066 mmol), the corresponding keto-acid (0.132 mmol) and sodium triacetoxyborohydride (28 mg, 0.132 mmol) was stirred in 1.5 mL 1,2-dichloroethane for 6 h. The solvent was removed and the products were purified by preparative HPLC (Zorbax SB-C18 9.4×250 mm column, gradient: 5:95 CH$_3$CN/H$_2$O+ 0.1% TFA for 5 min, then ramp to 70:30 v/v CH$_3$CN/H$_2$O+ 0.1% TEA over 25 min, 10 mL/min). The solvent was removed by lyophilization to give the products as mixtures of diastereomers.

TABLE 1

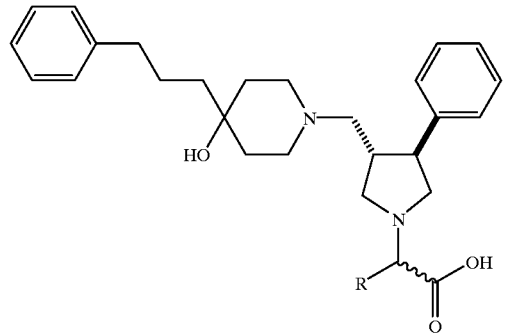

| EXAMPLE # | R | ESI-MS M/z (M + H) |
|---|---|---|
| 37 | ⤴Me | 465 |
| 38 | ⤴⤴Me | 479 |

TABLE 1-continued

| EXAMPLE # | R | ESI-MS M/z (M + H) |
|---|---|---|
| 39 | Me-CH(Me)- (isopropyl) | 493 |
| 40 | -CH2-CH(Me)2 (isobutyl) | 493 |
| 41 | n-hexyl | 521 |
| 42 | 2-furyl | 503 |
| 43 | 2-thienyl | 519 |
| 44 | phenyl | 513 |
| 45 | 3-indolyl | 552 |
| 46 | -CH2CH2-Ph | 541 |

EXAMPLES 42–46

There are no Examples 42 to 46.

EXAMPLES 47–67

The compounds in Table 2 were prepared according to the following general procedure. A solution the appropriate aldehyde (1.0 equiv), the appropriate piperidine.HCl (1.3 equiv), sodium triacetoxyborohydride (2.0 equiv) and TEA (1.5 equiv) in 1 mL 1,2-dichloroethane was stirred for 3h. The crude mixture was filtered through a pad of silica (3 g) eluting with 19:1 v/v $CH_2Cl_2$/MeOH. The solvent was removed and the residue was dissolved in 2 mL MeOH and stirred with 10% palladium on carbon (12 mg, 0.011 mmol) under 1 atm of hydrogen for 1–20 h. The reaction mixture was filtered through a 0.45 micron nylon filter. Pure product was obtained by flash chromatography (3 g silica gel, 19:1 v/v $CH_2Cl_2$/MeOH, then 19:1:0.2 v/v/v $CH_2Cl_2$/MeOH/ $NH_4OH$ as the eluant) or by preparative HPLC (Zorbax SB-C18 9.4×250 mm column, gradient: 5:95 $CH_3CN$/$H_2O$+ 0.1% TFA for 5 min, then ramp to 70:30 v/v $CH_3CN$/$H_2O$+ 0.1% TFA over 25 min, 10 mL/min).

For cases that were incompatible to catalytic hydrogenation the (4-methoxy)benzyl ester of the appropriate aldehyde was used. The (4-methoxy)benzyl group was removed by stirring in formic acid overnight. Pure products were isolated as described above.

TABLE 2

| EXAMPLE # | Rᵃ | Rᵇ | Z | ESI-MS M/z (M + H) |
|---|---|---|---|---|
| 47 | phenyl-(CH₂)₄- | cyclohexyl | H | 517.4 |
| 48 | phenyl-CH=CH-CH₂- (cis) | cyclohexyl | H | 501.4 |
| 49 | phenyl-CH=CH-CH₂- (trans) | cyclohexyl | H | 501.5 |
| 50 | phenyl-(CH₂)₂-CH(CH₃)- | cyclohexyl | H | 517.5 |
| 51 | 4-NC-phenyl-(CH₂)₂- | cyclohexyl | H | 514.4 |
| 52 | 4-NC-phenyl-(CH₂)₃- | isopropyl | H | 488.4 |
| 53 | benzofurazan-5-yl-(CH₂)₃- | isopropyl | H | 505.4 |
| 54 | 3-F-4-NC-phenyl-(CH₂)₃- | cyclohexyl | F | 564.5 |

TABLE 2-continued
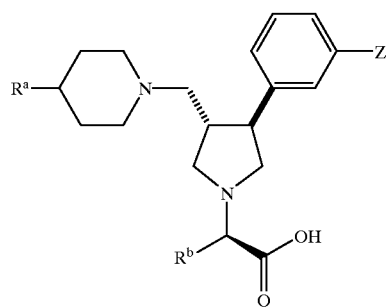
| EXAMPLE # | R<sup>a</sup> | R<sup>b</sup> | Z | ESI-MS M/z (M + H) |
|---|---|---|---|---|
| 55 | 3-CN-4-F-C6H3-(CH2)3- | cyclohexyl | H | 546.5 |
| 56 | 4-CN-3-F-C6H3-(CH2)3- | cyclohexyl | H | 546.5 |
| 57 | trans-2-phenylcyclopropyl-CH2- | cyclohexyl | H | 515.5 |
| 58 | 2-OMe-C6H4-(CH2)3- | cyclohexyl | F | 551.5 |
| 59 | 3-CN-C6H4-(CH2)3- | cyclobutyl-CH2- | F | 532.6 |
| 60 | 4-CN-C6H4-(CH2)3- | cyclobutyl-CH2- | H | 514.3 |
| 61 | 3-CN-C6H4-(CH2)3- | cyclobutyl-CH2- | H | 514.3 |

TABLE 2-continued
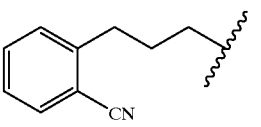
| EXAMPLE # | R$^a$ | R$^b$ | Z | ESI-MS M/z (M + H) |
|---|---|---|---|---|
| 62 | 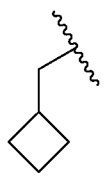 | 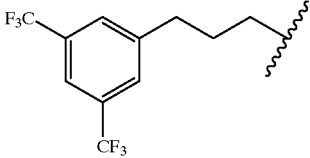 | H | 515.3 |
| 63 | 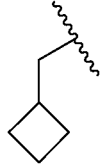 | 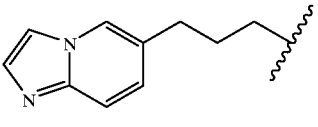 | F | 643.3 |
| 64 | 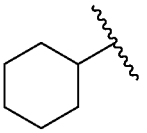 | 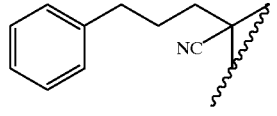 | H | 543.4 |
| 65 | 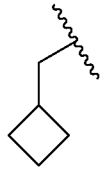 | 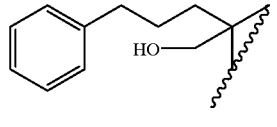 | H | 514.3 |
| 66 | 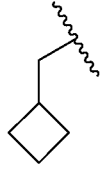 | 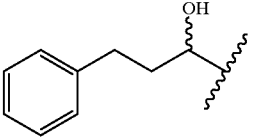 | H | 519.3 |
| 67 | 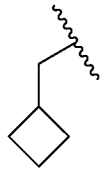 | 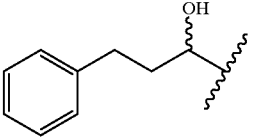 | H | 505.3 |

The compounds in Table 3 were prepared in a manner similar to those in Table 2 from 2-(S)-((3-(R)-formyl)-4-(S)-phenyl-pyrrolidin 1-yl)-3-cyclobutyl)propanoic acid, (4-methoxy)benzyl ester and the appropriate piperidine.

TABLE 3

| EXAMPLE # | R | ESI-MS M/z (M + H) |
|---|---|---|
| 68 | 2-CN-phenyl-propyl | 514.4 |
| 69 | 3-CN-phenyl-propyl | 514.4 |
| 70 | 4-CN-phenyl-propyl | 514.4 |

EXAMPLE 71
2-(R)-(3-(S((4-(3-Phenylpropyl)piperidin-1-yl)methyl)-4-(S)-phenyl-pyrrolidin-1-yl)-2-(cyclohexyl)acetic acid
Step A: 2-(R)-(3-(S)-((4—(3-Phenylpropyl)piperidin-1-yl)methyl)-4-(S)-phenylpyrrolidin-1-yl)-2-(cyclohexyl)acetic acid, benzyl ester To a solution of 34 mg (0.084 mmol) of 2-(R)-(3-(R)-formyl-4-(S)-phenylpyrrolidin-1-yl)-2-(cyclohexyl)acetic acid, benzyl ester (from EXAMPLE 1, Step I) and 19 mg (0.093 mmol) of 4-(3-phenylpropyl) piperidine in 2 mL of CH$_2$Cl$_2$ at rt was added 27 mg (0.13 mmol) of sodium triacetoxyborohydride. After stirring for 1 h, the reaction was diluted with 25 mL of CH$_2$Cl$_2$ and washed with 25 mL of sat'd NaHCO$_3$. After separating the phases, the aqueous layer was extracted with 25 mL of CH$_2$Cl$_2$. The combined organic phases were washed with 50 mL of sat'd NaCl, dried over MgSO$_4$ and concentrated. The residue was purified by flash chromatography eluting with 50:1 v/v CH$_2$Cl$_2$/MeOH to give 37 mg (74%) of the title compound: $^1$H NMR (500 MHz) δ 0.99–2.91 (32H), 3.20–3.27 (3H1), 5.19 (ABq, J=19.7, 2H), 7.17–7.43 (15H); NH$_3$-CI-MS 593 (M+H).
Step B: 2-(R)-(3-(S)-((4-(3-Phenylpropyl)piperidin-1-yl)methyl)-4-(S)-phenylpyrrolidin-1-yl)-2-(cyclohexyl)acetic acid A solution of 37 mg (0.062 mmol) of 2-(R)-(3-(S)-((4-(3-phenylpropyl)piperidin-1-yl)methyl)-4-(S)-phenylpyrrolidin-1-yl)-2-(cyclohexyl)acetic acid, benzyl ester (from EXAMPLE 71, Step A) and 19 mg (0.093 mmol) of 10% palladium on carbon in 4 mL of MeOH was hydrogenated (40 psi) on a Parr shaker for 1 h. The reaction mixture was filtered through a 0.45 micron nylon membrane polypropylene filter and concentrated to give 31 mg (100%) of the title compound: $^1$H NM (500 MHz) δ 0.85–4.11 (35H), 7.11–7.39 (10H); NH$_3$-CI-MS 503 (M+H).

EXAMPLE 72
2-(R)-(3-(S)-((4-(3-(2-Pyridyl)propyl)piperidin-1-yl)methyl)-4-(S)-phenylpyrrolidin-1-yl)-2-(cyclohexyl)acetic acid
Step A: 1-(t-Butoxycarbonyl)-4-(3-(2-pyridyl)propyl)piperidine The title compound was prepared using a procedure analogous to that described in EXAMPLE 31, Step A, substituting (2-bromo)pyridine for (3-bromo)quinoline. Flash chromatography on silica gel using 4:1 v/v hexanes/EtOAc, then 3:2 v/v hexanes/EtOAc as the eluant provided 135 mg (48%) of the title compound: $^1$H NMR (500 MHz) δ 1.05–1.81 (10H), 1.46 (9H), 2.67–2.82 (2H), 3.65 (m, 1H), 4.08–4.16 (12H), 7.14–7.18 (2H), 7.63 (m,1H), 8.54 (d, J=4.4, 1H); ESI-MS 304 (M+H).
Step B: 4-(3-(2-Pyridyl)propyl)piperidine.2 TFA To a solution of 128 mg (0.42 mmol) of 1-(t-butoxycarbonyl)-4-(3-(2-pyridyl)propyl)piperidine (from EXAMPLE 72, Step A) in 1 mL of CH$_2$Cl$_2$ was added 1 mL of TFA. After stirring for 2 h at rt, the reaction was concentrated to give the title compound: $^1$H NMR (500 MHz) 1.22–1.46 (5H), 1.46 (9H), 1.73–1.79 (4H), 2.68 (t, J=11.8, 2H), 2.78 (t, J=7.8, 2H), 3.19 (d, J=11.8, 2H), 5.32 (br s, 1H), 7.09–7.15 (2H), 7.59 (t, J=7.7, 2H), 8.52 (d, J=4.6, 1H).
Step C: 2-(R)-(3-(S)-((4-(3-(2-Pyridyl)propyl)piperidin-1-yl)methyl)-4-(S)-phenylpyrrolidin-1-yl)-2-(cyclohexyl) acetic acid, (4-methoxy)benzyl ester The title compound was prepared from 42 mg (0.096 mmol) of 2-(R)-(3-(R)-formyl-4-(S)-phenylpyrrolidin-1-yl)-2-(cyclohexyl)acetic acid, (4-methoxy)benzyl ester (from EXAMPLE 33, Step E) and 36 mg (0.18 mmol) of 4-(2-pyridylpropyl)piperidine.2 TFA (from EXAMPLE 72, Step B) using a procedure analogous to that described in EXAMPLE 71, Step A. Flash chromatography using 25:1 v/v CH$_2$Cl$_2$/MeOH provided 58 mg (97%) of the title compound: $^1$H NMR (500 MHz) δ 0.94–3.28(35H), 3.82 (s, 3H), 5.11 (ABq, J=11.9, 2H), 6.88–7.35 (11H), 7.58–7.61 (m, 1H), 8.52 (d, J=4.1, 1H); ESI-MS 624 (M+H).
Step D: 2-(R)-(3-(S)-((4-(3-(2-Pyridyl)propyl)piperidin-1-yl)methyl)-4-(S)-phenylpyrrolidin-1-yl)-2-(cyclohexyl) acetic acid The title compound was prepared from 58 mg (0.093 mmol) of 2-(R)-(3-(S)-((4-(3-(2-pyridyl)propyl)piperidin-1-yl)methyl)-4-(S)-phenylpyrrolidin-1-yl)-2-(cyclohexyl) acetic acid, (4-methoxy)benzyl ester (from EXAMPLE 72, Step C) using a procedure analogous to that described in EXAMPLE 10, Step F. Flash chromatography using 90:10:1 v/v/v CH$_2$Cl$_2$/MeOH/NH$_4$OH as the eluant afforded 44 mg (94%) of the title compound: $^1$H NMR (500 MHz) δ 0.82–3.90 (35H), 7.07–7.58 (8H), 8.49 (d, J=4.8 Hz, 11H); ESI-MS 504 (M+H).

EXAMPLE 73
2-(R)-(3-(S)-((4-(3-(Quinoxalin-2-yl)propyl)piperidin-1-yl)methyl)-4-(S)-phenylpyrrolidin-1-yl)-2-(cyclohexyl)acetic acid
Step A: 4-(3-(2-Quinoxalin-2-yl)propyl)piperidine.2 TFA The title compound was prepared using a procedure analogous to that described in EXAMPLE 31, Step A (substituting (2-chloro)quinoxaline for (3-bromo)quinoline) and EXAMPLE 72, Step B. For the title compound: $^1$H NMR (500 MHz) δ 0.79–3.51 (15H), 7.70–7.78 (2H), 8.03–8.10 (2H), 8.74 (s, 1H).

Step B: 2-(R)-(3-(S((4-(3-(Quinoxalin-2-yl)propyl) piperidin-1-yl)methyl)-4-(S)-phenylpyrrolidin-1-yl)-2-(cyclohexyl)acetic acid, (4-methoxy)benzyl ester The title compound was prepared from 50 mg (0.12 mmol) of 2-(R)-(3-(R)-formyl-4-(S)-phenylpyrrolidin-1-yl)-2-(cyclohexyl)acetic acid, (4-methoxy)benzyl ester (from EXAMPLE 33, Step E) and 55 mg (015 mmol) of 4-(3-(quinoxalin-2-yl)propyl)piperidine.2 TFA (from EXAMPLE 73, Step A) using a procedure analogous to that described in EXAMPLE 71, Step A. Flash chromatography using 19:1 v/v $CH_2Cl_2$/MeOH afforded 77 mg (100%) of the title compound: $^1$H NMR (500 MHz) 80.83–3.36(35H), 3.81 (s, 3H), 5.11 (ABq, J=11.9, 2H), 6.89 (d, J=8.7, 2H), 7.16–7.35 (7H), 7.70–7.78 (2H), 8.03–8.10 (2H), 8.73 (s, 1H).

Step C: 2-(R)-(3-(S)-((4-(3-(Quinoxalin-2-yl)propyl) piperidin-1-yl)methyl)-4-(S)-phenylpyrrolidin-1-vi)-2-(cyclohexyl)acetic acid The title compound was prepared from 77 mg (0.11 mmol) of 2-(R)-(3-(S)-((4-(3-(quinoxalin-2-yl)propyl) piperidin-1-yl)methyl)-4-(S)-phenylpyrrolidin-1-yl)-2-(cyclohexyl)acetic acid, (4-methoxy)benzyl ester (from EXAMPLE 73, Step B) using a procedure analogous to that described in EXAMPLE 10, Step F. Flash chromatography using 95:5:0.5 v/v/v $CH_2Cl_2$/MeOH/$NH_4$OH as the eluant afforded 55 mg (87%) of the title compound: $^1$H NMR (500 MHz) δ 0.874.00 (35H), 7.22–7.30 (5H), 7.69–7.76 (2H), 8.00–8.08 (2H), 8.70 (s, 1H); ESI-MS 555 (M+H); HPLC A: 2.27 min.

EXAMPLE 74

2-(R)-(3-(S)-((4-(3-((4-Trifluoromethyl)pyrimidin-2-yl) propyl)piperidin-1-yl)methyl)-4-(S)-(3-fluorophenyl) pyrrolidin-1-yl)-3-(cyclobutyl)propanoic acid Step A: 1-(t-Butoxycarbonyl)-4-(3,3-dibromoprop-2-enyl)piperidine To a solution of 286 mg (0.86 mmol) of carbon tetrabromide in 4 mL of $CH_2Cl_2$ at −10° C. was added 339 mg (1.29 mmol) of triphenylphosphine. After 10 min, a solution of 98 mg (0.43 mmol) of ((1-t-butoxycarbonyl)piperidin-4-yl) acetaldehyde (from EXAMPLE 33, Step A) and 0.060 mL (0.43 mmol) of TEA in 2 mL of $CH_2Cl_2$ was added. After stirring at rt for 2 h, the reaction mixture was concentrated. The residue was purified by flash chromatography eluting with 9:1 v/v hexanes/EtOAc, then 1:1 v/v hexanes/EtOAc to give 118 mg (72%) of the title compound: $^1$H NMR (500 MHz) δ 1.14–1.22 (2H), 1.47 (s, 9H), 1.57–1.60 (m, 1H), 1.67 (br d, J=12.6,22H), 2.08 (t, J=7.1,22H), 2.70 (t, J=12.7, 22H), 4.10 (br d, J=12.6, 2H), 6.42 (t, J=7.4, 1H).

Step B: 1-(t-Butoxycarbonyl)-4-(2-propynyl)piperidine

To a solution of 118 mg (0.31 mmol) of 1-(t-butoxycarbonyl)-4-(3,3-dibromoprop-2-enyl)piperidine (from EXAMPLE 74, Step A) in 4 mL of THF at −78° C. was added 0.370 mL (0.92 mmol) of a 2.5 M solution of butyllithium. After stirring at −78° C. for 45 min, the reaction mixture was quenched with 4 mL of sat'd $NH_4Cl$ and diluted with 25 mL of ether. After separating the phases, the aqueous layer was extracted with 25 mL of ether. The combined organic phases were washed with 50 mL of sat'd NaCl, dried over $MgSO_4$ and concentrated. The residue was purified by flash chromatography eluting with 4:1 v/v hexanes/ether to give 55 mg (80%) of the title compound: $^1$H NMR (500 MHz) δ 1.18–1.26 (2H), 1.47 (s, 9H), 1.60–1.67 (m, 11), 1.77 (br d, J=13.2, 2H), 1.99 (t, J=2.6, 11H), 2.16 (dd, J=6.6, 2.5, 2H), 2.68–2.74 (2H), 4.12 (br d, J=13.0, 22H).

Step C: 1-(t-Butoxycarbonyl)-4-(3-((4-trifluoromethyl) pyrimidin-2-yl)prop-2-ynyl)piperidine A solution of 86 mg (0.39 mmol) of 1-(t-butoxycarbonyl)-4-(2-propynyl)piperidine (from EXAMPLE 74, Step B) in 4 mL of TEA at 0° C. was treated with 0.070 mL (0.58 mmol) of a 2-chloro-4-(trifluoromethyl)pyrimidine, then flushed with argon. After stirring at 0° C. for 5 min, 27 mg (0.04 mmol) of dichlorobis(triphenylphosphine) palladium(II) and 4 mg (0.02 mmol) of copper iodide were added and the reaction vessel was flushed with argon. After 3 h at 60° C., the reaction mixture was cooled to rt, and quenched with 5 mL of 1.0 N NaOH and diluted with 25 mL of ether. After the separating phases, the aqueous layer was extracted with 25 mL of ether. The combined organic phases were washed with 50 mL of sat'd NaCl, dried over $MgSO_4$ and concentrated. The residue was purified by flash chromatography eluting with 9:1 v/v hexanes/EtOAc followed by 2:1 v/v hexanes/EtOAc to give 132 mg (93%) of the title compound: $^1$H NMR (400 MHz) 8 1.26–1.33 (2H), 1.46 (s, 9H), 1.80–1.88 (3H), 2.46 (d, J=6.4, 2H), 1.99 (br t, J=11.2, 1H), 4.104.40 (2H), 7.54 (d, J=5.0, 1H), 8.94 (d, J=5.0, 1H).

Step D: 1-(t-Butoxycarbonyl)-4-(3-((4-trifluoromethyl) pyrimidin-2-yl)propyl)piperidine The title compound was prepared from 1-(t-butoxycarbonyl)-4-(3-((4-trifluoromethyl)pyrimidin-2-yl) prop-2-ynyl)piperidine from (EXAMPLE 74, Step C) using a procedure analogous to that described in EXAMPLE 71, Step B. Flash chromatography using 9:1 v/v hexanes/EtOAc followed by 2:1 v/v hexanes/EtOAc afforded the title compound: $^1$H NMR (400 MHz) δ 1.04–1.15 (2H), 1.27–1.49 (3H), 1.46 (s, 9H), 1.68 (br d, J=12.7, 2H), 1.85–1.93 (2H), 2.68 (br t, J=12.1, 2H), 3.05 (t, J=7.7, 2H), 4.08 (br d, J=11.5, 2H), 7.47 (d, J=5.0, 1H), 8.92 (d, J=5.0, 1H).

Step E: 4-(3-((4-Trifluoromethyl)pyrimidin-2-yl)propyl) piperidine.TFA

The title compound was prepared from 17 mg (0.046 mmol) of 1-(t-butoxy-carbonyl)-4-(3-((4-trifluoromethyl) pyrimidin-2-yl)propyl)piperidine (from EXAMPLE 74, Step D) using a procedure analogous to that described in EXAMPLE 72, Step B. Flash chromatography eluting with 95:5:0.5 v/v/v $CH_2Cl_2$/MeOH/$NH_4$OH afforded 22 mg (96%) of the title compound: $^1$H NMR (300 MHz) δ 1.21–3.45 (15H), 7.52 (d, 5.0 Hz, 1H), 8.95 (d, 5.0 Hz, 1H).

Step F: 2-(R)-(3-(S)-(4-(3-((4-Trifluoromethyl)pyrimidin-2-yl)prop-1-yl)piperidin-1-yl)methyl)-4-(S)-(3-fluorophenyl) pyrrolidin-1-yl)-3-(cyclobutyl)propanoic acid, benzyl ester The title compound was prepared from 15 mg (0.037 mmol) of 2-(R)-(3-(R)-formyl-4-(S)-(3-fluorophenyl) pyrrolidin-1-yl)-3-(cyclobutyl)propanoic acid, benzyl ester (from EXAMPLE 26, Step A) and 22 mg (0.044 mmol) of 4-(3-((4-trifluoromethyl)pyrimidin-2-yl)propyl) piperidine.TFA (from EXAMPLE 74, Step E) using a procedure analogous to that described in EXAMPLE 71, Step A. Flash chromatography using 25:1 v/v $CH_2Cl_2$/MeOH afforded 22 mg (92%) of the title compound: $^1$H NMR (500 MHz) δ 1.20–3.29 (33H), 3.81 (s, 3H), 5.17 (ABq, J=12.2, 22H), 6.86–7.42 (9H), 7.47 (d, J=5.0, 1H), 8.91 (d, J=5.0, 1H).

Step G: 2-(R)-(3-(S(4-(3-((4-Trifluoromethyl)pyrimidin-2-yl)prop-1-yl)piperidin-1-yl)methyl)-4-(S)-(3-fluorophenyl) pyrrolidin-1-yl)-3-(cyclobutyl)propanoic acid The title compound was prepared from 22 mg (0.033 mmol) of 2-(R)-(3-(S)-(4-(3-((4-trifluoromethyl)pyrimidin-2-yl)propyl)piperidin-1-yl)methyl)-4-(S)-(3-fluorophenyl) pyrrolidin-1-yl)-3-(cyclobutyl)propanoic acid, benzyl ester (from EXAMPLE 74, Step F) using a procedure analogous to that described in EXAMPLE 71, Step B to give 15 mg (79%) of the title compound: $^1$H NMR (500 MHz) δ 0.86–4.00 (33H), 6.92–7.30 (4H), 7.45 (d, 5.0 Hz, 1H), 8.90 (d, J=5.0, 1H); ESI-MS 577.3 (M+H). HPLC A: 2.64 min.

EXAMPLE 75

2-(R)-(3-(S)-(4-(3-((5-Trifluoromethyl)pyridin-2-yl)propyl) piperidin-1-yl)methyl)-4-(S)-(3-fluorophenyl)pyrrolidin-1-yl)-3-(cyclobutyl)propanoic acid The title compound was prepared using procedures analogous to those described in EXAMPLE 74, substituting 2-bromo-5-trifluoromethyl pyridine for 2-chloro-4-trifluoromethyl pyrimidine in Step C. For the title compound: $^1$H NMR (500 MHz) δ 1.27–4.00 (33H), 6.90–7.28 (5H), 7.81 (dd, 8.2, 2.2 Hz, 1H), 8.77 (s, 1H); ESI-MS 576 (M+H); HPLC A: 2.64 min.

EXAMPLE 76
2-(R)-(3-(S)-(4-(3-((4-Trifluoromethylphenyl)propyl) piperidin-1-yl)methyl)-4-(S)-(3-fluorophenyl)pyrrolidin-1-yl)-3-(cyclobutyl)propanoic acid The title compound was prepared using a procedures analogous to those described in EXAMPLE 74, substituting 1-bromo-4-trifluoromethylbenzene for 2-chloro-trifluoromethyl pyrimidine in Step C. For the title compound:. $^1$H NMR (500 MHz) δ 1.27–4.00 (33H), 6.91–7.29 (6H), 7.51 (d, 8.0 Hz, 2H); ESI-MS 575.3 (M+H); HPLC A: 3.17 min.

EXAMPLE 77
2-(R)-(3-(S)-(4-(3-((5-Trifluoromethyl)pyridin-2-yl)propyl) piperidin-1-yl)methyl)-4-(S)-phenylpyrrolidin-1-yl)-2-(cyclohexyl)acetic acid The title compound was prepared using a procedure analogous to that described in EXAMPLE 75, substituting 2-(R)-(3-(R)-formyl-4-(S)-phenylpyrrolidin-1-yl)-2-(cyclohexyl)acetic acid, (4-methoxy)benzyl ester (from EXAMPLE 33, Step E) for 2-(R)-(3-(R)-formyl-4-(S)-phenylpyrrolidin-1-yl)-3-(cyclobutyl)propanoic acid, benzyl ester in Step F. For the title compound: $^1$H NMR (500 MHz) δ 1.11–4.00 (35H), 7.22 (d, J=8.0, 1H), 7.26–7.30 (5H), 7.80 (dd, J=8.0, 2.0, 1H), 8.77 (s, 1H); ESI-MS 572 (M+H).

EXAMPLE 78
2-(R)-(3-(S)-(4-((4-Trifluoromethylphenyl)propyl) piperidin-1-yl)methyl)-4-(S)-phenylpyrrolidin-1-yl)-2-(cyclohexyl)acetic acid The title compound was prepared using a procedure analogous to that described in EXAMPLE 76, substituting 2-(R)-(3-(R)-formyl-4-(S)-phenylpyrrolidin-1-yl)-2-(cyclohexyl)acetic acid, (4-methoxy)benzyl ester (from EXAMPLE 33, Step E) for 2-(R)-(3-(R)formyl-4-(S)-phenylpyrrolidin-1-yl)-3-(cyclobutyl)propanoic acid, benzyl ester in Step F. For the title compound: $^1$H NMR (500 MHz) δ 1.12–4.00 (35H), 7.23 (d, J=8.0, 1H), 7.28–7.30 (5H), 7.51 (d, J=8.0,2H); ESI-MS 571 (M+H); HPLC A: 3.17 min.

EXAMPLE 79
2-(R)-(3-(S)-((4-Hydroxy-4-(3-(tetrazolo[4,5-a]pyridin-5-yl)propyl) piperidin-1-yl)methyl)-4-(S)-phenylpyrrolidin-1-yl)-2-(cyclohexyl)acetic acid
Step A: 4-Hydroxy-4-(3-(tetrazolo[4,5-a]pyridin-5-yl)propyl)piperidine.HCl The title compound was prepared using a procedure analogous to those described in EXAMPLE 2, Steps A,B, D–F, substituting 5-bromo-tetrazolo[4,5-a]pyridine (from EXAMPLE 34, Step A) for 1-bromo-4-(1H-tetrazol-5-yl)benzene in Step D. For the title compound: $^1$H NMR (500 MHz, CD$_3$OD) δ 1.57–1.61 (m, 2H), 1.70–1.86 (6H), 2.83 (t, J=7.5, 2H), 3.19–3.33 (4H), 7.78 (dd, J=1.5, 9.0, 1H), 8.01 (d, J=9.0, 1H), 8.95 (app s, 11).
Step B: 2-(P)-(3-(S)-((4-Hydroxy-4-(3-(tetrazolo[4,5-a]pyridin-5-yl)propyl)piperidin-1-yl)methyl)-4-(S)-phenylpyrrolidin-1-yl)-2-(cyclohexyl)acetic acid, benzyl ester The title compound was prepared from 32 mg (0.079 mmol) of 2-(R)-(3-(R)-formyl-4-(S)-phenylpyrrolidin-1-yl)-2-(cyclohexyl)acetic acid, benzyl ester (from EXAMPLE 1, Step I) and 26 mg (0.087 mmol) of 4-hydroxy-4-(3-(tetrazolo[4,5-a]pyridin-5-yl)propyl)piperidine.HCl (from EXAMPLE 79, Step A) using a procedure analogous to that described in EXAMPLE 71, Step A. Flash chromatography using 9:1 v/v CH$_2$Cl$_2$/MeOH as the eluant afforded 41 mg (80%) of the title compound: $^1$H NMR (500 MHz) δ 0.88–3.27 (35H), 5.16 (ABq, J=12.1, 2H), 7.17–7.41 (10H), 7.53 (d, J=9.2, 2H), 7.93 (d, J=9.2, 2H), 8.62 (s, 11H); ESI-MS 651.6 (M+H).
Step C: 2-(R)-(3-(S)-((4-Hydroxy-4-(3-(tetrazolo[4,5-a]pyridin-5-yl)propyl)piperidin-1-yl)methyl)-4-(S)-phenylpyrrolidin-1-yl)-2-(cyclohexyl)acetic acid The title compound was prepared from 41 mg (0.063 mmol) of 2-(R)-(3-(S)-((4-hydroxy-4-(3-(tetrazolo[4,5-a]pyridin-5-yl)propyl)piperidin-1-yl)methyl)-4-(S)-phenylpyrrolidin-1-yl)-2-(cyclohexyl)acetic acid, benzyl ester (from EXAMPLE 79, Step B) using a procedure analogous to that described in EXAMPLE 71, Step B to give 35 mg (100%) of the title compound: $^1$H NMR (500 MHz) δ 0.92–4.00 (35H), 7.17–7.38 (5H), 7.51 (d, J=9.2, 2H), 7.91 (d, J=9.2, 2H), 8.64 (s, 1H);ESI-MS 561 (M+H).

EXAMPLE 80
2-(R)-(3-(S)-((4-Hydroxy-4-(3-(3,4-difluorophenyl)propyl) piperidin-1-yl)methyl)-4-(S)-phenylpyrrolidin-1-yl)-2-(cyclohexyl)acetic acid The title compound was prepared from 2-(R)-(3-(R)-formyl-4-(S)-phenylpyrrolidin-1-yl)-2-(cyclohexyl)acetic acid, benzyl ester (from EXAMPLE 1, Step I) and (3-(3,4-difluorophenyl)propyl)piperidine.HCl (from EXAMPLE 119, Step C) using procedures analogous to those described in EXAMPLE 71, Steps A and B. For the title compound: $^1$H NMR (500 MHz) B 0.90–3.90 (35H), 6.80–7.34 (8H); ESI-MS 555 (M+H).

EXAMPLE 81
2-(R)-(3-(S)-((4-Hydroxy-4-(3-(4-pyridyl)propyl)piperidin-1-yl)methyl)-4-(S)-phenylpyrrolidin-1-yl)-2-(cyclohexyl)acetic acid
Step A: 4-Hydroxy-4-(3-(4-pyridyl)propyl)piperidine.HCl The title compound was prepared using procedures analogous to those described in EXAMPLE 2, Steps A,B,D–F, substituting (4-bromo)pyridine for 1-bromo-4-(1H-tetrazol-5-yl)benzene in Step D. For the title compound: $^1$H NMR (500 MHz) δ 1.59–1.91 (8H), 2.98–3.31 (6H), 8.00 (d, J=6.6,22H), 8.74 (d, J=6.6, 2H); ESI-MS 221 (M+H).
Step B: 2-(R)-(3-(S)-((4-Hydroxy-4-(3-(4-pyridyl)prop-1-yl)piperidin-1-yl)methyl)-4-(S)-phenylpyrrolidin-1-yl)-2-(cyclohexyl)acetic acid The title compound was prepared from 2-(R)-(3-(R)-formyl-4-(S)-phenylpyrrolidin-1-yl)-2-(cyclohexyl)acetic acid, benzyl ester (from EXAMPLE 1, Step I) and 4-hydroxy-4-(3-(4-pyridyl)propyl)piperidine.HCl (from EXAMPLE 81, Step A) using procedures analogous to those described in EXAMPLE 71, Steps A and B. For the title compound: $^1$H NMR (500 MHz) δ 1.00–4.00 (35H), 7.04 (d, J=5.7, 2H), 7.24–7.31 (5H), 8.40 (d, J=5.7, 2H); ESI-MS 520 (M+H).

EXAMPLE 82
2-(R)-(3-(S)-((4-Hydroxy-4-(3-(2-napthyl)propyl)piperidin-1-yl)methyl)-4-(S)-phenylpyrrolidin-1-yl)-2-(cyclohexyl)acetic acid
Step A: 4-Hydroxy-4-(3-(2-naphthyl)propyl)piperidine.HCl The title compound was prepared using procedures analogous to those described in EXAMPLE 12, Steps A and B, substituting (2-bromo)napthalene for 3,4-difluoro-1-bromobenzene in Step B. For the title compound: HPLC (Zorbax SB-C8 4.6×100 mm column, gradient elution using 0:100 $CH_3CN/H_2O$ to 100:0 v/v $CH_3CN/H_2O$+0.1% TFA over 7.5 min 2.25 mL/min): 3.38 min; ESI-MS 270 (M+H).
Step B: 2-(R)-(3-(S)-((4-Hydroxy-443-(2-napthyl)propyl) piperidin-1-yl)methyl)-4-(S)-phenylpyrrolidin-1-yl)-2-(cyclohexyl)acetic acid The title compound was prepared from 2-(R)-(3-(R)-formyl-4-(S)-phenylpyrrolidin-1-yl)-2-(cyclohexyl)acetic acid, benzyl ester (from EXAMPLE 1, Step I) and 4-hydroxy-4-(3-(2-naphthyl)propyl)piperidine.HCl (from EXAMPLE 82, Step A) using procedures analogous to those described in EXAMPLE 71, Steps A and B. For the title compound: $^1$H NMR (500 MHz) δ 0.89–3.88 (35H), 7.22–7.77 (12H); ESI-MS 569.6 (M+H).

EXAMPLE 83
2-(R)-(3-(S)-((4-Hydroxy-4-(3-(3,5-difluoro-4hydroxyphenyl)propyl) piperidin-1-yl)methyl)-4-(S)-phenylpyrrolidin-1-yl)-2-(cyclohexyl)acetic acid
Step A: 1-Bromo-3,5-difluoro-4-(benzyloxy)benzene To a solution of 5.0 g (24.0 mmol) of 2,6 difluoro-4-bromophenol in 20 ml of DMF at rt was added 5 g (36.0 mmol) of $K_2CO_3$ followed by 4.5 g (26.3 mmol) of benzyl bromide. The mixture was stirred for 12 h, diluted with $H_2O$, the organic phase washed with sat'd NaCl, and the aqueous phase was then extracted 3× with $CH_2Cl_2$. The combined organic layers were dried over $Na_2SO_4$ and concentrated. Flash chromatography with a gradient of 0–15% ethyl acetate/hexanes (v/v) afforded 6.3 g (88%) of the title compound: $^1$H NMR (500 MHz) δ 5.17 (s, 21), 7.06–7.11 (2H). 7.34–7.45 (5H).
Step B: 4-Hydroxy-4-(3-(3,5-difluoro-4-hydroxyphenyl) propyl)piperidine.HCl The title compound was prepared using procedures analogous to those described in EXAMPLE 2, Steps A,B,D–F, substituting 1-bromo-3,5-difluoro-4-benzyloxy benzene (from EXAMPLE 83, Step A) for 1-bromo-4-(1H-tetrazol-5-yl)benzene in Step D. For the title compound: $^1$H NMR (500 MHz, $CD_3OD$) δ 1.48–1.52 (2H), 1.64–1.77 (6H). 2.54 (t, J=7.5 Hz, 2H), 3.18–3.27 (4H). 6.74 (d, J=8.0 Hz, 2H).
Step C: 2-(R)-(3-(S)-((4-Hydroxy-4-(3-(3,5-difluoro-4-hydroxyphenyl)prop-1-yl)piperidin-1-yl)methyl)-4-(S)-phenylpyrrolidin-1-yl)-2-(cyclohexyl)acetic acid The title compound was prepared from 2-(R)-(3-(R)-formyl-4-(S)-phenylpyrrolidin-1-yl)-2-(cyclohexyl)acetic acid, benzyl ester (from EXAMPLE 1, Step I) and 4-hydroxy-4-(3-(3,5-difluoro-4-hydroxyphenyl) propyl) piperidine.HCl (from EXAMPLE 83, Step B) using procedures analogous to those described in EXAMPLE 71, Steps A and B. For the title compound: $^1$H NMR (500 MHz) δ 0.95–3.42 (35H), 5.16 (ABq, J=12.0, 2H), 6.56 (d, J=8.0, 2H), 7.21–7.30 (5H); ESI-MS 571 (M+H).

EXAMPLE 84
2-(R)-(3-(S)-((4-Fluoro-4-(3-phenylpropyl)piperidin-1-yl) methyl)-4-(S)-phenylpyrrolidin-1-yl)-2-(cyclohexyl)acetic acid To a solution of DIEA (0.019 mL, 0.11 mmol) in 0.5 mL of 1,2-dichloroethane was added 4fluoro-4-(3-phenylpropyl) piperidine.HCl (21 mg, 0.08 mmol) To this solution, a solution of 2-(R)-((3-(R)-formyl)-4-(S)-phenylpyrrolidin-1-yl)-2-(cyclohexyl)acetic acid, (4-methoxy) benzyl ester (25 mg, 0.052 mmol, from EXAMPLE 33, Step E) was added. A slurry of sodium triacetoxyborohydride (35 mg, 0.17 mmol) in 0.5 mL of 1,2-dichloroethane was then added. The reaction mixture was allowed to stand at rt for 16 hours. The solvent was removed and the product was purified by preprative HPLC (column: YMC Combiprep ODS-A 20×50 mm, gradient: 10% acetonitrile/$H_2O$ w/0.1% TFA for 1.5 min then ramp to 90% acetonitrile/$H_2O$ w/0.1% TFA over 7.5 min, flow: 20 mL/min). The isolated material was stirred in 3 mL formic acid for 16 h. After removal of solvent, the residue was purified by ion exchange chromatography (0.5 grams Varian SCX resin, 100% MeOH→2.0 M $NH_3$/MeOH) to give 13 mg (48%) of the title compound: $^1$H NMR (400 MHz, $CD_3OD$) δ 1.15–1.37 (m, 4H), 1.41–1.59 (m, 5H), 1.62–1.69 (m, 5H), 1.72–1.91 (m, 5H), 2.04 (t, J=10, 1H), 2.24 (t, J=11, 1H), 2.32 (dd, J=4.5, 13, 1H), 2.46 (dd, J=10, 13 Hz, 2H), 2.58 (t, J=7.5 Hz, 2H), 2.62–2.65 (m, 1H), 2.77 (m, 1H), 3.16 (dd, J=11, 19, 1H), 3.45 (m, 2H), 3.51 (d, J=3.9, 1H), 3.58–3.64 (m, 2H), 7.12–7.16 (m, 3H), 7.22–7.29 (m, 3H), 7.33–7.37 (m, 4H); ESI-MS: 521 (M+H); HPLC A: 2.65 min.

EXAMPLE 85
2(-R)-(3-(S)-((4-Fluoro-4-(3-phenylpropyl)piperidin-1-yl) methyl)-4-(S)-(3-fluorophenyl)-pyrrolidin-1-yl)-3-methylbutanoic acid
Step A: 2-(S)-Hydroxy-3-methylbutanoic acid, (4-methoxy) benzyl ester The title compound was prepared from 2-(S)-hydroxy-3-methylbutanoic acid using a procedure analogous to that described in EXAMPLE 19, Step E. For the title compound: $^1$H NMR (500 MHz) δ 0.84 (d, J=6.5, 3H), 1.01 (d, J=6.5, 3H), 2.05–2.12 (m, 1H), 2.71 (d, J=6.0, 1H), 4.06–4.08 (m, 1H), 5.18 (ABq, J=11.5, 2H), 6.91 (d, J=8.5, 2H), 7.32 (d, J=6.5, 2H).
Step B: 2-(R)-((3-(R)-Formyl)(S)-(3-fluorophenyl)-pyrrolidin-1-yl)-3-methylbutanoic acid (4-methoxy)benzyl ester The title compound was prepared from 3-(R)-(t-butyldimethylsilyloxymethyl)-4-(S)-(3-fluorophenyl) pyrrolidine (from EXAMPLE 20, Step H) and 2-(S)-hydroxy-3-methylbutanoic acid, (4-methoxy)benzyl ester (from EXAMPLE 85, Step A) using procedures analogous to those described in EXAMPLE 1, Steps G–I. For the title compound: $^1$H NMR (500 MHz) δ 0.91 (d, J=6.5, 3H), 1.00 (d, J=6.5, 3H), 2.04–2.09 (m, 11H), 2.68 (t, J=8.5, 11H), 2.88–2.92 (m, 11H), 3.06 (d, J=10.0, 1H), 3.14–3.19 (2H), 3.26 (t, J=8.5, 1H), 3.55 (q, J=7.5, 1H), 3.82 (s, 3H), 5.13 (app s, 2H), 6.88–6.97 (4H), 7.18–7.34 (5H), 9.64 (d, J=1.5, 1H).
Step C: 2-(R)-(3-(S)-((4-Fluoro-4-(3-phenylpropyl) piperidin-1-yl)methyl)-4-(S)-(3-fluorophenyl)-pyrrolidin-1-yl)-3-methylbutanoic acid The title compound was prepared using a procedure analogous to that described in EXAMPLE 84, substituting 2-(R)-((3-(R)-formyl)-4-(S)-(3-fluorophenyl)-pyrrolidin-1-yl)-3-methylbutanoic acid, (4-methoxy)benzyl ester (from EXAMPLE 85, Step B) for 2-(R)-((3-(R)-formyl)-4-(S)-phenylpyrrolidin-1-yl)-2-(cyclohexyl)acetic acid, (4-methoxy) benzyl ester. For the title compound: ESI-MS: 499 (M+H); HPLC A: 2.51 min.

EXAMPLE 86
2-(R)-(3-(S)-((4-Fluoro-4-(3-(4-fluorophenyl)-propyl) piperidin-1-yl)methyl)-4-(S)-(3-fluorophenyl)-pyrrolidin-1-yl)-3-(cyclobutyl)propanoic acid
Step A: N-Benzyl-(4-hydroxy-4-(3-(4-fluorophenyl) propyl))piperidine 4-Hydroxy-4-(3-(4-fluorophenyl)propyl)piperidine.HCl (165 mg, 0.6 mmol) was dissolved in a solution of DIEA (0.122 mL, 0.7 mmol) in 10 mL of 1,2-dichloroethane. Benzaldehyde (0.076 mL, 0.75 mmol) was then added and the reaction mixture was mixed well. A slurry of sodium triacetoxyborohydride (318 mg, 1.5 mmol) in 5 mL of 1,2-dichloroethane was then added. The reaction mixture was allowed to stand at rt for 16 h. The solvent was removed, and the crude material purified by ion exchange chromatography (2 grams Varian SCX resin, 100% MeOH→2.0 M $NH_3$/MeOH) to give 180 mg (91%) of the title compound: ESI-MS: 328.0 (M+H); HPLC A: 2.74 min.

Step B: N-Benzyl-(4-fluoro-4-(3-(4-fluorophenyl)-propyl)) piperidine

A solution of N-benzyl-(4-hydroxy-4-(3-(4-fluorophenyl)-propyl))piperidine (180 mg, 0.55 mmol, from EXAMPLE 86, Step A) in 1 mL of $CH_2Cl_2$ was added to a solution of diethylaminosulfur trifluoride (0.092 mL, 0.7 mmol) in 1 mL of $CH_2Cl_2$ at −78° C. The resulting mixture was stirred cold for 1, then warmed to rt and stirred for an additional hour. The reaction was quenched with 3 mL of 2.0 N NaOH. The layers were separated and the aqueous was extracted with 4×3 mL of $CH_2Cl_2$. The extracts were combined, dried over $Na_2SO_4$ and concentrated. Flash chromatography using 3:1 v/v hexanes/EtOAc as the eluant) afforded 32 mg (32%) of the title compound: ESI-MS: 330 (M+H); HPLC A: 2.75 min.

Step C: 4-Fluoro-4-(3-(4-fluorophenyl) propylpiperidine.HCl

A solution of 1-chloroethyl chloroformate (0.011 mL, 0.1 mmol) and N-benzyl-(4-fluoro-4-(3-(4-fluorophenyl)-propyl))piperidine (32 mg, 0.1 mmol, from EXAMPLE 86, Step B) in 5 mL of 1,2-dichloroethane was heated at reflux for 1 h. The mixture was cooled to it, treated with 0.003 mL of 1-chloroethyl chloroformate then heated at reflux for 30 min. The mixture was cooled to rt and concentrated. The residue was dissolved in 5 mL of methanol and heated at reflux for 1 h. The mixture was cooled and concentrated. The product was triturated with EtOAc, filtered and dried to afford 28 mg (100%) of the title compound: ESI-MS: 240 (M+H); HPLC A: 2.25 min.

Step D: 2-(R)-(3-(S)-((4Fluoro-4-(3-(4-fluorophenyl) propyl)piperidin-1-yl)methyl)-4-(S)-(3-fluorophenyl)-pyrrolidin-1-yl)-3-(cyclobutyl)propanoic acid The title compound was prepared using a procedure analogous to that described in EXAMPLE 84, substituting 2-(R)-(3-(R)-(formyl)-4-(S)-(3-fluorophenyl)pyrrolidin-1-yl)-3-(cyclobutyl)propanoic acid, benzyl ester (from EXAMPLE 26, Step A) for 2-(R)-((3-(R)-formyl)-4-(S)-phenylpyrrolidin-1-yl)-2-(cyclohexyl)acetic acid, (4-methoxy) benzyl ester and 4-fluoro-4-(3-(4-fluorophenyl) propyl)piperidine.HCl (from EXAMPLE 86, Step C) for 4-fluoro-4-(3-phenylpropyl)piperidine.HCl. For the title compound: ESI-MS: 543 (M+H); HPLC A: 2.99 min.

EXAMPLE 87
2-(R)-(3-(S)-((4-(3-Phenylpropyl)piperidin-1-yl)methyl)-4-(S)-(3-thienyl)pyrrolidin-1-yl)-3-(cyclobutyl)propanoic acid Step A: 1-(Prop-2-enyl)-3-(R)-(hydroxymethyl)-4-(S)-(3-thienyl) pyrrolidine The title compound was prepared from trans-3-(3-thienyl) acrylic acid using procedures analogous to those described in EXAMPLE 1, Steps A–C, substituting N-methoxymethyl-N-trimethylsilylmethyl(prop-2-enyl) amine for N-methoxymethyl-N-trimethylsilylmethylbenzyl amine in Step B. For the title compound: $^1$H NMR (500 MHz) δ 2.30–2.34 (m, 1H), 2.44 (t, J=8.5, 1H), 2.67 (t, J=9.0, 1H), 2.77 (dd, J=5.0, 9.0, 1H), 3.02–3.15 (4H), 3.53 (dd, J=7.5, 10.0, 1H), 3.64 (dd, J=5.0, 10.0, 1H), 5.07 (d, J=10.0, 1H), 5.17 (d, J=17.5, 1H), 5.83–5.91 (m, 1H), 6.97–6.99 (2H), 7.20–7.22 (m, 1H); ESI-MS 224 (M+H).

Step B: 1-(Prop-2-enyl)-3-(R)-(t-butyldimethylsilyloxymethyl)-4-(S)-(3-thienyl)pyrrolidine A solution of 1.06 g (4.75 mmol) of 1-(prop-2-enyl)(3-(R)-(hydroxymethyl))-4-(S)-(3-thienyl)pyrrolidine (from EXAMPLE 87, Step A) in 12.0 mL of $CH_2Cl_2$ at 0° C. was treated with 0.99 mL (5.7 mmol) of DIEA and 855 mg (5.6 mmol) of t-butyldimethyl silyl chloride. After warming to rt and stirring for 20 h, the solution was partitioned between 100 mL of ether and 100 mL of $H_2O$. After separating the phases, the aqueous layer was extracted with 100 mL of ether. The combined organic phases were dried over $MgSO_4$ and concentrated. The residue was purified by flash chromatography eluting with 3:1 v/v hexanes/EtOAc to yield 1.24 g (77%) of the title compound: $R_F$: 0.54 (3:2 v/v hexanes/EtOAc); $^1$H NMR (300 MHz) δ 0.0 (s, 6H), 0.86 (s, 9H), 2.35 (m, 1H), 2.52–2.71 (m, 3H), 2.97–3.20 (m, 4H), 3.54–3.66 (m, 2H), 5.06–5.21 (m, 2H), 5.89 (m, 1H). 6.98–7.02 (m, 2H), 7.22 (m, 1H).

Step C: (3-(R)-(t-Butyldimethylsilyloxymethyl)-4-(S)-(3-thienyl)pyrrolidine

A solution of 3.7 g (11.0 mmol) of 1-(prop-2-enyl)-3-(R)-(t-butyldimethylsilyloxymethyl)-4-(S)-(3-thienyl) pyrrolidine (from EXAMPLE 87, Step B) in 16% aqueous acetonitrile (degassed with nitrogen) was treated with 540 mg (0.58 mmol) of chloro tris(triphenylphosphine)rhodium. The reaction was warmed to reflux and the propanal that formed was removed via azeotropic distillation with the solvents. Additional solvent was added periodically to maintain a constant reaction volume. After 6 h, TLC indicated the absence of starting material. The reaction was cooled to rt and concentrated. The residue was purified by flash chromatography eluting with a gradient of 97:2:1 v/v/v $CH_2Cl_2$/MeOH/$NH_4OH$, then 94:5:1 v/v/v $CH_2Cl_2$/MeOH/$NH_4OH$, then 89:10:1 v/v/v $CH_2Cl_2$/MeOH/$NH_4OH$ to yield 2.76 g (84%) of the title compound: $R_F$: 0.26 (97:2:1 v/v/v $CH_2Cl_2$/MeOH/$NH_4OH$); $^1$H NMR (300 Mhz) δ 0.0 (s, 6H), 0.86 (s, 9H), 2.36 (m, 1H), 2.93–3.70 (m, 7H), 6.99–7.06 (m, 2H), 7.28 (m, 1H).

Step D: 2-(R)-(3-(R)-(t-Butyldimethylsilyloxymethyl)-4-(S)-(3-thienyl)pyrrolidin-1-yl)-3-(cyclobutyl)propanoic acid, (4methoxy)benzyl ester The title compound was prepared from 274 mg (1.0 mmol) of 2-(S)-hydroxy-3-(cyclobutyl)propanoic acid, (4-methoxy)benzyl ester (from EXAMPLE 19, Step E) and 380 mg (1.35 mmol) of 3-(S)-(t-butyldimethyl silyloxymethyl)-4-(S)-(3-thienyl)pyrrolidine (from EXAMPLE 87, Step C) using a procedure analogous to that described in EXAMPLE 1, Step G to provide 449 mg (87%) of the title compound: $^1$H NMR (300 MHz) δ 0.0 (s, 6H), 0.86 (s, 9H), 1.52–2.09 (m, 9H), 2.23–2.33 (m, 2H), 2.59–2.70 (m, 21), 2.95–3.24 (m, 3H), 3.46–3.61 (m, 2H), 3.81 (s, 3H), 5.08 (br s, 2H), 6.85–6.95 (m, 4H), 7.21–7.33 (m, 3H).

Step E: 2-(R)(3-(R)-(Hydroxy)methyl)-4-(S)-(3-thienyl) pyrrolidin-1-yl)-3-(cyclobutyl)propanoic acid. (4-methoxy) benzyl ester The title compound was prepared from 449 mg (0.90 mmol) of 2-(R)-(3-(R)-(t-butydimethylsilyloxymethyl)-4-(S)-(3-thienyl)-pyrrolidin-1-yl)-3-(cyclobutyl)propanoic acid, (4-methoxy)benzyl ester (from EXAMPLE 87, Step D) using a procedure analogous to that described in EXAMPLE 1, Step H to provide 345 mg (89%) of the title compound: $R_F$: 0.43 (1:1 v/v hexanes/EtOAc); $^1$H NMR (300 Mhz) δ 1.56–2.10 (m, 9H), 2.22–2.33 (m, 2H), 2.55 (m, 1H), 2.77 (m, 1H), 3.01 (m, 1H), 3.22–3.27 (m, 21, 3.55–3.72 (m, 2H), 3.81 (s, 31), 5.09 (s, 2H), 6.86–6.94 (m, 4H), 7.23–7.34 (m, 3H).

Step F: 2-(R)(3-(R)-Formyl-4-(S)-(3-thienyl)pyrrolidin-1-yl)-3-(cyclobutyl)propanoic acid. (4-methoxy)benzyl ester The title compound was prepared from 337 mg (0.78 mmol) of 2-(R)-(3-(R)(hydroxymethyl)-4-(S)-(3-thienyl) pyrrolidin-1-yl)-3-(cyclobutyl)propanoic acid, (4-methoxy) benzyl ester (from EXAMPLE 87, Step E) using a procedure analogous to that described in EXAMPLE 1, Step I to provide 197.5 mg (59%) of the title compound: $R_F$: 0.56 (4:1 v/v hexanes/EtOAc); $^1$H NMR (300 Mhz) δ 1.56–2.05 (m, 8H), 2.27 (m, 1H), 2.69 (br t, 1H), 2.89 (m, 1H), 3.06–3.31 (m, 4H), 3.63 (br q, 1H), 3.81 (s, 3H), 5.09 (s, 2H), 6.86–6.96 (m, 4H), 7.25–7.33 (m, 3H), 9.63 (d, J=2.2, 1H).

Step G: 2-(R)-(3-(S)-((4-(3-Phenylpropyl)piperidin-1-yl) methyl)-4-(S)-(3-thienyl)pyrrolidin-1-yl)-3-(cyclobutyl) propanoic acid, (4-methoxy)benzyl ester The title compound was prepared from 20 mg (0.046 mmol) of 2-(R)-(3-(R)-formyl-4-(S)-(3-thienyl)pyrrolidin-1-yl)-3-(cyclobutyl)propanoic acid, (4-methoxy)benzyl ester (from EXAMPLE 87, Step F) and 12.9 mg (0.046 mmol) of 4-(3-phenylpropyl)piperidine.HCl using a procedure analogous to that described in EXAMPLE 1, Step J to provide 25.4 mg (88%) of the title compound: $R_F$: 0.47 (3:2 v/v hexanes/EtOAc); $^1$H NMR (300 Mhz) δ 1.10–3.22 (m, 3H), 3.80 (s, 3H), 5.07 (ABq, J=11.9,2H), 6.85–6.93 (m, 4H), 7.14–7.33 (m, 8H).

Step H: 2-(R)-(3-(S)-((4-(3-Phenylpropyl)piperidin-1-yl) methyl)-4-(S)-(3-thienyl)pyrrolidin-1-yl)-3-(cyclobutyl) propanoic acid The title compound was prepared from 25.4 mg (0.041 mmol) of 2-(R)-(3-(S)-((4-(3-phenylpropyl)piperidin-1-yl) methyl)-4-(S)-(3-thienyl)pyrrolidin-1-yl)-3-(cyclobutyl) propanoic acid, (4-methoxy)benzyl ester (from EXAMPLE 87, Step G) using a procedure analogous to that described in EXAMPLE 10, Step F to provide 16.4 mg (80%) of the title compound: $R_F$: 0.29 (90:10:1 v/v/v $CH_2Cl_2$/MeOH/ $NH_4OH$); HPLC A: 2.93 min. ESI-MS 495 (M+H). $^1$H NMR (300 MHz, $CD_3OD$) δ 1.02–3.49 (m, 33H), 6.96–7.33 (m, 8H).

EXAMPLE 88
2-(R)-(3-(S)-((4-(3-(3,4-Difluorophenyl)propyl)piperidin-1-yl)methyl)-4-(S)-(3-thienyl)pyrrolidin-1-yl)-3-(cyclobutyl)propanoic acid The title compound was prepared from 21 mg (0.046 mmol) of 2-(R)-(3-(R)-formyl-4-(S)-(3-thienyl)pyrrolidin-1-yl)-3-(cyclobutyl) propanoic acid, (4-methoxy)benzyl ester (from EXAMPLE 87, Step F) and 11.7 mg (0.046 mmol) of 4-(3-(3,4-difluorophenyl)propyl)piperidine.HCl (from EXAMPLE 119, Step C) using procedures analogous to those described in EXAMPLE 1, Step J and EXAMPLE 10, Step F to provide 15.9 mg (77%) of the title compound: $R_F$: 0.34 (90:10:1 v/v/v $CH_2Cl_2$/MeOH/$NH_4OH$); $^1$H NMR (300 MHz, $CD_3OD$) δ 1.00–3.48 (m, 33H), 6.79–7.01 (m, 4H), 7.18 (m, 1H), 7.32 (m, 1H); ESI-MS 531 (M+H); HPLC A: 3.01 min.

EXAMPLE 89
2-(R)-(3-(S)-((4-(3-(4-Fluorophenyl)propyl)piperidin-1-yl) methyl)-4-(S)-(3-thienyl)pyrrolidin-1-yl)-3-(cyclobutyl) propanoic acid The title compound was prepared from 21 mg (0.046 mmol) of 2-(R)-(3-(R)-formyl-4-(S)-(3-thienyl)pyrrolidin-1-yl)-3-(cyclobutyl) propanoic acid, (4-methoxy)benzyl ester (from EXAMPLE 87, Step F), 11.7 mg (0.046 mmol) of 4-(3-(4-fluorophenyl)propyl)piperidine.HCl (from EXAMPLE 96, Step B) using procedures analogous to those described in EXAMPLE 1, Step J and EXAMPLE 10, Step F to provide 17.6 mg (72%) of the title compound: $R_F$: 0.28 (90:10:1 v/v/v $CH_2Cl_2$/MeOH/$NH_4OH$); $^1$H NMR (300 MHz, $CD_3OD$) δ 1.01–3.48 (m, 33H), 6.80–6.86 (m, 2H), 6.99–7.05 (m, 3H), 7.18 (m, 1H), 7.33 (m, 1H); ESI-MS 513 (M+H); HPLC A: 2.72min.

EXAMPLE 90
2-(R)-(3-(S)-((4-(3-Phenylpropyl)piperidin-1-yl)methyl)-4-(S)-(3-thienyl)pyrrolidin-1-yl)-2-(cyclohexyl)acetic acid
Step A: 2-(R)-(3-(R)-Formyl-4-(S)-(3-thienyl)pyrrolidin-1-yl)-2-(cyclohexyl)acetic acid, 4-methoxybenzyl ester The title compound was prepared from (3-(R)-(t-butyl-dimethylsilyloxy)methyl)-4-(S)-(3-thienyl)pyrrolidine (from EXAMPLE 87, Step C) and 2-(S)-hydroxy-2-(cyclohexyl)acetic acid, (4methoxy)benzyl ester (from EXAMPLE 33, Step E) using procedures analogous to those described in EXAMPLE 1, Steps G–I.
Step B: 2-(R)(3-(S)-((4-(3-Phenylpropyl)piperidin-1-yl) methyl)-4-(S)-(3-thienyl)pyrrolidin-1-yl)-2-(cyclohexyl) acetic acid The title compound was prepared from 2-(R)-(3-(R)-formyl-4-(S)-(3-thienyl)pyrrolidin-1-yl)-2-(cyclohexyl) acetic acid, 4-methoxybenzyl ester (from EXAMPLE 90, Step A) and 4-(3-phenylpropyl)piperidine using procedures analogous to those described in EXAMPLE 1, Step J and EXAMPLE 10, Step F. For the title compound: $^1$H NMR (500 MHz) δ 0.85–4.20 (35H), 7.11–7.35 (8l); ESI-MS 509 (M+H).

EXAMPLE 91
2-(R)-(3-(S)-((4-(3-(3,4Difluorophenyl)propyl)piperidin-1-yl)methyl)-4-(S)-(3-thienyl)pyrrolidin-1-yl)-2-(cyclohexyl) acetic acid The title compound was prepared using procedures analogous to those described in EXAMPLE 90 substituting 4-(3-(3,4-difluoro)phenylpropyl)piperidine.HCl (from EXAMPLE 119, Step C) for 4-(3-phenylpropyl)piperidine in Step B. For the title compound: $^1$H NMR (500 MHz) δ 1.11–3.85 (35H), 6.81–7.30 (6H); ESI-MS 545 (M+H).

EXAMPLE 92
2-(S)-(3-(S)-((4-(3-Phenylpropyl)piperidin-1-methyl)-4-(S)-phenylpyrrolidin-1-yl)-3-(cyclobutyl)propanoic acid
Step A: (R/S)-2-Hydroxy-3-(cyclobutyl)propanoic acid, (4-methoxy)benzyl ester The title compound was prepared using procedures analogous to those described in EXAMPLE 17, Step A substituting bromomethylcyclobutane for bromomethylcyclohexane. For the title compound: $R_F$: 0.27 (4:1 v/v hexanes/EtOAc); $^1$H NMR (300 MHz) δ 1.57–2.08 (m, 8H), 2.30 (br, 1H), 2.51 (m, 1H), 3.82 (s, 3H), 4.11 (dd, J=7.7,4.3, 1H), 5.12 (ABq, J=11.8, 2H), 6.90 (d, J=8.8,22H), 7.29 (d, J=8.8, 2H).
Step B: 2-(S)-(3-(R)-(Hydroxymethyl)-4-(S)-phenylpyrrolidin-1-yl)-3-(cyclobutyl)propanoic acid, (4-methoxy)benzyl ester The title compound was prepared from 3-(R)-(t-butyldimethylsilyloxymethyl)-4-(S)-phenyl pyrrolidine (from EXAMPLE 1, Step E) and (R/S)-2-hydroxy-3-(cyclobutyl)propanoic acid (from EXAMPLE 92, Step A) using procedures analogous to those described in EXAMPLE 1, Steps G an H. The diastereomers were separated by HPLC in the second step using the following conditions: Chiralpak AD 2×25 cm column, 17:3 v/v hexanes/iPrOH, 9.0 mL/min, 220 nm) to provide the title compound.
Step C: 2-(S)-(3-(R)-Formyl-4-(S)-phenylpyrrolidin-1-yl)-3-(cyclobutyl)propanoic acid, (4-methoxy)benzyl ester The title compound was prepared from 69 mg (0.16 mmol) of 2-(S)-(3-(R)-(hydroxymethyl)-4-(S)- phenylpyrrolidin-1-yl)-3-(cyclobutyl)propanoic acid, (4-methoxy)benzyl ester (from EXAMPLE 92, Step B) using a procedure analogous to that described in EXAMPLE 1, Step I to provide 68 mg (100%) of the title compound: $R_F$: 0.28 (4:1 v/v hexanes/EtOAc); $^1$H NMR (300 MHz) δ 1.57–2.07 (m, 8H), 2.30 (m, 1H), 2.79–3.56 (m, 7H), 3.81 (s, 3H), 5.09 (s, 2H), 6.89 (d, J=8.8,22H), 7.19–7.34 (m, 7H), 9.65 (d, J=1.6, 1H).

Step D: 2-(S)-(3-(S)-((4-(3-Phenylpropyl)piperidin-1-yl)methyl)-4-(S)-phenylpyrrolidin-1-yl)-3-(cyclobutyl) propanoic acid The title compound was prepared from 25 mg (0.059 mmol) of 2-(S)-(3-(R)-formyl-4-(S)-phenylpyrrolidin-1-yl)-3-(cyclobutyl)propanoic acid, (4-methoxy)benzyl ester (from EXAMPLE 92, Step C) and 14.3 mg (0.059 mmol) of 4-(3-phenylpropyl)piperidine.HCl using a procedures analogous to those described in EXAMPLE 1, Step J and EXAMPLE 10, Step F to 18.4 mg (64%) of the title compound: $R_F$: 0.48 (90:10:1 v/v/v $CH_2Cl_2$/MeOH/$NH_4OH$); $^1$H NMR (300 MHz, $CD_3OD$) δ 0.99–3.67 (m, 33H), 6.96–7.23 (m, 10H); ESI-MS 489 (M+H); HPLC A: 2.69 min.

EXAMPLE 93

2-(R/S)(3-(S)-((4-(3-Phenylpropyl)piperidin-1-yl)methyl)-4-(S)-phenylpyrrolidin-1-yl)-2-(cyclohexyl) methylphosphonic acid Step A: 2-(R/S)-(3-(R)-(t-Butyldimethylsilyloxymethyl)-4-(S)-phenylpyrrolidin-1-yl)-2-(cyclohexyl) methylphosphonic acid, dibenzyl ester A suspension of 196 mg (0.67 mmol) of 3-(S)-(t-butyldimethylsilyloxymethyl)-4-(S)-phenylpyrrolidine (from EXAMPLE 1, Step E), 0.075 mL (0.61 mmol) of cyclohexane carboxaldehyde, 83 mg (0.68 mmol) of $MgSO_4$ and 43 mg (0.069 mmol) of $Yb(OTf)_3$ in 3 mL of $CH_2Cl_2$ was stirred at rt for 30 min. After adding 0.150 mL (approximately 0.67 mmol) of dibenzyl phosphite, the reaction was stirred for 15 h, then concentrated. The crude product was partitioned between 50 mL of EtOAc and 50 mL of $H_2O$. After separating the phases, the organic layer was dried over $Na_2SO_4$ and concentrated. The residue was purified by flash chromatography eluting with 4:1 v/v hexanes/EtOAc to give 280 mg (69%) of the title compound as a mixture of diastereomers: $R_F$: 0.40 (4:1 v/v hexanes/EtOAc); $^1$H NMR (300 Mhz) δ −0.042, −0.032 (2 s, 6H), 0.83 (s, 9H), 1.04–2.04 (m, 11H), 2.31 (m, 1H), 2.83–3.54 (m, 8H), 4.94–5.13 (m, 4H), 7.09–7.38 (m, 15H); ESI-MS 649 (M+H); HPLC A: 4.21 min.

Step B: 2-(R/S)-(3-(R)-(Hydroxymethyl)-4-(S)-phenylpyrrolidin-1-yl)-cyclohexylmethylphosphonic acid, dibenzyl ester The title compound was prepared from 273 mg (0.42 mmol) of 2-(R/S)-(3-(R)-(t-butyldimethylsilyloxymethyl)-4-(S)-phenylpyrrolidin-1-yl)-2-(cyclohexyl) methylphosphonic acid, dibenzyl ester (from EXAMPLE 93, Step A) using a procedure analogous to that described in EXAMPLE 1, Step H to provide 215 mg (96%) of the title compound as a mixture of diastereomers: $R_F$: 0.19 (1:1 v/v hexanes/EtOAc); $^1$H NMR (300 Mhz) δ 0.91–2.34 (m, 12H), 2.86–3.66 (m, 9H), 4.93–5.12 (m, 4H), 7.13–7.37 (m, 151H).

Step C: 2-(R/S)-(3-(R)-Formyl-4-(S)-phenylpyrrolidin-1-yl)-2-(cyclohexyl)methylphosphonic acid, dibenzyl ester The title compound was prepared from 215 mg (0.40 mmol) of 2-(R/S)-(3-(R)-(hydroxymethyl)-4-(S)-phenylpyrrolidin-1-yl)-2-(cyclohexyl)methylphosphonic acid, dibenzyl ester (from EXAMPLE 93, Step B) using a procedure analogous to that described in EXAMPLE 1, Step I to provide 171 mg (80%) of the title compound as a mixture of diastereomers: $R_F$: 0.40 (5.5:4.5 v/v hexanes/EtOAc); $^1$H NMR (300 Mhz) δ 1.04–1.98 (m, 11H), 2.86–3.01 (m, 2H), 3.21–3.50 (m, 5H), 4.91–5.12 (m, 4H), 7.12–7.38 (m, 15H), 9.52,9.57 (2 d, J=2.5, 1H).

Step D: 2-(R/S(3-(S(((4-(3-Phenylpropyl)piperidin-1-yl) methyl)-4-(S)phenylpyrrolidin-1-yl)-2-(cyclohexyl) methylphosphonic acid, dibenzyl ester The title compound was prepared from 40 mg (0.075 mmol) of 2-(R/S)-(3-(R)-formyl-4-(S)-phenylpyrrolidin-1-yl)-2-(cyclohexyl) methylphosphonic acid, dibenzyl ester (from EXAMPLE 93, Step C), 18.7 mg (0.075 mmol) and of 4-(3-phenylpropyl)piperidine.HCl using a procedure analogous to that described in EXAMPLE 1, Step J to provide 40.5 mg (75%) of the title compound as a mixture of diastereomers: $R_F$: 0.29 (5.5:4.5 v/v hexanes/EtOAc); $^1$H NMR (300 Mhz) δ 1.02–3.35 (m, 35H), 4.93–5.12 (m, 4H), 7.09–7.37 (m, 20H).

Step E: 2-(R/S)-(3-(S)-((4-(3-Phenylpropyl)piperidin-1-yl) methyl)-4-(S)-phenylpyrrolidin-1-yl)-cyclohexylmethylphosphonic acid A solution of 39 mg (0.054 mmol) 2-(R/S)-(3-(S)-((4-(3-phenylpropyl)piperidin-1-yl)methyl)-4-(S)-phenylpyrrolidin-1-yl)-cyclohexylmethylphosphonic acid, dibenzyl ester (from EXAMPLE 93, Step D) in 2.3 mL of MeOH was hydrogenated using 17 mg of 10% palladium on carbon under 47 psi of hydrogen gas on a Parr shaker. After TLC indicated the absence of the starting benzyl ester, the reaction was filtered through a 0.45 micron nylon membrane polypropylene filter and concentrated to give 21.1 mg (73%) of the title compound: $^1$H NMR (500 MHz, $CD_3OD$) δ 0.99–3.57 (m, 35H), 6.97–7.29 (m, 10H); ESI-MS 539 (M+H); HPLC A: 2.59 min.

EXAMPLE 94

1-(1-(R)-(1H-Tetrazol-5-yl)-1-(cyclohexyl)methyl)-3-(S)-((4-(3-phenylpropyl) piperidin-1-yl)methyl)-4-(S)-phenylpyrrolidine Step A: 1-((4-Methoxy)benzyl)tetrazole A mixture of 3.84 g (28.0 mmol) of (4-methoxy) benzylamine, 2.73 g (42.0 mmol) of sodium azide and 7.50 mL (45.0 mmol) triethyl orthoformate in 25 mL of HOAc was stirred at 80° C. for 20 h. The reaction was cooled and concentrated. The residue was partitioned between 100 mL of EtOAc and 100 mL of $H_2O$ and the layers were separated. The organic layer was washed with 100 mL of 2.0 N HCl, 100 mL of sat'd $NaHCO_3$, 100 mL of sat'd NaCl, dried over $MgSO_4$ and concentrated. Flash chromatography on 100 g of silica gel using 2:1 v/v hexanes/EtOAc, then 1:1 v/v hexanes/EtOAc as the eluant afforded 2.32 g of the title compound: $^1$H NMR (300 MHz) δ 3.82 (s, 3H), 5.53 (s, 2H), 6.93 (d, J=8.6, 2H), 7.27 (d, J=8.6, 2H), 8.46 (s, 1H).

Step B: 5-(R/S)-(1-Hydroxy-1-(cyclohexyl)methyl)-1-((4-methoxy) benzyl)tetrazole A solution of 380 mg (2.0 mmol) of 1-((4-methoxy) benzyl) tetrazole (from EXAMPLE 94, Step A) in 10 mL of 9:1 v/v THF/N,N,N',N'-tetramethylethylenediamine at −100° C. was treated with 1.40 mL of 1.6 M n-butyllithium solution in hexanes, maintaining the internal temperature at less than −95 ° C. The resulting mixture was stirred cold for 10 min, then treated with 0.30 mL (2.5 mmol) of cyclohexane carboxaldehyde, maintaining the internal temperature at less than −95° C. The resulting mixture was warmed to rt and quenched with 10 mL of sat'd $NH_4Cl$. The quenched mixture was partitioned between 75 mL of ether and 25 mL of $H_2O$ and the layers were separated. The organic layer was washed with 50 mL of 2.0 N HCl, 50 mL of sat'd $NaHCO_3$, 50 mL of sat'd NaCl, dried over $MgSO_4$ and concentrated.

Flash chromatography on 30 g of silica gel using 4:1 v/v hexanes/EtOAc as the eluant afforded 363 mg (60%) of the title compound: ¹H NMR (500 MHz) δ 0.91 (dq, J=3.0, 12.5, 1H), 0.98–1.17 (5H), 1.60–1.62 (m, 2H), 1.68–1.76 (2H), 1.93 (app d, J=12.5), 3.79 (s, 3H), 4.73 (d, J=7.5, 11H), 5.60 (ABq, J=15.0, 2H), 6.86 (d, J=8.5, 2H), 7.22 (d, J=8.5, 2H).

Step C: 1-(1-(R)-(1-((4-Methoxy)benzyl)tetrazol-5-yl)-1-(cyclohexyl) methyl)-3-(R)-(hydroxymethyl)piperidin-1-yl) methyl)-4-(S)-phenylpyrrolidine and 1-(1-(S)-(1-((4-Methoxy)benzyl) tetrazol-5-yl)-1-(cyclohexyl) methyl)-3-(R)-(hydroxymethyl) piperidin-1-yl)methyl)-4-(S)-phenylpyrrolidine The title compound was prepared from 3-(R)-t-butyl-dimethylsilyloxymethyl-4-(S)-phenyl pyrrolidine (from EXAMPLE 1, Step E) and 5-(R/S)-(1-hydroxy-1-(cyclohexyl)methyl)-1-((4-methoxy)benzyl) tetrazole (from EXAMPLE 94, Step B) using procedures analogous to those described in EXAMPLE 1, Steps G and H. The diastereomers were separated in the second step by HPLC using the following conditions: Chiralpak AD 2×25 cm column, 3:1 v/v hexanes/iPrOH, 9.0 mL/min, 220 nM. For 1-(1-(R)-(1-((4-methoxy)benzyl)tetrazol-5-yl)-1-(cyclohexyl) methyl)-3-(R)-(hydroxymethyl)piperidin-1-yl)methyl)-4-(S)-phenyl pyrrolidine: ¹H NMR (500 MHz) δ 0.35–0.42 (m, 1H), 0.88–1.26 (5H), 1.47–1.76 (4H), 2.03–2.31 (4H), 2.542.57 (m, 1H), 2.95 (app q, J=7.5, 1H), 3.08 (app q, J=9.5, 2H), 3.47 (dd, J=6.5, 9.5, 1H), 3.62 (dd, J=5.0, 9.5), 3.74 (s, 3H), 3.86 (d, J=9.5, 1H), 5.48 (ABq, J=15.0, 2H), 6.82 (d, J=8.5, 2H), 7.07–7.26 (71); HPLC retention time: 20.6 min. For 1-(1-(S)-(1-((4-methoxy)benzyl)tetrazol-5-yl)-1-(cyclohexyl) methyl)-3-(R)-(hydroxymethyl)piperidin-1-yl) methyl)-4-(S)-phenyl pyrrolidine: HPLC retention time: 14.3 min.

Step D: 1-(1-(R)-(1-((4Methoxy)benzyl)tetrazol-5-yl)-1-(cyclohexyl) methyl)-3-(S)-((4-(3-phenylpropyl) piperidin-1-yl)methyl)-4-(S)-phenylpyrrolidine The title compound was prepared from 1-(1-(R)-(1-((4-methoxy)benzyl)tetrazol-5-yl)-1-(cyclohexyl) methyl)-3-(R)-(hydroxymethyl)piperidin-1-yl)methyl)-4-(S)-phenylpyrrolidine (from EXAMPLE 94, Step C) using procedures analogous to those described in EXAMPLE 1, Steps I and J, substituting 4-(3-phenylpropyl)piperidine.HCl for 4-hydroxy-4-(3-phenylpropyl)-piperidine.HCl in the second step. For the title compound: ¹H NMR (500 MHz) δ 0.35–0.42 (m, 1H), 0.80–1.30 (11H), 1.45–1.80 (10H), 2.05–2.35 (6H), 2.50–2.60 (3H), 2.70–2.80 (m, 2H), 3.00–3.10 (m, 2H), 3.74 (s, 3H), 3.81 (d, J=10.0, 1), 5.48 (ABq, J=15.5, 2H), 6.82 (d, J=8.5, 2H), 7.10–7.27 (13H).

Step E: 1-(1-(R)-(1H-Tetrazol-5-yl)-1-(cyclohexyl)methyl)-3-(S)-((4-(3-phenylpropyl) piperidin-1-yl)methyl)-4-(S)-phenyl pyrrolidine A solution of 54 mg (0.08 mmol) of 1-(1-(R)-(1-((4-methoxy) benzyl)tetrazol-5-yl)-1-(cyclohexyl) methyl)-3-(S)-((4-(3-phenylpropyl)-piperidin-1-yl)methyl)-4-(S)-phenylpyrrolidine (from EXAMPLE 94, Step D) in 3 mL of TFA was heated at reflux for 6 h. The mixture was cooled and concentrated. Flash chromatography on 2 g of silica gel using $CH_2Cl_2$, then 20:1:0.1 v/v/v $CH_2Cl_2$/MeOH/NH$_4$OH, then 10:1:0.1 v/v/v $CH_2Cl_2$/MeOH/NH$_4$OH as the eluant afforded 20 mg (46%) of the title compound: ESI-MS 527 (M+H), HPLC A: 2.77 min; HPLC B: 7.77 min.

EXAMPLE 95

2-(R)-(3-(S)-((4-(3-(3,5-Difluorophenyl)propyl)piperidin-1-yl)methyl)-4-(S)-(3 -fluorophenyl)pyrrolidin-1-yl)-3-(cyclobutyl)propanoic acid Step A: 1-t-Butoxycarbonyl-4-(2-iodoethyl)piperidine To a solution of 6.6 g (25 mmol) of triphenylphosphine in 125 mL of $CH_2Cl_2$ was added 1.7 g (25 mmol) of imidazole followed by 6.3 g (25 mmol) of iodine, and the mixture was stirred at rt for 30 min, after which 2.0 g (8.32 mmol) of 1-t-butoxycarbonyl-4-(2-hydroxyethyl) piperidine (from EXAMPLE 113, Step A) was added in $CH_2Cl_2$ and the mixture was stirred overnight at rt . The mixture was diluted with $H_2O$, the phases were separated, and the organic phase washed with sat'd NaCl and 0.25 M $Na_2SO_3$ solution. The aqueous phase was then extracted 3× with $CH_2Cl_2$, and the combined organic layers were dried over $Na_2SO_4$, filtered and the filtrate concentrated to provide a white solid. The solid was taken up in hexane, filtered and washed with hexane. The filtrate was concentrated. Flash chomatography on 100 g of silica gel using 17:3 v/v hexanes/EtOAc as the eluant afforded 2.8 g (96%) of the title compound: ¹H NMR (500 MHz) δ 1.11 (dq, J=4.4, 8.2, 2H), 1.46 (s, 2H), 1.55–1.63 (m, 1H). 1.66 (d, J=12.6, 2H), 1.78 (q, J=7.1, 2H), 2.65–2.75 (2H), 5.22 (2H), 3.22 (t, J=7.1, 2H), 4.1 14.15 (5H).

Step B: (2-((1-t-Butoxycarbonyl)piperidin-4-yl)ethyl)-triphenylphosphonium iodide A mixture of 2.8 g (8.0 mmol) of 1-t-butoxycarbonyl-4-(2-iodoethyl)piperidine and 2.1 g (8.0 mmol) of triphenylphosphine in 40 mL of toluene was heated at 100° C. for 36 h. A beige precipitate formed. The mixture was cooled and concentrated to provide a solid which was washed 2× with ether to give 1.72 g (35%) of the title compound: ¹H NMR (500 MHz, $CD_3OD$) δ 1.07 (dq, J=4.0,7.3, 2H), 1.42 (s, 9H), 1.58–1.64 (3H). 1.76 (d, J=12.4, 2H),2.65–2.78 (2H). 3.42–3.48 (2H). 4.05 (d, J=13.5, 2H),7.73–7.91 (15H), Step C: 1-t-Butoxycarbonyl-4-(3-(3,5-difluorophenyl)prop-2-enyl) piperidine To a solution of 1.2 g (2.0 mmol) of (2-((1-t-butoxycarbonyl) piperidin-4-yl)-ethyl) triphenylphosphonium iodide in 10 mL of toluene at 0° C. was added 6 mL (3.0 mmol) of an 0.5 M solution of potassium bis(trimethylsilyl)amide in toluene. After stirring at 0° C. for 30 min, 313 mg (1.1 mmol) of 3,5-difluorobenzaldehyde in 5 mL toluene was added. The mixture was stirred at 0° C. for 30 min, warmed to rt and stirred for 2 h. The mixture was diluted with $H_2O$ and the organic phase was washed with sat'd NaCl. The aqueous phase was then extracted 3× with $CH_2Cl_2$. The combined organic layers were dried over $Na_2SO_4$ and concentrate. Column chomatography using a gradient of 0–15% EtOAc in hexanes as the eluant afforded the title compound, which was used immediately in Step D.

Step D: 1-t-Butoxycarbonyl-4-(3-(3,5-difluorophenyl) propyl) piperidine

A mixture of 1-t-butoxycarbonyl-4-(3-(3,5-difluorophenyl) prop-2-enyl)piperidine (from EXAMPLE 95, Step C) and 50 mg of 10% palladium on carbon in MeOH (10 mL) was hydrogenated at 50 psi for 2 h. The suspension was filtered though Celite, the cake washed with MeOH and the filtrate was concentrated. Flash chomatography using 0–15% EtOAc in hexanes (v/v) as the eluant afforded the title compound: ¹H NMR (500 MHz ) δ 1.10 (dq, J=4.4, 8.2, 21), 1.25–1.30 (21), 1.37–1.45 (m, 1H), 1.47 (s, 9H), 1.62–1.67 (4H). 2.59 (t, J=7.8, 2H), 2.62–2.78 (2H), 4.08 (bs, 2H), 6.61–6.70 (3H).

Step E: 4-(3-(3,5-Difluorophenyl)propyl)piperidine.HCl

A solution of 1-t-butoxycarbonyl-4-(3-(3,5-difluorophenyl)propyl)piperidine (from EXAMPLE 95, Step D) in 2.0 N HCl in MeOH was stirred at rt for 20 h. The solution was concentrated. Ether was added and the mixture was concentrated to remove excess HCl to afford 381 mg (70% yield from EXAMPLE 95, Step C) of the title compound: ¹H NMR (500 MHz, $CD_3OD$) δ 1.32–1.37 (4H), 1.64–1.68 (1H), 1.94 (d, J=14.2, 2H), 2.64 (t, J=7.3, 2H), 2.95 (t, J=13.1, 2H), 3 35 (d, J=12.6, 2H), 6.69–6.78 (m, 1H). 6.80 (d, J=8.2, 2H).

Step F: 2-(R)-(3-(S)-((4-(3-(3,5-Difluorophenyl)propyl)piperidin-1-yl)methyl)-4-(S)-(3-fluorophenyl)pyrrolidin-1-yl)-3-cyclobutyl-propanoic acid, benzyl ester A mixture of 30 mg (0.07 mmol) of 2-(R)-(3-(R)-formyl-4-(S)-(3-fluorophenyl)pyrrolidin-1-yl)-3-(cyclobutyl)propanoic acid, benzyl ester (from EXAMPLE 26, Step A) and 21 mg (0.08 mmol) of 4-(3-(3,5-difluorophenyl)propyl)piperidine.HCl (from EXAMPLE 95, Step E) in 2 mL of $CH_2Cl_2$ at 0° C. was treated with 22 mg (0.11 mmol) of sodium triacetoxyborohydride. The bath was removed and the reaction was stirred at rt for 3 h. The mixture was diluted with $H_2O$, sat'd $NaHCO_3$ and $CH_2Cl_2$. The phases were separated and the aqueous phase was extracted 3× with $CH_2Cl_2$. The combined organic layers were dried over $Na_2SO_4$ and concentrated. Flash chromatography on 10 g silica using a gradient of 0–5% MeOH in $CH_2Cl_2$ (v/v) afforded the title compound: $^1$H NMR (500 MHz) δ 1.15–1.26 (5H), 1.52–1.67 (6H), 1.76–1.94 (6H), 2.01–2.07 (2H), 2.28–2.37 (4H), 2.54–2.58 (2H), 2.62 (d, J=10.3, 1H), 2.73 (dd, J=1.2, 7.8, 1H), 2.80 (d, J=10.5, 1H), 2.89 (q, J=7.7, 1H), 3.13–3.17 (2H). 3.27 (dd, J=2.0,6.4, 1H), 5.17 (d, J=2.5, 2H), 6.63 (tt, J=2.5,6.6, 1 F), 6.68–6.70 (21), 6.88 (dt, J=2.2,6.1, 1H, 6.96 (dt, J=2.3,6.4, 1H), 7.00 (d, J=7.8, 1H), 7.19–7.24 (m, 1H), 7.35–7.42 (5H).

Step G: 2-(R)-(3-(S)-((4-(3-(3,5-Difluorophenyl)propyl)piperidin-1-yl)methyl)-4-(S)-(3-fluorophenyl)pyrrolidin-1-yl)-3-cyclobutyl-propanoic acid A mixture of 2-(R)-(3-(S)-((4-(3-(3,5-difluorophenyl)propyl) piperidin-1-yl)methyl)-4-(S)-(3-fluorophenyl) pyrrolidin-1-yl)-3-(cyclobutyl)propanoic acid, benzyl ester (from EXAMPLE 95, Step F) and 20 mg 10% palladium on carbon in MeOH (5 mL) was hydrogenated at 50 psi for 90 min. The reaction mixture was filtered though Celite, the filter cake washed with MeOH, and the filtrate concentrated to afford 31 mg (84%, two steps) of the title compound: ESI-MS 543 (M+H); HPLC A: 2.85 min.

EXAMPLE 96

2-(R)-(3-(S)-((4-(3-(4-Fluorophenyl)propyl)piperidin-1-yl) methyl)-4-(S)-phenylpyrrolidin-1-yl)-3-(cyclobutyl) propanoic acid Step A: 1-t-Butoxycarbonyl-4-(3-(4-fluorophenyl)propen-2-yl) piperidine The title compound was prepared from 1.5 g (2.5 mmol) of (2-((1-t-butoxycarbonyl)piperidin-4-yl)ethyl) triphenylphosphonium iodide (from EXAMPLE 95, Step B) using a procedure analogous to that described in EXAMPLE 95, Step C, substituting (4-fluoro)benzaldehyde for 3,5-difluoro(benzaldehyde. 743 mg (84%) of the title compound was obtained: $^1$H NMR (500 MHz) δ 1.13 (dq, J=3.9, 8.3, 2H), 1.46 (s, 9H), 1.50–1.55 (m, 1H). 1.70 (d, J=12.5, 2H), 2.25 (dt, J=1.8, 5.3, 2H), 2.69 (t, J=11.9, 2H), 4.08 (d, J=9.6, 2H), 5.66 (dt, J=4.3, 7.4, 11H), 6.45 (d, J=11.7, 1H), 7.03 (t, J=8.7, 2H), 2.62–2.78 (2H), 7.22 (dd, J=3.0, 5.5, 2H).

Step B: 4-(3-(4-Fluorophenyl)propyl)piperidine.HCl

The title compound was prepared from 743 mg (2.33 mmol) of 1-t-butoxycarbonyl-4-(3-(4-fluorophenyl)propen-2-yl)piperidine (from EXAMPLE 96, Step A) using procedures analogous to those described in EXAMPLE 95, Steps D and E. 424 mg (66%) of the title compound was obtained: $^1$H NMR (500 MHz, $CD_3OD$) δ 1.29–1.38 (4H). 1.58–1.68 (3H). 1.92 (d, J=14.0, 2H), 2.60 (t, J=7.6, 2H), 2.95 (t, J=12.2, 2H), 3.33–3.36 (2H). 6.97 (t, J=8.7, 2H), 7.17 (dd, J=3.0, 5.7, 2H).

Step C: 2-(R)-(3-(S((4-(3-(4-Fluorophenyl)propyl) piperidin-1-yl)methyl)-4-(S)-phenylpyrrolidin-1-yl)-3-cyclobutyl-propanoic acid The title compound was prepared from 25 mg (0.06 mmol) of 2-(R)-(3-(R)-formyl-4-(S)-phenylpyrrolidin-1-yl)-3-(cyclobutyl)propanoic acid, benzyl ester (from EXAMPLE 25, Step B) and 16 mg (0.06 mmol) of 4-(3-(4-fluorophenyl)propyl)piperidine.HCl (from EXAMPLE 96, Step B) using procedures analogous to those described in EXAMPLE 95, Steps F and G. 26 mg (81%) of the title compound was obtained: ESI-MS 507 (M+H); HPLC A: 2.69 min.

EXAMPLE 97

2-(R)-(3-(S)-((4-(3-(4-Fluorophenyl)propyl)piperidin-1-yl) methyl)-4-(S)-(3-fluorophenyl pyrrolidin-1-yl)-3-(cyclobutyl)propanoic acid The title compound was prepared from 25 mg (0.06 mmol) of 2-(R)-(3-(R)-formyl-4-(S)-(3-fluorophenyl) pyrrolidin-1-yl)-3-(cyclobutyl) propanoic acid, benzyl ester (from EXAMPLE 26, Step A) and 15 mg (0.06 mmol) of 4-(3-(4-fluorophenyl)propyl)piperidine.HCl (EXAMPLE 96, Step B) using procedures analogous to those described in EXAMPLE 95, Steps F and G. 17 mg (53%) of the title compound was obtained: $^1$H NMR (500 MHz, $CD_3OD$) δ 1.08–1.23 (5H). 1.54–1.76 (5H). 1.81–1.96 (5H). 2.04 (t, J=11.4, 1H), 2.09–2.19 (2H). 2.38 (dd, J=4.1, 12.3, 1H), 2.47–2.56 (4H). 2.69–2.72 (m, 1H). 2.78 (d, J=11.0, 1H), 2.91 (d, J=11.0, 1H), 3.14 (q, J=8.0, 1H), 3.24–3.31 (4H). 3.38 (dd, J=4.8, 9.3, 1H), 3.53–3.62 (2H). 6.93–6.96 (2H). 6.99–7.03 (m,1H). 7.13–7.16 (4H). 7.34–7.39 (m, 1H); ESI-MS 525 (M+H); HPLC A: 2.83 min; HPLC B: 7.57 min.

EXAMPLE 98

2-(R)-(3-(S)-((4-(2,2-Dimethyl-3-phenylpropyl)piperidin-1-yl)methyl)-4-(S) phenylpyrrolidin-1-yl)-2-(cyclohexyl) acetic acid Step A: (3-Carboxypropyl)triphenylphosphonium chloride A solution of 1 g (9.2 mmol) of 3-chloropropanoic acid and 2.4 g (9.2 mmol) of triphenylphosphine was refluxed in 10 mL of toluene overnight. After cooling, the mixture was concentrated to give 3.25 g (95%) of the title compound.

Step B: 3-(1-(t-Butoxycarbonyl)-4-piperidylidene)propionic acid

A mixture of 7.53 g (37.8 mmol) of 1-t-butoxycarbonyl-piperidin-4 one and 14 g (37.8 mmol) of (3-carboxypropyl) triphenyl-phosphonium chloride (from EXAMPLE 98, Step A) were dissolved in 100 mL of 1:1 v/v DMSO/THF. The mixture was cooled to 0° C. and was then added to 2 g (83.2 mmol) of dry 95% sodium hydride powder at 0° C. over a 10 min period. After stirring this mixture at 0 ° C. for 20 h, the reaction was quenched with $H_2O$, treated with sat'd NaCl and extracted 2× with $CH_2Cl_2$. The aqueous phase was acidified to pH 1 with 1 N HCl, and extracted 3× with $CH_2Cl_2$. The combined organic layers were washed with sat'd NaCl and $H_2O$, dried over $Na_2SO_4$, filtered and the filtrate concentrated. The residue was purified by column chomatography on 150 g of silica using a gradient of 25–50% acetone/hexanes (v/v), to give 2.4 g (25%) of the title compound: $^1$H NMR (500 _MHz) δ 1.47 (s, 9H1.2.21 (d, J=5.5,44H), 3.12 (d, J=7.3,22H), 3.42 (d, J=5.7, 4H), 5.41 (t, J=7.1, 11H).

Step C: (3-(1-t-Butoxycarbonylpiperidin-4-yl)propanoic acid

A mixture of 2.1 g (8.3 mmol) of 3-(1-(t-butoxycarbonyl)-4-piperidylidene)propionic acid (from EXAMPLE 98, Step B) in 20 mL of EtOAc and 500 mg of 10% palladium on carbon was hydrogenated (50 psi) on a Parr shaker for 6 h. The mixture was filtered through Celite, the filter cake washed with EtOAc and the filtrate concentrated to give 1.72 g (82%) of the title compound: ¹H NMR (500 MHz) δ 1.12 (dq, J=4.1, 8.5, 2H). 1.46 (s, 10H), 1.61 (q, J=7.5, 2H), 1.66 (d, J=13.3, 2H), 2.38 (t, J=7.8, 2H), 2.65–2.73 (2H), 4.09 (bs, 2H).

Step D: (3-(1-t-Butoxycarbonylpiperidin-4-yl)propanoic acid, methyl ester

A solution of 200 mg (0.79 mmol) of (3-(1-t-butoxycarbonylpiperidin-4-yl)propanoic acid (from EXAMPLE 98, Step C) in 2 mL of 1:1 v/v MeOH/THF was treated with a 2 M trimethylsilyl-diazomethane solution in THF until a yellow color persisted. After stirring the mixture at rt for 1 h, the solution was concentrated and the residue purified by column chomatography on 15 g silica gel with a gradient of 0–25% acetone/hexanes (v/v) to give 205 mg (97%) of the title compound: ¹H NMR (500 MHz) δ 1.11 (dq,J=4.3,8.3,2H). 1.38–1.44 (m, 1H), 1.46(s,9H), 1.59 (q, J=7.5, 2H), 1.65 (d, J=13.3, 2H), 2.35 (t, J=7.6, 2H), 2.62–2.73 (2H), 3.68 (s, 3H), 4.09 (bs, 2H).

Step E: (3-(1-t-Butoxycarbonylpiperidin-4-yl)-2-(RS)-methylpropanoic acid, methyl ester A solution of 0.38 mL (0.38 mmol) of a 1.0 M solution of sodium bis(trimethylsilyl)amide in THF at −70° C. was treated with a solution of 50 mg (0.19 mmol) of (3-(1-t-butoxycarbonylpiperidin-4-yl)propanoic acid, methyl ester (from EXAMPLE 98, Step D) in 1 mL THF. The mixture was stirred for 20 min, treated with 0.033 mL (0.52 mmol) of methyl iodide and stirred at −70° C. for 1 h. The reaction was quenched with $H_2O$ and sat'd NaCl and extracted 3× with $CH_2Cl_2$. The combined organic layers were dried over $Na_2SO_4$, filtered and the filtrate concentrated. The residue was purified by column chomatography on 10 g of silica eluting with a gradient of 0–25% EtOAc /hexanes (v/v), to give 34 mg (70%) of the title compound: ¹H NMR (500 MHz) δ 1.03–1.12 (2H), 1.15 (d, J=6.9, 3H). 1.25–1.31 (m, 1H), 1.38–1.43 (m, 1H), 1.45 (s, 9H), 1.59–1.70 (3H), 2.53–2.58 (m, 1H), 2.65 (t, J=12.2, 2H), 3.68 (s, 3H), 4.06 (bs, 2H).

Step F: (3-(1-t-Butoxycarbonylpiperidin-4-yl)-2,2-dimethylpropanoic acid, methyl ester A solution of 0.37 mL (0.38 mmol) of a 2.0 M solution of lithium diisopropylamide in THF at −70° C. was treated with a solution of 82 mg (0.25 mmol) of (3-(1-t-butoxycarbonylpiperidin-4-yl)-2-(RS)-methylpropanoic acid, methyl ester (from EXAMPLE 98, Step E) in 1 mL THF. The mixture was stirred for 30 min, treated with 0.047 mL (0.75 mmol) of methyl iodide and stirred at −70° C. for 2 h. The reaction was diluted with $H_2O$ and sat'd NaCl and extracted 3× with $CH_2Cl_2$. The combined organic layers were dried over $Na_2SO_4$, filtered and the filtrate concentrated. The residue was purified by column chomatography on 10 g of silica eluting with a gradient of 0–25% EtOAc/hexanes (v/v), to give 70 mg (81%) of the title compound: ¹H NMR (500 z) δ 1.11 (dq, J=4.3, 8.3, 2H). 1.19 (s, 6H), 1.45 (s, 10H), 1.50–1.54 (4H), 2.66 (t, J=11.4,22H), 3.61 (s, 3H), 4.01 (bs, 2H).

Step G: 1-(t-Butoxycarbonyl)-4-(3-hydroxy-2,2-dimethylpropyl)-piperidine

A solution of 70 mg (0.24 mmol) of (3-(1-t-butoxycarbonylpiperidin-4-yl)-2,2-dimethylpropanoic acid, methyl ester (from EXAMPLE 98, Step F) in 1 mL of $CH_2Cl_2$ at 0° C. was treated with 1.18 mL (1.18 mmol) of a 1.0 M solution of DIBALH in THF. The mixture was warmed to rt and stirred for 2 h. The reaction was quenched with $H_2O$ and sat'd sodium potassium tartrate solution. The mixture was diluted with $CH_2Cl_2$, stirred for 1 h and the layers were separated. The aqueous layer extracted 3× with $CH_2Cl_2$. The combined organic layers were washed with sat'd NaCl, dried over $Na_2SO_4$, filtered, and the filterate concentrated. The residue was purified by column chomatography on 15 g silica eluting with a gradient of 0–25% acetone/hexanes (v/v), to give 40 mg (60%) the title compound: ¹H NMR (500 MHz) δ 0.92 (s, 6H), 1.14–1.19 (m, 2H), 1.21 (d, J=5.3, 2H). 1.46 (s, 10H), 1.67 (d, J=12.6, 2H). 2.72 (t, J=11.6, 2H), 3.34 (s, 2H), 4.02 (d, J=12.6, 2H).

Step H: 1-(t-Butoxycarbonyl)-4-(3-iodo-2,2-dimethylpropyl)-piperidine

A solution of 102 mg (0.39 mmol) of triphenylphosphine and 27 mg (0.39 mmol) of imidazole in 2 mL of toluene was treated with 98 mg (0.39 mmol) of iodine. The mixture was stirred at rt for 30 min, then treated with a solution of 35 mg (0.13 mmol) of 1-(t-butoxycarbonyl)-4-(3-hydroxy-2,2-dimethylpropyl)piperidine (from EXAMPLE 98, Step F) in 5 mL of toluene. The resulting mixture was stirred at rt overnight. The reaction was quenched with $H_2O$ and sat'd NaCl and extracted 3× with $CH_2Cl_2$. The combined extracts were washed with 2 M $Na_2SO_3$, dried over $Na_2SO_4$ and concentrated. The residue was purified by column chomatography on 10 g of silica eluting with $CH_2Cl_2$ to provide 36 mg (73%) of the title compound: ¹H NMR (500 MHz) δ 1.06 (s, 6H), 1.11 (dq, J=3.4, 8.7, 2H). 1.31 (d, J=5.0, 2H). 1.46 (s, 10H), 1.67 (d, J=12.6, 2H). 2.72 (t, J=12.4, 2H), 3.18 (s, 3H), 4.02 (d, J=13.1, 2H).

Step I: 4-(3-Phenyl-2.2-dimethylpropyl)piperidine

A mixture of 26 mg (0.07 mmol) of 1-(t-butoxycarbonyl)-4-(3-iodo-2,2-dimethylpropyl)piperidine (from EXAMPLE 98, Step H) and 2 mg (0.007 mmol) of [1,1'-bis(diphenylphosphino)ferrocene]nickel (II) chloride in ether (5 mL) at reflux was treated with phenylmagnesium bromide (0.13 mL of 3.0 M solution in ether). The resulting mixture was heated at reflux for 12 h, cooled and quenched with $H_2O$ and sat'd NaCl. The mixture was extracted 3× with $CH_2Cl_2$ and the combined organic layers were dried over $Na_2SO_4$, filtered and the filtrate concentrated. The residue was purified by column chomatography on 10 g of silica using a gradient of 0–5% MeOH/$CH_2Cl_2$ (v/v), then 10% MeOH/$CH_2Cl_2$+2% $NH_{401}H$ (v/v), to give 9 mg (56%) of the title compound: ¹H NMR (500 MHz) δ 0.89 (s, 6H), 1.18–1.27 (4H), 1.52–1.59 (m, 1H), 1.71 (d, J=12.3,21).2.46 (bs, 1H) 2.52 (s, 2H), 2.65 (t, J=11.9, 2H). 3.06 (d,J=12.2, 2H), 7.13 (d, J=7.3, 2H), 7.22 (t, J=7.1, 11H), 7.28 (t, J=6.7, 2H).

Step J: 2-(R)-(3-(S)-((4-(2,2-Dimethyl-3-phenylpropyl)piperidin-1-yl)methyl)-4-(S)-phenylpyrrolidin-1-yl)-2-(cyclohexyl)acetic acid The title compound was prepared from 9 mg (0.05 mmol) of 4-(3-phenyl-2,2-dimethylpropyl)piperidine (from EXAMPLE 98, Step I) and 20 mg (0.05 mmol) of 2-(R)-(3-(R)-formyl-4-(S)-phenylpyrrolidin-1-yl)-2-(cyclohexyl) acetic acid, 4-methoxybenzyl ester (from EXAMPLE 33, Step E) using procedures analogous to those described in EXAMPLE 1, Step J and EXAMPLE 10, Step F. For the title compound: ESI-MS 531 (M+H).

EXAMPLE 99

2-(R)-(3-(S)-((4-(2-(R)-Methyl-3-phenylpropyl)piperidin-1-yl)methyl)-4-(S)-phenylpyrrolidin-1-yl)-2-(cyclohexyl) acetic acid Step A: 3-(3-(1-t-Butoxycarbonylpiperidin-4-yl)-2-(R)-methyl-propionyl)-4-(S)-benzyloxazolidin-2-one The title compound was prepared from (3-(1-t-butoxycarbonylpiperidin-4-yl)propanoic acid (from EXAMPLE 98, Step C) using procedures analogous to those described in EXAMPLE 30, Steps A and B. For the title compound: ¹H NMR (500 MHz) δ 1.07–1.15 (2H), 1.23 (d, J=6.8, 3H). 1.31–1.36 (m, 1H), 1.46 (s, 10H), 1.67 (bt, 2H), 1.741.79 (2H), 2.67 (bt, 2H), 2.77 (dd, J=3.8, 9.6, 2H). 3.27

(dd, J=3.2, 10.0, 2H). 3.84–3.88 (m, 1H), 4.07 (bd, 2H), 4.184.23 (2H), 4.68–4.71 (m, 1H), 7.21–7.36 (5H).

Step B: 1-t-Butoxycarbonyl-4-(3-hydroxy-2-(R)-methylpropyl) piperidine

A solution of 156 mg (0.36 mmol) of (3-(1-t-butoxycarbonyl-piperidin-4-yl)-2-(R)methylpropyl)-4-(S)-benzyloxazolidin-2-one (from EXAMPLE 99, Step A) in 3 mL of THF at 0° C. was treated with 0.03 mL (0.73 mmol) of MeOH followed by 16 mg (0.73 mmol) of lithium borohydride. The cooling bath was removed, the mixture was warmed to rt and stirred for 3 h. The reaction was quenched with $H_2O$ and sat'd sodium potassium tartrate. The quenched mixture was diluted with $CH_2Cl_2$ and stirred for 1 h, then extracted 3x with $CH_2Cl_2$. The combined organic layers were washed with sat'd NaCl, dried over $Na_2SO_4$, filtered and the filtrate concentrated. Purification by silica gel column chomatography with 0–25% EtOAc/hexanes (v/v) provided 72 mg (77%) of the title compound: $^1H$ NMR (500 MHz) δ 0.92 (d, J=6.8,33H). 1.01–1.12 (3H), 1.27–1.33 (m, 1H), 1.45 (s, 9H), 1.46–1.50 (m, 1H), 1.61–1.75 (4H), 2.69 (bq, 2H), 3.41 (dd, J=3.9,6.6 Hz, 1H). 3.49 (dd, J=4.8, 5.7, 1H). 4.07 (bd, 2H).

Step C: 4-(3-Phenyl-2-(R)methylpropyl)piperidine

The title compound was prepared from 1-t-butoxycarbonyl-4-(3-hydroxy-2-(R)-methylpropyl)piperidine (from EXAMPLE 99, Step B) using procedures analogous to those described in EXAMPLE 98, Steps H and I. For the title compound: $^1H$ NMR (500 MHz) δ 0.84 (d, J=6.4,33H). 1.02–1.15 (3H), 1.46–1.56 (m, 1H), 1.55–1.69 (2H), 1.82–1.86 (m, 1H), 2.35 (dd, J=5.1, 8.2, 1H). 2.42 (bs, 1H), 2.56–2.67 (3H), 3.07–3.09 (2H), 7.147.29 (5H).

Step D: 2-(R)-(3-(S)-4-(4-(2-(R)-Methyl-3-phenylpropyl)piperidin-1-yl)methyl)-4-(S)-phenylpyrrolidin-1-yl)-cyclohexaneacetic acid The title compound was prepared from 15 mg (0.07 mmol) of 4-(3-phenyl-2-(R)-methylpropyl)piperidine (from EXAMPLE 99, Step C) and 31 mg (0.07 mmol) of 2-(R)-(3-(R)-formyl-4-(S)-phenylpyrrolidin-1-yl)-2-(cyclohexyl)acetic acid, (4-methoxy)benzyl ester (from EXAMPLE 33, Step E) using procedures analogous to those described in EXAMPLE 1, Step J and EXAMPLE 10, Step F. For the title compound: ESI-MS 517 (M+H).

EXAMPLE 100

2-(R)-(3-(S)-((4-(2-(S)-Methyl-3-phenylpropyl)piperidin-1-yl)methyl)-4-(S)-phenylpyrrolidin-1-yl)-2-(cyclohexyl) acetic acid The title compound was prepared using procedures analogous to those described in EXAMPLE 99, substituting 4-(R)-benzyloxazolidin-2-one for 4-(S)-benzyloxazolidin-2-one in Step A. For the title compound: ESI-MS 517 (M+H), HPLC A: 2.85 min.

EXAMPLE 101

2-(R)-(3-(S)-((4-(3-(3,5-Difluorophenyl)propyl)piperidin-1-yl)methyl)-4-(S)-phenylpyrrolidin-1-yl)-2-(cyclohexyl) acetic acid The title compound was prepared from 2-(R)-(3-(R)-formyl-4-(S)-phenylpyrrolidin-1-yl)-2-(cyclohexyl)acetic acid, benzyl ester (from EXAMPLE 1, Step I) and 4-(3-(3,5-difluorophenyl)propyl)piperidine.HCl (from EXAMPLE 95, Step E) using procedures analogous to those described in EXAMPLE 1, Steps J and K. For the title compound: $^1H$ NMR (500 MHz, $CD_3OD$) δ 1.14–1.47 (10H). 1.58–1.68 (6H). 1.77–1.84 (6H). 2.06 (t, J=11.0, 1H), 2.36 (d, J=12.3, 1H), 2.53–2.59 (3H). 2.75–2.81 (2H). 2.96 (d, J=10.5, 1H), 3.11 (q, J=10.5, 1H), 3.30–3.42 (3H). 3.57–3.60 (2H). 6.67–6.72 (m, 1H). 6.74–6.76 (2H). 7.25–7.28 (m, 1H). 7.34–7.89 (4H); ESI-MS 539 (M+H).

EXAMPLE 102

2-(R)-(3-(S)-((4-(3-(3,5-Difluorophenyl)propyl)piperidin-1-yl)methyl)-4-(S)-(3-fluorophenyl)pyrrolidin-1-yl)-2-(cyclohexyl)acetic acid Step A: 2-(R)-(3-(R)Formyl-4-(S)-(3-fluoro)phenylpyrrolidin-1-yl)-2-(cyclohexyl)acetic acids benzyl ester The title compound was prepared from 3-(R)-(t-butyl-dimethylsilyloxymethyl)-4-(S(3-fluoro)phenylpyrrolidine (from EXAMPLE 20, Step H) using procedures analogous those described in EXAMPLE 1, Steps G–I.

Step B: 2-(R)-(3-(S)-((4-(3-(3,5-Difluorophenyl)propyl)piperidin-1-yl)methyl)-4-(S)-(3-fluorophenyl)pyrrolidin-1-yl)-2-(cyclohexyl)acetic acid The title compound was prepared from 2-(R)-(3-(R)-formyl-4-(S)-(3-fluoro)phenylpyrrolidin-1-yl)-2-(cyclohexyl)acetic acid, benzyl ester (from EXAMPLE 102, Step A) and 4-(3-(3,5-difluorophenyl)propyl) piperidine-.HCl (from EXAMPLE 95, Step E) using procedures analogous to those described in EXAMPLE 1, Steps J and K. For the title compound: ESI-MS 557 (M+H).

EXAMPLE 103

2-(R)(3-(S)-((4-(3-(Imidazol-2-yl)propyl)piperidin-1-yl)methyl)-4-(S)-(3-fluorophenyl)pyrrolidin-1:-1)-2-(cyclohexyl)acetic acid Step A: 4-(3-(1-t-Butoxycarbonylpiperidin-4-yl)butanoic acid The title compound was prepared from 4-chlorobutanoic acid using procedures analogous to those described in EXAMPLE 98, Steps A–C.

Step B: 4-(1-t-Butoxycarbonylpiperidin-4-yl)butan-1-ol

The title compound was prepared from 400 mg (1.5 mmol) of 4-(1-t-butoxycarbonylpiperidin-4-yl)butanoic acid (from EXAMPLE 103, Step A) using a procedure analogous to that described in EXAMPLE 30, Step D. 200 mg (53%) of the title compound was obtained: $^1H$ NMR (500 MHz) δ 1.16 (dq, J=3.9, 8.3, 2H). 1.26–1.29 (2H), 1.47–1.42 (3H), 1.46 (s, 10H), 1.55–1.58 (2H), 1.65 (bd, 2H), 2.67 (bt, 2H), 3.65 (t, J=6.6, 1H). 4.07 (bd, 2H).

Step C: 4-(1-t-Butoxycarbonylpiperidin-4-yl)butanal

The title compound was prepared from 200 mg (0.79 mmol) of 4-(1-t-butoxycarbonylpiperidin-4-yl)butan-1-ol (from EXAMPLE 103, Step B) using a procedure analogous to that described in EXAMPLE 1, Step I. 153 mg (77%) of the title compound was obtained: $^1H$ NMR (500 MHz) δ 1.10 (dq, J=4.4, 8.2, 2H). 1.25–1.30 (2H), 1.38–1.44 (m, 1H), 1.46 (s, 9H), 1.63–1.69 (4H), 2.44 (dt, J=1.7, 5.7, 2H). 2.67 (bt, 2H), 4.8 (bs, 2H), 9.77 (t, J=1.8, 1H).

Step D: 2-(3-(1-t-Butoxycarbonylpiperidin-4-yl)propyl) imidazole

A solution of 153 mg (0.61 mmol) of 4-(1-t-butoxycarbonylpiperidin-4-yl)butanal (from EXAMPLE 103, Step C) in 4 mL of MeOH at 0° C. was treated with 38 mg (0.18 mmol) of glyoxal trimer powder and stirred for 15 min. The reaction was treated with 0.46 mL (0.92 mmol) of a 2.0 M solution of ammonia in MeOH and the resulting mixture was stirred at rt overnight. The mixture was quenched with $H_2O$ and sat'd $NaHCO_3$ and extracted 3x with $CH_2Cl_2$. The combined extracts were dried over $Na_2SO_4$, filtered and the filtrate was concentrated. The residue was purified by column chomatography on silica eluting with 0–8% $MeOH/CH_2Cl_2$ (v/v), then 10% MeOH/$CH_2Cl_2$+2% $NH_4OH$ (v/v/v) to give 45 mg (26%) of the title compound: $^1H$ NMR (500 MHz) d 1.03 (dq, J=3.9, 8.5, 2H). 1.23–1.28 (2H), 1.33–1.39 (m, 1H), 1.45 (s, 9H), 1.60 (bd, 2H), 1.72–1.76 (2H), 2.59–2.68 (2H), 2.73 (t, J=7.7, 2H). 4.03 (bs, 2H), 6.93 (s, 2H), 8.88 (bs, 1H).

Step E: 2-(3-(peridin-4-yl)propyl)imidazole -2 HCl

The title compound was prepared from 2-(3-(1-t-butoxycarbonylpiperidin-4-yl)propyl)imidazole (from EXAMPLE 103, Step D) using a procedure analogous to that described in EXAMPLE 95, Step E. For the title compound: $^1$H NMR (500 MHz,CD$_3$OD) d 1.36–1.43 (4H), 1.64–1.72 (m, 1H), 1.82–1.93 (2H), 1.95 (bd, 2H), 2.99–3.04 (2H), 7.44 (s, 2H).

Step F: 2-(R)-3-(S((4-(3-(Imidazol-2-yl)propyl)piperidin-1-yl)methyl)-4-(S)-(3-fluorophenyl)pyrrolidin-1-yl)-2-(cyclohexyl)acetic acid The title compound was prepared from 2-(3-(piperidin-4-yl)propyl)imidazole.2 HCl (from EXAMPLE 103, Step E) and 2-(R)-(3-(R)-formyl-4-(S)-phenylpyrrolidin-1-yl)-2-(cyclohexyl) acetic acid, 4-methoxybenzyl ester (from EXAMPLE 33, Step E) using procedures analogous to those described in EXAMPLE 1, Step J and EXAMPLE 10, Step F. For the title compound: ESI-MS 494 (M+H); HPLC A: 1.73 min.

EXAMPLE 104

2-(R)-(3-(S)-((4-(3-(R)-Phenylbutyl)piperidin-1-yl)methyl)-4-(S)-phenylpyrrolidin-1-yl)-2-(cyclohexyl)acetic acid Step A: 3-(R)-Phenylbutan-1-ol The title compound was prepared from 1.3 g (7.92 mmol) of 3-(R)-phenylbutanoic acid using a procedure analogous to that described in EXAMPLE 30, Step D. 900 mg (75%) of the title compound was obtained: 1$^1$H NMR (500 MHz) o 1.31 (d, J=6.8,33H), 1.48 (bs, 1H), 1.86–1.90 (2H), 2.88–2.94 (m, 1H), 3.54–3.61 (2H). 7.22–7.34 (5H).

Step B: 1-Iodo-3-(R)-phenylbutane

A solution of 900 mg (6.0 mmol) of 3-(R)-phenylbutan-1-ol (from EXAMPLE 104, Step A) and 3.0 mL (18.0 mmol) of DIEA in 10 mL of CH$_2$Cl$_2$ was treated with 0.7 mL (9.0 mmol) of methanesulfonyl chloride and the resulting mixture was stirred at rt for 1 h. The reaction was quenched with H$_2$O and 50 mL of 1.0 N HCl. The quenched mixture was extracted 3× with CH$_2$Cl$_2$. The organic extracts were washed with sat'd NaCl, dried over Na$_2$SO$_4$, filtered and the filtrate concentrated. A mixture of the residue and 9.0 g (60.0 mmol) of NaI in 10 mL of acetone was heated at reflux for 2 h. The reaction mixture cooled and concentrated. The residue was diluted with H$_2$O and extracted 3× with CH$_2$Cl$_2$. The extracts were washed with sat'd NaCl, dried over Na$_2$SO$_4$, filtered and the filtrate concentrated. The residue was purified by flash chomatography on 50 g of silica eluting with 0–20% EtOAc/hexanes (v/v) to give 1.4 g (90%) of the title compound: $^1$H NMR (500 MHz) δ 1.31 (d, J=6.9, 31), 2.10–2.14 (2H), 2.87–2.92 (m, 1H), 2.96–3.01 (m, 1H). 3.11–3.15 (m, 1H), 7.22–7.35 (5H).

Step C: 1-(t-Butoxcarbonyl)-4-(3-(R)-phenylbutyl)piperidine

The title compound was prepared from 1-iodo-3-(R)-phenylbutane (from EXAMPLE 104, Step B) using procedures analogous to those described in EXAMPLE 98, Steps A–C. For the title compound: $^1$H NMR (500 MHz) δ 0.99–1.14 (3H), 1.18–1.23 (m, 11H), 1.25 (d, J=6.8, 3H), 1.28–1.36 (m, 1H), 1.46 (s, 9H), 1.48–1.65 (4H), 2.63–2.67 (3H), 4.06 (bs, 2H), 7.18–7.32 (5H).

Step D: 4-(3-(R)-Phenylbutyl)piperidine.HCl

The title compound was prepared from 1-(t-butoxycarbonyl)-4-(3-(R)-phenylbutyl)piperidine (from EXAMPLE 104, Step C) using a procedure analogous to that described in EXAMPLE 95, Step E.

Step E: 2-(R)-(3-(S)-((4-(3-(R)-Phenylbutyl)piperidin-1-yl)methyl)-4-(S)-phenylpyrrolidin-1-yl)-2-(cyclohexyl)acetic acid The title compound was prepared from 30 mg (0.13 mmol) of 4-(3-(R)-phenylbutyl)piperidine.HCl and 50 mg (0.13 mmol) of 2-(R)-(3-(R)-formyl-4-(S)-phenylpyrrolidin-1-yl)-2-(cyclohexyl)acetic acid, benzyl ester (from EXAMPLE 1, Step I) using procedures analogous to those described in EXAMPLE 1, Steps J and H. 36 mg (54%) of the title compound was obtained: $^1$H NMR (500 MHz, CD$_3$OD) δ 0.94–1.84 (23H). 2.06–2.14 (m, 1H). 2.36–2.42 (m, 1H). 2.57–2.60 (2H). 2.74–3.02 (3H). 3.10–3.12 (m, 1H). 3.30–3.60 (7H). 7.10–7.13 (3H). 7.21–7.29 (3H), 7.34–7.39 (4H); ESI-MS 517 (M+H).

EXAMPLE 105

2-(R)-(3-(S)-((4-(3-(S)-Phenylbutyl)piperidin-1-yl)methyl)-4-(S)-phenylpyrrolidin-1-yl)-2-(cyclohexyl)acetic acid The title compound was prepared using procedures analogous to those described in EXAMPLE 104, substituting 3-(S)-phenylbutanoic acid for 3-(R)-phenylbutanoic acid in Step A. For the title compound: $^1$H NMR (500 MHz, CD$_3$OD) δ 0.94–1.88 (23H). 2.10–2.16 (1H). 2.40 (d, J=12.2, 1H), 2.57–2.68 (2H). 2.75–2.79 (m, 1H). 2.86 (d, J=10.0, 1H), 3.00 (d, J=10.1, 1H), 3.09–3.11 (m, 1H). 3.30–3.42 (41). 3.55–3.61 (3H). 7.10–7.13 (3H). 7.21–7.29 (3H), 7.34–7.38 (4H); ESI-MS 517(M+H).

EXAMPLE 106

2-(R)-(3-(S)-((4-(3-(4-Nitrophenyl)propyl)piperidin-1-yl)methyl)-4-(S)-phenylpyrrolidin-1-yl)-2-(cyclohexyl)acetic acid Step A: 4-(3-(4-Nitrophenyl)prop l)piperidine.HCl A solution of 50 mg (0.25 mmol) of 4-(3-phenylpropyl)piperidine in 1.2 mL of formic acid was treated with 0.5 mL of nitric acid and 0.5 mL of sulfuric acid and the resulting mixture was heated at 60° C. for 4 h. The mixture was cooled to rt, poured onto ice and diluted with H$_2$O. The aqueous mixture was adjusted to pH=7 with 5.0 N NaOH. The mixture was then extraced 3× with CH$_2$Cl$_2$. The combined extracts were washed with sat'd NaCl, dried over Na$_2$SO$_4$ and concentrated.

The crude product and 0.14 mL (0.08 mmol) of DIEA in 3 mL of CH$_2$Cl$_2$ was treated with 48 mg (0.22 mmol) of di-t-butyldicarbonate and the resulting mixture was stirred at rt for 3 h. The mixture was diluted with aqueous NaCl and extracted 3× with CH$_2$Cl$_2$. The extracts were dried over Na$_2$SO$_4$, filtered and the filtrate concentrated. The residue was purified by column chomatography on 25 g of silica eluting with 0–10% EtOAc/hexanes (v/v) to give 92 mg of impure 1-t-butylcarbonyl-4-(3-(4-nitrophenyl)propyl) piperidine. HPLC (Chiralpak AD 2×25 cm column, 95/5 v/v hexanes/EtOH, 9 ml/min, 220 nm. Retention Time=17.4 min) afforded 19 mg of pure 1-t-butylcarbonyl-4-(3-(4-nitrophenyl)propyl)piperidine. A solution of the t-butyl carbamate in 2 mL of 0.4 N HCl in MeOH was stirred at rt for 4 h. The solution was concentrated. Ether was added and the resulting mixture was concentrated to remove excess HCl. 19 mg of the title compound was obtained: $^1$H NMR (500 MHz, CD$_3$OD) δ 1.33–1.38 (4H). 1.59–1.68 (m, 1H). 1.70–1.74 (2H). 1.93 (bd, 2H). 2.76 (t, J=7.5, 2H), 2.96 (bt, 2H). 3.34 (bd, 2H), 7.43 (d, J=8.7, 2H), 8.14-(d,J=8.7,2H).

Step B: 2-(R)-(3-(S)-((4-(3-(4-Nitrophenyl)propyl)piperidin-1-yl)methyl)-4-(S)-phenylpyrrolidin-1-yl)-2-(cyclohexyl)acetic acid The title compound was obtained from 19 mg (0.07 mmol) of 4-(3-(4-nitrophenyl)propyl)piperidine.HCl (from EXAMPLE 106, Step A) and 30 mg (0.07 mmol) of 2-(R)-(3-(R)-formyl-4-(S)-phenylpyrrolidin-1-yl)-2-(cyclohexyl) acetic acid, 4-methoxybenzyl ester (from EXAMPLE 33, Step E) using procedures analogous to those described in EXAMPLE 1, Step J and EXAMPLE 10, Step F. 12 mg (31%) of the title compound was obtained: $^1$H NMR (500

MHz, CD₃OD) δ 0.83–0.89 (3H), 1.12–1.32 (9H). 1.43–1.45 (m, 1H). 1.61–1.92 (9H). 2.14–2.26 (m, 1H). 2.43 (d, J=11.7, 1H), 2.69–2.72 (3H). 2.79–2.81 (m, 1H), 2.91 (d, J=10.1, 1H), 3.05–3.13 (2H), 3.30–3.45 (2H), 3.57–3.63 (2H), 7.28–7.30 (m, 1H), 7.35–7.36 (4H), 7.39 (d, J=8.7, 2H), 8.12(d, J=8.7,22H); ESI-MS 548 (M+H); HPLC B: 7.49 min.

EXAMPLE 107

2-(R)-(3-(S)-((4-Hydroxy-(3-(4-fluorophenyl)propyl) piperidin-1-yl)methyl)-4-(S)-phenylpyrrolidin-1-yl)-3-methylbutanoic acid Step A: 4-Hydroxy-(3-(4-fluorophenyl)propyl) piperidine.HCl The title compound was prepared using procedures analogous to those described in EXAMPLE 2, Steps A,B, D–F, substituting 1-iodo-4-fluorobenzene for 1-bromo-4-(1H-tetrazol-5-yl)benzene in Step D.

Step B: 2-(R)-(3-(S)-((4-Hydroxy-(3-(4-fluorophenyl)propyl)piperidin-1-yl)methyl)-4-(S)-phenylpyrrolidin-1-yl)-3-methylbutanoic acid The title compound was prepared from 30 mg (0.08 mmol) of 2-(R)-(3-(R)-formyl-4-(S)-phenylpyrrolidin-1-yl)-3-methylbutanoic acid, benzyl ester (from EXAMPLE 5, Step D) and 25 mg (0.09 mmol) of 4-hydroxy-(3-(4-fluorophenyl)propyl)piperidine.HCl from EXAMPLE 107, Step A) using procedures analogous to those described in EXAMPLE 1, Steps J and K. 22 mg (55%) of the title compound was obtained: ESI-MS 497 (M+H).

EXAMPLE 108

2-(R)-(3-(S)-((4-(3-(3,4-Difluorophenyl)propyl)-4-hydroxypiperidin-1-yl)methyl)-4-(S)-phenylpyrrolidin-1-yl)-3-methylbutanoic acid Step A: 4-Hydroxy-(3-(3,4-difluorophenyl)propyl) piperidine.HCl The title compound was prepared using procedures analogous to those described in EXAMPLE 2, Steps A,B, D–F, substituting 1-bromo-3,4-difluorobenzene for 1-bromo-4-(1H-tetrazol-5-yl)benzene in Step D.

Step B: 2-(R)(3-(S)-((4-Hydroxy-(3-(3,4-difluorophenyl) propyl) piperidin-1-yl)methyl)-4-(S)-phenylpyrrolidin-1-yl)-3-methylbutanoic acid The title compound was prepared from 30 mg (0.08 mmol) of 2-(R)-(3-(R)-formyl-4-(S)-phenylpyrrolidin-1-yl)-3-methylbutanoic acid, benzyl ester (from EXAMPLE 5, Step D) and 25 mg (0.09 mmol) of 4hydroxy-(3-(3,4-difluorophenyl)propyl)piperidine.HCl from EXAMPLE 108, Step A) using procedures analogous to those described in EXAMPLE 1, Steps J and K. 22 mg (55%) of the title compound was obtained: ESI-MS 515 (M+H).

EXAMPLE 109

2-(R)-(3-(S)-((4-(3-(3,5-Difluorophenyl)propyl)piperidin-1-yl)methyl)-4-(S)-(3-fluorophenyl)pyrrolidin-1-yl)-2-(cyclohexyl)acetic acid The title compound was prepared from 2-(R)-((3-(R)-formyl)-4-(S)-3-(fluoro)phenylpyrrolidin-1-yl)-2-(cyclohexyl)acetic acid, benzyl_ester (from EXAMPLE 102, Step A) and 4-(3-(3,5-difluorophenyl)propyl) piperidine.HCl (from EXAMPLE 95, Step E) using procedures analogous to those described in EXAMPLE 1, Steps J and K. For the title compound: ESI-MS 557 (M+H).

EXAMPLE 110

2-(R)-(3-(S)-((4-(3-(4-Fluorophenyl)propyl)-4-hydroxypiperidin-1-yl)methyl)-4-(S)-phenylpyrrolidin-1-yl)-2-(cyclohexyl)acetic acid Step A 4-Hydroxy-4-(3-(4-fluorophenyl)propyl) piperidine.HCl The title compound was prepared using procedures analogous to those described in EXAMPLE 1, Steps A,B, D–F substituting 1-iodo-4-fluorobenene for 1-bromo-4-(1H-tetrazol-5-yl)benzene in Step D.

Step B 2-(R)-(3-(S)-((4-(3-(4-Fluorophenyl)propyl)-4-hydroxy-piperidin-1-yl)methyl)-4-(S)-phenylpyrrolidin-1-yl)-2-(cyclohexyl)acetic acid The title compound was prepared from 2-(R)-(3-(R)-Formyl-4-(S)-phenylpyrrolidin-1-yl)-2-(cyclohexyl)acetic acid, benzyl ester (from EXAMPLE 1, Step I) and 4-hydroxy-4-(3-(4-fluorophenyl)propyl) piperidine.HCl (from EXAMPLE 110, Step A) using procedures analogous to those described in EXAMPLE 1, Steps J and K. For the title compound: ESI-MS 537 (M+H).

EXAMPLE 111

2-(R)-(3-(S)-((4-(2,2-Dimethyl-3-(4-fluorophenyl)propyl) piperidin-1-yl)methyl)-4-(S)-(3-fluorophenyl)pyrrolidin-1-yl)-3-(cyclobutyl)propanoic acid The title compound was prepared using procedures analogous to those described in EXAMPLE 98, substituting 4-fluorophenylmagnesium bromide for phenylmagnesium bromide in Step I and 2-(R)-(3-(R)-formyl-4-(S)-(3-fluorophenyl)pyrrolidin-1-yl)-3-(cyclobutyl)propanoic acid, benzyl ester (from EXAMPLE 26, Step A) for 2-(R)-(3-(R)-formyl-4-(S)-phenylpyrrolidin-1-yl)-2 -(cyclohexyl)acetic acid, (4-methoxy)benzyl ester in Step J. For the title compound: ESI-MS 553 (M+H); HPLC A: 3.12 min.

EXAMPLE 112

2-(R)-(3-(S)-((4-(1-(R)-Methyl-3-(4-fluorophenyl)propyl) piperidin-1-yl)methyl)-4-(S)-(3-fluorophenyl)pyrrolidin-1-yl)-3-(cyclobutyl)propanoic acid The title compound was prepared using procedures analogous to those described in EXAMPLE 30, substituting 4-fluorobenzaldehyde for benzaldehyde in Step G and 2-(R)-(3-(R)-formyl-4-(S(3-fluorophenyl)pyrrolidin-1-yl)-3-(cyclobutyl)propanoic acid, benzyl ester (from EXAMPLE 26, Step A) for 2-(R)-(3-(R)-formyl-4-(S)-phenylpyrrolidin-1-yl)-2-(cyclohexyl)acetic acid, (4-methoxy)benzyl ester in Step I. For the title compound: ESI-MS 539 (M+H); HPLC A: 3.07 min.

EXAMPLE 113

2-(R)-(3-(S)-((4-(3-(2,4-Difluorophenyl)propyl)piperidin-1-yl)methyl)-4-(S)-(3-fluorophenyl)pyrrolidin-1-yl)-3-(cyclobutyl)propanoic acid Step A 4-(2-Hydroxyethyl)-1-(t-butoxycarbonyl)piperidine To a solution of 4-carboxymethyl-1-(t-butoxycarbonyl)-piperidine (5.1 g, 22.2 mmol) in dioxane (under nitrogen), was added 11.1 mL (111.2 mmol, 10 M solution) of borane dimethyl sulfide. The mixture was heated to 50° C. for 2.5 h. The solution was concentrated and the residue diluted with 1:1 v/v ether/EtOAc and washed with H₂O, 1 M NaOH and sat'd NaCl. The organic portion was dried over MgSO₄ and concentrated to provide 4.5 g (88%) of the title compound: ¹H NMR (300 MHz) δ 1.0–1.2 (m, 2H), 1.45 (s, 9H), 1.45–1.6 (m, 3H), 1.6–1.7 (m, 2H), 2.6–2.8 (m, 2H), 3.6–3.8 (t, 2H), 4.04.2 (m, 2H).

Step B 1-t-Butoxycarbonyl(2-iodoethyl)piperidine

A solution of 4-(2-hydroxyethyl)-1-(t-butoxycarbonyl)-piperidine (4.5 g, 19.6 mmol, from EXAMPLE 113, Step A), imidazole (1.8 g, 27 mmol) and triphenylphosphine (7.1 g, 27 mmol) in 60 mL of 2:1 v/v ether/CH₃CN at 0° C. was treated with 7.4 g (29 mmol) of iodine. The mixture was warmed to rt and stirred for 15 min. The mixture was diluted with 200 mL of ether and washed with sat'd $Na_2SO_4$ (2×200 mL), sat'd $CaSO_4$ (100 mL) and sat'd NaCl. The organic phase was dried over $Na_2SO_4$ and concentrated. The material was filtered through a pad of silica to remove the triphenylphosphine oxide providing 6.1 g (92%) of the title compound: $^1$H NMR (300 MHz) δ 1.0–1.2 (m, 2H), 1.45 (s, 9H), 1.55 (m, 1H), 1.7–1.8 (m, 4H), 2.6–2.8 (m, 2H), 3.19–3.25 (t, 2H), 4.04.2 (m, 2H).

Step C: 2-(((1-t-Butoxycarbonyl)piperidin-4yl)ethyl) triphenyl phosphonium iodide A mixture of 2.8 g (8.0 mmol) 1-t-butoxycarbonyl-4-(2-iodoethyl)piperidine (from EXAMPLE 113, Step B) and 2.1 g (8.0 mmol) of triphenylphosphine in 40 mL of toluene was heated at 100° C. for 36 hr. A beige precipitate formed. The mixture was cooled and concentrated. The solid was filtered, washed with ether and dried to provide 1.72 g (36%) of the title compound.

Step D: 1-(t-Butoxycarbonyl)-(4-(3-(2,4-difluorophenyl) prop-2-enyl)-piperidine

A solution of 400 mg (0.66 mmol) (2-((1-t-butoxycarbonyl)-piperidin-4-yl)ethyl) triphenylphosphonium iodide (from EXAMPLE 113, Step C) in 2 mL dry THF at 0° C. was added sodium bis (trimethylsilyl) amide (0.726 mL, 0.726 mmol, 1.0 M in THF. The mixture was stirred at 0° C. for 20 mn and treated with 2,4-difluorobenzaldehyde (0.079 mL, 0.726 mmol). The reaction mixture was warmed to rt and stirred for 2 h. The mixture was diluted with 100 mL of EtOAc and washed with $H_2O$ and sat'd NaCl. After separating the phases, the organic phase was dried over $NaSO_4$ and concentrated. Flash chromatography eluting with 9:1 v/v hexanes/EtOAc to give 90 mg (45%) of the title compound: Rf: 0.25 (9:1 v/v hexanes/EtOAc); HPLC (YMC ODS-A 4.6×50 mm column, gradient elution using 10:90 v/v $CH_3CN/H_2O$+0.1% TFA to 100% $CH_3CN$+0.1% TFA over 2.0 min, hold 1 min, 5.0 mL/min, 220 nm): Retention Time: 2.04 min.

Step E: 4-(3-(2,4-Difluorophenyl)propyl)-1-t-butoxycarbonyl piperidine

The title compound was prepared from 4-(3-(2,4-difluorophenyl)prop-2-enyl)-1-t-butoxycarbonylpiperidine (90 mg, 0.27 mmol, from EXAMPLE 113, Step D) using a procedure analogous to that described in EXAMPLE 95, Step D to provide 70 mg (77%) of the title compound: HPLC (YMC ODS-A 4.6×50 mm column, gradient elution using 10:90 v/v $CH_3CN/H_2O$+0.1% TFA to 100% $CH_3CN$ over 2.0 min, hold 1 min, 5.0 mL/min, 220 nm): Retention Time: 2.076 min.

Step F: 4-(3-(2,4-Difluorophenyl)propyl)piperidine.HCl

A solution of 4-(3-(2,4-difluorophenyl)propyl)-1-t-butoxycarbonylpiperidine (90 mg, 0.27 mmol, from EXAMPLE 113, Step E) in 2 mL of 1% HCl in MeOH was heated to 50° C. for 2 h. After cooling to rt, the material was concentrated to provide 70 mg (93%) of the title compound: HPLC (YMC ODS-A 4.6×50 mm column, gradient elution using 10:90 v/v $CH_3CN/H_2O$+0.1% TFA to 100% $CH_3CN$+0.1% TFA over 2.0 min, hold 1 min, 5.0 mL/min, 220 nm): Retention Time: 1.18 min.

Step G: 2-(R)-(3-(S)-((4-(3-(2,4-Difluorophenyl)propyl) piperidin-1-yl)methyl)-4-(S)-(3-fluorophenyl)pyrrolidin-1-yl)-3-(cyclobutyl)propanoic acid, benzyl ester The title compound was prepared from 2-(R)-(3-(R)-formyl-4-(S)-(3-fluorophenyl)pyrrolidin-1-yl)-3-(cyclobutyl)propanoic acid, benzyl ester (53 mg, 0.13 mmol, from EXAMPLE 26, Step A) and 4-(3-(2,4-difluorophenyl) propyl)piperidine.HCl (35 mg, 0.13 mmol, from EXAMPLE 113, Step F) using a procedure analogous to that described in EXAMPLE 1, Step J to provide 75 mg (91%) of the title compound: HPLC (YMC ODS-A 4.6×50 mm column, gradient elution using 10:90 v/v $CH_3CN/H_2O$+0.1% TFA to 100% $CH_3CN$ +0.1% TFA over 2.0 min, hold 1 min, 5.0 mL/min, 220 nm): Retention Time: 1.55 min; ESI-MS 633.0 (M+H).

Step H: 2-(R)-(3-(S)-((4-(3-(2,4-Difluorophenyl)propyl) piperidin-1-yl)methyl)-4-(S)-(3-fluorophenyl)pyrrolidin-1-yl)-3-(cyclobutyl)propanoic acid The title compound was prepared from 2-(R)-(3-(S)-((4-(3-(2,4-difluorophenyl)propyl)piperidin-1-yl)methyl)-4-(S)-(3-fluorophenyl)pyrrolidin-1-yl)-3-(cyclobutyl) propanoic acid, benzyl ester (75 mg, 0.13 mmol, from EXAMPLE 113, Step G) using a procedure analogous to that described in EXAMPLE 1, Step K to provide 70 mg (99%) the title compound: $^1$H NMR (500 MHz) δ 1.20–3.90 (33H), 6.60–7.40 (7H); HPLC (YMC ODS-A 4.6×50 mm column, gradient elution using 10:90 v/v $CH_3CN/H_2O$+ 0.1% TFA to 100% $CH_3CN$+0.1% TFA over 2.0 min, hold 1 min, 5.0 mL/min, 220 nm): Retention Time: 1.34 min; ESI-MS 543.0 (M+H).

EXAMPLE 114

2-(R)-(3-(S)-((4-(3-(2,6-Difluorophenyl)propyl)piperidin-1-yl)methyl)-4-(S)-(3-fluorophenyl)pyrrolidin-1-yl)-3-(cyclobutyl)propanoic acid Step A: 4-(3-(2,6-Difluorophenyl)propyl)piperidine.HCl The title compound was prepared using procedures analogous to those described in EXAMPLE 113, Steps A–F, substituting 2,6-difluorobenzaldehyde for 2,4-difluorobenzaldehyde in Step D. For the title compound: HPLC (YMC ODS-A 4.6×50 mm column, gradient elution using 10:90 v/v $CH_3CN/H_2O$+0.1% TFA to 100% $CH_3CN$+ 0.1% TFA over 2.0 min, hold 1 min, 5.0 mL/min, 220 nm): Retention Time: 1.17 min.

Step B: 2-(R)(3-(S)-((4-(3-(2,6-Difluorophenyl)propyl) piperidin-1-yl)methyl)-4-(S)-(3-fluorophenyl)pyrrolidin-1-yl)-3-cyclobutylpropanoic acid The title compound was prepared from 2-(R)-(3-(R)-formyl-4-(S)-(3-fluorophenyl)pyrrolidin-1-yl)-3-(cyclobutyl)propanoic acid, benzyl ester (from EXAMPLE 26, Step A) and 4-(3-(2,6-difluorophenyl)propyl) piperidine-.HCl (from EXAMPLE 114, Step A) using procedures analogous to those described in EXAMPLE 1, Steps J and K to provide the title compound: ESI-MS 543 (M+H); HPLC (YMC ODS-A 4.6×50 mm column, gradient elution using 10:90 v/v $CH_3CN/H_2O$+0.1% TFA to 100% $CH_3CN$ +0.1% TFA over 2.0 min, hold 1 min, 5.0 mL/min, 220 nm): Retention Time: 1.34 min.

EXAMPLE 115

2-(R)-(3-(S)-((4-(3-(2,4,6-Trifluorophenyl)propyl) piperidin-1-yl)methyl)-4-(S)-(3-fluorophenyl)pyrrolidin-1-yl)-3-(cyclobutyl)propanoic acid Step A 4-(3-(2,4,6-Triifluorophenyl)propyl)piperidine.HCl The title compound was prepared using procedures analogous to those described in EXAMPLE 113, Steps A–F substituting 2,6-difluorobenzaldehyde for 2,4,6-trifluorobenzaldebyde in Step D. For the title compound: HPLC (YMC ODS-A 4.6×50 mm column, gradient elution using 10:90 v/v $CH_3CN/H_2O$+0.1% TFA to 100% $CH_3CN$ +0.1% TFA over 2.0 min, hold 1 min, 5.0 mL/min, 220 nm): Retention Time: 1.22 min.

Step B: 2-(R)-(3-(S)-((4-(342,4,6-Trifluorophenyl)propyl) piperidin-1-yl)methyl)-4-(S)(3-fluorophenyl)pyrrolidin-1-yl)-3-cyclobutylpropanoic acid The title compound was prepared from 2-(R)-(3-(R)-formyl-4-(S)-(3-fluorophenyl)pyrrolidin-1-yl)-3-(cyclobutyl)propanoic acid, benzyl ester (from EXAMPLE 26, Step A) and 4-(3-(2,6-difluorophenyl)propyl) piperidine-.HCl (from EXAMPLE 115, Step A) using procedures analogous to those described in EXAMPLE 1, Steps J and K to provide the title compound: ESI-MS 561 (M+H); HPLC (YMC ODS-A 4.6×50 mm column, gradient elution using 10:90 v/v $CH_3CN/H_2O$+0.1% TFA to 100% $CH_3CN$ over 2.0 min, hold 1 min, 5.0 mL/min, 220 nm): Retention Time: 1.36 min.

EXAMPLE 116

2-(R)-(3-(S)-((4-(3-(4-Cyanophenyl)propyl)piperidin-1-yl) methyl)-4-(S)-phenylpyrrolidin-1-yl)-2-(cyclohexyl)acetic acid Step A: 4-(3-(4-cyanophenyl)propyl)piperidine.HCl The title compound was prepared using procedures analogous to those described in EXAMPLE 113, Steps A–F, substituting 4-cyanobenzaldehyde for 2,4-difluorobenzaldehyde in Step D. For the title compound: HPLC (Zorbax SB-C8 4.6 mm×7.5 cm column, gradient elution using 10:90 v/v $CH_3CN/H_2O$+0.1% TFA to 100% $CH_3CN$ over 7.5 min, hold for 45 sec, 2.25 mL/min, 220 nm): Retention Time: 3.29 min.

Step E: 2-(R)-(3-(S)-((4-(3-(4Cyanophenyl)propyl) piperidin-1-yl)methyl)-4-(S)-phenylpyrrolidin-1-yl)-2-(cyclohexyl)acetic acid The title compound was prepared from 2-(R)-(3-(R)-formyl-4-(S)-phenylpyrrolidin-1-yl)-2-(cyclohexyl)acetic acid, benzyl ester (from EXAMPLE 1, Step 1) and 4-(3-(4-cyanophenyl)propyl)piperidine×HCl (from EXAMPLE 116, Step A) using procedures analogous to those described in EXAMPLE 1, Steps J and K. For the title compound: HPLC (Zorbax SB-C8 4.6 mm×7.5 cm column, gradient elution using 10:90 v/v $CH_3CN/H_2O$+0.1% TFA to 100% $CH_3CN$ over 7.5 min, hold for 45 sec, 2.25 mL/min, 220 nm): Retention Time: 4.13 min; ESI-MS 528 (M+H).

EXAMPLE 117

2-(R)-3-(S)-((4-(3-(Benzofurazan-4-yl)propyl)piperidin-1-yl)methyl)-4-(S)-(3-fluorophenyl)pyrrolidin-1-yl)-2-(cyclohexyl)acetic acid Step A: 4-(Trifluoromethylsulfonyloxy)benzofurazan A solution of 4-hydroxybenzofurazan (680 mg, 5 mmol) and pyridine (2.02 mL, 25 mmol) in 8 mL $CH_2Cl_2$ under nitrogen at 0° C. was treated with trifluoromethanesulfonic anhydride (1.02 mL, 6 mmol). The resulting mixture was stirred at 0° C. for 1 h. The mixture was diluted with 100 mL $CH_2Cl_2$, washed with 50 mL of 0.5 M NaOH, 50 mL of $H_2O$, 5% AcOH (2×50 mL), and 50 mL of $H_2O$. The organic layer was dried over $Na_2SO_4$ and concentrated. Flash chromatography on 30 g of silica gel using, 9:1 v/v hexanes/EtOAc as the eluant afforded 940 mg (70%) of the title compound.

Step B 4-(3-(Benzofurazan-4-yl)propyl)piperidine.HCl

The title compound was prepared using procedures analogous to those described in EXAMPLE 33, Steps A,B and D, substituting 4 (trifluoromethylsulfonyloxy)benzofurazan (from EXAMPLE 117, Step A) for 4-bromobenzofurazan in Step D.

Step C: 2-(R)-(3-(S)-(4-(3-(Benzofurazan-4-yl)propyl) piperidin-1-yl)methyl)-4-(S)-(3-fluorophenyl)pyrrolidin-1-yl)-2-(cyclohexyl)acetic acid The title compound was prepared from 30 mg (0.071 mmol) 2-(R)-((3-(R)-formyl-4-(S)-(3-fluorophenyl) pyrrolidin-1-yl)-2-(cyclohexyl)acetic acid, benzyl ester (from EXAMPLE 102, Step A) and 4-(3-(benzofurazan-4-yl)propyl)piperidine. HCl (from EXAMPLE 117, Step B) using procedures analogous to those described in EXAMPLE 1, Steps J and K. For the title compound: HPLC (Zorbax SB-C8 4.6 mm×7.5 cm column, gradient elution using 10:90 v/v $CH_3CN/H_2O$+0.1% TFA to 100% $CH_3CN$ over 7.5 min, hold for 45 sec, 2.25 mL/min, 220 nm): Retention Time: 4.31 min; ESI-MS 563.0 (M+H).

EXAMPLE 118

2-(R)-(3-(S)-((4-(3-phenylpropyl)piperidin-1-yl)methyl)-4-(S)-(3-fluorophenyl)pyrrolidin-1-yl)-2-(cyclohexyl)acetic acid The title compound was prepared using procedures analogous to those described in EXAMPLE 71, substituting 2-(R)-(3-(R)-formyl)-4-(S)-(3-fluorophenyl)pyrrolidin-1-yl)-2-(cyclohexyl)acetic acid, benzyl ester (from Example 102, Step A) for 2-(R)-(3-(R)-formyl)-4-(S)-phenylpyrrolidin-1-yl)-2-(cyclohexyl)acetic acid, benzyl ester in Step A. For the title compound: HPLC (Zorbax SB-C8 4.6 mm×7.5 cm column, gradient elution using 10:90 v/v $CH_3CN/H_2O$+0.1% TFA to 100% $CH_3CN$ over 7.5 min, hold for 45 sec, 2.25 mL/min, 220 nm): Retention Time: 4.43 min. ESI-MS 521 (M+H).

EXAMPLE 119

2-(R)-(3-(S)-((4-(3-(3,4-Difluorophenyl)propyl)piperidin-1-yl)methyl)-4-(S)-(phenylpyrrolidin-1-yl)-3-methylbutanoic acid Step A 3-(3,4-Difluorophenyl propanol A solution of 5.0 g (27.0 mmol) of 3-(3,4-difluorophenyl) propanoic acid in 200 mL dioxane was treated with 13.5 mL of 2.0 M borane×dimethylsulfide solution in THF. The resulting mixture was heated at 50° C. for 2 h. The mixture cooled and concentrated. The residue was dissolved in 1:1 v/v ether/EtOAc, washed with $H_2O$, 1.0 M NaOH, sat'd NaCl, dried over over $MgSO_4$ and concentrated to provide 4.6 g (94%) of the title compound.

Step B 1-Iodo-3-(3,4-difluorophenyl)propane

A solution of 2.00 g (11.6 mmol) of 3-(3,4difluorophenyl) propanol (from EXAMPLE 199, Step A), 3.96 g (15.1 mmol) of triphenylphosphine and 1.03 g (15.1 mmol) of imidazole in 2:1 v/v ether/$CH_3CN$ at 0° C. was treated with 4.10 g (16.3 mmol) of iodine. The resulting mixture was warmed to rt and stirred for 1 h. The mixture was diluted with 200 mL ether, and washed with sat'd $Na_2S_2O_3$ (2×30 mL) and sat'd $CuSO_4$ (30 mL). The organic phase was dried over $MgSO_4$ and concentrated. The residue was partially dissolved in ether and filtered to remove triphenylphosphine oxide. The filtrate was concentrated. Flash chromatography on silica gel using 4:1 v/v hexanes/EtOAc afforded 3.25 g (99%) of the title compound.

Step C: ((4-(3-(3,4-Difluorophenyl)propyl)piperidine.HCl

The title compound was prepared from 1-iodo-3-(3,4-difluorophenyl)propane (from EXAMPLE 119, Step B) using procedures analogous to those described in EXAMPLE 98, Steps A–C and EXAMPLE 95, Step E.

Step D: 2-(R(3-(S)-(4-(3-(3,4-Difluorophenyl)propyl) piperidin-1-yl)methyl)-4-(S)-(phenylpyrrolidin-1-yl)-3-methylbutanoic acid The title compound was prepared from 2-(R)-(3-(R)-formyl-4-(S)-(phenylpyrrolidin-1-yl)-3-methylbutanoic acid, benzyl ester (from EXAMPLE 5, Step D) and 4-(3-(3,4-difluorophenyl)propyl)piperidine.HCl (from EXAMPLE 119, Step C) using procedures analogous to those described in EXAMPLE 1, Steps J and K. For the title compound: HPLC (Zorbax SB-C8 4.6 mm×7.5 cm column, gradient elution using 10:90 v/v $CH_3CN/H_2O$+0.1% TFA to 100% $CH_3CN$ over 7.5 min, hold for 45 sec, 2.25 mL/min, 220 nm): Retention Time: 4.04 min; ESI-MS 499 (M+H)

EXAMPLES 120–148

The compounds in Table 4 were prepared according to the following general procedure. A solution the appropriate aldehyde (1.0 equiv), the appropriate piperidine.HCl (1.3 equiv), sodium triacetoxyborohydride (2.0 equiv) and TEA (1.5 equiv) in 1 mL 1,2-dichloroethane was stirred for 3 h. The crude mixture was filtered through silica gel (3 g) eluting with 19:1 v/v $CH_2Cl_2$/MeOH. The solvent was removed and the residue was dissolved in 2 mL MeOH and stirred over 10% palladium on carbon (12 mg, 0.011 mmol) under 1 atm of hydrogen for 1–20 h. The reaction mixture was filtered through a 0.45 micron nylon filter. Pure product was obtained by flash chromatography (3 g silica gel, 19:1 v/v $CH_2Cl_2$/MeOH, then 19:1:0.2 v/v/v $CH_2Cl_2$/MeOH/ $NH_4OH$ as the eluant) or by preparative HPLC (Zorbax SB-C18 9.4×250 mm column, gradient: 5:95 $CH_3CN$/$H_2O$+ 0.1% TFA for 5 min, then ramp to 70:30 v/v $CH_3CN$/$H_2O$+ 0.1% TFA over 25 min, 10 mL/min).

For cases that were incompatible with catalytic hydrogenaton the (4-methoxy)benzyl ester of the appropriate aldehyde was used. The (4methoxy)benzyl group was removed by stirring in formic acid overnight. Pure products were isolated as described above.

TABLE 4

| EXAMPLE # | $R^a$ | $R^b$ | X | ESI-MS M/z (M + H) |
|---|---|---|---|---|
| 120 | 3,4-difluorophenyl-propyl | cyclohexyl | F | 557 |
| 121 | 2-cyanophenyl-propyl | cyclohexyl | F | 546 |
| 122 | 3-cyanophenyl-propyl | cyclohexyl | F | 546 |
| 123 | 4-cyanophenyl-propyl | cyclohexyl | F | 546 |
| 124 | 2-cyanophenyl-propyl | cyclohexyl | H | 528 |
| 125 | 4-cyanophenyl-(methyl)propyl | cyclohexyl | F | 560 |

TABLE 4-continued
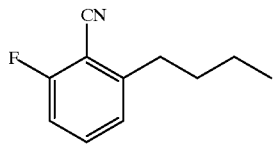
| EXAMPLE # | R$^a$ | R$^b$ | X | ESI-MS M/z (M + H) |
|---|---|---|---|---|
| 126 | 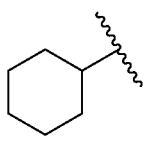 | 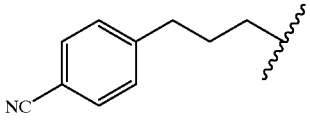 | F | 564 |
| 127 | 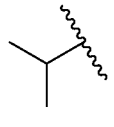 | 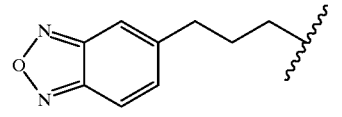 | F | 506 |
| 128 | 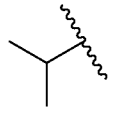 | 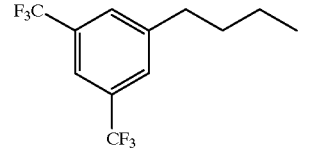 | F | 523 |
| 129 | 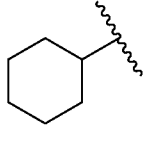 | 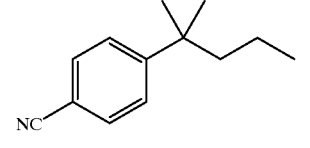 | F | 657 |
| 130 | 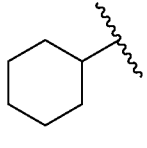 | 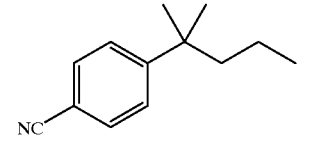 | H | 556 |
| 131 | 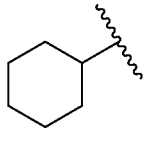 | 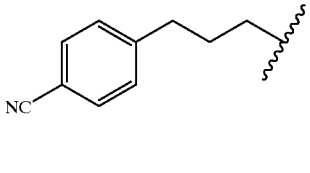 | F | 574 |
| 132 | 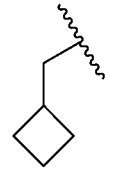 | | F | 532 |

TABLE 4-continued
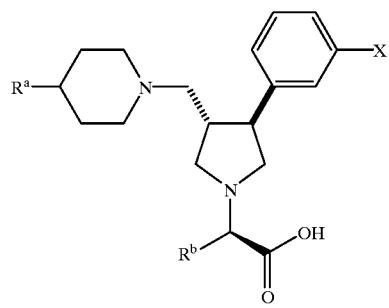
| EXAMPLE # | Rᵃ | Rᵇ | X | ESI-MS M/z (M + H) |
|---|---|---|---|---|
| 133 | NC, F-phenyl-propyl | isopropyl | F | 524 |
| 134 | F, NC-phenyl-propyl | isopropyl | F | 524 |
| 135 | benzofurazan-propyl | isopropyl | F | 533 |
| 136 | CN, F-phenyl-propyl | isopropyl | F | 524 |
| 137 | NC, CF₃-phenyl-propyl | isopropyl | F | 574 |
| 138 | NC, CF₃-phenyl-propyl | cyclohexyl | F | 614 |
| 139 | Cl, Cl-phenyl-propyl | cyclobutylmethyl | H | 556 |

TABLE 4-continued

| EXAMPLE # | Rᵃ | Rᵇ | X | ESI-MS M/z (M + H) |
|---|---|---|---|---|
| 140 | 2-Cl, 4-F phenyl-(CH₂)₃- | cyclobutyl-CH₂- | F | 541 |
| 141 | 2-CF₃, 4-CF₃ phenyl-(CH₂)₃- | cyclohexyl- | F | 643 |
| 142 | 3,4-di-F phenyl-(CH₂)₃- | cyclohexyl- | H | 539 |
| 143 | phenyl-(CH₂)₃- | isopropyl- | H | 474 |
| 144 | 3,4-di-F phenyl-(CH₂)₃- | isopropyl- | H | 513 |
| 145 | 4-Cl phenyl-(CH₂)₃- | cyclohexyl- | H | 537 |
| 146 | 3,5-di-CF₃ phenyl-(CH₂)₃- | cyclohexyl- | H | 639 |

TABLE 4-continued

| EXAMPLE # | R$^a$ | R$^b$ | X | ESI-MS M/z (M + H) |
|---|---|---|---|---|
| 147 | 4-fluorophenylpropyl | cyclohexyl | H | 521 |
| 148 | benzofurazan-5-yl-propyl | cyclohexyl | H | 545 |

EXAMPLES 149–153

The compounds in Table 5 were prepared using procedures analogous to those described for the preparation of the compounds in Table 1.

TABLE 5

| EXAMPLE # | R$^a$ | R$^b$ | X | ESI-MS M/z (M + H) |
|---|---|---|---|---|
| 149 | phenylpropyl | cyclohexyl | F | 537 |
| 150 | 3,4-difluorophenylpropyl | propyl | H | 515 |
| 151 | 3,4-difluorophenylpropyl | isopropyl | H | 529 |

TABLE 5-continued

| EXAMPLE # | R$^a$ | R$^b$ | X | ESI-MS M/z (M + H) |
|---|---|---|---|---|
| 152 | 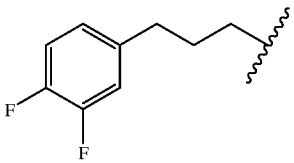 | 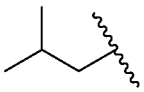 | H | 529 |
| 153 | 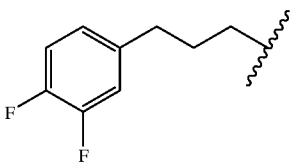 | 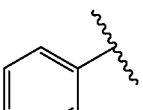 | H | 549 |

EXAMPLE 154

2-(R)-(3-(S)-((4-(3,3-Difluoro-3-phenylpropyl)piperidin-1-yl)methyl)-4-(S)-phenylpyrrolidin-1-yl)-2-(cyclohexyl) acetic acid Step A: 1-(Benzyloxycarbonyl)-4-(3-oxo-3-phenylprop-1-enyl)piperidine DIEA (4.6 mL, 3.4 g, 26 mmol) was added to a solution of 4-(hydroxymethyl)piperidine (2.00 g, 17.4 mmol) dissolved in CH$_2$Cl$_2$ (20 mL). The solution was cooled in an ice bath and benzyl chloroformate (2.5 mL, 3.0 g, 18 mmol) was added dropwise over 10 min. After warming to RT and stirring for 96 h, the mixture was diluted with EtOAc (50 mL) and washed in succession with 25 mL each of saturated aq. NaHCO$_3$, 2 N HCl, saturated aq. NaHCO$_3$, and saturated aq. NaCl. The organic layer was dried (Na$_2$SO$_4$), decanted, and evaporated to give 4.14 g of 1-(benzyloxycarbonyl)-4-(hydroxymethyl)piperidine.

1,1,1-Triacetoxy-1,1-dihydro-1,2-benzoiodoxol-3(1H)-one (1.92 g, 4.53 mmol) was added to a solution of 1-(benzyloxycarbonyl)-4-(hydroxymethyl)piperidine (1.00 g, 4.01 mmol) in CH$_2$Cl$_2$ (20 mL) and the mixture was stirred at RT for 45 min. Ether (75 mL) and 1.3 N NaOH (25 mL) were added and stirring was continued for 15 min. The mixture was transferred to a separatory funnel with additional ether (30 mL) and 1.3 N NaOH (20 mL). The organic layer was separated, washed with saturated aq. NaCl (20 mL, dried (Na$_2$SO$_4$), decanted,and evaporated to give 846 mg of 1-(benzyloxycarbonyl)-4-piperidine carboxaldehyde as a colorless syrup.

Diethyl (2-oxo-2-phenylethyl)phosphonate (0.96 mL,1.1 g, 4.4 mmol) was added in one portion to a stirred suspension of sodium hydride (60% oil dispersion, 158 mg, 3.95 mmol) in THF (20 mL). After 15 min. at RT, the clear solution was cooled in an ice bath and 1-(benzyloxycarbonyl)-4-piperidinecarboxaldehyde (840 mg, 3.40 mmol) was added in THF (1.0 mL) with additional THF (2×1.0 mL) for rinsing. Stirring was continued for a total of 2 h, with slow warming to RT. The mixture was then partitioned between ether (120 ml) and 2.5 N NaOH (60 mL). The organic layer was washed with saturated aq. NaCl (60 mL), dried (Na$_2$SO$_4$), decanted, and evaporated. The crude product was purified by flash column chromatography on silica gel eluting with 85:15 v/v to 80:20 v/v hexanes/EtOAc to give 0–95 g of the title compound as a colorless syrup: $^1$H NMR (400 MHz) δ 7.82 (d, J=8, 21), 7.57 (t, J=8, 1H), 7.48 (t, J=8, 2H), 7.39–7.29 (m, 51), 6.99 (dd, J=15, 6, 1H), 6.87 (dd, J=15, 1, 1H), 5.15 (s, 2H), 2.97–2.82 (m, 2H), 2.50–2.39 (m, 1H), 1.89–1.77 (m, 2H), 1.54–1.39 (m, 2H); ESI-MS 367 (M+NH$_3$+H).

Step B: 2-(2-(1-(Benzyloxycarbonyl)piperidin-4-yl)ethyl)-2-phenyl-1,3-dithiolane 1-(Benzyloxycarbonyl)-4-(3-oxo-3-phenylprop-1-enyl)piperidine (0.95 g, 2.7 mmol, from EXAMPLE 154, Step A) was hydrogenated using 5% Pd/C (10 mg) in 95% ethanol (20 mL) at atmospheric pressure. After 3.5 h, the mixture was filtered and the catalyst was washed with 95% ethanol. Evaporation of the filtrate gave 0.95 g of 1-(benzyloxycarbonyl)-4-(3-oxo-3-phenylpropyl)piperidine as a colorless syrup.

Boron trifluoride-acetic acid complex (BF$_3$.2CH$_3$CO$_2$H, 0.370 mL, 501 mg, 2.67 mmol) was added to a solution of 1,2-ethanedithiol (0.440 mL, 494 mg, 5.25 mmol) and (1-(benzyloxycarbonyl)-4-(3-oxo-3-phenylpropyl)piperidine (930 mg, 2.65 mmol) in CH$_2$Cl$_2$ (4.0 mL) at RT. After 6 h, the mixture was diluted with ether (50 mL) and washed with saturated aq. NaHCO$_3$ (2×25 mL), 2.5 N NaOH (25 mL), and saturated aq. NaCl (25 mL). The organic layer was dried (Na$_2$SO$_4$), decanted, and evaporated. The crude product was purified by flash column chromatography on silica gel eluting with 9:1 v/v hexanes/EtOAc to give 1.05 g of the title compound as a colorless liquid: $^1$H NMR (400 MHz) S 7.66 (d, J=8, 2H), 7.38–7.26 (m, 7H), 7.22 (t, J=8), 1H), 5.10 (s, 2H), 4.18–4.02 (m, 2H), 3.41–3.32 (m, 2H), 3.29–3.20 (m, 2H), 2.79–2.62 (m, 2H), 2.40–2.32 (m, 2H), 1.65–1.54 (m, 2H), 1.40–1.27 (m, 1H), 1.24–1.16 (m, 2H), 1.10–0.97 (m, 2H); ESI-MS 428 (M+H); HPLC A: 4.21 min.

Step C: 1-(t-Butoxycarbonyl)-4-(3,3-difluoro-3-phenylpropyl)piperidine 1,3-Dibromo-5,5-dimethylhydantion (74 mg, 0.26 mmol) was stirred with CH$_2$Cl$_2$ (0.50 mL) at RT, and the suspension was then cooled in a dry ice/2-PrOH bath. After 5 min., hydrogen fluoride-pyridine (70% HF, 0.18 mL) was added over 1 min. After 5 min., a solution of 2-(2-(1-(benzyloxycarbonyl)piperidin-4-yl)ethyl)-2-phenyl-1,3-dithiolane (100 mg, 0.234 mmol, from EXAMPLE 154, Step B) in CH$_2$Cl$_2$ (0.20 mL) was added over 1 min. After 10 min., the reaction mixture was diluted into CH$_2$Cl$_2$ (25 mL) and washed with H$_2$O (10 mL) containing NaHSO$_3$ (0.5 g). The organic layer was washed with saturated aq. NaHCO$_3$ (2×10 mL) followed by saturated aq. NaCl (10 mL), dried (Na$_2$SO$_4$), decanted, and evaporated to give 98 mg of colorless syrup. This material was combined with 195 mg of crude product from two similar reactions and purified by flash column chromatography on silica gel eluting with 9218 v/v hexanes/EtOAc to give 247 mg of 1-(benzyloxycarbonyl)-4-(3,3-difluoro-3-phenylpropyl) piperidine ($R_F$: 0.3 using 10% EtOAc in hexane) containing some residual impurity.

The partially purified 1-(benzyloxycarbonyl)-4-(3,3-difluoro-3-phenylpropylpiperidine (247 mg) was hydrogenated at atmospheric pressure in 95% ethanol (4.0 mL) containing 20% Pd(OH)$_2$/C (60 mg). After 6 h, additional 20% Pd(OH)$_2$/C (32 mg) was added and the hydrogenation was continued for another 16 h. The mixture was filtered and the catalyst was washed with 95% ethanol. Evaporation of the filtrate gave 164 mg of crude 4-(3,3-difluoro-3-phenylpropyl)piperidine as a colorless syrup.

Di-t-butyl dicarbonate (178 mg, 0.816 mmol) was transferred with CH$_2$Cl$_2$ (2×0.5 mL) to a solution of crude 4-(3,3-difluoro-3-phenylpropyl)piperidine (164 mg) in CH$_2$Cl$_2$ (2.0 mL). After stirring at RT for 1 h, the solution was stored at −20° C. for 48 h. The mixture was then diluted into EtOAc (25 mL) and washed with saturated aqueous NaHCO$_3$ (10 mL) followed by saturated aqueous NaCl (10 mL). The organic layer was dried (Na$_2$SO$_4$), decanted, and evaporated. The crude product was purified by flash column chromatography on silica gel, eluting with 94:6 v/v hexanes/EtOAc to give the title compound as 112 mg of colorless syrup: $R_F$: 0.25 (19:1 v/v hexanes/EtOAc). $^1$H NMR (400 MHz) δ 7.50–7.40 (m, 5H), 4.24–3.99 (m, 2H), 2.64 (bt, J=12, 2H), 2.14 (tm, J=16, 2H), 1.62 (bd, J=12, 2H), 1.45 (s, 9H), 1.42–1.33 (m, 3H), 1.13–1.00 (m, 2H).

Step D: 4-(3,3-Difluoro-3-phenylpropyl)piperidine

TFA (2.5 mL, 3.7 g, 32 mmol) was added dropwise to a solution of 1-(t-butoxycarbonyl)-4-(3,3-difluoro-3-phenylpropyl)piperidine (42 mg, 0.12 mmol, from EXAMPLE 154, Step C) in CH$_2$Cl$_2$ (2.5 mL) at 0° C. After 80 min., the solution was transferred using a double-ended needle to a rapidly stirred solution of NaHCO$_3$ (5.0 g, 60 mmol) in H$_2$O (50 mL). Ether (50 mL) and 2.5 N NaOH (20 mL) were added, followed by solid NaCl to saturate the aqueous layer. The aqueous layer was separated and extracted with ether (50 mL). The organic layers were washed in succession with saturated aq. NaCl (20 mL), combined, dried (Na$_2$SO$_4$), decanted,and evaporated to give the title compound as 27 mg of colorless oil. $^1$H NMR (400 MHz, CD$_3$OD) δ 7.51–7.40 (m, 5H), 2.98 (dm, J=12,22H), 2.53 (td, J=12, 3, 2H), 2.24–2.10 (m, 2H), 1.65 (bd, J=12, 2H), 1.42–1.26 (m, 3H), 1.06 (qd, J=12,4,2H); ESI-MS 240 (M+H); HPLC A: 2.25 min.

Step E: 2-(R)-(3-(S)-((4-(3,3-Difluoro-3-phenylpropyl) piperidin-1-yl)methyl)-4-(S)-phenylpyrrolidin-1-yl)-2-(cyclohexyl)acetic acid (4-methoxy)benzyl ester Molecular sieve pellets (3 A) were added to a solution of 2-(R)-(3-(R)-formyl-4-(S)-phenylpyrrolidin-1-yl)-2-(cyclohexyl)acetic acid (4-methoxy)benzyl ester (34 mg, 0.078 mmol, from EXAMPLE 33, Step E) and 4-(3,3-difluoro-3-phenylpropyl)piperidine (20 mg. 0.084 mmol, from EXAMPLE 154, Step D) in 1,2-dichloroethane (0.75 mL). The mixture was stirred for 45 min. at RT before the addition of sodium triacetoxyborohydride (19.9 mg, 0.094 mmol). After 4 h, the mixture was diluted with EtOAc (20 mL) and washed with saturated aq. NaHCO$_3$ (10 mL) followed by saturated aq. NaCl (10 mL). The organic layer was dried (Na$_2$SO$_4$), decanted, and evaporated. Purification by flash column chromatography on silica gel, eluting with 92:8 v/v, then 86:14 v/v hexanes/EtOAc, gave 34 mg of the title compound as a colorless film. $^1$H NMR (400 MHz, CD$_3$OD) δ 7.47–7.40 (m, 5H), 7.36 (d, J=8,22H), 7.23 (t, J=7, 2H), 7.15 (t, J=7, 1H), 7.10 (d, J=7, 1H), 6.90 (d, J=8, 2H), 5.12 (s, 2H), 3.18 (dd, J=9, 7, 1H), 3.12–3.06 (m, 2H), 2.80–2.56 (m, 4H), 2.51 (dd, J=9, 7, 11H), 2.30–2.19 (m, 3H), 2.12 (tm, J=16, 2H), 1.94 (bd, J=12, 1H), 1.86–1.50 (m, 9H), 1.31–0.89 (m, 10H); ESI-MS 659 (M+H).

Step F: 2-(R)-(3-(S)-((4-(3,3-Difluoro-3-phenylpropyl) piperidin-1-yl)methyl)-4-(S)-phenylpyrrolidin-1-yl)-2-(cyclohexyl)acetic acid 2-(R)-(3-(S)-((4-(3,3-Difluoro-3-phenylpropyl)piperidin-1-yl)methyl)-4-(S)-phenylpyrrolidin-1-yl)-2-(cyclohexyl) acetic acid (4-methoxy)benzyl ester (32 mg, 0.049 mmol) dissolved in 95% ethanol (2.5 mL) was hydrogenated at atmospheric pressure using 20% Pd(OH)$_2$/C (5.8 mg). After 3 h, additional Pd(OH)$_2$/C (3.5 mg) was added and the reaction was continued for 1 h. The mixture was filtered, the catalyst was washed with 95% ethanol, and the filtrate was evaporated. The crude product was purified by flash column chromatography on silica gel packed in CH$_2$Cl$_2$. Elution with 95:5:1 v/v/v CH$_2$Cl$_2$/CH$_3$OH/NH$_4$OH followed by 90:10:1 v/v/v CH$_2$Cl$_2$/CH$_3$OH/NH$_4$OH gave 26 mg of the title compound as a colorless brittle glass: $R_F$: 0.5 (10% CH$_3$OH/2% conc. aq. NH$_4$OH/CH$_2$Cl$_2$). $^1$H NMR (400 MHz, CD$_3$OD) δ 7.48–7.30 (m, 4H), 7.38–7.30 (m, 4H), 7.30–7.23 (m, 1H), 3.62–3.51 (m, 2H), 3.44 (d, J=4, 11), 3.10 (td, J=10, 8, 1H), 2.88 (bd, J=12, 1H), 2.73 (bd, J=10, 2H), 2.46 (dd, J=12, 10, 1H), 2.30 (dd, J=13,4, 1H), 2.11 (tm, J=16, 2H), 1.96 (bt, J=12, 1H), 1.90–1.64 (m, 8H), 1.59 (bt, J=12, 2H), 1.50–1.00 (m, 11H); ESI-MS 539 (M+H).

EXAMPLE 155

2-(R)-(3-(S)-((4-(3,3-Difluoro-3-(4-fluorophenyl)propyl) piperidin-1-yl)methyl)-4-(S)-(3-fluorophenyl)pyrrolidin-1-yl)-3-(cyclobutyl)propanoic acid Step A: 1-(t-Butoxycaronyl)-4-(hydroxymethyl)piperidine Di-t-butyl dicarbonate (4.69 g, 21.5 mmol) was transferred in CH$_2$Cl$_2$ (9 mL) over 10 min. to a solution of 4-(hydroxymethyl)piperidine (2.47 g, 21.4 mmol) in CH$_2$Cl$_2$ (16 mL). After stirring at RT for 1 h, the solution was diluted with ether (50 mL) and washed with 2 N HCl, saturated aq. NaHCO$_3$, and saturated aq. NaCl (25 mL of each). The organic layer was dried (Na$_2$SO$_4$), decanted, and evaporated to give 4.57 g of the title compound as a crystalline solid. $^1$H NMR (500 MHz, CD$_3$OD) δ 4.08 (d, J=14,2H), 3.40 (d, J=6, 2H), 2.81–2.67 (m, 2H), 1.71 (d, J=13, 2H), 1.67–1.58 (m, 1H), 1.44 (s, 9H), 1.09 (qd, J=12, 4, 2H).

Step B: 1-(t-Butoxycarbonyl)-4-(iodomethyl)piperidine

Methanesulfonyl chloride (4. 10 mL, 6.07 g, 52.9 mmol) was added dropwise to a solution of 1-(t-butoxycarbonyl)-4-(hydroxymethyl)piperidine (10.0 g, 46.4 mmol, from EXAMPLE 155, Step A) and TEA (9.80 mL, 7.11 g, 70.3 mmol) in CH$_2$Cl$_2$ (140 mL) at 5–8° C. After 1 h, the mixture was diluted with EtOAc (400 mL) and washed with H$_2$O (200 mL). The aqueous layer was extracted with EtOAc (2×150 mL) and the combined organic layers were washed with 1 N HCl (200 mL), saturated aq. NaHCO$_3$ (200 mL), and saturated aq. NaCl (200 mL). The organic layer was dried (Na$_2$SO$_4$), decanted, and evaporated to give 13.58 g of 1-(t-butoxycarbonyl)piperidin-4-yl methanesulfonate as a pale yellow solid.

A mixture of 1-(t-butoxycarbonyl)piperidin-4-yl methanesulfonate (13.58 g, 46.4 mmol) and sodium iodide (34.68 g, 232 mmol) in acetone (80 mL) was heated to reflux for 3 h. The mixture was partitioned between ether (350 mL) and H$_2$O (350 mL). The organic layer was washed with saturated aq. NaCl (250 mL), and the aqueous layers were extracted in succession with ether (250 mL). The combined organic layers were dried (Na$_2$SO$_4$), decanted, and evaporated to give 14.8 g of 1-(t-butoxycarbonyl)-4-(iodomethyl)

piperidine as a pale yellow oil. ¹H NMR (500 MHz) δ 4.25–4.00 (m, 2H), 3.12 (d, J=4, 2H), 2.78–2.52 (m, 2H), 1.85 (d, J=13, 2H), 1.68–1.56 (m, 1H), 1.48 (s, 9H), 1.15 (qd, J=12, 4, 2H).

Step C: ((1-(t-Butoxycarbonyl)piperidin-4-yl)methyl)triphenylphosphonium iodide

A solution of triphenylphosphine (6.63 g, 25.3 mmol) and 1-(t-butoxycarbonyl)-4-(iodomethyl)piperidine (7.96 g, 24.5 mmol, from EXAMPLE 155, Step B) in $CH_3CN$ (40 mL) was heated to reflux for 72 h. The solution was evaporated to give 13.35 g of white solid. A portion (12.34 g) of this material was dissolved in $CH_3CN$ (25 mL) at 65° C. EtOAc (35 mL) was added and the mixture was allowed to cool slowly to RT and then to −20° C. The supernatant was decanted, and the colorless crystals were washed with EtOAc (5×5 mL) and dried under vacuum to give 9.25 g of the title compound. ¹H NMR (500 MHz, $CD_3OD$) δ 7.89 (t, J=8, 3H), 7.86 (dd, J=12,8,66H), 7.76 (td, J=8,4,66H), 3.91 (bd, J=13, 2H), 3.44 (dd, J=14, 6, 2H, 2.72–2.58 (m, 2H), 2.08–1.96 (m, 1H), 1.49 (bd, J=12, 2H), 1.41 (s, 9H), 1.43 (qd, J=13, 4, 2H).

Step D: Methyl (4-fluorobenzoyl)formate

Dimethyl oxalate (5.90 g, 50 mmol) was dissolved in THF (50 mL) and ether (50 mL) in a 3-neck round bottom flask fitted with a mechanical stirrer. The solution was stirred vigorously at −65° C. as a 1.0 M THF solution of 4-fluorophenylmagnesium bromide (60 mL, 60 mmol) was added dropwise over 40 min. The mixture was stirred 30 min. at −65° C. and allowed to warm to −20° C. over 30 min. before being poured into 2 N HCl (50 mL) with stirring. The layers were separated and the aq. layer was extracted with ether (3×50 mL). The combined organic layers were washed with saturated aq. NaCl (2×50 mL), dried ($Na_2SO_4$), decanted, and evaporated. The residue was dissolved in EtOAc, dried ($Na_2SO_4$), filtered, and evaporated to give a yellow solid. The crude product was dissolved in warm hexane (25 mL), filtered, and cooled to −20° C. Filtration followed by washing with cold hexane (15 mL) gave 4.95 g of the title compound as light tan crystals. ¹H NMR (500 MHz) δ 8.11 (dd, J=9.0,5.0,2H), 7.21 (t, J=9,22H), 4.00 (s, 3H); HPLC A: 2.59 min.

Step E: Methyl difluoro(4-fluorophenyl)acetate

Methyl (4-fluorobenzoyl)formate (4.75 g, 26.1 mmol, from EXAMPLE 155, Step D) was added to (diethylamino)sulfur trifluoride (7.0 mL, 8.5 g, 53 mmol). The mixture was stirred rapidly and an ice bath was used briefly to reduce the temperature to 15° C. After the ice bath was removed, the reaction temperature rose to 48° C. over 10 min. and then slowly returned to RT. After a total of 2.75 h, the solution was carefully poured onto crushed ice (30 g) and the mixture was extracted with $CH_2Cl_2$ (2×25 mL). The organic layers were washed in succession with saturated aq. $NaHCO_3$ (2×25 mL) and saturated aq. NaCl (10 mL), combined, dried ($Na_2SO_4$) decanted, and evaporated. The residue was distilled to give the title compound as 4.16 g of light yellow liquid, B.p. 46–48° C. (0.5 mm Hg). ¹H NMR (500 MHz) δ 7.63 (dd, J=9, 5, 2H), 7.16 (d, J=9, 20, 3.88 (s, 3H); HPLC A: 3.05 min.

Step F: 1-(t-Butoxycarbonyl)-4-(3,3-difluoro-3-(4-fluorophenyl)prop-1-enyl)piperidine A solution of methyl difluoro(4-fluorophenyl)acetate (2.04 g, 10.0 mmol, from EXAMPLE 155, Step E) in $CH_3OH$ (10.0 mL) was cooled to −60° C. Sodium borohydride (380 mg, 10.0 mmol) was added in 5 portions at 10 to 15 min. intervals. The mixture was cooled to −60 to −55° C. prior to each addition and allowed to warm to −45° C. following each addition. After the last addition, the mixture was stirred 1.25 h at −50 to 45° C. The mixture was cooled to −60° C. and quenched with 1 N HCl (30 mL), with the temperature rising to −20° C. near the end of the addition. After warming to 0° C., the mixture was extracted with ether (3×20 mL). The combined ether layers were washed with $H_2O$ (2×20 mL), dried ($Na_2SO_4$), decanted, and evaporated to give 1.95 g of crude 2,2-difluoro-2-(4-fluorophenyl)-1-methoxyethanol as a pale yellow oil.

A suspension of ((1-(t-butoxycarbonyl)piperidin-4-yl)methyl)triphenylphosphonium iodide (500 mg, 0,92 mmol, from EXAMPLE 155, Step C) in THF (7.2 mL) was stirred at RT for 30 min. A 0.5 M toluene solution of potassium bis(trimethylsilyl)amide (1.8 mL, 0.90 mmol) was added over 3 min., giving an orange suspension. After 30 min., crude 2,2-difluoro-2-(4-fluorophenyl)-1-methoxyethanol (95 mg, 0.46 mmol) was added in THF (1.0 mL). After an additional 30 min., the mixture was quenched by the addition of saturated aq. $NH_4Cl$ (2 mL). The mixture was partitioned between EtOAc (50 mL) and $H_2O$ (75 ml), and the aqueous layer was extracted with EtOAc (50 mL). The organic layers were washed in succession with saturated aq. NaCl (25 mL), dried ($Na_2SO_4$), decanted, and evaporated. The crude product was purified by flash column chromatography on silica gel, eluting with 10% ether in hexane to give 117 mg of 1-(t-butoxycarbonyl)-4-(3,3-difluoro-3-(4-fluorophenylprop-1-enyl)piperidine as a 95:5 mixture of cis and trans isomers, respectively. ¹H NMR (500 MHz) δ 7.55 (dd, J=9, 5, 2H), 7.13 (t, J=9, 2H), 5.76 (q, J=12, 1H), 5.64 (dd, J=12, 10, 1H), 4.20–3.95 (m, 2H), 2.80–2.54 (m, 3H), 1.54 (bd, J=12, 2H), 1.47 (s, 9H), 1.26 (qd, J=12, 4, 2H); HPLC A: 3.96 min.

Step G: 1-(t-Butoxycarbonyl)-4-(3,3-difluoro-3-(4-fluorophenyl)proyl)piperidine

Potassium azodicarboxylate (695 mg, 3.58 mmol) was added to a solution of 1-(t-butoxycarbonyl)-4-(3,3-difluoro-3-(4-fluorophenyl)prop-1-enyl)piperidine (424 mg, 1.19 mmol, from EXAMPLE 155, Step F) in $CH_3OH$ (3.3 mL). The mixture was stirred at RT as a 9.0 M solution of acetic acid in methanol (0.80 ml, 7.2 mmol) was added over 3 h using a syringe pump. After 30 min., a second portion of potassium azodicarboxylate (695 mg, 3.58 mmol) was added followed by the addition of 9.0 M acetic acid in methanol (0.80 mL, 7.2 mmol) over 3 h. After 20 min., a third portion of potassium azodicarboxylate (695 mg, 3.58 mmol) was added followed by the addition of 9.0 M acetic acid in methanol (0.80 mL, 7.2 mmol) over 3 h. After stirring for 20 h at RT, the mixture was diluted with EtOAc (80 mL), and washed with 2 N HCl (40 mL), saturated aq. $NaHCO_3$ (40 mL), and saturated aq. NaCl (40 mL). The organic layer was dried ($Na_2SO_4$), decanted, and evaporated to give 417 mg of a mixture containing the title compound and 20–25% of unreduced 1-(t-butoxycarbonyl)-4-(3,3-difluoro-3-(4-fluorophenyl)prop-1-enyl)piperidine.

A portion (365 mg) of the crude mixture containing residual olefin was hydrogenated at atmospheric pressure for 16 h using iridium black (30 mg) in a mixture of tert-butanol (24 mL) and EtOAc (2.4 mL). The mixture was filtered, the catalyst was washed with $CH_3OH$, and the filtrate was evaporated to give 371 mg of the title compound as a pale yellow syrup. $R_F$: 0.2 (19:1 v/v hexanes/EtOAc). ¹H NMR (500 MHz) δ 7.46 (dd, J=9, 5, 211, 7.12 (t, J=9, 2H), 4.184.00 (m, 2H), 2.73–2.61 (m, 2H), 2.14 (tm, J=16, 21), 1.64 (bd, J=12, 2H), 1.46 (s, 9H), 1.46–1.33 (m, 3H), 1.08 (qd, J=12, 4, 2H); HPLC A: 4.01 min.

Step H: 4-(3.3-Difluoro-3-(4-fluorophenyl)propyl)piperidine 1-(t-Butoxycarbonyl)-4-(3,3-difluoro-3-(4-fluorophenyl)propyl)piperidine (122 mg, 0.34 mmol, from EXAMPLE 155, Step G) was dried by evaporation of a toluene solution at reduced pressure. The residue was dissovlved in chloroform (7.6 mL) and iodotrimethylsilane (0.100 mL, 141 mg, 0.70 mmol) was added. After stirring 30 min at RT, the solution was poured into a mixture of saturated aqueous NaHCO$_3$ (15 mL) and 2.5 N NaOH (5 mL), and extracted with ether (50 mL). The organic layer was washed with saturated aq. NaCl (15 ml), dried (Na$_2$SO$_4$), decanted, and evaporated to give the title compound as 88 mg of colorless oil. $^1$H NMR (500 MHz, CD$_3$OD) δ 7.51 (dd, J=9, 5,22H), 7.17 (t, J=9, 2H), 2.98 (dm, J=12, 2H), 2.52 (td, J=12, 3, 2H), 2.17 (tin, J=16, 2H), 1.65 (bd, J=13, 2H), 1.42–1.26 (m, 3H), 1.07 (qd, J=12, 4, 2H); ESI-MS 258 (M+H); HPLC A: 2.64 min.

Step I: 2-(R)-(3-(S)-((4-(3,3-Difluoro-3-(4-fluorophenyl) propyl)piperidin-1-yl)methyl)-4-(S)-(3-fluorophenyl) pyrrolidin-1-yl)-3-(cyclobutyl propanoic acid benzyl ester Molecular sieve pellets (3 A) were added to a solution of 2-(R)-(3-(R)-formyl-4-(S)-(3-fluorophenyl)pyrrolidin-1-yl)-3-(cyclobutyl)propanoic acid benzyl ester (160 mg, 0.39 mmol, from EXAMPLE 26, Step A) and 4-(3,3-difluoro-3-(4-fluorophenyl)propyl) piperidine (110 mg. 0.43 mmol, from EXAMPLE 155, Step H). in 1,2-dichloroethane (4.0 mL). The mixture was stirred for 10 min. at RT before the addition of sodium triacetoxyborohydride (103 mg, 0.49 mmol). After 7 h, the mixture was diluted with EtOAc (50 mL) and washed with saturated aq. NaHCO$_3$ (25 ml) followed by saturated aq. NaCl (25 mL). The organic layer was dried (Na$_2$SO$_4$), decanted, and evaporated. The crude product was purified by flash column chromatography on silica gel, eluting with 90:10:1 v/v/v hexanes/EtOAc/MeOH.

Further purification by preparative PLC on a 20×250 mm Chiralcel OD column, eluting with 99:1 v/v hexanes/iPrOH gave 171 mg of the title compound. $^1$H NMR 500 MHz, CD$_3$OD) δ 7.49 (dd, J=9,5, 2H), 7.41 (d, J=8,22H), 7.38–7.29 (m, 3H), 728–7.22 (m, 1H), 7.16 (t, J=9,22H), 7.00 (d, J=8, 1H), 6.97 (d, J=10, 1H), 6.90 (td, J=8, 2, 1H), 5.18 (d, J=12, 1H), 5.15 (d, J=12, 1H), 3.20 (dd, J=9,6, 1H), 3.15–3.05 (m, 2H), 2.86–2.74 (m, 2H), 2.68–2.60 (m, 2H), 2.52 (dd, J=9,7, 1H), 2.38–2.22 (m, 4H), 2.12 (tm, J=16,2H), 2.07–1.94 (m, 4H), 1.90–1.68 (m, 6H), 1.68–1.50 (m, 4H), 1.34–1.00 (m, 5H).

Step J: 2-(R)-(3-(S)(4-(3,3-Difluoro-3-(4-fluorophenyl) propyl)piperidin-1-yl)methyl)-4-(S)-(3-fluorophenyl) pyrrolidin-1-yl)-3-(cyclobutyl)propanoic acid 2-(R)-(3-(S)-((4-(3,3-Difluoro-3-(4fluorophenyl)propyl) piperidin-1-yl)methyl)-4-(S)-(3-fluorophenyl)pyrrolidin-1-yl)-3-(cyclobutyl)propanoic acid benzyl ester (170 mg, 0.261 mmol, from EXAMPLE 155, Step I) dissolved in 95% ethanol (15 mL) was hydrogenated at atmospheric pressure using 20% Pd(OH)$_2$/C (35 mg). After 1 h, the mixture was filtered, the catalyst was washed with 95% ethanol, and the filtrate was evaporated. The crude product was purified by flash column chromatography on silica gel eluting with 95:5:1 v/v/v CH$_2$Cl$_2$/CH$_3$OH/NH$_4$OH followed by 90:10:1 v/v/v CH$_2$Cl$_2$/CH$_3$OH/NH$_4$OH to give the title compound as 137 mg of amorphous glass which could be recrystallized from CH$_3$OH: $^1$H NMR (500 MHz, CD$_3$OD) δ 7.49 (dd, J=9, 5, 2H), 7.39–7.33 (m, 1H), 7.19–7.11 (m, 4H), 7.01 (td, J=8, 2, 1H), 3.63 (dd, J=11, 8, 1H), 3.57 (bt, J=10, 1H), 3.42 (dd, J=9,4, 1H), 3.39–3.26 (m, 2H), 3.15 (bq, J=10, 1H), 2.89 (d, J=11, 1H), 2.77–2.66 (m, 2H), 2.54–2.44 (m, 2H), 2.35 (dd, J=13, 4, 1H), 2.22–2.06 (m, 4H), 2.03–1.54 (m, 10H), 1.31–1.00 (m, 5H); ESI-MS 561 (M+H); HPLC A: 2.72 min.

EXAMPLE 156
2-(R)-(3-(S)-((4-(3,3-Difluoro-3-phenylpropyl)piperidin-1-yl)methyl)-4-(S)-(3-fluorophenyl)pyrrolidin-1-yl)-3-(cyclobutyl)propanoic acid The title compound was prepared using procedures analogous to those described in EXAMPLE 154, substituting 2-(R)-(3-(R)-formyl-4-(S)-(3-fluorophenyl)pyrrolidin-1-yl)-3-(cyclobutyl)propanoic acid benzyl ester (from EXAMPLE 26, Step A) for 2-(R)-(3-(R)-formyl-4-(S)-phenylpyrrolidin-1-yl)-2-cyclohexyl)acetic acid (4-methoxy)benzyl ester in Step E. For the title compound: $^1$H NMR (500 MHz, CD$_3$OD) δ 7.47–740 (m, 1H), 7.16–7.10 (m, 2H), 7.00 (td, J=8, 2, 1H), 3.59–3.48 (m, 2H), 3.37–3.15 (m, 3H), 3.12 (q, J=9, 1H), 2.87 (bd, J=12, 1H), 2.74–2.61 (m, 2H), 2.52–2.43 (m, 2H), 2.34 (dd, J=12,4, 1H), 2.21–2.06 (m, 4H), 2.00–1.76 (m, 6H), 1.76–1.65 (m, 2H), 1.64–1.53 (m, 2H), 1.30–1.13 (m, 3H), 1.09 (qd, J=12,4, 1H), 1.03 (qd, J=12,4, 1H); ESI-MS 543 (M+H); HPLC A: 2.54 min.

EXAMPLE 157
2-(R)-(3-(S)-((4-(3,3-Difluoro-3-(4-fluorophenyl)propyl) piperidin-1-yl)methyl)-4-(S)-phenylpyrrolidin-1-yl)-3-(cyclobutylpropanoic acid The title compound was prepared using procedures analogous to those described in EXAMPLE 155, substituting 2-(R)-(3-(R)-formyl-4-(S)-phenylpyrrolidin-1-yl)-3-(cyclobutyl)propanoic acid (4-methoxy)benzyl ester (from EXAMPLE 19, Step F) for 2-(R)-(3-(R)-formyl-4-(S)-(3-fluorophenyl)pyrrolidin-1-yl)-3-(cyclobutyl)propanoic acid benzyl ester in Step I. For the title compound: $^1$H NMR (500 MHz, CD$_3$OD) δ 7.49 (dd, J=9, 5,2H), 7.36–7.30 (m, 3H), 7.28–7.23 (m, 2H), 7.16 (t, J=9, 2H), 3.79–3.20 (m, 5H), 3.09 (q, J=9, 1O), 2.86 (bd, J=12, 1H), 2.75–2.65 (m, 2H), 2.54–2.41 (m, 2H), 2.32 (dd, J=12,4, 1H), 2.22–2.05 (m, 4H), 2.00–1.66 (m, 8H), 1.63–1.53 (m, 2H), 1.30–1.01 (m, 5H); ESI-MS 543 (M+H); HPLC A: 2.75 min.

EXAMPLE 158
2-(R)-(3-(S)-((4-(3,3-Difluoro-3-phenylpropyl)piperidin-1-yl)methyl)-4-(S)-phenylpyrrolidin-1-yl)-3-(cyclobutyl) propanoic acid The title compound was prepared using procedures analogous to those described in EXAMPLE 154, substituting 2-(R)-(3-(R)-formyl-4-(S)-phenylpyrrolidin-1-yl)-3-(cyclobutyl)propanoic acid (4-methoxy)benzyl ester (from EXAMPLE 19, Step F) for 2-(R)-(3-(R)-formiyl+(S)-phenylpyrrolidin-1-yl)-2-(cyclohexyl)acetic acid (4-methoxy)benzyl ester in Step E. For the title compound: $^1$H NMR (500 MHz, CD$_3$OD) δ 7.46–7.40 (m, 4H), 7.37–7.30 (m, 4H), 7.29–7.24 (m, 2H), 3.79–3.20 (m, 5H), 3.10 (q, J=9, 1H), 2.86 (bd, J=12, 1H), 2.75–2.65 (m, 2H), 2.542.41 (m, 2H), 2.32 (dd, J=12,4, 1H), 2.22–2.06 (m, 4H), 2.01–1.66 (m, 8H), 1.63–1.53 (m, 2H), 1.29–1.00 (m, 5H); ESI-MS 525 (M+H); HPLC A: 2.69 min.

EXAMPLE 159
(2-(S)-(3-(S)-((4-(3,3-Difluoro-3-(4fluorophenyl)propyl) piperidin-1-yl)methyl)-4-(S)-phenylpyrrolidin-1-yl)-3-(cyclobutyl)propanoic acid The title compound was prepared using procedures analogous to those described in EXAMPLE 155, substituting 2-(S)-(3-(R)-formyl-4-(S)-phenylpyrrolidin-1-yl)-3-(cyclobutyl)propanoic acid (4-methoxy)benzyl ester (from EXAMPLE 92) for 2-(R)-(3-R)-formyl-4-(S)-(3-fluorophenyl)pyrrolidin-1-yl)-3-(cyclobutyl)propanoic acid benzyl ester in Step I. For the title compound: ESI-MS 543 (M+H); HPLC A: 2.54 min.

EXAMPLE 160
2-(S)-(3-(S)-((4-(3,3-Difluoro-3-phenylpropyl)piperidin-1-yl)methyl)-4-(S)-phenylpyrrolidin-1-yl)-3-(cyclobutyl) propanoic acid The title compound was prepared using procedures analogous to those described in EXAMPLE 154, substituting 2-S)-(3-(R)-formyl-4-(S)-phenylpyrrolidin-1-yl)-3-(cyclobutyl)propanoic acid (4-methoxy)benzyl ester (from EXAMPLE 92, Step C) for 2-(R)-(3-(R)-formyl-4-(S)-phenylpyrrolidin-1-yl)-2-(cyclohexyl)acetic acid (4-methoxy)benzyl ester in Step E. For the title compound: ESI-MS 525 (M+H); HPLC A: 3.00 min.

EXAMPLE 161

2-(R)-(3-(S)-((4-(3,3-Difluoro-3-(4-fluorophenyl)propyl)piperidin-1-yl)methyl)-4-(S)-(3-fluorophenyl)pyrrolidin-1-yl)-3-(cyclopropyl)propanoic acid The title compound was prepared using procedures analogous to those described in EXAMPLE 155, substituting 2-(R)-(3-(R)-formyl-4-(S) phenylpyrrolidin-1-yl)-3-(cyclopropyl)propanoic acid (4-methoxy)benzyl ester (from EXAMPLE 21, Step E) for 2-(R)-(3-(R)formyl-4-(S)-(3-fluorophenyl)pyrrolidin-1-yl)-3-(cyclobutyl)propanoic acid benzyl ester in Step I. For the title compound: $^1$H NMR (300 MHz, CD$_3$OD) δ 0.03–0.07 (m, 2H), 0.36–0.42 (m, 2H), 0.70 (m, 1H), 0.89–1.17 (m, 51), 1.43–2.07 (m, 8H), 2.22 (m, 1H), 2.37 (m, 1H), 2.55–2.63 (m, 2H), 2.77 (m, 1H), 3.04 (m, 1H), 3.16–3.27 (m, 2H), 3.42–3.53 (m, 3H), 6.88 (m, 1H), 7.01–7.06 (m, 4H), 7.23 (m, 1H), 7.34–7.39 (m, 2H). ESI-MS 547 (M+H); HPLC A: 2.61 min.

EXAMPLE 162

2-(R)-(3-(S)-((4-(2-(1-Naphthyl))ethyl)piperidin-1-yl)methyl)-4-(S)-phenylpyrrolidin-1-yl)-2-(cyclohexyl)acetic acid Step A: (1-Benzyl)piperidine-4-carboxaldehyde To a suspension of 4.08 g of (methoxymethyl)triphenylphosphonium chloride in 20 mL of THF was added 8.11 mL of n-butyllithium(1.6 M in hexane) at 0° C. The reaction was stirred at 0° C. for 0.5 h. To the resulting solution was added 2.05 g of 1-benzyl-4-piperidone at 0° C. After stirring at rt for 1 h, the reaction was refluxed for 3 h. The reaction was cooled to rt and partitioned between EtOAc and H$_2$O. The organic layer was washed with sat'd NaCl, dried over MgSO$_4$ and concentrated to afford 5.48 g of viscous oil. The oil was dissolved in 20 mL of formic acid (96%). After stirring at rt for 4 h, the mixture was concentrated. The residue was dissolved in EtOAc and washed with sat'd NaHCO$_3$ followed by sat'd NaCl. The organic layer was dried over MgSO$_4$ and concentrated. The residue was purified by flash chromatography eluting with 1:1 v/v hexanes/EtOAc followed by EtOAc to give 877 mg of the title compound.

Step B: (E/Z)-1-Benzyl-4-(2-(2-(1-napthyl))vinyl)piperidine

To a suspension of 1.01 g of 1-naphthylmethyl triphenylphosphonium chloride in 5 mL of THF was added 1.73 mL of n-butyllithium(1.6 M in hexane) at 0° C. To the above solution was added 467 mg of (1-benzyl)piperidine-4-carboxaldehyde (from EXAMPLE 162, Step A) in 5 mL of THF. The reaction was stirred at 0° C. for 0.5 h, at rt for 0.5 h and at reflux for 3 h. The reaction was cooled to rt and partitioned between EtOAc and H$_2$O. The aqueous phase was was extracted with EtOAc (3×). The combined organic phases were washed with sat'd NaCl and dried over MgSO$_4$. Concentration afforded a viscous oil which was purified by flash chromatography eluting with 91:9 v/v hexanes/EtOAc followed by 1:1 v/v hexanes/EtOAc to give 473 mg of the title compound (E:Z=2:1) as a white solid.

Step C: 4-(2-((1-Naphthyl))ethyl)piperidine

A solution of 465 mg of (1)-1-benzyl-4-(2-((1-naphthyl)vinyl)piperidine (from EXAMPLE 162, Step B) in 10 mL of MeOH and 3 mL of THF was hydrogenated using 1 g 10% palladium on carbon under one atmosphere of hydrogen gas. After stirring at rt for 18 h, the mixture was filtered through celite. Concentration of the filtrate afforded 178 mg of the title compound as a viscous oil, which was used for the next step without further purification.

Step D: 2-(R)-(3-(S)-((4-(2-((1-Naphthyl))ethyl)piperidin-1-yl)methyl)-4-(S)-phenylpyrrolidin-1-yl)-2-(cyclohexyl) acetic acid The title compound was prepared from 2-(R)-(3-(R)-formyl-4-(S)-phenylpyrrolidin-1-yl)-2-(cyclohexyl)acetic acid, benzyl ester (from EXAMPLE 1, Step I) and 4-(2-napthylethyl)piperidine (from EXAMPLE 162, Step C) using procedures analogous to those described in EXAMPLE 1, Steps J and K. For the title compound: $^1$H NMR (500 MHz, CD$_3$OD) a 1.103.80 (m, 33H), 7.10–7.60 (m, 9H), 7.68 (d, J=7.7, 1H), 7.83 (d, J=8.0, 1H), 7.99 (d, J=8.5, 1H); ESI-MS 539 (M+H); HPLC A: 2.83 min.

EXAMPLE 163

2-(R)-(3-(S)-((Benzothiazol-2-yl)methyl)piperidin-1-yl)methyl)-4-(S)-phenylpyrrolidin-1-yl)-2-(cyclohexyl)acetic acid Step A: ((1-Benzyl)piperidin-4-ylidene)acetic acid, t-butyl ester To a solution of 1.68 g of t-butyl diethylphosphonoacetate in 5 mL of THF was added 400 mg of sodium hydride (60% dispersion in mineral oil) at 0° C. The reaction was warmed to rt and stirred at rt for 20 min. To the resulting solution was added a solution of 1.05 g of 1-benzyl-4-piperidone in 5 mL of THF. The solution was refluxed for 3 h and cooled to rt. After quenching with aqueous NH$_4$Cl, the aqueous phase was extracted with EtOAc (3×). The combined organic phases were dried over MgSO$_4$ and concentrated to give 1.05 g of the title compound as a oil, which was used for the next step without further purification.

Step B: ((1-Benzyl)piperidin-4-yl)acetic acid, t-butyl ester

To a solution of 1 g of ((1-benzyl)piperidin-4-ylidene)acetic acid, t-butyl ester (from EXAMPLE 163, Step A) in 10 mL of EtOH was added 100 mg of platinum oxide at rt. The solution was hydrogenated for 3 h under one atmosphere of hydrogen gas. After filtering through celite, the filtrate was concentrated under reduced pressure to give 936 mg of the title compound as a viscous oil.

Step C: (1-Benzyl-piperidin-4-yl)acetic acid TFA

A solution of 936 mg of ((1-benzyl)piperidin-4-yl)acetic acid, t-butyl ester (from EXAMPLE 163, Step B) in 2 mL of TFA was stirred at rt for 18 h. The solution was concentrated to afford the title compound.

Step D: 1-Benzyl-4-((benzothiazol-2-yl)methyl)piperidine

A mixture of 1.2 g of (1-benzyl-piperidin-4-yl)acetic acid.TFA, (from EXAMPLE 163, Step C) and 433 mg of 2-aminothiophenol was treated with 10 mL of polyphosphoric acid. After stirring at 120° C. for 18 h, the syrup was poured onto ice and H$_2$O, maintaining the temperature of the aqueous mixture below 10° C. The resulting dark brown solution was made basic with ammonium hydroxide. The aqueous mixture was extracted with EtOAc (3×). The combined organic extracts were washed with sat'd NaCl and dried over MgSO$_4$. Concentration afforded 962 mg of the title compound as a oil.

Step E: 1-Ethoxycarbonyl-4-((Benzothiazol-2-yl)methyl)piperidine

A solution of 500 mg of 1-benzyl-4-((benzothiazol-2-yl)methyl)piperidine (from EXAMPLE 163, Step D) in 10 mL of THF was added 185 mg of ethyl chloroformate at rt. The reaction was stirred at rt for 5 h. The reaction mixture was partitioned between H$_2$O and EtOAc. The aqueous phase was extracted with EtOAc (3x). The combined organic phases were washed with sat'd NaCl and dried over MgSO$_4$. Concentration afforded 320 mg of the title compound as a oil.

Step F: 4-((Benzothiazol-2-yl)methyl)piperidine

A solution of 300 mg of 1-ethoxycarbonyl-4-((benzothiazol-2-yl)methyl)piperidine (from EXAMPLE 163, Step E) in 5 mL of EtOH and 5 mL of KOH (50 wt. % solution) was refluxed for 18 h. The reaction mixture was partitioned between H$_2$O and EtOAc. Aqueous phase was extracted with EtOAc (3x). The combined organic phases were washed with sat'd NaCl and dried over anhydrous MgSO$_4$. Concentration afforded 180 mg of the title compound as a brown solid.

Step G: 2-(R)-(3-(S)-(4-((Benzothiazol-2-yl)methyl) piperidin-1-yl)methyl)-4-(S)-phenylpyrrolidin-1-yl)-2-(cyclohexyl)acetic acid The title compound was prepared from 4-((benzothiazol-2-l)methyl)piperidine (from EXAMPLE 163, Step F) and 2-(R)-(3-(R)-formyl-4-(S)-phenylpyrrolidin-1-yl)-2-(cyclohexyl)acetic acid, 4methoxybenzyl ester (EXAMPLE 33, Step E) using procedures analogous to those described in EXAMPLE 1, Step J and EXAMPLE 10, Step F. For the title compound: $^1$H NMR (500 MHz, CD$_3$OD) δ 1.10–1.96 (m, 9H), 2.07 (br t, 2H), 2.35 (br d, 2H), 2.51 (br t, 2H), 2.77 (br d, 4H), 2.94 (br d, 2H), 3.01 (d, J=7.1, 2H), 3.14 (q, H=8.7, 21), 3.35–3.65 (m, 6H), 7.23–7.35 (m, 5H), 7.39 (t, J=7.3, 1H), 7.48 (t, J=7.3, 1H), 7.89 (d, J=8.2, 1H), 7.92 (d, J=7.6, 1H); ESI-MS 532 (M+H); HPLC A: 2.23 min.

EXAMPLE 164

2-(R)-(3-(S)-(4-(((1-H-Benzimidazol-2-yl)methyl) piperidin-1-yl)methyl)-4-(S)-phenylpyrrolidin-1-yl)-2-(cyclohexyl)acetic acid Step A: 1-Benzyl-4-((1H-benzimidazol-2-yl)methyl) piperidine The title compound using procedures analogous to those described in EXAMPLE 163, Steps A–D, substituting 1,2-phenylenediamine for 2-aminothiophenol in Step D.

Step B: 4-((1H-Benzimidazol-2-yl)methyl)piperidine HCOOH

A mixture of 66 mg of 1-benzyl-4-((1H-benzimidazol-2-yl)methyl)piperidine (from EXAMPLE 164, Step A), 66 mg of 10% palladium on carbon and 68 mg of ammonium formate in 10 mL of MeOH was heated at reflux for 3 h. The mixture was cooled and filtered through celite. Concentration afforded 37 mg of the title compound as a foamy solid.

Step C: 2-(R)-(3-(S)-(4-((1-H-benzoimidazol-2-yl)methyl) piperidin-1-yl)methyl)-4-(S)-phenylpyrrolidin-1-yl)-2-(cyclohexyl)acetic acid The title compound was prepared from 2-(R)-(3-(R)-formyl-4-(S)-phenylpyrrolidin-1-yl)-2-(cyclohexyl)acetic acid, 4-methoxybenzyl ester (from EXAMPLE 33, Step E) and 4-((1H-benzimidazol-2-yl)methyl) piperidine.HCOOH (from EXAMPLE 164, Step B) using a procedures analogous to those described in EXAMPLE 1, Step J and EXAMPLE 10, Step F. For the title compound: ESI-MS 515 (M+H); HPLC A: 1.79 min.

EXAMPLE 165

2-(R)-(3-(S)-(4-((3-H-hnidazo[4,5-b]pyridin-2-yl)methyl) piperidin-1-yl)methyl)-4-(S)-phenylpyrrolidin-1-yl)-2-(cyclohexyl)acetic acid The title compound was prepared using procedures analogous to those described in EXAMPLE 164, except that 2,3-diaminopyridine was substituted for 1,2-phenylenediamnine in Step A. For the title compound: ESI-MS 516 (M+H); HPLC A: 2.21 min.

EXAMPLE 166

2-(R(3-(S(4-((1-H-Benzoimidazol-2-yl)ethyl)piperidin-1-yl)methyl)-4-(S)-phenylpyrrolidin-1-yl)-2-(cyclohexyl) acetic acid The title compound was prepared using procedures analogous to those described in EXAMPLE 164, except that 1-benzyl-piperidine-4-carboxaldehyde (from EXAMPLE 162, Step A) was substituted for 1-benzyl-4-piperidinone in Step A. For the title compound: ESI-MS 529 (M+H); HPLC A: 2.43 min.

EXAMPLE 167

2-(R)-(3-(S)-(4-((3-H-Imidazo[4,5-b]pyridin-2-yl)ethyl) piperidin-1-yl)methyl)-4-(S)-phenylpyrrolidin-1-yl)-2-(cyclohexyl)acetic acid The title compound was prepared using procedures analogous to those described in EXAMPLE 164, except that 1-benzyl-piperidine-4-carboxaldehyde (from EXAMPLE 162, Step A) was substituted for 1-benzyl-4-piperidinone in Step A and 2,3-diaminopyridine was substituted for 1,2-phenylenediamine in Step A. For the title compound: ESI-MS 530 (M+H); HPLC A: 1.65 min.

EXAMPLE 168

2-(R)-(3-(S)-((4-Hydroxy-4-(phenylethynyl)piperidin-1-yl) methyl)-4-(S)-phenylpyrrolidin-1-yl)-2-(cyclohexyl)acetic acid Step A: 4-Hydroxy-4-(phenylethynyl)piperidine A solution of 1.03 g of phenylacetylene in 10 mL of THF was treated with 12 mL of ethyl magnesium bromide (1.0 M solution in THF) at 0° C. The resulting mixture was stirred at 0° C. for 10 min, then treated with a solution of 2 g of 1-t-butoxycarbonyl-piperidin-4-one in 10 mL of THF. The reaction was warmed to rt and stirred for 18 h. The reaction was quenched with sat'd NH$_4$Cl and extracted with EtOAc (3x). The combined organic phases were dried over MgSO$_4$ and concentrated to give 1.98 g of a viscous oil. A solution of the oil in 5 mL of CH$_2$Cl$_2$ and 1 mL of anisole was treated with 2 mL of TFA and the resulting mixture was stirred at rt for 48 h. The reaction was concentrated and the residue was partitioned between EtOAc and sat'd NaHCO$_3$. The aqueous phase was extracted with EtOAc (3x). The combined organic phases were washed with sat'd NaCl, dried over MgSO$_4$ and concentrated. Flash chromatography eluting with 1:1 v/v hexanes/EtOAc, then 9:1 v/v CH$_2$Cl$_2$/MeOH and then 80:15:1 v/v/v CHCl$_3$MeOH/NH$_4$OH afforded 160 mg of the title compound.

Step B: 2-(R)-(3-(S)-((4-Hydroxy-4-(phenylethynyl) piperidin-1-yl)methyl)-4-(S)-phenylpyrrolidin-1-yl)-cyclohexaneacetic acid The title compound was prepared from of 2-(R)-(3-(R)-formyl-4-(S)-phenylpyrrolidin-1-yl)-2-(cyclohexyl)acetic acid, 4methoxybenzyl ester (EXAMPLE 33, Step E) and of 4-hydroxy-4-(phenylethynyl)piperidine (from EXAMPLE 168, Step A) using a procedures analogous to those described in Example 1, Step J and Example 10, Step F. For the title compound: ESI-MS 501 (M+H); HPLC A: 2.29 min.

EXAMPLE 169

α-(R)-(3-(S)-((4-(3-(pyrid-2-yl)-3,3-difluororprop-1-yl) piperidin-1-yl)methyl)-4-(S)-(3-fluorophenyl) pyrrolidin-1 -yl)tert-butylacetic acid Step A: 3,3-dimethyl-2-(S)-hydroxybutyric acid benzyl ester (S)-3,3-dimethyl-2-hydroxybutyric acid (2.1 grams, 15.9 mmol) and triethylamine (3.3 mL, 23.8 mmol) were dissolved in 15 mL DMF. Benzyl bromide (2.8 mL, 23.8 mmol) was added and the mixture was stirred overnight. Ethyl acetate was added and the mixture was washed with water (3×) and sat'd NaCl then dried over sodium sulfate and concentrated. Flash chromatography (150 g silica, 7/1 Hexane/EtOAc) afforded 3.4 grams (96%) of the title compound. $^1$H NMR (300 MHz, CDCl$_3$). δ 0.98 (s, 9H), 2.75 (d, 1H), 3.85 (d, 1H), 5.23, (s, 21), 7.27–7.3 (m, 5H).

Step B: 3.3-dimethyl-2-(S)-(trifluoromethanesulfonyl) butyric acid benzyl ester

A solution of (3,3-dimethyl-2-(S)hydroxybutyric acid benzyl ester (3.4 grams, 15.3 mmol, from Step A) in 60 mL dichloromethane was cooled to −78 C under nitrogen. 2,6-lutidine (2.3 mL, 19.9 mmol) then trifluoromethanesulfonic andydride (3.1 mL, 18A mmol) were added dropwise via syringe. The mixture was warmed to room temperature and stirred for 1 h. Water was added and the mixture was extracted with ethyl acetate. The organic layer was dried over sodium sulfate and concentrated. Flash chromatography (150 g silica, 20/1 Hexane/EtOAc) afforded 3.3 grams (61%) of the desired triflate. $^1$H NMR (400 MHz, CDCl$_3$). S 1.05 (s, 9H), 4.8, (s, 1H), 5.25 (dd, 2H), 7.3–7.4 (m, 5H).

Step C: α-(R)-(3-(S)-tert-((butyldimethylsilyloxy)methyl)-4-(S)-(3-fluorophenyl)pyrrolidin-1-yl)-tert-butylacetic acid A dry flask was charged 10 mL DMF and (3,3-dimethyl-2-(S)-trifluoromethanesulfonylbutyric acid benzyl ester, (2.2 grams, 6.4 mmol). The vessel was purged with nitrogen and 3-(R)-(t-butyldimethylsilyloxymethyl)-4-(S)-(3-fluoro)phenyl pyrrolidine (2.7 grams, 8.9 mmol, from EXAMPLE 20 Step H) then diisopropylethyl amine (1.8 mL, 10.2 mmol) were added. The mixture was heated to 50 C overnight. Water (200 mL) was added and the mixture was extracted with ether (2×150 mL). The combined organics were dried over sodium sulfate and concentrated. Flash chromatography (150 g silica, 30/1 Hexane/EtOAc) afforded 2.0 grams (61%) of product. $^1$H NMR (400 MHz, CDCl$_3$). δ 0 (s, 6H), 0.84 (s, 9H), 1.05 (s, 9H), 2.25–2.35 (m, 1H), 2.8–2.94 (m, 3H), 3.1–3.22 (m, 3H), 3.45–3.58 (m, 2H), 5.1–5.25 (dd, 2H), 6.83–6.99 (m, 3H), 7.19–7.24 (m, 1H), 7.3–7.42 (m, 5H).

Step D: α-(R)-(3-(R)-Formyl-(S)-(3-fluorophenyl) pyrrolidin-1-yl)-tert-butylacetic acid, benzyl ester The title compound was prepared in two steps from a-(R)-(3-(S)-tert-((butyldimethylsilyloxy)methyl)-4-(S)-(3-fluorophenyl)pyrrolidin-1-yl)-tert-butylacetic acid (Step C) using procedures analogous to those in EXAMPLE 1 Steps H and I. $^1$H NMR (400 MHz, CDCl$_3$). S 1.05 (s, 9H), 2.88–2.96 (m, 2H), 3.2–3.35 (m, 4H), 3.484.53 (q, 1H), 6.89–6.99 (m, 3H), 7.21–7.26 (m, 1H). 7.35–7.45 (m, 5H), 9.61 (s, 1H).

Step E: α-(R)-(3-(S)-((4-(3-(pyrid-2-yl)-3,3-difluoroprop-1-yl)piperidin-1-yl)methyl)-4-(S)-(3-fluorophenyl)pyrrolidin-i:-l)-tert-butylacetic acid The title compound was prepared from a-(R)-(3-(R)-Formyl-4-(S)-(3-fluorophenyl)pyrrolidin-1-yl)-tert-butylacetic acid, benzyl ester (25 mg, 0.063 mmol, from Step D) and 4-(3-(pyrid-4-yl)-3,3-difluoroprop-1-yl) piperidine (18 mg, 0.075 mmol, from EXAMPLE 202 Step E) using the procedure described in EXAMPLE 35 Step C. 29 mg (87%) of desired product was obtained. $^1$H NMR (500 MHz, CD$_3$OD). δ 1.05–1.22 (m, 2H), 1.16 (s, 9H), 1.22–2.31 (m, 3H), 1.6–1.7 (t, 2H), 1.96–2.03 (t, 1H), 2.11–2.2 (m, 1H), 2.21–2.35 (m, 2H), 2.42–2.5 (dd, 1H), 2.6–2.68 (t, 1H), 2.69–2.73 (m, 1H), 2.85–2.91 (d, 1H), 2.99–3.04 (d, 1H), 3.1–3.18 (q, 1H), 3.23–3.38 (m, 3H), 3.75–3.85 (m, 2H), 6.98–7.02 (t, 1H), 7.13–7.17 (m, 2H), 7.33–7.37 (m, 1H), 7.47–7.5 (m, 1H), 7.6 (d, 1H), 7.92–7.96 (t, 1H), 8.6 (d, 1H). ESI-MS, M/z; (M+H) 532.4 (obs), 532.33 (calc.).

EXAMPLE 170

2-(RS)-(3-(S)-((4-(3-(4-cyanophenyl)prop-1-yl)piperidin-1-yl)methyl)-4-(S)-(3-fluorophenyl)pyrrolidin-1-yl)-4,4,4-trifluorobutyric acid Step A: 2-hydroxy-4,4,4-trifluorobutyric acid benzyl ester A suspension of 2-amino-4,4,4-trifluorobutyric acid (1.1 g, 7 mmol), in 5 mL water was cooled to 0 C. 2N sulfuric acid (3.9 mL, 7.7 mmol) was added followed by 2N sodium nitrite (3.9 mL, 7.7 mmol). After 3 h the mixture was warmed to room temperature and stiffed overnight. Water was added and the mixture was extracted with EtOAc and dichloromethane (100 mL each). The combined organics were dried over sodium sulfate and concentrated. DMF (5 mL) was added followed by triethylamine (1.5 ml, 10.5 mmol) and benzyl bromide (1.25 mL, 10.5 mmol). The resulting mixture was stirred overnight. The mixture was diluted with water and extracted with EtOAc. The organic layer was dried over sodium sulfate and concentrated. Flash chromatography (3/1 Hexane/EtOAc) afforded 438 mg (25 %) of desired product. $^1$H NMR (400 MHz, CDCl$_3$). δ 2.4–2.55 (m, 1H), 2.63–2.77 (m, 1H), 4.5–4.55 (m, 1H), 5.26 (dd, 2H), 7.35–7.41 (m, 5H)

Step B: 2-(RS(3-(R)-Formyl-4-(S)-(3-fluorophenyl) pyrrolidin-1-yl)-4,4,4-trifluorobutyric acid benzyl ester The title compound was prepared from 2-hydroxy-4,4,4-trifluorobutyric acid benzyl ester and 3-(R)-(t-butyldimethylsilyloxymethyl)-4-(S)-(3-fluoro)phenyl pyrrolidine (from EXAMPLE 20 Step H) following the procedures in EXAMPLE 1 Steps G–A.

Step C: 2-(RS)-(3-(S)-((4-(3-(4-cyanophenyl)prop-1-yl) piperidin-1-yl)methyl)-4-(S)-(3-fluorophenyl)pyrrolidin-1-Yl)-4,4,4-trifluorobutyric acid The title compound was prepared from 2-(RS)-(3-(R)-Formyl-4-(S)-(3-fluorophenyl)pyrrolidin-1-yl)-4,4,4-trifluorobutyric acid, benzyl ester (from Step B) and 4-(3-(4-cyanophenyl)prop-1-yl)piperidine (from EXAMPLE 36 Step A) using the procedure described in EXAMPLE 35 Step C. $^1$H NMR (500 MHz, CD$_3$OD). δ 1.25–1.54 (5H), 1.6–1.63 (m, 2H), 1.79–1.82 (d, 2H), 2.43–3.0 (9H), 3.08–3.45 (8H) 6.93–6.97 (m, 1H), 7.11–7.17 (m, 2H), 7.3–7.37 (m, 3H), 7.6 (d, 2H). ESI-MS, M/z; (M+H)=546.1 (obs), 546.27 (calc.).

EXAMPLE 171

2-(R)-(3-(S)-((4-(3-(2-methoxy-4,6-difluorophenyl)propyl) piperidin-1-yl)methyl)-4-(S)-(3-fluorophenyl)-pyrrolidin-1-yl)-3-(cyclopropyl)propanoic acid Step A: 2-Allyl-4,6-difluorophenol 3,5-difluorophenol (3.9 grams, 30 mmol), allyl bromide (3.4 mL, 39 mmol) and K$_2$CO$_3$ (12.4 grams, 90 mmol) were suspended in 75 mL acetone and the mixture was refluxed overnight. The mixture was diluted with water and extracted with EtOAc. The organic was dried over sodium sulfate and concentrated. 5.5 grams of crude allyl-3,5-difluorophenylether. The oil was heated to reflux for 6 h then cooled to room temperature. Flash chromatography (150 g silica, 1011 Hexane/EtOAc) afforded 5.2 grams (100%) of product. $^1$H NMR (400 MHz, CDCl$_3$). δ 3.4 (d, 2H), 5.1–5.2 (m, 2H), 5.6 (s, 1H), 5.9–6.0 (m, 1H), 6.46.5 (m, 2H).

Step B: (2-Allyl-4,6-difluorophenyl)methyl ether

A solution of iodomethane (1.8 mL, 29.4 mmol), K$_2$CO$_3$ (2.4 grams, 17.6 mmol) and 2-Allyl-4,6-difluorophenol (1.0 grams, 5.9 mmol) in 20 mL acetone was refluxed overnight. The mixture was diluted with water and extracted with EtOAc. The organic layer was dried over sodium sulfate and concentrated. Flash chromatography (Hexane) afforded 0.67 g (63%) of the title compound. $^1$H NMR (400 MHz, CDCl$_3$). S 3.36 (d, 21), 3.82 (s, 3H), 4.97–5.12 (m, 2H), 5.85–6.0 (m, 1H), 6.4–6.5 (m, 2H).

Step C: N-tert-butoxycarbonyl-1,2,3,6-tetrahydropyridine-4-trifluoromethane sulfonate.

A dry flask under nitrogen was charged with a solution of sodium hexamethyldisilazide (11 mL, 1.0 M in TH) and was cooled to −78 C. A solution of N-tert-butoxycarbonyl-4-piperidone (2.0 grams, 10 mmol) in 10 mL THF was added dropwise via cannula. After 30 min. a solution of 2-(N,N-bis(trifluoromethanesulfonyl) amino-5-chloropyridine (4.7 grams, 12 mmol) in 15 mL THF was added. The mixture was warmed to room temperature, quenched with sat'd ammonium chloride and extracted with EtOAc. The EtOAc layer was separated and washed with sat'd NaCl then dried over sodium sulfate and concentrated. Flash chromatography (100 g silica, 10/1 Hexane/EtOAc) afforded 1.9 grams (58%) of the title compound. $^1$H NMR (400 MHz, CDCl$_3$). δ 1.5 (s, 9H), 2A-2.48 (m, 2H), 3.62–3.68 (t, 2H), 4.054.07 (m, 2H), 5.77–5.8 (bs, 1H).

Step D: 4-(3-(2-methoxy-4,6-difluorophenyl)prop-1-yl) piperidine HCl

A solution of (2-Allyl-4,6-difluorophenyl)methyl ether (221 mg, 1.2 mmol, from Step B) in 0.5 mL THF was cooled to 0 C and a solution of 9-BBN (2.64 mL, 0.5 M in THF, 1.32 mmol). The mixture was warmed to room temperature and stirred for 5 h. N-tert-butoxycarbonyl-1,2,3,6-tetrahydropyridine-4-trifluoromethanesulfonate (437 mg, 1.32 mmol, from Step C), bis(diphenylphosphino)ferrocenyl palladium dichloride (49 mg, 0.06 mmol) and K$_2$CO$_3$ (332 mg, 2.4 mmol) were added followed by 5 mL DMF. The mixture was heated to 50 C overnight. The mixture was diluted with EtOAc and washed with water (3×) then sat'd NaCl. The organic portion was dried over sodium sulfate and concentrated. Flash chromatography (30 g silica, 10/1 Hexane/EtOAc) afforded 167 mg of desired product. This material was dissolved in 2 mL methanol and 48 mg (0.045 mmol) 10% Pd/C was added. The mixture was stirred under 1 atm of hydrogen for 2 h. The catalyst was filtered off and to the solution was added 10 mL 1 % conc HCl in methanol. The mixture was heated to 50 C for 2 h then concentrated to give the pure HCl salt. $^1$H NMR (400 MHz, CD$_3$OD) δ 1.25–1.4 (m, 4H), 1.5–1.63 (m, 3H), 1.88–1.98 (d, 2H), 2.58–2.63 (t, 2H), 2.9–3.0 (m, 2H), 3.3–3.4 (m, 2H), 3.82 (s, 3H), 6.42–6.52 (m, 1H), 6.58–6.61 (d, 1H).

Step E: 2-(R)-(3-(S)-((4-(3-(2-methoxy-4,6-difluorophenyl)propyl)piperidin-1-yl)methyl)-4-(S)-(3-fluorophenyl)-pyrrolidin-1-yl)-3-2(cyclopropyl)propanoic acid The title compound was prepared from 4-(3-(2-methoxy-4,6-difluorophenyl)prop-1-yl)piperidine.HCl and 2-(R)-(3-(R)-formyl-4-(S)-(3-fluorophenyl)pyrrolidin-1-yl)-3-(cyclopropyl)propanoic acid benzyl ester using a procedure as described in EXAMPLE 35 Step C. $^1$H NMR (500 MHz, CD$_3$OD). δ 0.5 (d, 2H), 0.8–0.85 (m, 1H), 1.07–2.03 (5H), 1.43–1.5 (m, 2H), 1.58–1.71 (m, 3H), 1.83–1.93 (m, 2H), 2.02–2.08 (m, 1H), 2.38–2.41 (dd, 1H), 2.52–2.59 (m, 3H), 2.7–2.81 (m, 2H), 2.90–2.95 (d, 1H), 3.1–3.2 (q, 1H), 3.3–3.4 (m, 2H), 3.57–3.65 (m, 3H), 3.8 (s, 3H), 6.4–6.44 (t, 1H), 6.55–6.6 (d, 1H), 6.99–7.05 (t, 1H), 7.13–7.2 (m, 2H), 7.3–7.4 (m, 1H1). ESI-MS, M/z; (M+H)=559.3 (obs), 559.31 (calc.).

EXAMPLE 172

α-(R)-(3-(S)-((4-(3-(4-fluorophenyl)-3,3-difluoroprop-1-yl) piperidin-1-yl)methyl)-4-(S)-(3-fluorophenyl)pyrrolidin-1-yl)-3-(R)-cyclobutylbutyric acid Step A: Cyclobutylacetic acid A solution of bromomethyl cyclobutane (26.5 grams, 178 mmol) and potassium cyanide (2.34 grams, 359 mmol) in 90 mL DMSO was heated to 50 C for 48 h. The mixture was diluted with ethyl acetate and washed with 1 N NaOH. The organic layer was dried and concentrated. The crude material was suspended in 6 N HCl and the mixture was refluxed overnight. The mixture was cooled and extracted with ether. The organic layer was dried over sodium sulfate and concentrated to afford 11.7 grams of product (25%) $^1$H NMR (400 MHz, CDCl$_3$). δ 1.5–1.6 (m, 2H), 1.63–1.8 (m, 2H), 1.95–2.05 (m, 2H), 2.25 (d, 2H), 2.45–2.6 (m, 1H).

Step B: (R)-N-cyclobutylacetyl-4-benzyloxazolidinone

A round bottom flask was charged with cyclobutyl acetic acid (6.8 grams, 59.8 mmol, from Step A) and 200 mL dry THF. The mixture was cooled to −78 C and triethylamine (10 mL, 71.8 mmol) was added. Pivaloyl chloride (8.1 mL, 65.8 mmol) was added and the mixture was warmed to 0° C. and stirred for 1.5 h. A separate flask was charged with R)-benzyloxazolidinone and 100 mL THF. The solution was cooled to −78 C and a solution of n-butyllithium (44.9 mL, 1.6 M in hexane, 71.8 mmol) was added dropwise via syringe. After warming to 0 C and stirring for 30 min this solution was added via cannula to the above flask contianing the mixed anhydride. The resulting mixture was warmed to room temperature and stirred for 2.5 h. EtOAc was added and the mixture was washed with water and sat'd NaCl. The organic portion was dried over sodium sulfate and concentrated. Flash chromatography (15/1 hexane/EtOAc) afforded 11 grams (67%) of the desired acyl oxazolidinone. $^1$H NMR (400 MHz, CDCl$_3$). δ 1.72–1.81 (m, 2H), 1.85–1.99 (m, 2H), 2.18–2.28 (m, 2H), 2.72–2.82 (m, 2H), 3.0–3.18 (m, 2H), 3.27–3.33 (dd, 1H), 4.154.23 (m, 2H), 4.634.7 (m, 1H), 7.18–7.38 (m, 5H).

Step C: N-((R)-2-cyclobutyl propionyl-(R)-4-benzyloxazolidinone (R)-N-cyclobutylacetyl-4-benzyloxazolidinone (11 grams, 40.2 mmol, from Step B) was dissolved in 200 mL dry THF. The solution was cooled to −78 C under a nitrogen atmosphere. A solution of lithium hexamethyldisilazide (48.2 mL, 1.0 M in THF, 48.2 mmol) was added and the mixture was stirred for 30 min. Iodomethane (3.75 mL, 60.3 mmol) was added and the mixture was gradually warmed to room temperature and quenched by adding water. The mixture was extracted with ethyl acetate and the organic portion was dried over sodium sulfate and concentrated. Flash chromatography (20/1 hexane/ethyl acetate) afforded 7.5 grams (65%) of the title compound. $^1$H NMR (400 MHz, CDCl$_3$) δ 1.16 (d, 3H), 1.62–1.93 (m, 4H), 2.02–2.16 (m, 2H), 2.58–2.7 (m, 11H), 2.75–2.82 (dd, 1H), 3.22–3.3 (dd, 1H), 3.7–3.8 (m, 1H), 4.174.23 (m, 2H), 4.684.73 (m, 1H), 7.2–7.4 (m, 5H).

Step D: N-Methyl-N-methoxy-(R)-2-cyclobutylpropionamide

A flask was charged with 60 mL THF, N-((R)-2-cyclobutyl)propionyl-(R)-4-benzyloxazolidinone (7.5 grams, 26.1 mmol, from Step C), and 32 mL water. The solution was cooled to 0 C and hydrogen peroxide (11.7 mL, 30%, 104 mmol) was added. Lithium hydroxide (1.25 grams, 52.2 mmol) was added and the mixture was stirred for 6 h at room temperature. The reaction was quenched with aqueous sodium sulfite and partitioned between water and methylene chloride. Sodium bicarbonate was added and the layers were separated. The aqueous layer was acidified with 2 N HCl and extracted with ether. The ether layers were combined and dried over sodium sulfate then concentrated to give 2.9 grams (87%) of the desired acid. The acid (2.9 grams, 18.7 mmol) was dissolved in 25 mL NMP and HBTU (17.7 grams, 46.8 mmol), HOBt (9.5 grams, 70.1 mmol) and diisopropylethylamine (16.3 mL, 93.5 mmol) was added. N-O-dimethylhydroxylamine hydrochloride (3.65 grams, 37.4 mmol) was added and the mixture was stirred for 5 h.

The mixture was then diluted with ether and washed with water and sat'd NaCl. The ether was removed to give a precipitate which was filtered off and washed with 1/1 ether/pentane. The ether/pentane washes were combined and concentrated. Flash chromatography (1/1 pentane/ether) afforded 2.62 grams (71%) of the desired amide. $^1$H NMR (400 MHz, CDCl$_3$). δ 1.05 (d, 3H), 1.62–1.93 (m, 4H), 1.98–2.12 (m, 2H), 2.5–2.3 (m, 1H), 3.18 (s, 3H), 3.72 (s, 3H).

Step E: 2(R)-Cyclobutylpropiophenone

A dry flask was charged with N-Methyl-N-methoxy-(R)-2-cyclobutylpropionamide (2.62 grams, 15.4 mmol, from Step D). The vessel was purged with nitrogen and 40 mL THF was added. The mixture was cooled to –10 C and a solution of phenyllithium (30 mL, 1.8 M, 53.9 mmol) was added. The solution was stirred for 1 h at –10 C then the reaction was quenched with sat'd ammonium chloride. The mixture was extracted with ethyl acetate and the organic portion was dried over sodium sulfate and concentrated. Flash chromatography (99/1 hexane/ethyl acetate) afforded 2.06 grams (70%) of the title compound. $^1$H NMR 400 MHz, CDCl$_3$). δ 1.13 (d, 3H), 1.59–1.7 (m, 1H), 1.73–2.0 (m, 5H), 2.05–2.15 (m, 1H), 2.6–2.7 (m, 1H), 3.43–3.53 (m, 1H), 7.44–7.5 (t, 2H), 7.55–7.6 (m, 1H), 7.97–8.0 (d, 2H).

Step F: 1-(R)phenyl-2-(R)-cyclobutyl propanol

A dry flask was charged with 25 mL THF and a solution of L-Selectride® (12.6 mL, 1 M in THF, 12.6 mmol) was added. The solution was cooled to –78 C and a solution of (R)-Cyclobutylpropiophenone (2.38 grams, 12.6 mmol, from Step E) in 5 mL THF was added. After stirring at –78 C for 1 h the was warmed to room temperature gradually overnight. Sat'd sodium bicarbonate was added and the mixture was extrated with ethyl acetate. The organic portion was washed with water and sat'd NaCl. The solvent was removed and the residue was dissolved in methanol (100 mL). Concentrated HCl (1 mL) was added and the mixture was stirred at 50 C for 15 hours. After removal of the solvent the product was purified by flash chromatography (100/1 hexane/ethyl acetate →20/1 hexane ethyl acetate) to afford 1.4 grams (58%/o) of product. $^1$H NMR (500 MHz, CDCl$_3$). δ 0.68 (d, 3H), 1.64–1.98 (m, 6H), 2.02–2.09 (m, 1H), 2.11–2.19 (m, 1H), 4.58 (d, 1H), 7.23–7.38 (m, 5H).

Step G: 1-(R)-phenyl-2(S)-cyclobutyl propyl acetate

A solution of (R)-1-phenyl-(R)-2-cyclobutyl propanol (1.12 grams, 5.9 mmol, from Step F), triphenylphosphine (3.86 grams, 14.7 mmol), and acetic acid (0.84 mL, 14.7 mmol) in 20 mL dry THF was cooled to –78 C. Diisopropylazodicarboxylate (2.9 mL, 14.7 mmol) was added and the mixture was warmed to room temperature over 1 hour and stirred for 30 min. The solvent was removed and the residue was suspended in 95/5 hexane/ethyl acetate and filtered through a plug of silica eluting until all product had come through (to remove triphenylphosphine oxide). After removal of the solvent the product was purified by flash chromatography (99/1 hexane/ethyl acetate) to give 0.86 grams (67%) of the title compound. $^1$H NMR (500 MHz, CDCl$_3$). δ 0.81 (d, 3H), 1.59–2.0 (m, 7H), 2.1 (s, 3H), 2.1–2.2 (m, 1H), 5.68 (d, 1H), 7.23–7.31 (m, 3H), 7.36–7.38 (m, 2H).

Step H: Benzyl-(2S)-hydroxy-(3R)-cyclobutyl butyrate

A solution of (R)-1-phenyl-(S)-2-cyclobutyl propyl acetate (0.98 grams, 4.49 mmol, from Step G), periodic acid (14.3 grams, 62.9 mmol) in 21 mL 1/1/1 CCl4/acetonitrile/water was heated to 32 C. Ruthenium trichloride (47 mg, 0.22 mmol) was added in three portions over 5 h. The mixture was cooled to 0 C, diluted with ethyl acetate and stirred for 20 min. The layers were separated and the organic portion was washed with water and sat'd sodium chloride then dried over sodium sulfate and concentrated. The residue was dissolved in 30 mL of methanol and 6 mL water. Potassium carbonate (2.5 grams, 18 mmol) was added and the mixture was stirred at 50 C overnight. The mixture was diluted with ether and the layers were separated. The aqueous layer was acidified with HCl and extracted with ethyl acetate (3×). The ethyl acetate portions were combined, dried over sodium sulfate and concentrated. The crude hydroxyacid was dissolved in 2 mL DMF and triethyl amine (1 mL, 7.2 mmol) was added. Benzyl bromide (0.86 mL, 7.2 mmol) was added and the mixture was stirred overnight. Ethyl acetate was added and the mixture was washed with water and sat'd sodium chloride. The organic portion was dried over sodium sulfate and concentrated Flash chromatography (99/1→97/3 hexane/ethyl acetate) afforded 0.41 grams (37%) of the title compound. $^1$H NMR (500 MHz, CDCl$_3$). δ 0.86 (d, 3H), 1.6–1.7 (m, 1H), 1.71–1.78 (m, 2H), 1.81–1.9 (m, 2H), 2.01–2.11 (m, 2H), 2.32–2.41 (m, 1H), 2.62 (bs, 1H), 4.2 (s, 1H), 5.22 (dd, 2H), 7.33–7.41 (m,5H).

Step I: 2-(R)-(3-(R)-Formyl-4-(S)-(3-fluorophenyl)pyrrolidin-1-yl)-3-(R)-cyclobutylbutyric acid, benzyl ester The title compound was prepared in a manner analogous to that described in EXAMPLE 169 Steps B–D from Benzyl-(2S)-hydroxy-(3R)-cyclobutyl butyrate (from Step H) and except that dichloromethane as used in place of DMF in the triflate displacement step (EXAMPLE Step C). $^1$H NMR (500 MHz, CDCl$_3$). δ 0.86 (d, 3H), 1.6–2.05 (m, 9H), 2.16–2.23 (m, 1H), 2.61–2.7 (t, 1H), 2.92–2.98 (m, 1H), 3.08–3.17 (m, 2H), 3.2–3.23 (t, 1H), 3.52–3.6 (q, 1H), 5.19 (s, 2H), 6.88–7.02 (m, 3H), 7.21–7.26 (m, 1H), 7.31–7.41 (m, 5H) 9.65 (s, 1H).

Step J: α-(R)(3-(S)-((4-(3-(4-fluorophenyl)-3,3-difluoroprop-1-yl)piperidin-1-yl)methyl)-4-(S)-(3-fluorophenyl)pyrrolidin-1-yl)-3-(R)-cyclobutylbutyric acid The title compound was prepared from 2-(R)-(3-(R)-Formyl-4-(S)-(3-fluorophenyl)pyrrolidin-1-yl)-3-R)-cyclobutylbutyric acid, benzyl ester (20 mg, 0.047 mmol) and 4-(3-(4-fluorophenyl)-3,34difluoroprop-1-yl)piperidine (16 mg, 0.06 mmol, from EXAMPLE 155 Step H ) using the procedure described in EXAMPLE 35 Step C. $^1$H NMR (500 Mz, CDCl$_3$). δ 0.80 (d, 3H), 1.2–3.55 (30H), 6.9–6.98 (t, 1H), 6.98–7.02 (d, 1H), 7.03–7.14 (m, 3H), 7.22–7.28 (m, 1H), 7.39–7.42 (m, 2H). ESI-MS, M/z; (M+H)=575.6 (obs), 575.3 (calc.).

EXAMPLES 173–175

Examples 173–175 in Table 6 were prepared using procedures analogous to those described in Example 172.

TABLE 6

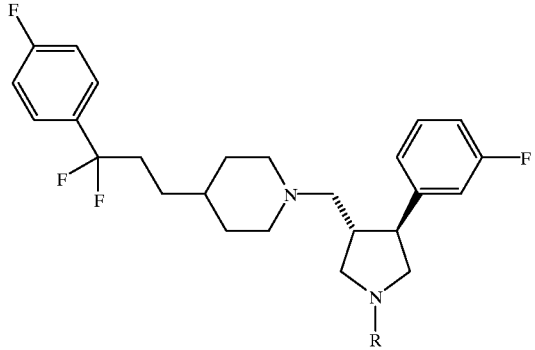

| EXAMPLE # | R | ESI-MS M/z (M + H) |
|---|---|---|
| 173 | (structure with CO₂H, cyclobutyl) | 575.6 |
| 174 | (structure with CO₂H, cyclobutyl) | 575.6 |
| 175 | (structure with CO₂H, cyclobutyl) | 575.6 |

EXAMPLE 176

2-(R)-(3-(S)-((3-(4-Fluorophenyl)-3-oxo-2,2-difluoropropyl)piperidin-1-yl)methyl)-4-(S)-(3-fluorophenyl)pyrrolidin-1-yl)-3-(cyclopropyl)propanoic acid Step A: Ethyl 3-(1-(t-butoxycarbonyl)-piperidin-4-yl)-3-hydroxy-2,2-difluoropropionate A suspension of 4.38 g (67.0 mmol) of Zn powder in 40 mL of THF was treated with 0.58 mL (6.7 mmol) of 1,2-dibromoethane. The resulting mixture was heated at reflux for 2 min, then cooled to rt. Trimethylsilyl chloride (0.43 mL 3.4 mmol) was then added, the resulting mixture was stirred at ambient temperature for 20 min, the cooled to −5° C. A solution of 2.88 g (13.4 mmol) of 1-(t-butoxycarbonyl)-4-formyl piperidine and 9.52 g (46.9 mmol) of ethyl bromodifluoroacetate in 10 mL of THF was gradually added to the activated Zn. After the resulting exotherm subsided, the cooling bath was removed and the resulting mixture was stirred at rt for 20 h. The reaction was quenched with 50 mL of sat'd NH₄Cl and the resulting mixture was partitioned between 300 mL of ether and 100 mL of H₂O. The organic layer was separated, washed with 50 mL of sat'd NaHCO₃, 50 mL of sat'd NaCl, dried and concentrated. Flash chromatography on 200 g of silica gel using 4:1 v/v, then 2:1 v/v hexanes/EtOAc as the eluants afforded 2.25 g (52%) of the title compound as an oil: ¹H NMR (500 MHz, CDCl₃) δ 1.31–1.34 (m, 1H), 1.37 (t, J=7.0, 3H), 1.45 (s, 9H), 1.69–1.72 (m, 2H), 1.86–1.92 (m, 2H), 2.40 (d, J=7.0, 1H), 2.68–2.72 (m, 2H), 3.83–3.90 (m, 1H), 4.104.20 (m, 2H), 4.36 (q, J=7.0, 2H).

Step B: Ethyl 3-(1-(t-butoxycarbonyl)-piperidin-4-yl)-2,2-difluoropropionate

A solution of 2.25 g (6.7 mmol) of ethyl 3-(1-(t-butoxycarbonyl)-piperidin-4-yl)-3-hydroxy-2,2-difluoropropionate (from EXAMPLE 176, Step A) and 2.50 g (20.5 mmol) of 4-(N,N-dimethylamino)pyridine in 40 mL of CH₂Cl₂ at 0° C. was treated with 1.10 mL (12.0 mmol) of methyl chlorooxoacetate. The resulting mixture was warmed to rt, stirred for 1 h, then quenched with 100 mL of 0.5 N KHSO₄. The quenched mixture was extracted with 250 mL of EtOAc; the extract was dried and concentrated. The crude oxalate ester, 3.70 mL (12.0 mmol) of tris(trimethylsilyl)silane and 500 mg (3.0 mmol) of 2,2'-azobisisobutyronitrile in 20 mL of toluene was heated at reflux under an Ar atmosphere for 1.5 h. The reaction mixture was cooled and concentrated. Flash chromatography on 75 g of silica gel using 10:1 v/v, then 4:1 v/v hexanes/ether as the eluants afforded 922 mg (43%) of the title compound as an oil: ¹H NMR (500 MHz, CDCl₃) δ 1.16–1.25 (m, 2H), 1.36 (t, J=7.0, 3I), 1.46 (s, 9H), 1.74 (app d, J=15.0, 2H), 1.75–1.81 (m, 1H), 2.02 (dt, J=6.0, 18.0,22H), 2.68–2.73 (m, 2H), 4.05–4.09 (m, 2H), 4.33 (q, J=7.0, 2H).

Step C: 4-(3-(4-Fluorophenyl)-3-oxo-2,2-difluoropropyl)-1-(t-butoxycarbonyl)piperidine A solution of 0.35 mL (3.0 mmol) of 1-fluoro-4-iodobenzene in 8 mL of ether at −78° C. was treated with 3.7 mL of 1.7 M t-butyllithium soln in pentane.

The resulting solution was stirred cold for 30 min, then added via cannula to a solution of 550 mg (1.7 mmol) of ethyl 3-(1-(t-butoxycarbonyl)-piperidin-4-yl)-2,2-difluoropropionate (from EXAMPLE 176, Step B) in 8 mL of ether at −78° C. The resulting mixture was stirred cold for 15 min, then quenched with 15 mL of sat'd NH₄Cl. The resulting mixture was partitioned between 75 mL of ether and 25 mL of H₂O and the layers were separated. The organic layer was washed with 25 mL of sat'd NaHCO₃, 25 mL of sat'd NaCl, dried and concentrated. Flash chromatography on 40 g of silica gel using 10:1 v/v hexanes/ether afforded 602 mg (95%) of the title compound as an oil: ¹H NMR (500 MHz, CDCl₃) δ 1.20–1.29 (m, 2H), 1.46 (s, 9H), 1.79 (app d, J=16.5, 2H), 1.85–1.91 (m, 1H), 2.14 (dt, J=8.0, 23.5, 2H), 2.72 (app t, J=11.5, 2H), 4.05–4.09 (m, 2H) 7.15–7.20 (m, 2H), 8.13–8.17 (m, 2H).

Step D: 2-(R)-(3-(S)-((3-(4-Fluorophenyl)-3-oxo-2,2-difluoropropyl)piperidin-1-yl)methyl)-4-(S)-(3-fluorophenyl)pyrrolidin-1-yl))-3-(cyclopropyl) propanoic acid A solution of 50 mg (0.13 mmol) of 4-(3-(4-fluorophenyl)-3-oxo-2,2-difluoropropyl)-1-(t-butoxycarbonyl)piperidine (from EXAMPLE 176, Step C) in 3 mL of CH₂Cl₂ at 0° C. was treated with 3 mL of TEA. The resulting mixture was stirred cold and concentrated. The crude piperidine TEA was salt was converted to the title compound using procedures analogous to those described in EXAMPLE 21, Steps F and G: ESI-MS 561 (M+H); HPLC A: 2.64 min.

EXAMPLE 177

2-(R)-(3-(S)-((3-(4-Fluorophenyl)-3-(RS)-hydroxy-2,2-difluoropropyl)piperidin-1-yl)methyl)-4-(S)-(3-fluorophenyl)pyrrolidin-1-yl))-3-(cyclopropyl)propanoic acid Step A: 4-(3-(4-Fluorophenyl-3-(RS)-hydroxy-2,2difluoropropyl)-1-(t-butoxycarbonyl)piperidine A solution of 186 mg (0.5 mmol) of 4-(3-(4-fluorophenyl)-3-oxo-2,2-difluoropropyl)-1-(t-butoxycarbonyl)piperidine (from EXAMPLE 176, Step C) in 4 mL of MeOH at 0° C. was treated with 38 mg (1.0 mmol) of NaBH₄ and stirred cold for 20 min. The reaction was quenched with 10 mL of 1.0 N NaOH and the quenched mixture was extracted with 2×50 mL of ether. The extracts were dried, combined and concentrated. Flash chromatography on 10 g of silica gel using 3:1 v/v hexanes/ether as the eluant afforded 162 mg of the title compound: $^1$H NMR (500 MHz, CDCl$_3$) δ 1.07–1.15 (m, 2H), 1.43 (s, 9H), 1.71 (app t, J=13.5, 2H), 1.81–1.85 (m, 1H), 2.58 (d, J=3.0, 1H), 2.64–2.72 (m, 2H), 3.96–4.08 (m, 2H), 4.82 (dt, J=3.0, 10.0, 1H), 7.05–7.08 (m, 2H), 7.40–7.43 (m, 2H).

Step B: 2-(R)-(3-(S)-((3-(4-Fluorophenyl)-3-(RS)-hydroxy-2,2-difluoropropyl)piperidin-1-yl)methyl)-4-(S)-(3-fluorophenyl)pyrrolidin-1-yl))-3-(cyclopropyl)propanoic acid The title compound was prepared from 4-(3-(4-fluorophenyl)-3-(RS)-hydroxy-2,2-difluoropropyl)-1-(t-butoxycarbonyl)piperidine (from EXAMPLE 177, Step A) using procedures analogous to those described in EXAMPLE 176, Step D: ESI-MS 563 (M+H); HPLC A: 2.29 min.

EXAMPLE 178
2-(R)-(3-(S)-((3-(4-Fluorophenyl)-2,2difluoropropyl)piperidin-1-yl)methyl)-4-(S)-(3-fluorophenyl)pyrrolidin-1-yl))-3-(cyclopropyl)propanoic acid Step A: 4-(3-(4-Fluorophenyl)-2,2-difluoropropyl-1)-1-(t-butoxycarbonyl)piperidine The title compound was prepared from 4-(3-(4fluorophenyl)-3-(RS)-hydroxy-2,2-difluoropropyl)-1-(t-butoxycarbonyl)piperidine (from EXAMPLE 177, Step A) using a procedure analogous to that described in EXAMPLE 176, Step B: $^1$H NMR (500 MHz, CDCl$_3$) δ 1.10–1.18 (m, 21), 1.43 (s, 91), 1.57–1.72 (41), 1.80–1.85 (m, 1H), 2.65–2.75 (m, 21), 3.10 (t, J=16.0, 2H), 3.98–4.08 (m, 2H), 6.99–7.03 (m, 2H), 7.19–7.22 (m, 2H).

Step B: 2-(R)-(3-(S)-((3-(4-Fluorophenyl)-2,2-difluoropropyl)piperidin-1-yl)methyl)-4-(S)-(3-fluorophenyl)pyrrolidin-1-yl))-3-(cyclopropyl)propanoic acid The title compound was prepared from 4-(3-(4-fluorophenyl)-2,2-difluoropropyl)-1-(t-butoxycarbonylpiperidine (from EXAMPLE 178, Step A) using procedures analogous to those described in EXAMPLE 176, Step D: ESI-MS 547 (M+H); HPLC A: 2.53 min.

EXAMPLES 179–187

The following compounds were prepared procedures described in EXAMPLES 176, 177, and 178 substituting the appropriate aryl halide in EXAMPLE 176, Step C and the appropriate pyrrolidine aldehyde intermediate in EXAMPLE 178, Step B. In cases where the pyrrolidine aldehyde intermediates were protected as benzyl esters, the final deprotection was carried out using catalytic hydrogenation (1 atm H$_2$, 10% Pd/C, MeOH).

| EXAMPLE | R1 | R2 | ESI MS (M + H) | HPLC A |
|---|---|---|---|---|
| 179 | —F | cyclobutyl-CH$_2$- | 561 | 2.75 |
| 180 | —CN | cyclopropyl-CH$_2$- | 554 | 2.32 |
| 181 | —CN | t-Bu-CH$_2$- | 556 | 2.35 |
| 182 | —SO$_2$CH$_3$ | t-Bu-CH$_2$- | 609 | 2.11 |
| 183 | —SO$_2$CH$_3$ | cyclopropyl-CH$_2$- | 607 | 2.08 |
| 184 | —CF$_3$ | cyclopropyl-CH$_2$- | 597 | |

-continued

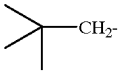

| EXAMPLE | R1 | R2 | ESI MS (M + H) | HPLC A |
|---|---|---|---|---|
| 185 | —CF₃ | 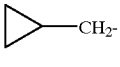—CH₂- | 599 | |
| 186 | —OCF₃ | —CH₂- | 613 | 2.77 |
| 187 | —OCF₃ | —CH₂- | 615 | |

EXAMPLE 188
2-(R)-(3-(S)-((3-(4-Fluorophenyl)-3-(RS)-hydroxypropyl) piperidin-1-yl)methyl)-4-(S)-(3-fluorophenyl)pyrrolidin-1-yl))-3-(cyclopropyl)propanoic acid
Step A: N-Methoxy-N-methyl-3-(1-(t-butoxycarbonyl) piperidin-4-yl)propionamide A mixture of 1.29 g (5.0 mmol) of 3-(1-(t-butoxycarbonyl)piperidin-4-yl)propionamide (from EXAMPLE 98, Step B) and 1.65 mL (15.0 mmol) of 4-methylmorpholine in 25 mL of CH₂Cl₂ at 0° C. was treated with 0.70 mL of isobutyl chloroformate. The resulting mixture was stirred cold for 15 min, then treated with 0.78 g (8.0 mmol) of O,N-dimethylhydroxylamine×HCl. The resulting mixture was stirred cold for 3.5 h, quenched with 100 mL of 0.5 N KHSO₄, then extracted with 200 mL of ether. The extract was washed with 100 mL of 1.0 N NaOH, 50 mL of sat'd NaCM, dried and concentrated. Flash chromatography on 60 g of silica gel using 10:1 v/v, then 3:1 v/v CH₂Cl₂/EtOAc as the eluant afforded 1.31 g (91%) of the title compound: ¹H NMR (300 MHz, CDCl₃) δ 1.07–1.18 (m, 2H), 1.38–1.69 (5H), 1.45 (s, 9H), 2.45 (t, J=7.6, 2H), 2.68 (app t, J=12.4, 2H), 3.18 (s, 3H), 3.69 (s, 3H), 4.05–4.11 (m, 2H).
Step B: 4-(3-(4-Fluorophenyl)-3-(RS)-hydroxypropyl)-1-(t-butoxycarbonyl) piperdine A solution of 1.30 g (4.5 mmol) of N-methoxy-N-methyl-3-(1-(t-butoxycarbonyl)piperidin-4-yl)propionamide (from EXAMPLE 188, Step A) in 25 (of THF at 0° C. was treated with 3.0 mL of 2.0 M (4-fluoro)phenylmagnesium bromide in ether and stirred cold for 1 h. The reaction was quenched with 100 mL of 0.5 N HCl and extracted with 150 mL of ether. The extract was washed with 50 mL of sat'd NaCl, dried and concentrated. The crude ketone in 10 mL of MeOH at 0° C. was treated with 110 mg (2.2 mmol) of NaBH₄ and the resulting mixture was stirred cold for 30 min. The reaction was quenched with 5 mL of 1.0 N NAOH. The quenched mixture was partitioned between 100 mL of ether and 25 m of H₂O and the layers were separated. The organic layer was dried; the aqueous layer was extracted with 100 mL of ether, the extract dried and the organic layers combined and concentrated. Flash chromatography on 40 g of silica gel using 3:2 v/v hexanes/ether as the eluant afforded 566 mg (37%) of the title compound.
Step C: 4-(3-(4-Fluorophenyl)-3-(RS)-hydroxypropyl)-piperidine A solution of 117 mg (0.35 mmol) of 4-(3-(4-fluorophenyl)-3-(RS-hydroxypropyl)-1-(t-butoxycarbonyl) piperidine (from EXAMPLE 188, Step B) in 4 mL of 1.0 M HCl in MeOH was stirred at rt for 20 h. The solution was concentrated. Flash chromatography on 5 g of silica gel using 90:10:1 v/v/v CH₂Cl₂/MeOH/NH₄OH as the eluant aforded 50 mg (52%) of the title compound.
Step D: 2-(R)-(3-(S)-((3-(4-Fluorophenyl)-3-(RS)-hydroxypropyl)piperidin-1-yl)methyl)-4-(S)-(3-fluorophenyl)pyrrolidin-1-yl))-3-(cyclopropyl) propanoic acid The title compound was prepared from 4-(3-(4-fluorophenyl)--3-(RS)-hydroxypropyl)-piperidine (from EXAMPLE 188, Step C) and 2-(R)-(3-(R)-formyl-4 (S)-(3-fluorophenyl)pyrrolidin-1-yl)-3-(cyclopropyl)propanoic acid, 4-(methoxy)benzyl ester (from EXAMPLE 21, Step E) using procedures analogous to those described in EXAMPLE 21, Step F and EXAMPLE 1, Step K: ESI-MS 527 (M+H); HPLC A: 2.77 min.

EXAMPLE 189
2-(R)-(3-(S)-((3-(4-Fluorophenyl)-3-(RS)-hydroxy-3-(R/S)-methylpropyl)piperidin-1-yl)methyl)-4-(S)-(3-fluorophenyl)pyrrolidin-1-yl))-3-(cyclopropyl)propanoic acid Step A: 4-(3-(4-Fluorophenyl)-3-oxo-propyl)-1-(t-butoxycarbonyl) piperidine A mixture of 500 mg (1.5 mmol) of 4-(3-(4-fluorophenyl)-3-(RS)-hydroxypropyl)-1-(t-butoxycarbonyl) piperidine (from EXAMPLE 188, Step B), 351 mg (3.0 mmol) of 4-(methyl)morpholine and 800 mg of 4 Å molecular sieves in 10 _mL of $CH_2Cl_2$ at 0° C. was treated with 35 mg (0.1 mmol) of tetrapropylammonium perruthenate. The cooling bath was removed and the mixture was stirred at rt for 1 h. The mixture was filtered and the filtrate was concentrated. Flash chromatography on 15 g of silica gel using 3:1 v/v hexanes/ether afforded 386 mg (78%) of the title compound: $^1$H NMR (500 MHz, $CDCl_3$) δ 1.10–1.19 (m, 2H), 1.43–1.49 (m, 1H), 1.45 (s, 9H), 1.58–1.70 (4H), 2.65–2.70 (m, 2H), 2.70 (t, J=7.5, 2H), 4.054.1 1 (m, 2H), 7.11–7.15 (m, 21), 7.97–8.00 (m, 2H).

Step B: 4-(3-(4-Fluorophenyl)-3-oxo-propyl)-1-(benzyloxycarbonyl) piperidine

A solution of 188 mg (0.56 mmol) of 4-(3-(4-fluorophenyl)-3-oxo-propyl)-1-(t-butoxycarbonyl) piperidine (from EXAMPLE 189, Step A) in 5 mL of $CH_2Cl_2$ at 0° C. was treated with 3 mL of TFA and the resulting mixture was stirred cold for 30 min. The solution was concentrated. A solution of the crude piperidine in 5 mL THF/5 mL of 1.0 N NaOH at 0° C. was treated with 0.09 mL (0.63 mmol) of benzyl chloroformate and the resulting mixture was stirred cold for 30 min. The reaction mixture was partitioned between 50 mL of ether and 10 mL of $H_2O$ and the layers were separated. The organic layer was washed with 10 mL of sat'd NaCl, dried and concentrated. Flash chromatography on 10 g of silica gel using 2:1 v/v hexanes/ether as the eluant afforded 196 mg (95%) of the title compound: $^1$H NMR (500 MHz, $CDCl_3$) δ 1.10–1.20 (m, 21), 1.43–1.53 (m, 1H), 1.60–1.71 (4H), 2.72–2.82 (m, 2H), 2.97 (t, J=7.5, 21), 4.154.21 (m, 2H), 5.12 (s, 2H), 7.11–7.15 (m, 2H), 7.26–7.36 (5H), 7.96–8.00 (m, 2H).

Step C: 4-(3-(4-Fluorophenyl)-3-(RS)-hydroxy-3-(RS)methylpropyl)-1-(benzyloxycarbonyl) piperidine 4-(3-(4-Fluorophenyl)-3-oxo-propyl)-1-(benzyloxycarbonyl) piperidine (from EXAMPLE 189, Step B) was added as a solid to a solution of 2.0 mL of 1.5 M MeMgBr in THF at 0° C. and the resulting mixture was stirred cold for 30 min. The reaction was quenched with 5 mL of sat'd NHCl and the quenched mixture was partitioned between 30 mL of ether and 5 mL of $H_2O$. The organic layer was separated, dried and concentrated. Flash chromatography on 4 g of silica gel using 3:2 v/v hexanes/ether as the eluant afforded 61 mg (81%) of the title compound.

Step D: 4-(3-(4-Fluorophenyl)-3-(RS)-hydroxy-3-(RS)methylpropyl)piperidine

A mixture of 61 mg (0.16 mmol) of 4-(3-(4-fluorophenyl)-3-(RS)-hydroxy-3-(RS)methylpropyl)-1-(benzyloxycarbonyl)piperidine (from EXAMPLE 189, Step C) and 10 mg of 10% Pd/C in 6 mL of MeOH was stirred under an atmosphere of hydrogen for 30 min. The reaction mixture was filtered and the filtrate concentrated to afford 40 mg (100%) of the title compound: ESI-MS 252 (M+H); HPLC A: 1.76 min.

Step E: 2-(R)-(3-(S)-((3-(4-Fluorophenyl)-3-(RS)-hydroxy-3-(RS)-methylpropyl) piperidin-1-yl)methyl)-4-(S)-(3-fluorophenyl)pyrrolidin-1-yl))-3-(cyclopropyl)propanoic acid The title compound was prepared from 4-(3-(4-fluorophenyl)-3-(RS)-hydroxy-3-(RS)methylpropyl) piperidine (from EXAMPLE 189, Step D) and and 2-(R)-(3-(R)-formyl-4-(S)-(3-fluorophenyl)pyrrolidin-1-yl)-3-(cyclopropyl)propanoic acid, 4-(methoxy)benzyl ester (from EXAMPLE 21, Step E) using procedures analogous to those described in EXAMPLE 21, Step F and EXAMPLE 1, Step K: ESI-MS 541 (M+H); HPLC A: 2.32 min.

EXAMPLE 190

2-(R)-(3-(S)-((3-(4-Fluorophenyl)-3,3-(ethylenedioxy)propyl)piperidin-1-yl)methyl)-4-(S)-(3-fluorophenyl)pyrrolidin-1-yl))-3-(cycloyropyl)propanoic acid Step A: 4-(3-(4-Fluorophenyl)-3,3-(ethylenedioxy)propyl)-1-(benzyloxycarbonyl) piperidine A solution of 71 mg (0.19 mmol) of 4-(3-(4-fluorophenyl)-3-oxo-propyl)-1-(benzyloxycarbonyl) piperidine (from EXAMPLE 189, Step B), 0.05 mL (0.9 mmol) of ethylene glycol and 5 mg (0.26 mmol) of p-toluene sulfonic acid x $H_2O$ in 3 mL of toluene was heated at 80° C. After 1 h, and additional 5 mg of p-toluene sulfonic acid×$H_2O$ was added and the resulting mixture was heated at reflux. After 2 h, the mixture was cooled and partitioned between 30 mL of ether and 10 mL of 1.0 N NaOH. The organic layer was separated, dried and concentrated. Flash chromatography on 4 g of silica gel using 3:1 v/v hexanes/ether afforded 66 mg of the title compound: $^1$H NMR (500 MHz, $CDCl_3$) δ 1.00–1.10 (m, 2H), 1.261.36 (3H), 1.50–1.60 (m, 2H), 1.86–1.89 (m, 2H), 2.65–2.75 (m, 2H), 3.71–3.78 (m, 2H), 3.96–4.03 (m, 2H), 4.064.16 (m, 2H), 5.10 (s, 2H), 6.99–7.04 (m, 2H), 7.26–7.40 (7H).

Step B: 2-(R)-(3-(S((3-(4-Fluorophenyl)-3,3-(ethylenedioxy)propyl)piperidin-1-yl)methyl)-4-(S)-(3-fluorophenyl)pyrrolidin-1-yl))-3-(cyclopropyl) propanoic acid The title compound was prepared from 4-(3-(4-fluorophenyl)-3,3-(ethylenedioxy)propyl)-1-(benzyloxycarbonyl) piperidine (from EXAMPLE 190, Step A) using procedures analogous to those described in EXAMPLE 189, Steps D and E: ESI-MS 569 (M+H); HPLC A: 2.56 min.

EXAMPLES 191–197

The following compounds were prepared using procedures analogous to those described in EXAMPLE 74 and substituting the appropriate heteroaryl halide in Step C and the appropriate pyrrolidine aldehyde intermediate in Step F. In cases where the pyrrolidine aldehyde intermediates were preotected as (4-methoxy)benzyl esters, the final deprotection was carried out using acid hydrolysis (96% HCOOH, rt).

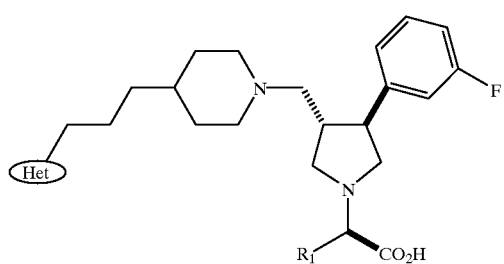
| EXAMPLE | Het | R₁ | ESI MS (M + H) | HPLC A |
|---|---|---|---|---|
| 191 | 6-methylpyridazin-3-yl | cyclobutyl-CH₂— | 505 | 2.21 |
| 192 | 5-fluoropyrimidin-2-yl | cyclopropyl-CH₂— | 513 | 2.56 |
| 193 | 5-fluoropyridin-2-yl | cyclopropyl-CH₂— | 512 | 1.84 |
| 194 | 5-methylpyrazin-2-yl | cyclopropyl-CH₂— | 505 | |
| 195 | 6-trifluoromethylpyridin-3-yl | cyclopropyl-CH₂— | 548 | |
| 196 | 1-methylimidazol-2-yl | cyclopropyl-CH₂— | 483 | |
| 197 | 2-trifluoromethylpyrimidin-5-yl | cyclopropyl-CH₂— | 549 | |

EXAMPLE 198

2R)-(3-(R)-((4-(3,3-Difluoro-3-(4-fluorophenyl)propyl)piperidin-1-yl)methyl)-4-(S)(3-fluorophenyl)pyrrolidin-1-yl)-3-(cyclobutyl)propanoic acid

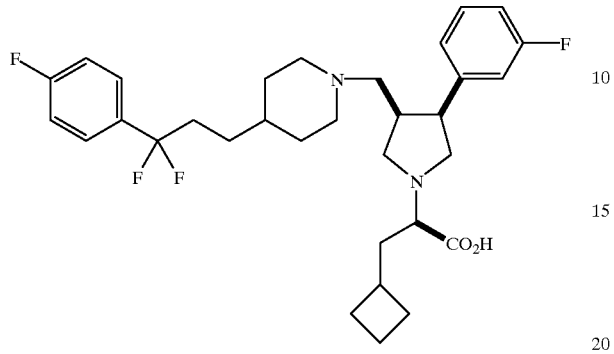

Step A: 2-(R)-(3-(R)-((4-(3,3-difluoro-3-(4-fluorophenyl)propyl)piperidin-1-yl)methyl)-4-(S)-(3-fluorophenyl)pyrrolidin-1-yl)-3-(cyclobutyl)propanoic acid benzyl ester The title compound was a by-product (29 mg) isolated from the HPLC purification described in EXAMPLE 155, Step J. For the title compound: $^1$H NMR (500 MHz, CD$_3$OD) δ 7.50 (dd, J=9,6, 2H), 7.40 (d, J=8, 2H), 7.38–7.28 (m, 3H), 7.23 (td, J=8, 6, 1H), 7.16 (t, J=9, 2H), 7.08–7.01 (m, 2H), 6.90 (td, J=9, 2, 1H), 5.19 (d, J=12, 1H), 5.16 (d, J=12, 1H), 3.38 (bq, J=7, 1H), 3.22 (dd, J=9,7, 1H), 3.00 (dd, J=9, 8, 1H), 2.82 (dd, J=10, 6, 1H), 2.50 (dd, J=10, 8, 1H), 2.67–2.54 (m, 3H), 2.34 (septet, J=8, 1H), 2.19–1.98 (m, 4H), 1.92–1.74 (m, 7H), 1.70–1.59 (m, 3H), 1.59–1.52 (m, 1H), 1.30–1.23 (m, 2H), 1.19–0.99 (m, 3H).

Step B: 2-(R)-(3-(R)-((4-(3,3-difluoro-3-(4-fluorophenyl)propyl)piperidin-1-yl)methyl)-4-(S)-(3-fluorophenyl)pyrrolidin-1-yl)-3-(cyclobutyl)propanoic acid The title compound was prepared using procedures analogous to those described in EXAMPLE 155, Step J, substituting 2-(R)-(3-(R)-((4-(3,3-difluoro-3-(4-fluorophenyl)propyl)piperidin-1-yl methyl)-4-(S)-(3-fluorophenyl)pyrrolidin-1-yl)-3-(cyclobutyl)propanoic acid benzyl ester (from EXAMPLE 198, Step A) for 2-(R)-(3-(S)-((4-(3,3-difluoro-3-(4-fluorophenyl)propyl)piperidin-1-yl)methyl)-4-(S)-(3-fluorophenyl)pyrrolidin-1-yl)-3-(cyclobutyl) propanoic acid benzyl ester. For the title compound: $^1$H NMR (500 MHz, CD$_3$OD) δ 7.49 (dd, J=9, 6, 2H), 7.35 (td, J=8, 6, 1H), 7.16 (t, J=9,22H), 7.11–7.06 (m, 2H), 7.00 (td, J=9,2, 1H), 3.76 (q, J=8, 1H), 3.72–3.62 (m, 2H), 3.44 (t, J=10, 1H), 3.36 (dd, J=9, 6, 11H), 3.21 (dd, J=11, 7, 1H), 2.92–2.73 (m, 3H), 2.50 (septet, J=8, 1H), 2.22–2.06 (m, 5H), 2.02–1.67 (m, 9H), 1.60 (bd, J=12, 2H), 1.31–1.01 (m, 5H); ESI-MS 561 (M+H); HPLC A: 2.64 min.

EXAMPLE 199

2-(R)-(3-(S)-((4-(3,3-Difluoro-3-(4-fluorophenyl)propyl)piperidin-1-yl)methyl)-4-(S)-(3-thienyl)-pyrrolidin-1-yl)-3-(cyclobutyl)propanoic acid

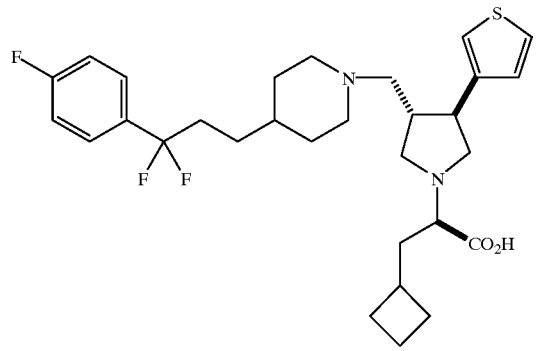

Step A: 2-(R)-(3-(S)-((4-(3,3-Difluoro-3-(4fluorophenyl)propyl)piperidin-1-yl)methyl)(S)-(3-thienyl)pyrrolidin-1-yl)-3-(cyclobutyl)propanoic acid (4-methoxy)benzyl ester The title compound was prepared using procedures analogous to those described in EXAMPLE 155, Step I, substituting 2-(R)-(3-(R)-formyl-4-(S)-(3-thienyl)pyrrolidin-1-yl)-3-(cyclobutyl)propanoic acid (4-methoxy)benzyl ester (from EXAMPLE 87, Step F) for 2-(R)-(3-(R)-formyl-4-(S)-(3-fluorophenyl)pyrrolidin-1-yl)-3-(cyclobutyl)propanoic acid benzyl ester. For the title compound: $^1$H NMR (500 MHz, CD$_3$OD) δ 7.50 (dd, J=9, 5, 2H), 7.34 (d, J=8, 2H), 7.30 (dd, J=5, 3, 1H), 7.16 (t, J=9, 2H), 7.04–7.00 (m, 1H), 6.93 (dd, J=5, 1, 1H), 6.90 (d, J=8, 2H), 5.12 (d, J=12, 1H), 5.09 (d, J=12, 1H), 3.78 (s, 3H), 3.14 (dd, J=9, 6, 1H), 3.10–3.02 (m, 2H), 2.90 (bq, J=8, 1H), 2.79 (bd, J=11, 1H), 2.65 (bd, J=11, 1H), 2.58 (t, J=9, 11H), 2.52 (dd, J 9, 6, 11H), 2.35–2.21 (m, 4H), 2.20–2.07 (m, 2H), 2.07–1.94 (m, 2H), 1.88–1.70 (m, 6H), 1.68–1.53 (m, 4H), 1.31–1.24 (m, 2H), 1.23–1.05 (m, 3H); ESI-MS 669 (M+H); HPLC A: 3.43 min.

Step B: 2-(R)-(3-(S)-((4-(3,3-Difluoro-3-(4-fluorophenyl)propyl)piperidin-1-yl)methyl)-4-(S)-(3-thienyl)pyrrolidin-1-yl)-3-(cyclobutyl)propanoic acid A solution of 2-(R)-(3-(S)-((4-(3,3-difluoro-3-(4-fluorophenyl)propyl)piperidin-1-yl)methyl)-4-(S)-(3-thienyl)pyrrolidin-1-yl)-3-(cyclobutyl)propanoic acid (4-methoxy)benzyl ester (24.1 mg, 0.036 mmol, from EXAMPLE 199, Step A) dissolved in 2.0 mL of 96% formic acid was stirred at RT for 8 h. The solution was evaporated, toluene (5 mL) was added to the residue, and the mixture was evaporated again. The crude product was purified by flash column chromatography on silica gel silica gel packed in CH$_2$Cl$_2$. Elution with 95:5:1 v/v/v CH$_2$Cl$_2$/CH$_3$OH/NH$_4$OH followed by 90:10:2 v/v/v CH$_2$Cl$_2$/CH$_3$OH/NH$_4$OH gave 18.3 mg of the title compound as a colorless glass. For the title compound: $^1$H NMR (500 MHz, CD$_3$OD) δ 7.50 (dd, J=9,5,22H), 7.43 (dd, J=5,3, 1H), 7.31–7.27 (m, 1H), 7.16 (t, J=9, 2H), 7.11 (dd, J=5, 1, 1H), 3.62–3.50 (m, 2H), 3.39 (dd, J=8, 4, 1H), 3.30–3.21 (m, 1H), 2.90 (d, J=12, 1H), 2.76 (d, J=12, 1H), 2.54–2.38 (m, 3H), 2.22–2.07 (m, 4H), 2.06–1.77 (m, 7H), 1.77–1.58 (m, 4H), 1.32–1.07 (m, 6H); ESI-MS 549 (M+H); HPLC A: 2.82 min.

EXAMPLE 200

2-(R)-(3-(S)-((4-(3,3-Difluoro-3-(4fluorophenyl)propyl)piperidin-1-yl)methyl)-4-(S)-(3-fluorophenyl)pyrrolidin-1-yl)-3-methylbutanoic acid

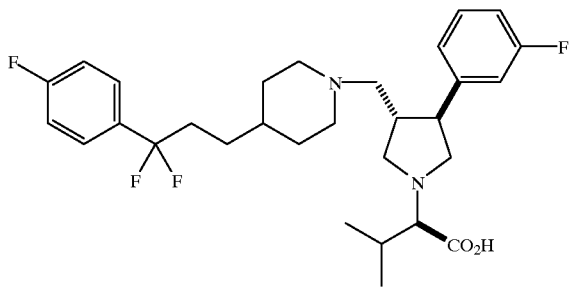

The title compound was prepared using procedures analogous to those described in EXAMPLE 155, Steps I and J, substituting 2-(R)-(3-(R)-formyl-4-(S)-(3-fluorophenyl) pyrrolidin-1-yl)-3-methylbutanoic acid (4-methoxy)benzyl ester (from EXAMPLE 85, Step B) for 2-(R)-(3-(R)-formyl-4-(S)-(3-fluorophenyl)pyrrolidin-1-yl)-3-(cyclobutyl) propanoic acid benzyl ester in Step I. For the title compound: $^1$H NMR (500 MHz, CD$_3$OD) δ 7.49 (dd, J=9, 5, 2H), 7.36 (td, J=8, 6, 1H), 7.19–7.12 (m, 4H), 7.11 (td, J=8,2,1H), 3.61 (dd, J=11, 8, 1H), 3.55 (bt, J=10, 11), 3.47 (d, J=5, 1H), 3.42–3.32 (m, 2H), 3.16 (q, J=10, 1H), 2.90 (d, J=11, 1H), 2.78–2.68 (m, 2H), 2.50 (dd, J=13, 10, 1H), 2.36 (dd, J=13,4, 1H), 2.26–2.17 (m, 1H), 2.17–2.06 (m, 2H), 2.01 (bt, J=12, 1H), 1.83 (bt, J=12, 1H), 1.65–1.55 (m, 2H), 1.30–1.02 (m, 5H), 1.16 (d, J=7, 3H), 1.03 (d, J=7, 3H); ESI-MS 535 (M+H); HPLC A: 3.10 min.

EXAMPLE 201
2-(R)-(3-(S)-((4-(3,3-Difluoro-3-(4-fluorophenyl)propyl) piperidin-1-yl)methyl)-4-(S)-phenylpyrrolidin-1-yl)-2-(cyclohexyl)acetic acid

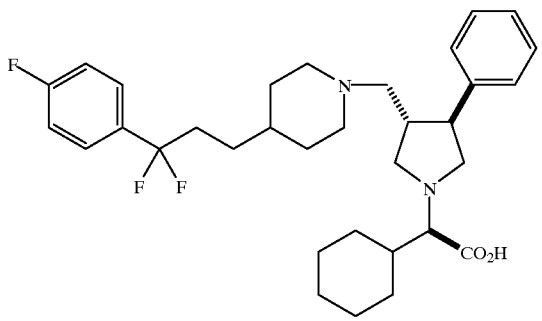

The title compound was prepared using procedures analogous to those described in EXAMPLE 155, Steps I and J, substituting 2-(R)-(3-(R)-formyl-4-(S)-phenylpyrrolidin-1-yl)-2-(cyclohexyl)acetic acid (4methoxy)benzyl ester (from EXAMPLE 33, Step E) for 2-(R)-(3-(R)-formyl-4-(S)-(3-fluorophenyl)pyrrolidin-1-yl)-3-(cyclobutyl)propanoic acid benzyl ester in Step I. For the title compound: $^1$H NMR (500 MHz, CD$_3$OD) δ 7.50 (dd, J=9, 5, 2H), 7.39–7.31 (m, 4H), 7.31–7.24 (m, 1H), 7.16 (t, J=9, 2H), 3.63–3.52 (m, 2H), 3.49–3.24 (m, 2H), 3.12 (q, J=10, 1H), 2.88 (bd, J=11, 1H), 2.72 (bd, J=11,2H), 2.46 (t, J=10, 1H), 2.31 (dd, J=12,2, 1H), 2.18–2.06 (m, 2H), 1.97 (bt, J=11, 1H), 1.90–1.64 (m, 7H), 1.64–1.53 (m, 2H), 1.50–1.39 (m, 1H), 1.37–1.01 (m, 10H); ESI-MS 557 (M+H); HPLC A: 3.11 min.

EXAMPLE 202
2-(R)-(3-(S)-((4-(3,3-Difluoro-3-(2-pyridyl)propyl) piperidin-1-yl)methyl)-4-(S)-(3-fluorophenyl)pyrrolidin-1-yl)-3-(cyclopropyl)propanoic acid

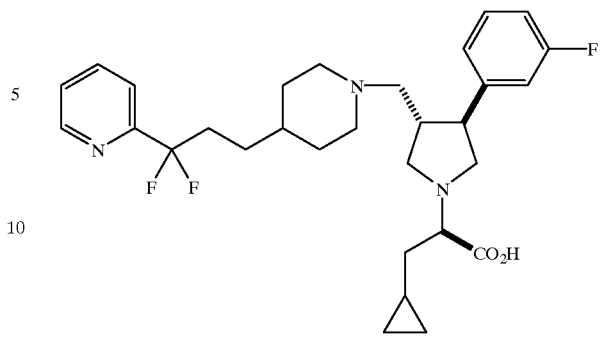

Step A: Ethyl oxo(2-pyridyl)acetate
A solution of n-butyllithium (100 mL, 1.6 M, 160 mmol) in hexanes was added over 2 min. to a stirred solution of 2-bromopyridine (15.0 mL, 24.9 g, 157 mmol) in 500 mL of ether cooled in a dry ice/i-PrOH bath, causing a temporary rise in temperature to 47° C. After 25 min., the solution was transferred rapidly to a stirred 0° C. solution of diethyl oxalate (75 mL, 81 g, 550 mmol) in 1000 mL of ether. After 2 h at 0° C., the mixture was washed with saturated aq. NaHCO$_3$ (900 ml), water (900 mL), and saturated aq. NaCl (450 mL). The organic layer was dried (MgSO$_4$), filtered, and evaporated. Distillation gave the title compound as 11.68 g of yellow liquid, B.p. 96–108° C. (0.3 mm Hg pressure). For the title compound: $^1$H NMR (500 MHz, CDCl$_3$) δ 8.78 (d, J=5, 1H), 8.13 (d, J=8, 1H), 7.93 (td, J=8, 2, 1H), 7.56 (ddd, J=8, 5, 1, 11H), 4.51 (q, J=7,22H), 1.44 (t, J=7, 3H).

Step B: Ethyl difluoro(2-pyridyl)acetate
Ethyl oxo(2-pyridyl)acetate (11.59 g, 64.7 mmol, from EXAMPLE 202, Step A) was added to a flask containing (diethylamino)sulfur trifluoride (18.0 mL, 22.0 g, 136 mmol) and the solution was heated to 45° C. overnight. An additional portion of (diethylamino)sulfur trifluoride (24.9 g, 154 mol) was added and the solution was heated to 55° C. for 2 days. After cooling to RT, the solution was added carefully to a stirred mixture of EtOAc (600 mL), ice (500 g), water (500 mL), and NaHCO$_3$ (100 g). After the resulting reaction had subsided, the layers were separated and the organic layer was washed with 250 mL each of saturated aq. NaHCO$_3$, water, and saturated aq. NaCl. The organic layer was dried (Na$_2$SO$_4$), decanted, and evaporated. Distillation gave 8.45 g of yellow liquid, B.p. 5063° C. (0.1 mm Hg), containing a residual impurity. Further purification by flash column chromatography on silica gel, eluting with 80:20 v/v to 75:25 v/v hexanes/EtOAc, gave the title compound as 6.54 g of yellow oil. For the title compound: $^1$H NMR (500 MHz, CDCl$_3$) δ 8.68 (d, J=5, 1H), 7.88 (td, J=8,2, 1H), 7.76 (d, J=8, 1H), 7.44 (dd, J=8,5, 1H), 4.40 (q,J=7, 2H), 1.35 (t, J=7,3H).

Step C: 1-(t-Butoxycarbonyl)-4-(3,3-difluoro-3-(2-pyridyl) prop-1-enyl)piperidine
Ethyl difluoro(2-pyridyl)acetate (1.00 g, 4.97 mmol, from EXAMPLE 202, Step B) was dissolved in CH$_3$OH (15 mL) in a 3-neck round bottom flask fitted with a mechanical stirrer, and the resulting solution was cooled in a dry iceli-PrOH bath. Sodium borohydride (114 mg, 3.0 mmol) was added in 2 portions 15 min. apart. After an additional 55 min., the cold reaction was quenched by the addition of saturated aq. NH$_4$Cl (6.5 mL) over 12 min. After 10 min., the cooling bath was removed and the mixture was stirred for 35 min. before being diluted with saturated aq. NaCl (100 mL)

and extracted with EtOAc (4×75 mL). The combined organic layers were dried (Na$_2$SO$_4$), decanted, and evaporated to give 1.02 g of crude 2,2-difluoro-2-(2-pyridyl)-1-methoxyethanol as an amber oil.

A suspension of ((1-(t-butoxycarbonyl)piperidin-4-yl)methyl)triphenylphosphonium iodide (5.29 g, 9.00 mmol, from EXAMPLE 155, Step C) in THF (70 mL) was stirred at RT for 40 min. A toluene solution of potassium bis(trimethylsilyl)amide (18 mL, 0.5 M, 9.0 mmol) was added, giving an orange suspension. After 40 min., crude 2,2difluoro-2-(2-pyridyl)-1-methoxyethanol (940 mg, 4.97 mmol) was added in THF (20 mL). After an additional 50 min., the mixture was quenched by the addition of saturated aq. NH$_4$Cl (10 mL). The mixture was partitioned between EtOAc (100 mL) and H$_2$O (100 ml), and the aqueous layer was extracted with EtOAc (3×100 mL). The organic layers were washed in succession with saturated aq. NaCl (100 mL), dried (Na$_2$SO$_4$), decanted, and evaporated. Purification by flash column chromatography on silica gel, eluting with 90:10 v/v to 80:20 v/v hexanes/EtOAc, gave 1.18 mg of the title compound (approximately 95:5 cis/trans mixture) as an oil which soldified upon standing. For the title compound: $^1$H NMR (500 MHz, CDCl$_3$) S 8.68 (d, J=5, 1H), 7.84 (td, J=8, 2, 1H), 7.70 (d, J=8, 1H), 7.39 (dd, J=8, 5, 1H), 5.93 (td, J=14, 11, 1H), 5.70 (ddt, J=11, 10, 2, 1H), 4.17–3.99 (bs, 2H), 2.80–2.62 (m, 3H), 1.58 (d, J=12,22H), 1.46 (s, 9H), 1.26 (qd, J=12, 4, 2H); ESI-MS 339 (M+H); HPLC A: 4.28 min.

Step D: 1-(t-Butoxycarbonyl)-4-(3,3-difluoro-3-(2-pyridyl)propyl)piperidine

Potassium azodicarboxylate (246 mg, 1.27 mmol) was added to a stirred solution of 1-(t-butoxycarbonyl)-4-(3,3-difluoro-3-(2-pyridyl)prop-1-enyl)piperidine (143 mg, 0.42 mmol, from EXAMPLE 202, Step C) in methanol (1.4 mL) at RT. A solution (0.58 mL) of 75:25 v/v CH$_3$OH/AcOH was added in three portions at 30 min. intervals. After two hours, an additional portion of potassium azodicarboxylate (246 mg, 1.27 mmol) was added, followed by a solution (0.58 mL) of 75:25 v/v CH$_3$OH/AcOH added in three portions at 30 min. intervals. After another two hours, a third portion of potassium azodicarboxylate (246 mg, 1.27 mmol) was added, followed by a solution (0.58 mL) of 75:25 v/v CH$_3$OH/AcOH added in the same manner as before. After stirring overnight, the mixture was diluted with EtOAc (50 mL) and washed with saturated aq. NaHCO$_3$ (30 mL) followed by saturated aq. NaCl (30 mL). The organic layer was dried (Na$_2$SO$_4$), decanted, and evaporated to give the crude product containing approximately 30% starting olefin. This material was combined with crude product similarly obtained from 1-(t-butoxycarbonyl)-4-(3,3-difluoro-3-(2-pyridyl)prop-1-enyl)piperidine (20 mg, 0.059 mmol) and purified by preparative HPLC on a 20×250 mm Chiralcel OD column, eluting with 98:2 v/v hexanes/i-PrOH, to give 105 mg of the title compound: $^1$H NMR (500 MHz, CDCl$_3$) δ 8.68 (d, J=5, 1H), 7.82 (td, J=8, 2, 1H), 7.64 (d, J=8, 1H), 7.38 (dd, J=8, 5, 1H), 4.174.00 (bs, 2H), 2.75–2.62 (m, 2H), 2.42–2.30 (m, 2H), 1.67 (d, J=12, 2H), 1.46 (s. 9H), 1.45–1.38 (m, 3H), 1.15–1.04 (m, 2H); ESI-MS 241 (M+H-100); HPLC A: 4.36 min.

Step E: 4-(3,3-Difluoro-3-(2-pyridyl)propyl)piperidine

The title compound was prepared using procedures analogous to those described in EXAMPLE 155, Step H, substituting 1-(t-butoxycarbonyl)-4-(3,3-difluoro-3-(2-pyridyl)propyl)piperidine (from EXAMPLE 202, Step D) for 1-(t-butoxycarbonyl)-4-(3,3-fluoro-3-(4-fluorophenyl)propyl)piperidine. For the title compound: $^1$H NMR (500 MHz, CD$_3$OD) δ 8.62 (d, J=5, 1H), 7.95 (td, J=8, 2, 1H), 7.68 (d, J=8, 1H), 7.50 (dd, J=8, 5, 1H), 2.99 (d,J=12, 2H), 2.53 (td, J=12, 3, 2H), 2.37–2.26 (m, 2H), 1.67 (d, J=12, 2H), 1.42–1.28 (m, 3H), 1.08 (dq, J=12, 4, 2H); ESI-MS 241 (M+H); HPLC A: 2.21 min.

Step F: 2-(R)(3-(S((4-(3,3-Difluoro-3-(2-pyridyl)propyl)piperidin-1-yl)methyl)-4-(S)-(3-fluorophenyl)pyrrolidin-1-yl)-3-(cyclopropyl)propanoic acid (4-methoxy)benzyl ester ester A solution of 4-(3,3-difluoro-3-(2-pyridyl)propyl) piperidine (20 mg. 0.083 mmol, from EXAMPLE 202, Step E) and AcOH (0.0050 mL, 5.2 mg, 0.087 mmol) in 1,2-dichloroethane (1.1 mL) was transferred to a vial containing 2-(R)-(3-(R)-formyl-4-(S)-(3-fluorophenyl)pyrrolidin-1-yl)-3-(cyclopropyl)propanoic acid (4-methoxy)benzyl ester (30 mg, 0.076 mmol, from EXAMPLE 21, Step E). Molecular sieve pellets (100 mg, 3 Å) were added and the mixture was stirred for 10 min. at RT before the addition of sodium triacetoxyborohydride (19 mg, 0.090 mmol). After 3 h, the mixture was diluted with EtOAc (40 mL) and washed with saturated aq. NaHCO$_3$ (20 mL) followed by saturated aq. NaCl (20 mL). The aq. layers were extracted with EtOAc (40 mL) and the combined organic layers were dried (Na$_2$SO$_4$), decanted, and evaporated. The crude product was purified by flash column chromatography on silica gel, eluting with 50:50 v/v CH$_2$Cl$_2$/EtOAc, to give 36 mg of the title compound. Further purification by preparative HPLC on a 20×250 mm Chiralcel OD column, eluting with 98:2 v/v hexanes/i-PrOH, gave 23 mg of the title compound: $^1$H NMR (500 MHz, CD$_3$OD) δ 8.60 (d, J=5, 1H), 7.94 (td, J=8, 2, 1H), 7.66 (d, J=8, 1H), 7.48 (dd, J=8, 5, 1H), 7.35 (d, J=8, 2H), 7.25 (td, J=8, 6, 1H), 7.01–6.95 (m, 2H), 6.92–6.87 (m, 2H), 5.13 (s, 2H), 3.77 (s, 3H), 3.33 (dd, J=9, 6, 1H), 3.10 (q, J=9, 2H), 2.84–2.74 (m, 2H), 2.66–2.59 (m, 2H), 2.52 (dd, J=9,7, 1H), 2.36–2.21 (m, 5H), 1.81 (bt, J=12, 1H), 1.73 (bt, J=12, 1H), 1.71–1.51 (m, 4H), 1.30–1.24 (m, 2H), 1.21–0.99 (m, 3H), 0.72–0.64 (m, 1H), 0.45–0.55 (m, 2H), 0.07–0.00 (m, 2H); ESI-MS 650 (M+H); HPLC A: 3.33 min.

Step G: 2-(R)(3-(S)-((4-(3,3-Difluoro-3-(2-pyridyl)propyl)piperidin-1-yl)methyl)-4-(S)-(3-fluorophenyl)pyrrolidin-1-yl)-3-(cyclopropyl)propanoic acid 2-(R)-(3-(S((4-(3,3-Difluoro-3-(2-pyridyl)propyl)piperidin-1-yl)methyl)-4-(S)-(3-fluorophenyl)pyrrolidin-1-yl)-3-(cyclopropyl)propanoic acid (4-methoxy)benzyl ester ester (19 mg, 0.029 mmol, from EXAMPLE 202, Step F) dissolved in 95% ethanol (1.0 mL) was hydrogenated at atmospheric pressure using 10% Pd/C (2.5 mg). After 3 h, the mixture was filtered, the catalyst was washed with 95% ethanol, and the filtrate was evaporated. Purification by flash column chromatography on silica gel, eluting with 50:50 v/v CH$_2$Cl$_2$/EtOAc followed by 90:10:2 v/v/v CH$_2$Cl$_2$/CH$_3$OH/NH$_4$OH, gave 14 mg of the title compound: $^1$H NMR (500 MHz, CD$_3$OD) δ 8860 (d, J=5, 1H), 7.94 (td, J=8, 2, 1H), 7.66 (d, J=8, 1H, 7.49 (dd, J=8, 5, 1H), 7.36 (td, J=8, 6, 1H), 7.18–7.12 (m, 2H), 7.01 (td, J=8, 2, 1H), 3.68–3.56 (m, 3H), 3.44–3.27 (m, 2H), 3.16 (q, J=11, 1H), 2.88 (bd, J=11, 1H), 2.77–2.67 (m, 2H), 2.49 (dd, J=12, 10, 1H), 2.35 (dd, J=12,4, 1H), 2.33–2.21 (m, 2H), 1.99 (td, J=12, 2, 1H), 1.94–1.86 (m, 1H), 1.81 (bt, J=12, 1H), 1.69 (ddd, J=14, 8, 5, 1H), 1.66–1.55 (m, 2H), 1.31–1.00 (m, 5H), 0.88–0.78 (m, 1H), 0.56–0.49 (m, 2H), 0.24–0.14 (m, 2H); ESI-MS 530 (M+H); HPLC A: 2.80 min.

EXAMPLE 203

2-(R)-(3-(S)-((4-(3,3-Difluoro-3-(2-pyridyl)propyl)piperidin-1-yl)methyl)-4-(S)-(3-fluorophenyl)pyrrolidin-1-yl)-3-(cyclobutyl)propanoic acid

233

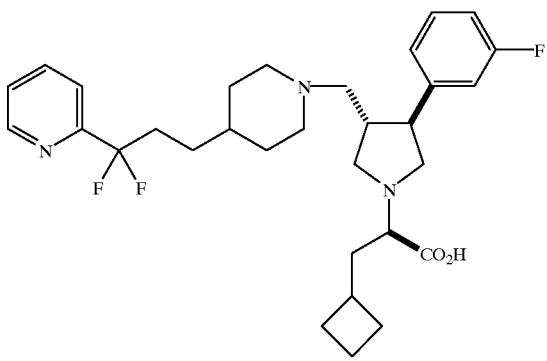

The title compound was prepared using procedures analogous to those described in EXAMPLE 202, Steps F and G, substituting 2-(R)-(3-(R)-formyl-4-(S)-(3-fluorophenyl) pyrrolidin-1-yl)-3-(cyclobutyl)propanoic acid (4-methoxy) benzyl ester for 2-(R)-(3-(R)-formyl-4-(S)-(3-fluorophenyl) pyrrolidin-1-yl)-3-(cyclopropyl)propanoic acid (4-methoxy) benzyl ester in Step F. 2-(R)-(3-(R)-Formyl-4-(S)-(3-fluorophenyl)pyrrolidin-1-yl)-3-(cyclobutyl)propanoic acid (4-methoxy)benzyl ester was prepared from 3-R)-(t-butyldimethylsilyloxymethyl)-4 (S)-(3-fluorophenyl) pyrrolidine (from EXAMPLE 20, Step H) and 4-(methoxy) benzyl 2-(S)-hydroxy-3-(cyclobutyl)propanoate (from EXAMPLE 19, Step E) using procedures analogous to those described in EXAMPLE 1, Steps G–I. For the title compound: $^1$H NMR (500 MHz, CD$_3$OD) δ 8.60 (d, J=5, 1H), 7.94 (td, J=8,2, 1H), 7.66 (d, J=8, 1H), 7.49 (dd, J=8,4, 1H), 7.36 (td, J=8,6, 1), 7.18–7.11 (m, 2H), 7.01 (td, J=8, 2, 1H), 3.62 (dd, J=11, 8, 1H), 3.56 (dd, J=11, 8, 1H), 3.41 (dd, J=9,4, 1H), 3.38–3.22 (m, 2H), 3.15 (q, J=10, 1H), 2.89 (bd, J=11, 1H), 2.77–2.66 (m, 2H), 2.54–2.43 (m, 2H), 2.35 (dd, J=12,4, 1H), 2.33–2.07 (m, 4H), 2.03–1.55 (m, 10H), 1.31–0.99 (m, 51); ESI-MS 544 (M+H); HPLC A: 1.49 min.

EXAMPLE 204
2-(R)-(3-(S)-((4-(3,3-Difluoro-3-(6-methylpyridazin-3-yl) propyl)piperidin-1-yl)methyl)-4-(S)-(3-fluorophenyl) pyrrolidin-1-yl)-3-(cyclopropyl)propanoic acid

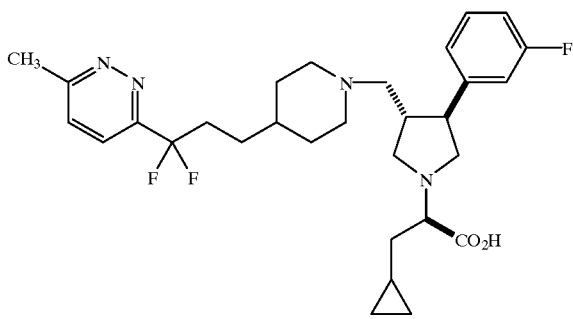

Step A: 3-Bromo-6-methylpyridazine
A solution (3.0 mL) containing 30%HBr in acetic acid was added to 3-(trifluoromethanesulfonyloxy)-6-methylpyridazine (prepared as described by M. Rohr, et al., *Heterocycles,* 1996, 43, 1459–64) and the mixture was heated in a 100° C. oil bath for 2.5 h. The mixture was cooled in an ice bath, adjusted to pH ≧9 (as determined using pH paper) by the careful addition of 20% aqueous NaOH, and extracted with ether (3×20 mL). The organic layers were dried (Na$_2$SO$_4$), decanted, and evaporated to give title compound as 359 mg of pale tan crystals. For the title compound: $^1$H NMR (500 MHz, CDCl$_3$) δ 7.56 (d, J=9, 1H), 7.22 (d, J=9, 1H), 2.70 (s, 3H).

Step B: Ethyl difluoro(6-methylpyridazin-3-yl)acetate
This procedure is derived from the general method of T. Taguchi, et al. (*Tetrahedron Lett.,* 1986,27,6103–6106). Ethyl difluoroiodoacetate (0.355 mL, 651 mg, 2.60 mmol) was added to a rapidly stirred suspension of copper powder (333 mg, 5.24 mmol) in DMSO (6.5 mL) at RT. After 50 min., 3-bromo-6-methylpyridazine (300 mg, 1.73 mmol) was added in DMSO (1.0 mL). After 20 h, the mixture was transferred to a separatory funnel containing water (25 mL) and saturated aq. NH$_4$Cl (25 mL), and extracted with EtOAc (2×50 mL). The organic extracts were washed with saturated aq. NaCl, dried (Na$_2$SO$_4$), decanted, and evaporated. Purification by flash column chromatography on silica gel, eluting with 70:30 v/v hexanes/EtOAc, gave 363 mg of the title compound as an amber liquid. For the title compound: $^1$H NMR (500 MHz, CDCl$_3$) δ 7.79 (d, J=9, 1H), 7.53 (d, J=9, 1H), 4.43 (q, J=7, 2H), 2.82 (s, 3H), 1.38 (t, J=7, 3H).
Steps C–G: 2-(R)(3-(S)-((4-(3,3-Difluoro-3-(6-methylpyridazin-3-yl)propyl)piperidin-1-yl)methyl)-4-(S)-(3-fluorophenyl)pyrrolidin-1-y)-3-(cyclopropyl)propanoic acid The title compound was prepared using procedures analogous to those described in EXAMPLE 202, Steps C–G, substituting ethyl difluoro(6-methylpyridazin-3-yl)acetate (from EXAMPLE 204, Step B) for ethyl difluoro(2-pyridyl) acetate in Step C. For the title compound: $^1$H NMR (500 MHz, CD$_3$OD) δ 7.85 (d, J=9, 1H), 7.73 (d, J=9, 1H), 7.37 (td, J=8, 6, 1H), 7.18–7.12 (m, 2H), 7.01 (td, J=8, 2, 1H), 3.68–3.55 (m, 3H), 3.46–3.30 (m, 2H), 3.16 (q, J=10, 1H), 2.90 (bd, J=11, 1H), 2.78–2.68 (m, 2H), 2.74 (s, 3H), 2.50 (dd, J=12, 10, 1H), 2.47–2.33 (m, 3H), 2.00 (td, J=12, 2, 1H), 1.95–1.87 (m, 1H), 1.82 (td, J=12, 2, 1H), 1.73–1.58 (m, 3H), 1.38–1.31 (m, 2H), 1.30–1.02 (m, 3H), 0.88–0.79 (m, 1H), 0.56–0.50 (m, 2H), 0.24–0.14 (m, 2H); ESI-MS 545 (M+H); HPLC A: 1.28 min.

EXAMPLES 205–210

The compounds in Table 7 were prepared using procedures analogous to those described in EXAMPLE 204, substituting the appropriate heteroaryl halide (R-X) for 3-bromo-6-methylpyridazine in Step B. In the case of EXAMPLE 208, α-(R)-(3-(R)formyl-4-(S)-(3-fluorophenylpyrrolidin-1-yl)-tert-butylacetic acid (4-methoxy)benzyl ester was substituted for 2-(R)-(3-(R)-formyl-4-(S)-(3-fluorophenyl)pyrrolidin-1-yl)-3-(cyclopropyl)propanoic acid (4-methoxy)benzyl ester in Step F. α-(R(3-(R)-Formyl-4-(S)-(3-fluorophenyl) pyrrolidin-1-yl)-tert-butylacetic acid (4-methoxy)benzyl ester was prepared using procedures analogous to those described in EXAMPLE 169, Steps A–D, substituting 4-methoxybenzyl chloride for benzyl bromide in Step A.

TABLE 7

[Structure: piperidine bearing R-CF2-CH2CH2- chain, connected via CH2 to a pyrrolidine substituted with 3-fluorophenyl, N-CH(R')CO2H]

| EXAMPLE # | R | X | R' | ESI-MS | HPLC A (min.) |
|---|---|---|---|---|---|
| 205 | 2-thiazolyl | Br | CH2-cyclopropyl | 536 (M + H) | 2.17 |
| 206 | 2-pyrimidinyl | Br | CH2-cyclopropyl | 531 (M + H) | 1.94 |
| 207 | 5-CF3-2-pyridyl | Br | CH2-cyclopropyl | 598 (M + H) | 2.67 |
| 208 | 5-CF3-2-pyridyl | Br | C(CH3)3 | 600 (M + H) | 1.73 |
| 209 | 5-F-2-pyridyl | Br | CH2-cyclopropyl | 548 (M + H) | 2.32 |
| 210 | 2-thienyl | I | CH2-cyclopropyl | 535 (M + H) | 1.68 |

EXAMPLES 211–212

The compounds in Table 8 were prepared using procedures analogous to those described in EXAMPLE 204, substituting the appropriate heteroaryl bromide (R-Br) for 3-bromo-6-methylpyridazine in Step B. These compounds are derived from the minor stereoisomers isolated as by-products in Step F using a Chiralcel OD HPLC column eluting with hexanes/i-PrOH.

TABLE 8

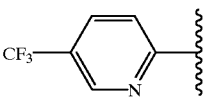

| EXAMPLE # | R | ESI-MS | HPLC A (min.) |
|---|---|---|---|
| 211 | 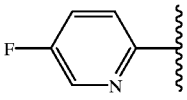 | 598 (M + H) | 2.64 |
| 212 | 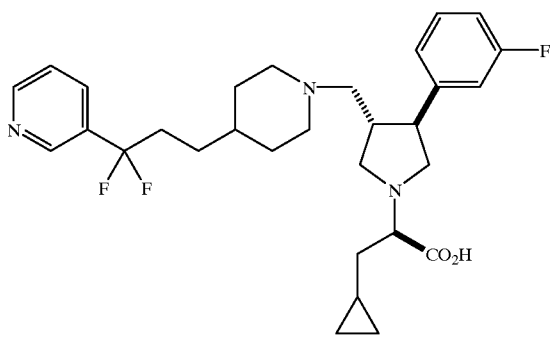 | 548 (M + H) | 2.29 |

EXAMPLE 213

2-(R)-(3-(S)-((4-(3,3-Difluoro-3-(3-pyridyl)propyl)piperidin-1-yl)methyl)-4-(S)-(3-fluorophenyl)pyrrolidin-1-yl)-3-(cyclopropyl)propanoic acid Step A: Dimethyl (2-oxo-2-(3-pyridyl)ethyl)phosphonate A solution of n-butyllithium in hexanes (9.0 mL, 1.6 M, 14 mmol) was added over 10 min. to a solution of dimethyl methylphosphonate (1.50 mL, 1.72 g, 13.8 mmol) in THF (60 mL) cooled in a dry ice/i-PrOH bath. After 30 min., a solution of methyl nicotinate (757 mg, 5.52 mmol) in THF (6 mL) was added over 2 min. The solution was stirred in the cooling bath for 45 min. before being allowed to warm to 0° C. over 1 h. The reaction was quenched with saturated aq. NH$_4$Cl (50 mL) and then partitioned between saturated aq. NaCl (50 1L) and CH$_2$Cl$_2$ (200 mL). The aq. layer was extracted with CH$_2$Cl$_2$ (2×100 1L). The combined organic layers were dried (Na$_2$SO$_4$) decanted, and evaporated. Purification by flash column chromatography on silica gel, eluting with EtOAc followed by 97:3 v/v CH$_2$Cl$_2$/CH$_3$OH, gave material containing some residual impurity. Further purification by flash column chromatography on silica gel, eluting with 50:50:5 v/v/v to 50:50:10 v/v/v toluene/EtOAc/CH$_3$OH gave 1.15 g of the title compound. For the title compound: $^1$H NMR (500 MHz, CDCl$_3$) δ 9.26–9.20 (bs, 1H), 8.83 (d, J=4, 1H), 8.34 (dt, J=8, 2, 1H), 7.70 (dd, J=8, 4, 1H), 3.82 (d, J=11, 6H), 3.67 (d, J=24,2H).

Step B: 1-(t-Butoxycarbonyl)-4-(3-oxo-3-(3-pyridyl)prop-1-enyl)piperidine 1,1,1-Triacetoxy-1,1dihydro-1,2-benzoiodoxol-3(1H)-one (750 mg, 1.77 mmol) was added to a solution of 1-(t-butoxycarbonyl)-4-(hydroxymethyl)-piperidine (339 mg, 1.57 mmol, from EXAMPLE 155, Step A) in CH$_2$Cl$_2$ (10 mL) and the mixture was stirred at RT. After 45 min., and additional portion of 1,1,1-triacetoxy-1,1-dihydro-1,2-benzoiodoxol-3(1H)-one (150 mg, 0.35 mmol) was added. After an additional 30 min., ether (30 mL) and 1.3 N NaOH (10 1L) were added and stirring was continued for 20 min. The mixture was transferred to a separatory funnel with additional ether (30 mL) and 1.3 N NaOH (15 mL). The organic layer was separated, washed with water (20 mL), dried (Na$_2$SO$_4$), decanted, and evaporated to give 291 mg of 1-(t-butoxycarbonyl)-4piperidinecarboxaldehyde as a colorless oil.

A solution of dimethyl (2-oxo-2-(3-pyridyl)ethyl) phosphonate (150 mg, 0.65 mmol, from EXAMPLE 213, Step A) in THF (1.8 mL) was added to a stirred suspension of sodium hydride (60% oil dispersion, 15 mg of NaH, 0.63 mmol) in THF (3.0 mL). The resulting suspension was warmed in a 45° C. oil bath for 30 min. After the mixture had cooled to RT, 1-(t-butoxycarbonyl)-4 piperidinecarboxaldehyde (112 mg, 0.53 mmol) was added in THF (1.5 mL). After stirring overnight at RT, the mixture was diluted with ether (20 mL) and washed with 2.5 N NaOH (20 mL) followed by saturated aq. NaCl (20 mL). The aq. layers were extracted in succession with ether (20 mL), and the combined organic layers were dried (Na$_2$SO$_4$), decanted, and evaporated. Purification by flash column chromatography on silica gel, eluting with 80:20 v/v to 60:40 v/v hexanes/EtOAc, gave 135 mg of the title compound (trans isomer) as a yellow syrup. For the title compound: $^1$H NMR (500 M , CDCl$_3$) δ 9.17–9.13 (bs, 1H), 8.81 (bd, J=4, 1H), 8.27 (d, J=8, 1H), 7.49 (dd, J=8, 4, 1H), 7.07 (dd, J=15, 7, 1H), 6.85 (dd, J=15, 1, 1H), 4.254.13 (bs, 2H), 2.87–2.78 (m, 2H), 2.51–2.41 (m, 1H), 1.83 (d, J=12, 2H), 1.49 (s, 9H), 1.45 (qd, J=12, 4, 2H); ESI-MS 261 (M+H–56), 217 (M+H–100); HPLC A: 1.73 min.

Step C: 1-(t-Butoxycarbonyl)-4-(3-oxo-3-(3-pyridyl)propyl piperidine 1-(t-Butoxycarbonyl)-4-(3-oxo-3-(3-pyridyl)prop-1-enyl) piperidine (940 mg, 2.97 mmol, from EXAMPLE 213, Step B) was hydrogenated using 5% Pd/C in 95% ethanol at atmospheric pressure. Purification by flash column chromatography on silica gel, eluting with 90:10 v/v to 50:50 v/v hexanes/EtOAc gave 884 mg of the title compound as a colorless syrup. For the title compound: 1H NMR (500 MHz, CDCl$_3$) δ 9.23–9.15 (bs, 1H), 8.81 (bd, J=4, 1H), 8.28 (dt, J=8, 1, 1H), 7.48 (dd, J=8,4, 1H), 4.19–4.04 (bs, 2H), 3.04 (t, J=8,22H), 2.70 (bt, J=11, 2H), 1.78–1.70 (m, 4H), 1.56–1.45 (m, 1H), 1.47 (s, 9H), 1.17 (qd, J=12,4,22H); ESI-MS 263 (M+H–56), 219 (M+H–100); HPLC A: 1.78 min.

Step D: 1-(t-Butoxycarbonyl)-4-(3,3-difluoro-3-(3-pyridyl) propyl)piperidine

A solution of 1-(t-butoxycarbonyl)-4-(3-oxo-3-(3-pyridyl)propyl)piperidine (810 mg, 2.54 mmol, from EXAMPLE 213, Step C) in (diethylamino)sulfur trifluoride (3.30 mL, 3.66 g, 23 mmol) was stirred in a teflon tube at 40° C. for 2 days. The reaction was diluted with CH$_2$Cl$_2$ (20 mL) and the resulting solution was added in portions to a stirred mixture of water (150 mL), ice (150 g) and NaHCO$_3$ (29.3 g). After the resulting reaction had subsided, the mixture was extracted with EtOAc (2×200 mL). The organic layers were washed in succession with saturated aq. NaCl (100 mL), dried (Na$_2$SO$_4$), decanted, and evaporated. Flash column chromatography on silica gel, eluting with 80:20 v/v to 50:50 v/v toluene/ether, gave material containing some residual impurity. Further purification by preparative HPLC on a 20×250 mm Chiralcel OD column, eluting with 80:20 v/v hexanes/i-PrOH, gave 395 mg of the title compound: $^1$H NMR (500 MHz, CD$_3$OD) δ 8.69 (s, 1H), 8.64 (d, J=5, 1H), 7.97 (d, J=8, 1H), 7.54 (dd, J=8, 5, 1H), 4.04 (d, J=13, 21), 2.78–2.62 (bs, 2H), 2.31–2.20 (m, 2H), 1.68 (d, J=12, 2H), 1.50–1.40 (m, 1H), 1.43 (s, 9H), 1.40–1.34 (m, 2H), 1.02 (qd, J=12,4, 2H); ESI-MS 285 (M+H–56), 241 (M+H–100); HPLC A: 2.10 min.

Steps E–G: 2-(R)-(3-(S)-((4-(3,3-Difluoro-3-(3-pyridyl) propyl)piperidin-1-yl)methyl)-4-(S)-(3-fluorophenyl) pyrrolidin-1-yl)-3-(cyclopropyl)propanoic acid The title compound was prepared using procedures analogous to those described in EXAMPLE 202, Steps E–G, substituting 1-(t-butoxycarbonyl)-4-(3,3-difluoro-3-(3-pyridyl)propyl)piperidine (from EXAMPLE 213, Step D) for 1-(t-butoxycarbonyl)-4-(3,3-difluoro-3-(2-pyridyl) propyl)piperidine in Step E. For the title compound: $^1$H NMR (500 MHz, CD$_3$OD) S 8.66 (s, 1H), 8.63 (d, J=5, 1H), 7.95 (d, J=8, 1H), 7.53 (dd, J=8, 5, 1H), 7.36 (td, J=8,6, 1H), 7.18–7.12 (m, 2H), 7.01 (td, J=8, 2, 1H), 3.68–3.56 (m, 3H), 3.44–3.30 (m, 2H), 3.16 (q, J=10, 1H), 2.89 (d, J=11, 1H), 2.76–2.68 (m, 2H), 2.49 (dd, J=12, 10, 1H), 2.35 (dd, J=12,4, 1H), 2.25–2.13 (m, 2H), 1.98 (td, J=12, 2, 1H), 1.90 (ddd, J=14, 8, 7, 1H), 1.81 (td, J=12, 2, 1H), 1.66–1.56 (m, 2H), 1.34–1.27 (m, 2H), 1.27–1.17 (m, 11H), 1.12 (qd, J=12,4, 1H), 1.05 (qd, J=12,4, 1H), 0.88–0.79 (m, 1H), 0.56–0.50 (m, 2H), 0.22–0.15 (m, 2H); ESI-MS 530 (M+H); HPLC A: 1.20 min.

EXAMPLES 214–217

The compounds in Table 9 were prepared using procedures analogous to those described in EXAMPLE 213. In EXAMPLE 214, α-(R)-(3-(R)-formyl-4-(S)-(3-fluorophenyl)pyrrolidin-1-yl)-tert-butylacetic acid (4-methoxy)benzyl ester was substituted for 2-(R)-(3-(R)-formyl-4-(S)-(3-fluorophenyl)pyrrolidin-1-yl)-3-(cyclopropyl)propanoic acid (4-methoxy)benzyl ester in Step F. α-(R)-(3-(R)-Formyl-4-(S)-(3-fluorophenyl) pyrrolidin-1-yl)-tert-butylacetic acid (4-methoxy)benzyl ester was prepared using procedures analogous to those described in EXAMPLE 169, Steps A–D, substituting 4-methoxybenzyl chloride for benzyl bromide in Step A. In EXAMPLES 215 and 216, the appropriate heterocyclic ester (R—CO$_2$CH$_3$), obtained by treatment of the carboxylic acid (R—CO$_2$H) with (trimethylsilyl)diazomethane (see N. Hashimoto, et al., *Chem Pharm Bull.*, 1981, 29, 1475–1478) was substituted for methyl nicotinate in Step A. In EXAMPLE 217, the appropriate ester (R—CO$_2$CH$_2$CH$_3$), obtained by methylation of ethyl 4-pyrazolecarboxylate with iodomethane and K$_2$CO$_3$ in CH$_3$CN at RT, was substituted for methyl nicotinate in Step A.

TABLE 9

| EXAMPLE # | R | R' | ESI-MS | HPLC A (min.) |
|---|---|---|---|---|
| 214 | 3-pyridyl | C(CH$_3$)$_3$ | 532 (M + H) | 1.22 |

TABLE 9-continued

| EXAMPLE # | R | R' | ESI-MS | HPLC A (min.) |
|---|---|---|---|---|
| 215 | CF$_3$-pyridyl | CH$_2$-cyclopropyl | 598 (M + H) | 1.68 |
| 216 | CH$_3$-pyrazolyl (1,3) | CH$_2$-cyclopropyl | 533 (M + H) | 1.77 |
| 217 | CH$_3$-pyrazolyl (1,4) | CH$_2$-cyclopropyl | 533 (M + H) | 1.42 |

EXAMPLE 218
2-(R)-((3-(S)-(4-((1,1-Dioxo-1,2,3,4-tetrahydro-1lambda-6-thieno[2,3-B]thiopyran-2-yl)methyl)piperidin-1-yl)methyl)-4-(S)-(3-fluorophenyl)-pyrrolidin-1-yl)-3-(cyclopropyl) propionic acid Step A: (+)- and (−)-4-((1,1-Dioxo-1,2,3,4-tetrahydro-1lambda-6-thieno[2,3-B]thiopyran -2-yl)methyl)-1-tert-butoxycarbonylpiperidine 1,1-Dioxo-1,2,3,4-tetrahydro-1lambda-6-thieno[2,3-B]thiopyran (220 mg, 1.2 mmol) was used in a procedure analogous to that described in Example 94, Step A to afford the title compound as a mixture of enantiomers, which were then separated via preparative chiral HPLC (column: Chiralpack AD 0.46×25 cm, eluant: 15% isopropanol in hexane, flow: 9 ml/min) to afford 39 mg (8% yield) and 34 mg (7% yield) of the pure enantiomers. ESI-MS. M/z; (M+H)=386.2.

Step B: 2-(R)-((3-(S)-(4-((1,1-Dioxo-1,2,3,4-tetrahydro-1lambda-6thieno[2,3-B]thiopyran-2-yl)methyl)piperidin-1-yl)methyl)-4-(S)-(3-fluorophenyl)pyrrolidin-1-yl)-3-(cyclopropyl)propionic acid Aldehyde 19 (28 mg, 0.068 mmol) and each enantiomer of 4-((1,1-dioxo-1,2,3,4-tetrahydro-1lambda-6-thieno[2,3-B]thiopyran -2-yl)methyl)-1-tert-butoxycarbonylpiperidine (36 mg, 0.09 mmol, from Step A) were reacted in a manner analogous to that described in Example 89, Step B to afford 19.1 mg (49% yield) of one diastereomer and 20.7 mg(53% yield) of the other diastereomer of the title compound. ESI-MS. M/z; (M+H)=575.2 and 575.4, respectively.

EXAMPLE 219
2-(R)-((3-(S)-(4-((1,1-Dioxo-thiochroman-2-yl)methyl) piperidin-1-yl)methyl)-4-(S)-(3-fluorophenyl)-pyrrolidin-1-yl)-3-(cyclopropyl)propionic acid Step A: 4-((1,1-Dioxo-thiochroman-2-yl)methyl)-1-tert-butoxycarbonylpiperidine A solution of 1,1dioxo-thiocroman (120 mg, 0.66 mmol) in 1 mL of dry THF was slowly added to a solution of LiN(SiMe$_3$)$_2$ (0.7 mL, 1 M in THF, 0.7 mmol) in 2 mL of dry THF at −78° C. under nitrogen. The reaction mixture was stirred at −78° C. for 4 h., then warmed to room temperature for 2 h. The mixture was then diluted with diethyl ether and washed with 1N HCl, 1N NaOH and brine. The solution was dried over MgSO$_4$, filtered, and purified by preparative HPLC (column: YMC combiprep ODS-A 20×50 mm, gradient: 10% acetonitrile/water w/ 0.1% TPA to 100 % acetonitrile/water w/ 0.1% TFA over 8 min, then ramp to 10% acetonitrile/water w/0.1% TFA over 2 min, flow: 20 ml/min) to afford 40 mg (16% yield) of the title compound. ESI-MS. M/z; (M+H)=380.1.

Step B: 2-(R)-((3-(S)-(4-((1,1-Dioxo-thiochroman-2-yl) methyl)piperidin-1-yl)methyl)-(S)-(3-fluorophenyl)-pyrrolidin-1-yl)-3-(cyclopropyl)propionic acid Aldehyde 14 (25 mg, 0.063 mmol) and 4-((1,1-Dioxo-thiochroman-2-yl)methyl)-1-tert-butoxycarbonylpiperidine (30 mg, 0.08 mmol, from Step A) were reacted in a manner analogous to that described in Example 89, Step B to afford 12.9 mg (38% yield) of the title.compound as an unresolvavble mixture of diastereomers. ESI-MS. M/z; (M+H)= 569.2.

EXAMPLE 220
2-(R)-(3-(S)-((4-(2-Naphthyl)methyl-piperidin-1-yl) methyl)-4-(S)-phenylpyrrolidin-1-yl)-(cyclohexyl)acetic acid The title compound was prepared using a procedure analogous to that described in Example 162, except that 2-naphthyl triphenylphosphonium bromide and 1-benzyl-4-piperidone were employed in place of 1-naphthyl triphenylphosphonium bromide and 1-benzyl-piperidine-4-carboxaldehyde, respectively, in Step B. For the title compound: ESI-MS 525 (M+1); HPLC A: 2.75 min.

EXAMPLE 221
2-(R)-(3-(S)-((4-(3-(Benzoimidazol-1-yl)-propyl)-piperidin-1-yl)methyl)-4-(S)-phenylpyrrolidin-1-yl) (cyclohexyl)acetic acid Step A: 3-(1-Benzyl-piperidin-4yl)-acrylic acid, ethyl ester To a solution of 15.5 mL of 1 M sodium bis(triemthylislyl)amide in 20 ml of THF was added 2.8 g triethyl phosphonoacetate at 0° C., and stirred at 0° C. for 15 min. After the addition of 1-benzyl-piperidine-4-carbaldehyde (from Example 162, step A) in 10 mL of 1BF, the reaction was stirred at 0° C. for 15 min. The reaction was warmed up to rt and stirred for 14 hr. The mixture was diluted with 35 ml of EtOAc and washed with H₂O. Aqueous phase was extracted with 2×30 mL EtOAc. The combined organic phases were washed with brine and dried over MgSO₄. Concentration gave a 2.43 g of title compound as a viscous oil.

Step B: 3-(1-Benzyl-piperidin-4-yl)-propionic acid, ethyl ester

The title compound was prepared from 3-(1-benzyl-piperidin-4-yl)-acrylic acid, ethyl ester (from Step A) using a procedure analogous to that described in Example 163, Step B.

Step C: 3-(1-Benzyl-piperidin-4-yl)-propan-1-ol

To a solution of 1.78 g 3-(o-benzyl-piperidin-4-yl)-propionic acid, ethyl ester (from Step B) in THF was added 7.11 mL of lithium aluminum hydride (1 M solution in THF) at 0° C. After stirring at 0° C. for 30 min, the reaction was warmed up to rt and stirred at rt overnight. The reaction was quenched with 5-N NaOH and diluted with H₂O. Aqueous layer was extracted with 250 mL of EtOAc. The combined organic phases were washed with brine, dried over MgSO₄ and concentrated to give 1.5 g of title compound as a viscous oil.

Step D: 3-(1-Benzyl-piperidin-4-yl)-propionaldehyde

To a solution of 0.93 mL of oxalyl chloride in 20 mL of $CH_2Cl_2$ at −78° C. was added 1.13 mL of DMSO in 0.1 mL of $CH_2Cl_2$ dropwise. After stirring 5 min, a solution of 3-(1-benzyl-piperidin)yl)propan-1-ol (form Step C) in 8 mL of $CH_2Cl_2$ was added dropwise. After stirring 15 minutes, 0.75 mL of diisopropylethylamine was added. The reaction was warmed to 0° C. and stirred for 20 min. After quenching with H₂O, the reaction was diluted with 50 mL of $CH_2Cl_2$. The aqueous layer was extracted with 2×50 mL Of $CH_2Cl_2$. The combined organic phases were dried over MgSO₄ and concentrated to give 612 mg the title compound, which was used for the next step without further purification Step E: N-(3-(1-Benzyl-piperidin-4-yl)-propyl)-benzene-1,2-diamine The title compound was prepared from 300 mg 3-(1-benzyl-piperidin-4-yl)-propionaldehyde (from Step D), 300 mg of 1,2-phenylenediamine and 200 mg sodium triacetoxyborohydride in THF and DMF using a procedure analogous to that described in Example 1, Step J.

Step F: 1-(3-(1-Benzyl-piperidin-4yl)-propyl)-1-H-benzoimidazole

To a solution of 160 mg of N-(3-(1-benzyl-piperidin-4-yl)-propyl)-benzene-1,2-diamine (from Step E) in 4.3 mL of trimethyl orthoformate was added 0. 16 mL concentrated HCl. After stirring at 80° C. for 16 hr, the reaction was diluted with EtOAc and washed with sat'd NaHCO₃ solution. Aqueous phase was extracted with 2×20 mL EtOAc. The combined organic phases were washed with brine, dried over MgSO₄ and concentrated to give 198 mg of oil, which was used for the next step without further purification.

Step G: 1-(3-Piperidin-4-yl-propyl)-1H-benzoimidazole $HCO_2H$

The title compound was prepared from 1-(3-(1-benzyl-piperidin-4-yl)-1-H-benzoimidazole (from Step F) using a procedure analogous to that described in Example 164, Step B.

Step H: 2-()-(3-(S)-(4-(3-(Benzoimidazol-1-yl)propyl)-piperidin-1-ylmethyl)-4-(S)-phenylpyrrolidin-1-yl)-(cyclohexyl)eacetic acid The title compound was prepared from 2-(R)(3-(R)-formyl-4-(S)-phenylpyrrolidin-1-yl)-(cyclohexyl)acetic acid, 4-methoxyl-benzyl ester (from Example 33, Step E) and 1-(3-piperidin-4-yl-propyl)-1-H-benzoimidazole (from Step G) using procedures analogous to those described in Example 1, Step J and Example 10, Step F, except that TFA and anisole were used in place of $HCO_2H$ in Example 10, Step F. For the title compound: ESI-MS 543 (M+1); HPLC A: 1.89 min.

EXAMPLE 222

2-(R)-(2-(3-(S)-((4-(3-Benzoimidazol-1-yl-propyl)-piperidin-1-yl)methyl)-4-(S)-(3-fluoro-phenyl)-pyrrolidin-1-yl)-3-cyclobutyl-propionic acid Step A: 2-(R)-(2-(3-(S)-((4-(3-Benzoimidazol-1-yl-propyl)-piperidin-1-yl)methyl)-4-(S)-(3-fluoro-phenyl)-pyrrolidin-1-yl)-3-cyclobutyl-propionic acid, benzyl ester The title compound was prepared from 2-(R)-(3-(R)-formyl-4-(S)-(3-fluoro-phenyl)pyrrolidin-1-yl)-3-cyclobutylpropionic acid, benzyl ester (from Example 26,Step A) and 1-(3-piperidin-4-yl-propyl)-1H-benzoimidazole (from Example 221, , Step G ) using procedures analogous to those described in Example 1, Steps J and K. For the title compound: ESI-MS 547 (M+1); HPLC A: 1.80 min

EXAMPLE 223

2-(R)-(3-(S)-((4-(3,4-Dihydro-1-H-isoquinolin-2-yl)methyl)-piperidin-1-ylmethyl)-4-(S)-phenylpyrrolidin-1-yl)-(cyclohexyl)acetic acid Step A: 2-((1-Benzyl-piperidin-4-yl)methyl)-1,2,3,4-tetrahydro-isoquinoline The title compound was prepared from 1,2,3,4-tetrahydroisoquinoline, 1-benzyl-piperidine-4-carbaldehyde (from Example 162, step A), diisopropylethylamine and sodium triacetoxyborohydride using a procedure analogous to that described in Example 1,, Step J.

Step B: 2-(R)-(3-(S)-((4-(3,4-Dihydro-1-H-isoquinolin-2-yl)methyl)-piperidin-1-ylmethyl)-4-(S)-phenylpyrrolidin-1-yl)-(cyclohexyl)acetic acid The title compound was prepared from 2-((1-benzyl-piperidin-4-yl)methyl)-1,2,3,4-tetrahydro-isoquinoline (from Step A) and 2-(R)-(3-(R)-formyl-4-(S)-phenylpyrrolidin-1-yl)-(cyclohexyl)acetic acid, 4-methoxy-benzyl ester (from Example 33, Step E), using procedures analogous to those described in Example 162, Step C and Example 10, Step F. For the title compound: ESI-MS 530 (M+1); HPLC A: 1.89 min

EXAMPLE 224

2-(R)-(3-(S)-((4-(2-Ethyl-5,7-dimethyl-imidazo[4,5-b]pyridin-3-yl)methyl)-piperidin-1-ylmethyl)-4-(S)-phenylpyrrolidin-1-yl)-(cyclohexyl)acetic acid Step A: 4-Formyl-piperidine-1-carboxylic acid, tert-butyl ester To a solution of 15.9 mL of LDA (2 M solution in THF) in 25 mL of THF at −78° C. was added 36.6 mL of diisopropylamine followed by 15.9 ml of (trimethylsilyl)diazomethane dropwise. After stirring at −78° C. for 30 min, 5.25 g of tert-butyl-4oxo-1-piperidinecarboxylate in 10 mL of THF was added slowly over 10 min. The reaction was stirred at −78° C. for 1 hr. After refluxing for 4 hr, the reaction was quenched with cold water and extracted with 3×70 mL of EtOAc. The combined organic phases were dried over MgSO₄ and concentrated. The residue was dissolved in 150 mL of EtOAc, then 10 g of silica gel was added. After stirring at rt for 16 hr, silica gel was filtered off. Concentration of filtrate followed by flash chromatography eluting with 25% EtOAc in hexane followed by 100% EtOAc afforded 3.66 g of the title compound as an oil.

Step B: 4-Hydroxymethyl-piperidine-1-carboxylic acid, tert-butyl ester

To a solution of 0.434 g of 4-formyl-piperidine-1-carboxylic acid, tert-butyl ester (from Step A) in 15 ml THF was added sodium borohydrid at 0° C. and stirred at 0° C. for 20 mn. The reaction was warmed to rt and stirred at rt for 14 hours. After quenching with CH$_3$OH, the reaction mixture was concentrated, then partitioned between EtOAc and H$_2$O. The aqueous layer was extracted with 2×20 mL of EtOAc. The combined organic phases were washed with brine, dried over MgSO$_4$ and concentrated. The residue was purified by flash chromatography eluting with 50% EtOAc in hexane, then 100% EtOA to give 390 mg of the title compound as an oil.

Step C: 4-(2-Ethyl-5,7-dimethyl-imidazo[4,5-b]pyridin-3-ylmethyl)-piperidine-1-carboxylic acid, tert-butyl ester To a solution of 0.216 g of 4-hydroxymethyl-piperidine-1-carboxylic acid, tert-butyl ester (from Step B) in 6 mL of CH$_2$Cl$_2$ at −78° C. was added 0.202 mL of triflic anhydride. After stirring at −78° C. for 5 minutes, 0.151 mL of 2,6-lutidine was added dropwise. The temperature was maintained below −70° C. throughout the reaction. After stirring for 15 minutes, 0.35 mL of diisopropylethylamine was added dropwise. After 15 minutes, a solution of 0.35 g 2-ethyl-5,7-dimethyl-3-H-imidazo[4,5-b]pyridine (prepared as described by Mantlo et al. U.S. Pat. No. 5, 412,097 and J. Med. Chem. 1991, 34, 2919 ) in 4 mL of CH$_2$Cl$_2$ was added dropwise. After warming to 0° C., the reaction was stirred at rt for 5 hr. The reaction was diluted with Et$_2$O, then washed with H$_2$O. The aqueous phase was extracted with 2×25 mL Et$_2$O. The combined organic phases were dried over MgSO$_4$ and concentrated. The residue was purified by flash chromatography eluting with 50% EtOAc in hexane to give 73 mg of the title compound as an oil.

Step D: 4-(2-Ethyl-5,7-dimethyl-imidazo[4,5-b]pyridin-3-yl)methyl)-piperidine, TFA salt To 70 mg of 4-(2-ethyl-5,7-dimethyl-imidazo[4,5-b]pyridin-3-ylmethyl)-piperidine-1-carboxylic acid, tert-butyl ester (from Step C) was added 2 mL of TFA. After stirring at rt for 1.5 hr, the reaction was concentrated to give 62 mg of viscous oil.

Step E: 2-(R)-(3-(S)-((4-(2-Ethyl-5,7-dimethyl-imidazo[4,5-b]pyridin-3-ylmethyl)-piperidin-1-ylmethyl)-4-(S)phenylpyrrolidin-1-yl)-(cyclohexyl)acetic acid The title compound was prepared from 2-(R)-(3-(R)-formyl-4-(S)-phenylpyrrolidin-1-yl)cyclohexaneacetic acid, 4-methoxy-benzyl ester (from Example 33, step E) and 4-(2-ethyl-5,7-dimethyl-imidazo[4,5-b]pyridin-3-ylmethyl)-piperidine, TFA salt (from Step D), using a procedure analogous to that described in Example 1 , Step J and Example 10, Step F. For the title compound: ESI-MS 572 (M+H); HPLC A: 2.37 min

EXAMPLES 225–227

Examples 225–227 in Table A were prepared according to the general procedure given in Example 221, employing the appropriate commercially available phenylene-1,2-diamines and appropriate aldehydes.

TABLE A

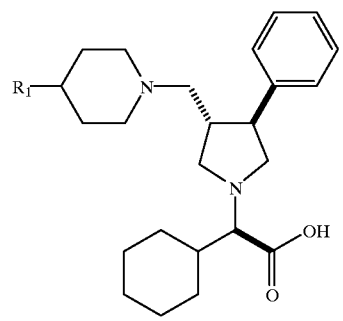

| EXAMPLE # | R$^1$ | MS m/Z (M + 1) |
|---|---|---|
| 225 | | 529 |
| 226 | | 600 |
| 227 | | 561 |

Examples 228–230 in Table B were prepared according to the general procedure given in Example 223, employing the approproiate amines and appropriate commercially available amines, 1,2,3,4-tetra hydroquinoline or indoline in place of 1,2,3,4-tetrahydroisoquinoline in Step A.

TABLE B

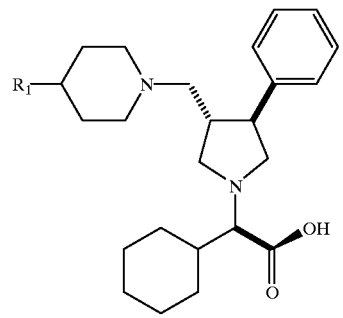

| EXAMPLE # | R$^1$ | MS m/Z (M + 1) |
|---|---|---|
| 228 | | 530 |

TABLE B-continued

| EXAMPLE # | R¹ | MS m/Z (M + 1) |
|---|---|---|
| 229 | (indoline-CH₂-) | 516 |
| 230 | (tetrahydroquinoline-propyl-) | 544 |

Examples 231–232 in Table C were prepared according to the general procedure given in Example 224, employing 2-ethyl-5,7-dimethyl-imidazo[4,5-b]pyridine and the appropriate alkylating agents such as 4-(3-hydroxypropyl)-piperidine-1-carboxylic acid, tert-butyl ester.

TABLE C

| EXAMPLE # | R¹ | MS m/Z (M + 1) |
|---|---|---|
| 231 | (2-ethyl-5,7-dimethyl-imidazo[4,5-b]pyridine-ethyl-) | 586 |

TABLE C-continued

| EXAMPLE # | R¹ | MS m/Z (M + 1) |
|---|---|---|
| 232 | (2-ethyl-5,7-dimethyl-imidazo[4,5-b]pyridine-butyl-) | 600 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

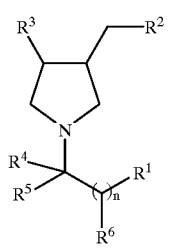

I wherein:
R$^1$ is —CO$_2$H;
R$^2$ is:

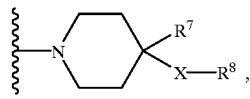

wherein
R$^7$ is selected from:
(1) hydrogen,
(2) C$_{1-6}$ alkyl, which is unsubstituted or substituted with 1–4 substituents where the substituents are independently selected from: hydroxy, cyano, and halo,
(3) cyano,
(4) hydroxy, and
(5) halo,
wherein
X is selected from:
C$_{1-10}$ alkyl and -(C$_{0-6}$ alkyl)C$_{3-6}$cycloalkyl(C$_{0-6}$ alkyl)-,
which is unsubstituted or substituted with 1–7 substituents where the substituents are independently selected from:
(a) halo,
(b) hydroxy,
(c) —O—C$_{1-3}$ alkyl,
(d) trifluoromethyl,
(e) -(C$_{1-3}$ alkyl)hydroxy, and
(f) ethylenedioxy
and wherein
R$^8$ is selected from:
phenyl, naphthyl, biphenyl, indanyl, tetrahydronapthyl and heterocycle,
which is unsubstituted or substituted with 1–7 of R$^{11}$
where R$^{11}$ is independently selected from:
(a) halo,
(b) cyano,
(c) hydroxy,
(d) C$_{1-6}$ alkyl, which is unsubstituted or substituted with 1–5 of R$^{12}$ where R$^{12}$ is independently selected from: halo, cyano, hydroxy, C$_{1-6}$ alkoxy, —CO$_2$H, —CO$_2$(C$_{1-6}$ alkyl), phenyl, trifluoromethyl, and —NR$^9$R$^{10}$, wherein R$^9$ is defined above and R$^{10}$ is independently selected from the definitions of R$^9$,
(e) —O—C$_{1-6}$ alkyl, which is unsubstituted or substituted with 1–5 of R$^{12}$,
(f) —CF$_3$,
(g) —CHF$_2$,
(h) —CH$_2$F,
(i) —NO$_2$,
(j) phenyl,
(k) —CO$_2$R$^9$,
(l) tetrazolyl,
(m) —NR$^9$R$^{10}$,
(n) —NR$^9$—COR$^{10}$,
(o) —NR$^9$—CO$_2$R$^{10}$,
(p) —CO—NR$^9$R$^{10}$,
(q) —OCO—NR$^9$R$^{10}$,
(r) —NR$^9$CO—NR$^9$R$^{10}$,
(s) —S(O)$_m$—R$^9$, wherein m is an integer selected from 0, 1 and 2,
(t) —S(O)$_2$—NR$^9$R$^{10}$,
(u) —NR$^9$S(O)$_2$—R$^{10}$,
(v) —NR$^9$S(O)$_2$—NR$^9$R$^{10}$, and
(w) C$_{1-6}$ fluoroalkoxy;
R$^3$ is selected from the group consisting of:
phenyl and thienyl,
which is unsubstituted or substituted with 1 7 substituents where the substituents are independently selected from:
(a) halo,
(b) trifluoromethyl,
(c) hydroxy,
(d) C$_{1-3}$ alkyl,
(e) —O—C$_{1-3}$ alkyl,
(f) —CO$_2$R$^9$,
(g) —NR$^9$R$^{10}$, and
(h) —CONR$^9$R$^{10}$;
R$^4$ is selected from:
C$_{1-10}$ alkyl, C$_{3-8}$ cycloalkyl, -(C$_{1-3}$ alkyl)-C$_{3-8}$ cycloalkyl,
C$_{2-10}$ alkenyl, C$_{2-10}$ alkynyl, phenyl, -(C$_{1-6}$ alkyl)-phenyl, naphthyl, biphenyl, hydrogen, cyclohexenyl, dihydronaphthyl, tetrahydronaphthyl, and octahydronaphthyl,
which is unsubstituted or substituted with 1–7 of R$^{11}$
where R$^{11}$ is independently as defined above;
R$^5$ is selected from:
hydrogen or C$_{1-6}$ alkyl, wherein the alkyl is unsubstituted or substituted with 1–7 substituents where the substituents are independently selected from:
(a) halo,
(b) trifluoromethyl,
(c) hydroxy,
(d) C$_{1-3}$ alkyl,
(e) —O—C$_{1-3}$ alkyl,
(f) —CO$_2$R$^9$,
(g) —NR$^9$R$^{10}$, and
(h) —CONR$^9$R$^{10}$,
or where R$^4$ and R$^5$ may be joined together to form a C$_{3-8}$ cycloalkyl ring which may be unsubstituted or substituted with 1–7 of R$^{11}$;
R$^6$ is independently selected from:
hydrogen or C$_{1-6}$ alkyl, wherein the alkyl is unsubstituted or substituted with 1–7 substituents where the substituents are independently selected from:
(a) halo,
(b) trifluoromethyl,
(c) hydroxy,
(d) C$_{1-3}$ alkyl,
(e) —O—C$_{1-3}$ alkyl,
(f) —CO$_2$R$^9$,
(g) —NR$^9$R$^{10}$, and
(h) —CONR$^9$R$^{10}$;
n is an integer selected from 0, 1, 2 and 3;
and pharmaceutically acceptable salts thereof and individual diastereomers thereof.
2. The compound of claim 1, wherein:
X is selected from:
C$_{1-10}$ alkyl and -(C$_{0-6}$ alkyl)C$_{3-6}$cycloalkyl(C$_{0-6}$ alkyl)-,
which is unsubstituted or substituted with 1–7 substituents where the substituents are independently selected from:
(a) halo,
(b) hydroxy,
(c) —O—C$_{1-3}$ alkyl, and
(d) trifluoromethyl; and R⁸ is selected from:
  phenyl, naphthyl, biphenyl, indanyl, tetrahydronapthyl and heterocycle,
    which is unsubstituted or substituted with 1–7 of $R^{11}$ where $R^{11}$ is independently selected from:
      (a) halo,
      (b) cyano,
      (c) hydroxy,
      (d) $C_{1-6}$ alkyl, which is unsubstituted or substituted with 1–5 of $R^{12}$ where $R^{12}$ is independently selected from: halo, cyano, hydroxy, $C_{1-6}$ alkoxy, —$CO_2H$, —$CO_2(C_{1-6}$ alkyl), phenyl, trifluoromethyl, and —$NR^9R^{10}$, wherein $R^9$ is defined above and $R^{10}$ is independently selected from the definitions of $R^9$,
      (e) —O—$C_{1-6}$ alkyl, which is unsubstituted or substituted with 1–5 of $R^{12}$,
      (f) —$CF_3$,
      (g) —$CBF_2$,
      (h) —$CH_2F$,
      (i) —$NO_2$,
      (j) phenyl,
      (k) —$CO_2R^9$,
      (l) tetrazolyl,
      (m) —$NR^9R^{10}$,
      (n) —$NR^9$—$COR^{10}$,
      (o) —$NR^9$—$CO_2R^{10}$,
      (p) —CO—$NR^9R^{10}$,
      (q) —OCO—$NR^9R^{10}$,
      (r) —$NR^9CO$—$NR^9R^{10}$,
      (s) —$S(O)_m$—$R^9$, wherein m is an integer selected from 0, 1 and 2,
      (t) —$S(O)_2$—$NR^9R^{10}$,
      (u) —$NR^9S(O)_2$—$R^{10}$, and
      (v) —$NR^9S(O)_2$—$NR^9R^{10}$.

3. The compound of claim 1 wherein $R^3$ is selected from the group consisting of:
  phenyl and thienyl,
    which may be unsubstituted or substituted with 1–5 substituents where the substituents are independently selected from:
      (a) halo,
      (b) trifluoromethyl,
      (c) hydroxy,
      (d) $C_{1-3}$ alkyl, and
      (e) —O—$C_{1-3}$ alkyl.

4. The compound of claim 1 wherein $R^3$ is selected from the group consisting of:
  phenyl and thienyl,
    which may be unsubstituted or substituted with 1–5 substituents where the substituents are independently selected from:
      (a) fluoro,
      (b) chloro,
      (c) trifluoromethyl,
      (d) hydroxy, and
      (e) $C_{1-3}$ alkyl.

5. The compound of claim 1 wherein $R^3$ is selected from the group consisting of:
  phenyl, which may be unsubstituted or substituted with 1–5 substituents where the substituents are independently selected from:
    (a) fluoro, and
    (b) chloro; and
  unsubstituted thienyl.

6. The compound of claim 1 wherein $R^3$ is unsubstituted phenyl, (3-fluoro)phenyl or 3-thienyl.

7. The compound of claim 2 wherein $R^3$ is unsubstituted phenyl, (3-fluoro)phenyl or 3-thienyl.

8. The compound of claim 1 wherein $R^4$ is $C_{1-10}$ alkyl, $C_{3-8}$ cycloalkyl, or -($C_{1-3}$ alkyl)-$C_{3-8}$ cycloalkyl,
  which is unsubstituted or substituted with 1–5 substituents where the substituents are independently selected from:
    (a) halo,
    (b) hydroxy,
    (c)-$C_{1-6}$ alkyl, which is unsubstituted or substituted with halo, cyano, —$CO_2H$, hydroxy or trifluoromethyl,
    (d) —O—$C_{1-6}$ alkyl, which is unsubstituted or substituted with halo, cyano, —$CO_2H$, hydroxy or trifluoromethyl,
    (e) —$CF_3$,
    (f) —$CHF_2$,
    (g) —$CH_2F$, and
    (h) —$CO_2H$.

9. The compound of claim 1 wherein $R^4$ is selected from: isopropyl, isobutyl, sec-butyl, t-butyl, cyclohexyl, cyclopentyl, cyclobutyl, cyclopropyl, —$CH_2$-cyclohexyl, —$CH_2$-cyclopentyl, —$CH_2$-cyclobutyl, and —$CH_2$—cyclopropyl.

10. The compound of claim 1 wherein $R^4$ is selected from: isopropyl, sec-butyl, t-butyl, cyclohexyl, cyclopentyl, cyclobutyl, cyclopropyl, —$CH_2$-cyclobutyl, and —$CH_2$-cyclopropyl.

11. The compound of claim 1 wherein $R^4$ is selected from: cyclohexyl, isopropyl, sec-butyl, t-butyl, —$CH_2$-cyclobutyl and —$CH_2$-cyclopropyl.

12. The compound of claim 1 wherein $R^5$ is hydrogen.

13. The compound of claim 1 wherein $R^6$ is hydrogen or unsubstituted $C_{1-6}$ alkyl.

14. The compound of claim 1 wherein $R^6$ is hydrogen.

15. The compound of claim 1 wherein $R^7$ is hydrogen, fluoro, hydroxy or $C_{1-6}$ alkyl.

16. The compound of claim 1 wherein $R^7$ is hydrogen or fluoro.

17. The compound of claim 1 wherein $R^7$ is hydrogen.

18. The compound of claim 1 wherein X is $C_{1-6}$ alkyl, which is unsubstituted or substituted with 1–7 substituents where the substituents are independently selected from:
  (a) halo,
  (b) hydroxy,
  (c) —O—$C_{1-3}$ alkyl, and
  (d) trifluoromethyl.

19. The compound of claim 1 wherein X is $C_{2-4}$ alkyl, which is unsubstituted or substituted with 1–6 substituents where the substituents are independently selected from:
  (a) halo,
  (b) —O—$C_{1-3}$ alkyl, and
  (c) trifluoromethyl.

20. The compound of claim 1 wherein X is $C_{2-4}$ alkyl, which is unsubstituted or substituted with 1–6 substituents where the substituents are fluoro.

21. The compound of claim 1 wherein X is n-propyl or —$CH_2CH_2CF_2$—.

22. The compound of claim 1 wherein $R^8$ is selected from: phenyl, naphthyl, benzoimiidazolyl, benzofurazanyl, isoxazolyl, pyrazinyl, pyridazinyl, pyridyl, pyridyl, and tetrazolopyridyl,
  which is unsubstituted or substituted with 1–7 substituents where the substituents are independently selected from:

(a) halo,
(b) cyano,
(c) hydroxy,
(d) $C_{1-6}$ alkyl, which is unsubstituted or substituted with 1–5 of $R^{12}$ where $R^{12}$ is independently selected from: halo, cyano, hydroxy, $C_{1-6}$ alkoxy, —$CO_2H$, phenyl, —$CO_2(C_{1-6}$ alkyl), trifluoromethyl, and —$NR^9R^{10}$, wherein $R^9$ and $R^{10}$ are independently selected from: hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$ alkyl,
$C_{1-3}$ alkoxy and trifluoromethyl;
(e) —O—$C_{1-6}$ alkyl, which is unsubstituted or substituted with 1–5 of $R^{12}$,
(f) —$CF_3$,
(g) —$CHF_2$,
(h) —$CH_2F$,
(i) —$NO_2$,
(j) phenyl,
(k) —$CO_2R^9$,
(l) tetrazolyl,
(m) —$NR^9R^{10}$,
(n) —$NR^9$—$COR^{10}$,
(o) $NR^9$—$CO_2R^{10}$,
(p) —CO—$NR^9R^{10}$,
(q) —OCO—$NR^9R^{10}$,
(r) —$NR^9CO$—$NR^9R^{10}$,
(s) —$S(O)_m$—$R^9$, wherein m is an integer selected from 0, 1 and 2,
(t) —$S(O)_2$—$NR^9R^{10}$,
(u) —$NR^9S(O)_2$—$R^{10}$, and
(v) —$NR^9S(O)_2$—$NR^9R^{10}$.

23. The compound of claim 1 wherein $R^8$ is selected from: phenyl, benzofurazanyl, benzoimdazolyl, isoxazole, pyridyl, and tetrazolopyridyl;
which is unsubstituted or substituted with 1–5 substituents where the substituents are independently selected from:
(a) halo,
(b) cyano,
(c) —$NO_2$,
(d) —$CF_3$,
(e) —$CHF_2$,
(f) —$CH_2F$,
(g) tetrazolyl,
(h) $C_{1-6}$ alkyl, which is unsubstituted or substituted with phenyl,
(i) —O—$C_{1-6}$ alkyl, and
(j) —$SO_2CH_3$.

24. The compound of claim 1 wherein $R^8$ is phenyl, which is unsubstituted or substituted with 1–3 substituents where the substituents are independently selected from:
(a) fluoro,
(b) chloro,
(c) cyano,
(d) —$NO_2$, and
(e) —$CF_3$.

25. The compound of claim 1 wherein $R^8$ is selected from: phenyl, 2-cyanophenyl, 3-cyanophenyl, 4-cyanophenyl, 4-fluorophenyl, 2,4-difluorophenyl, 3,4-difluorophenyl, 3,5-difluorophenyl, 2,6-difluorophenyl, 2,4,6-trifluorophenyl, 4nitrophenyl, 4-chlorophenyl, 3-chlorophenyl, 4-trifluoromethylphenyl, and 3,5-bis(trifluoromethyl)phenyl.

26. The compound of claim 1 wherein n is an integer selected from 0 and 1.

27. The compound of claim 1 wherein n is an integer which is 0.

28. The compound of claim 1 which is of the stereochemical configuration:

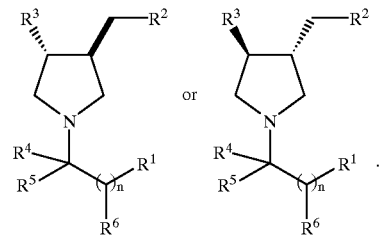

29. The compound of claim 1, which is a compound of formula (II):

(II)

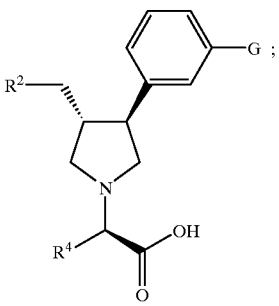

wherein $R^2$ is selected from the group consisting of

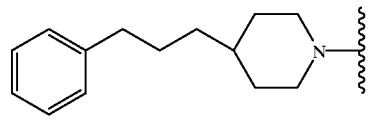

,

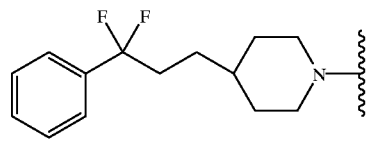

,

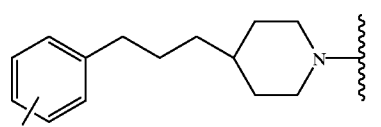

,

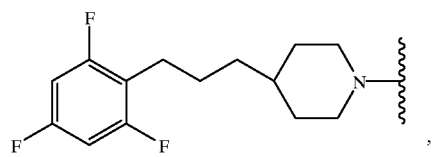

,

-continued

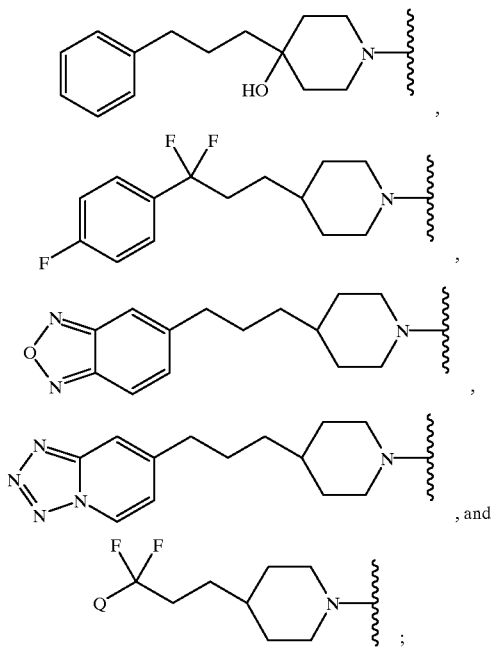

R⁴ is selected from the group consisting of

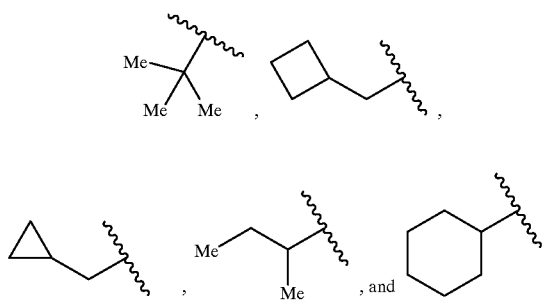

Q is pyridyl, pyrazinyl, pyrimidinyl, thiazolyl, thienyl, or pyrazolyl, any one of which is unsubstituted or substituted with methyl or trifluoromethyl; and G is hydrogen or fluoro;

and pharmaceutically acceptable salts thereof and individual diastereomers thereof.

30. A pharmaceutical composition which comprises an inert carrier and a compound of claim 1.

31. A method for modulation of chemokine receptor activity in a mammal which comprises the administration of an effective amount of the compound of claim 1.

32. A method for preventing infection by HIV, treating infection by HIV, delaying of the onset of AIDS, or treating AIDS comprising the administration to a patient of an effective amount of the compound of claim 1.

33. A method for the prevention or treatment of an inflammatory and immunoregulatory disorder or disease which comprises the administration to a patient of an effective amount of the compound of claim 1.

34. A method for the prevention or treatment of asthma, allergic rhinitis, dermatitis, conjunctivitis, atherosclerosis or rheumatoid arthritis which comprises the administration to a patient of an effective amount of the compound of claim 1.

35. A compound according to claim 1, which is a compound selected from the group consisting of:

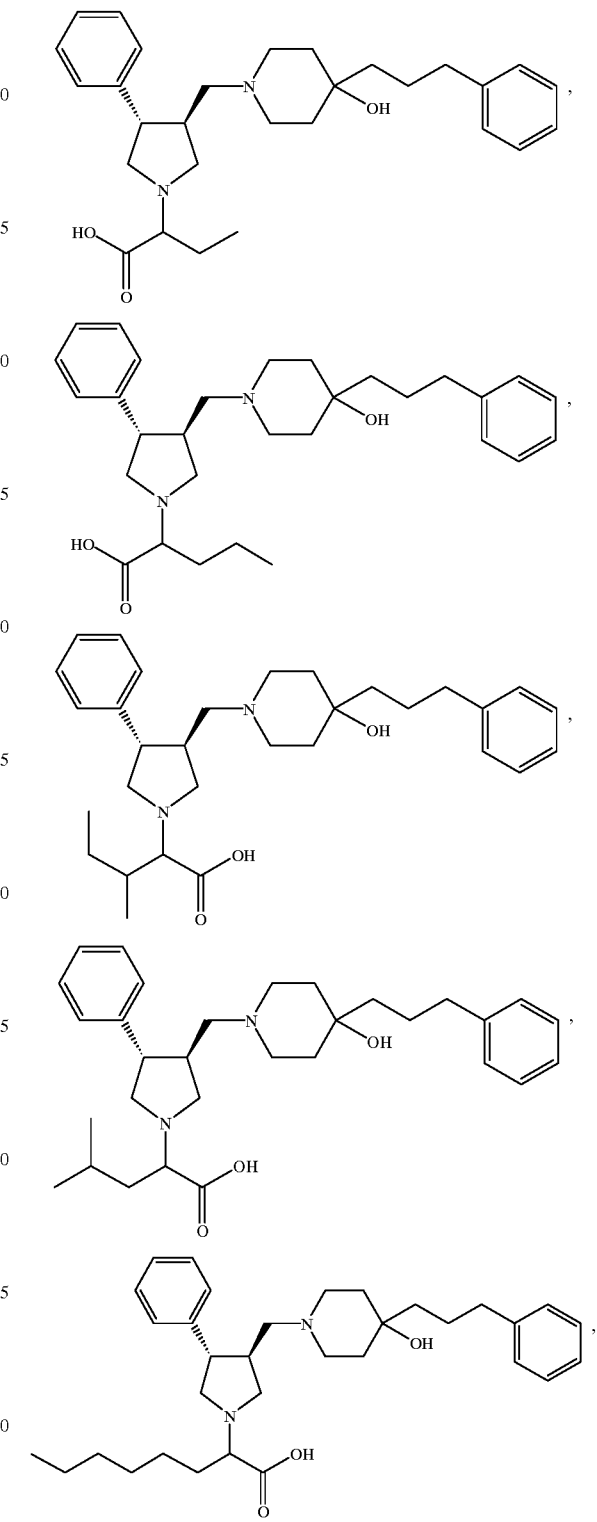

257
-continued
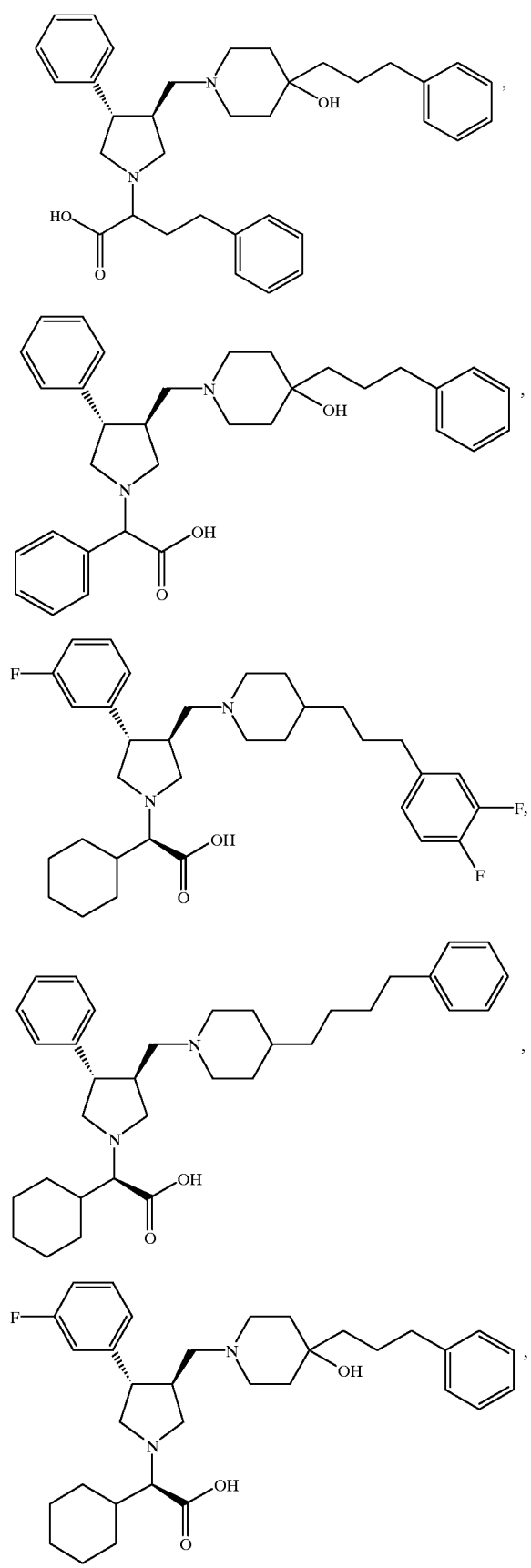
258
-continued
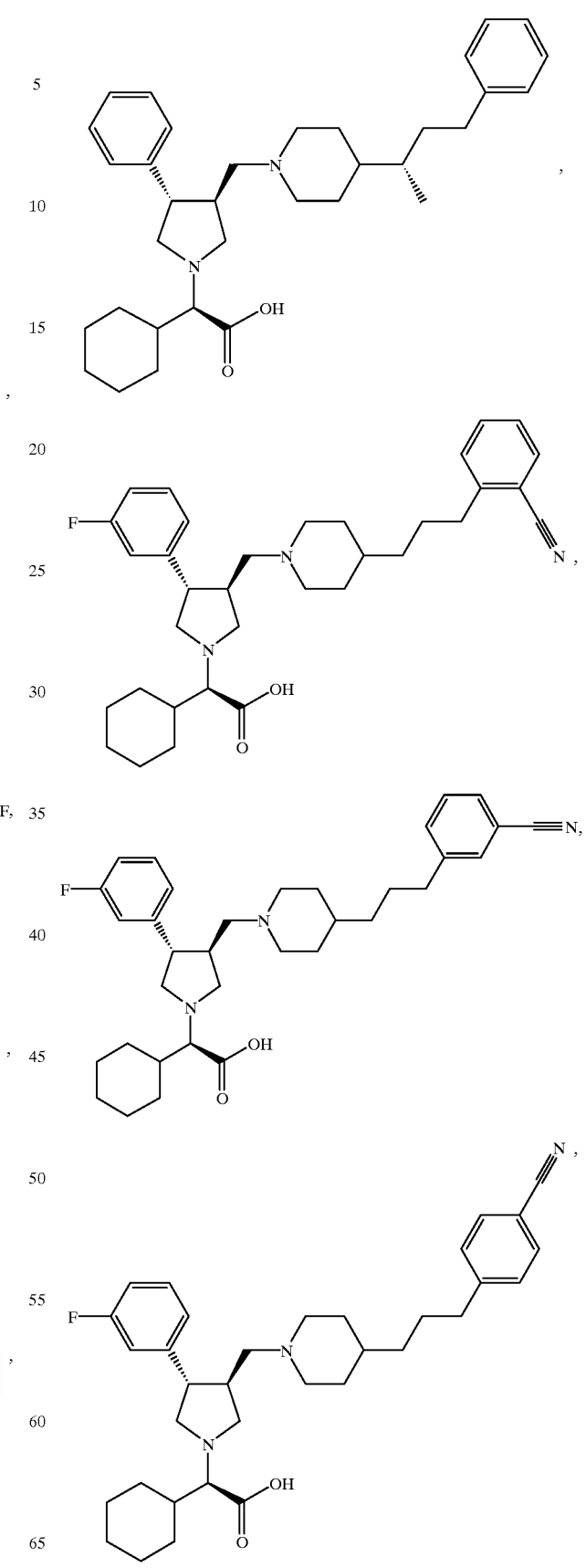

259 260
-continued -continued
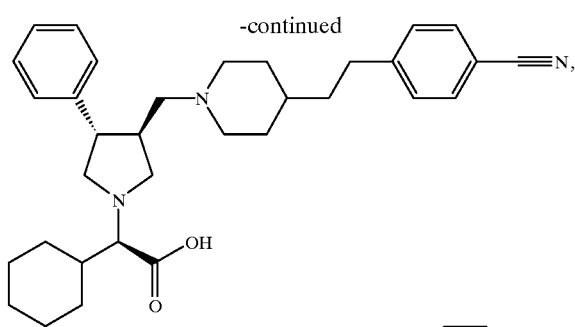
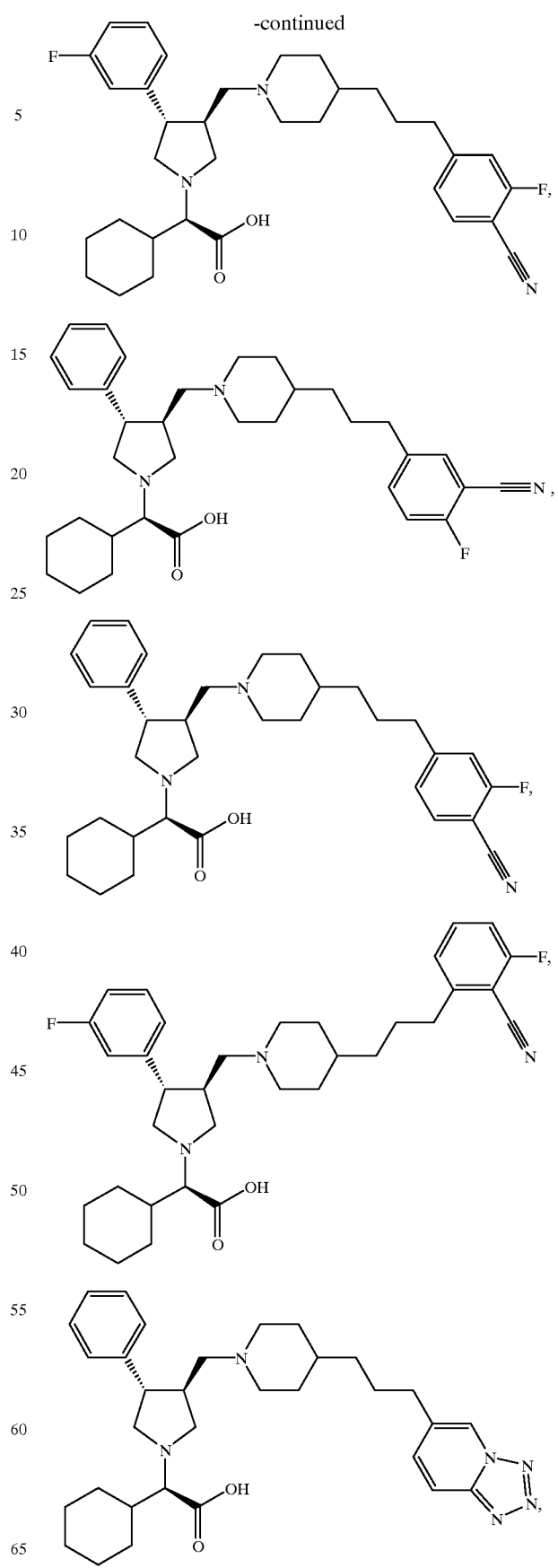

261
-continued
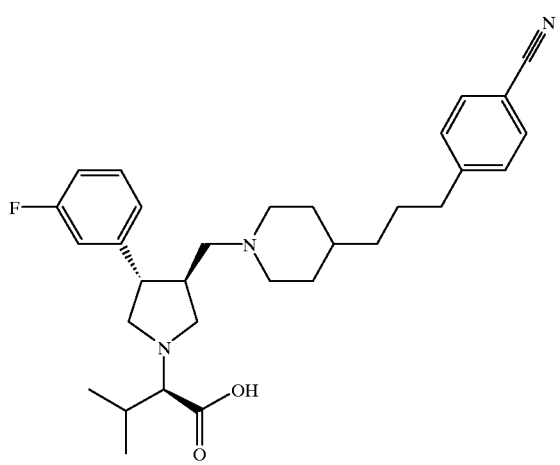
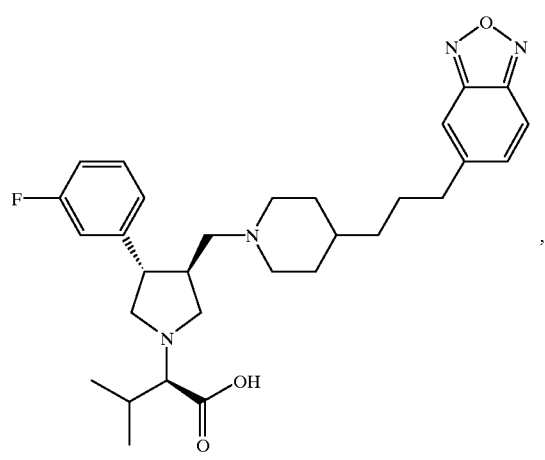
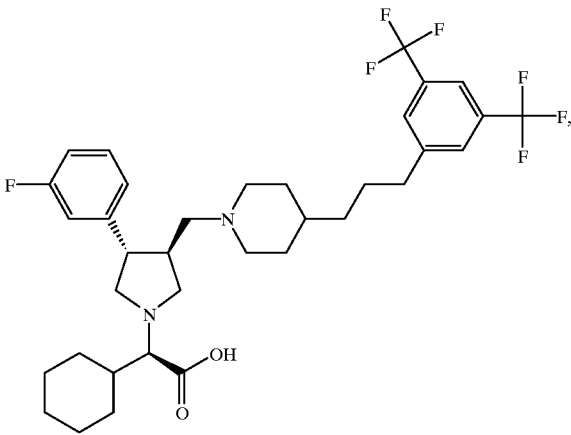
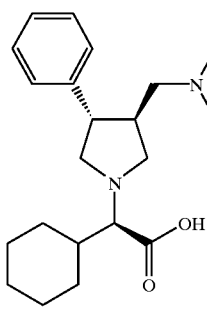
262
-continued
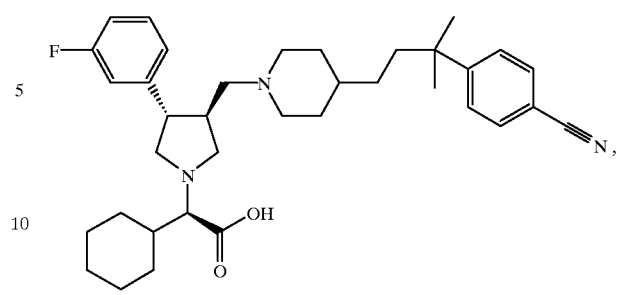
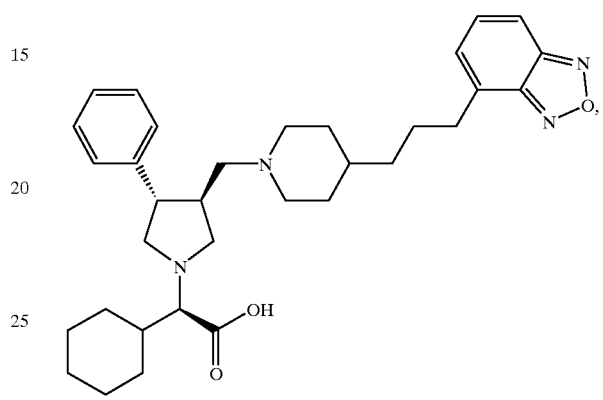
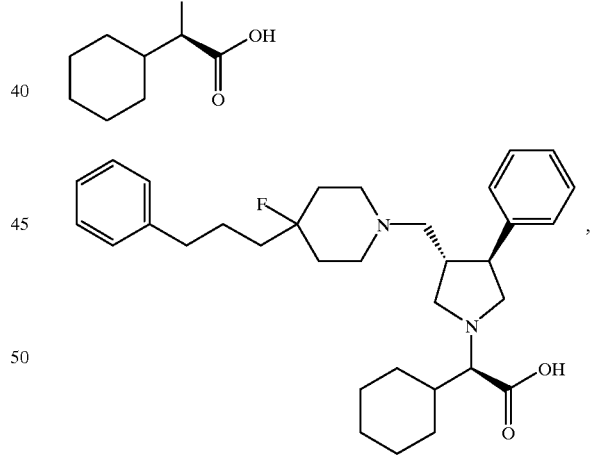
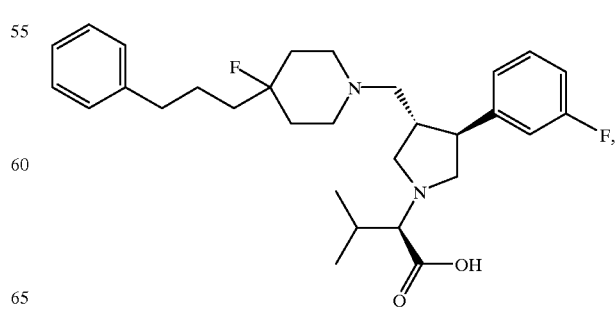

263
-continued
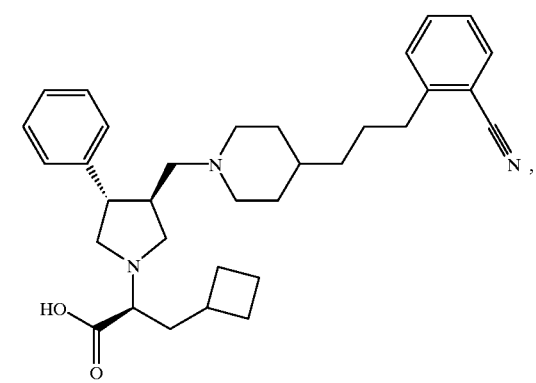
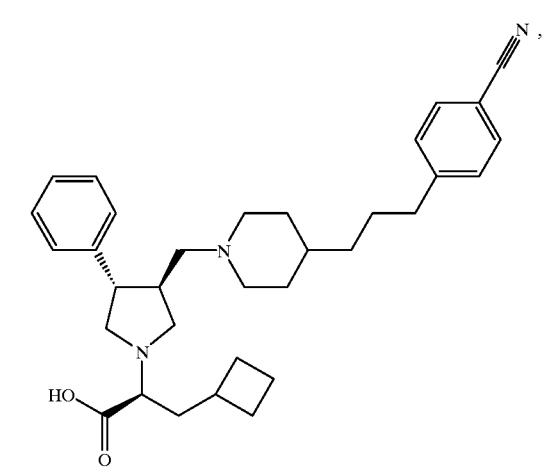
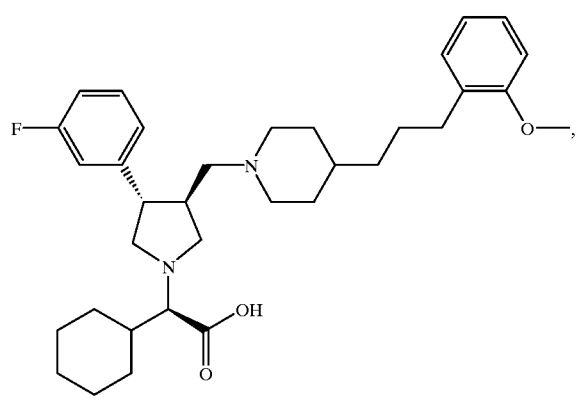
264
-continued
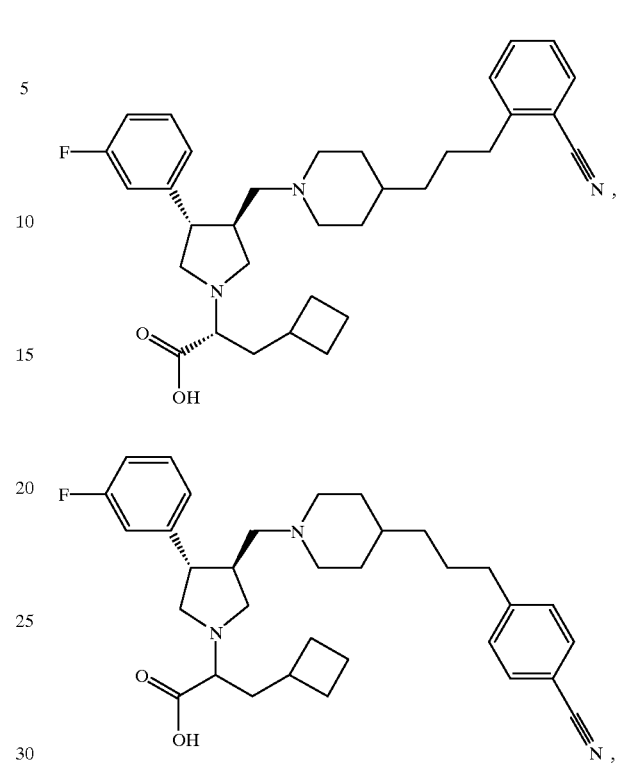
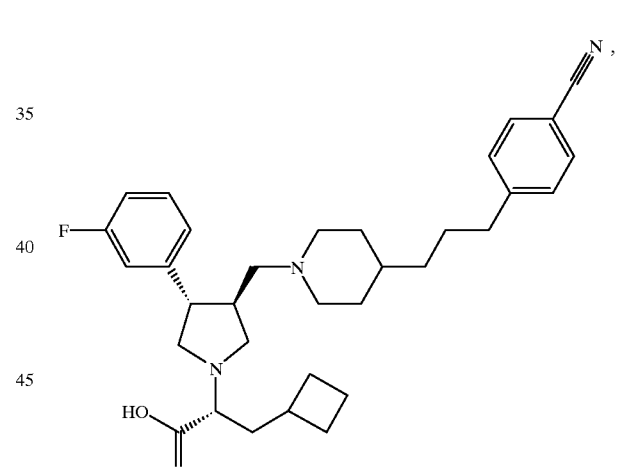

265
-continued
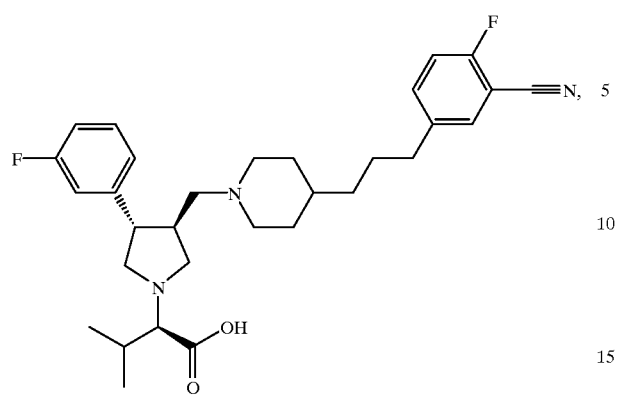
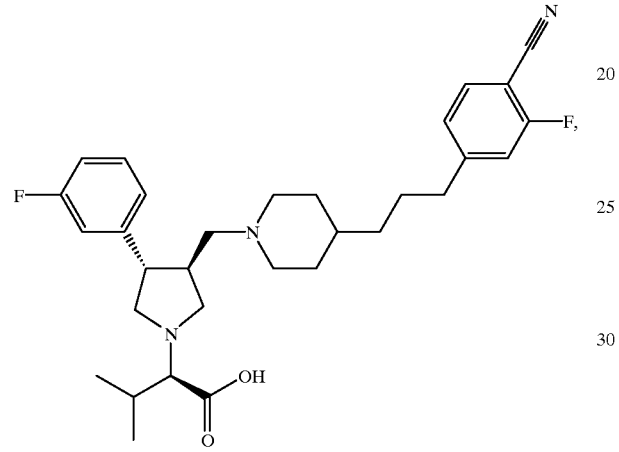
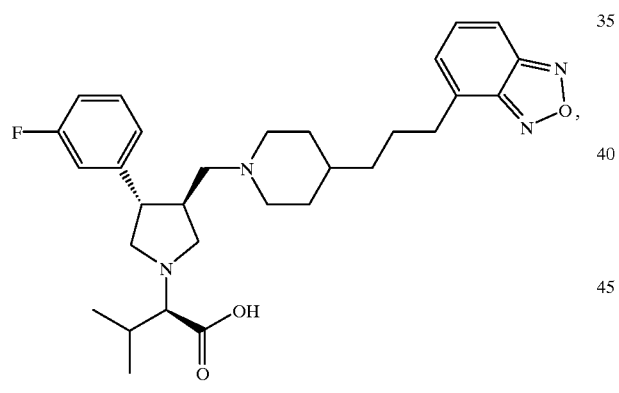
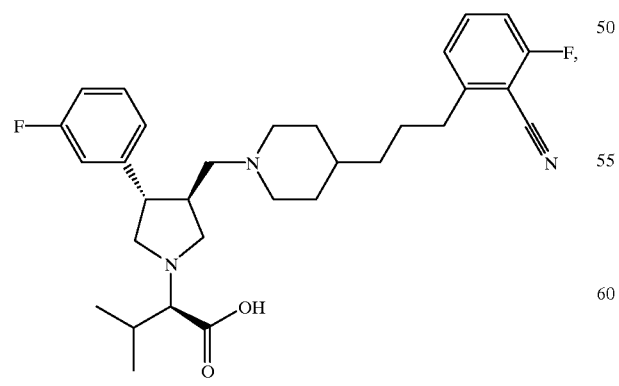
266
-continued
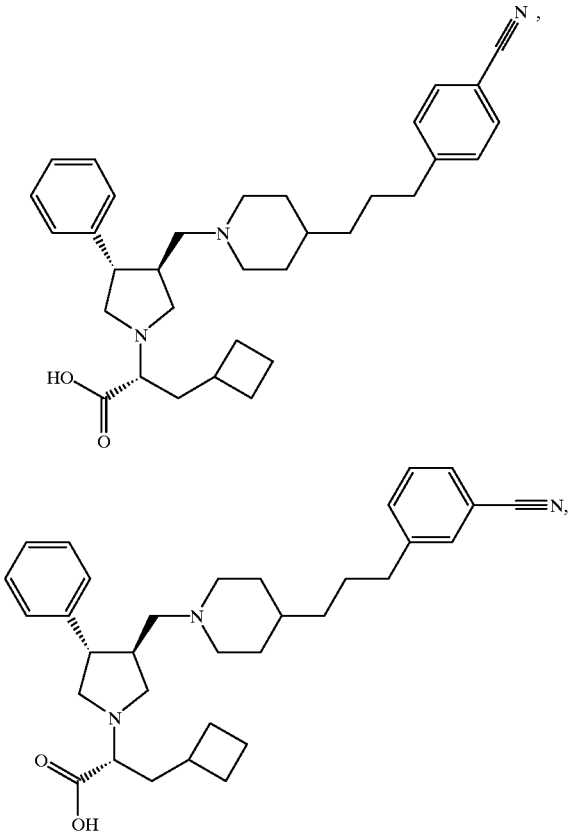
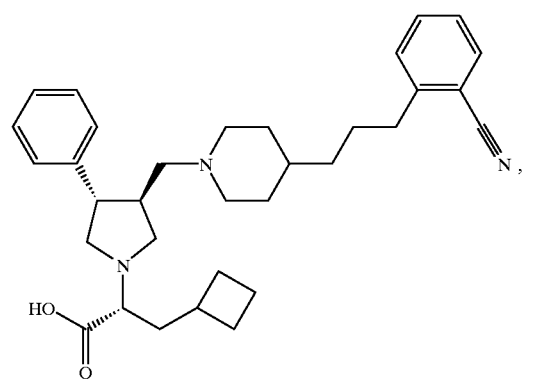
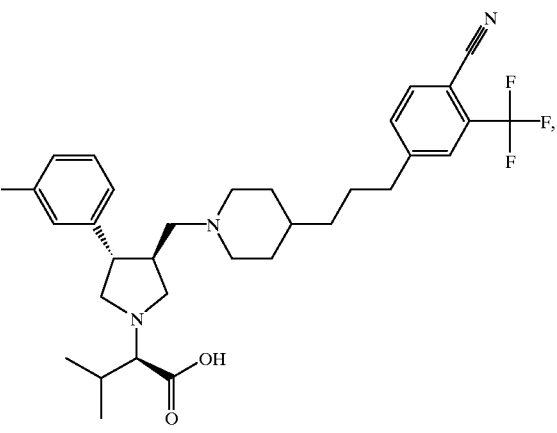

267
-continued
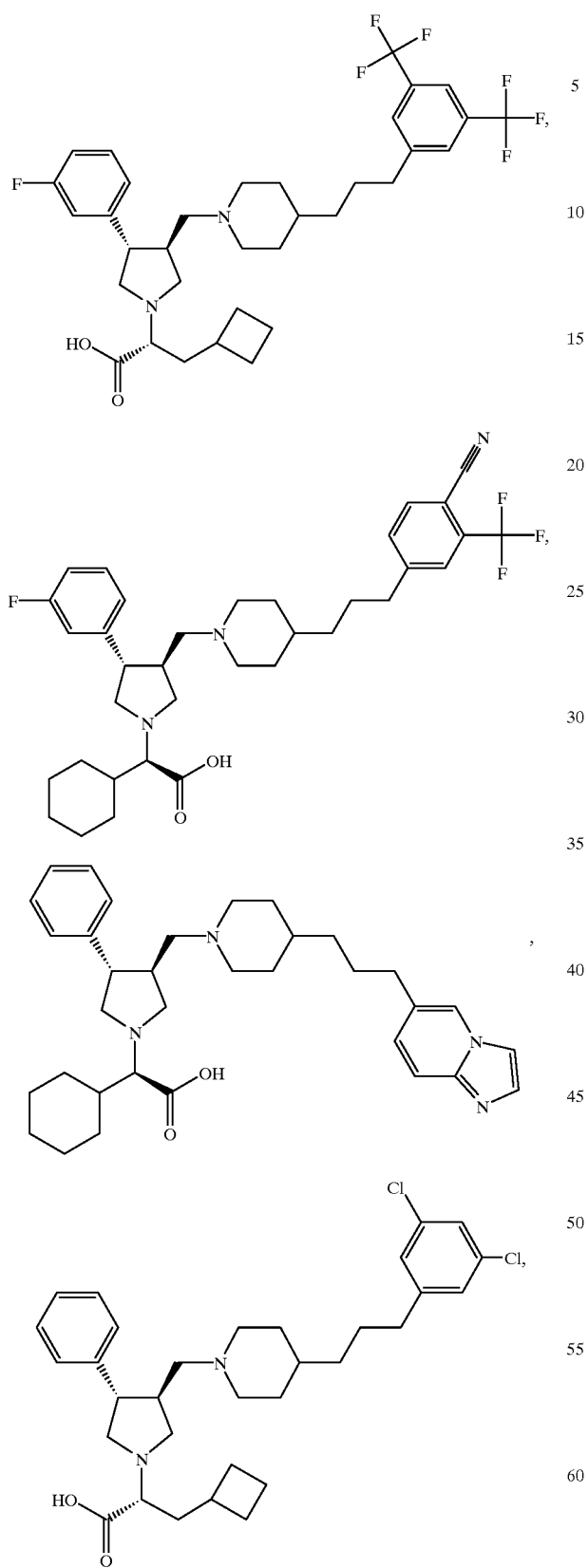
268
-continued
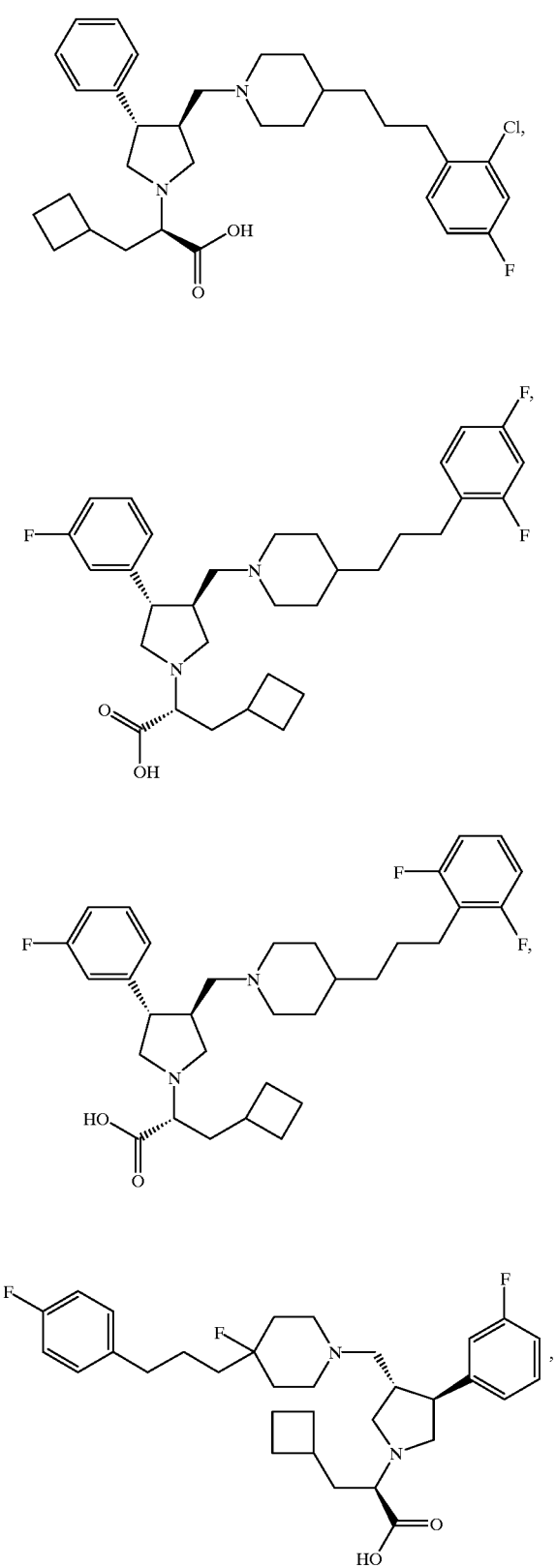

-continued
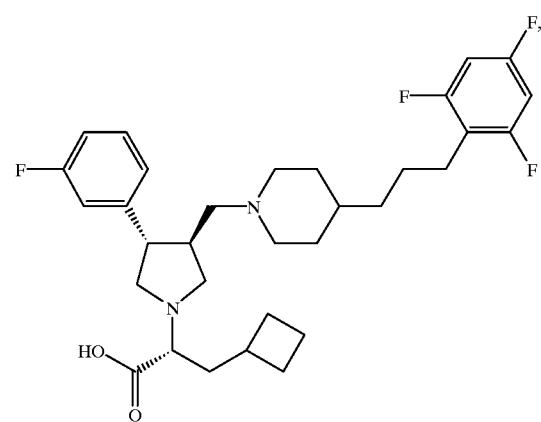
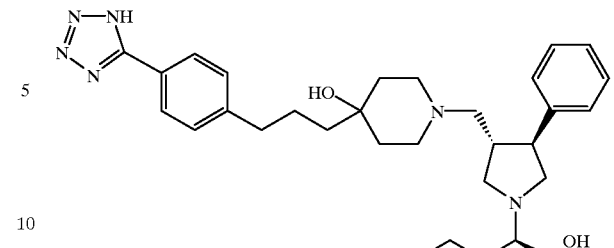
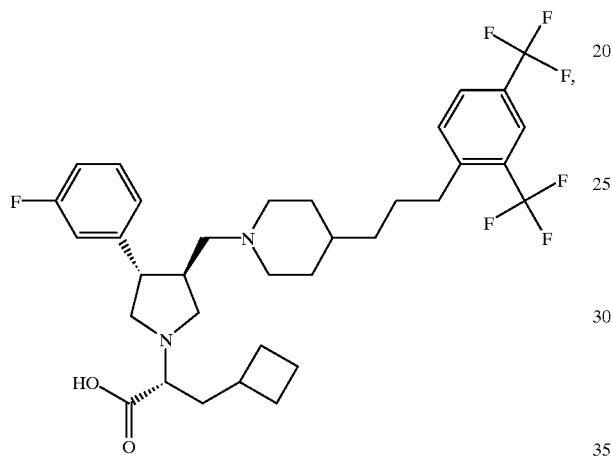
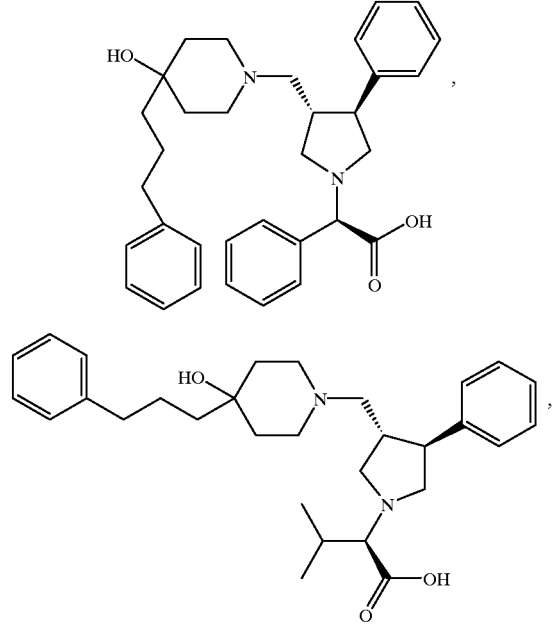
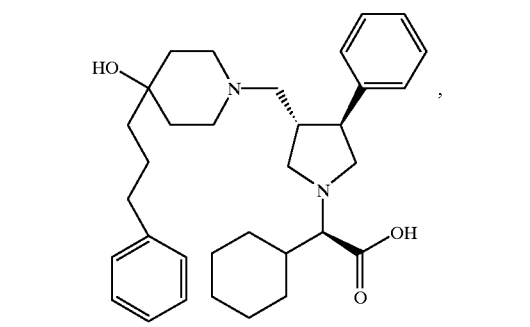
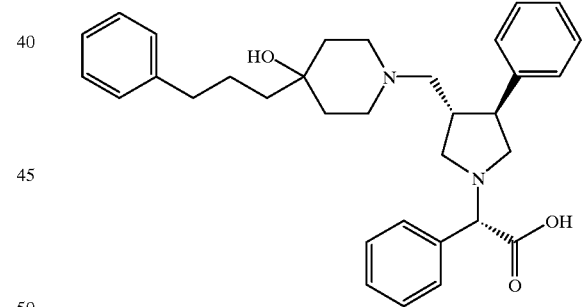
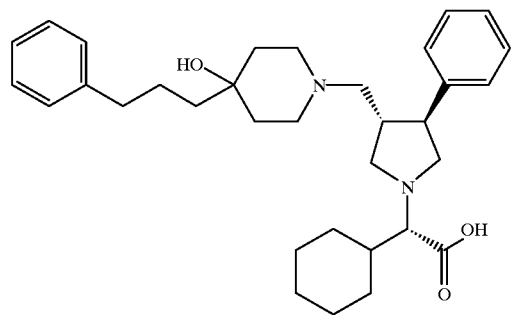
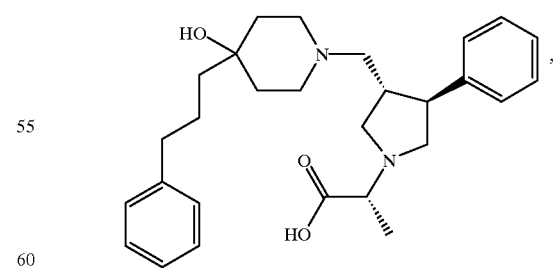

271
-continued
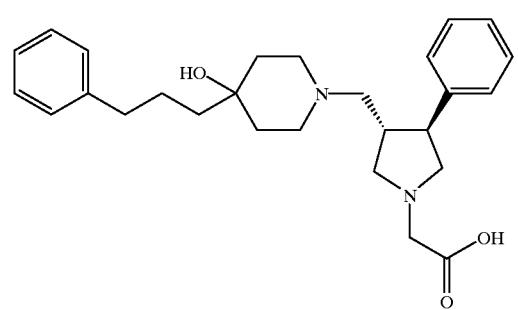
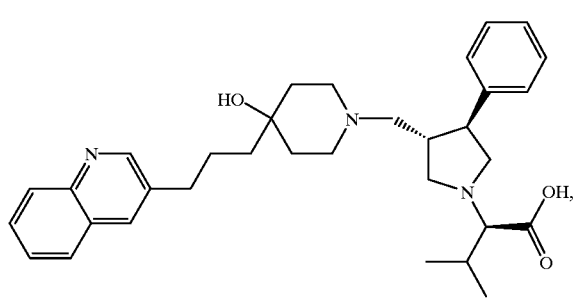
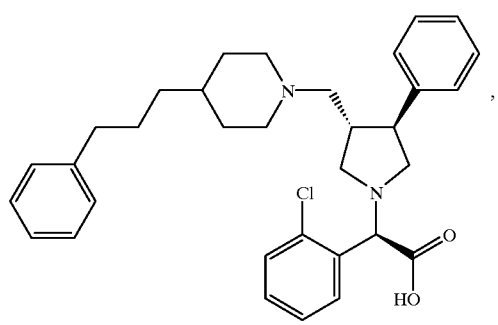
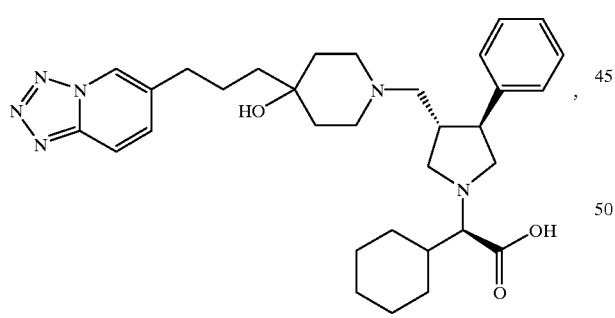
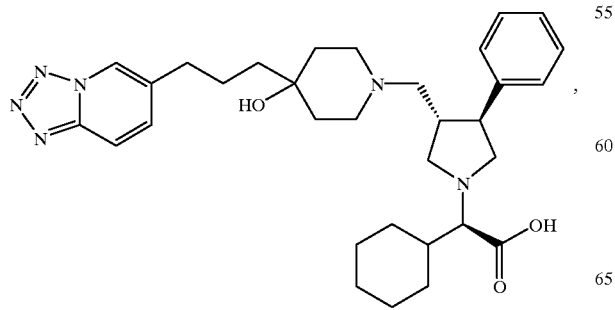
272
-continued
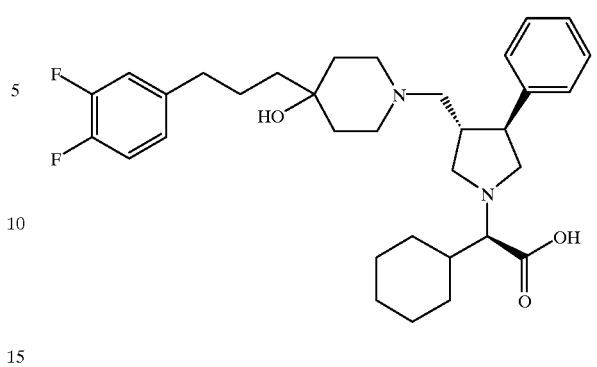
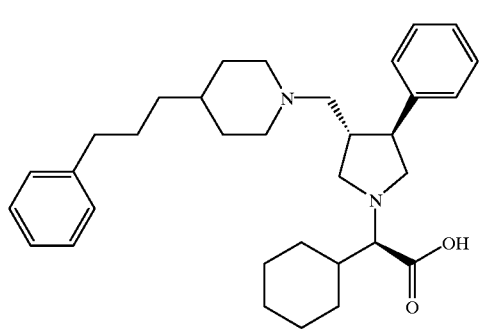
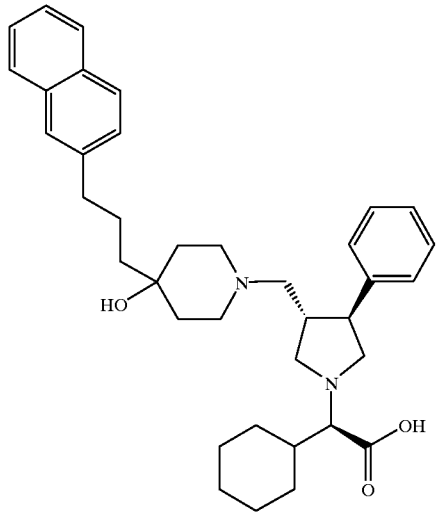
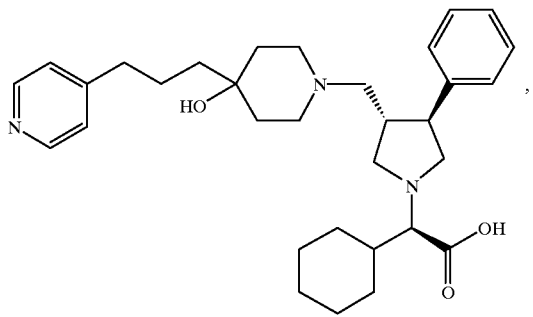

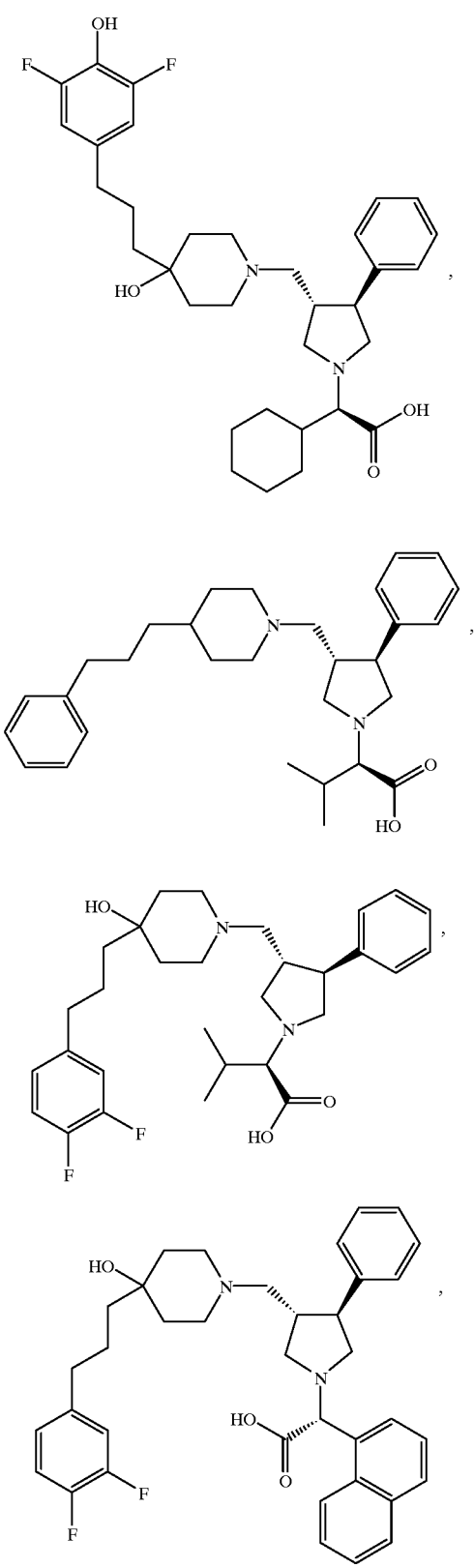
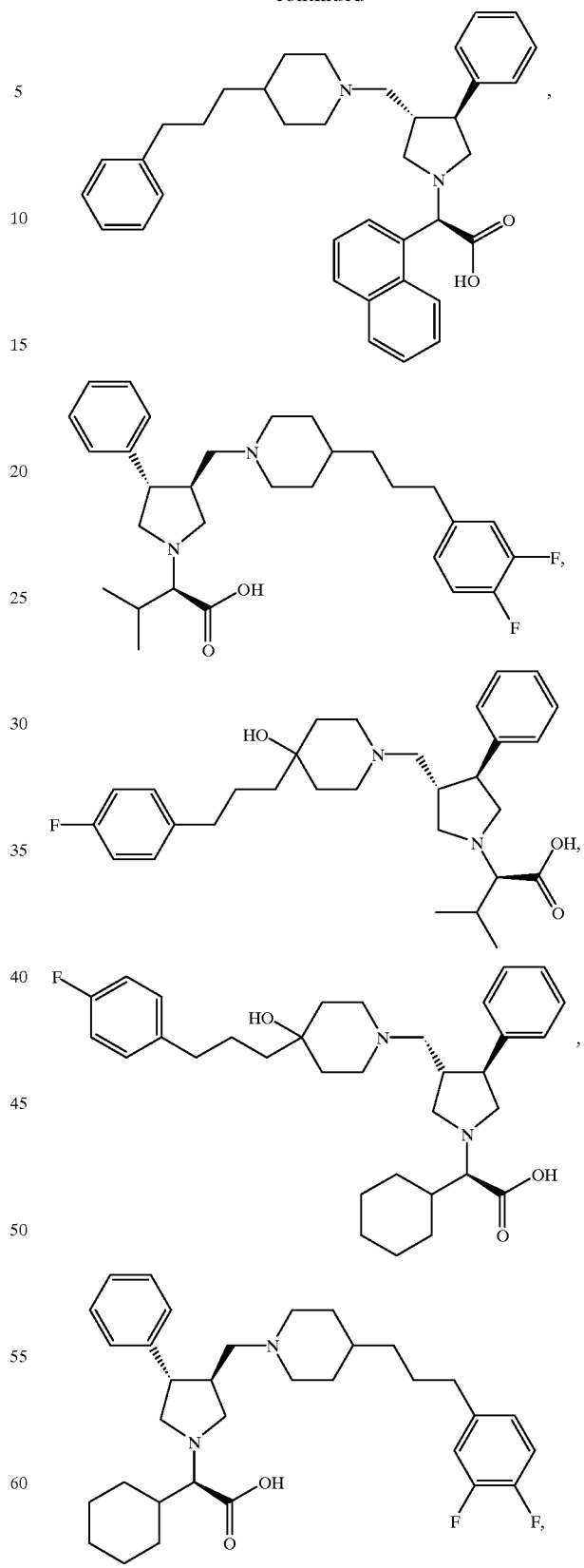

275
-continued
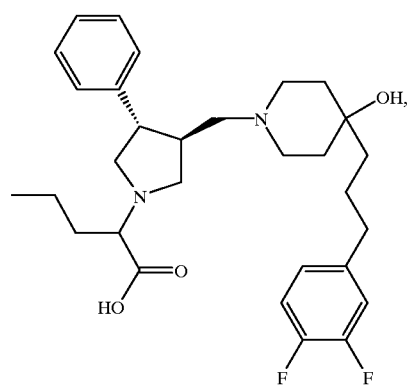
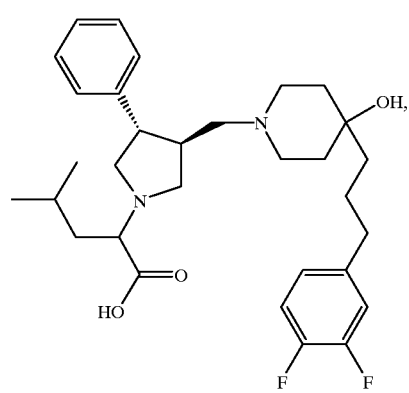
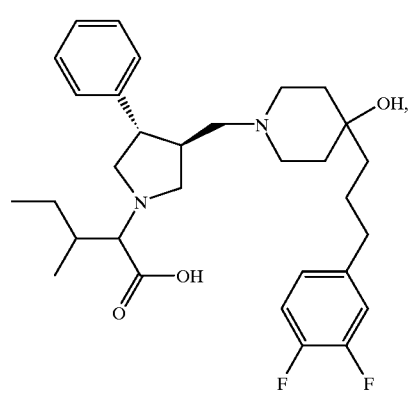
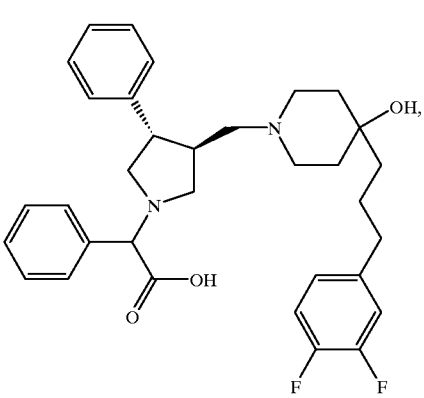
276
-continued
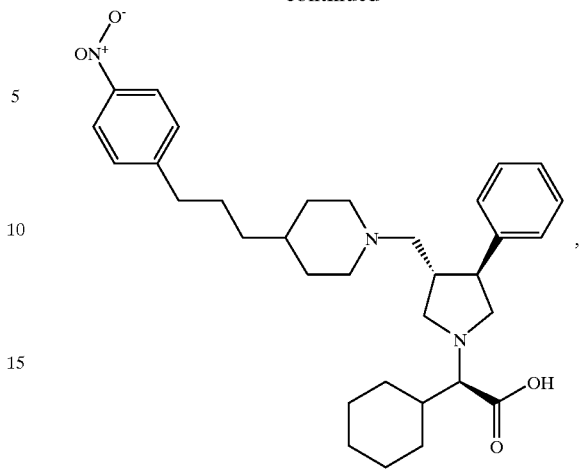
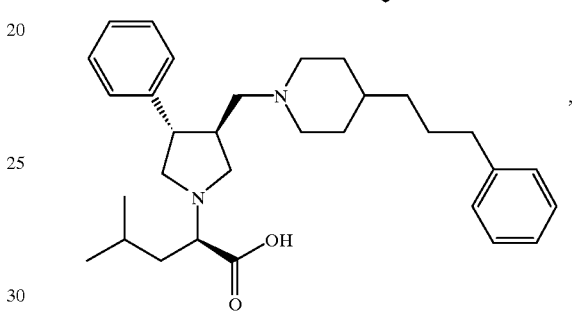
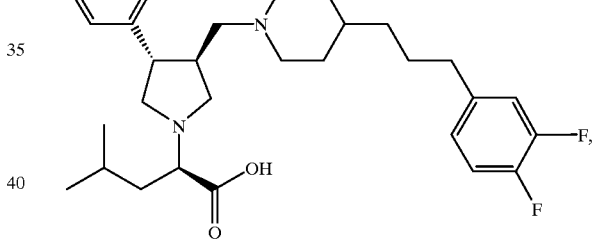
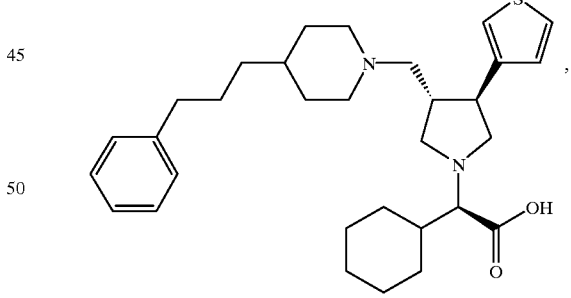
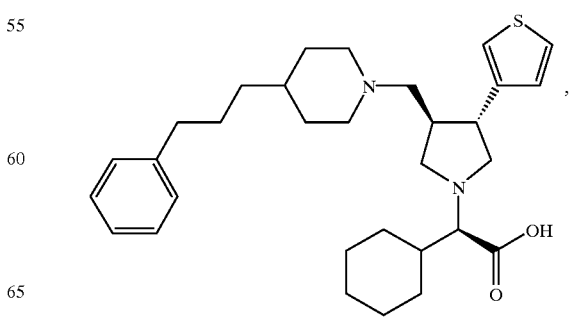

-continued
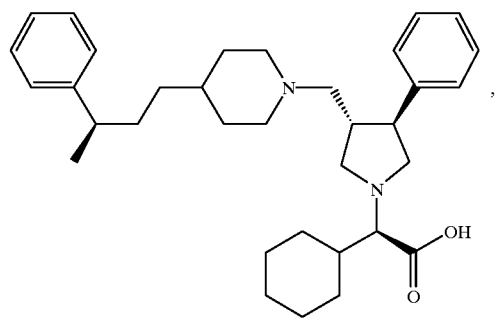
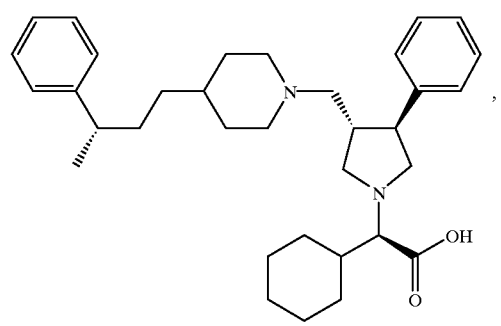
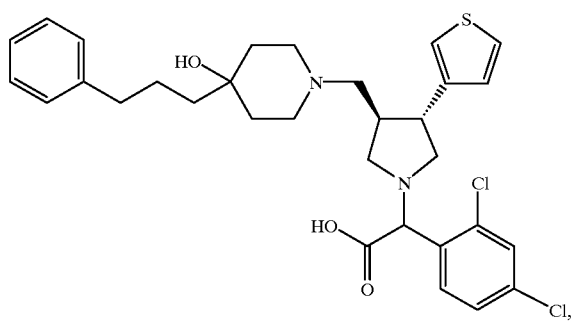
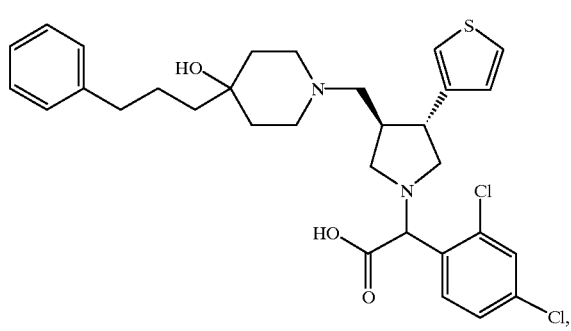
-continued
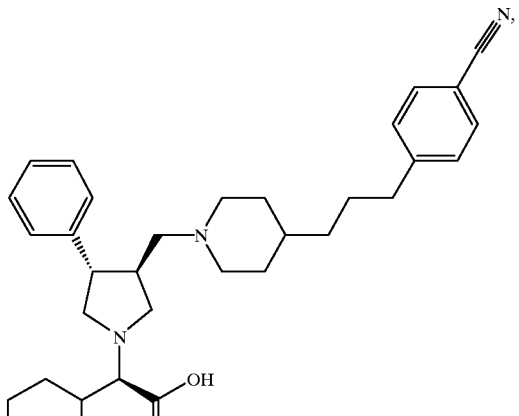
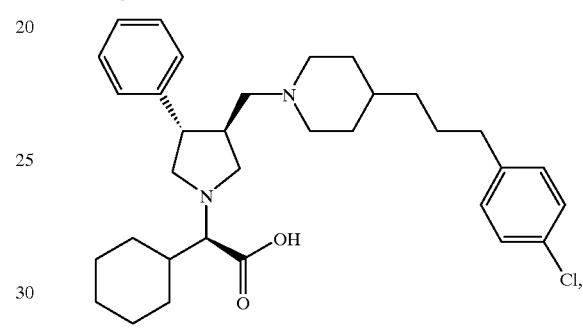
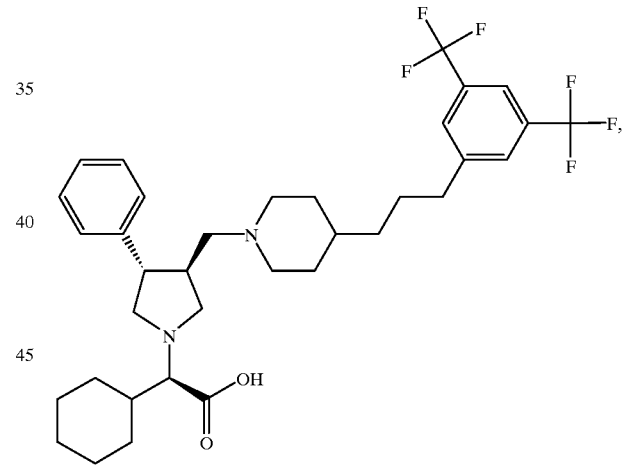
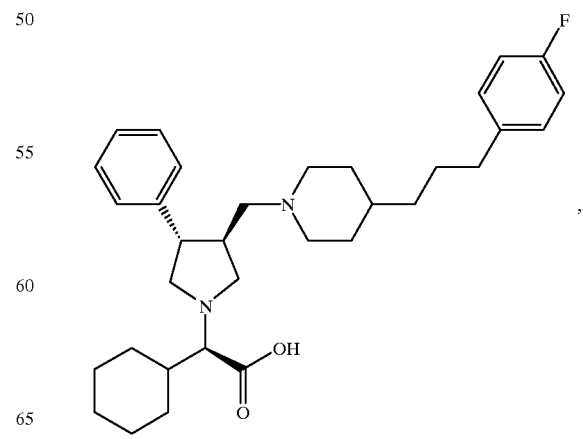

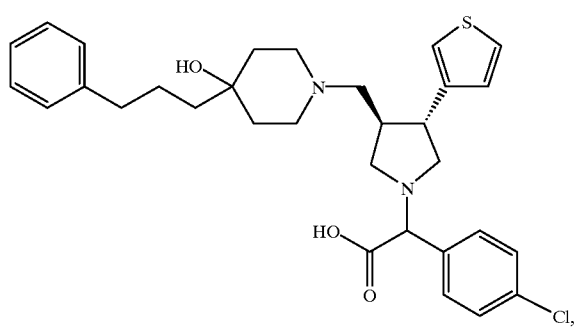
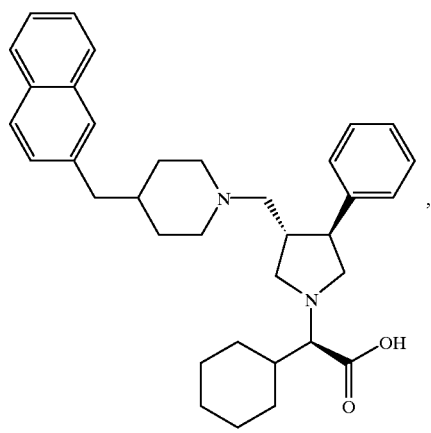
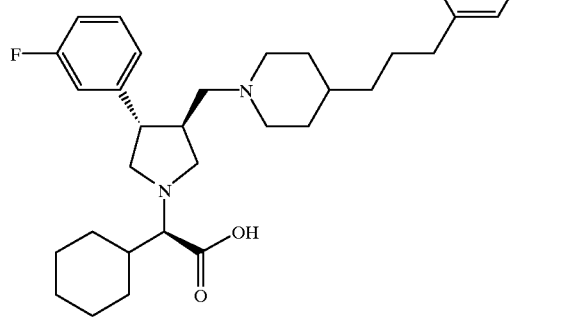
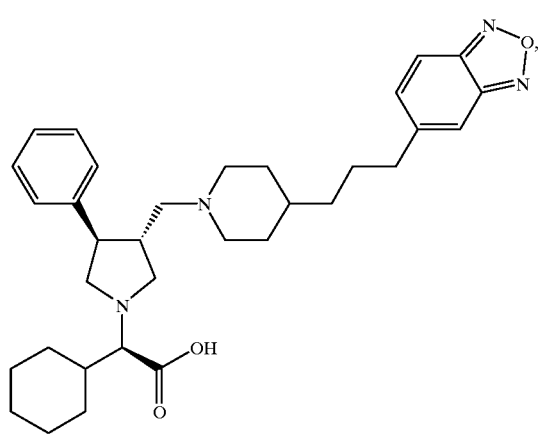
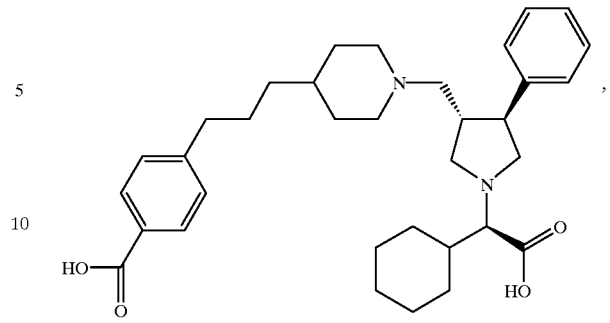
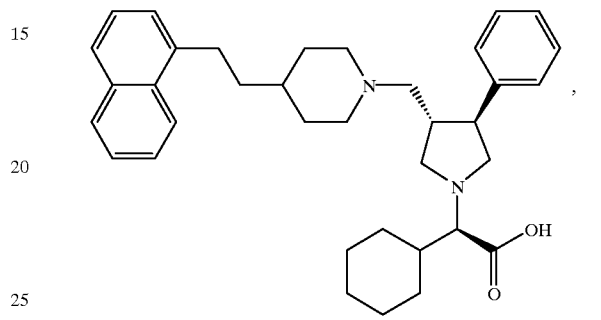
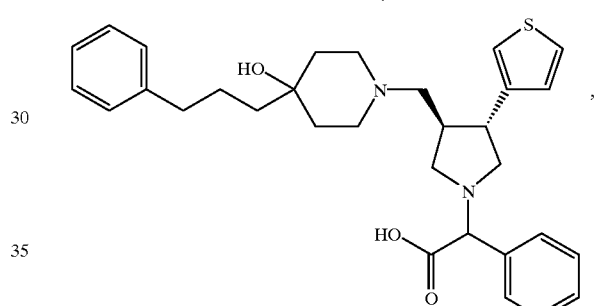
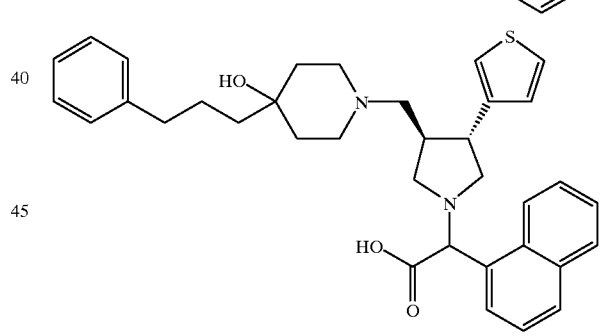
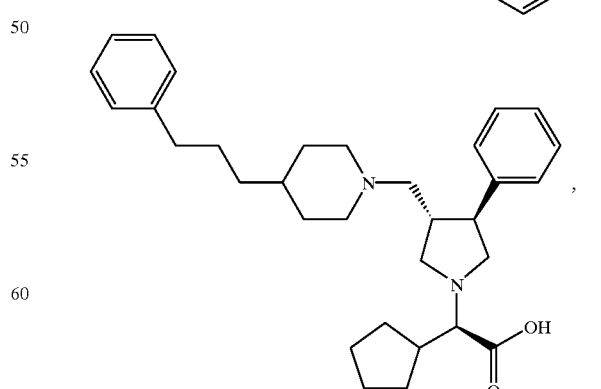

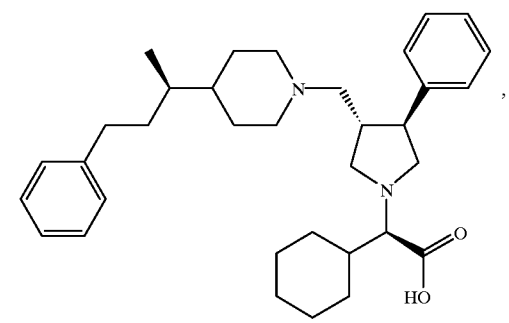
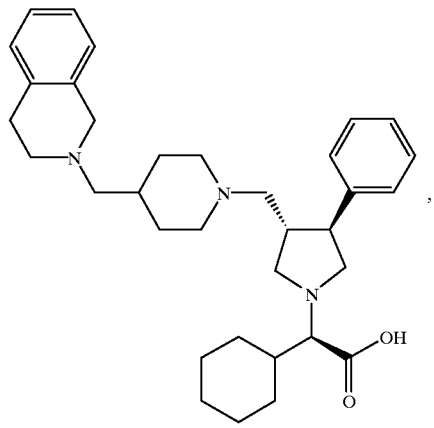
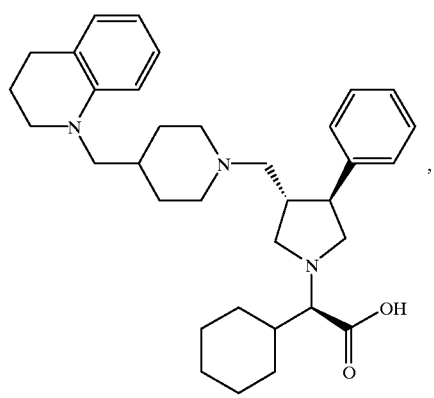
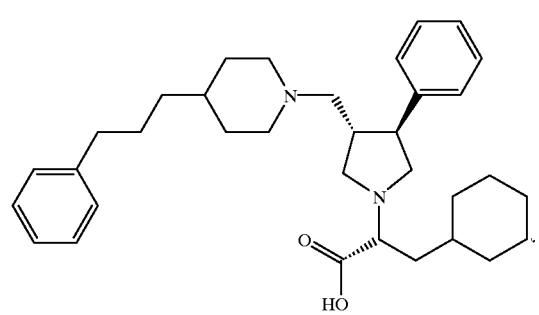
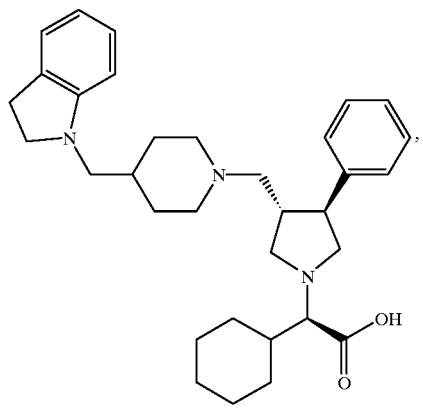

283
-continued
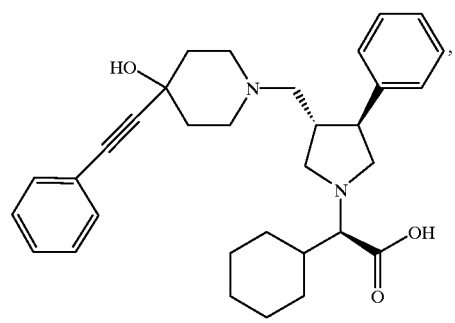
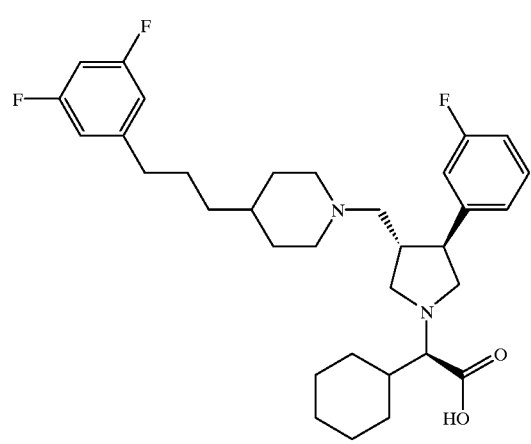
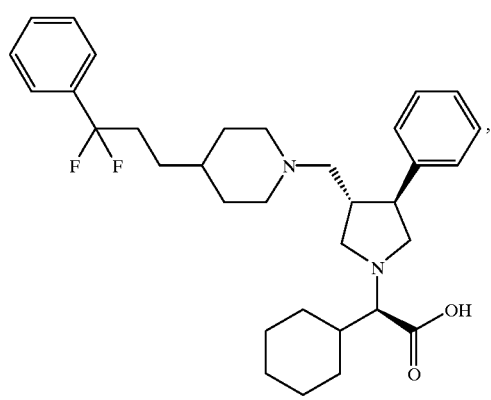
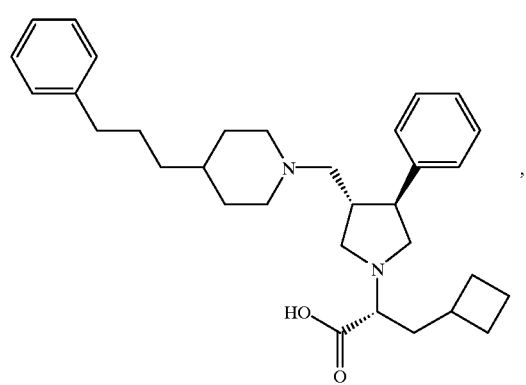
284
-continued
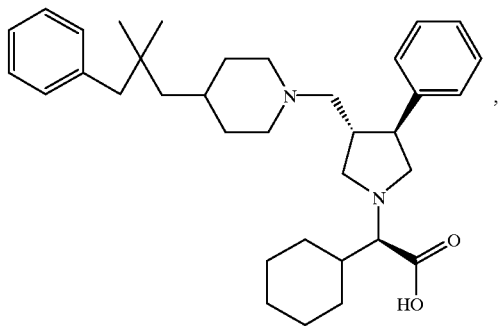
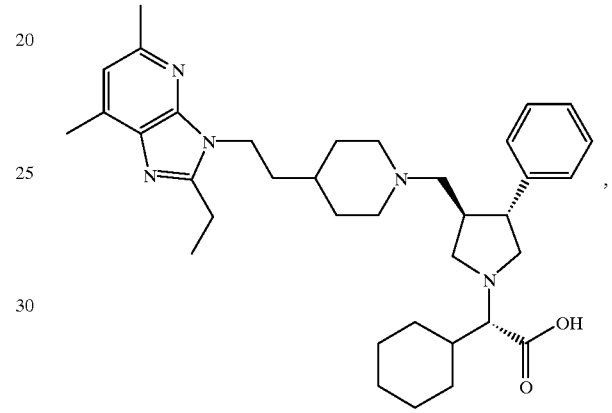
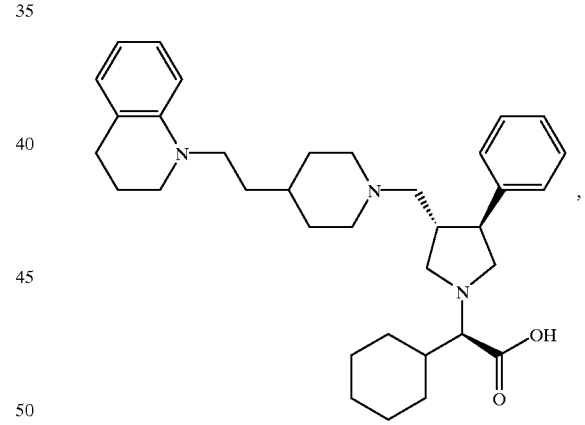
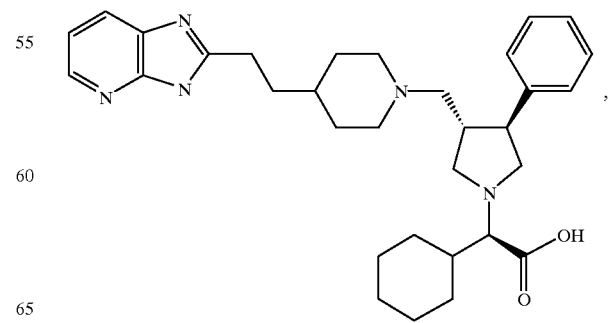

285
-continued
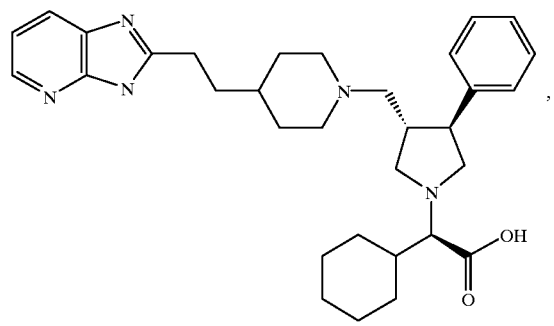
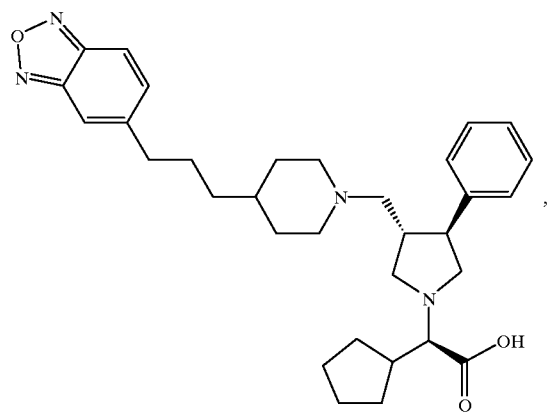
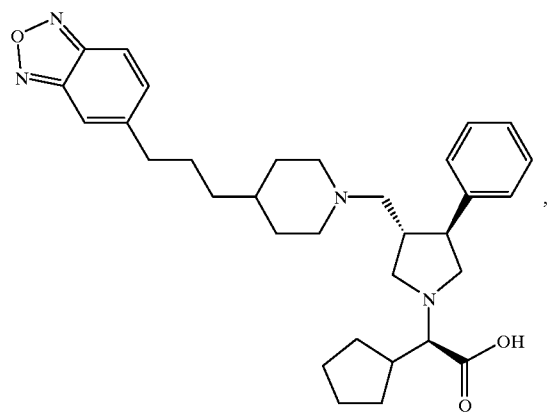
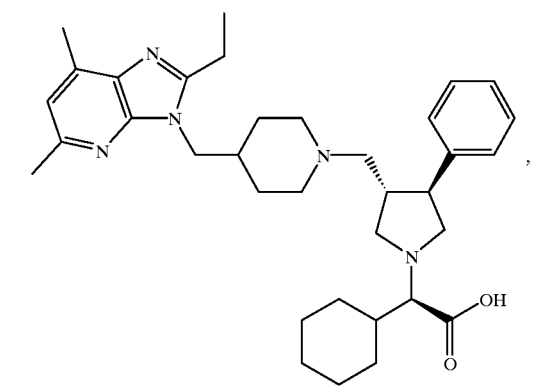
286
-continued
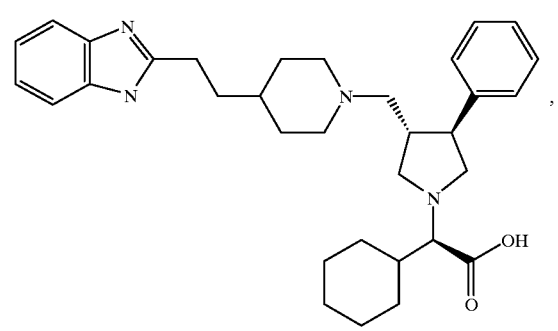
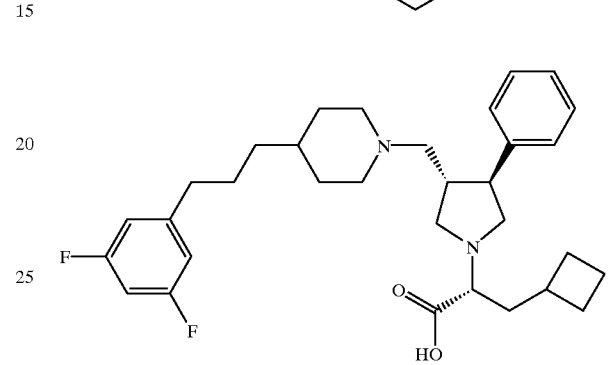
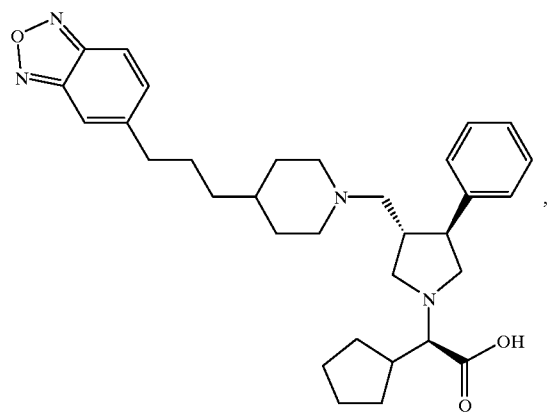
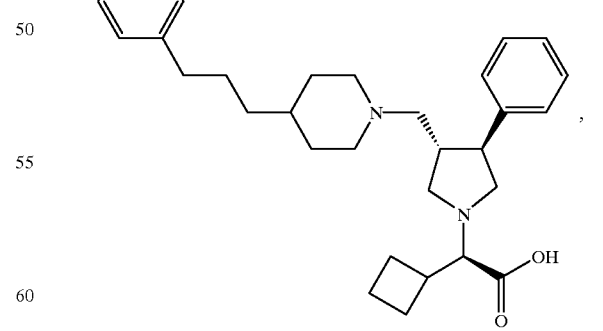

287
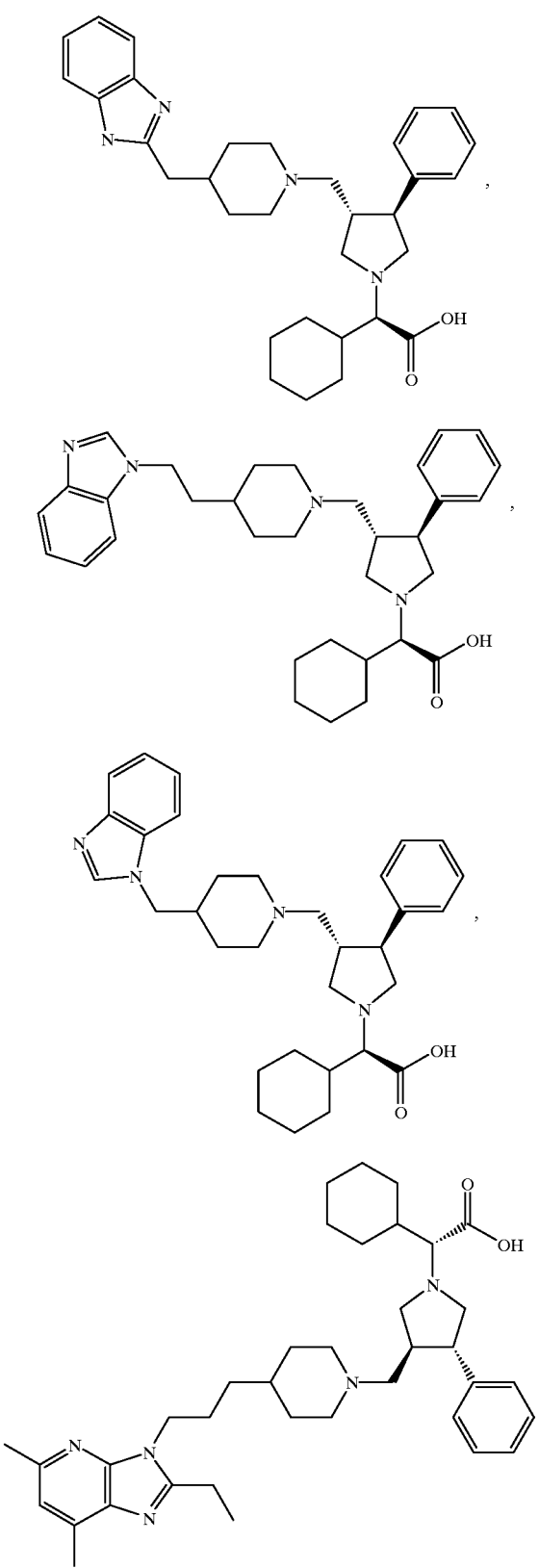
288
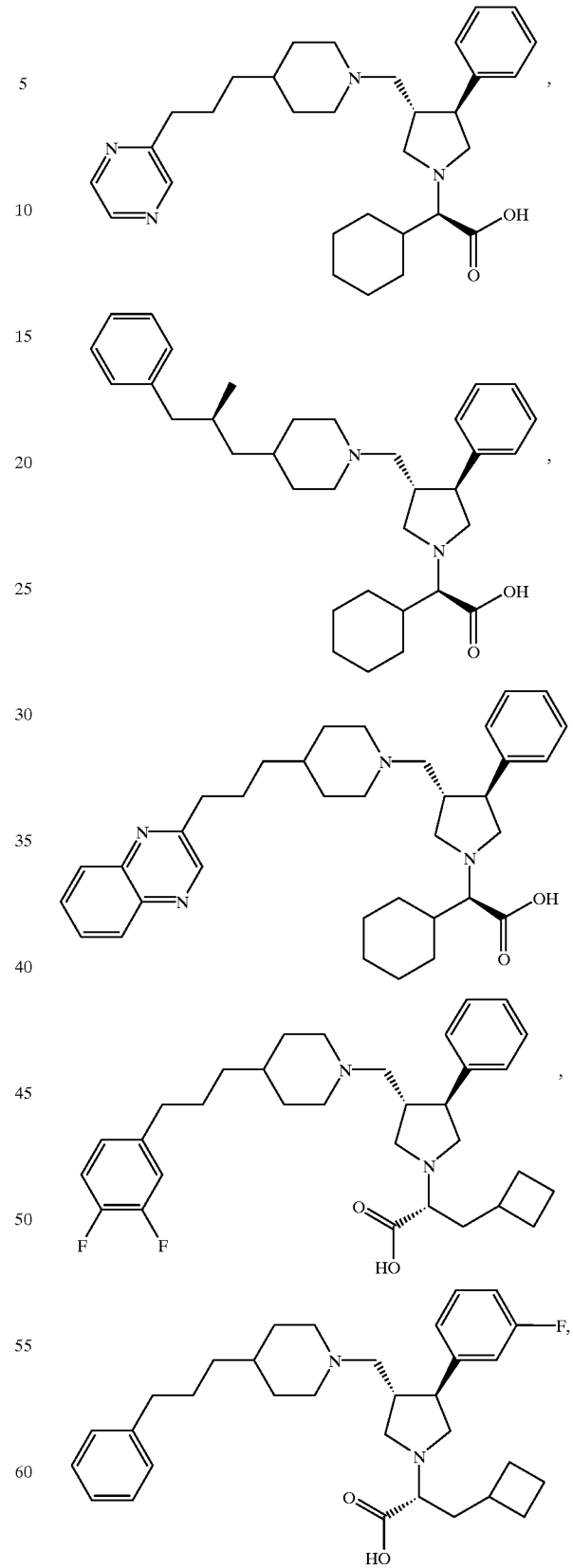

289
-continued
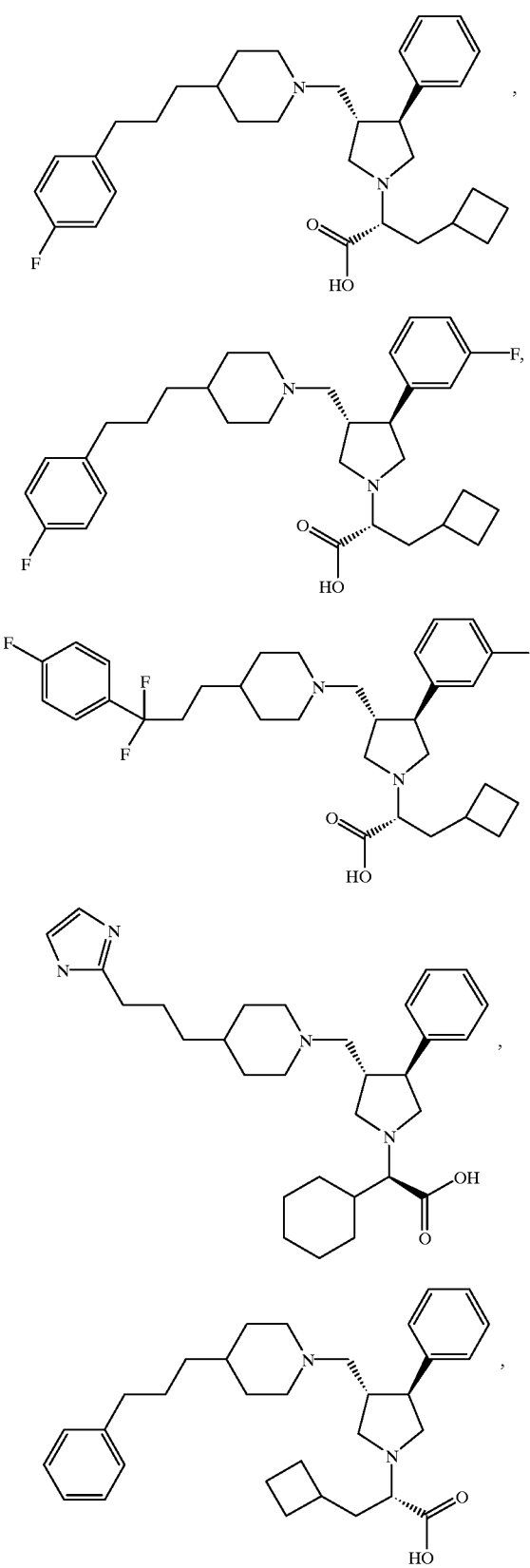
290
-continued
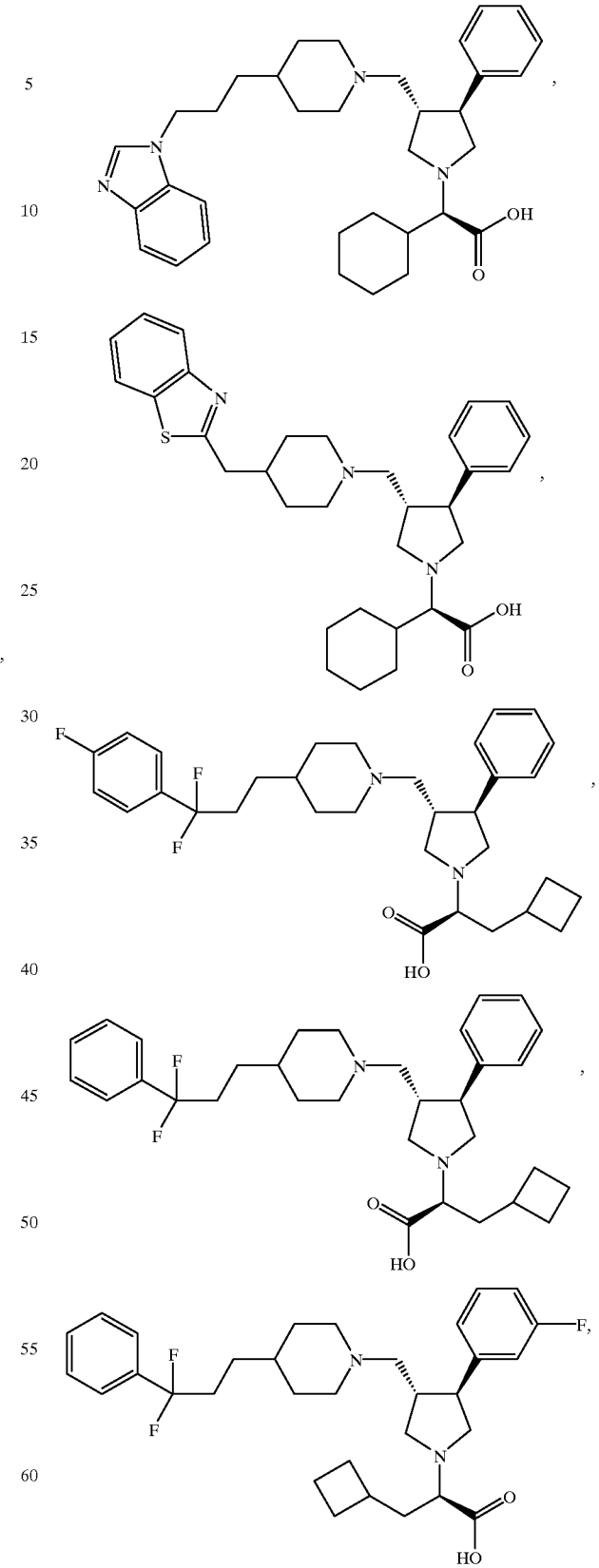

291
-continued
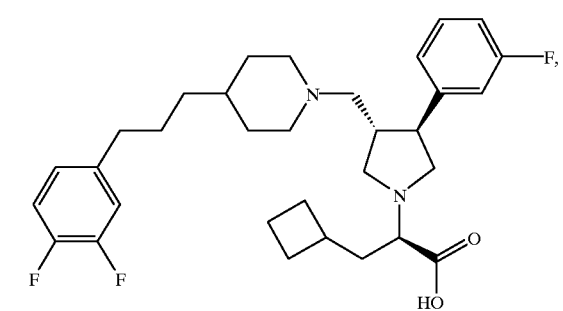
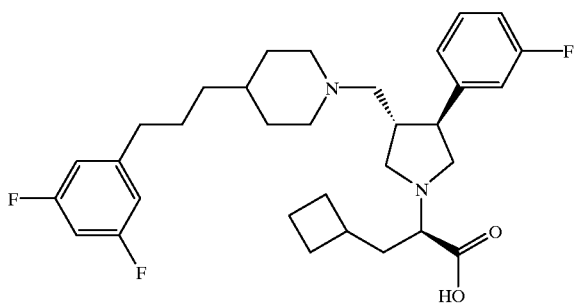
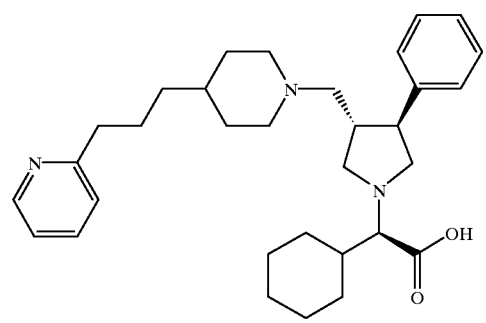
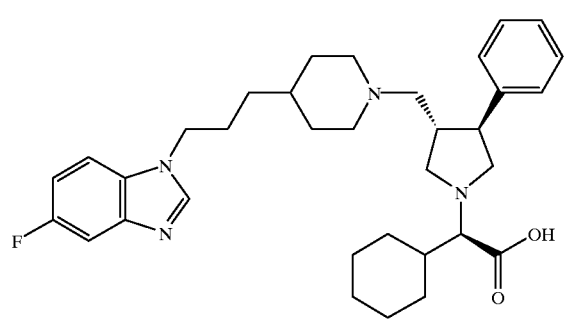
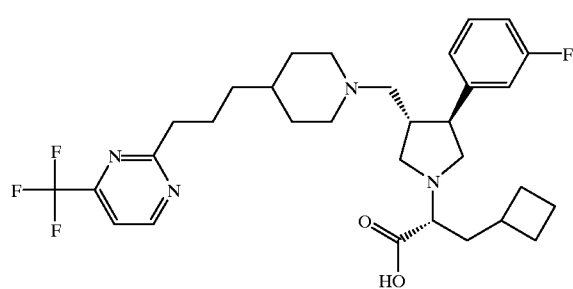
292
-continued
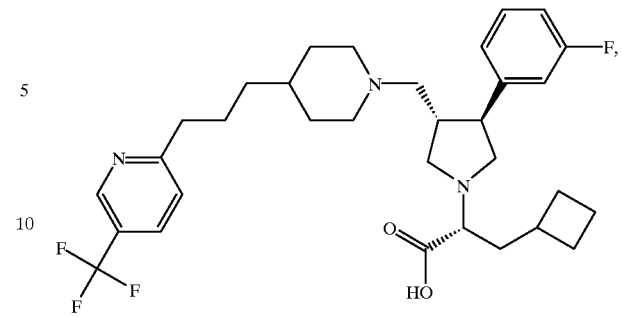
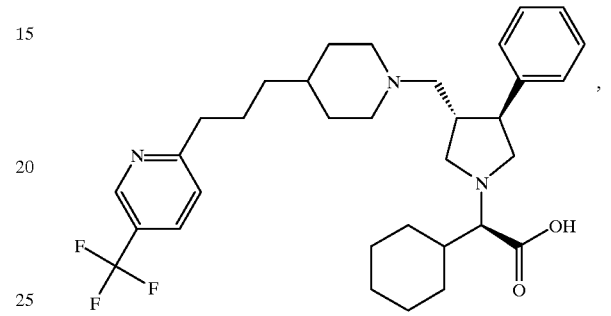
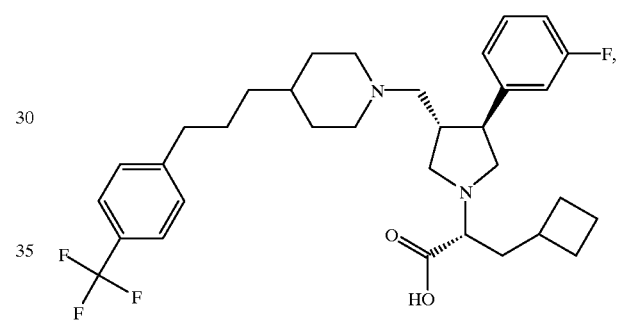
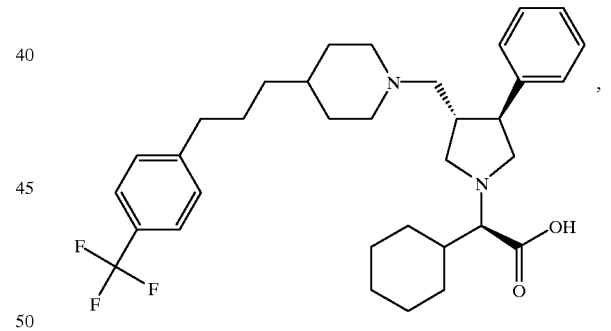
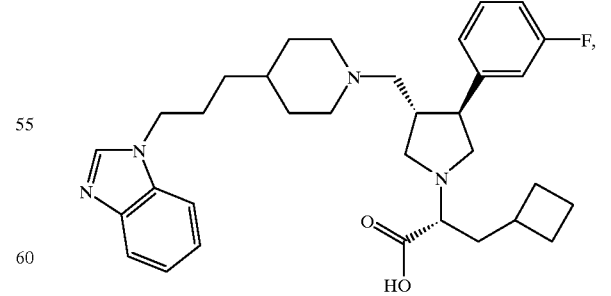

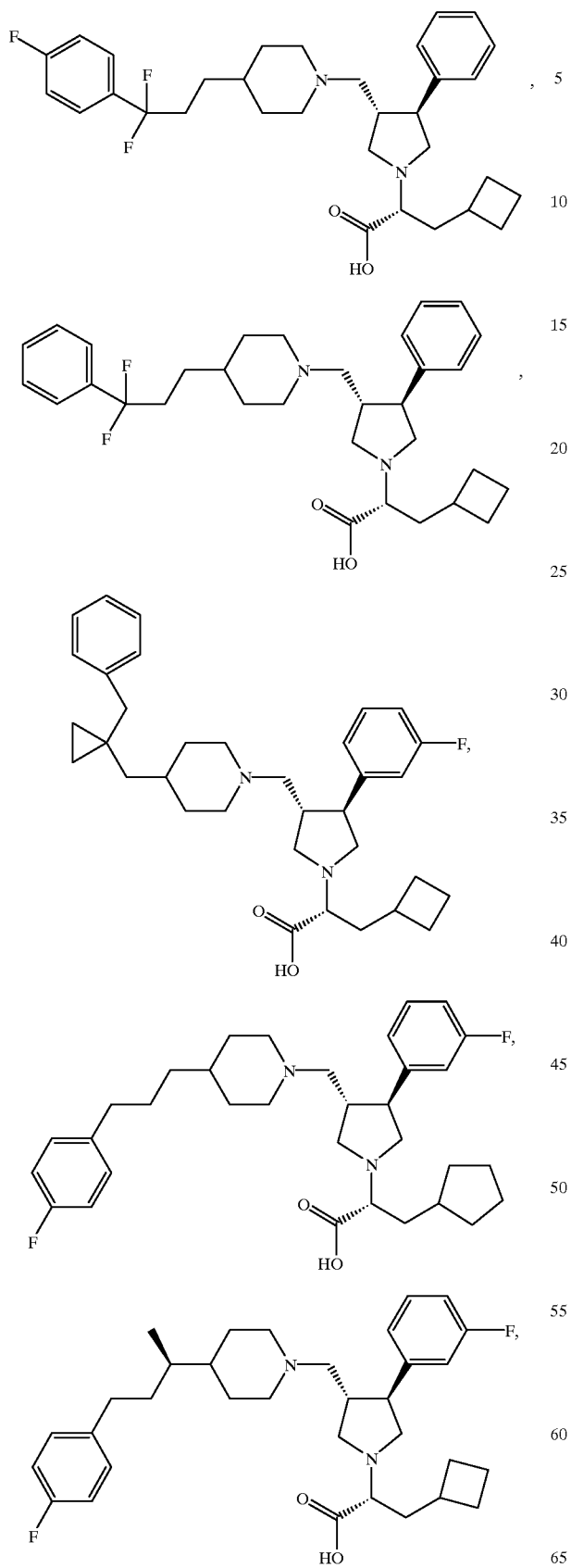
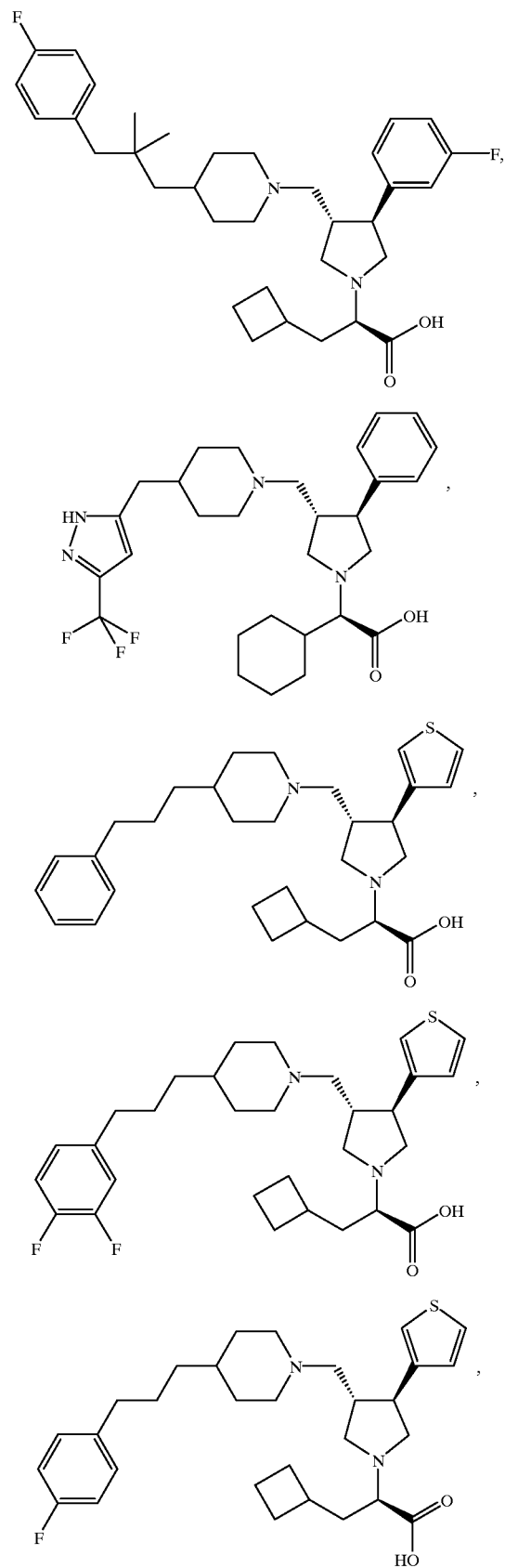

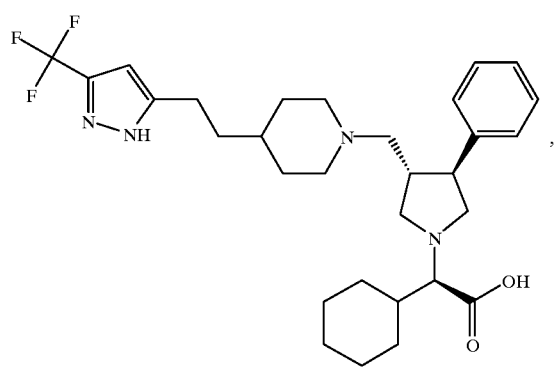
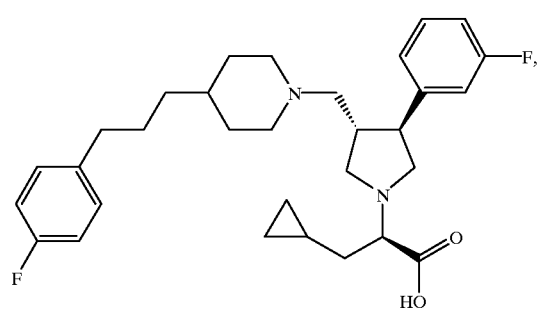
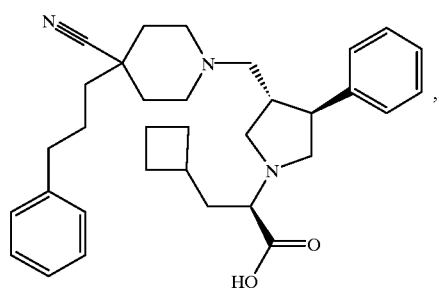
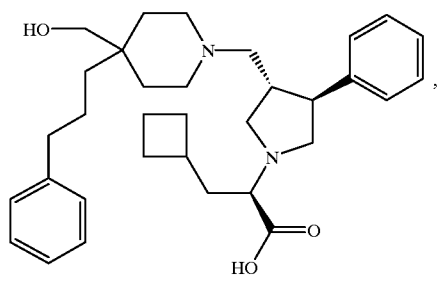
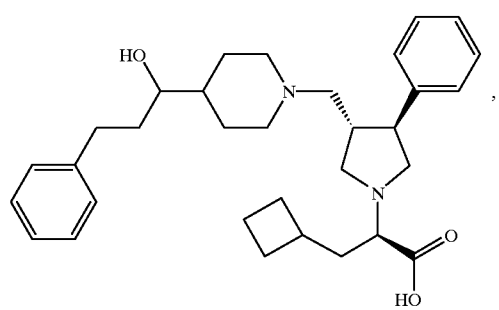
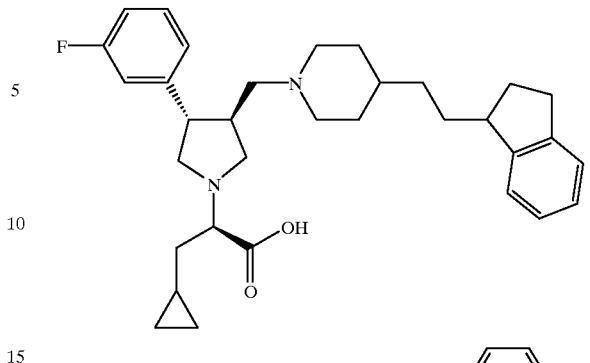
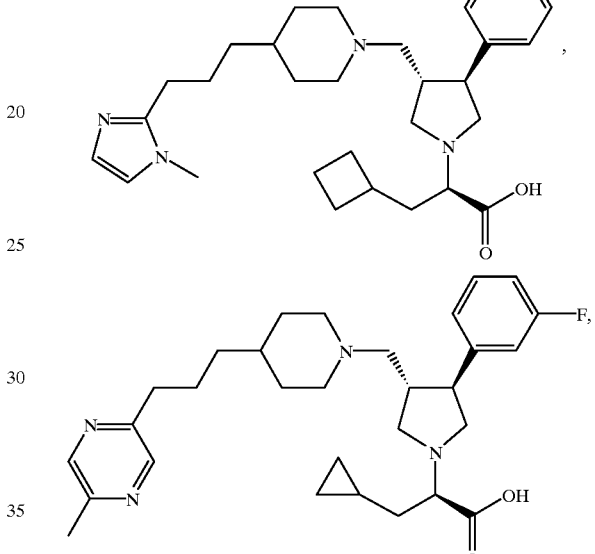
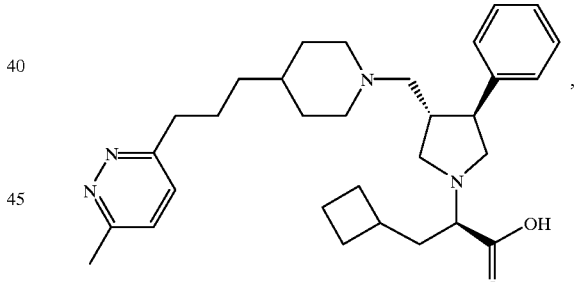
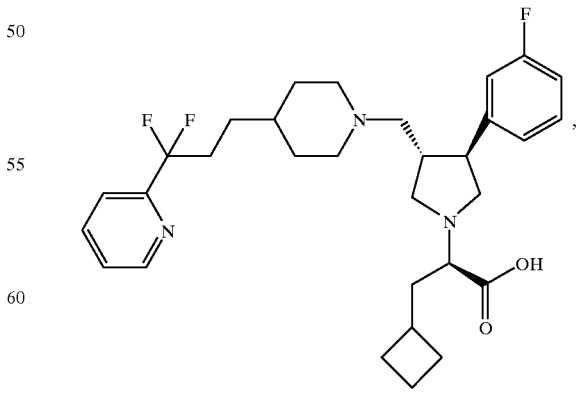

297
-continued
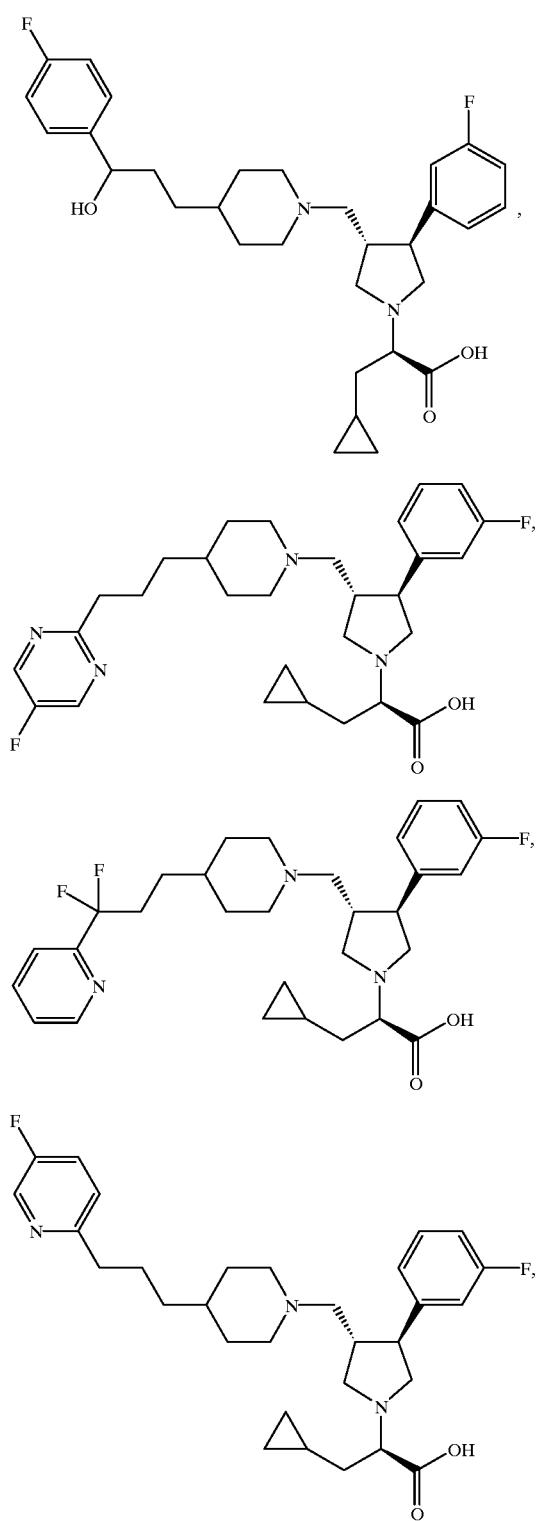
298
-continued
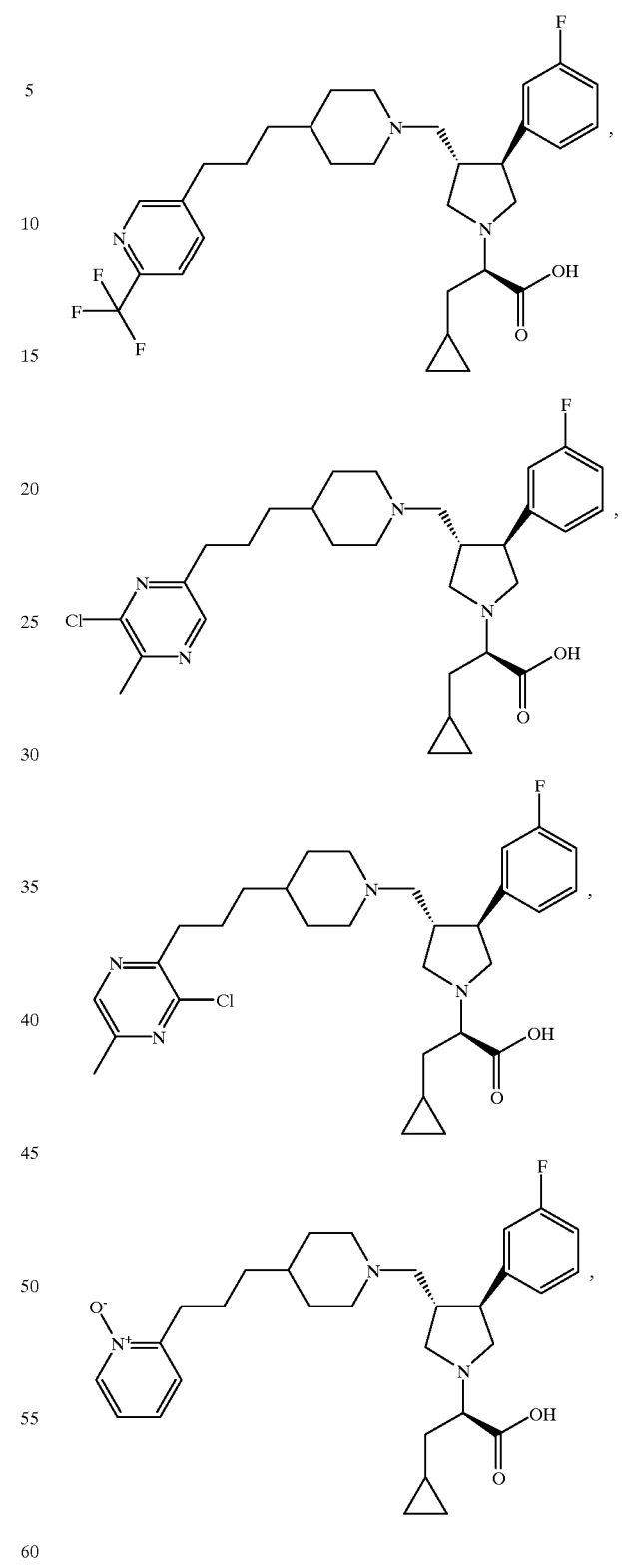

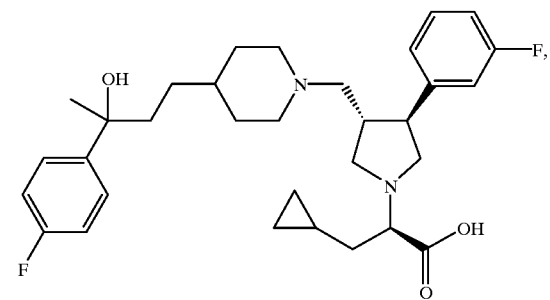
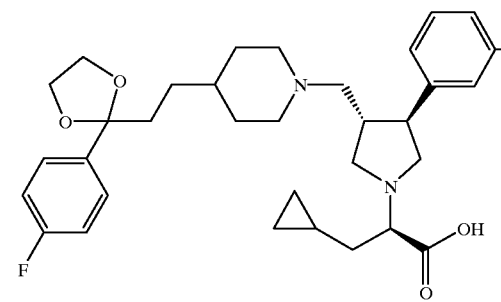
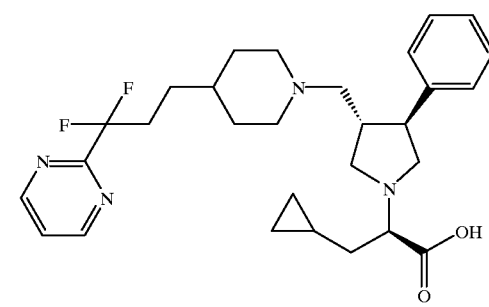
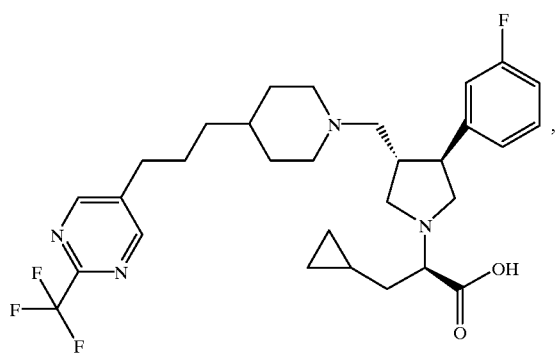
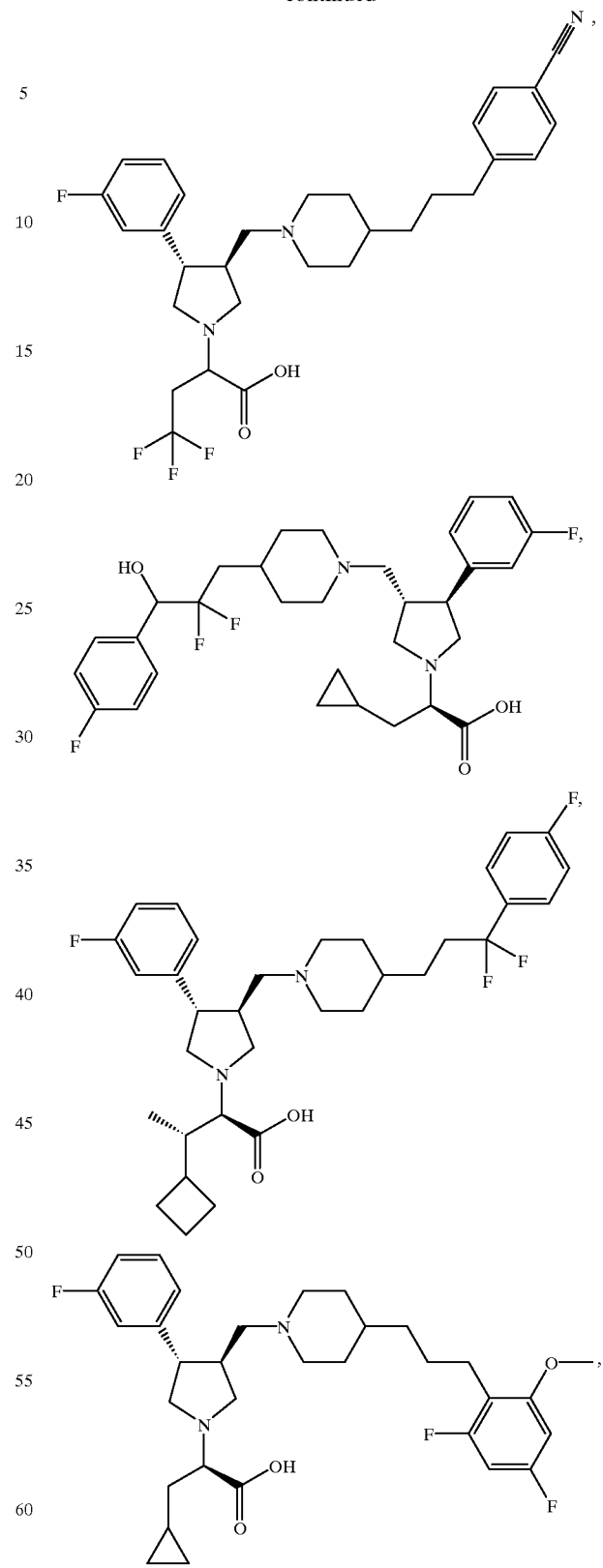

301
-continued
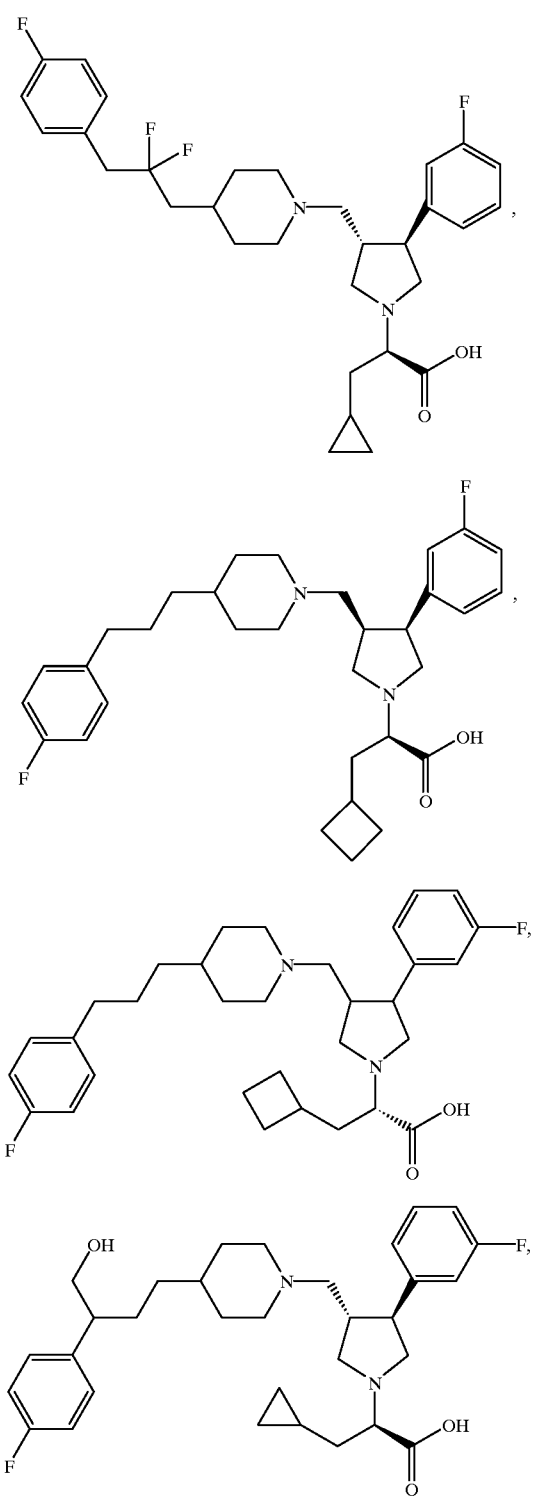
302
-continued
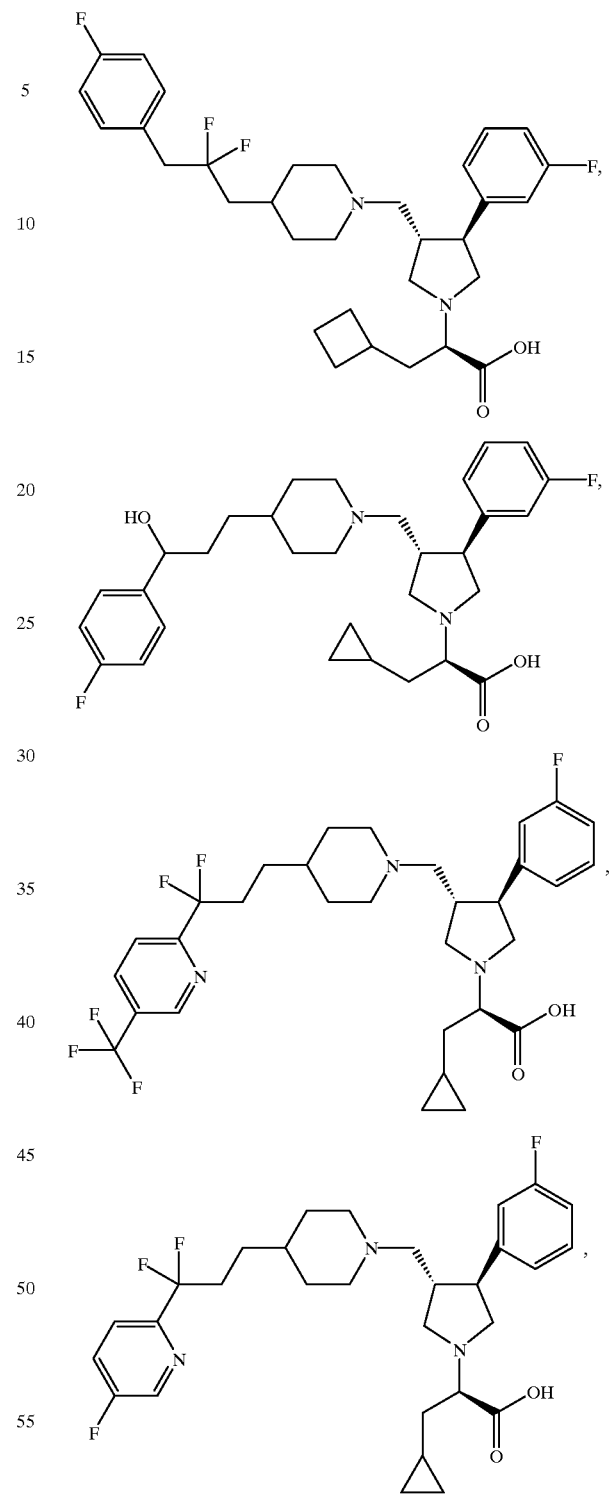

303
-continued
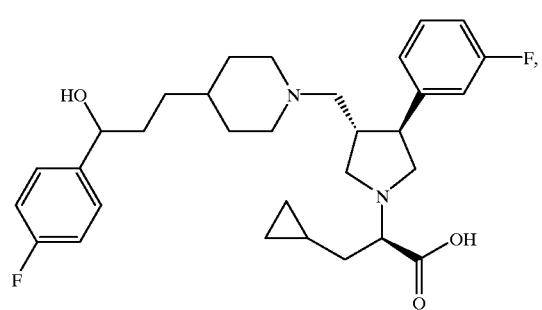
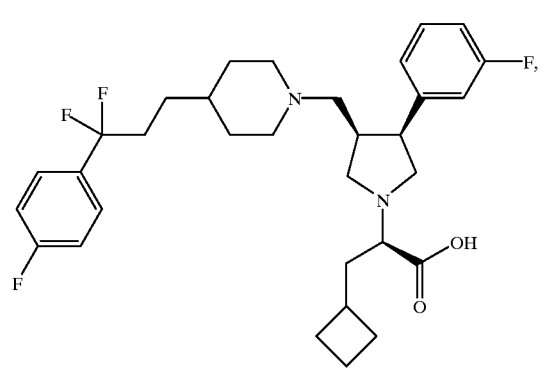
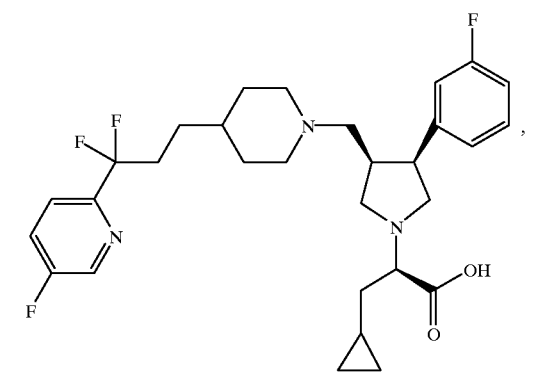
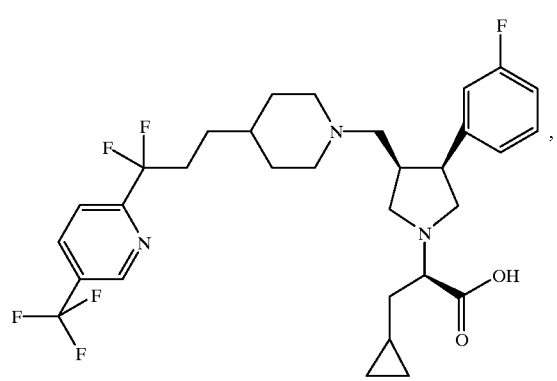
304
-continued
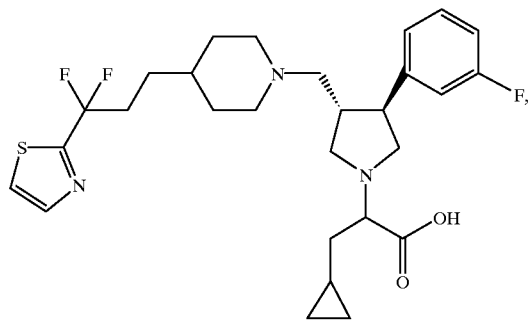
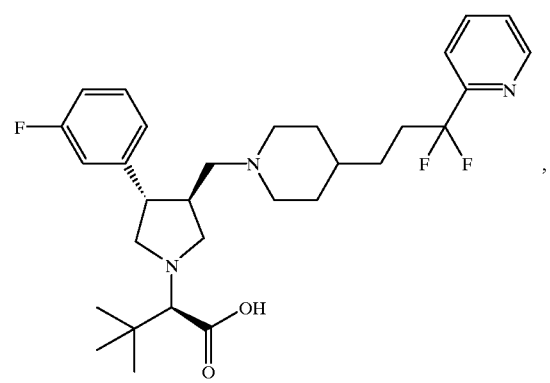
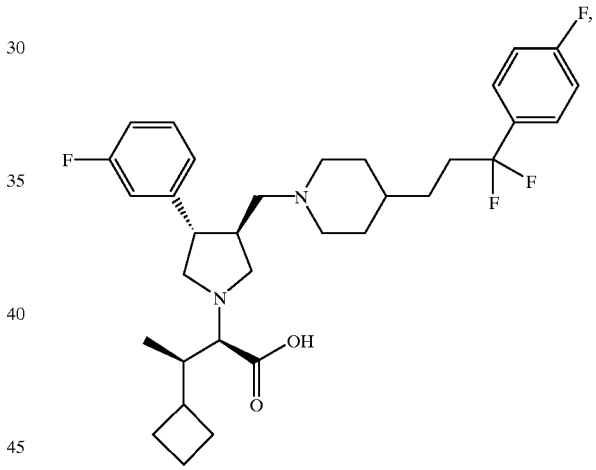
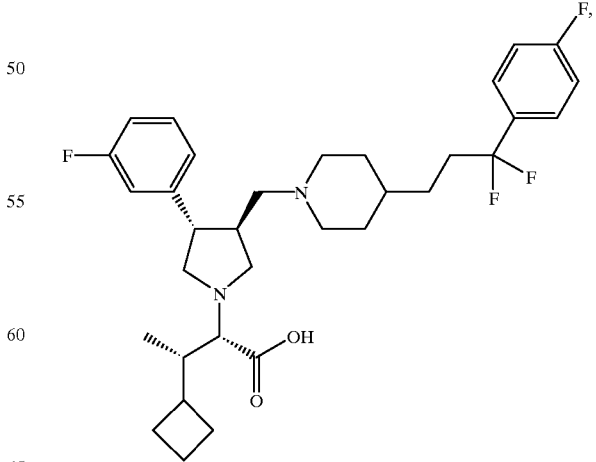

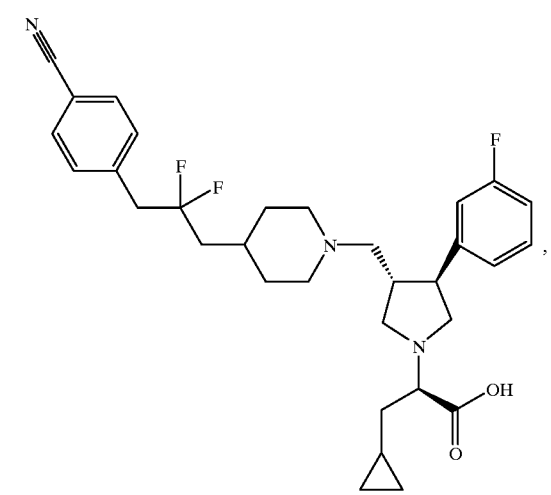
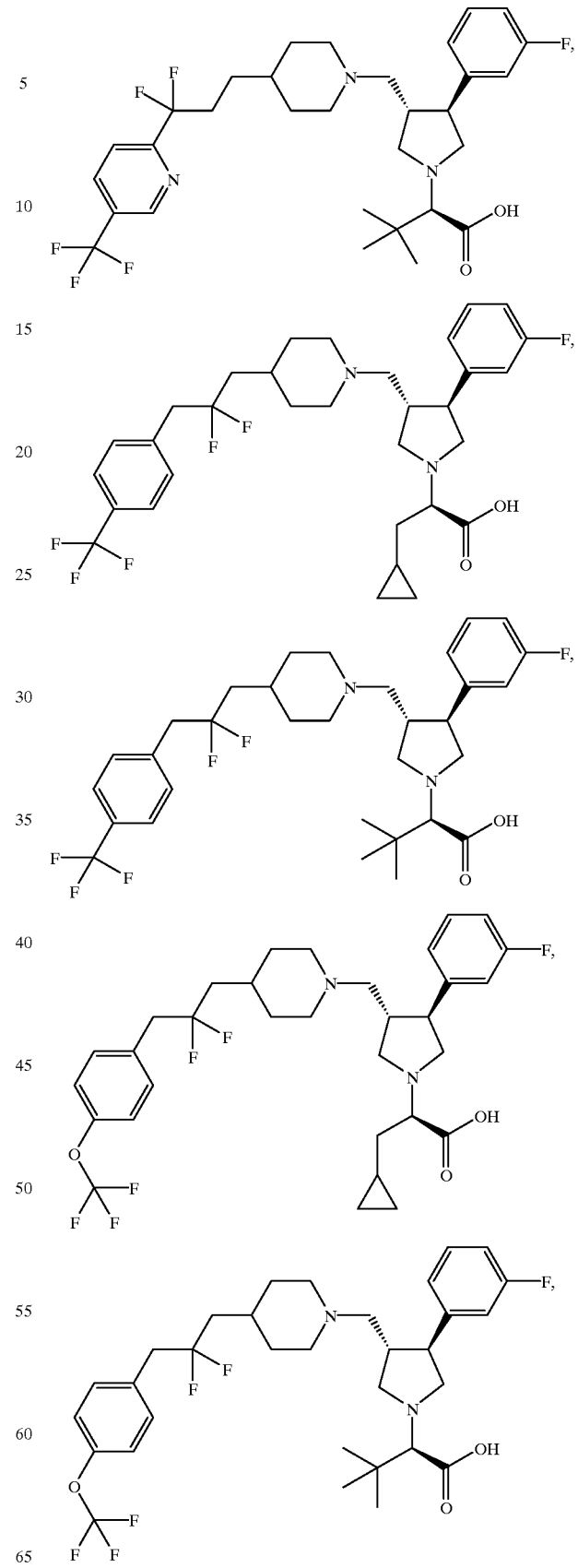

307
-continued
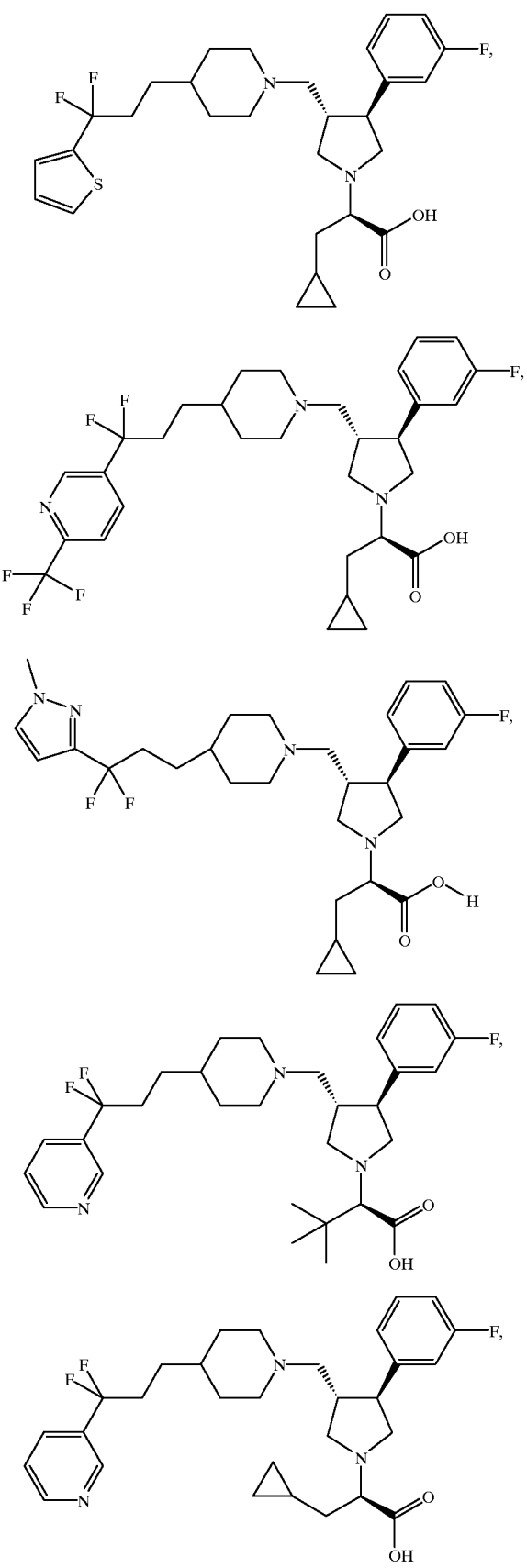
308
-continued
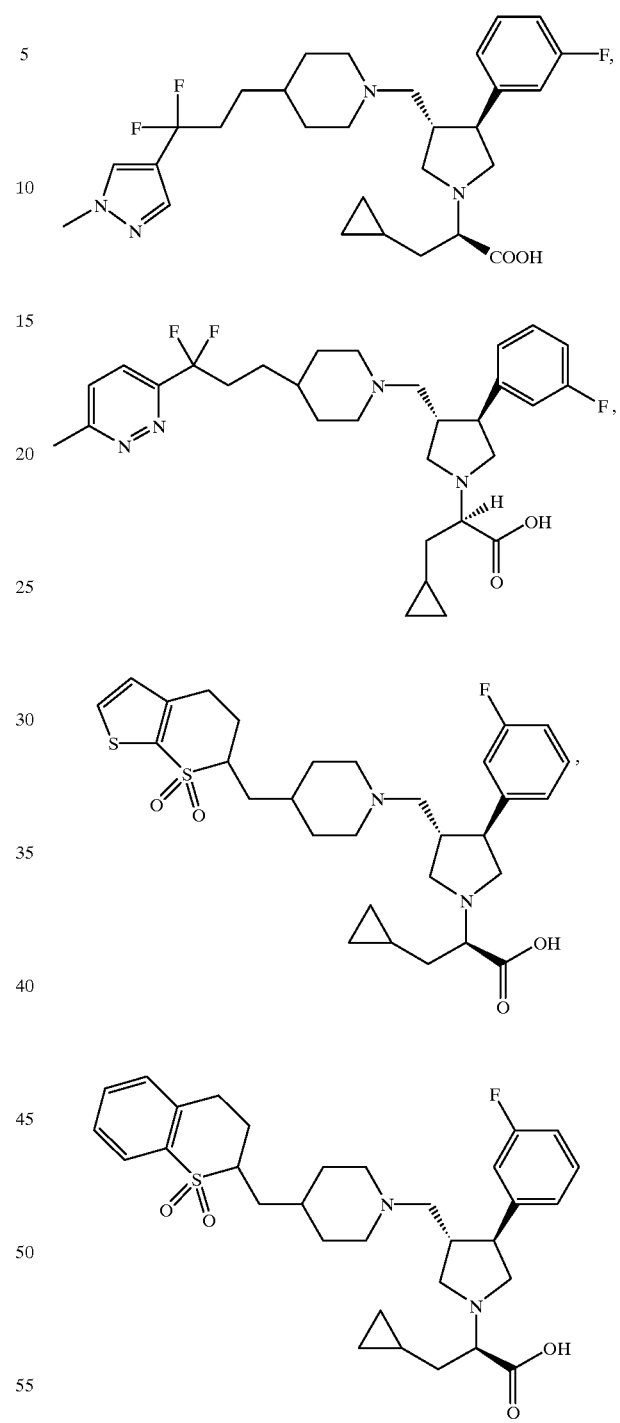
and pharmaceutically acceptable salts and individual diastereomers thereof.
36. A compound according to claim 29, which is a compound selected from the group consisting of:

309
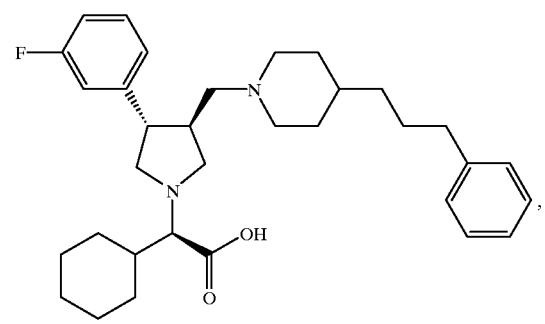
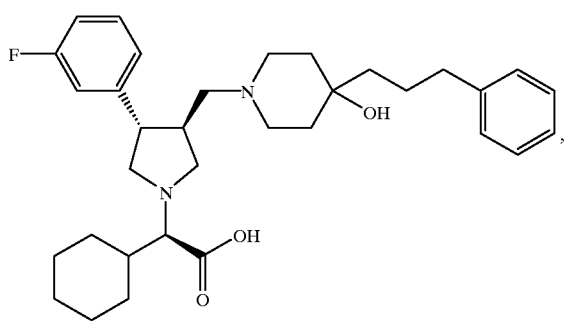
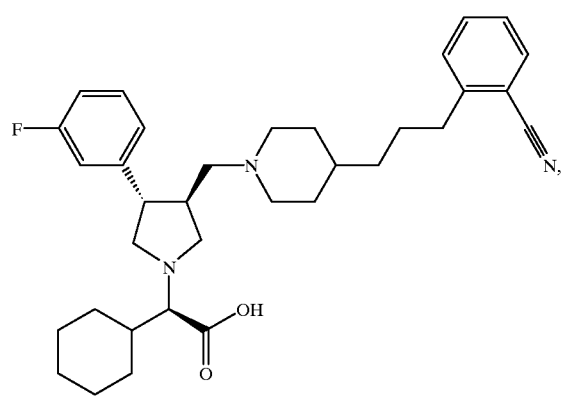
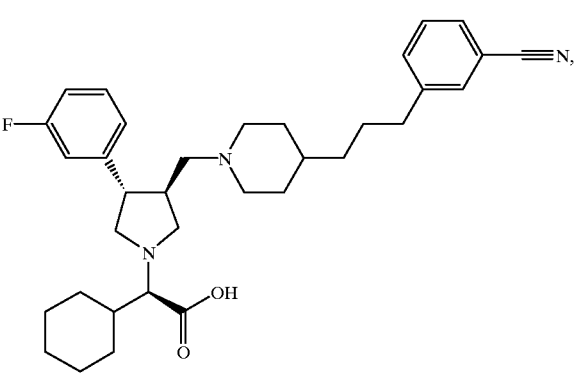
310
-continued
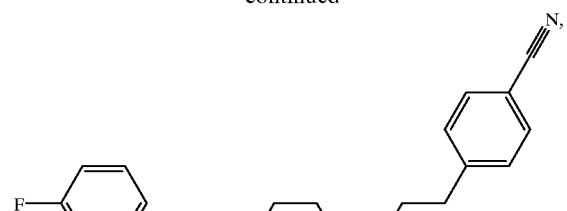
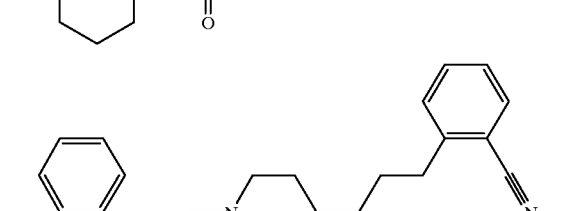
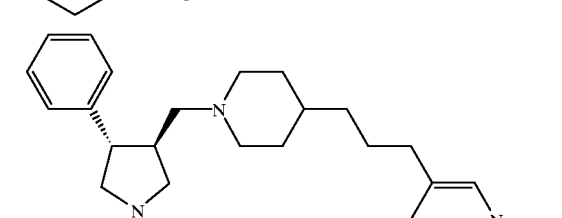
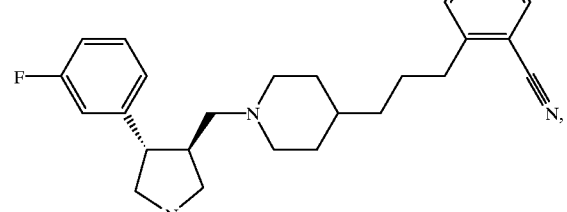

311
-continued
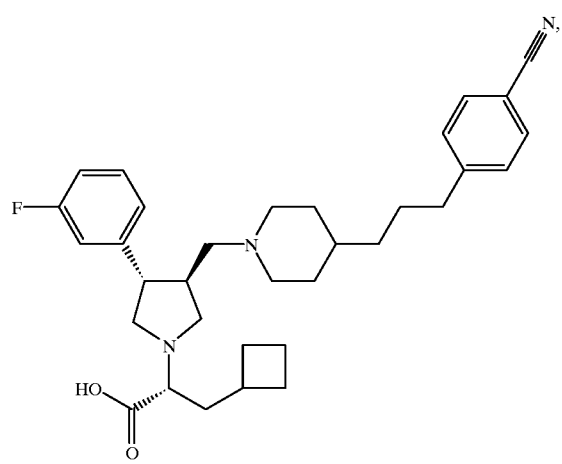
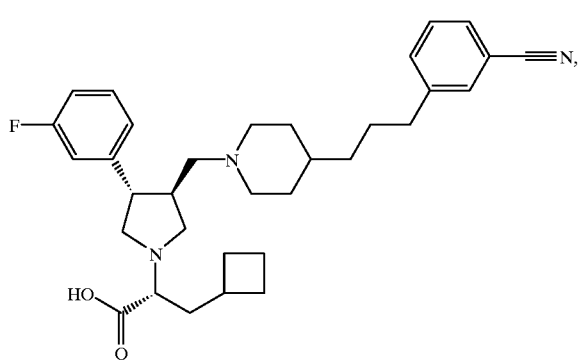
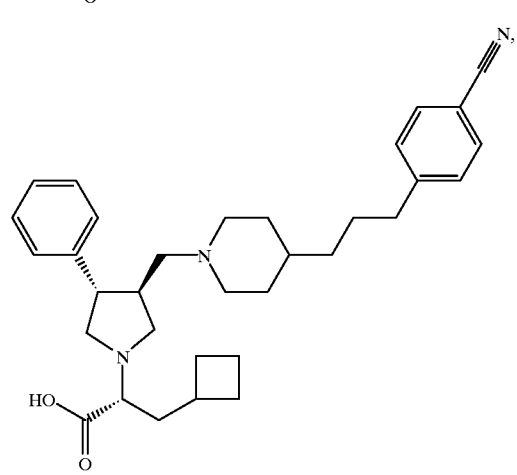
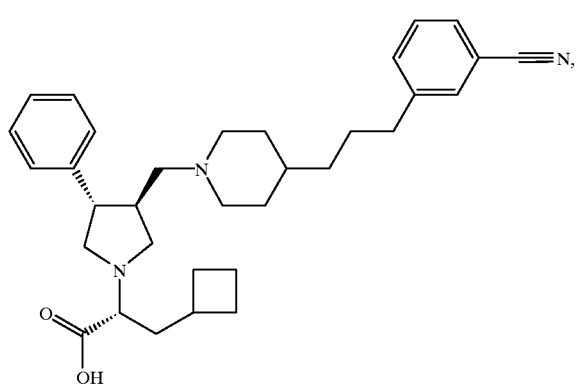
312
-continued
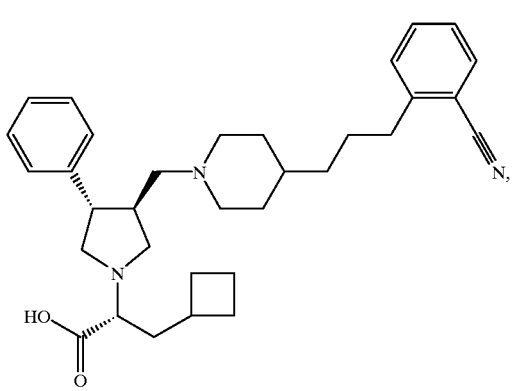
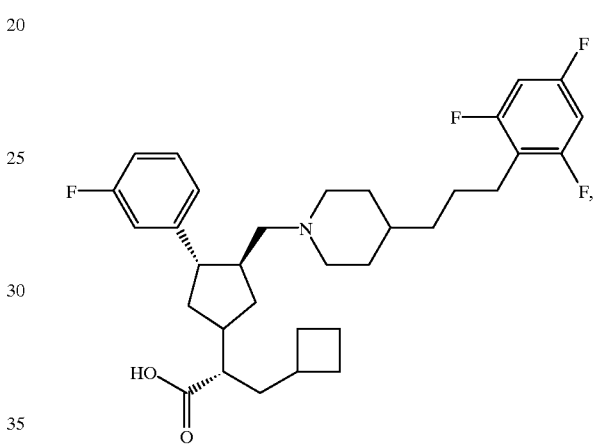
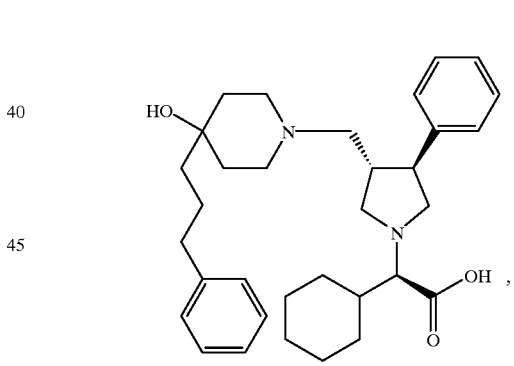
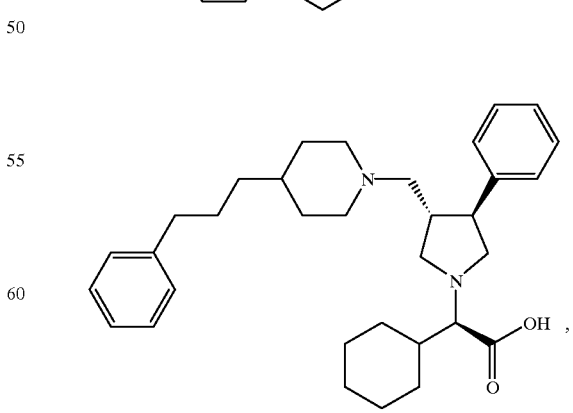

313
-continued
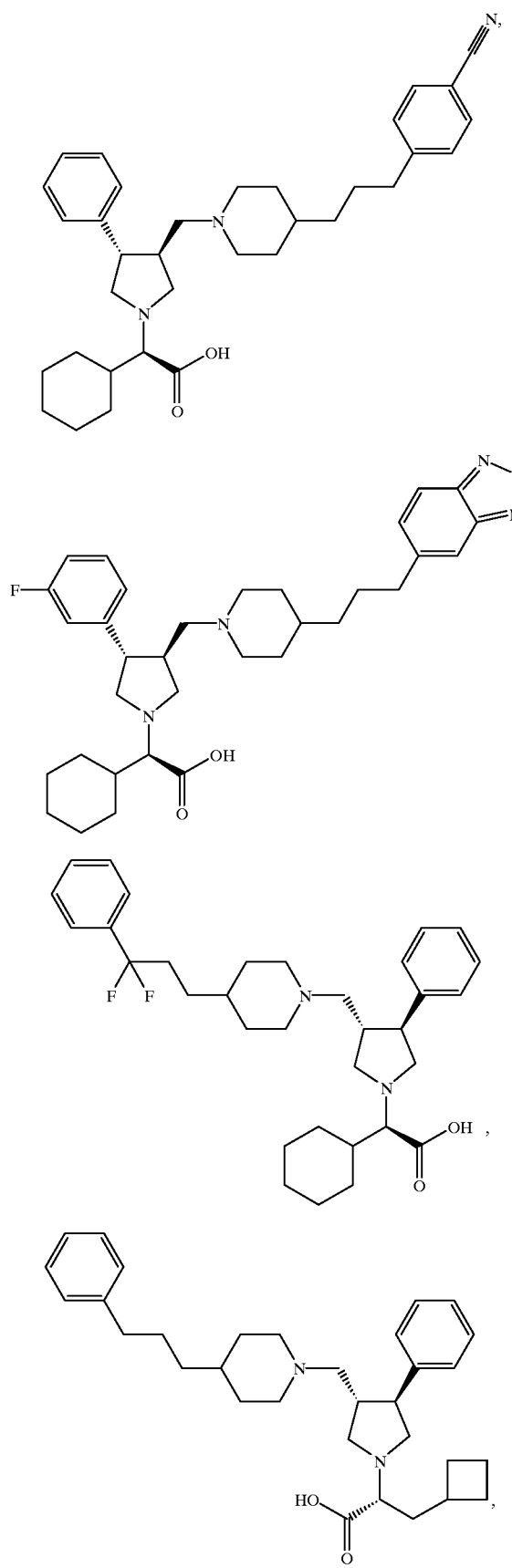
314
-continued
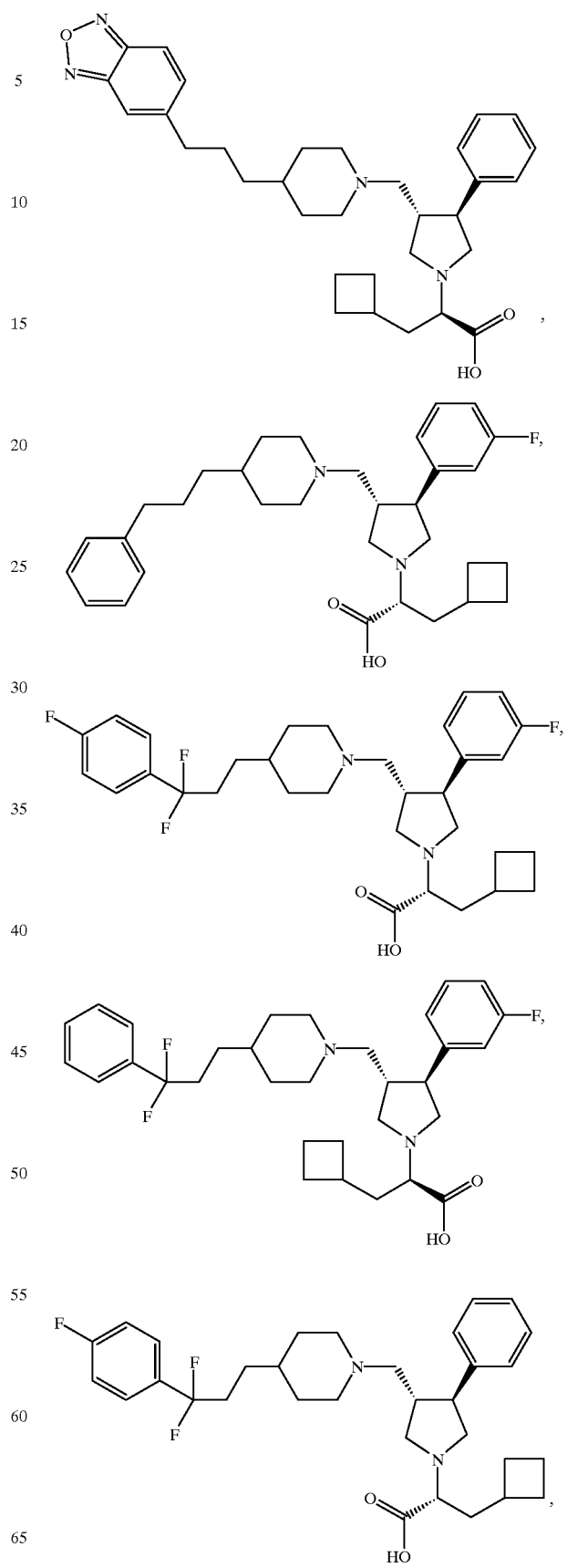

315
-continued
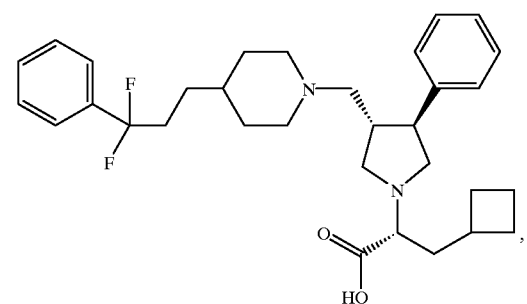
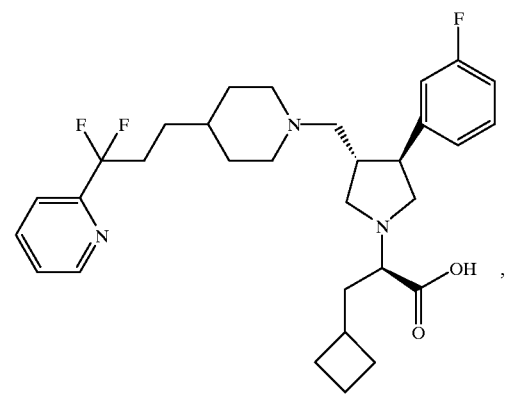
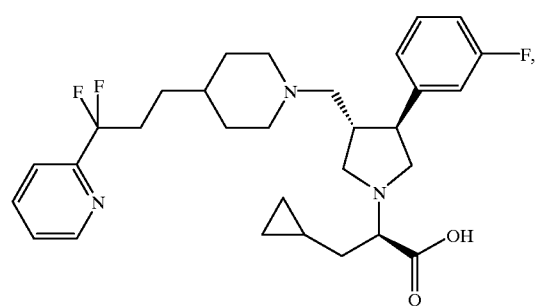
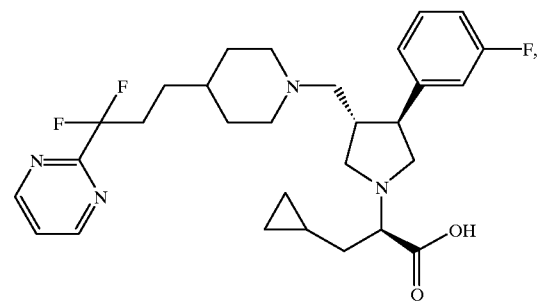
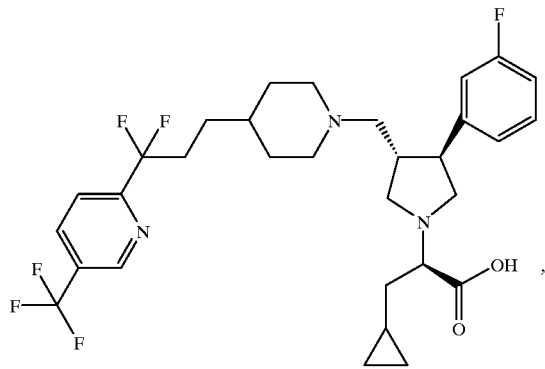
316
-continued
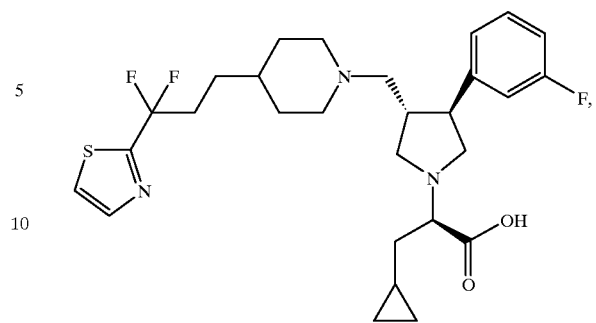
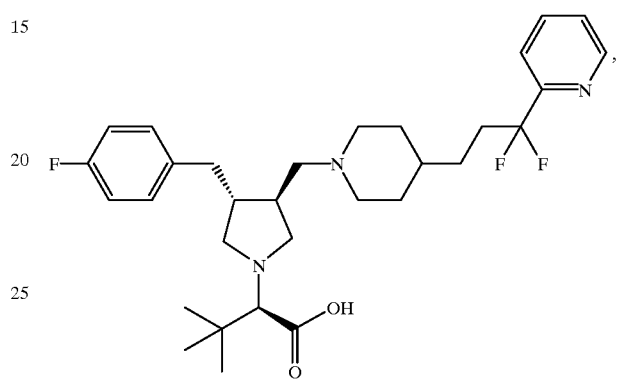
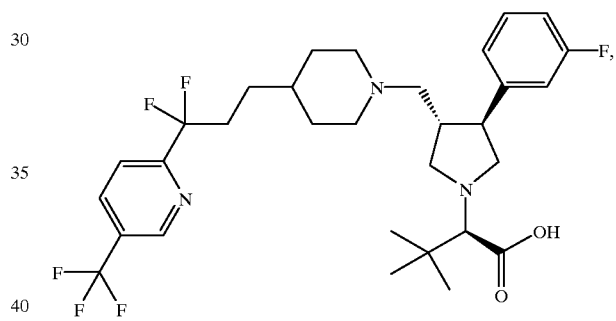
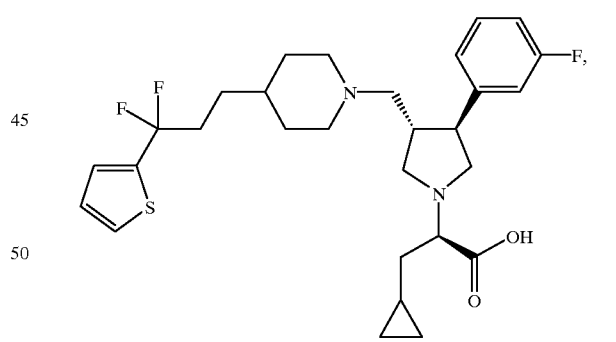
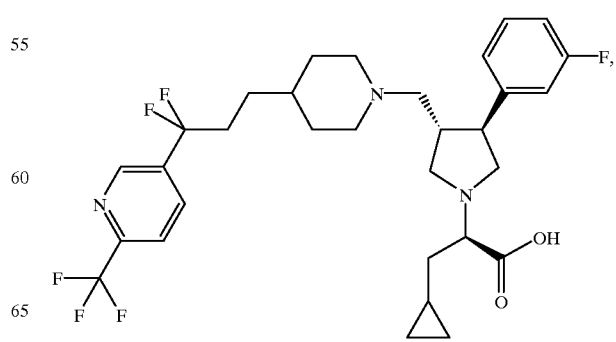

317
-continued
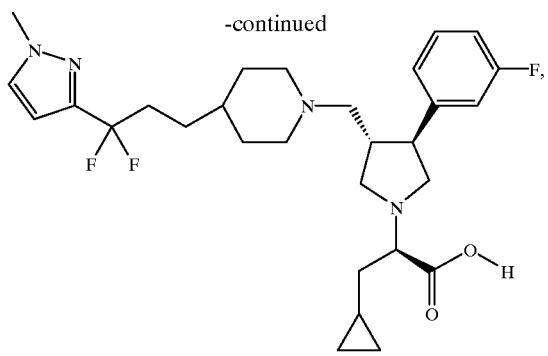
318
-continued
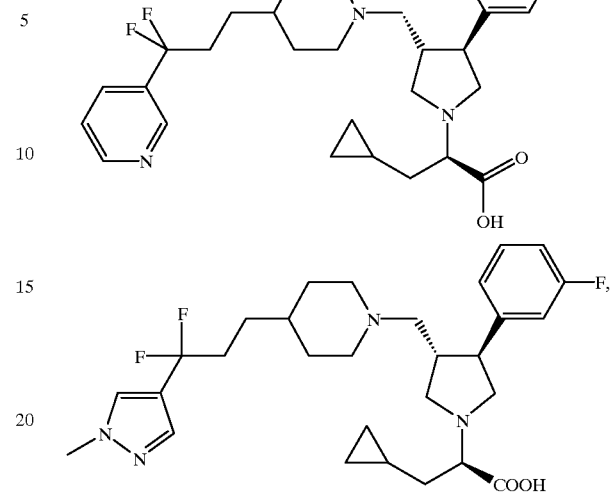
and pharmaceutically acceptable salts and individual diastereomers thereof.
* * * * *